United States Patent
Cai et al.

(10) Patent No.: US 11,970,506 B2
(45) Date of Patent: Apr. 30, 2024

(54) BIOACTIVE MOLECULE CONJUGATE, PREPARATION METHOD AND USE THEREOF

(71) Applicant: SICHUAN KELUN-BIOTECH BIOPHARMACEUTICAL CO., LTD., Chengdu (CN)

(72) Inventors: Jiaqiang Cai, Chengdu (CN); Shuai Song, Chengdu (CN); Tongtong Xue, Chengdu (CN); Liang Xiao, Chengdu (CN); Hanwen Deng, Chengdu (CN); Qiang Tian, Chengdu (CN); Guoqing Zhong, Chengdu (CN); Lichun Wang, Chengdu (CN); Jingyi Wang, Chengdu (CN)

(73) Assignee: SICHUAN KELUN-BIOTECH BIOPHARMACEUTICAL CO., LTD., Chengdu (CN)

( * ) Notice: Subject to any disclaimer, the term of this patent is extended or adjusted under 35 U.S.C. 154(b) by 599 days.

(21) Appl. No.: 16/758,980

(22) PCT Filed: Dec. 10, 2018

(86) PCT No.: PCT/CN2018/120125
§ 371 (c)(1),
(2) Date: Apr. 24, 2020

(87) PCT Pub. No.: WO2019/114666
PCT Pub. Date: Jun. 20, 2019

(65) Prior Publication Data
US 2020/0347075 A1 Nov. 5, 2020
US 2021/0101906 A2 Apr. 8, 2021

(30) Foreign Application Priority Data

Dec. 15, 2017 (CN) .......................... 201711347535.6
Mar. 20, 2018 (CN) .......................... 201810230346.9
Sep. 14, 2018 (CN) .......................... 201811071947.6

(51) Int. Cl.
| | |
|---|---|
| *C07D 491/22* | (2006.01) |
| *A61K 45/06* | (2006.01) |
| *A61K 47/68* | (2017.01) |
| *A61P 35/00* | (2006.01) |
| *C07D 401/14* | (2006.01) |
| *C07D 403/12* | (2006.01) |
| *C07D 403/14* | (2006.01) |
| *C07K 5/062* | (2006.01) |
| *C07K 16/30* | (2006.01) |
| *C07K 16/32* | (2006.01) |

(52) U.S. Cl.
CPC ........ *C07D 491/22* (2013.01); *A61K 47/6803* (2017.08); *A61K 47/6851* (2017.08); *A61K 47/6885* (2017.08); *A61P 35/00* (2018.01); *C07D 401/14* (2013.01); *C07D 403/12* (2013.01); *C07D 403/14* (2013.01); *C07K 5/06052* (2013.01); *C07K 16/30* (2013.01); *C07K 16/32* (2013.01); *A61K 45/06* (2013.01)

(58) Field of Classification Search
CPC .... C07K 5/06052; C07K 16/32; C07K 16/30; C07D 401/14; C07D 491/22; C07D 487/04; C07D 403/12; C07D 403/14; A61P 35/00; A61K 47/6885; A61K 47/6851; A61K 47/6803; A61K 47/6889; A61K 47/6855; A61K 45/06
See application file for complete search history.

(56) References Cited

U.S. PATENT DOCUMENTS

| | | |
|---|---|---|
| 5,410,024 A | 4/1995 | Pettit et al. |
| 5,767,237 A | 6/1998 | Sakakibara et al. |
| 2011/0020343 A1 | 1/2011 | Senter et al. |
| 2014/0017265 A1 | 1/2014 | Yurkovetskiy et al. |
| 2019/0076438 A1 | 3/2019 | Xue et al. |

FOREIGN PATENT DOCUMENTS

| | | | |
|---|---|---|---|
| CN | 1938046 A | 3/2007 | |
| CN | 104379168 A | 2/2015 | |
| CN | 106729743 A | 5/2017 | |
| CN | 107029244 A | 8/2017 | |
| CN | 110903395 | 3/2020 | |
| WO | WO-9411377 A2 * | 5/1994 | ........... C07D 317/66 |
| WO | WO 2009/117531 A1 | 9/2009 | |
| WO | WO 2011/097627 A1 | 8/2011 | |
| WO | WO 2013/072813 A2 | 5/2013 | |
| WO | WO2014092804 | 6/2014 | |
| WO | WO 2014/144878 | 9/2014 | |

(Continued)

OTHER PUBLICATIONS

Goldenberg DM et al. Trop-2 is a novel target for solid cancer therapy with sacituzumab govitecan (IMMU-132), an antibody-drug conjugate (ADC) Oncotarget. 2015; 6:22496-22512 (Year: 2015).*

(Continued)

*Primary Examiner* — Karen A. Canella
*Assistant Examiner* — John J Skoko, III
(74) *Attorney, Agent, or Firm* — Jones Day

(57) ABSTRACT

Provided herein are bioactive molecule conjugates, preparation methods and use thereof, particularly bioactive molecule conjugates (such as antibody-drug conjugates and small molecule drug conjugates) obtained by improved coupling of a drug and a targeting moiety, as well as their preparation method and use for the treatment of a disease associated with an abnormal cell activity.

22 Claims, 18 Drawing Sheets
Specification includes a Sequence Listing.

(56) References Cited

FOREIGN PATENT DOCUMENTS

| WO | WO-2014144878 A2 * | 9/2014 | ....... A61K 47/48215 |
|---|---|---|---|
| WO | WO 2016/205738 A2 | 12/2016 | |
| WO | WO2017/004144 | 1/2017 | |
| WO | WO-2017031034 A2 * | 2/2017 | ........... A61K 31/426 |
| WO | WO 2017/088734 | 6/2017 | |
| WO | WO2018025168 | 2/2018 | |
| WO | WO2018/183041 | 10/2018 | |
| WO | WO-2018227023 A1 * | 12/2018 | ......... A61K 47/6849 |
| WO | WO 2019/114666 A1 | 6/2019 | |

OTHER PUBLICATIONS

Li F et al. Camptothecin (CPT) and its derivatives are known to target topoisomerase I (Top1) as their mechanism of action: did we miss something in CPT analogue molecular targets for treating human disease such as cancer? Am J Cancer Res. 2017; 7(12): 2350-2394 (Year: 2017).*

Verma RP et al. Camptothecins: A SAR/QSAR Study Chem. Rev. 2009, 109, 213-235 (Year: 2009).*

Jain N et al. Current ADC Linker Chemistry. Pharm Res (2015) 32:3526-3540 (Year: 2015).*

Govindan SV et al. Milatuzumab-SN-38 conjugates for the treatment of CD74+ cancers. Mol Cancer Ther. 2013 12:968-978 (Year: 2013).*

Gupta N et al. Development of a facile antibody-drug conjugate platform for increased stability and homogeneity. Chem Sci. Mar. 1, 2017; 8(3): 2387-2395. (Year: 2017).*

Ren T et al. Antibody disulfide bond reduction and recovery during biopharmaceutical process development—A review Biotechnology and Bioengineering 2021 118(8) 2829-2844 (Year: 2021).*

Thomas A et al. Antibody-drug conjugates for cancer therapy. Lancet Oncol. Jun. 2016; 17(6): e254-e262 (Year: 2016).*

International Search Report for International Application No. PCT/CN2018/082809, dated Jul. 9, 2018.

Written Opinion of the International Searching Authority for International Application No. PCT/CN2018/082809, dated Jul. 9, 2018.

Fosgerau K et al., Peptide Therapeutics: Current Status and Future Directions, Drug Discovery Today, vol. 20, pp. 122-128 (Jan. 2015).

Non-Final Office Action dated Mar. 29, 2021, for U.S. Appl. No. 16/497,415.

European Search Report for EP Application No. 18787805.3, dated Mar. 12, 2021.

Cardillo et al., "Humanized Anti-Trop-2 IgG-SN-38 Conjugate for Effective Treatment of Diverse Epithelial Cancers: Preclinical Studies in Human Cancer Xenograft Models and Monkeys", Clin Cancer Res. 17: 3157-3169 (2017).

Toda et al., "Rapid, Stable, Chemoselective Labeling of Thiols with Julia-Kocieński Like Reagents: A Serum-Stable Alternative to Maleimide-Based Protein Conjugation", Angew. Chem. Int. Ed. 52: 12592-12596 (2013).

Bauer et al., "2-Sulfonylpyrimidines: Mild alkylating agents with anticancer activity toward p53-compromised cells", Proceedings of the National Academy of Science, 2016, 5271-5280.

International Search Report for International Application No. PCT/CN2018/120125, dated Mar. 18, 2019.

Written Opinion of the International Searching Authority for International Application No. PCT/CN2018/120125, dated Mar. 18, 2019.

Narihiro Toda et al., "Rapid, Stable, Chemoselective Labeling of Thiols with Julia-Kocieński-Like Reagents: A Serum-Stable Alternative to Maleimide-Based Protein Conjugation," *Angew. Chem. Int. Ed.* 2013, vol. 52(48), pp. 12592-12596.

Xiuling Li et al., "Site-Specific Dual Antibody Conjugation via Engineered Cysteine and Selenocysteine Residues," *Bioconjug Chem.* 2015, vol. 26(11), pp. 2243-2248.

James T. Patterson et al., "Improving the Serum Stability of Site-Specific Antibody Conjugates with Sulfone Linkers," *Bioconjugate Chem.* 2014, vol. 25, pp. 1402-1407.

Xiaofei Liang et al., "Discovery of 2-((3-Amino-4-methylphenyl)amino)-N-(2-methyl-5-(3-(trifluoromethyl)benzamido)phenyl)-4-(methylamino)pyrimidine-5-carboxamide (CHMFL-ABL-053) as a Potent, Selective, and Orally Available BCR-ABL/SRC/p38 Kinase Inhibitor for Chronic Myeloid Leukemia," *J. Med. Chem.* 2016, vol. 59, pp. 1984-2004.

Sung-Ju Moon et al., "Antibody Conjugates of 7-Ethyl-10-hydroxycamptothecin (SN-38) for Targeted Cancer Chemotherapy," *J. Med. Chem.*, 2008, vol. 51 (21), 6916-6926.

* cited by examiner

SEQUENCE LISTING

```
<160> NUMBER OF SEQ ID NOS: 20

<210> SEQ ID NO 1
<211> LENGTH: 7
<212> TYPE: PRT
<213> ORGANISM: artificial
<220> FEATURE:
<223> OTHER INFORMATION: Heavy chain CDR1 of antibodies of M1, M2 and M3

<400> SEQUENCE: 1

Gly Tyr Thr Phe Thr Asn Tyr
1               5

<210> SEQ ID NO 2
<211> LENGTH: 6
<212> TYPE: PRT
<213> ORGANISM: artificial
<220> FEATURE:
<223> OTHER INFORMATION: Heavy chain CDR2 of antibodies of M1, M2 and M3

<400> SEQUENCE: 2

Asn Thr Asp Ser Gly Glu
1               5

<210> SEQ ID NO 3
<211> LENGTH: 12
<212> TYPE: PRT
<213> ORGANISM: artificial
<220> FEATURE:
<223> OTHER INFORMATION: Heavy chain CDR3 of antibodies of M1, M2 and M3

<400> SEQUENCE: 3

Gly Gly Phe Gly Ser Ser Tyr Trp Tyr Phe Asp Val
1               5                   10

<210> SEQ ID NO 4
<211> LENGTH: 11
<212> TYPE: PRT
<213> ORGANISM: artificial
<220> FEATURE:
<223> OTHER INFORMATION: Light chain CDR1 of antibodies of M1 and M2

<400> SEQUENCE: 4

Lys Ala Ser Gln Asp Val Ser Ser Ala Val Ala
1               5                   10

<210> SEQ ID NO 5
<211> LENGTH: 7
```

```
<212> TYPE: PRT
<213> ORGANISM: artificial
<220> FEATURE:
<223> OTHER INFORMATION: Light chain CDR2 of antibodies of M1, M2 and M3

<400> SEQUENCE: 5

Ser Ala Ser Tyr Arg Tyr Thr
1               5

<210> SEQ ID NO 6
<211> LENGTH: 9
<212> TYPE: PRT
<213> ORGANISM: artificial
<220> FEATURE:
<223> OTHER INFORMATION: Light chain CDR3 of antibodies of M1 and M3

<400> SEQUENCE: 6

Gln Gln His Tyr Ser Thr Pro Leu Thr
1               5

<210> SEQ ID NO 7
<211> LENGTH: 9
<212> TYPE: PRT
<213> ORGANISM: artificial
<220> FEATURE:
<223> OTHER INFORMATION: Light chain CDR3 of antibody M2

<400> SEQUENCE: 7

Gln Gln His Tyr Ile Thr Pro Leu Thr
1               5

<210> SEQ ID NO 8
<211> LENGTH: 11
<212> TYPE: PRT
<213> ORGANISM: artificial
<220> FEATURE:
<223> OTHER INFORMATION: Light chain CDR1 of antibody M3

<400> SEQUENCE: 8

Lys Ala Ser Gln Asp Val Ser Ile Ala Val Ala
1               5                   10

<210> SEQ ID NO 9
<211> LENGTH: 107
<212> TYPE: PRT
<213> ORGANISM: artificial
<220> FEATURE:
<223> OTHER INFORMATION: Light chain constant region of antibodies of
      M1, M2 and M3

<400> SEQUENCE: 9

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105
```

100                 105

<210> SEQ ID NO 10
<211> LENGTH: 330
<212> TYPE: PRT
<213> ORGANISM: artificial
<220> FEATURE:
<223> OTHER INFORMATION: Heavy chain constant region of antibodies of
      M1, M2 and M3

<400> SEQUENCE: 10

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 11
<211> LENGTH: 121

```
<212> TYPE: PRT
<213> ORGANISM: artificial
<220> FEATURE:
<223> OTHER INFORMATION: Heavy chain variable region of antibody M1

<400> SEQUENCE: 11

Gln Val Gln Leu Gln Gln Ser Gly Ser Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Lys Gln Ala Pro Gly Gln Gly Leu Lys Trp Met
        35                  40                  45

Gly Trp Ile Asn Thr Asp Ser Gly Glu Pro Thr Tyr Thr Asp Asp Phe
    50                  55                  60

Lys Gly Arg Phe Ala Phe Ser Leu Asp Thr Ser Val Ser Thr Ala Tyr
65                  70                  75                  80

Leu Gln Ile Ser Ser Leu Lys Ala Asp Asp Thr Ala Val Tyr Phe Cys
                85                  90                  95

Ala Arg Gly Gly Phe Gly Ser Ser Tyr Trp Tyr Phe Asp Val Trp Gly
            100                 105                 110

Gln Gly Ser Leu Val Thr Val Ser Ser
        115                 120

<210> SEQ ID NO 12
<211> LENGTH: 107
<212> TYPE: PRT
<213> ORGANISM: artificial
<220> FEATURE:
<223> OTHER INFORMATION: Light chain variable region of antibody M1

<400> SEQUENCE: 12

Asp Ile Gln Leu Thr Gln Ser Pro Ser Ser Leu Ser Ala Ser Val Gly
1               5                   10                  15

Asp Arg Val Ser Ile Thr Cys Lys Ala Ser Gln Asp Val Ser Ser Ala
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Asp Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Val Tyr Tyr Cys Gln Gln His Tyr Ser Thr Pro Leu
                85                  90                  95

Thr Phe Gly Ala Gly Thr Lys Val Glu Ile Lys
            100                 105

<210> SEQ ID NO 13
<211> LENGTH: 121
<212> TYPE: PRT
<213> ORGANISM: artificial
<220> FEATURE:
<223> OTHER INFORMATION: Heavy chain variable region of antibody M2

<400> SEQUENCE: 13

Gln Val Gln Leu Gln Gln Ser Gly Ser Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Lys Gln Ala Pro Gly Gln Gly Leu Lys Trp Met
```

```
                35                  40                  45
Gly Trp Ile Asn Thr Asp Ser Gly Glu Pro Thr Tyr Thr Asp Asp Phe
    50                  55                  60

Lys Gly Arg Phe Ala Phe Ser Leu Asp Thr Ser Val Ser Thr Ala Tyr
65                  70                  75                  80

Leu Gln Ile Ser Ser Leu Lys Ala Asp Asp Thr Ala Val Tyr Phe Cys
                85                  90                  95

Ala Arg Gly Gly Phe Gly Ser Ser Tyr Trp Tyr Phe Asp Val Trp Gly
            100                 105                 110

Gln Gly Ser Leu Val Thr Val Ser Ser
            115                 120

<210> SEQ ID NO 14
<211> LENGTH: 107
<212> TYPE: PRT
<213> ORGANISM: artificial
<220> FEATURE:
<223> OTHER INFORMATION: Light chain variable region of antibody M2

<400> SEQUENCE: 14

Asp Ile Gln Leu Thr Gln Ser Pro Ser Ser Leu Ser Ala Ser Val Gly
1               5                   10                  15

Asp Arg Val Ser Ile Thr Cys Lys Ala Ser Gln Asp Val Ser Ser Ala
                20                  25                  30

Val Ala Trp Tyr Gln Gln Lys Pro Gly Lys Ala Pro Lys Leu Leu Ile
            35                  40                  45

Tyr Ser Ala Ser Tyr Arg Tyr Thr Gly Val Pro Asp Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Val Tyr Tyr Cys Gln Gln His Tyr Ile Thr Pro Leu
                85                  90                  95

Thr Phe Gly Ala Gly Thr Lys Val Glu Ile Lys
            100                 105

<210> SEQ ID NO 15
<211> LENGTH: 121
<212> TYPE: PRT
<213> ORGANISM: artificial
<220> FEATURE:
<223> OTHER INFORMATION: Heavy chain variable region of antibody M3

<400> SEQUENCE: 15

Gln Val Gln Leu Gln Gln Ser Gly Ser Glu Leu Lys Lys Pro Gly Ala
1               5                   10                  15

Ser Val Lys Val Ser Cys Lys Ala Ser Gly Tyr Thr Phe Thr Asn Tyr
                20                  25                  30

Gly Met Asn Trp Val Lys Gln Ala Pro Gly Gln Gly Leu Lys Trp Met
            35                  40                  45

Gly Trp Ile Asn Thr Asp Ser Gly Glu Pro Thr Tyr Thr Asp Asp Phe
    50                  55                  60

Lys Gly Arg Phe Ala Phe Ser Leu Asp Thr Ser Val Ser Thr Ala Tyr
65                  70                  75                  80

Leu Gln Ile Ser Ser Leu Lys Ala Asp Asp Thr Ala Val Tyr Phe Cys
                85                  90                  95

Ala Arg Gly Gly Phe Gly Ser Ser Tyr Trp Tyr Phe Asp Val Trp Gly
            100                 105                 110
```

```
Gln Gly Ser Leu Val Thr Val Ser Ser
        115                 120

<210> SEQ ID NO 16
<211> LENGTH: 107
<212> TYPE: PRT
<213> ORGANISM: artificial
<220> FEATURE:
<223> OTHER INFORMATION: Light chain variable region of antibody M3

<400> SEQUENCE: 16

Asp Ile Gln Leu Thr Gln Ser Pro Ser Ser Leu Ser Ala Ser Val Gly
1               5                   10                  15

Asp Arg Val Ser Ile Thr Cys Lys Ala Ser Gln Asp Val Ser Ile Ala
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Asp Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Val Tyr Tyr Cys Gln Gln His Tyr Ser Thr Pro Leu
                85                  90                  95

Thr Phe Gly Ala Gly Thr Lys Val Glu Ile Lys
            100                 105

<210> SEQ ID NO 17
<211> LENGTH: 450
<212> TYPE: PRT
<213> ORGANISM: artificial
<220> FEATURE:
<223> OTHER INFORMATION: Heavy chain amino acid sequences of Trastuzumab

<400> SEQUENCE: 17

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190
```

```
Ser Ser Ser Leu Gly Thr Gln Thr Tyr Ile Cys Asn Val Asn His Lys
        195                 200                 205

Pro Ser Asn Thr Lys Val Asp Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
        290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
        340                 345                 350

Thr Leu Pro Pro Ser Arg Glu Glu Met Thr Lys Asn Gln Val Ser Leu
            355                 360                 365

Thr Cys Leu Val Lys Gly Phe Tyr Pro Ser Asp Ile Ala Val Glu Trp
        370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 18
<211> LENGTH: 214
<212> TYPE: PRT
<213> ORGANISM: artificial
<220> FEATURE:
<223> OTHER INFORMATION: Light chain amino acid sequences of Trastuzumab

<400> SEQUENCE: 18

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95
```

```
Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 19
<211> LENGTH: 451
<212> TYPE: PRT
<213> ORGANISM: artificial
<220> FEATURE:
<223> OTHER INFORMATION: Heavy chain amino acid sequences of Sacituzumab

<400> SEQUENCE: 19

Gln Val Gln Leu Gln Gln Ser Gly Ser Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Lys Gln Ala Pro Gly Gln Gly Leu Lys Trp Met
        35                  40                  45

Gly Trp Ile Asn Thr Tyr Thr Gly Glu Pro Thr Tyr Thr Asp Asp Phe
    50                  55                  60

Lys Gly Arg Phe Ala Phe Ser Leu Asp Thr Ser Val Ser Thr Ala Tyr
65                  70                  75                  80

Leu Gln Ile Ser Ser Leu Lys Ala Asp Asp Thr Ala Val Tyr Phe Cys
                85                  90                  95

Ala Arg Gly Gly Phe Gly Ser Ser Tyr Trp Tyr Phe Asp Val Trp Gly
            100                 105                 110

Gln Gly Ser Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Leu Leu Gly
225                 230                 235                 240
```

```
Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 20
<211> LENGTH: 214
<212> TYPE: PRT
<213> ORGANISM: artificial
<220> FEATURE:
<223> OTHER INFORMATION: Light chain amino acid sequences of Sacituzumab

<400> SEQUENCE: 20

Asp Ile Gln Leu Thr Gln Ser Pro Ser Ser Leu Ser Ala Ser Val Gly
1               5                   10                  15

Asp Arg Val Ser Ile Thr Cys Lys Ala Ser Gln Asp Val Ser Ile Ala
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Asp Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Val Tyr Tyr Cys Gln Gln His Tyr Ile Thr Pro Leu
                85                  90                  95

Thr Phe Gly Ala Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125
```

```
Thr Ala Ser Val Val Cys Leu Leu Asn Asn Phe Tyr Pro Arg Glu Ala
    130             135             140

Lys Val Gln Trp Lys Val Asp Asn Ala Leu Gln Ser Gly Asn Ser Gln
145             150              155             160

Glu Ser Val Thr Glu Gln Asp Ser Lys Asp Ser Thr Tyr Ser Leu Ser
            165             170             175

Ser Thr Leu Thr Leu Ser Lys Ala Asp Tyr Glu Lys His Lys Val Tyr
        180             185             190

Ala Cys Glu Val Thr His Gln Gly Leu Ser Ser Pro Val Thr Lys Ser
    195             200             205

Phe Asn Arg Gly Glu Cys
    210
```

BIOACTIVE MOLECULE CONJUGATE, PREPARATION METHOD AND USE THEREOF

This application is a national stage filing under 35 U.S.C. § 371 of International Application No. PCT/CN2018/120125, filed on Dec. 10, 2018, which claims the benefit of the filing date of Chinese Patent Application No. 201711347535.6, filed on Dec. 15, 2017; Chinese Patent Application No. 201810230346.9, filed on Mar. 20, 2018; and Chinese Patent Application No. 201811071947.6, filed on Sep. 14, 2018; each of which is incorporated herein by reference.

FIELD OF THE INVENTION

Reference to an Electronic Sequence Listing

The contents of the electronic sequence listing are herein incorporated by reference in their entirety.

The disclosure belongs to the technical field of medical technology, and relates to a bioactive molecule conjugate, preparation method thereof, and use in the prevention and/or treatment of a disease associated with an abnormal cell activity, including but not limited to the use in the prevention and/or treatment of a neoplastic disease.

BACKGROUND ART

Chemotherapy was once a standard therapy for cancer, but bioactive molecules having high killing effect can mistakenly kill normal cells, resulting in serious side effects. Targeted therapy has become a hot research topic in the field of oncology due to the targetability and anti-tumor activity. Since the 20th century, breakthroughs have been made in the development of anti-tumor drugs and tumor targeted therapies using bio-macromolecular drugs (e.g., therapeutic antibodies or antibody fragments) and targeted small molecule ligands. However, despite of their high targetability, bio-macromolecular drugs have limited curative effects on solid tumors; in addition, bioactive molecules often lack targetability and accidentally injure normal cells and cause serious toxic and side effects, despite of their high killing effect on cancer cells.

Recent studies have found that therapeutic antibodies can be linked to bioactive molecules to form antibody-drug conjugates (ADCs). The ADC combine the targeting effect of antibodies and the activity of bioactive molecules making it a "biological missile". The ADC is guided by antibodies to bind to target cells, and then is internalized by cells to release drugs thereby treating relevant diseases. Due to the specificity and targetability to tumor cell related targets, the application values of antibodies not only are reflected in the treatment, but also become an ideal carrier for drug targeted delivery, and reduce side effects of drugs. Small molecule drug conjugates (SMDCs) are designed on the basis of same principle as antibody-drug conjugates (ADCs); that is, coupling bioactive molecules with some small molecule ligands which can selectively bind to receptors on the surfaces of tumor cells through chemical processes, thereby improving the targetability of effector molecules (bioactive molecules) to tumor cells. The difference between the SMDCs and the ADCs is that the SMDCs use small molecule ligands instead of antibodies, and there is not yet SMDC available on the market.

Currently, there are four commercially available ADCs: Mylotarg (Gemtuzumab Ozogamicin), Adcetris (Brentuximab Vedotin, CD30 monoclonal antibody-MMAE), Kadcyla (Trastuzumab Emtansine) and Besponsa (Inotuzumab ozogamicin, CD22 monoclonal antibody-calicheamicin). An ADC generally consists of an antibody, a bioactive molecule and a linker. The bioactive molecule is covalently coupled to the antibody via the linker; the antibody (e.g., monoclonal antibodies) can specifically recognize a specific target on the surface of a tumor cell, thus guiding the ADC to reach the surface of cancer cell and enabling the ADC to enter the cancer cell through endocytosis effect; then the bioactive molecule is released in the cancer cell to achieve the effect of specifically killing the cancer cell without damaging normal tissue cells.

Lysine is the most common linking site in antibodies, and ε-amino groups thereof can react with activated carboxyl groups of linkers to form amide bonds. Techniques for site-specific coupling are currently available, that is, carboxyl groups of linkers are activated, and then form amide bonds with specific lysine ε-amino groups in antibodies to complete the coupling. However, such amide bonds are prone to hydrolysis under the action of enzymes in vivo, as a result, bioactive molecules and antibodies dissociate before reaching target cells resulted in increasing toxicity while losing targetability of ADCs.

Thio groups of antibody cysteine usually exist in the form of disulfide bonds. The disulfide bonds in the antibody can be opened to provide multiple free sulfhydryl groups as coupling sites. One method of coupling with the sulfhydryl groups of the antibody is Michael addition reaction between the free sulfhydryl groups of the antibody and maleimide, or two Michael addition reactions between a specific substrate and free sulfhydryl groups of the antibody to form a sulfur bridge bond in a unique structure. However, many literatures have reported that ADCs obtained by thiol-Michael addition methods will undergo reverse Michael additions in systemic circulation, resulting in toxic reactions. The patent WO2016142049 discloses amatoxins as bioactive molecules, and structure comprising bioactive molecules having the structure of methylsulfonyl-substituted benzobisoxadiazole and linkers, but details of coupling with antibodies are not specifically described.

CONTENTS OF THE INVENTION

The invention discloses a novel bioactive molecule conjugate, which is obtained by improving the coupling way of the drug and the targeting moiety in an ADC or SMDC. The conjugate has high stability, extremely high coupling efficiency (90%) and high DAR (5-8). The disclosure is based on the above findings. Through intensive research, it was surprisingly found that, the ADC of the invention, e.g. BT001021 (example 32), after intravenous administration, the exposure of the bioactive small molecular toxin in tumor is significantly higher than that in plasma, whereas Immu-132 has significantly higher plasma exposure than tumor exposure under the same administration route. Therefore, the ADC of the invention has a better therapeutic window than Immu-132. We were also surprised that the ADC of the invention has a better efficacy than Immu-132 in animal models of gastric cancer, breast cancer and non-small cell lung cancer.

A first aspect of the disclosure provides a compound as shown in formula (I) or a pharmaceutically acceptable salt thereof, $$T-[L_1-(L_2)_{m1}-(L_3)_{m2}-(L_4)_{m3}-E]-G \quad \text{formula (I)}$$

wherein, T is a fragment of a bioactive molecule, preferably a fragment of a molecule with antitumor bioactivity;
$L_1$ is selected from an amino acid, a peptide composed of 2-10 amino acids, an oligosaccharide, —$(CH_2)_{t1}$—, —$(CH_2CH_2O)_{t1}$—$(CH_2)_{t2}$—,
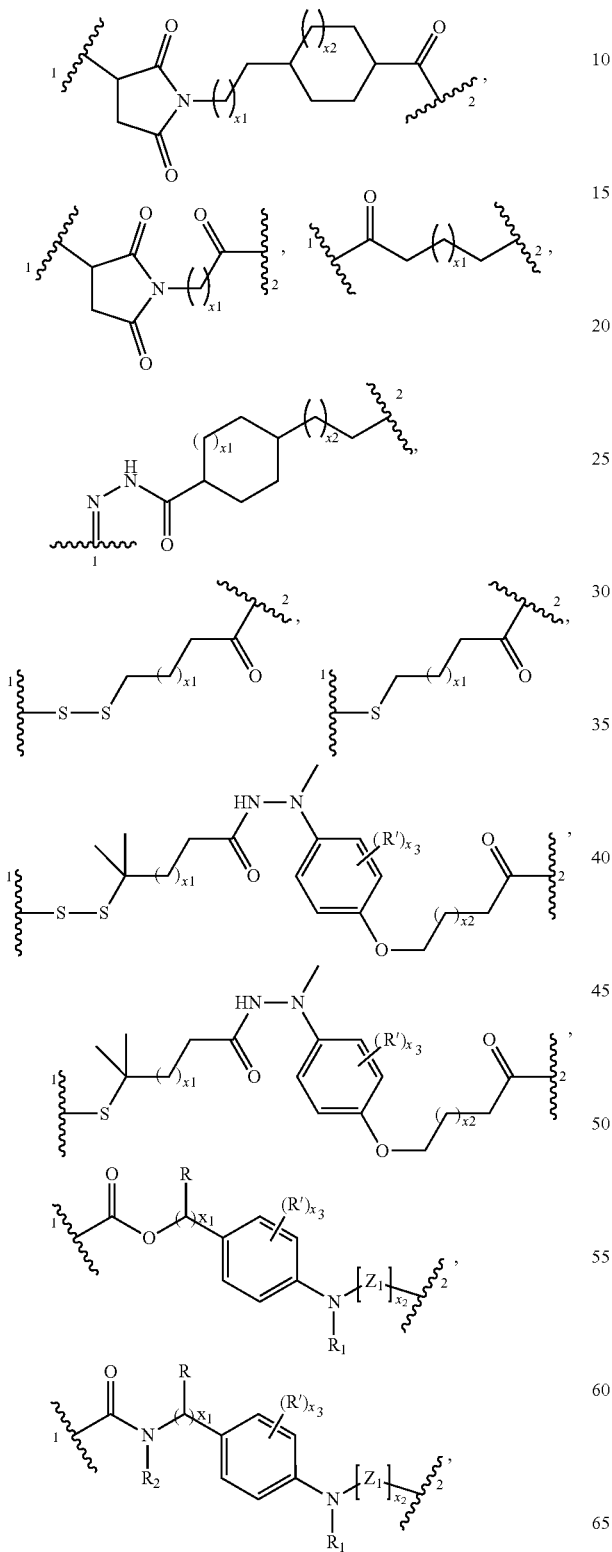
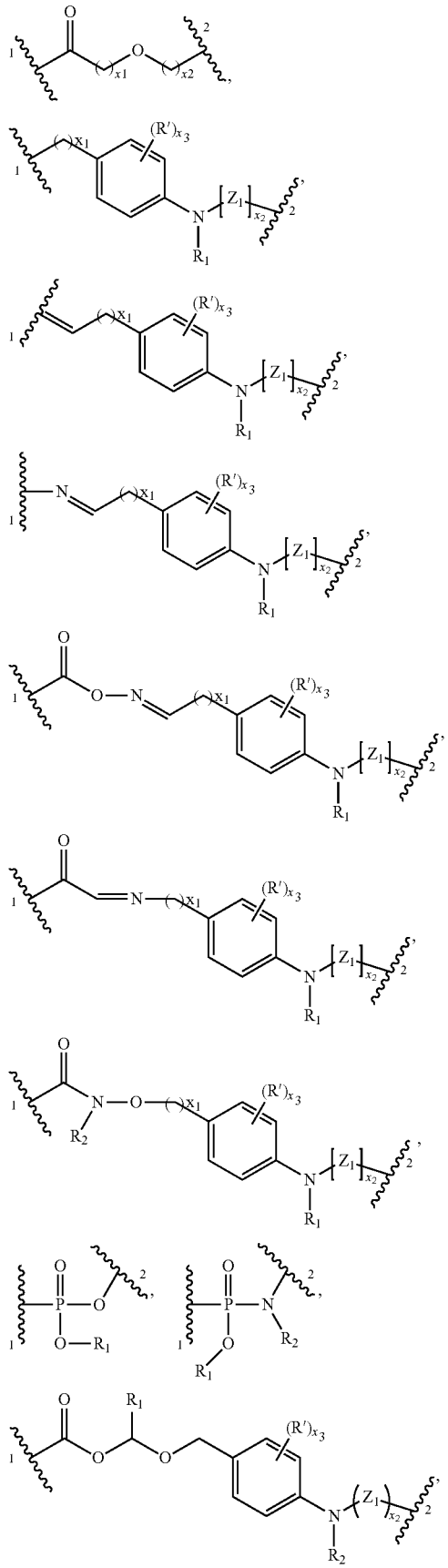

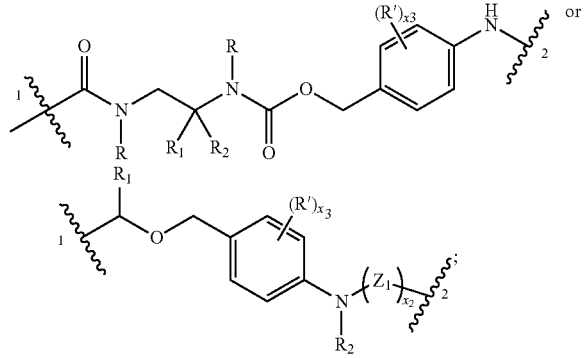
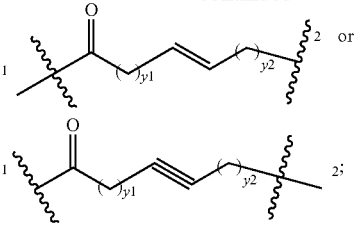

wherein each of R, R', $R_1$ and $R_2$ is independently H (hydrogen), D (deuterium), halogen, a carboxylic acid group, a sulfonic acid group, cyano, $C_{1-6}$ alkyl, halogenated $C_{1-6}$ alkyl (e.g., —$CF_3$), $C_{1-6}$ alkyl substituted with cyano (e.g., —$CH_2CN$), $C_{1-6}$ alkoxy, $C_{2-10}$ alkenyl, $C_{2-10}$ alkynyl, $C_{3-6}$ cycloalkyl, 6-10 membered aryl or 5-12 membered heteroaryl, each $Z_1$ is independently an amino acid or a peptide composed of 2-10 amino acids, each of $t_1$ and $t_2$ is independently 0, 1, 2, 3, 4, 5 or 6, each of $x_1$ and $x_2$ is independently 0, 1, 2, 3, 4, 5 or 6, each $x_3$ is independently 0, 1, 2, 3 or 4, and $L_1$ is bonded to T at the position 1 of $L_1$;

$L_2$ is selected from an amino acid, a peptide composed of 2-10 amino acids, an oligosaccharide, —$(CH_2)_{t1}$—, —$(CH_2CH_2O)_{t1}$—$(CH_2)_{t2}$—,

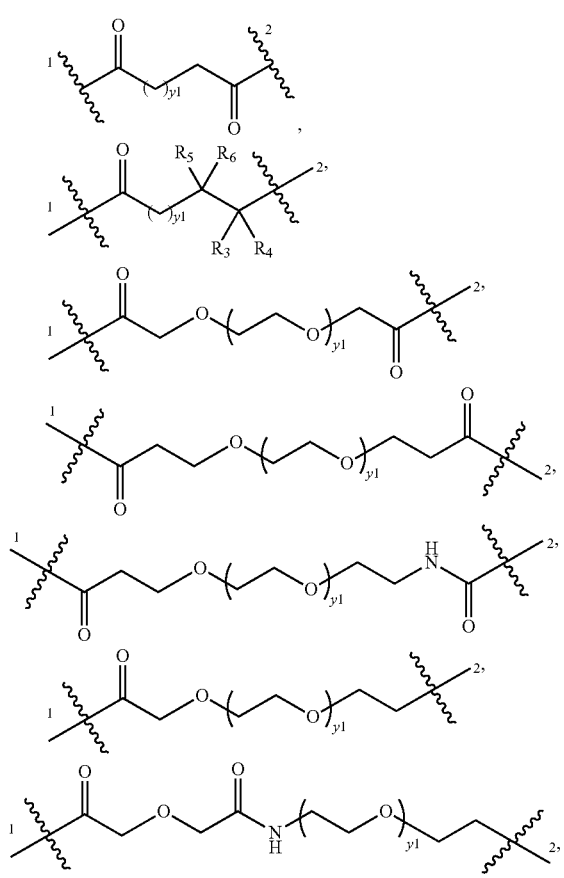

wherein each of $R_3$, $R_4$, $R_5$ and $R_6$ is independently selected from H (hydrogen), D (deuterium), halogen, a carboxylic acid group, a sulfonic acid group, CN, $C_{1-6}$ alkyl, halogenated $C_{1-6}$ alkyl, $C_{1-6}$ alkyl substituted with cyano, $C_{1-6}$ alkoxy, $C_{2-10}$ alkenyl, $C_{2-10}$ alkynyl or $C_{3-6}$ cycloalkyl, or $R_3/R_4$, $R_5/R_6$ or $R_3/R_5$ together with the carbon atoms attached thereto form a 3-8 membered ring, each of $t_1$ and $t_2$ is independently 0, 1, 2, 3, 4, 5 or 6, each of $y_1$ and $y_2$ is independently 0, 1, 2, 3, 4, 5, 6, 7, 8, 9 or 10, and $L_2$ is bonded to $L_1$ at the position 1 of $L_2$;

$L_3$ is selected from the following groups optionally substituted with one or more $R_7$: amino, 3-8 membered cycloalkylene, 3-8 aliphatic heterocyclylene, 6-12 membered bridged heterocyclylene, 6-12 membered spiroheterocyclylene, 6-12 membered fused heterocyclylene, 6-10 membered arylene (e.g., phenylene or naphthylene), 5-12 membered heteroarylene or 3-8 membered cycloalkylene-W—; wherein W is oxygen or $NR_8$, $R_7$ is independently selected from H (hydrogen), D (deuterium), halogen, =O, CN, carboxyl, sulfonic acid group, $C_{1-6}$ alkyl, halogenated $C_{1-6}$ alkyl, $C_{1-6}$ alkyl substituted with cyano, $C_{1-6}$ alkoxy, $C_{2-10}$ alkenyl or $C_{2-10}$ alkynyl, $R_8$ is independently selected from H (hydrogen), D (deuterium), $C_{1-6}$ alkyl, $C_{3-6}$ cycloalkyl, $C_{1-6}$ alkoxy or cyano $C_{1-2}$ alkyl, and $L_3$ is bonded to $L_2$ at the position 1 of $L_3$;

$L_4$ is selected from

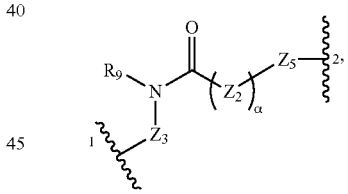

wherein $Z_5$ is preferably selected from $C_{2-6}$ alkenylidene, $C_{2-6}$ alkynylidene, amido group, sulfuryl, sulfinyl, 6-10 membered arylene or 5-6 membered heteroarylene; $Z_2$ is selected from $C_{1-6}$ alkylene, $C_{2-10}$ alkenylene, $C_{2-10}$ alkynylene, $C_{3-8}$ cycloalkylene, 6-10 membered arylene or 5-14 membered heteroarylene; $R_9$ is selected from H (hydrogen) or $C_{1-6}$ alkyl; $Z_3$ is absent or selected from $C_{1-6}$ alkylene, halogenated $C_{1-6}$ alkylene or $C_{1-6}$ alkylene substituted with alkoxy; or $R_9$ and $Z_3$ together with nitrogen atom attached thereto form a 4-8 membered heterocyclyl; α is independently 0, 1, 2, 3, 4, 5 or 6; and $L_4$ is bonded to E at the position 2 of $L_4$;

E is selected from the following groups optionally substituted with one or more $R_{12}$: 6-10 membered arylene or 5-14 membered heteroarylene; wherein $R_{12}$ is independently selected from H (hydrogen), D (deuterium), halogen, CN, nitro, $C_{1-6}$ alkyl or halogenated $C_{1-6}$ alkyl;

G is a leaving group for nucleophilic substitutions; such as, halogen, sulfonyl, sulfonic acid ester group, nitro, etc.;

each of $m_1$, $m_2$, and $m_3$ is independently 0, 1, 2, 3, 4, 5, 6, 7, 8, 9 or 10.

In some preferred embodiments, $L_1$ is selected from Val, Cit, Phe, Lys, D-Val, Leu, Gly, Ala, Asn, a peptide composed of 2-5 amino acids,

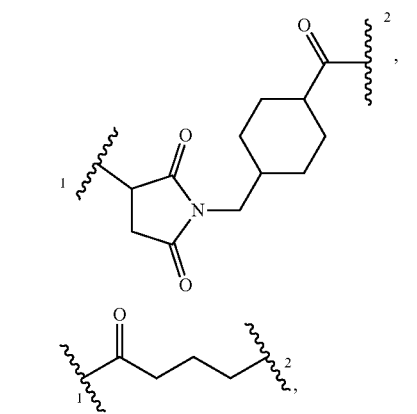

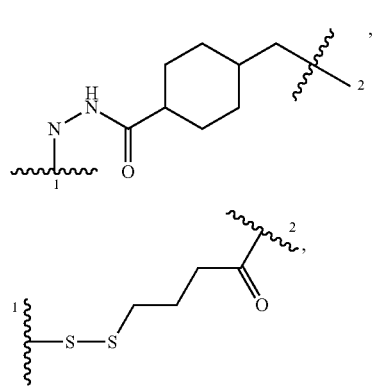

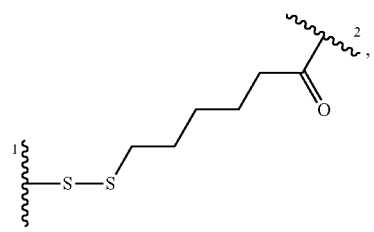

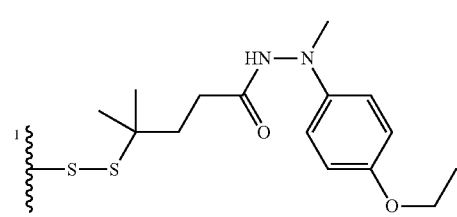

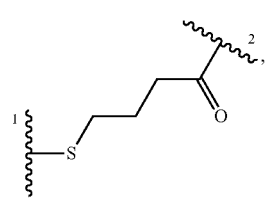

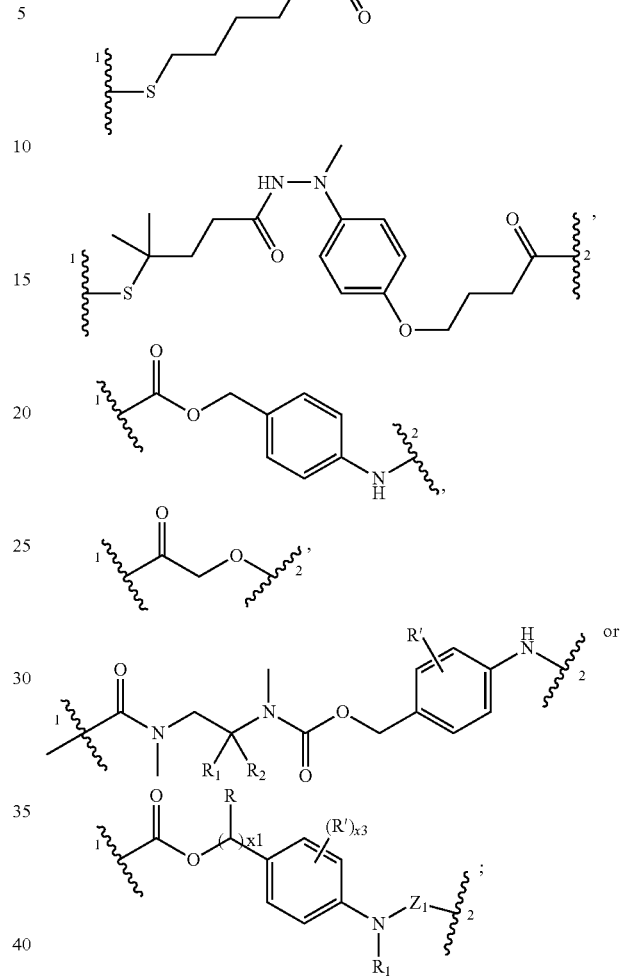

wherein each of R, R', $R_1$ and $R_2$ is independently H(hydrogen), D (deuterium), $C_{1-6}$ alkyl, $C_{2-10}$ alkenyl, $C_{2-10}$ alkynyl or $C_{3-6}$ cycloalkyl, $Z_1$ is Val, Cit, Phe, Lys, D-Val, Leu, Gly, Ala, Asn, Val-Cit, Cit-Val, Cit-Ala, Val-Ala, Lys-Val, Val-Lys(Ac), Phe-Lys, Phe-Lys(Ac), D-Val-Leu-Lys, Gly-Gly-Arg or Ala-Ala-Asn, $x_1$ is 0, 1, 2 or 3, and $x_3$ is 0, 1, 2, 3 or 4.

In some preferred embodiments, $L_1$ is selected from Val, Cit, Phe, Lys, D-Val, Leu, Gly, Ala, Asn, Cit-Val, Val-Ala, Lys-Val, Val-Lys(Ac), Phe-Lys, Phe-Lys(Ac), D-Val-Leu-Lys, Gly-Gly-Arg, Ala-Ala-Asn,

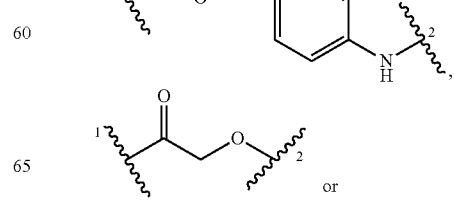

or

-continued

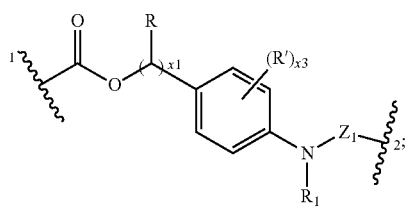

wherein each of R, R' and $R_1$ is independently H (hydrogen), D (deuterium), $C_{1-6}$ alkyl, $C_{2-10}$ alkenyl, $C_{2-10}$ alkynyl or $C_{3-6}$ cycloalkyl, $Z_1$ is Val, Cit, Phe, Lys, D-Val, Leu, Gly, Ala, Asn, Val-Cit, Cit-Val, Cit-Ala, Val-Ala, Lys-Val, Val-Lys(Ac), Phe-Lys, Phe-Lys(Ac), D-Val-Leu-Lys, Gly-Gly-Arg or Ala-Ala-Asn, and each of $x_1$ and $x_3$ is independently 0, 1, 2 or 3.

In some preferred embodiments, $L_1$ is selected from Lys, Cit, Cit-Val, Val-Ala, Lys-Val,

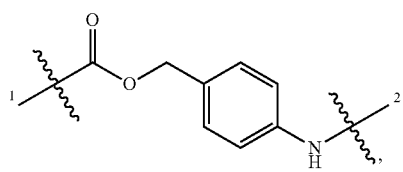 or

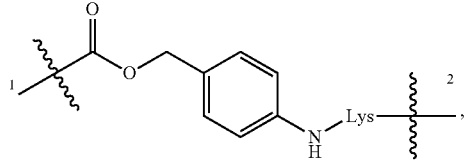

wherein each of R, R' and $R_1$ is independently H(hydrogen), D (deuterium) or $C_{1-4}$ alkyl, $Z_1$ is Cit, Lys, Cit-Val, Cit-Ala, Val-Ala or Lys-Val, and each of $x_1$ and $x_3$ is independently 0, 1 or 2.

In some preferred embodiments, $L_1$ is selected from Lys, Cit, Cit-Val, Val-Ala, Lys-Val,

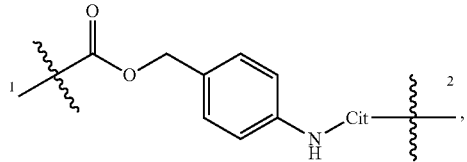

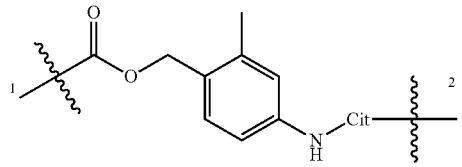

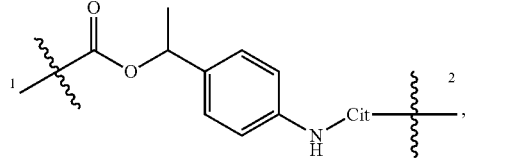

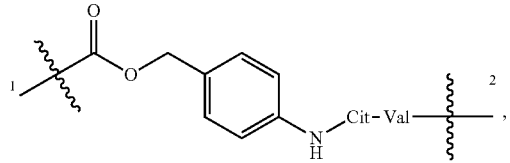

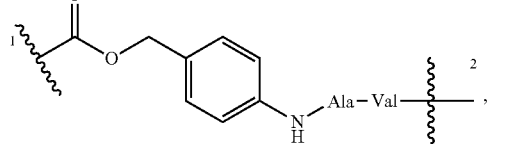

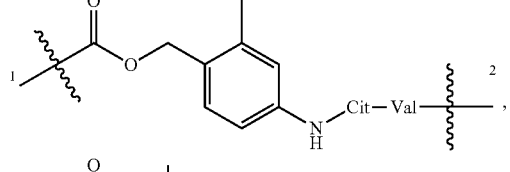

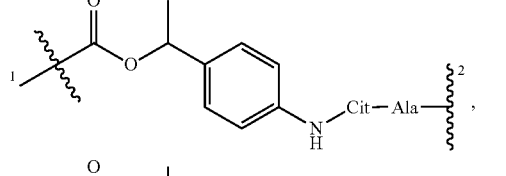

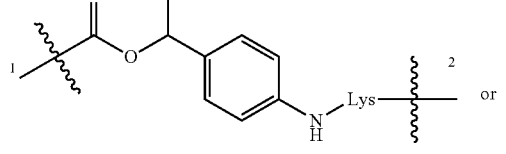

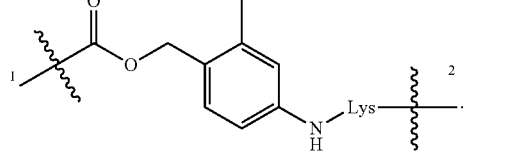 or

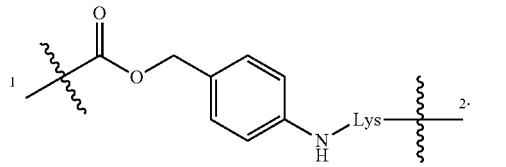

In some preferred embodiments, $L_1$ is selected from

In some preferred embodiments, $L_2$ is selected from Val, Cit, Phe, Lys, D-Val, Leu, Gly, Ala, Asn, a peptide composed of 2-5 amino acids,

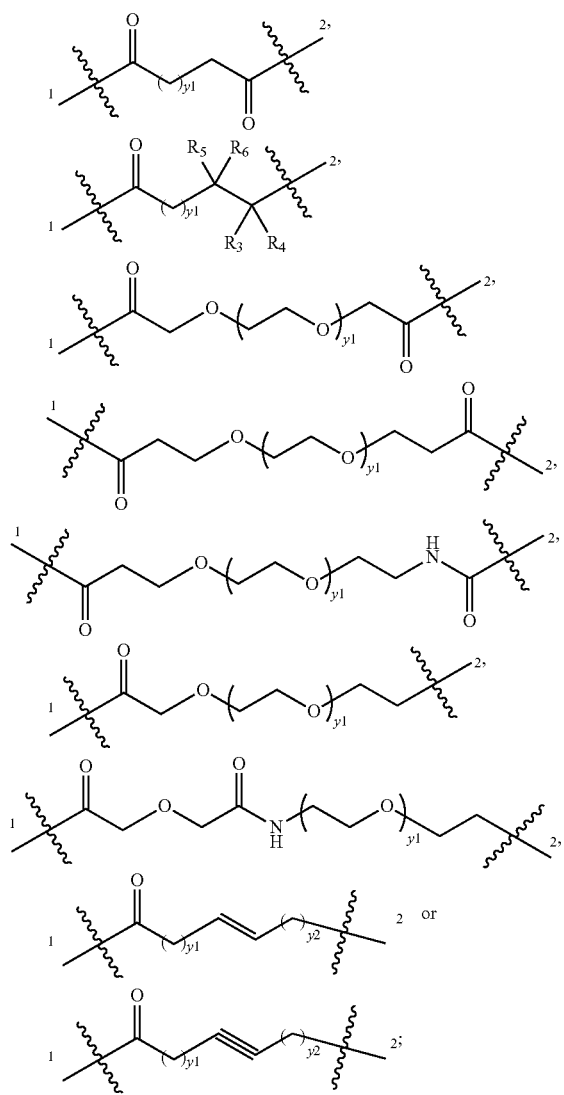

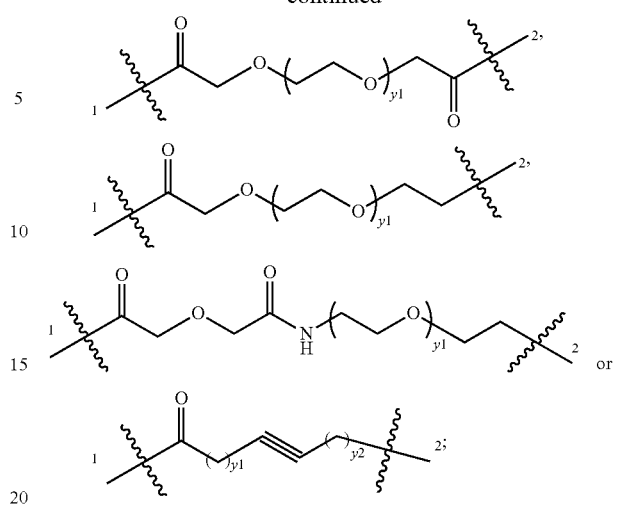

wherein each of $R_3$, $R_4$, $R_5$ and $R_6$ is independently selected from H (hydrogen), D (deuterium), halogen, a carboxylic acid group, a sulfonic acid group, $CF_3$, CN, $CH_2CN$, $C_{1-4}$ alkyl, $C_{1-4}$ alkoxy, $C_{2-6}$ alkenyl, $C_{2-6}$ alkynyl or $C_{3-6}$ cycloalkyl, each of $y_1$ and $y_2$ is independently 0, 1, 2, 3, 4, 5, 6, 7 or 8, and $L_2$ is bonded to $L_1$ at the position 1 of $L_2$;

$m_1$ is 0, 1 or 2.

In some preferred embodiments, $L_2$ is selected from

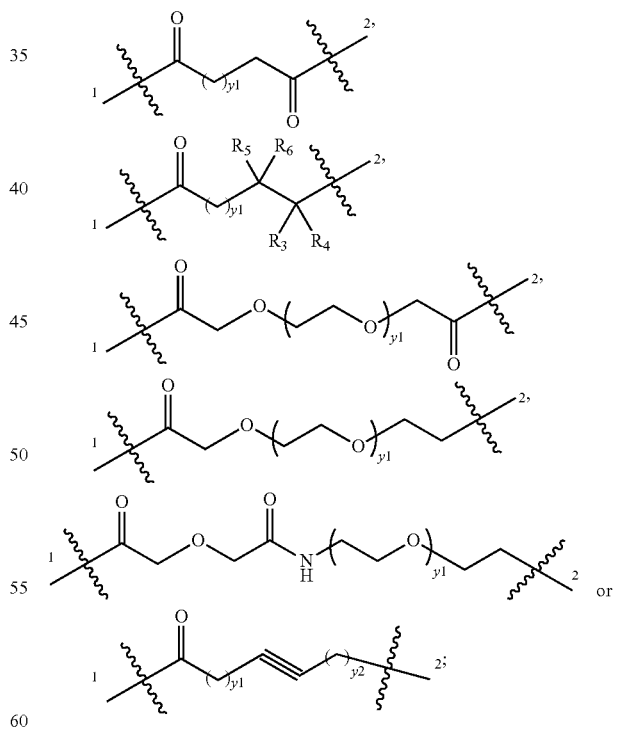

wherein each of $R_3$, $R_4$, $R_5$ and $R_6$ is independently selected from H (hydrogen), D (deuterium) or $C_{1-4}$ alkyl, each of $y_1$ and $y_2$ is independently 0, 1, 2, 3, 4, 5, 6, 7 or 8, and $L_2$ is bonded to $L_1$ at the position 1 of $L_2$;

$m_1$ is 1.

wherein each of $R_3$, $R_4$, $R_5$ and $R_6$ is independently selected from H (hydrogen), D (deuterium), halogen, a carboxylic acid group, a sulfonic acid group, $CF_3$, CN, $CH_2CN$, $C_{1-4}$ alkyl, $C_{1-4}$ alkoxy, $C_{2-6}$ alkenyl, $C_{2-6}$ alkynyl or $C_{3-6}$ cycloalkyl, each of $y_1$ and $y_2$ is independently 0, 1, 2, 3, 4, 5, 6, 7 or 8, and $L_2$ is bonded to $L_1$ at the position 1 of $L_2$;

$m_1$ is 0, 1, 2 or 3.

In some preferred embodiments, $L_2$ is selected from Val, Cit, Phe, Lys, D-Val, Leu, Gly, Ala, Asn, Val-Cit, Cit-Val, Val-Ala, Lys-Val, Val-Lys(Ac), Phe-Lys, Phe-Lys(Ac), D-Val-Leu-Lys, Gly-Gly-Arg, Ala-Ala-Asn,

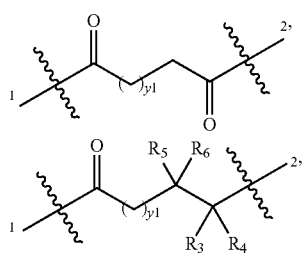

In some preferred embodiments, L₂ is selected from

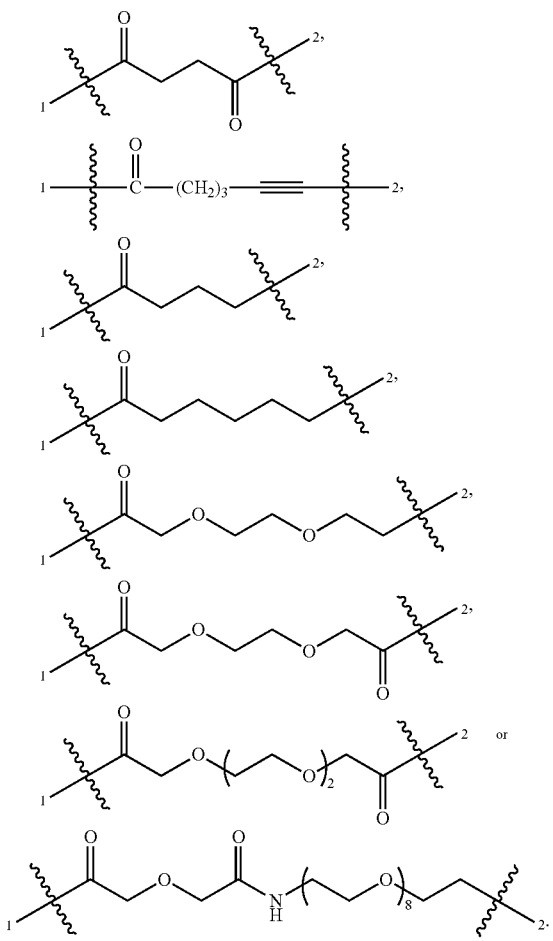

In some preferred embodiments, L₂ is selected from

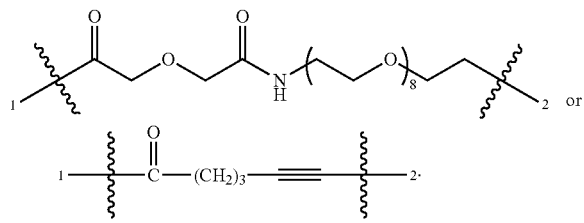

In some preferred embodiments, L₃ is selected from the following groups optionally substituted with one or more R₇: amino, 3-8 membered cycloalkylene, 3-8 aliphatic heterocyclylene, 6-12 membered bridged heterocyclylene, 6-12 membered spiroheterocyclylene, 6-12 membered fused heterocyclylene, 6-10 membered arylene, 5-12 membered heteroarylene or 3-8 membered cycloalkylene-W—; wherein W is oxygen or NR₈, R₇ is independently selected from H (hydrogen), D (deuterium), halogen, =O, CF₃, CN, CH₂CN, carboxyl, sulfonic acid group, $C_{1-4}$ alkyl, $C_{1-4}$ alkoxy, $C_{2-6}$ alkenyl or $C_{2-6}$ alkynyl; preferably, the 3-8 aliphatic heterocyclylene, 6-12 membered bridged heterocyclylene, 6-12 membered spiroheterocyclylene or 6-12 membered fused heterocyclylene has one or more nitrogen atoms; preferably, the 3-8 membered aliphatic heterocyclylene, 6-12 membered bridged heterocyclylene, 6-12 membered spiroheterocyclylene or 6-12 membered fused heterocyclylene has one or more quaternized nitrogen atoms; preferably, the 3-8 membered aliphatic heterocyclylene, 6-12 membered bridged heterocyclylene, 6-12 membered spiroheterocyclylene or 6-12 membered fused heterocyclylene has one or more nitrogen atoms, and at least one nitrogen atom is substituted with =O; R₈ is independently selected from H (hydrogen), D (deuterium), $C_{1-6}$ alkyl, $C_{2-6}$ alkenyl, $C_{3-6}$ alkynyl, $C_{3-6}$ cycloalkyl, $C_{1-6}$ alkoxy or cyano $C_{1-2}$ alkyl;

m₂ is 0, 1, 2 or 3.

In some preferred embodiments, L₃ is selected from the following groups optionally substituted with one or more R₇: amino, 3-6 membered aliphatic heterocyclylene or 5-10 membered heteroarylene; wherein R₇ is independently selected from H (hydrogen), D (deuterium), halogen, =O, CF₃, CN, CH₂CN, carboxyl, sulfonic acid group, $C_{1-4}$ alkyl, $C_{1-4}$ alkoxy, $C_{2-6}$ alkenyl or $C_{2-6}$ alkynyl; preferably, the 3-6 membered aliphatic heterocyclylene has one or more nitrogen atoms; preferably, the 3-6 membered aliphatic heterocyclylene has one or more quaternized nitrogen atoms; preferably, the 3-6 membered aliphatic heterocyclylene has one or more nitrogen atoms, and at least one nitrogen atom is substituted with =O;

m₂ is 0, 1 or 2.

In some preferred embodiments, L₃ is selected from the following groups optionally substituted with one or more R₇: amino or 5-6 membered heteroarylene; wherein R₇ is independently selected from H (hydrogen), D (deuterium), halogen, =O, CF₃, CN, CH₂CN, carboxyl, sulfonic acid group, $C_{1-4}$ alkyl, $C_{1-4}$ alkoxy, $C_{2-6}$ alkenyl or $C_{2-6}$ alkynyl; m₂ is 0 or 1.

In some preferred embodiments, L₃ is selected from the following groups optionally substituted with one or more R₇: amino, N-methylpiperidylene, pyrazolylene or triazolylene; wherein R₇ is independently selected from H (hydrogen), D (deuterium), halogen, =O, CF₃, CN, CH₂CN, carboxyl, sulfonic acid group, $C_{1-4}$ alkyl, $C_{1-4}$ alkoxy, $C_{2-6}$ alkenyl or $C_{2-6}$ alkynyl; m₂ is 0 or 1.

In some preferred embodiments, L₃ is selected from triazolylene; m₂ is 0 or 1.

In some preferred embodiments, L₃ is selected from

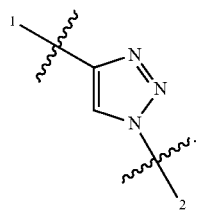

m₂ is 0 or 1. preferably, L₃ is bonded to L₂ at the position 1 of L₃.

In some preferred embodiments, L₃ is selected from the following groups optionally substituted with one or more R₇: amino,

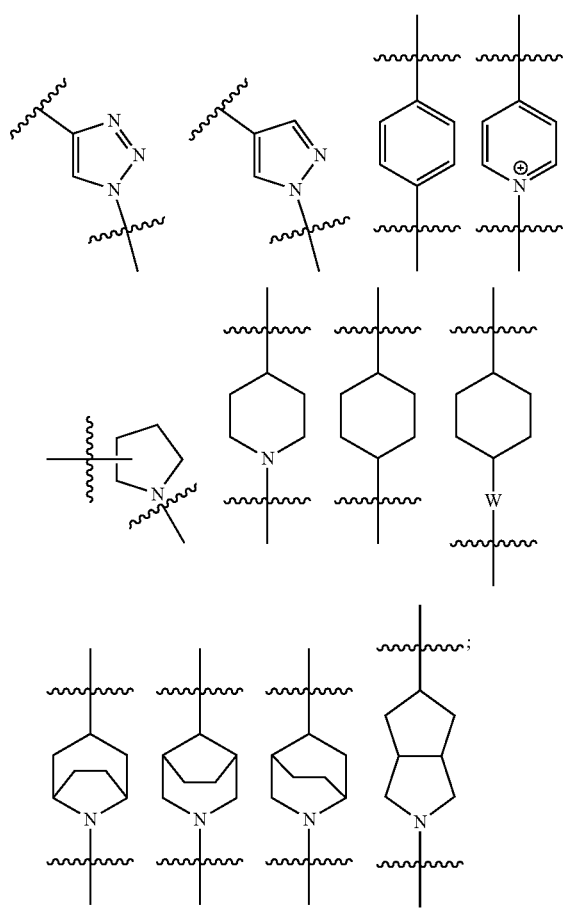

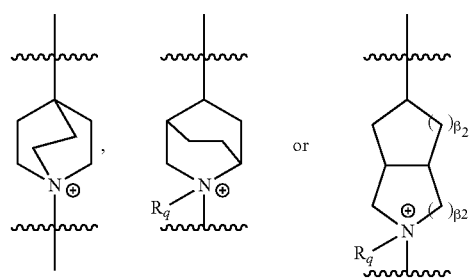

wherein each $R_q$ is independently selected from $C_{1-6}$ alkyl, $C_{2-6}$ alkenyl, $C_{3-6}$ alkynyl or $C_{3-8}$ cycloalkyl; $\beta_1$ is 0, 1 or 2; and $\beta_2$ is 1, 2 or 3.

$R_7$ is independently selected from H (hydrogen), D (deuterium), =O, CN, CH$_2$CN, methyl or CF$_3$;

W is NR$_8$, and R$_8$ is selected from H (hydrogen), D (deuterium), $C_{1-6}$ alkyl, $C_{2-6}$ alkenyl, $C_{3-6}$ alkynyl or $C_{3-6}$ cycloalkyl.

In some preferred embodiments, $L_3$ is selected from

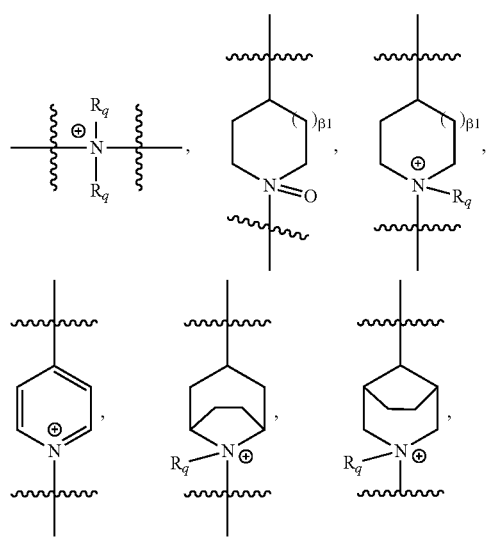

In some preferred embodiments, $L_3$ is selected from

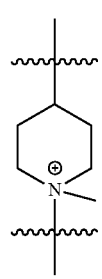

In some preferred embodiments, $L_4$ is selected from

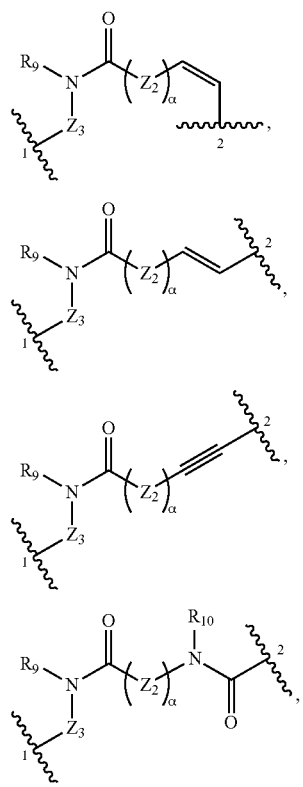

-continued

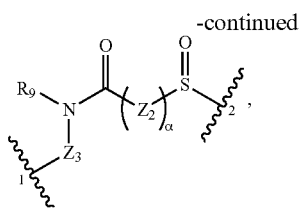

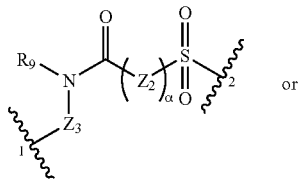 or

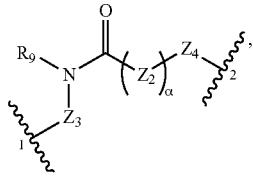

-continued

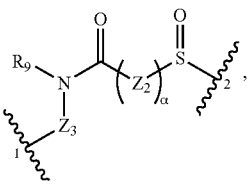

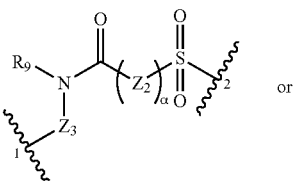 or

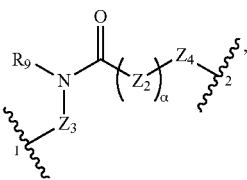

wherein $Z_4$ is 6-10 membered aryl or 5-6 membered heteroaryl; $R_{10}$ is selected from H (hydrogen) or $C_{1-6}$ alkyl; $Z_2$ is selected from $C_{1-6}$ alkylene, $C_{2-10}$ alkenylene, $C_{2-10}$ alkynylene or $C_{3-8}$ cycloalkylene; $R_9$ is selected from H (hydrogen) or $C_{1-6}$ alkyl; $Z_3$ is absent or selected from $C_{1-6}$ alkylene; or $R_9$ and $Z_3$ together with the nitrogen atom attached thereto form a 4-8 membered heterocyclylene; a is independently 0, 1, 2, 3, 4, 5 or 6, and $L_4$ is bonded to E at the position 2 of $L_4$;

$m_3$ is 0, 1, 2 or 3.

In some preferred embodiments, $L_4$ is selected from wherein $Z_4$ is a benzene ring, and $R_{10}$ is selected from H (hydrogen) and $C_{1-6}$ alkyl; $Z_2$ is selected from $C_{1-6}$ alkylene, $C_{2-10}$ alkenylene, $C_{2-10}$ alkynylene or $C_{3-8}$ cycloalkylene; $R_9$ is selected from H (hydrogen) or $C_{1-6}$ alkyl; $Z_3$ is absent or selected from $C_{1-6}$ alkylene or $R_9$ and $Z_3$ together with the nitrogen atom attached thereto form a 4-8 membered heterocyclylene; α is independently 0, 1, 2, 3, 4, 5 or 6, and $L_4$ is bonded to E at the position 2 of $L_4$;

$m_3$ is 0, 1, 2 or 3.

In some preferred embodiments, $L_4$ is selected from

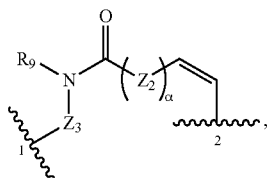

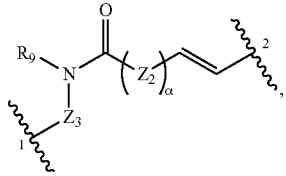

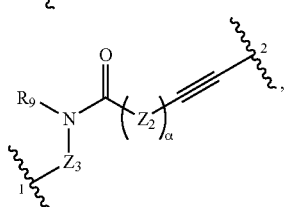

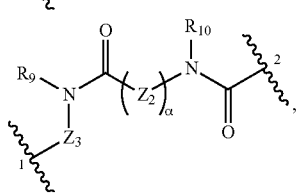

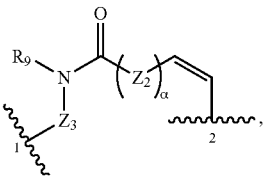

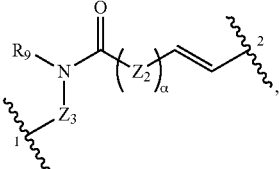

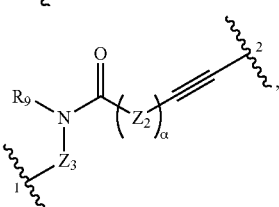

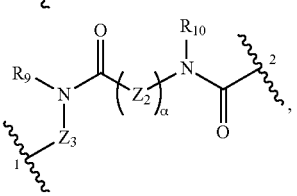

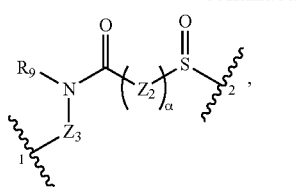

 or

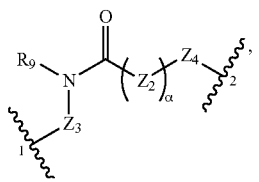

$Z_4$ is 5-6 membered heteroarylene; $R_{10}$ is selected from H (hydrogen) or $C_{1-6}$ alkyl; $Z_2$ is selected from $C_{1-6}$ alkylene, $C_{2-10}$ alkenylene, $C_{2-10}$ alkynylene or $C_{3-8}$ cycloalkylene; $R_9$ is selected from H (hydrogen) or $C_{1-6}$ alkyl; $Z_3$ is absent or selected from $C_{1-6}$ alkylene; or $R_9$ and $Z_3$ together with the nitrogen atom attached thereto form a 4-8 membered heterocyclylene; α is independently 0, 1, 2, 3, 4, 5 or 6; and $L_4$ is bonded to E at the position 2 of $L_4$;

m3 is 0, 1, 2 or 3.

In some preferred embodiments, $L_4$ is selected from

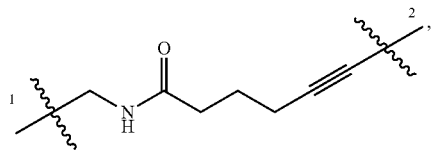

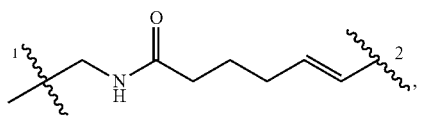

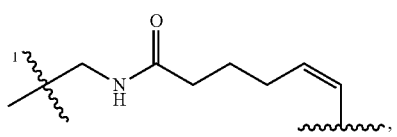

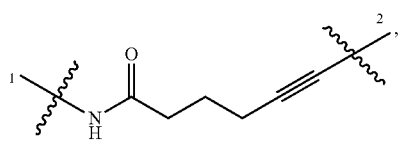

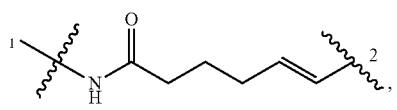

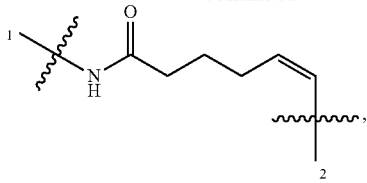

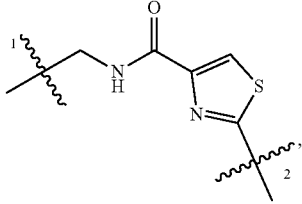

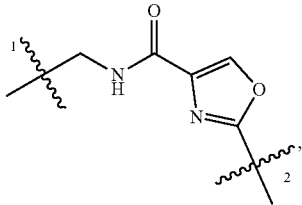

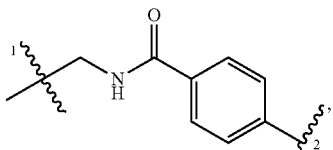

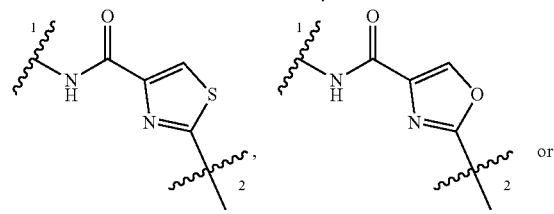 or

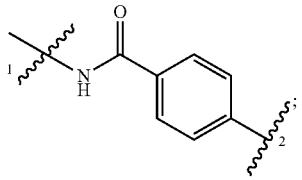 [SMILES: *NC(=O)c1ccc(*)cc1]

$m_3$ is 1.

In some preferred embodiments, $L_4$ is selected from

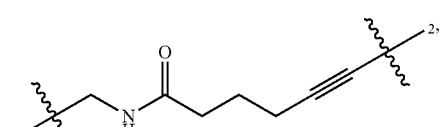

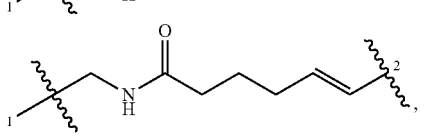

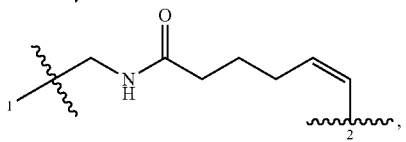

-continued

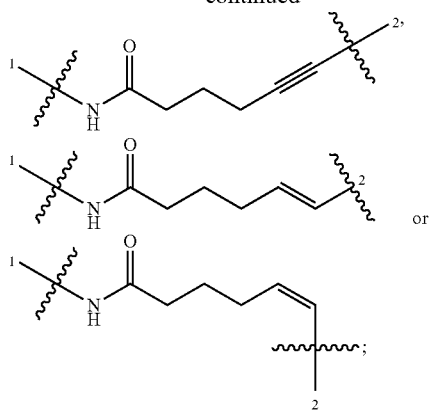

$m_3$ is 1.

In some preferred embodiments, $L_4$ is selected from

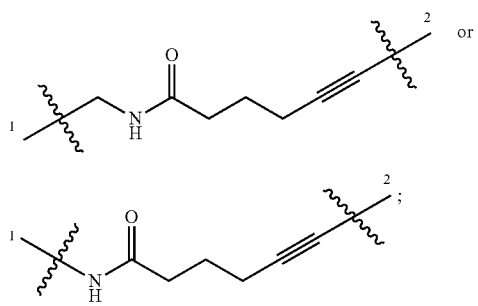

$m_3$ is 1.

In some preferred embodiments, E is selected from 5-10 membered heteroarylene optionally substituted with one or more $R_{12}$; wherein $R_{12}$ is independently selected from H (hydrogen), D (deuterium), halogen, CN, nitro, $C_{1-4}$ alkyl or halogenated $C_{1-4}$alkyl.

In some preferred embodiments, E is selected from the following groups optionally substituted with one or more $R_{12}$: pyrimidylene, quinolylene or pyrrolo[2,3-d] pyrimidylene; wherein $R_{12}$ is independently selected from H (hydrogen), D (deuterium), halogen, CN, nitro, $C_{1-2}$ alkyl or halogenated $C_{1-2}$ alkyl.

In some preferred embodiments, E is selected from pyrimidinyl optionally substituted with one or more $R_{12}$; wherein $R_{12}$ is independently selected from H(hydrogen) or D (deuterium).

In some preferred embodiments, G is selected from halogen, OMs, OTs, OTf, nitro, or anyone of the following groups which is optionally substituted with one or more $R_{13}$: alkylthio, arylthio, heteroarylthio, alkyl sulfinyl, aryl sulfinyl, heteroaryl sulfinyl, alkyl sulfonyl, aryl sulfonyl or heteroaryl sulfonyl; wherein $R_{13}$ is independently selected from H (hydrogen), D (deuterium), halogen, CN, nitro, $C_{1-6}$ alkyl, halogenated $C_{1-6}$ alkyl, $C_{1-6}$ alkoxy, 6-10 membered aryl or 5-12 membered heteroaryl.

In some preferred embodiments, G is selected from F, Cl, Br, I, OMs, OTs, OTf, methylsulfonyl, ethylsulfonyl, p-toluenesulfonyl or naphthalenesulfonyl.

In some preferred embodiments, G is selected from F, Cl, Br, OMs, OTs, methylsulfonyl or p-toluenesulfonyl.

In some preferred embodiments, G is selected from Cl or methylsulfonyl.

In some preferred embodiments, in

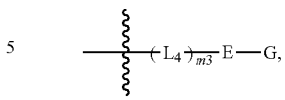

G is preferably methylsulfonyl, E is preferably pyrimidylene, $m_3$ is 1.

In some preferred embodiments,

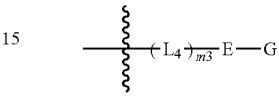

is

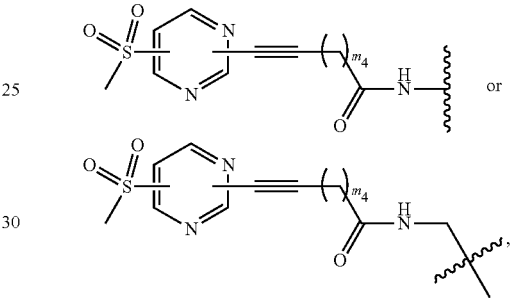

wherein $m_4$ is preferably an integer from 0 to 6, methylsulfonyl is a substituent on a carbon atom adjacent to a nitrogen atom in the pyrimidine ring.

In some preferred embodiments,

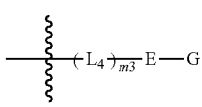

is

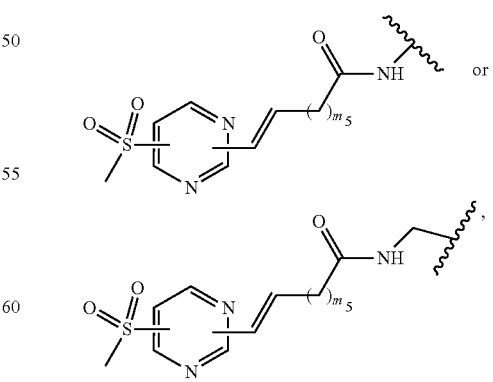

wherein $m_5$ is preferably an integer from 0 to 6, methylsulfonyl is a substituent on a carbon atom adjacent to a nitrogen atom in the pyrimidine ring.

In some preferred embodiments,

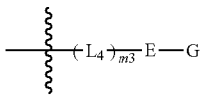

is

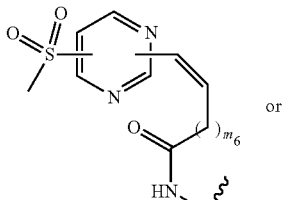

or

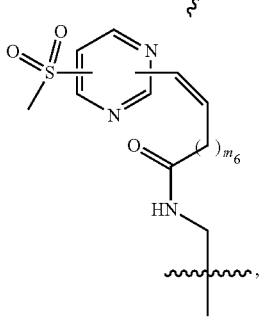

wherein $m_6$ is preferably an integer from 0 to 6, methylsulfonyl is a substituent on a carbon atom adjacent to a nitrogen atom in the pyrimidine ring.

In some preferred embodiments,

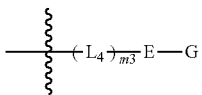

is

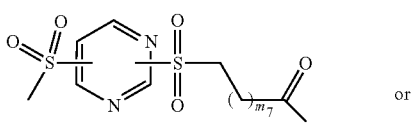

or

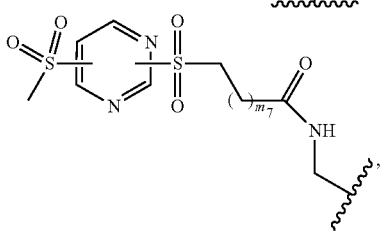

wherein $m_7$ is an integer from 1 to 5, methylsulfonyl is a substituent on a carbon atom adjacent to a nitrogen atom in the pyrimidine ring.

In some preferred embodiments,

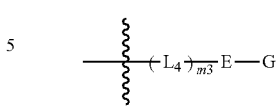

is

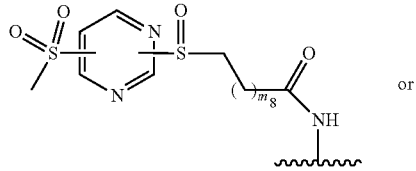

or

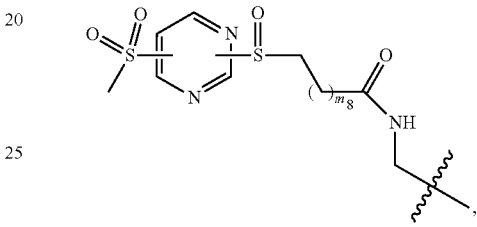

wherein $m_8$ is an integer from 1 to 5, methylsulfonyl is a substituent on a carbon atom adjacent to a nitrogen atom in the pyrimidine ring.

In some preferred embodiments,

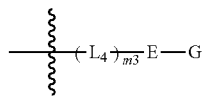

is

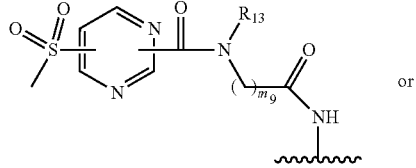

or

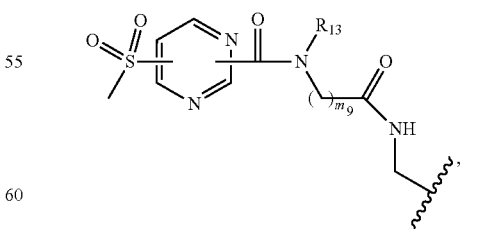

wherein $m_9$ is an integer from 1 to 5, $R_{13}$ is selected from hydrogen or $C_{1-6}$ alkyl, methylsulfonyl is a substituent on a carbon atom adjacent to a nitrogen atom in the pyrimidine ring.

In some preferred embodiments,

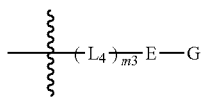

is

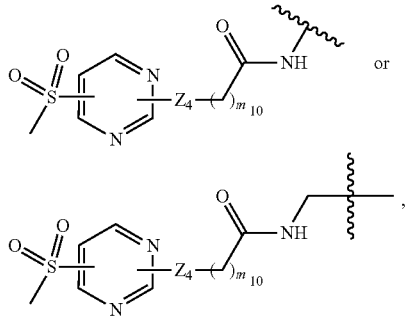

wherein $m_{10}$ is an integer from 0 to 6, and $Z_4$ is selected from 5-6 membered heteroarylene; methylsulfonyl is a substituent on a carbon atom adjacent to a nitrogen atom in the pyrimidine ring.

In some preferred embodiments,

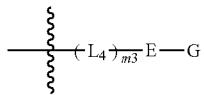

is

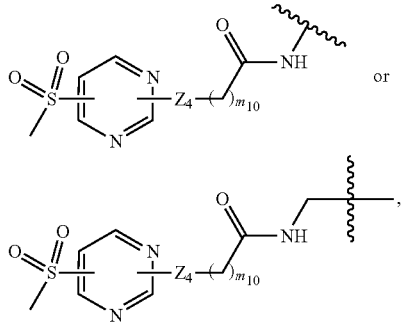

$Z_4$ is selected from pyridylene, pyrimidylene, pyrazolylene, thiazolylene, oxazolylene or triazolylene; methylsulfonyl is a substituent on a carbon atom adjacent to a nitrogen atom in the pyrimidine ring; more preferably, $m_{10}$ is an integer from 0-6.

In some preferred embodiments,

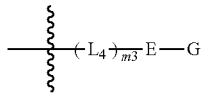

is

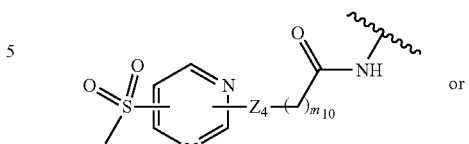

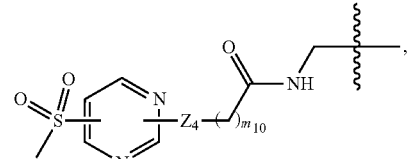

$Z_4$ is selected from pyridylene, pyrimidylene, pyrazolylene or triazolylene. More preferably, $m_{10}$ is an integer from 0-6.

In some preferred embodiments,

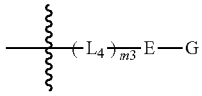

is

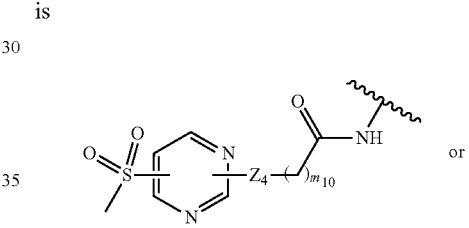

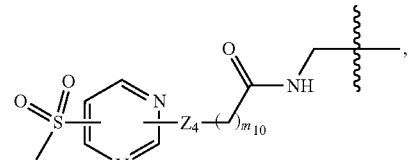

$Z_4$ is selected from oxazolylene or thiazolylene, and methylsulfonyl is a substituent of a carbon atom adjacent to a nitrogen atom in the pyrimidine ring. More preferably, $m_{10}$ is an integer from 0-6.

In some preferred embodiments,

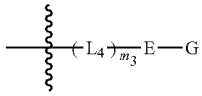

is

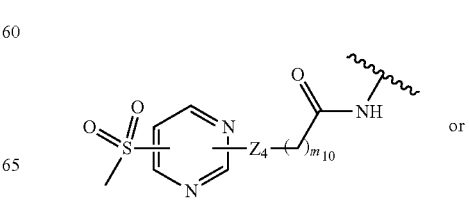

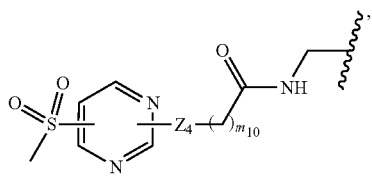

wherein $m_{10}$ is an integer from 0-6, and $Z_4$ is selected from 6-10 membered arylene; and methylsulfonyl is a substituent of a carbon atom adjacent to a nitrogen atom. More preferably, $m_{10}$ is an integer from 0-6.

In some preferred embodiments,

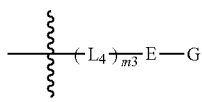

is

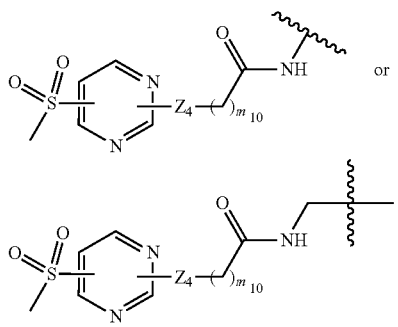

wherein $m_{10}$ is an integer from 0-6, and $Z_4$ is a benzene ring.

In some preferred embodiments,

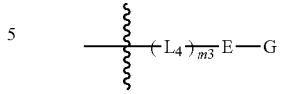

is

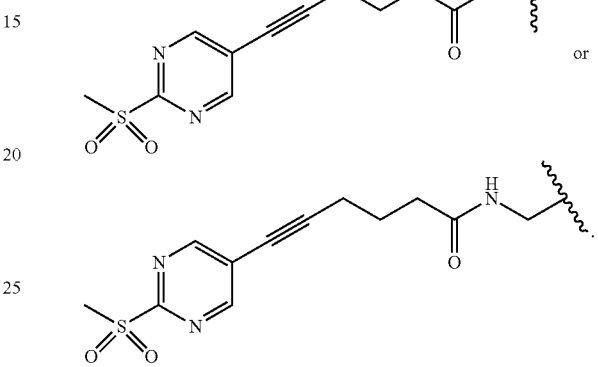

In some preferred embodiments,

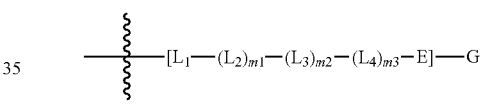

in formula (I) is selected from the following fragments:

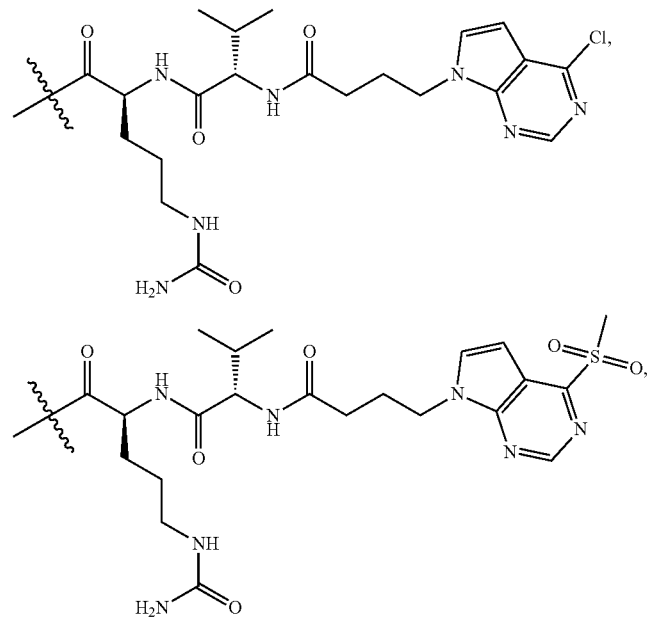

-continued
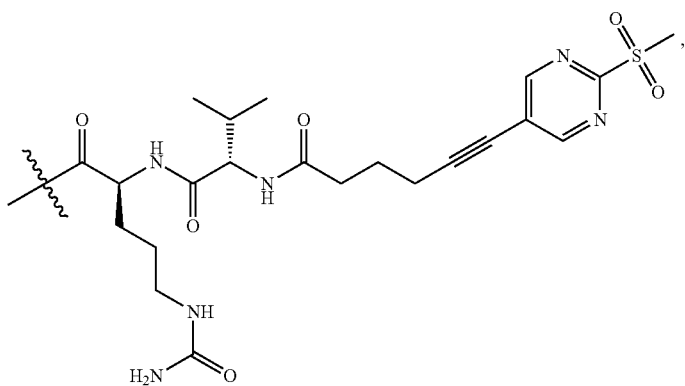
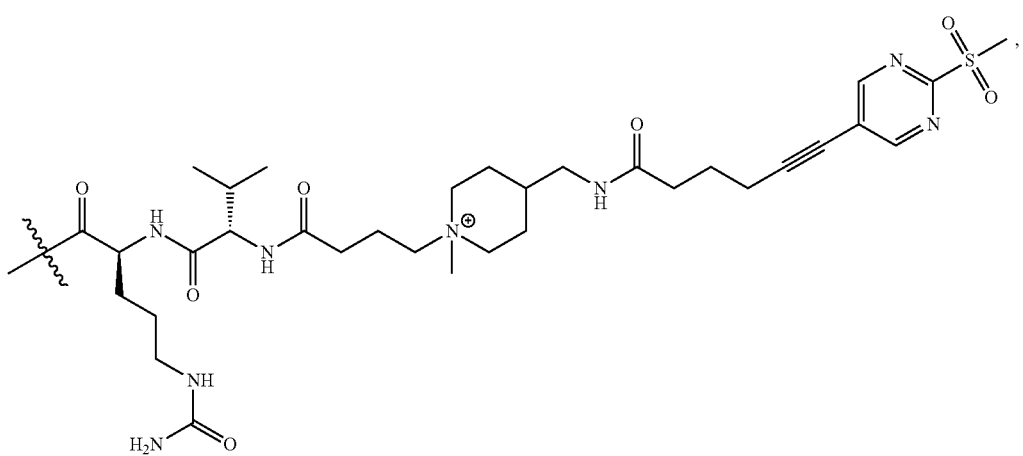
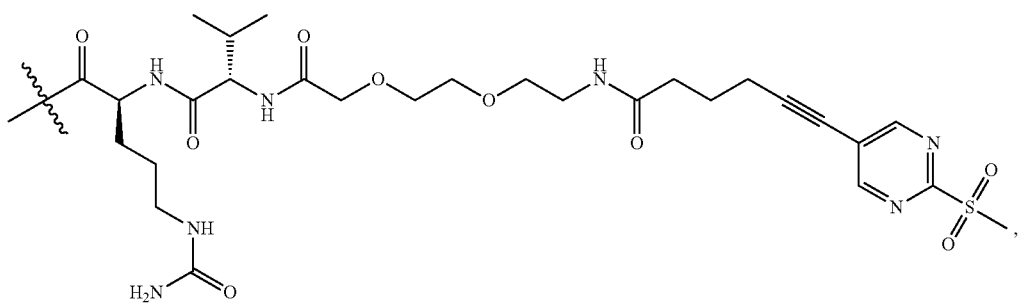
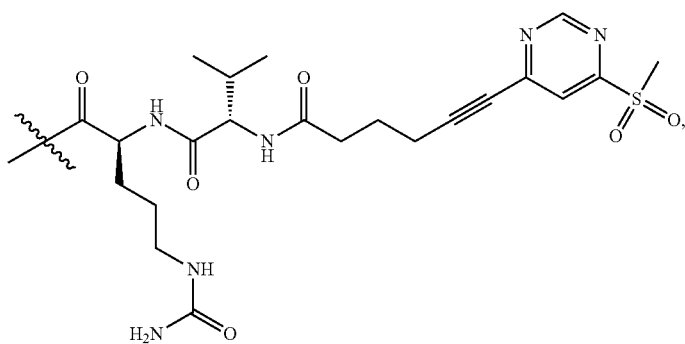

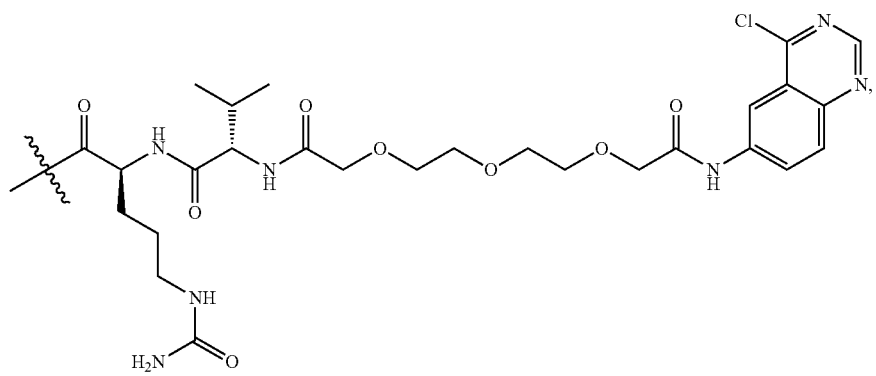
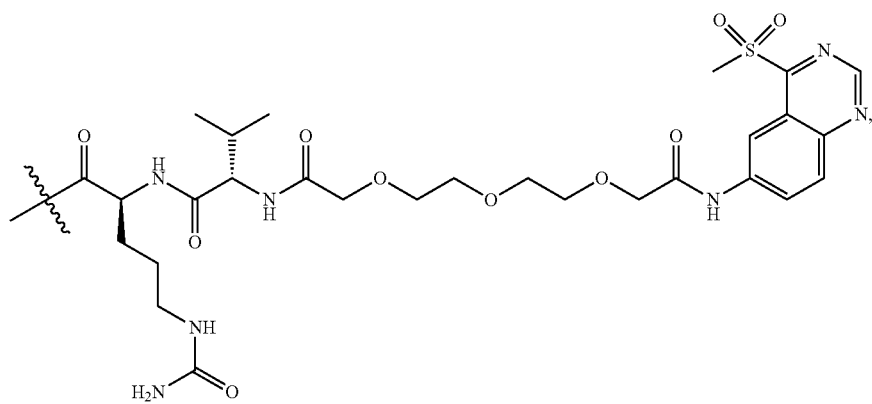
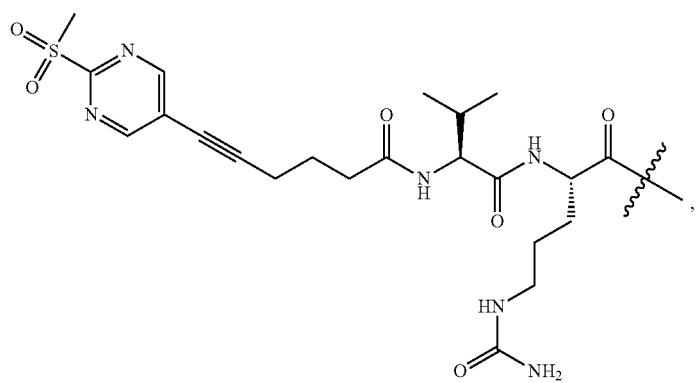
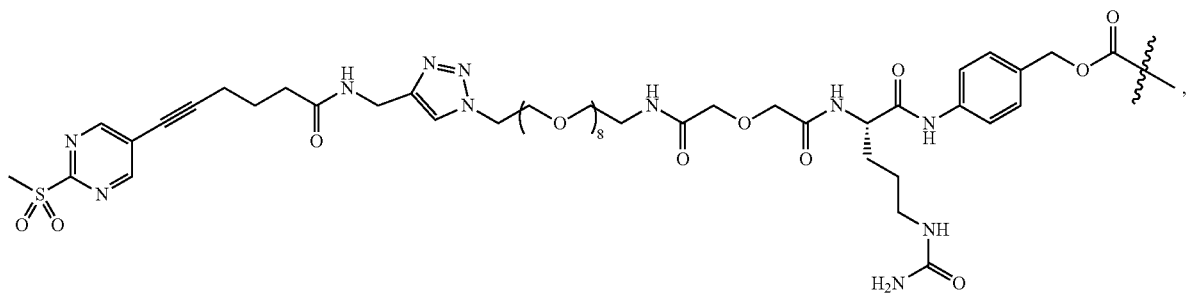

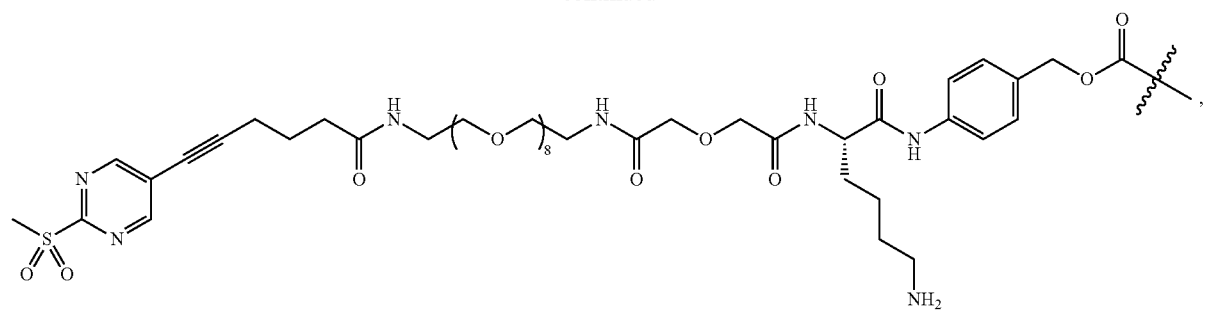
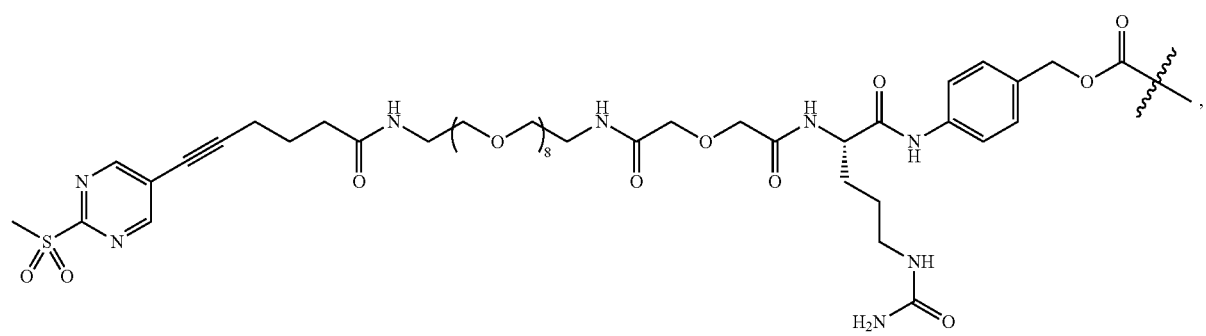
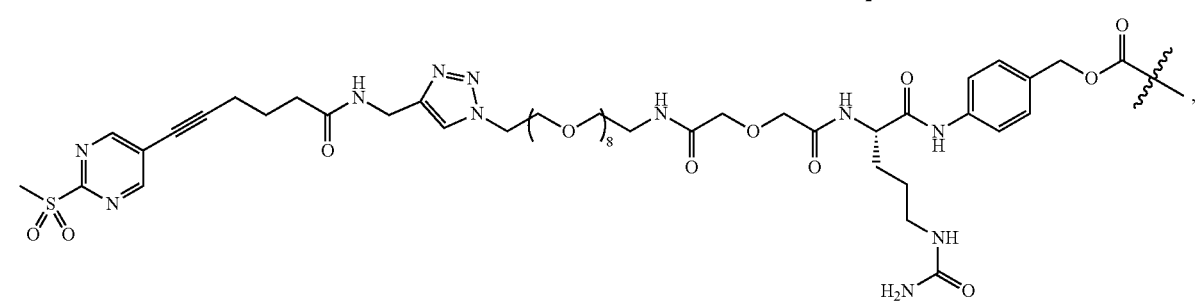
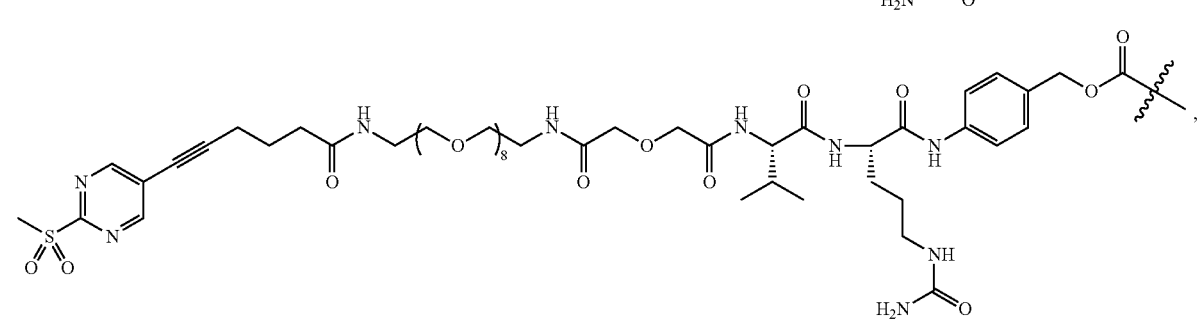
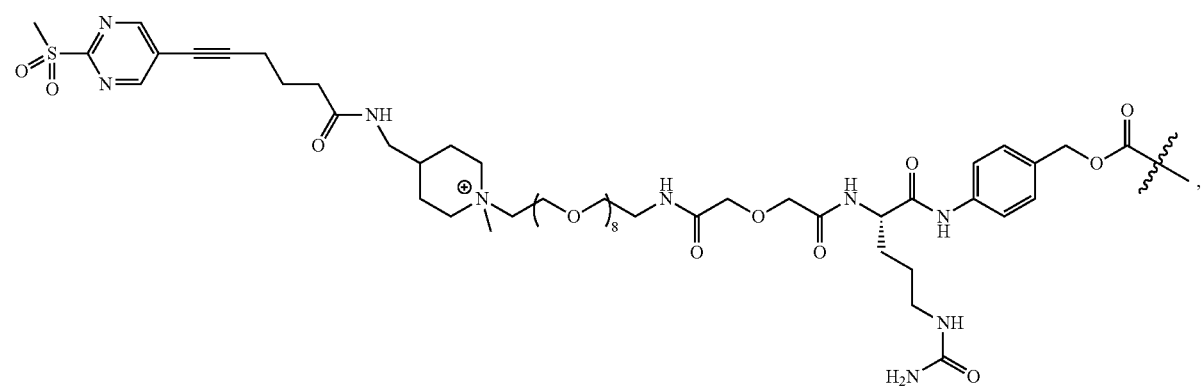

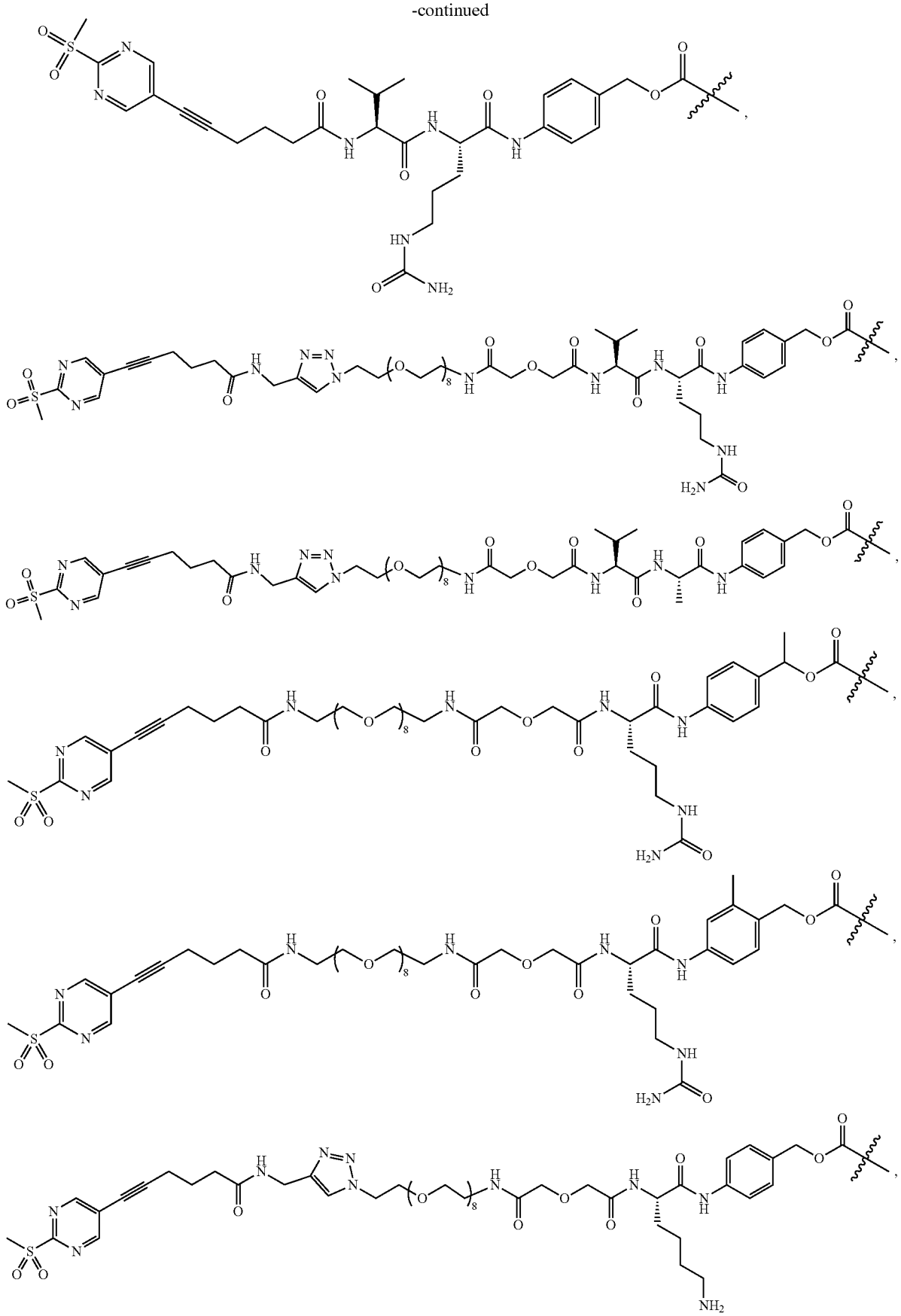

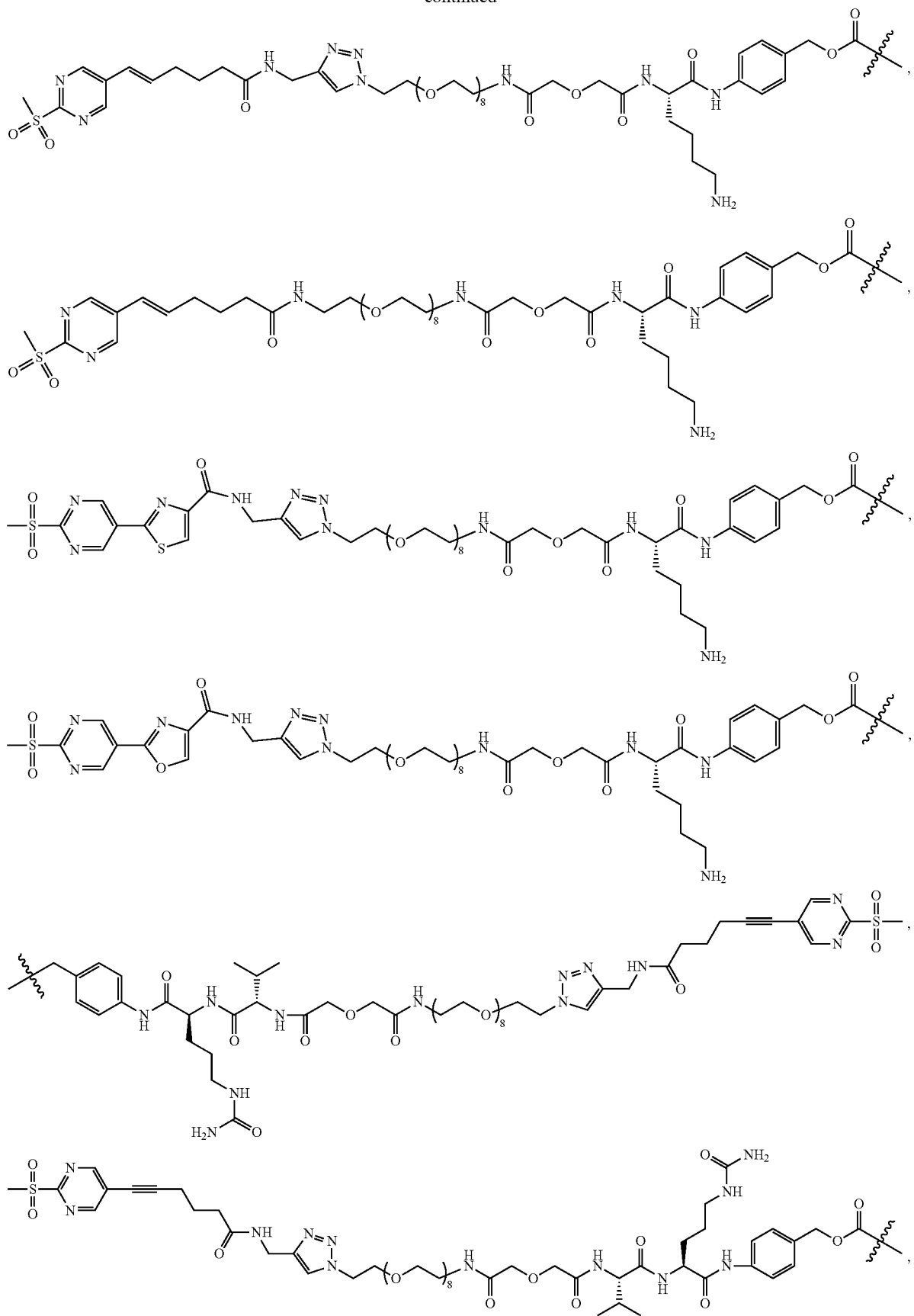

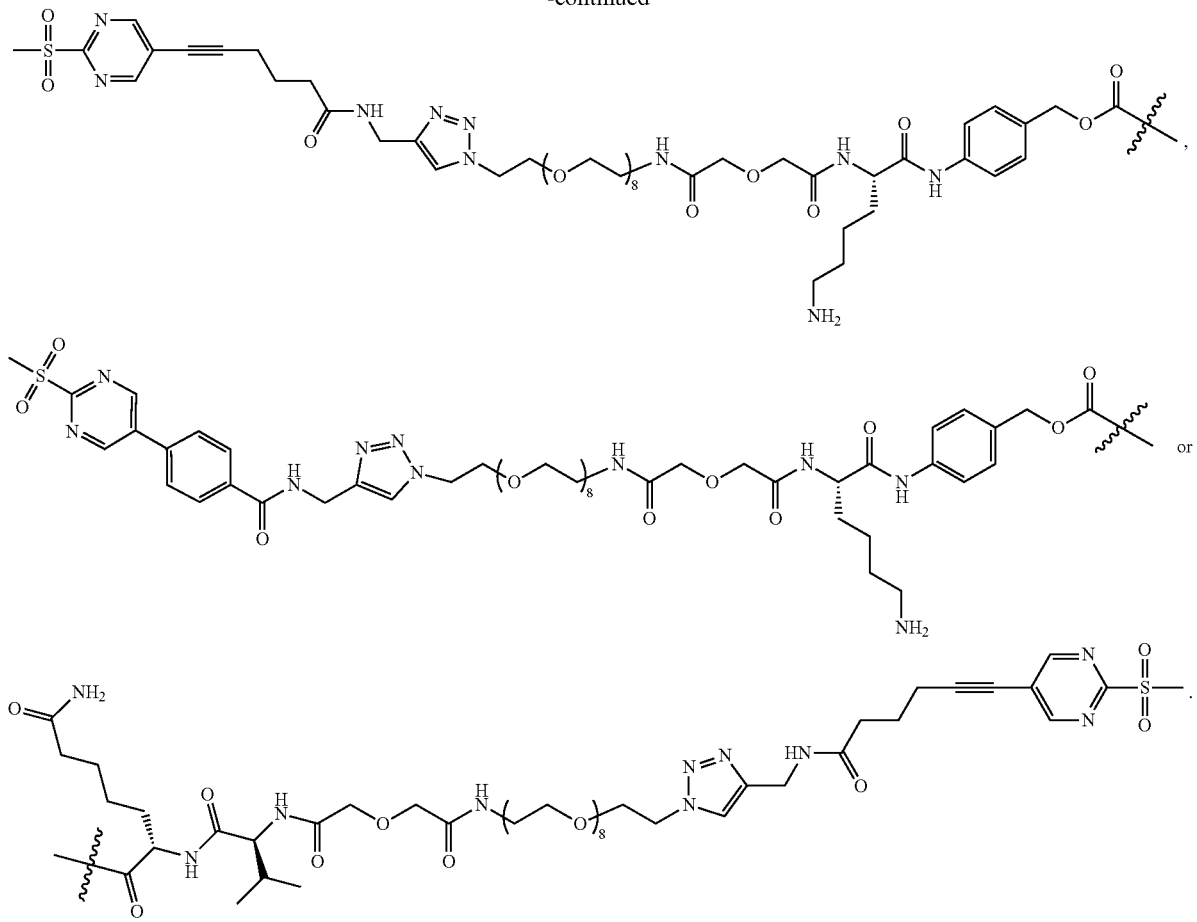

In some preferred embodiments, T is a fragment of a bioactive molecule. In some preferred embodiments, the bioactive molecule is selected from a metal complex, such as a platinum metal complex (e.g., oxaliplatin) or a gold metal complex; a glycopeptide antibiotic such as bleomycin or pingyangmycin; a DNA topoisomerase inhibitor, such as a topoisomerase I inhibitor (e.g., camptothecin, hydroxycamptothecin, 9-aminocamptothecin, SN-38, irinotecan, topotecan, bellotencian or rubitecan) or a topoisomerase II inhibitor (e.g., actinomycin D, doxorubicin, duocarmycin, daunorubicin, mitoxantrone, podophyllotoxin or etoposide); a drug interfering with DNA synthesis, such as methotrexate, 5-fluorouracil, cytarabine, gemcitabine, mercaptopurine, pentostatin, fludarabine, cladribine or narabine; a drugs acting on a structural protein, such as a tubulin inhibitor, a vinblastine alkaloid, a vincristine, vinblastine, paclitaxel, docetaxel or cabazitaxel; a tumor cell signaling pathway inhibitor, such as a serine/threonine kinase inhibitor, a tyrosine kinase inhibitor, a aspartokinase inhibitor or a histidine kinase inhibitor; a proteasome inhibitor; a histone deaceylase inhibitor; a tumor angiogenesis inhibitor; a cyclin inhibitor; a maytansine derivative; a calicheamicin derivative; a auristatin derivative; a pyrrolobenzodiazepine dimers (PBD) derivative; melphalan; mitomycin C; chlorambucil; and other active substances which inhibit the growth of tumor cells, promote the apoptosis or necrosis of tumor cells.

In some preferred embodiments, the bioactive molecule is selected from

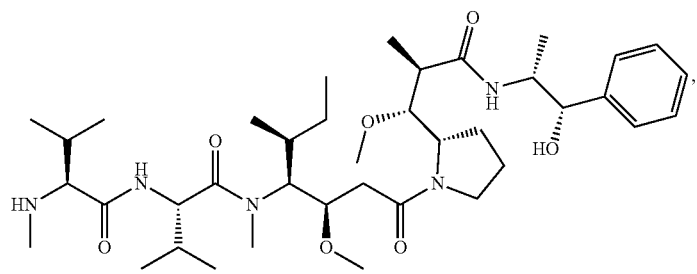

-continued

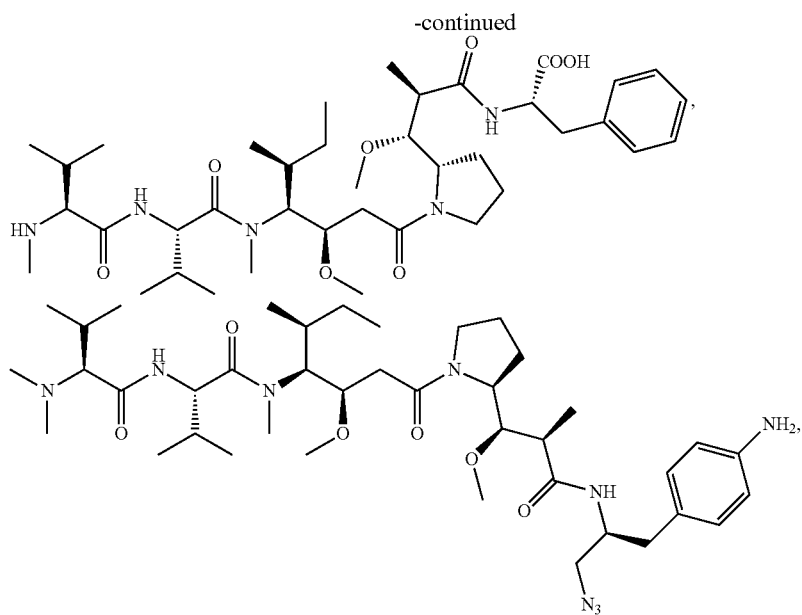

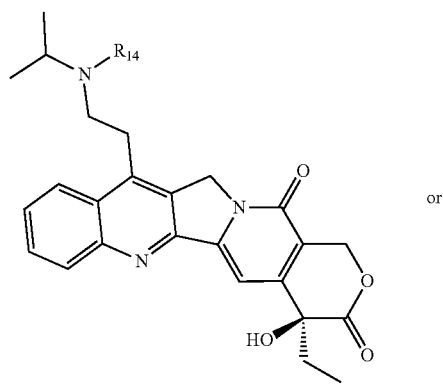

or

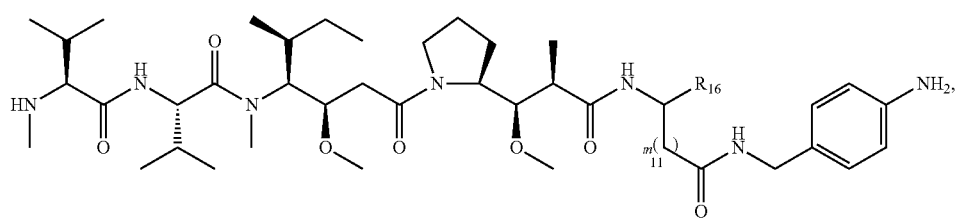

wherein $R_{14}$ is selected from acyl or sulfonyl, which is substituted with $R_{15}$, and $R_{15}$ is selected from $C_{1-6}$ alkyl, halogenated $C_{1-6}$ alkyl, 6-10 membered aryl or 5-12 membered heteroaryl; $R_{16}$ is selected from H (hydrogen), D (deuterium), $C_{1-6}$ alkyl or $C_{1-6}$ alkyl substituted with $R_{17}$, and $R_{17}$ is selected from aryl or heteroaryl, including but not limited to phenyl and pyridyl, and $m_{11}$ is 0, 1 or 2.

In some preferred embodiments, the bioactive molecule is selected from

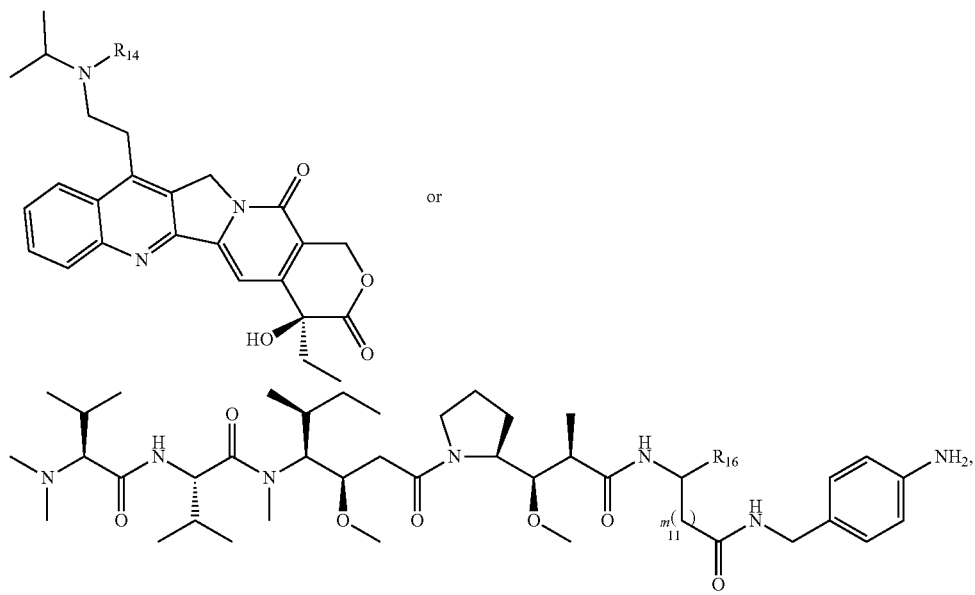

wherein $R_{14}$ is selected from acyl or sulfonyl, which is substituted with $R_{15}$, and $R_{15}$ is selected from $C_{1-6}$ alkyl, halogenated $C_{1-6}$ alkyl, 6-10 membered aryl or 5-12 membered heteroaryl; $R_{16}$ is selected from H (hydrogen), D (deuterium), $C_{1-6}$ alkyl, $C_{1-6}$ alkyl substituted with $R_{17}$, and $R_{17}$ is selected from aryl or heteroaryl, including but not limited to phenyl or pyridyl, and $m_{11}$ is 0, 1, or 2.

In some preferred embodiments, the bioactive molecule is selected from

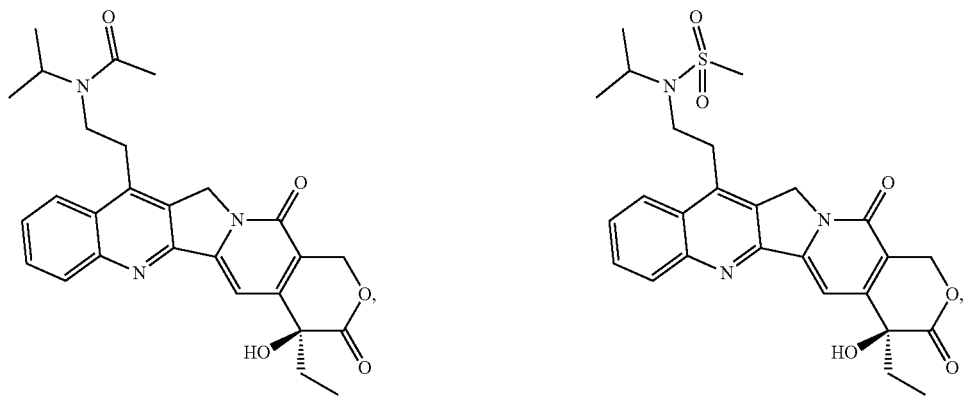

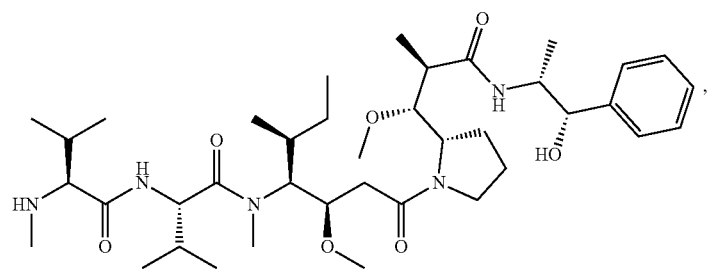

-continued
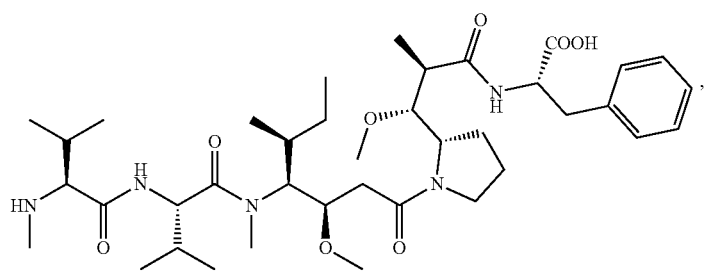
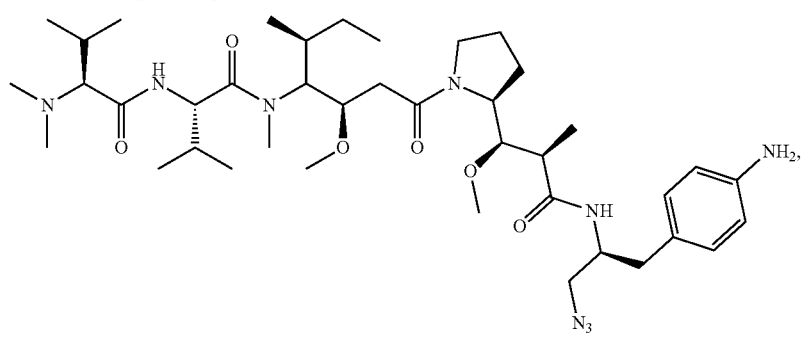
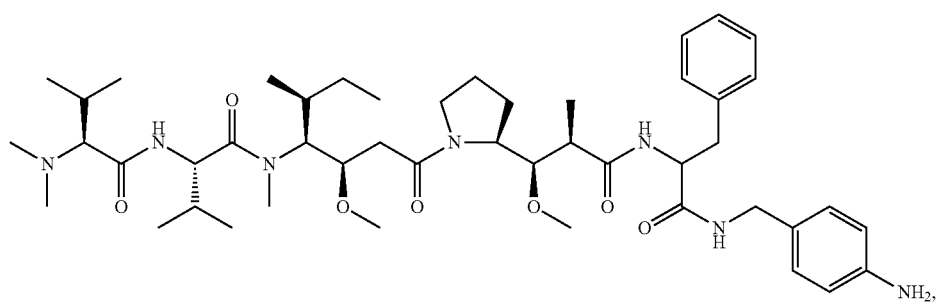
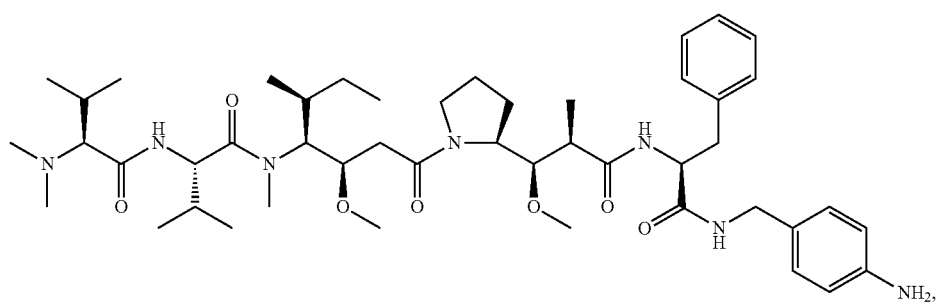
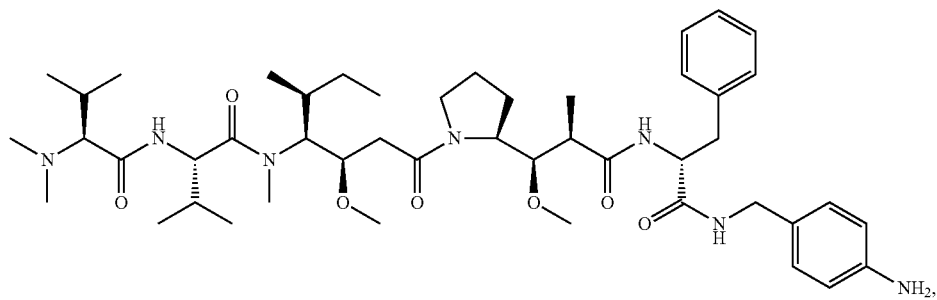

-continued
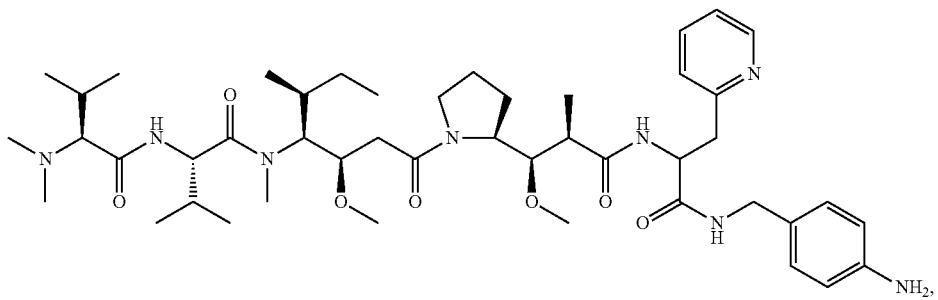
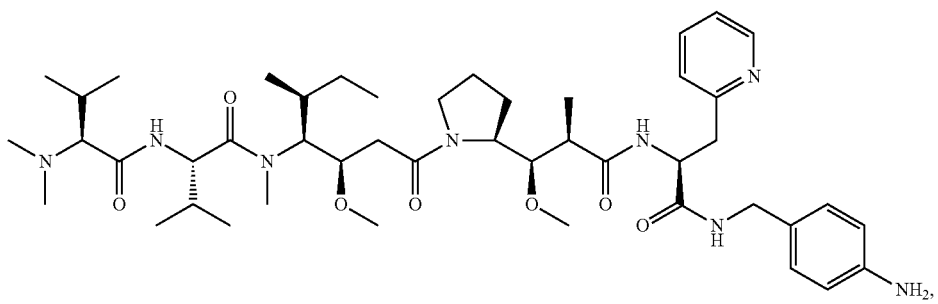
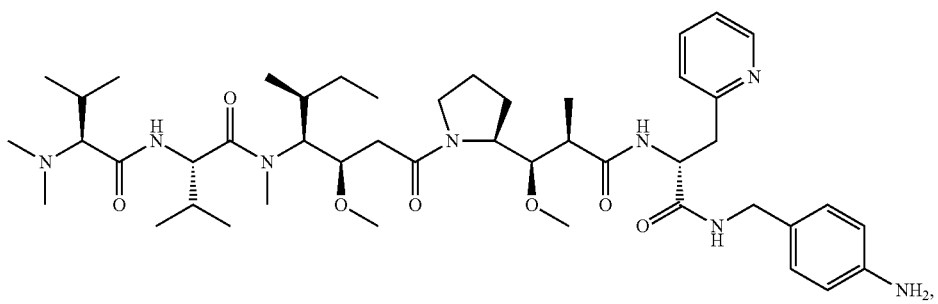
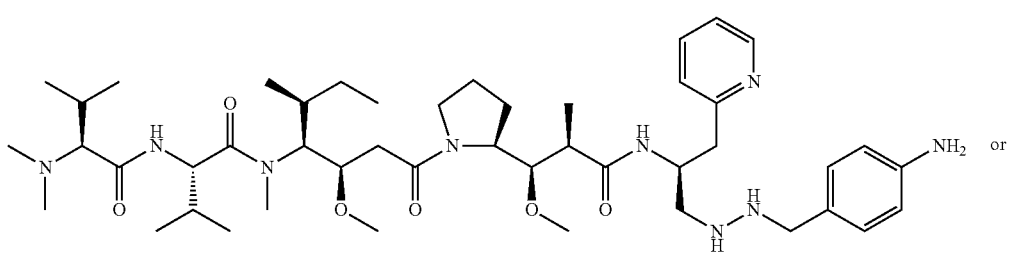
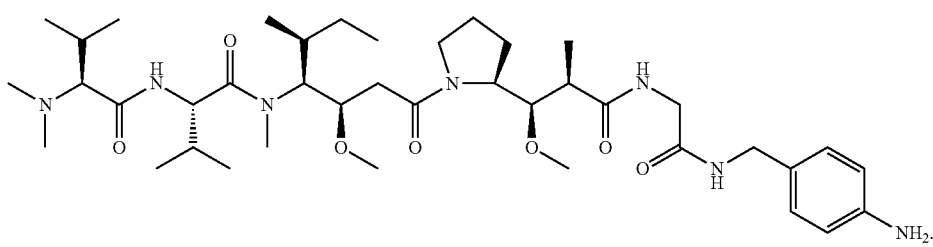

In some preferred embodiments, the bioactive molecule is selected from
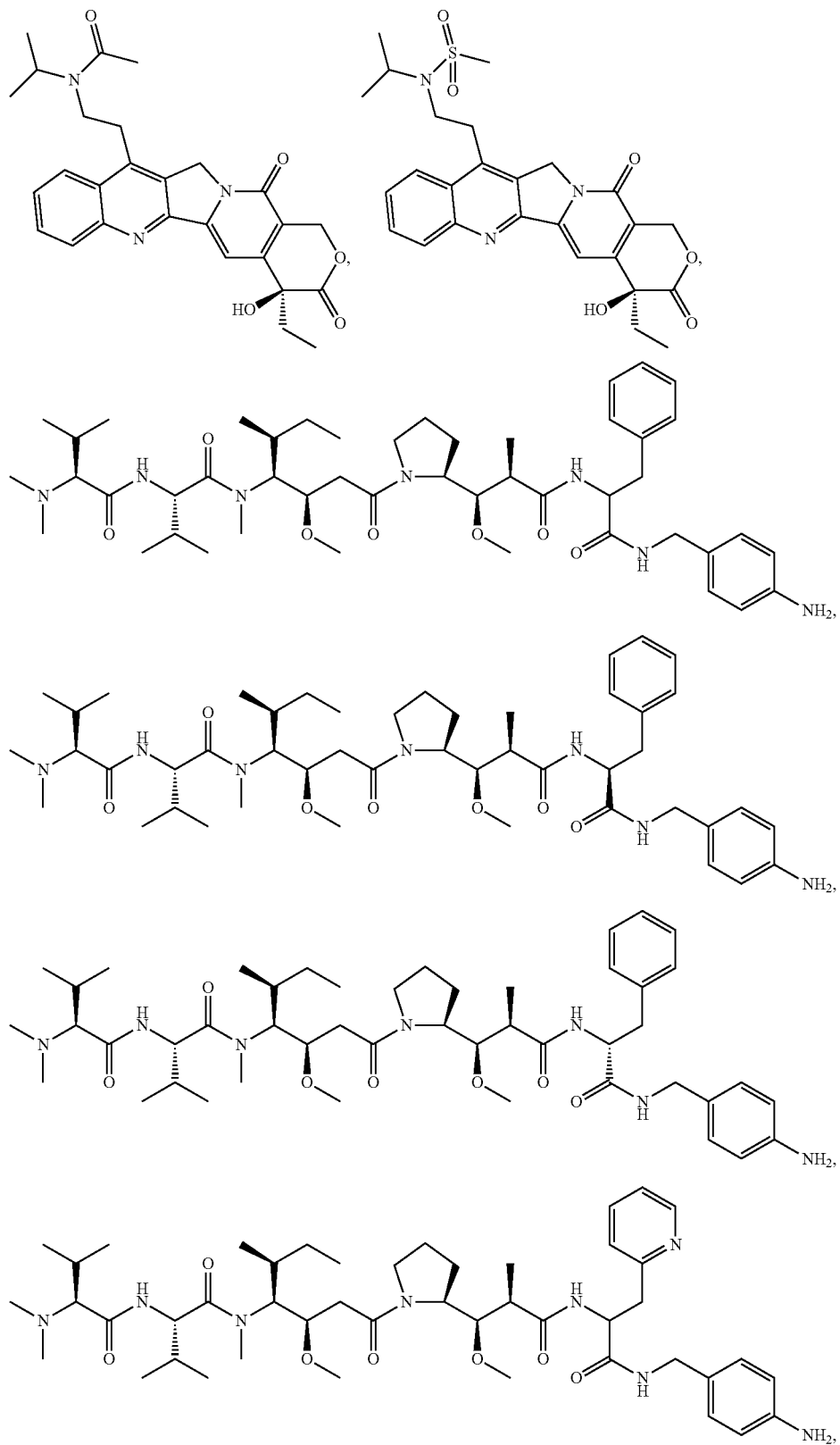

-continued
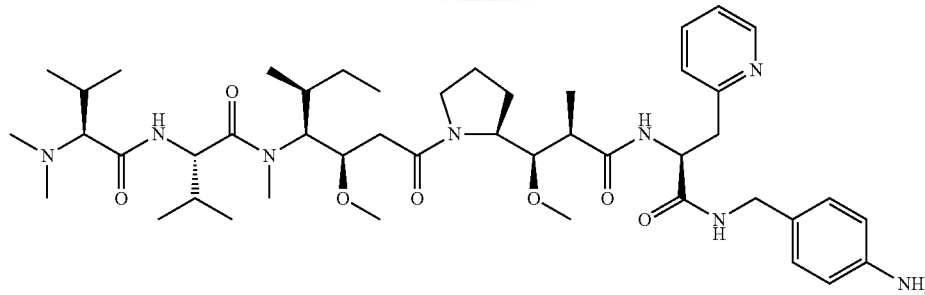
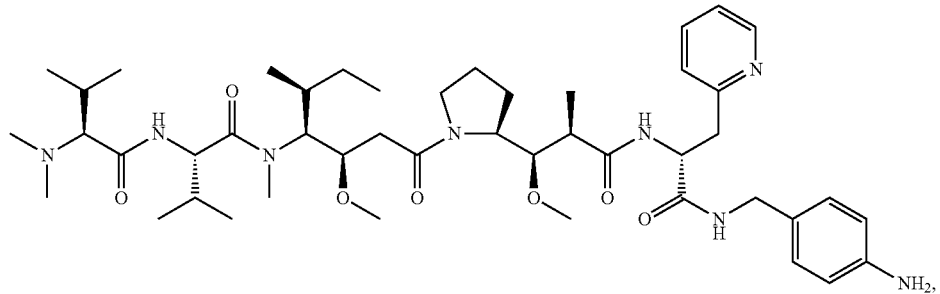
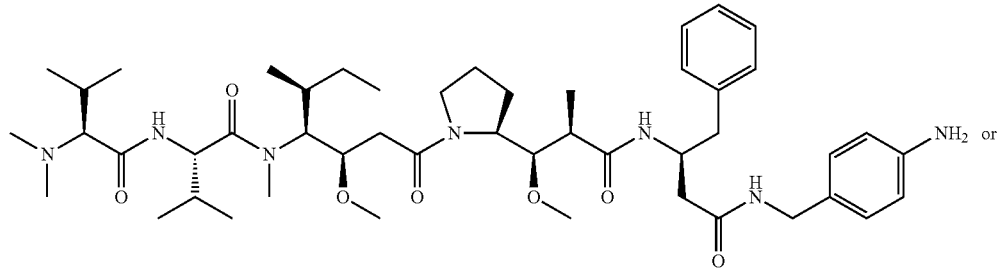
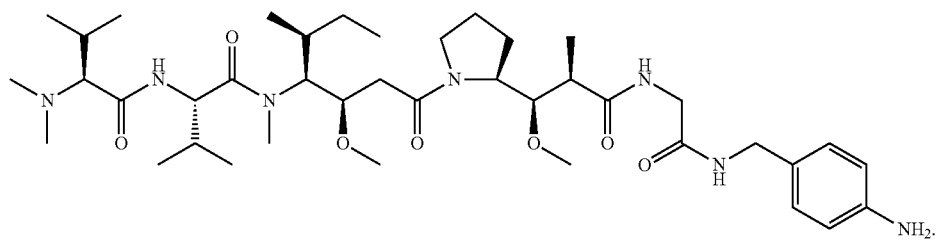
In some preferred embodiments, the bioactive molecule is selected from
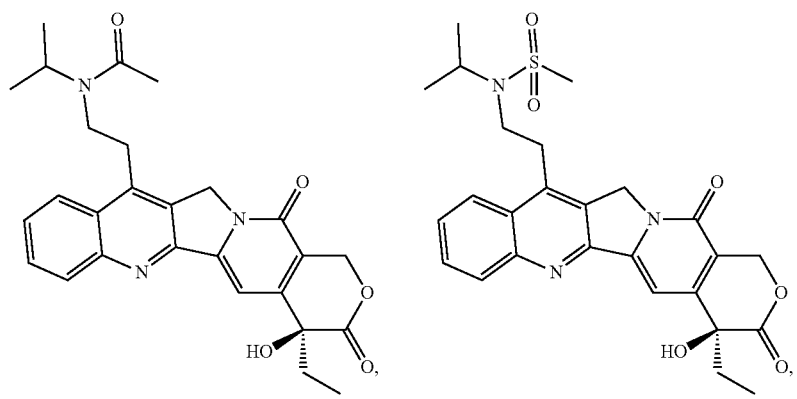

-continued
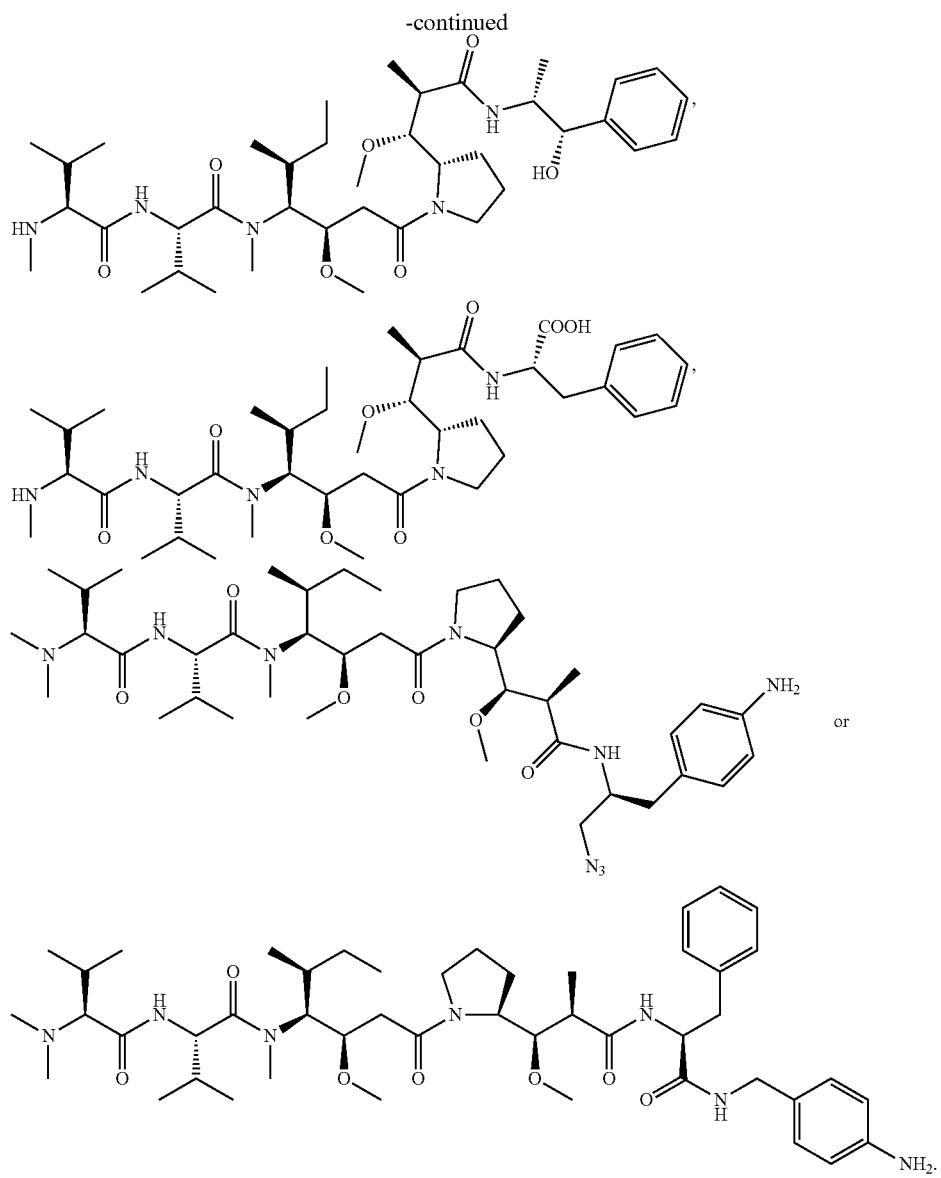
In some preferred embodiments, the bioactive molecule is selected from
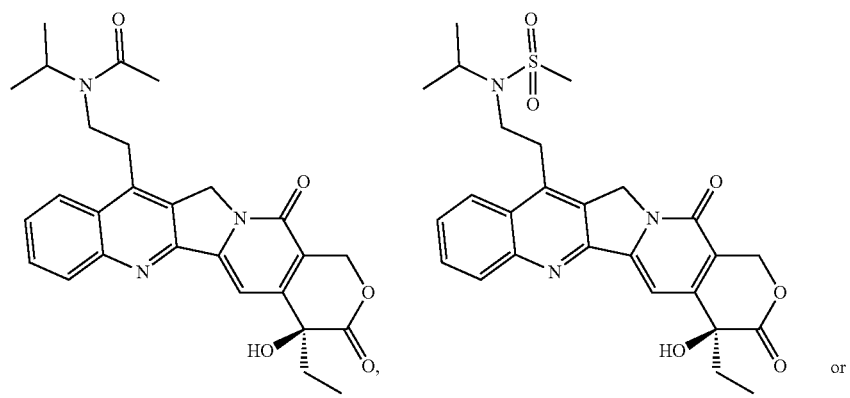

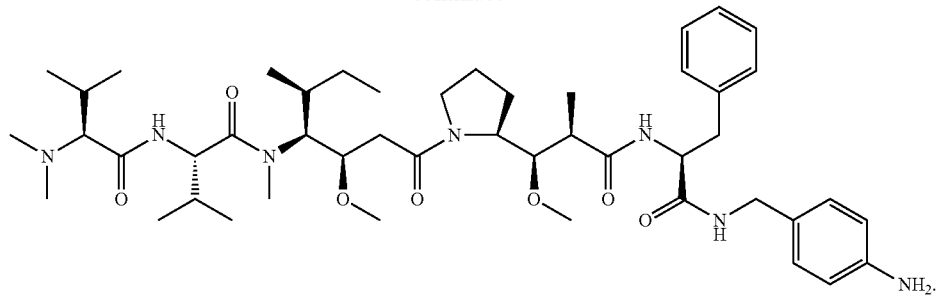
In some preferred embodiments, the bioactive molecule is selected from
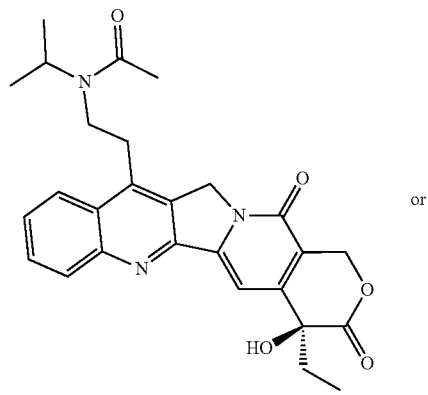 or 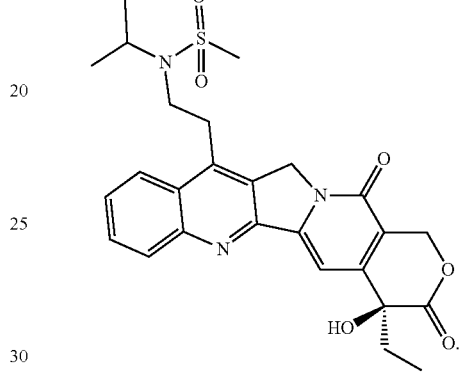
In some preferred embodiments, T is selected from
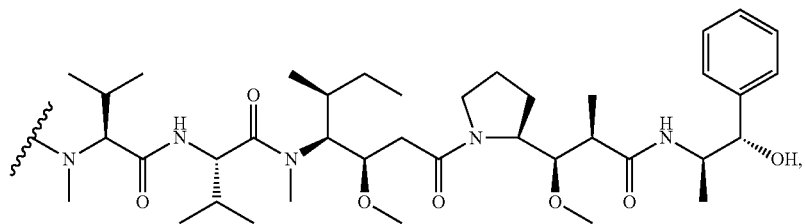
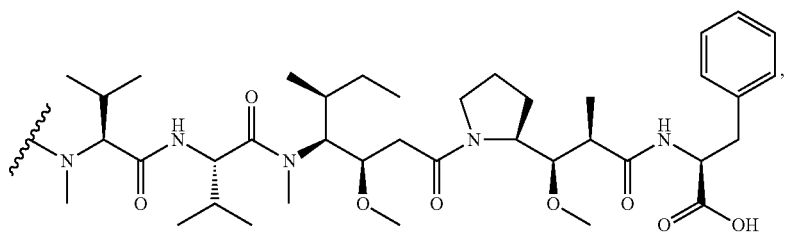

-continued
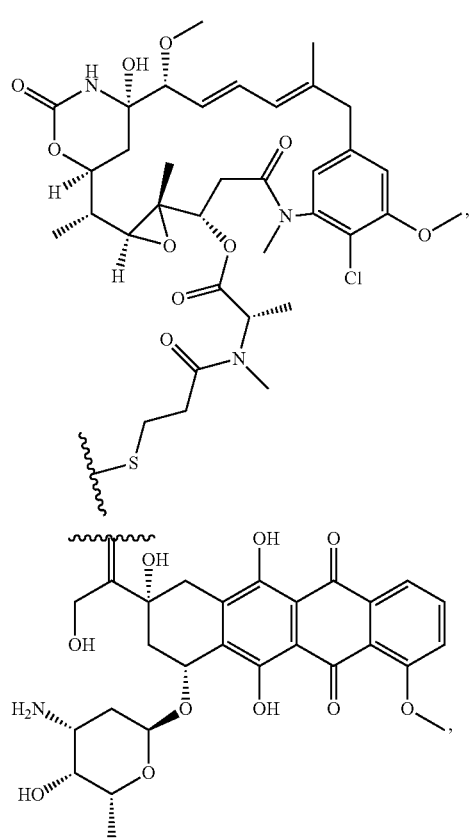
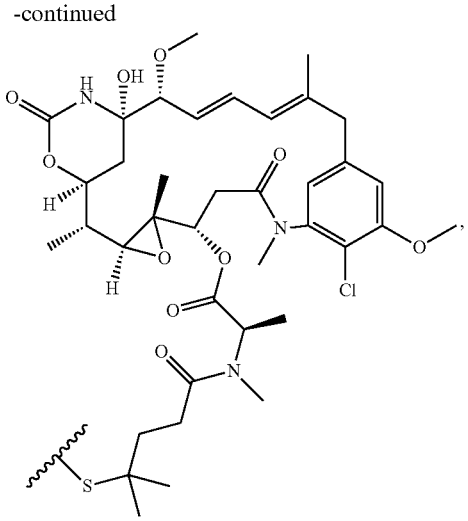
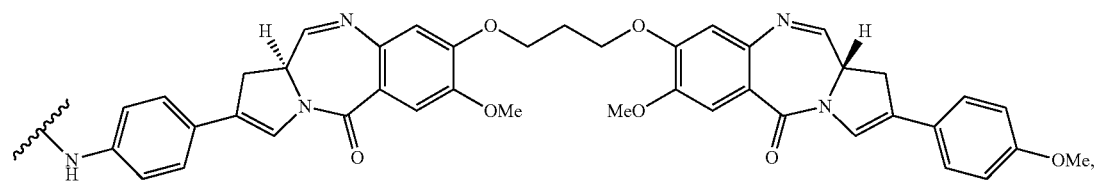
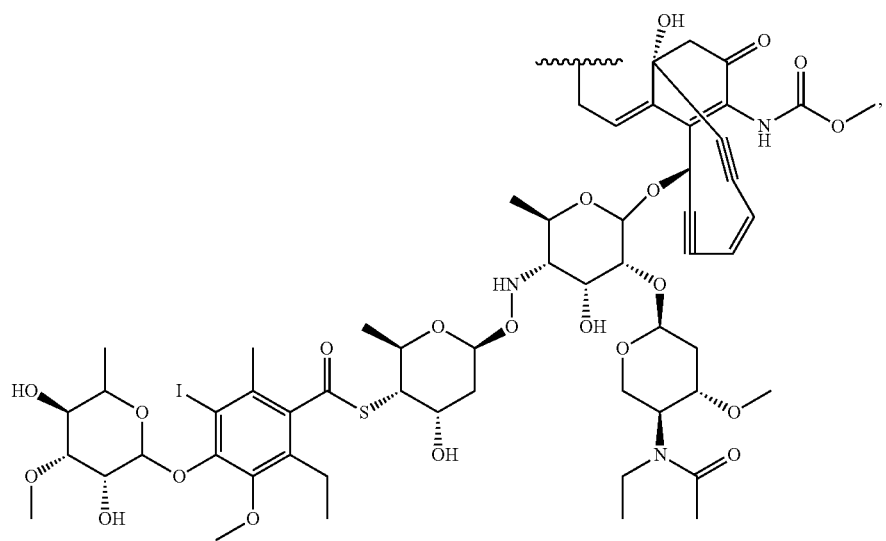

-continued
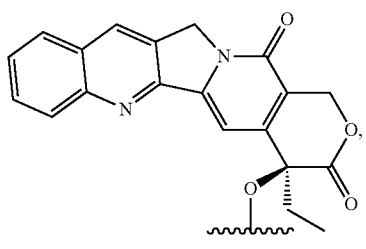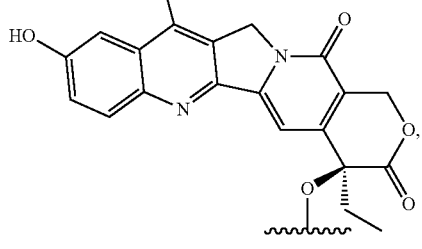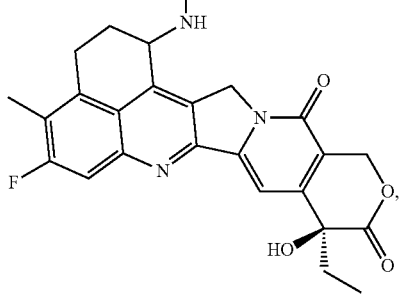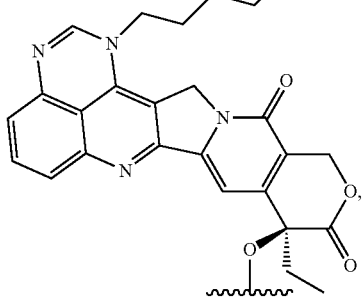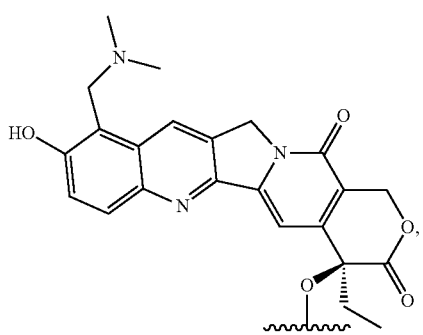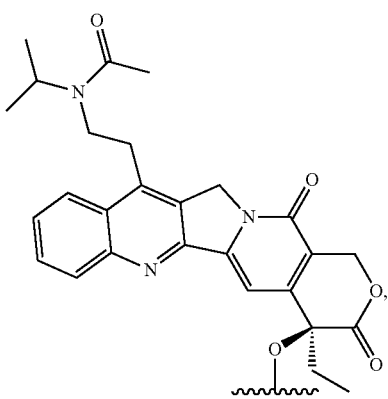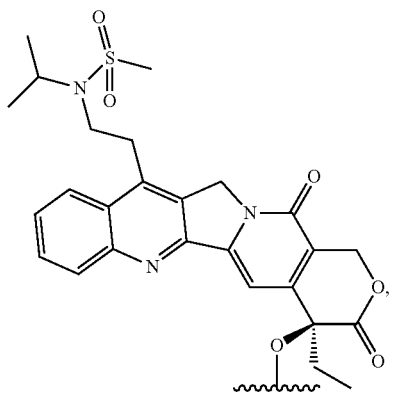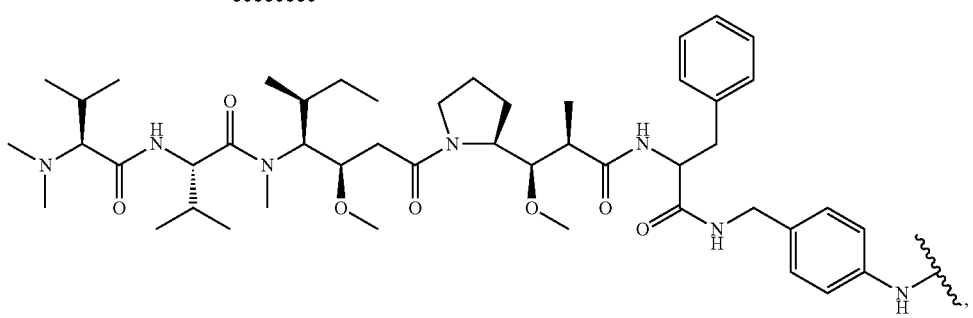

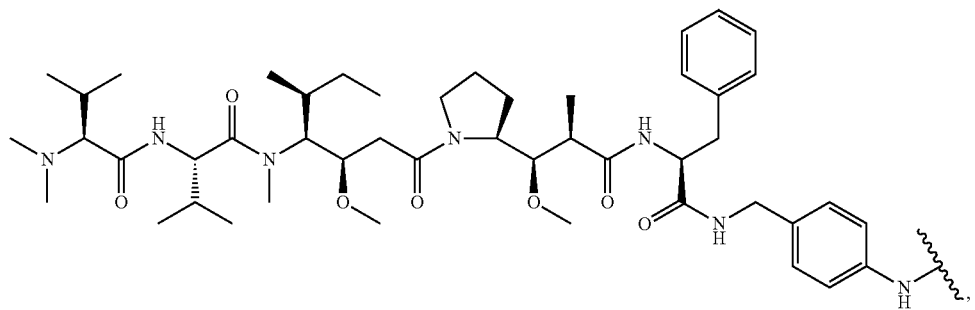
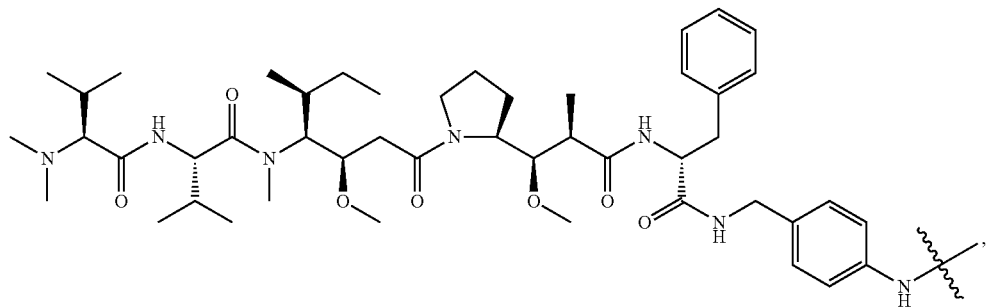
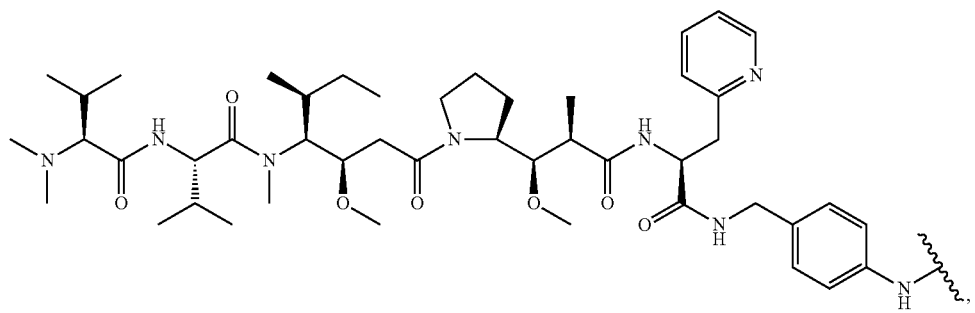
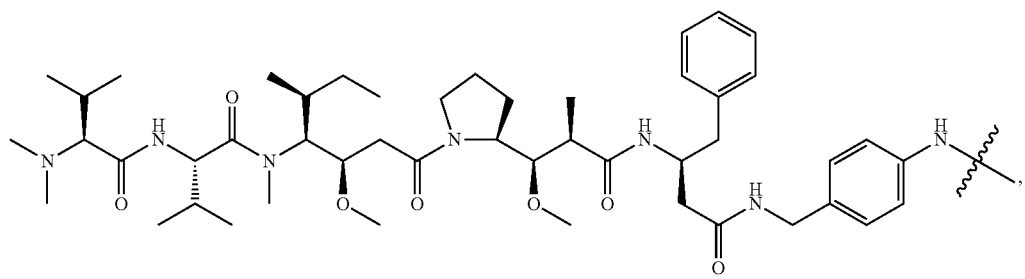
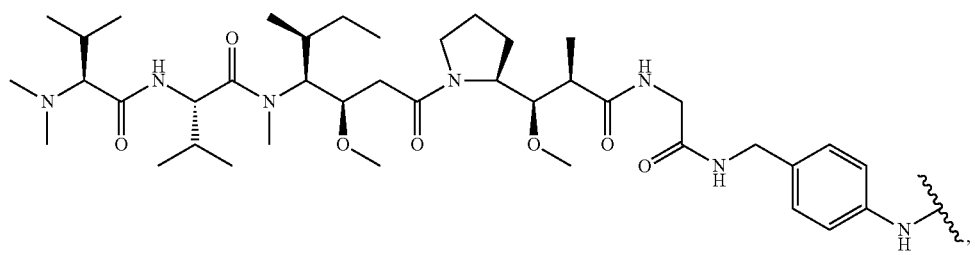

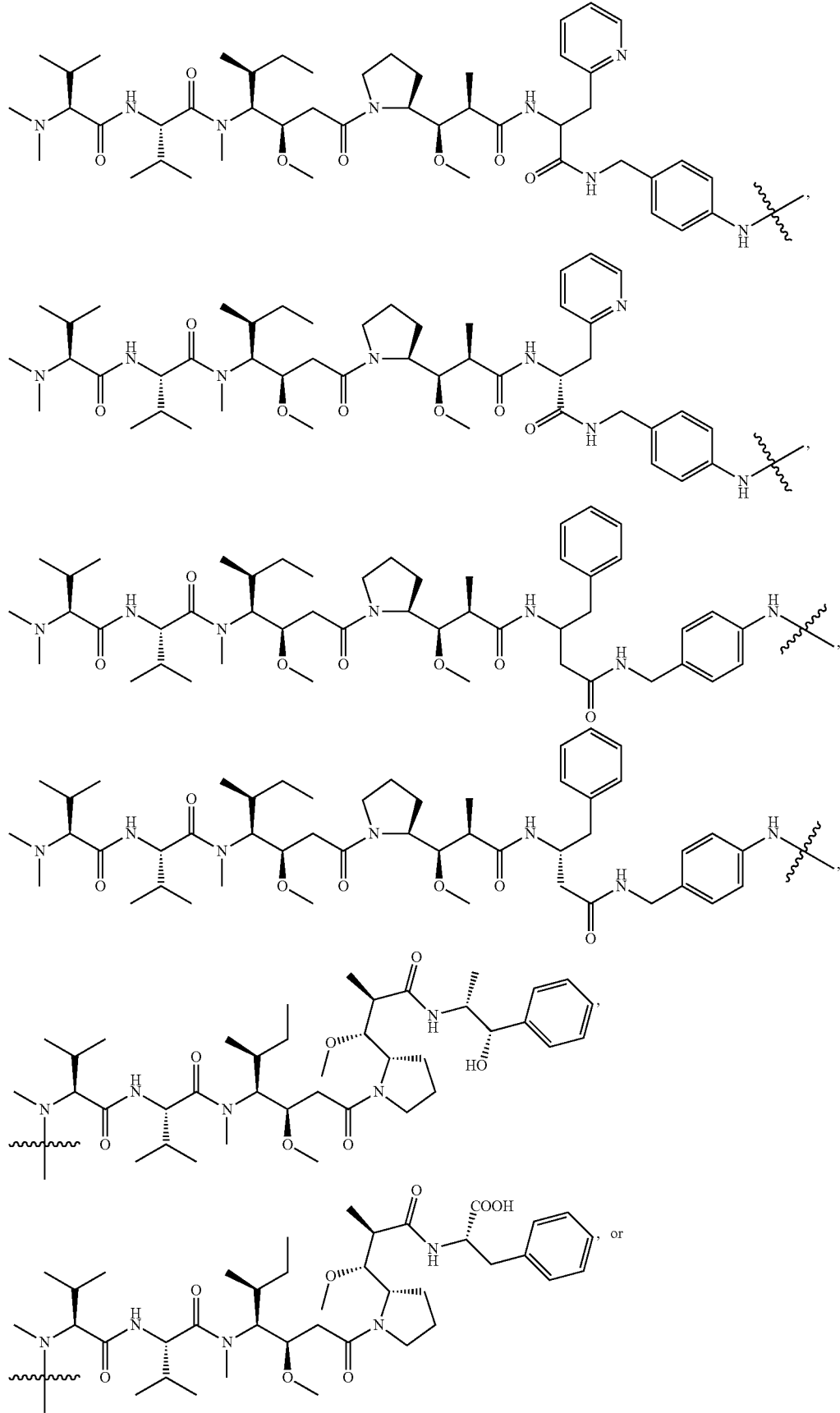

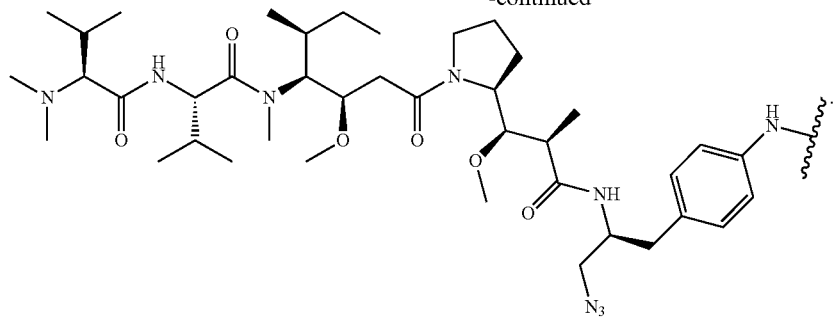
In some preferred embodiments, T is selected from
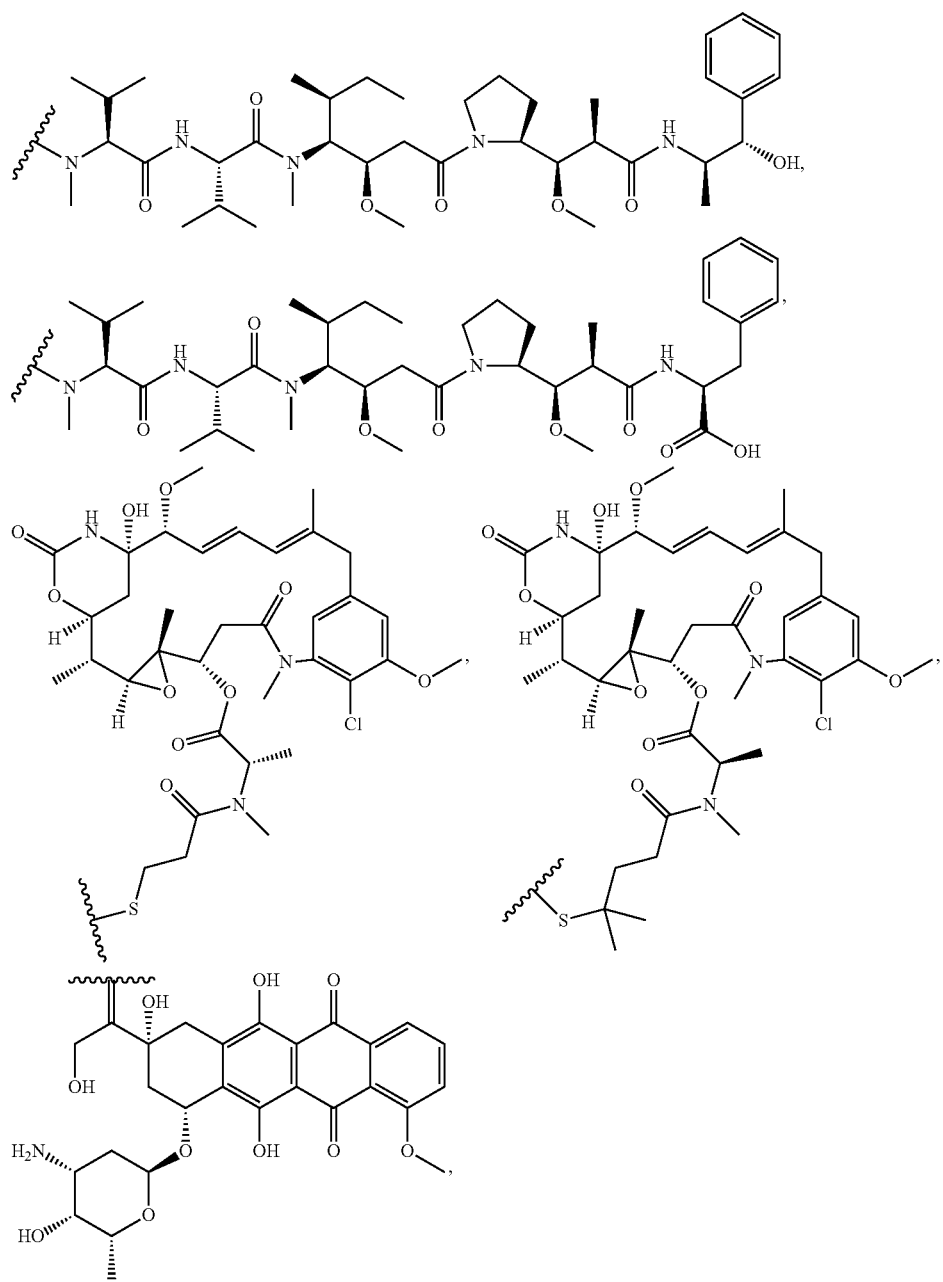

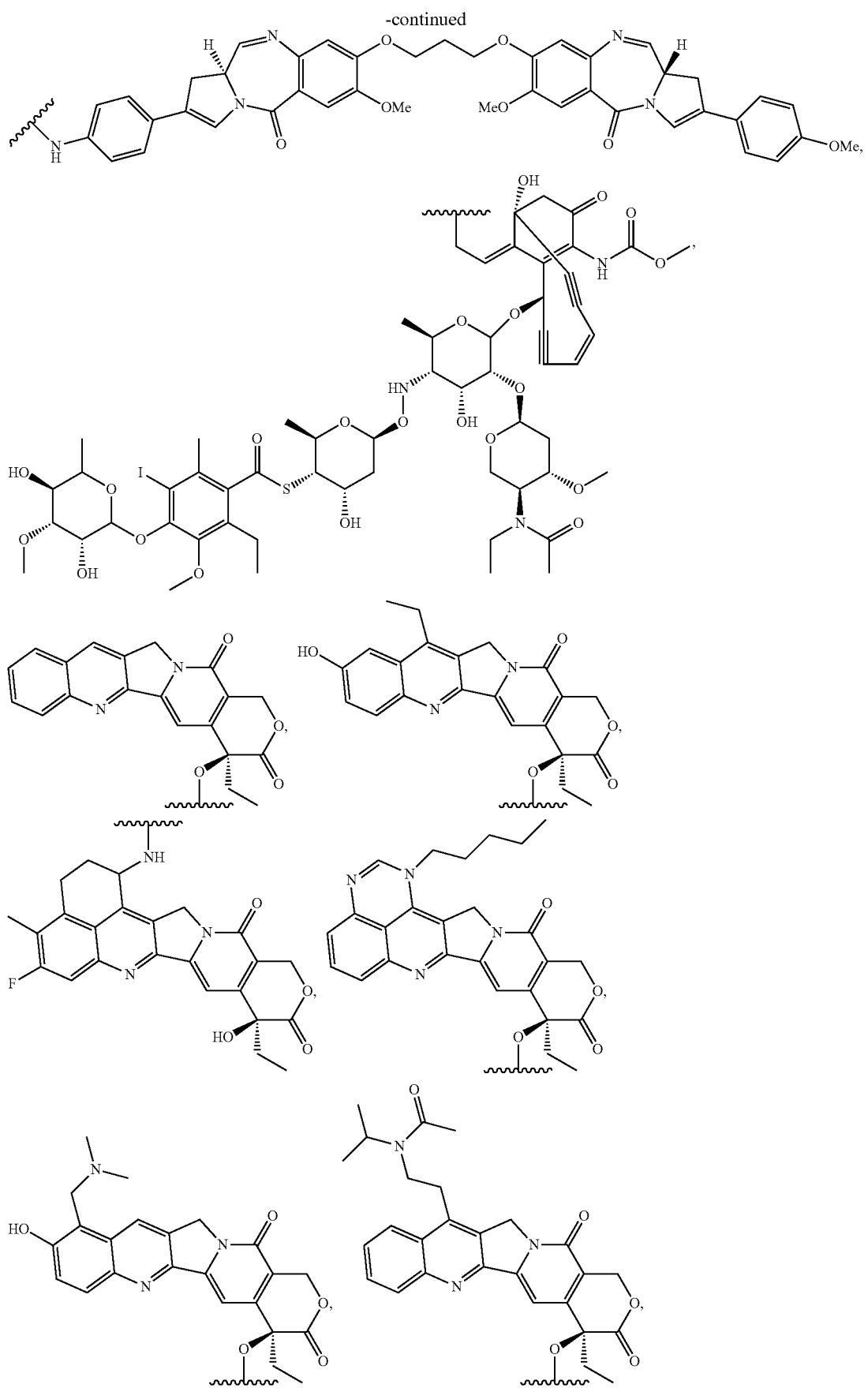

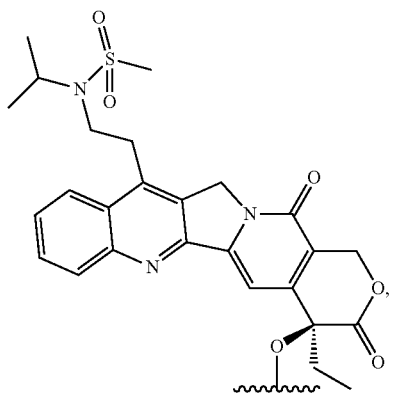
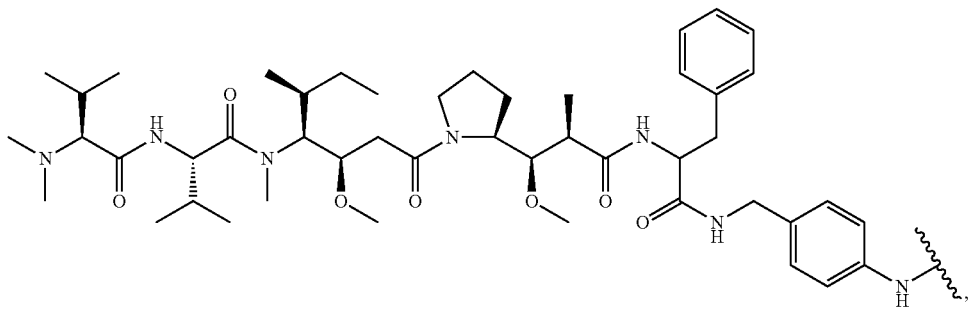
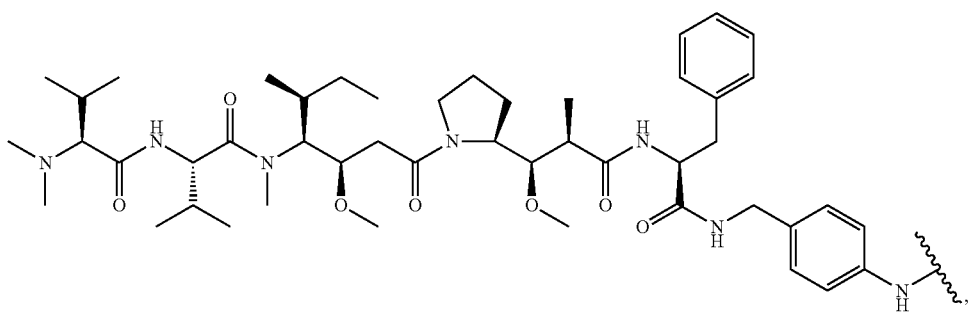
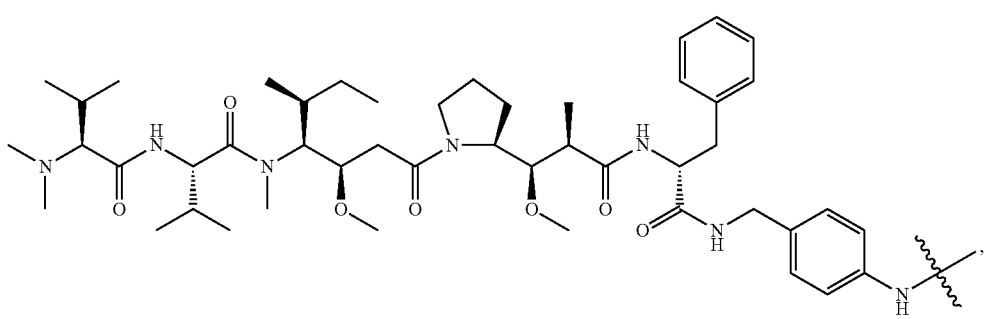
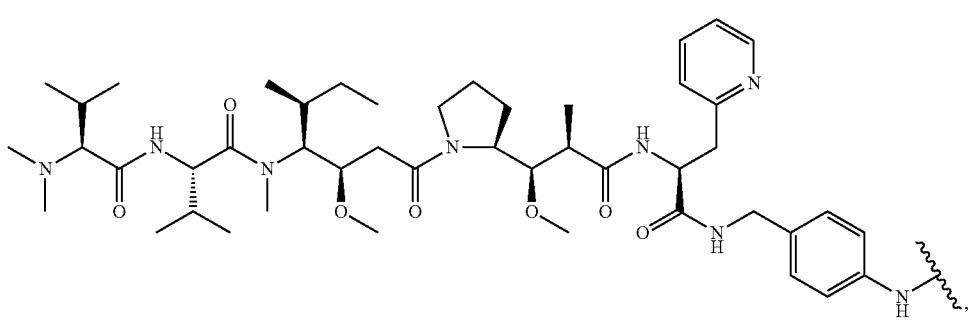

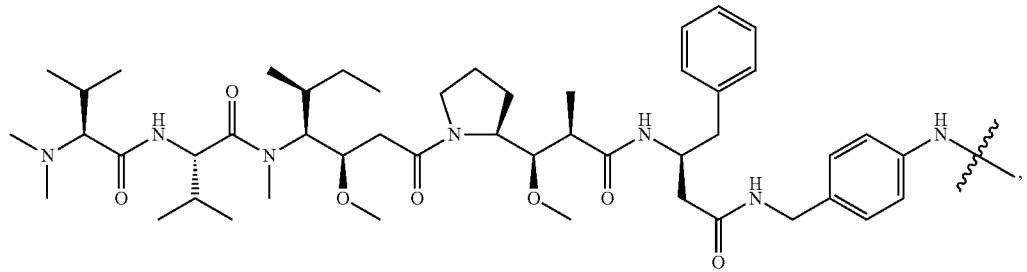,
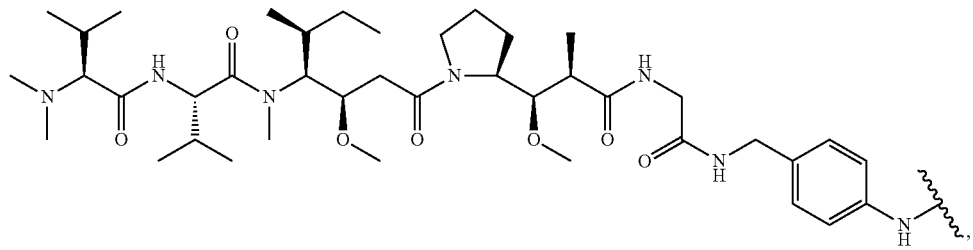,
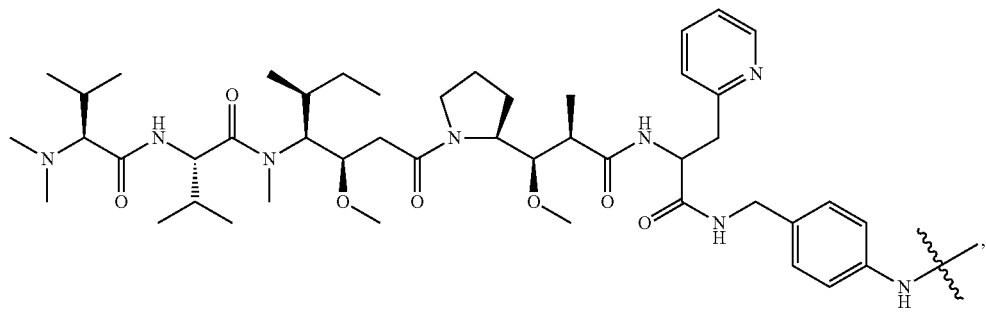,
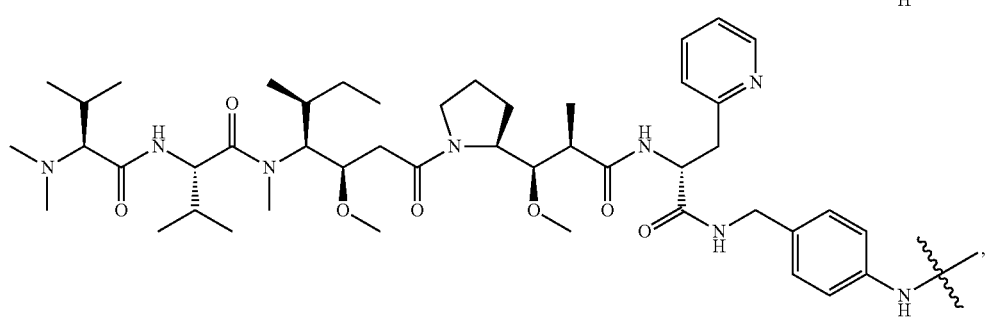,
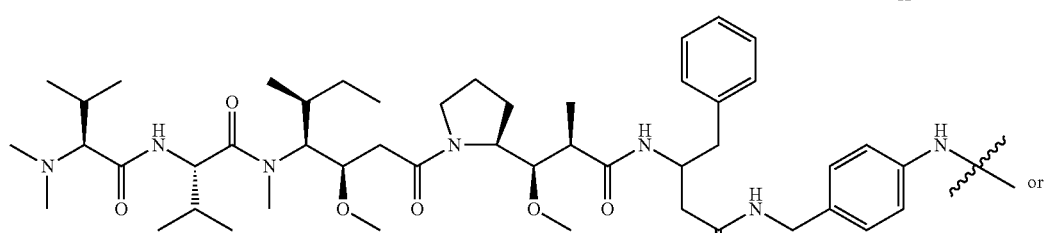 or
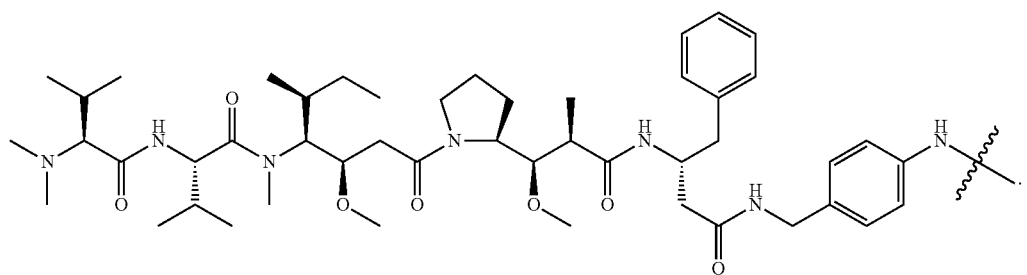.

In some preferred embodiments, T is selected from
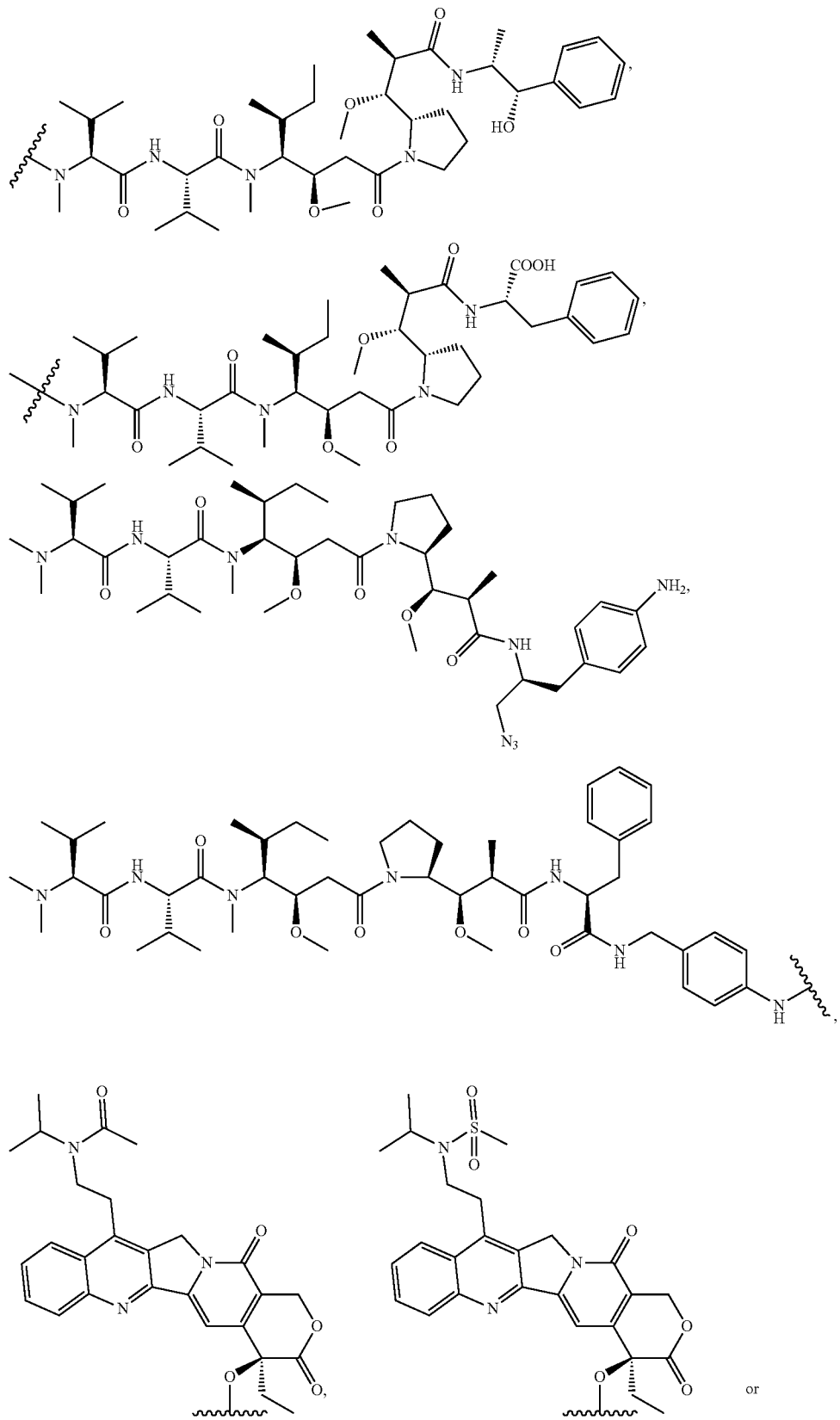

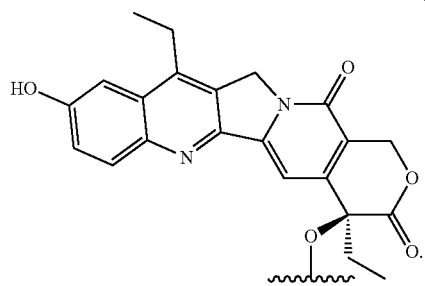
In some preferred embodiments, T is selected from
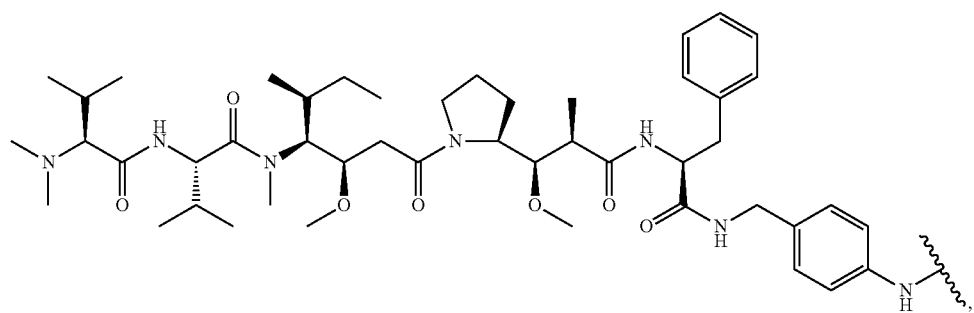
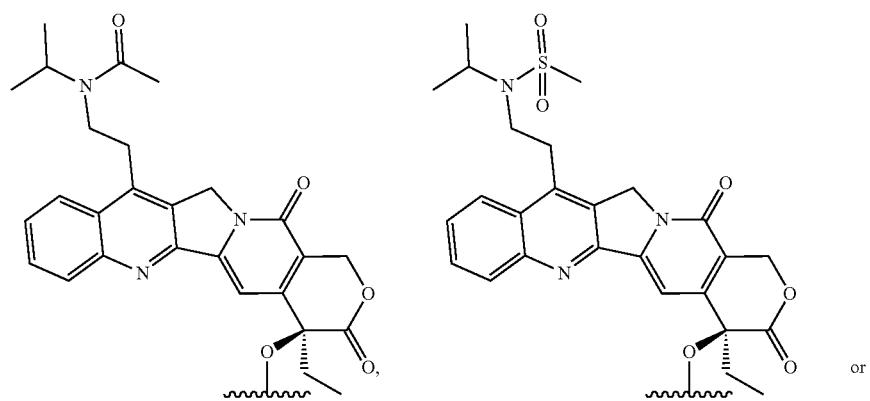
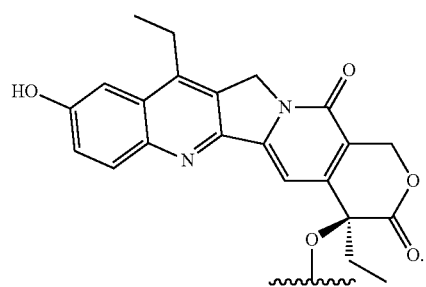 [SMILES: *O[C@]1(CC)C(=O)OCc2c1cc1n(c2=O)Cc2c-1nc1ccc(O)cc1c2CC]

In some preferred embodiments, T is selected from
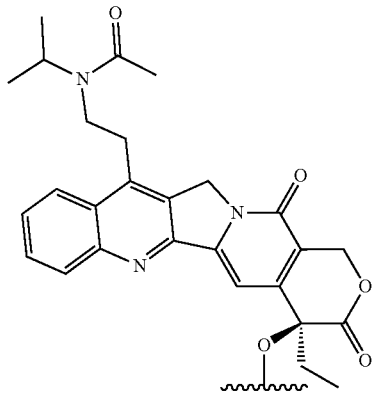
or
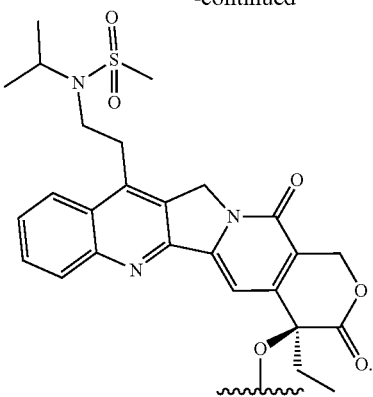
In some preferred embodiments, the compound shown in formula (I) is selected from
TL001
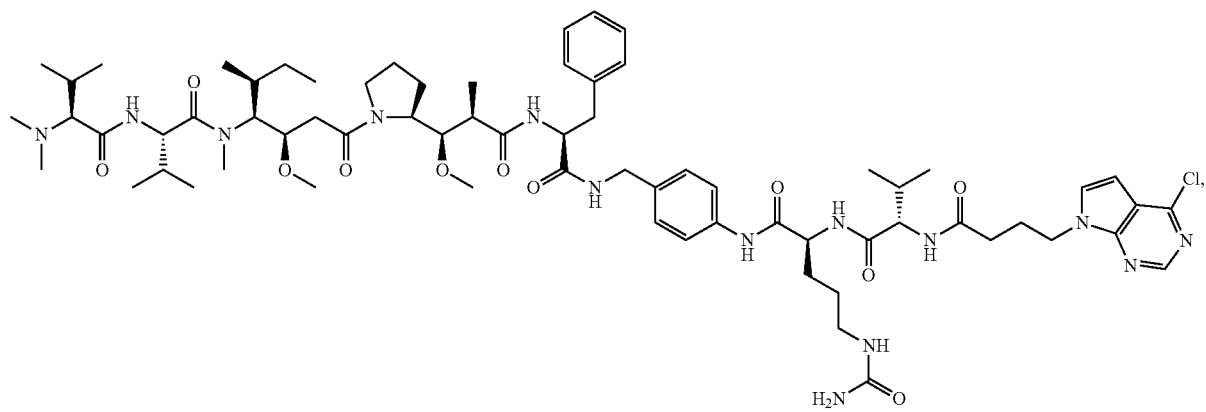
TL002
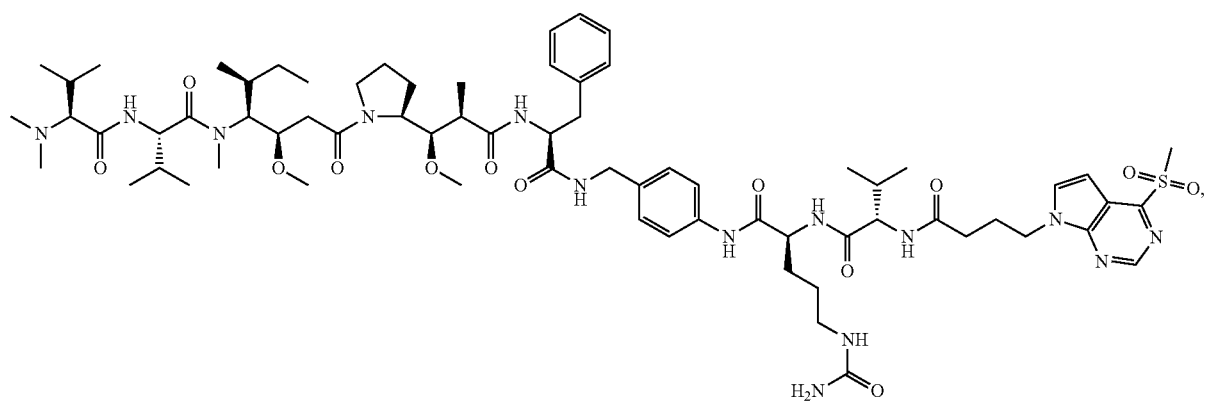

TL003
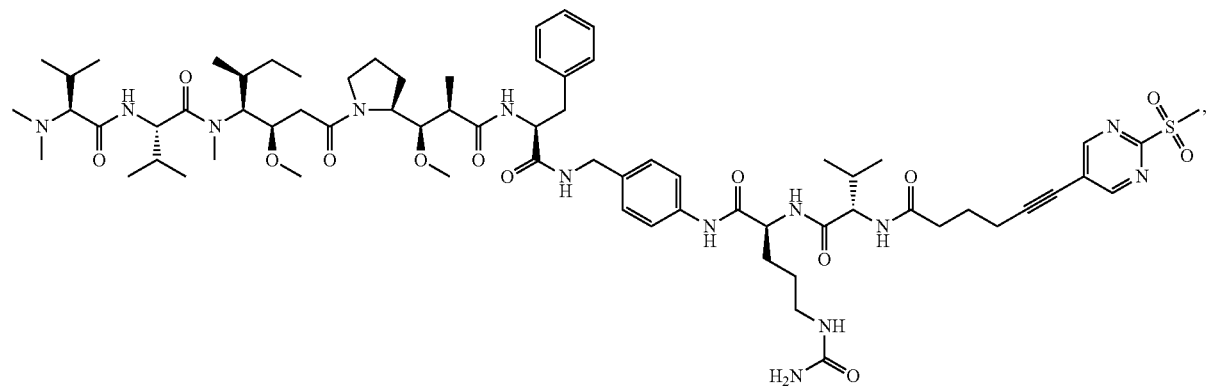
TL005
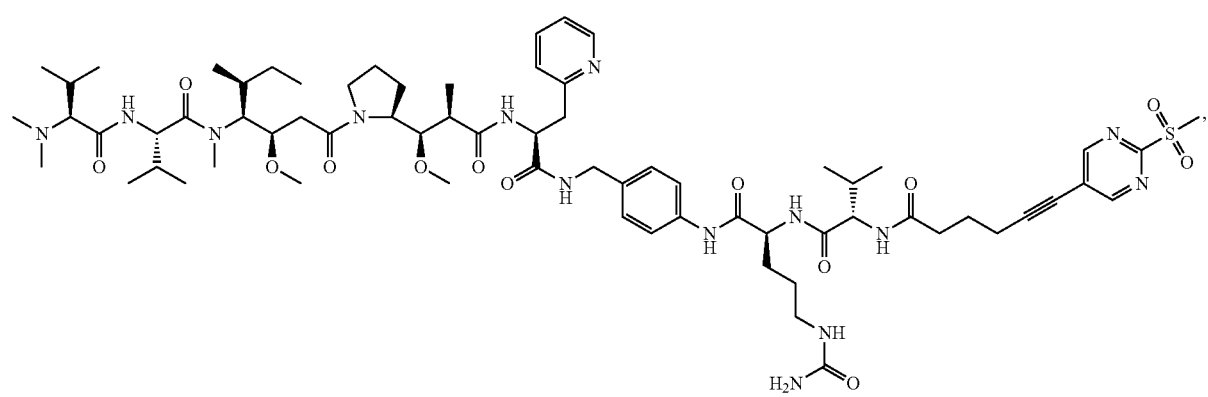
TL006
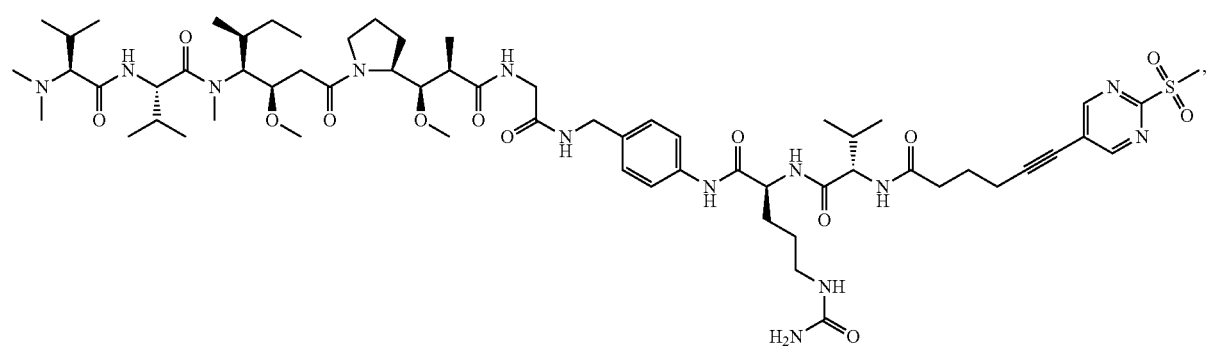
TL007
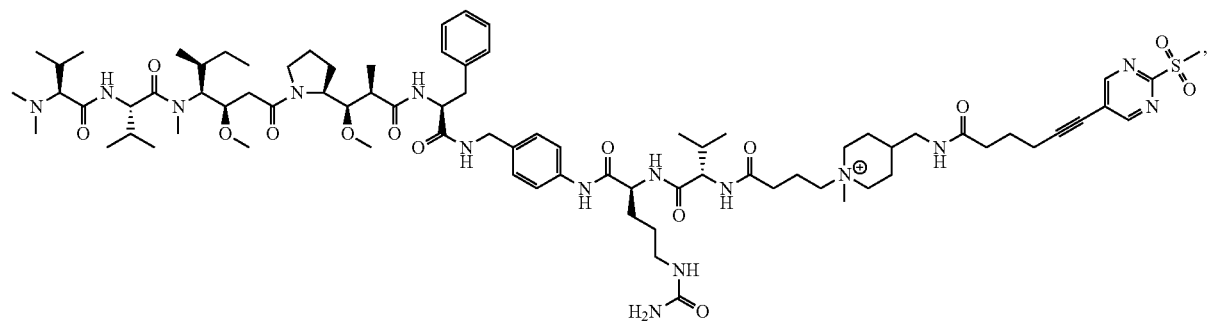

TL008
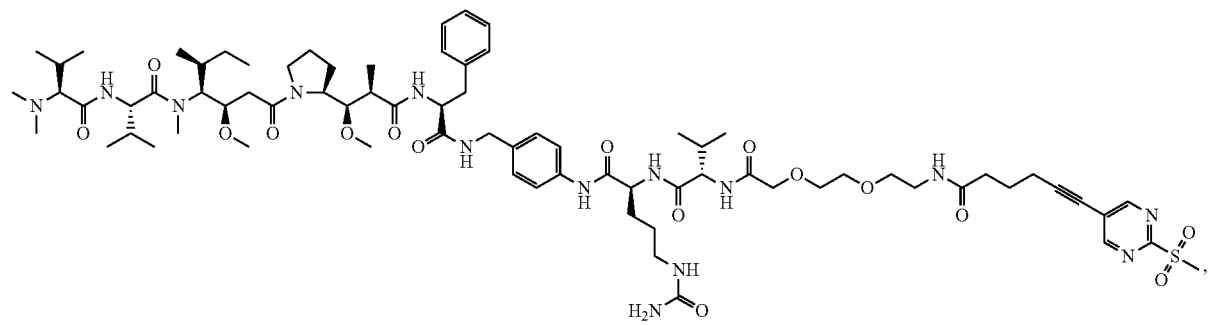
TL013
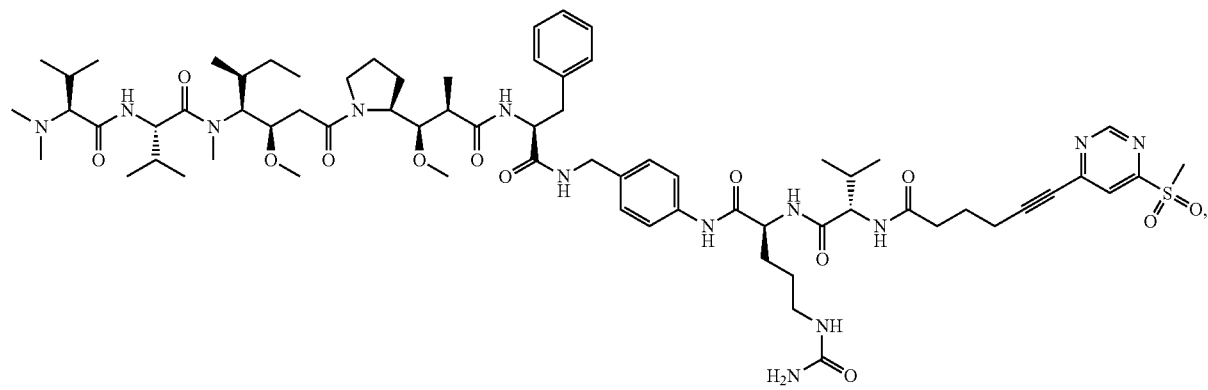
TL014
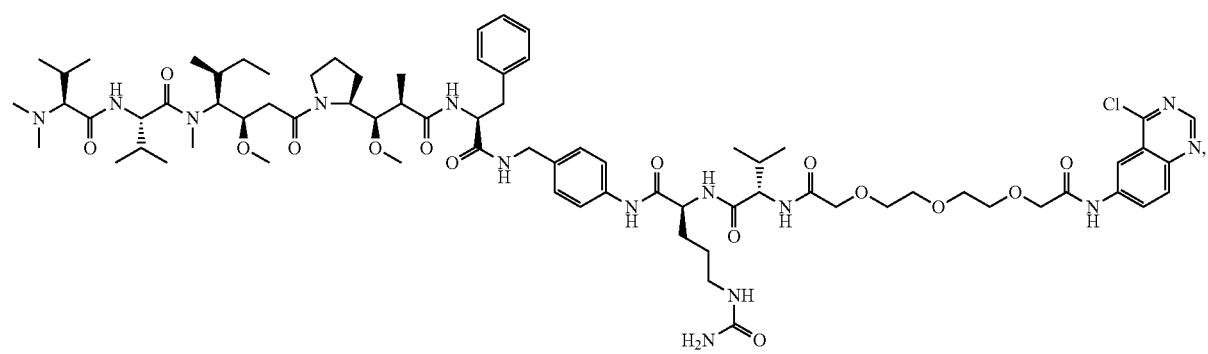
TL015
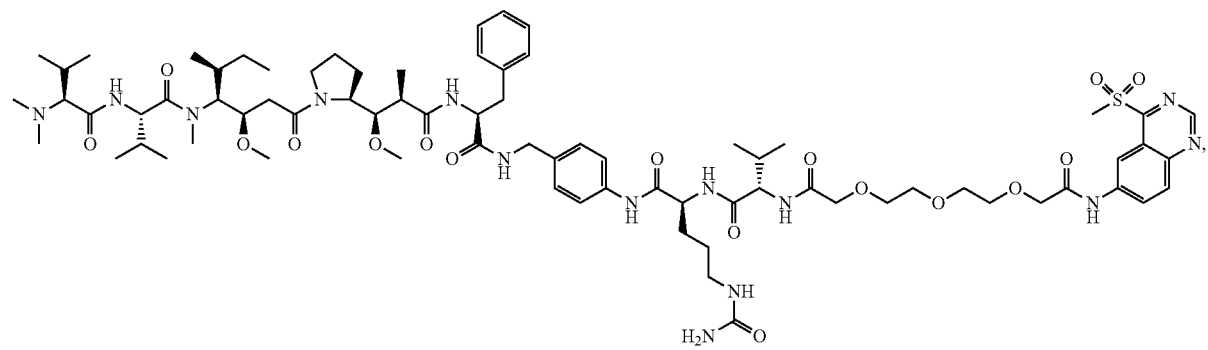

-continued
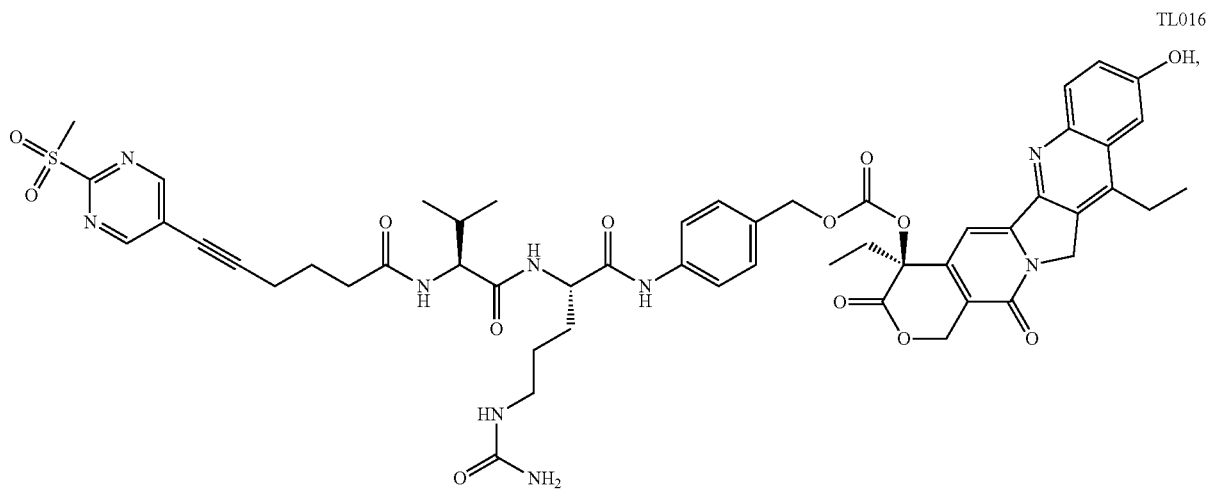
TL016
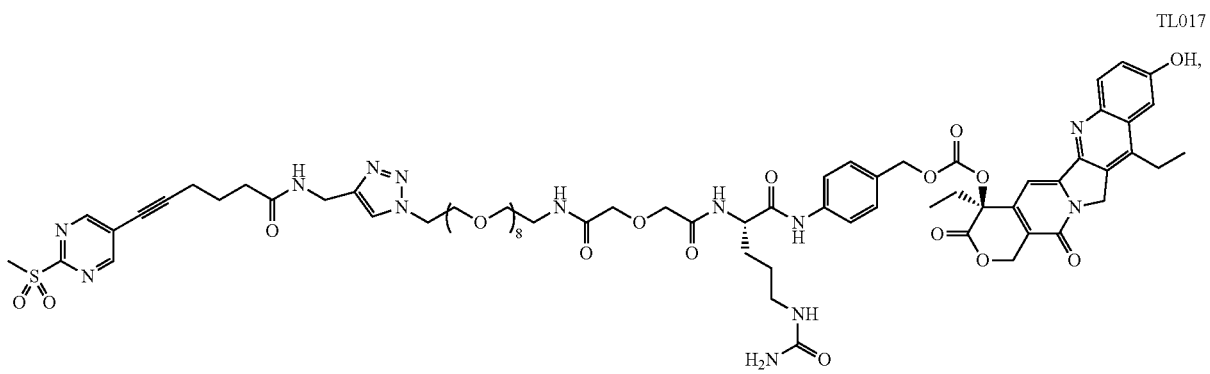
TL017
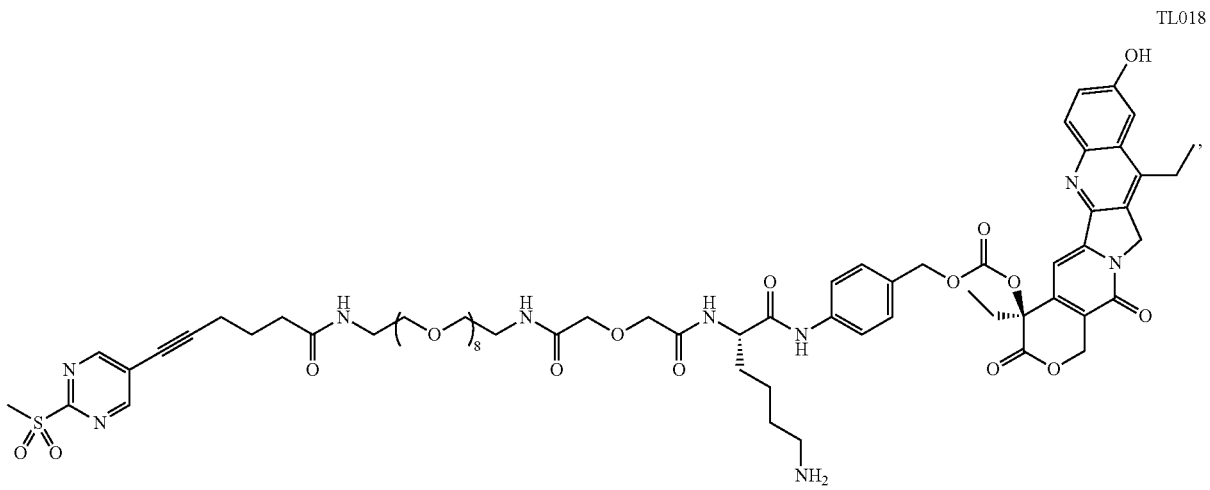
TL018

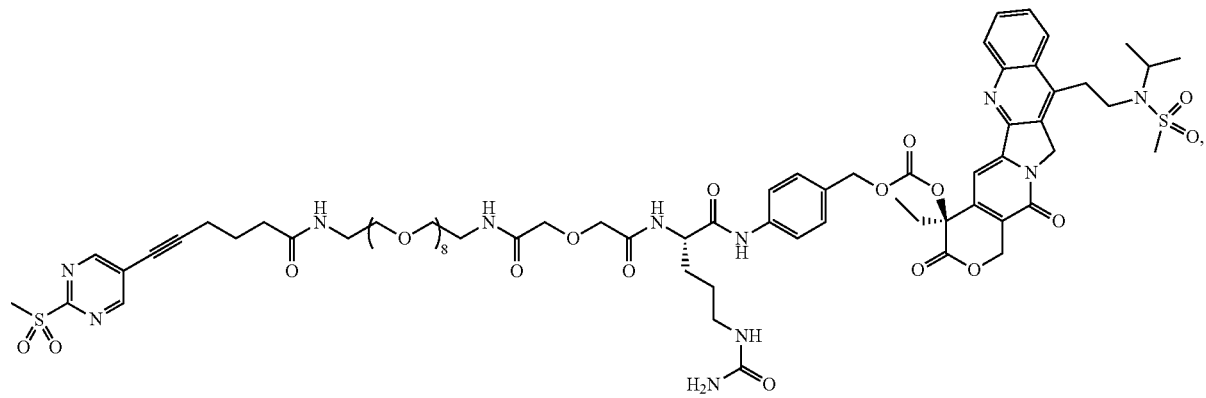
TL019
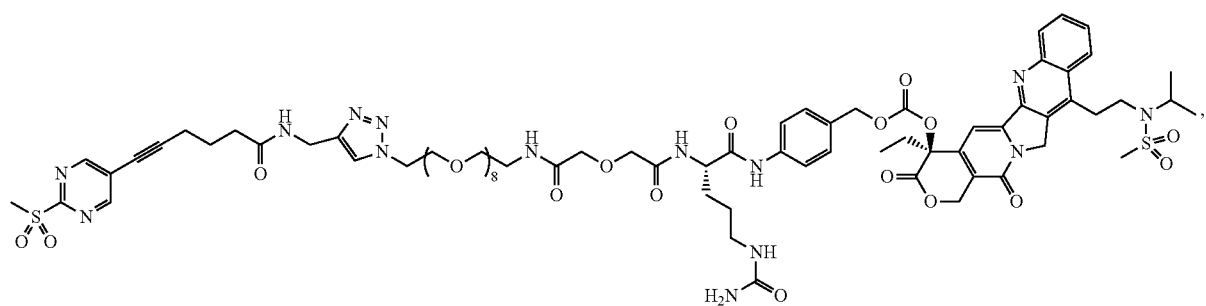
TL020
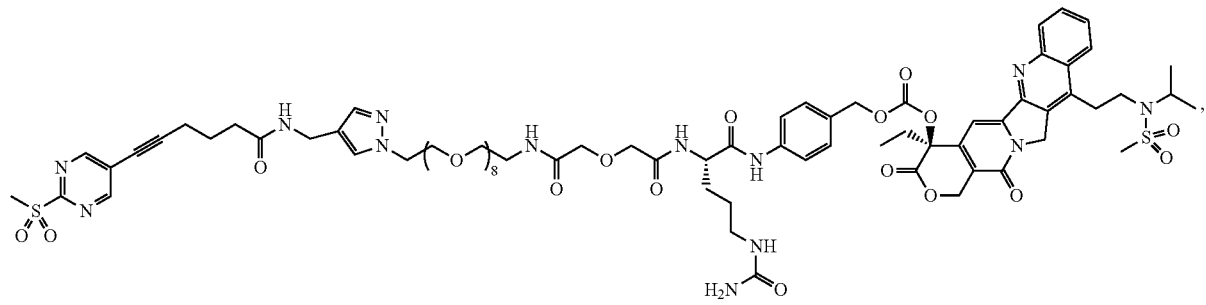
TL021
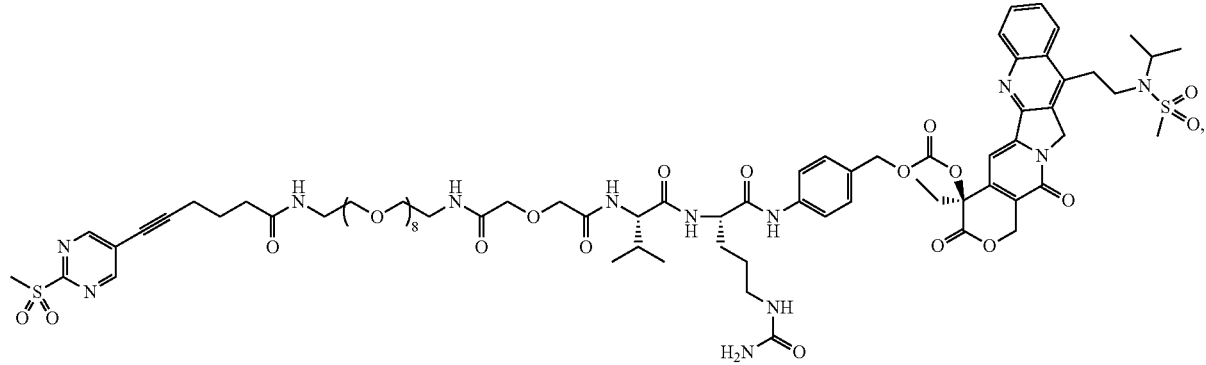
TL022

-continued
TL023
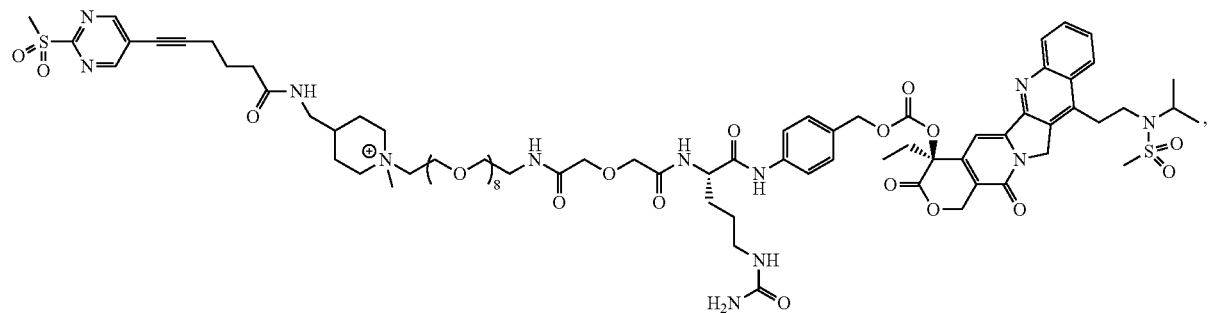
TL024
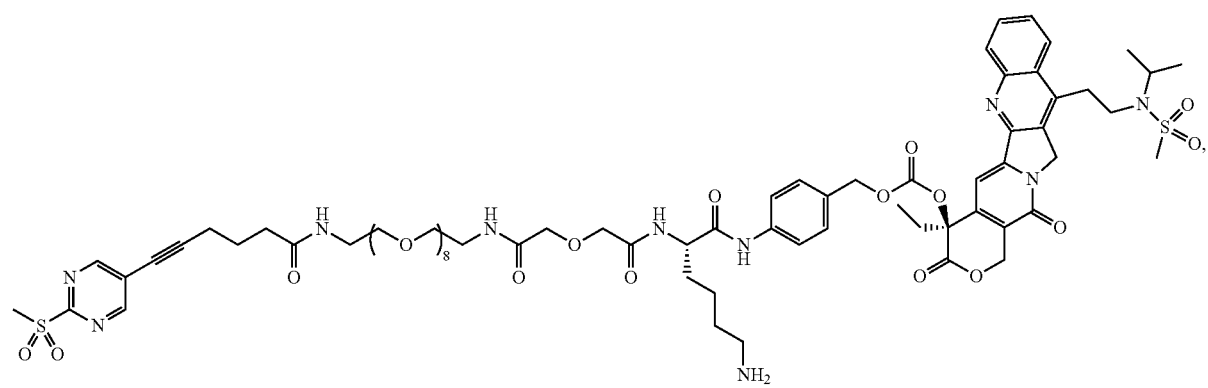
TL025
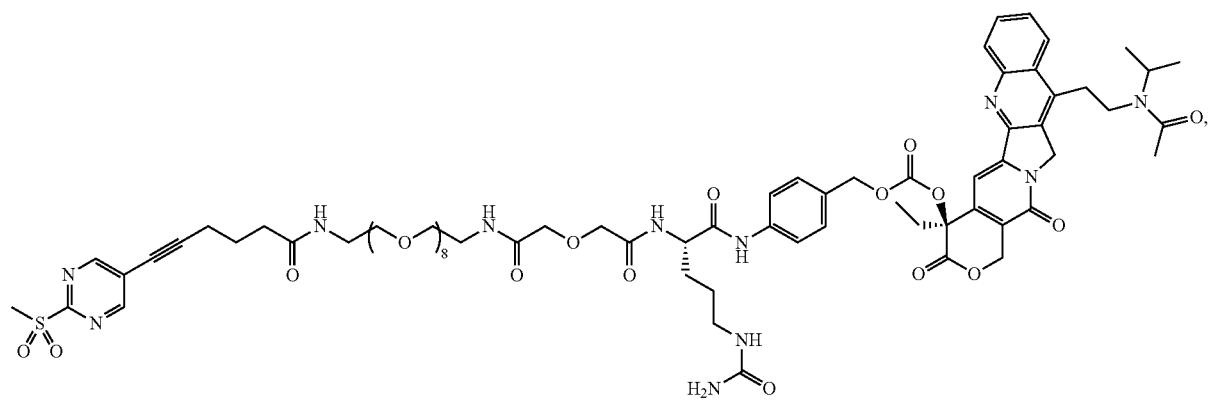
TL028
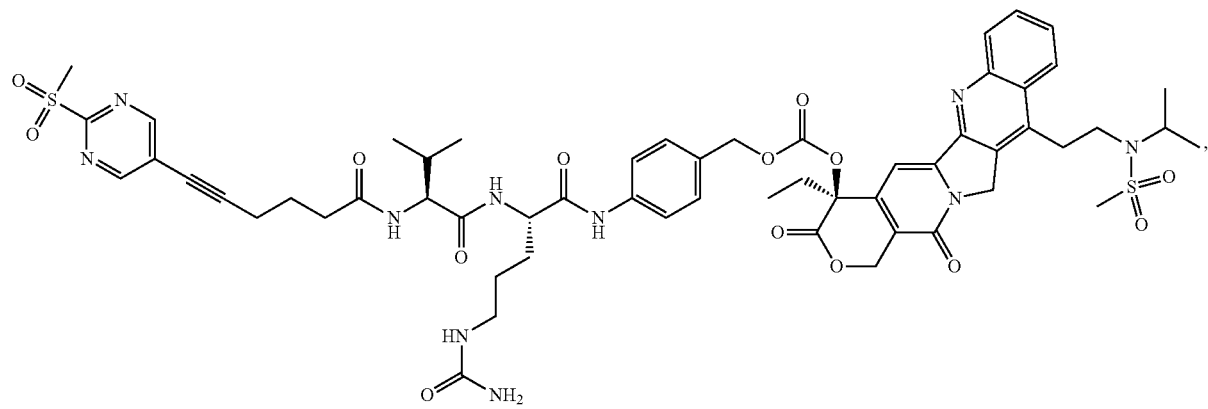

-continued
TL029
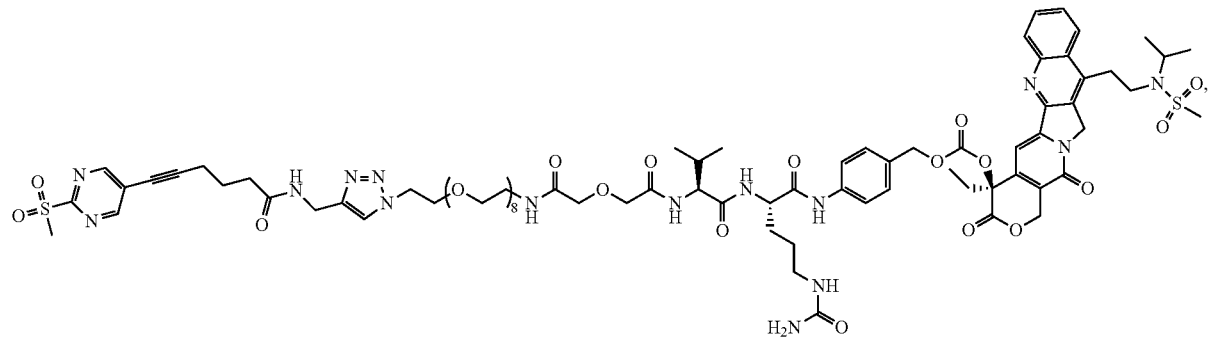
TL030
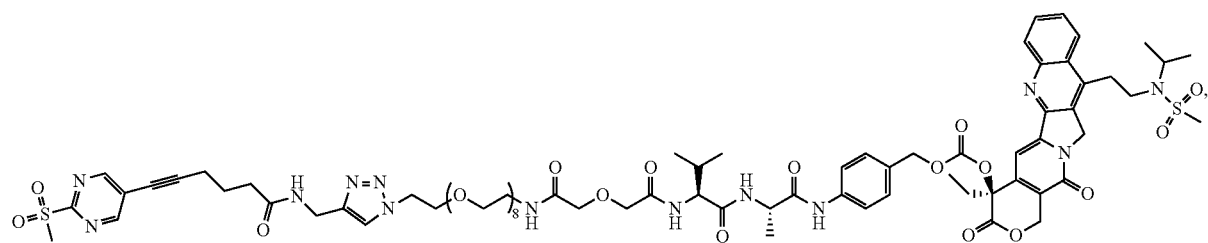
TL031
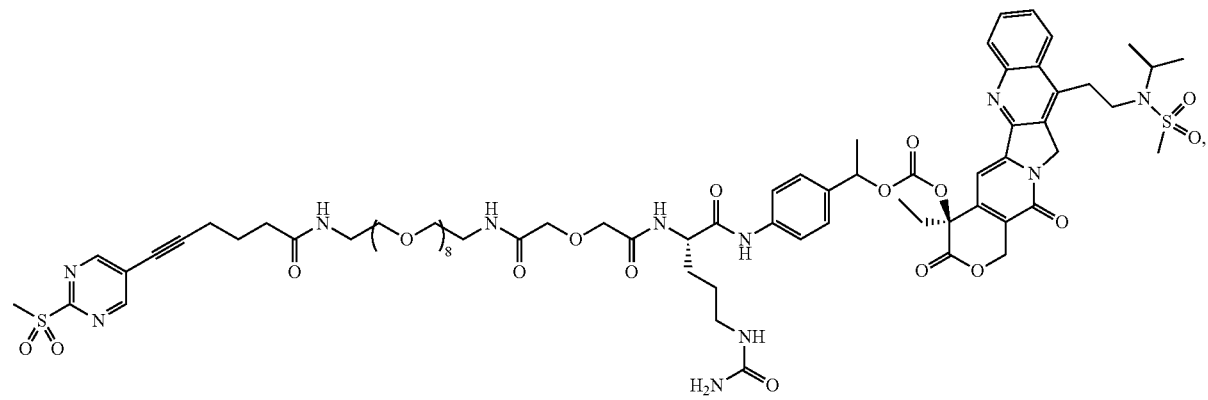
TL032
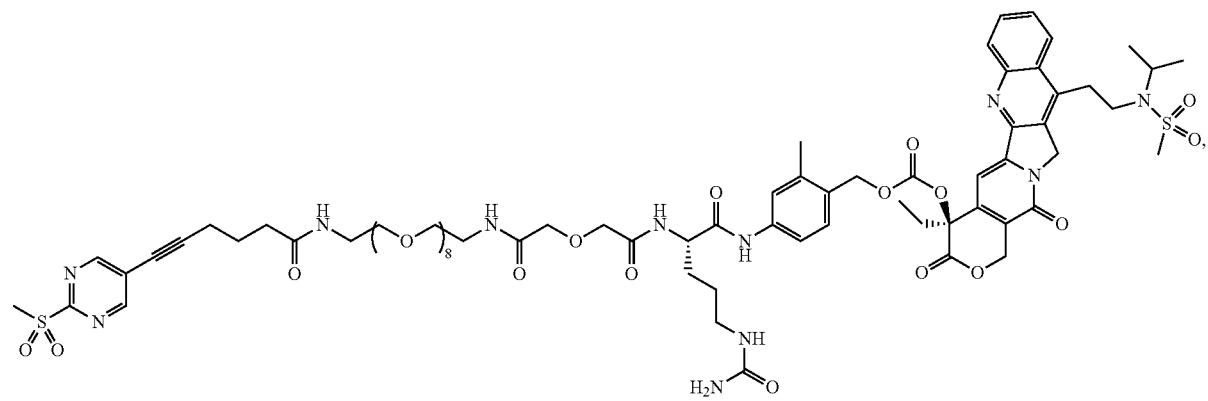

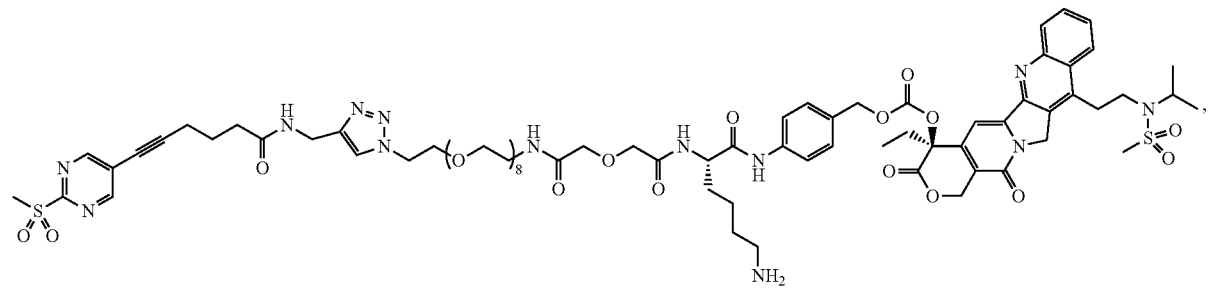
TL033
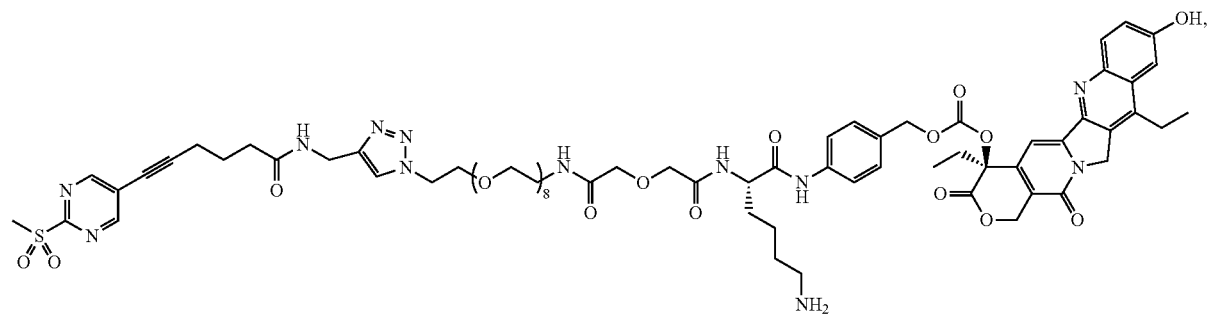
TL034
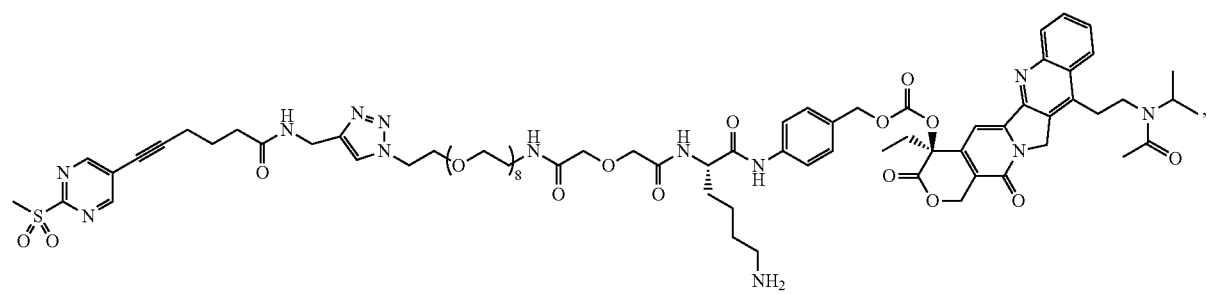
TL035
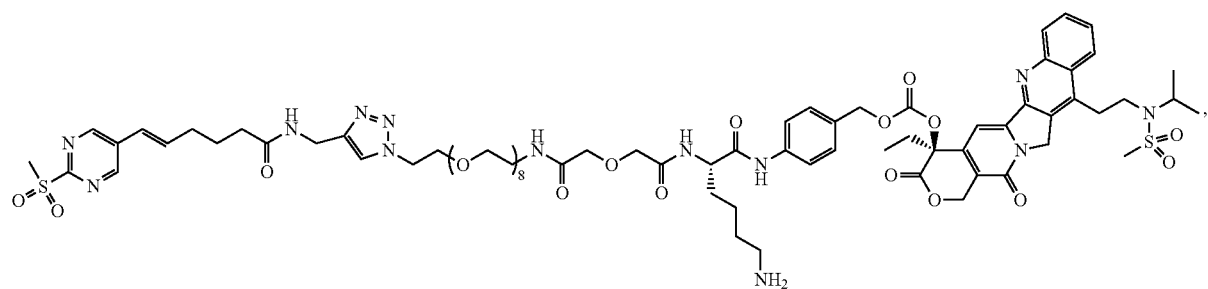
TL040
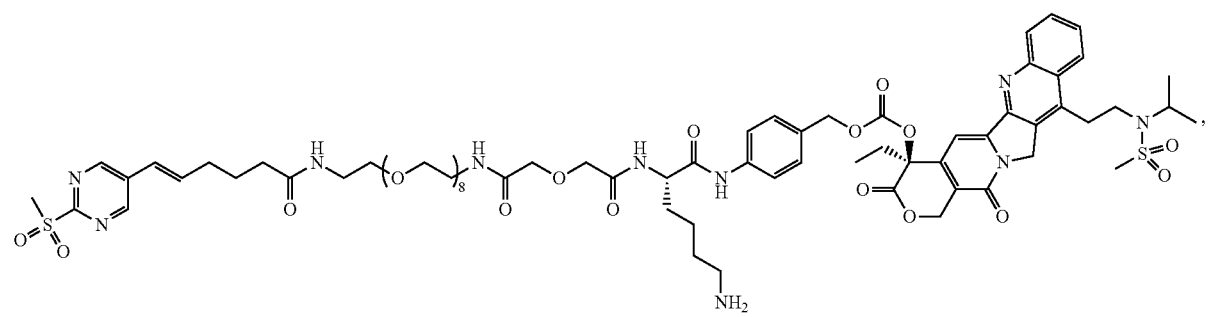
TL041

TL042
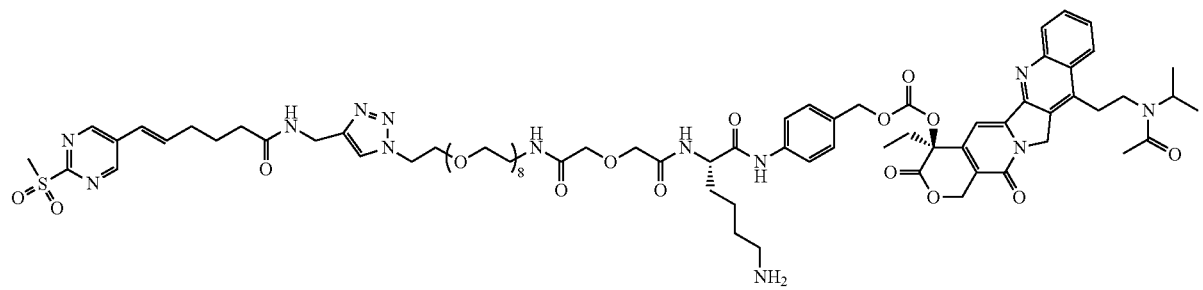
TL043
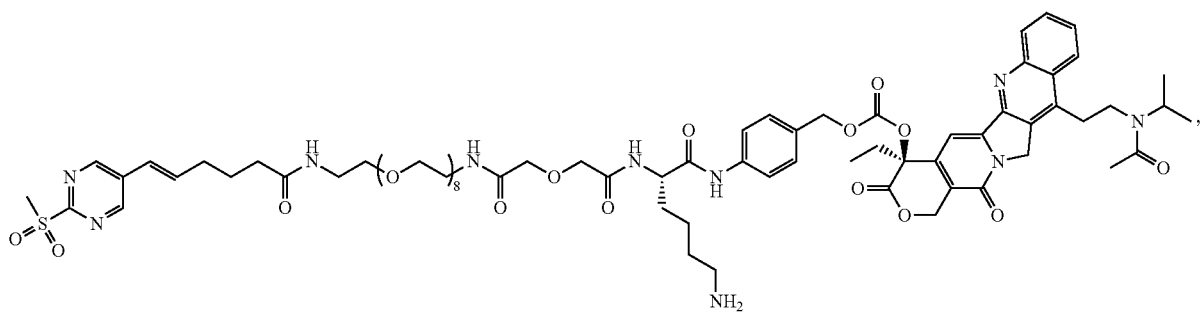
TL044
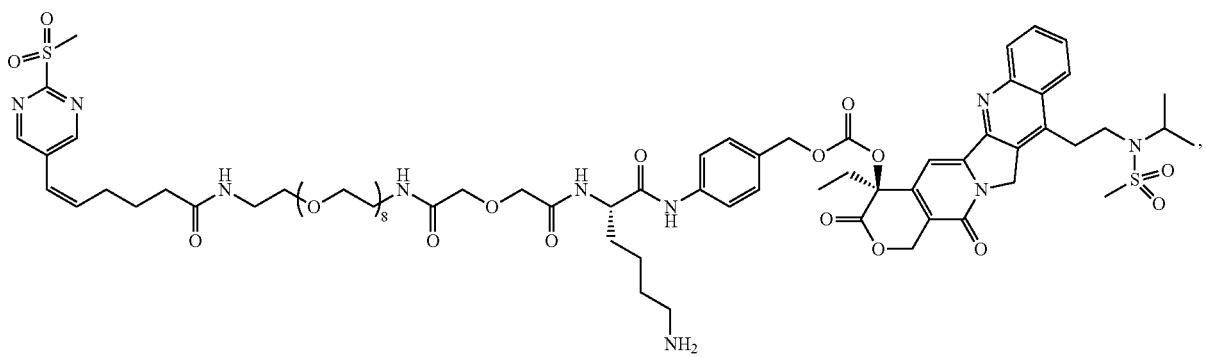
TL045
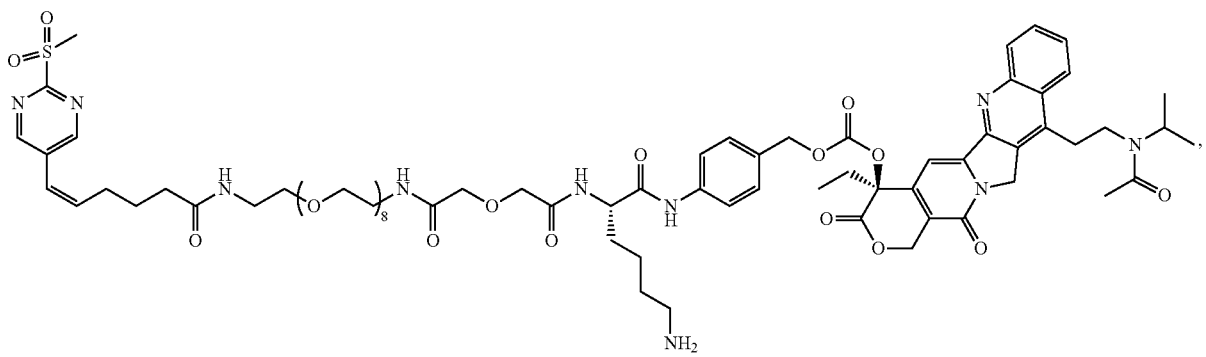

-continued
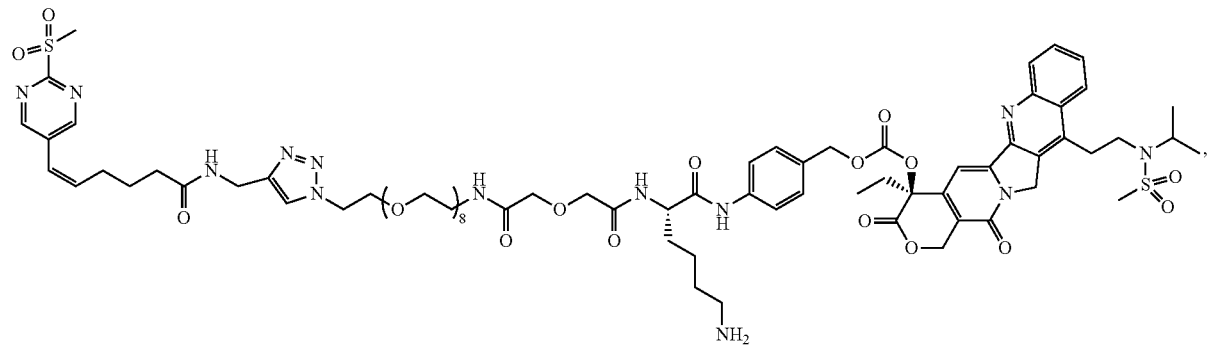
TL046
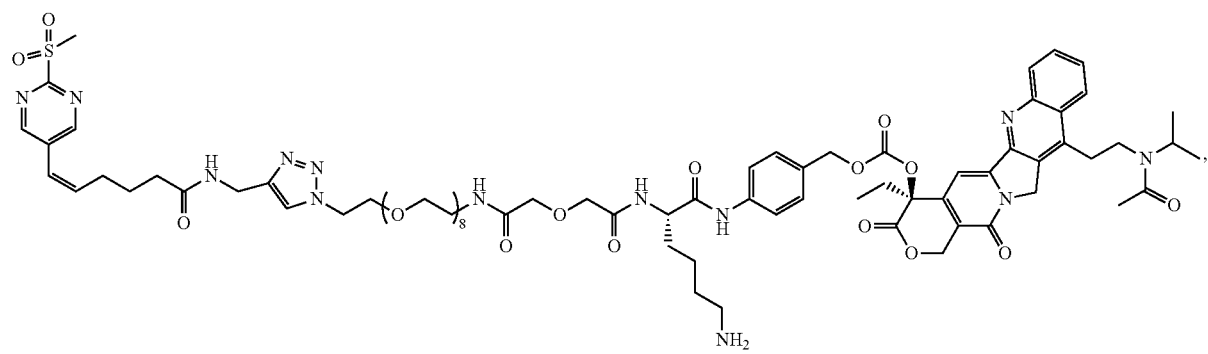
TL047
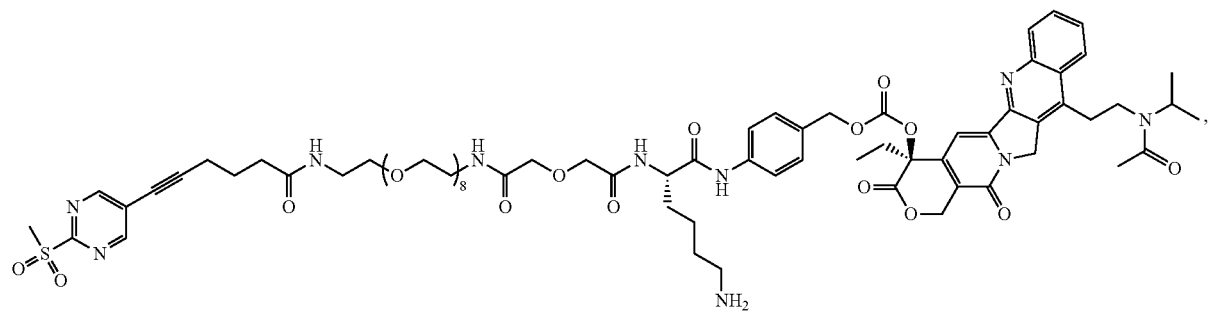
TL048
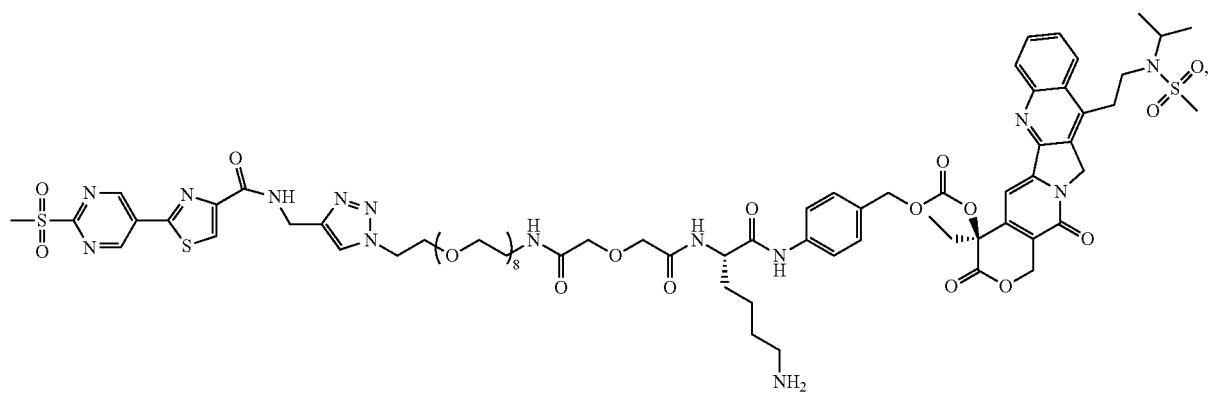
TL049

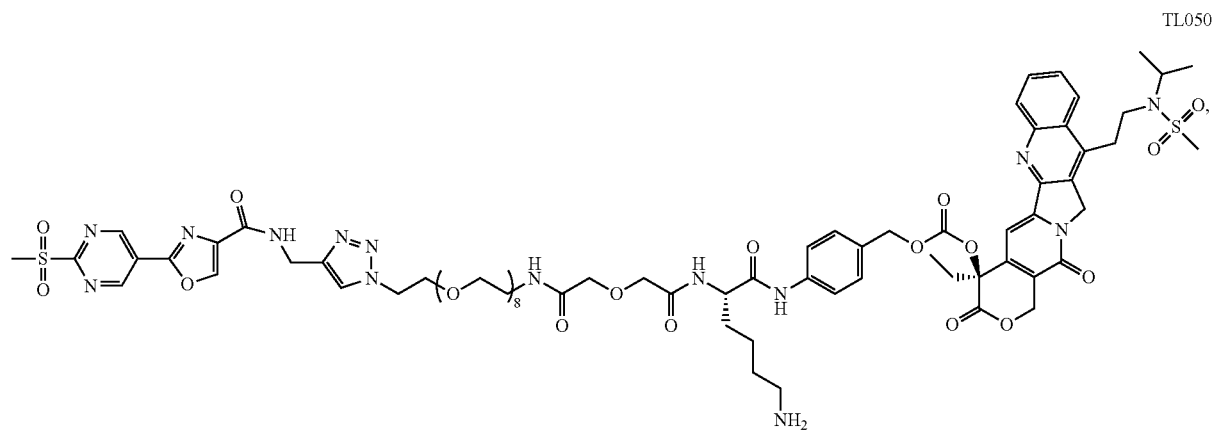
TL050
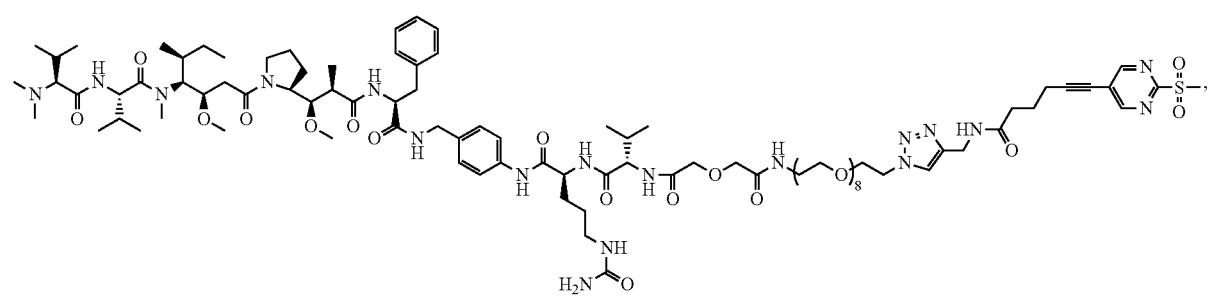
TL051
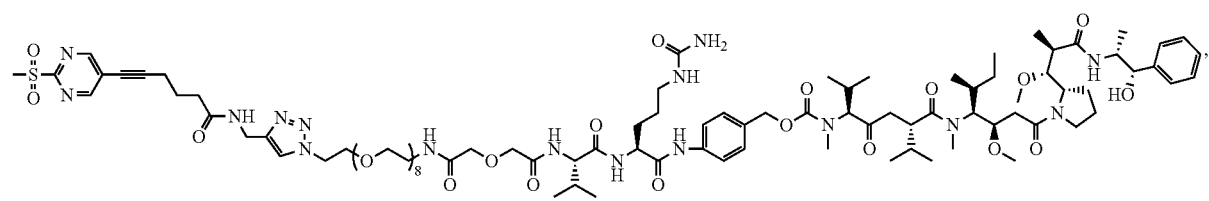
TL052
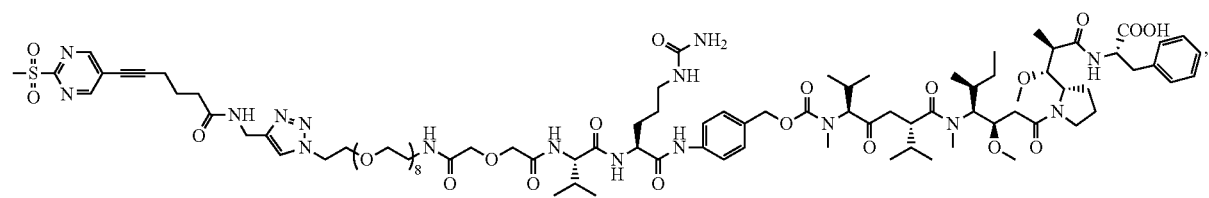
TL053
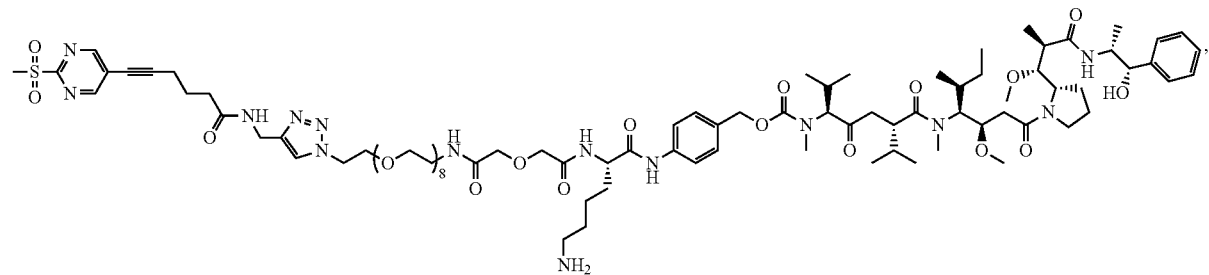
TL054

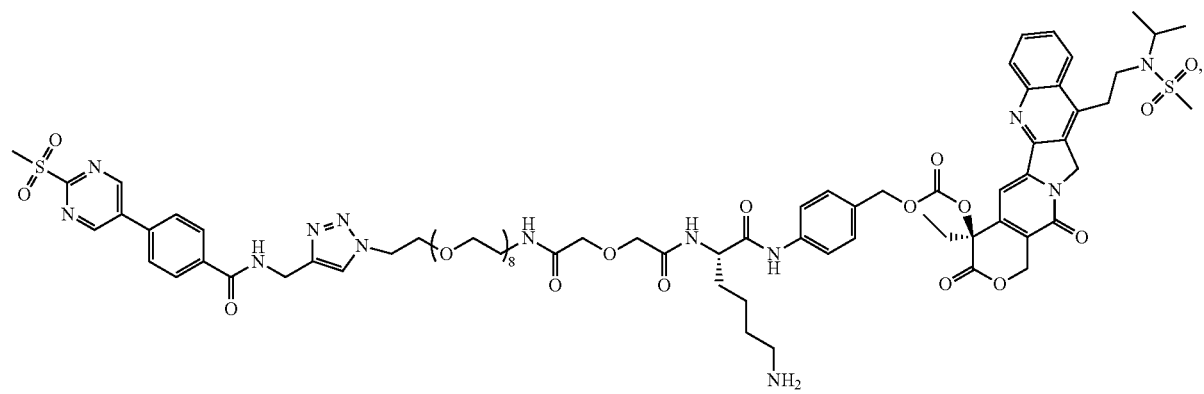
TL055
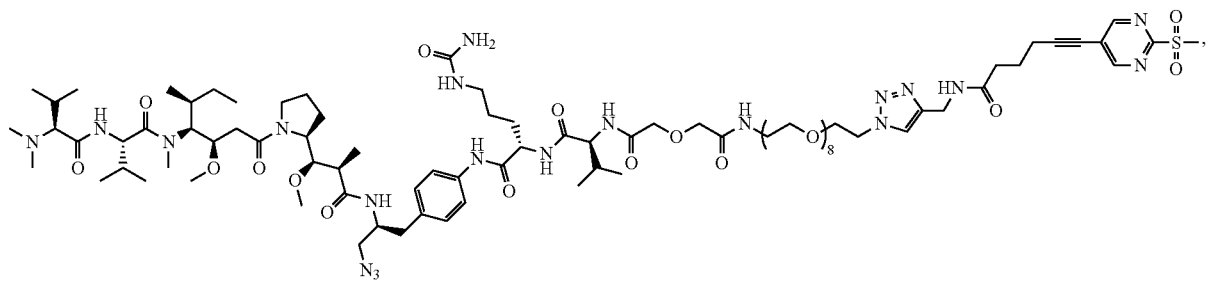
TL056
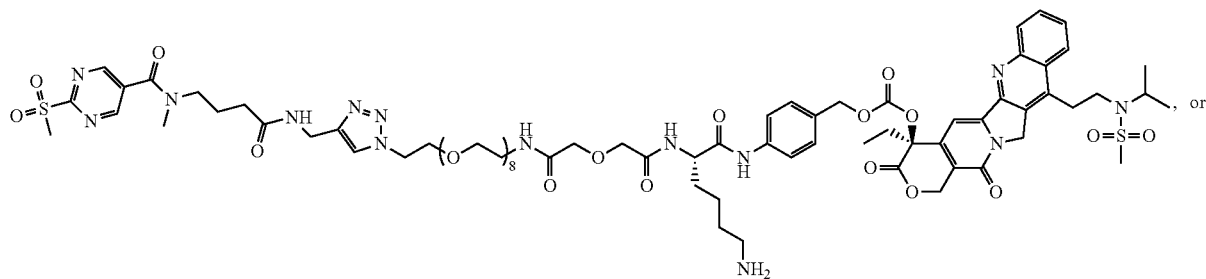
TL057
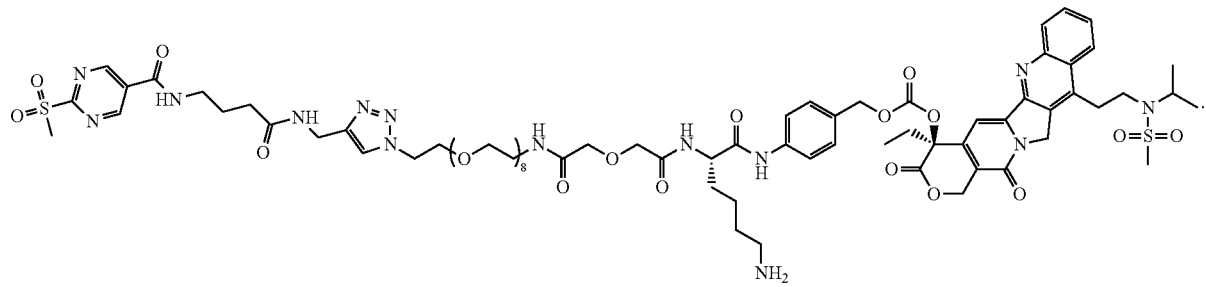
TL058

In some preferred embodiments, the compound is selected from
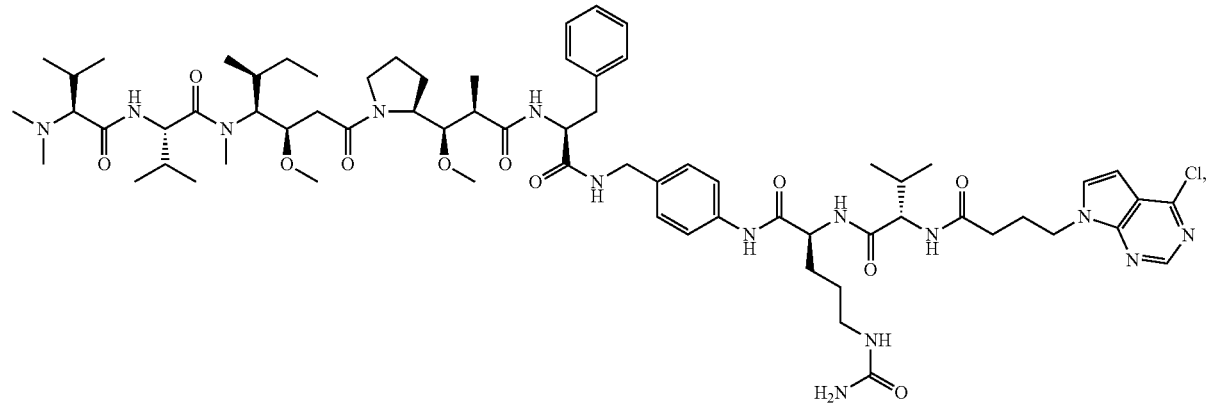
TL001
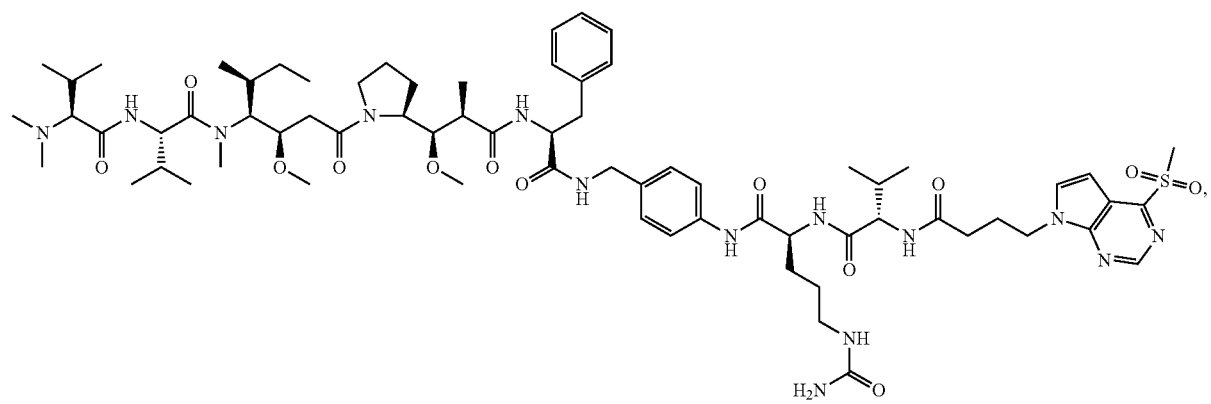
TL002
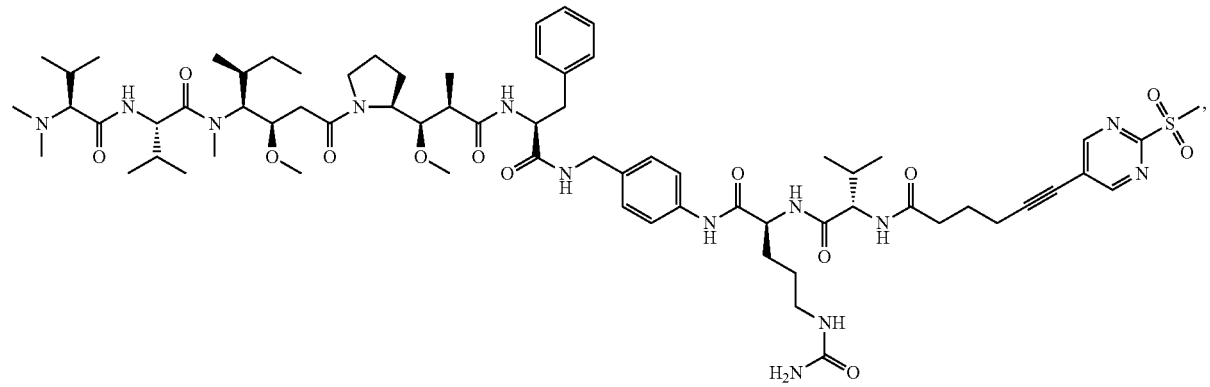
TL003

TL005
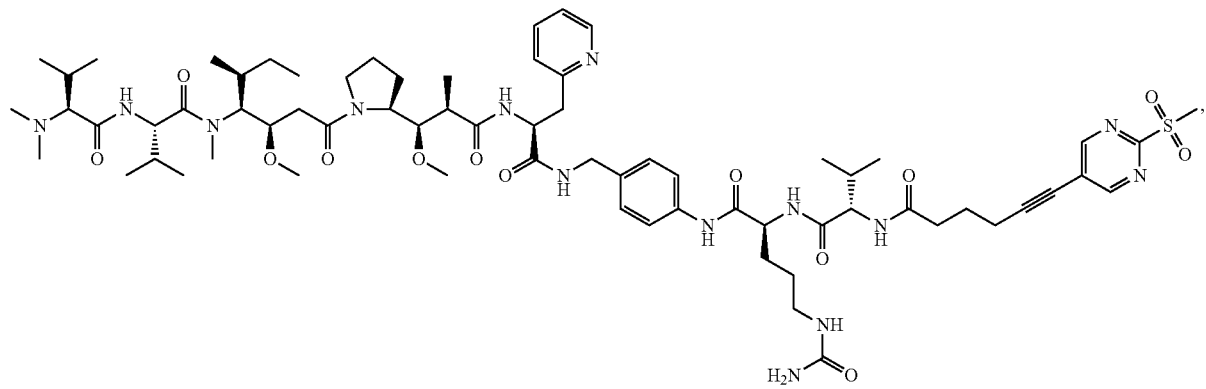
TL006
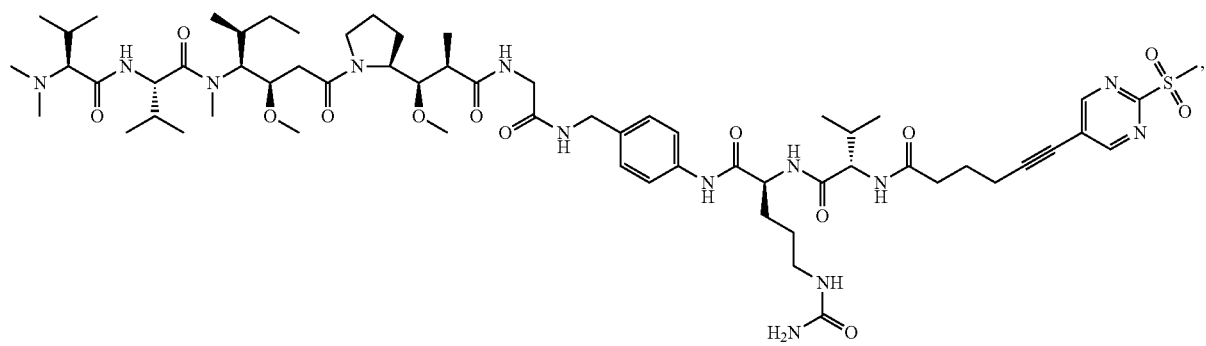
TL007
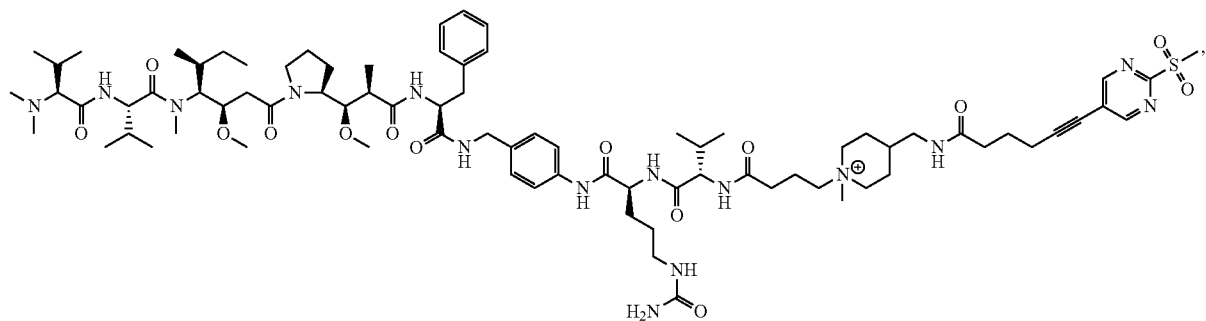
TL008
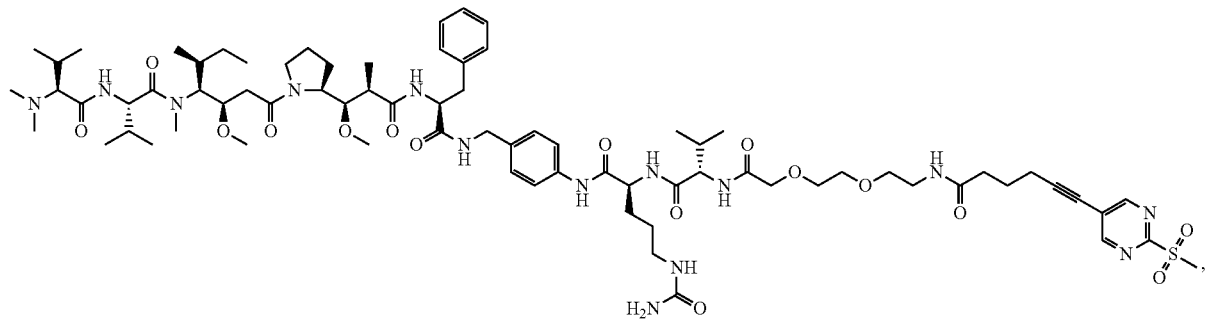

TL013
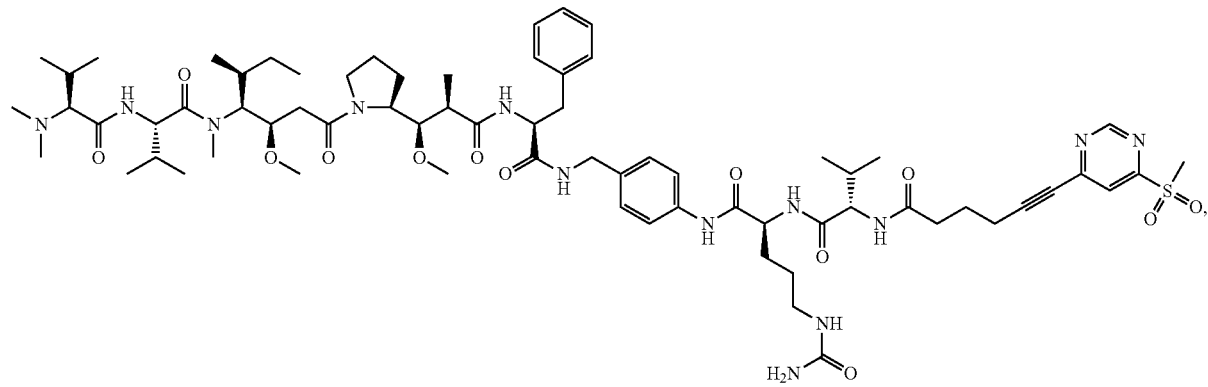
TL014
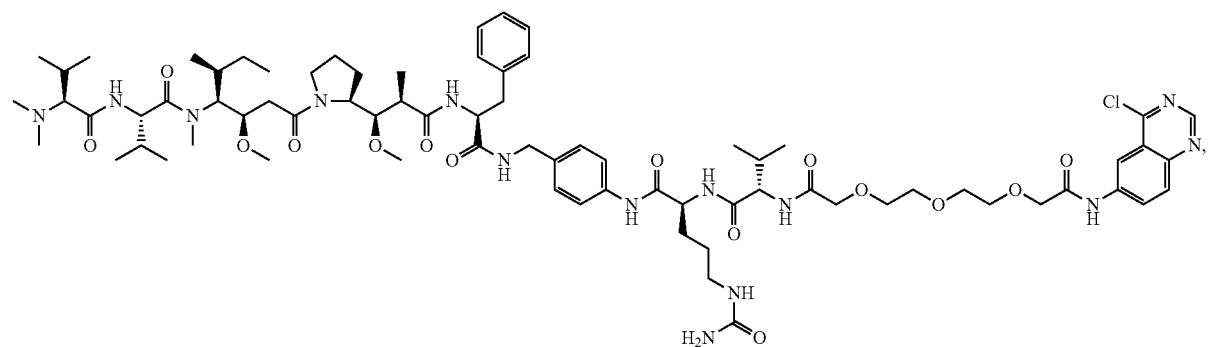
TL015
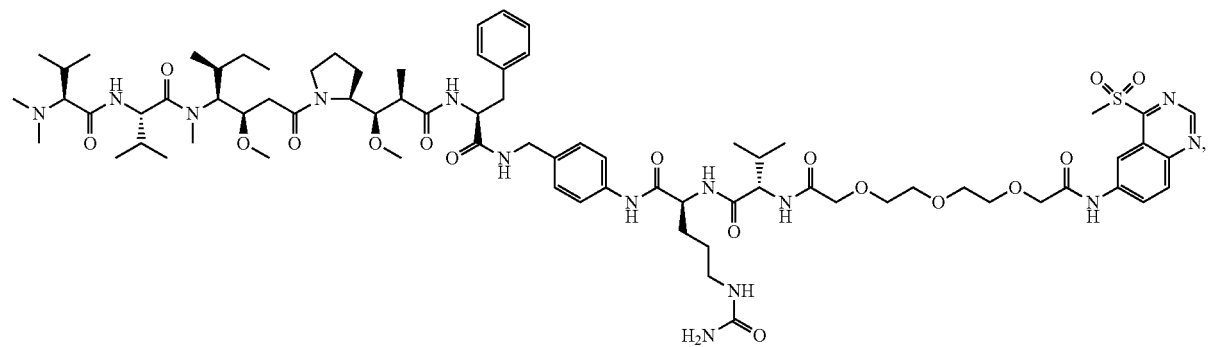
TL016
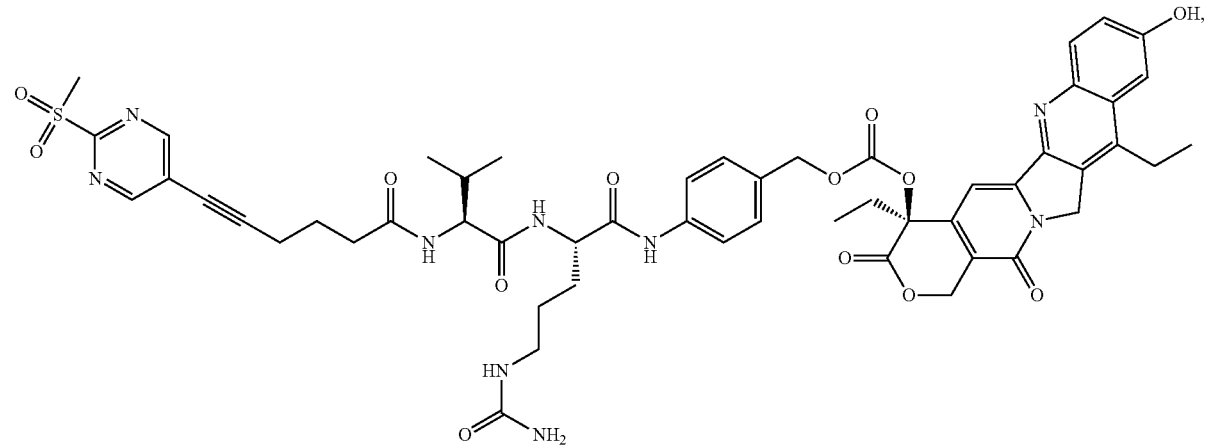

-continued
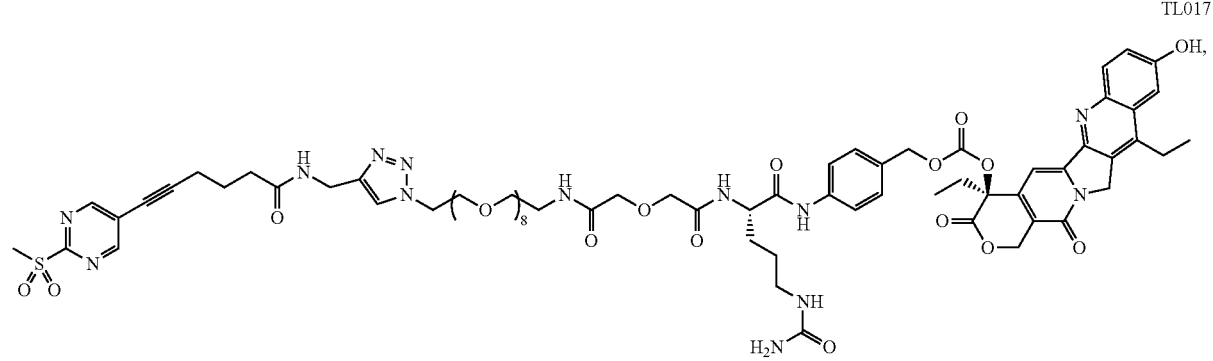
TL017
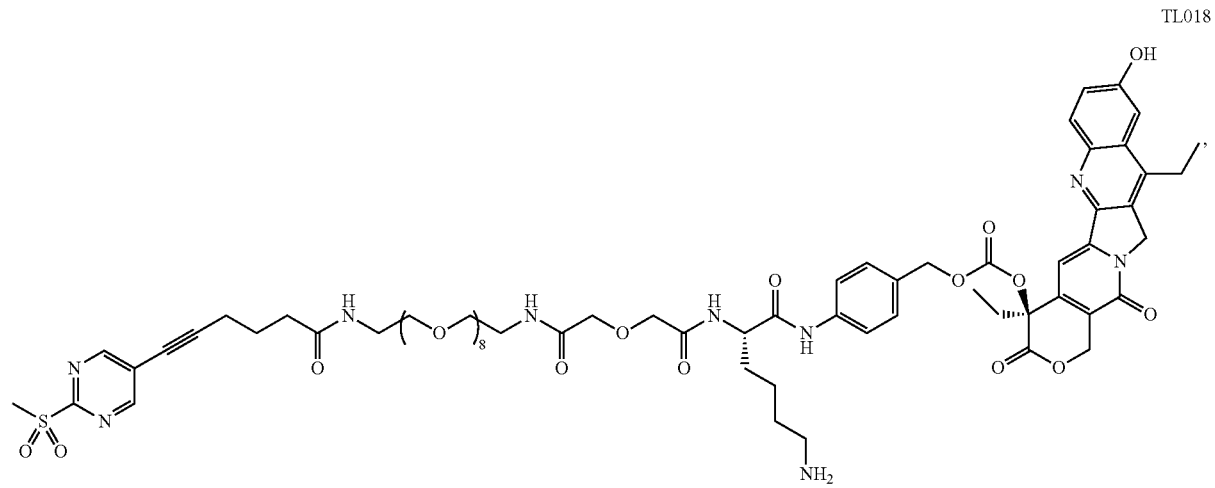
TL018
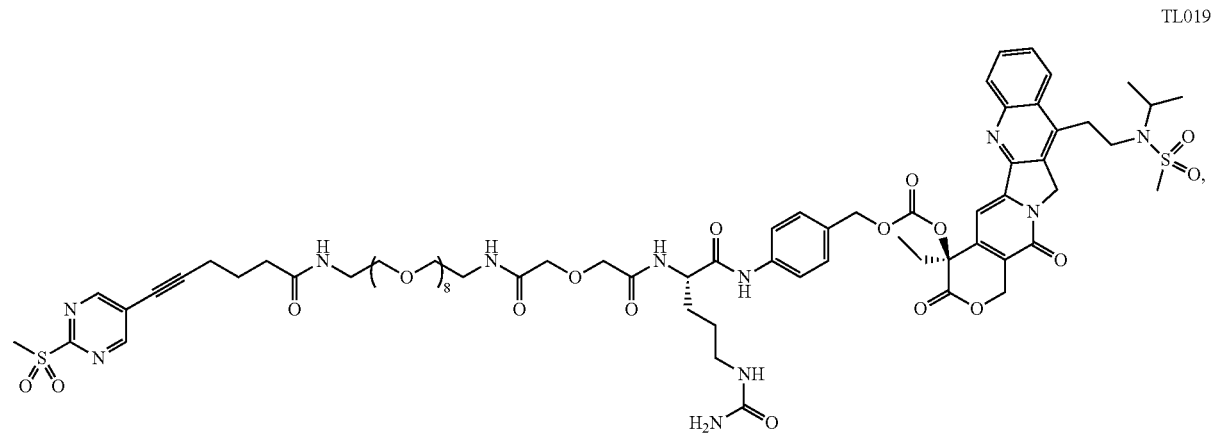
TL019
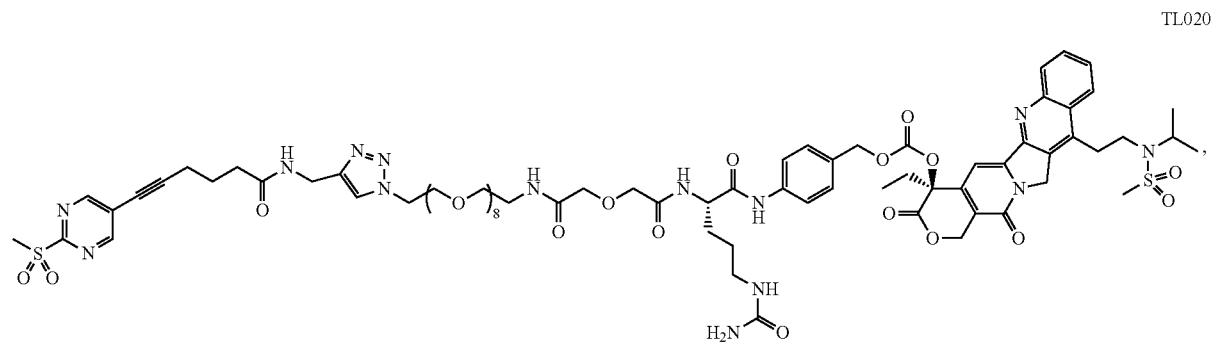
TL020

-continued
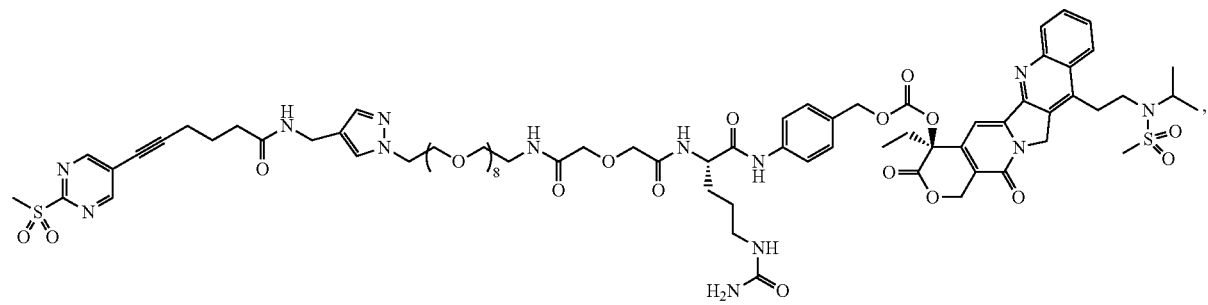
TL021
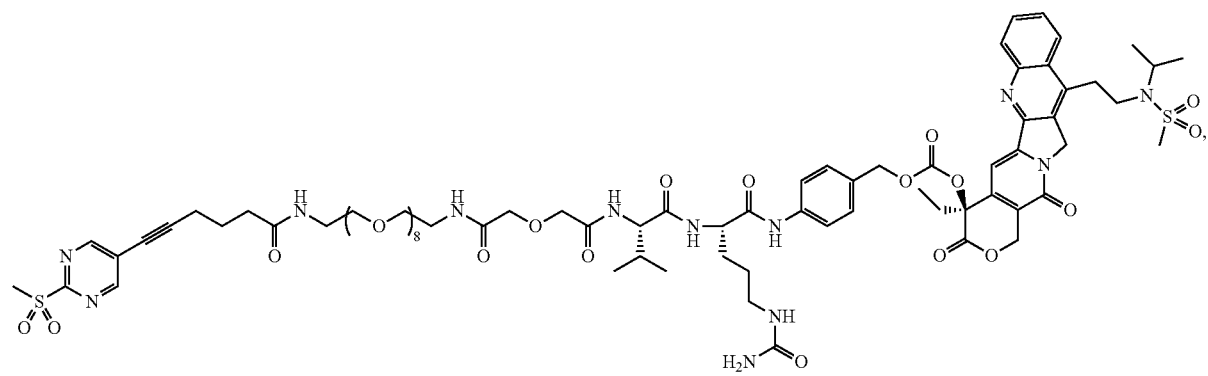
TL022
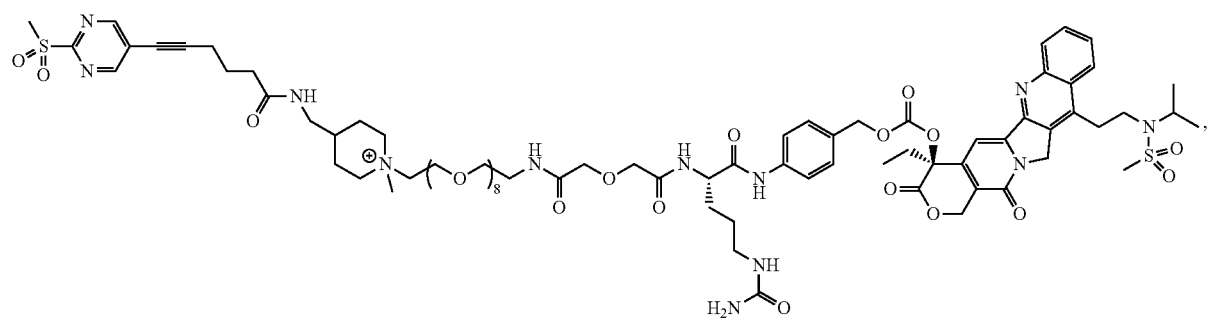
TL023
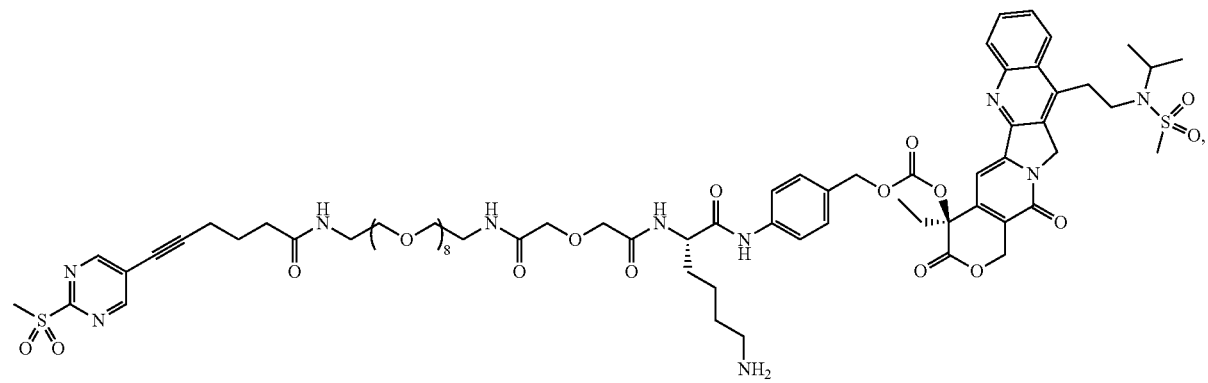
TL024

-continued
TL025
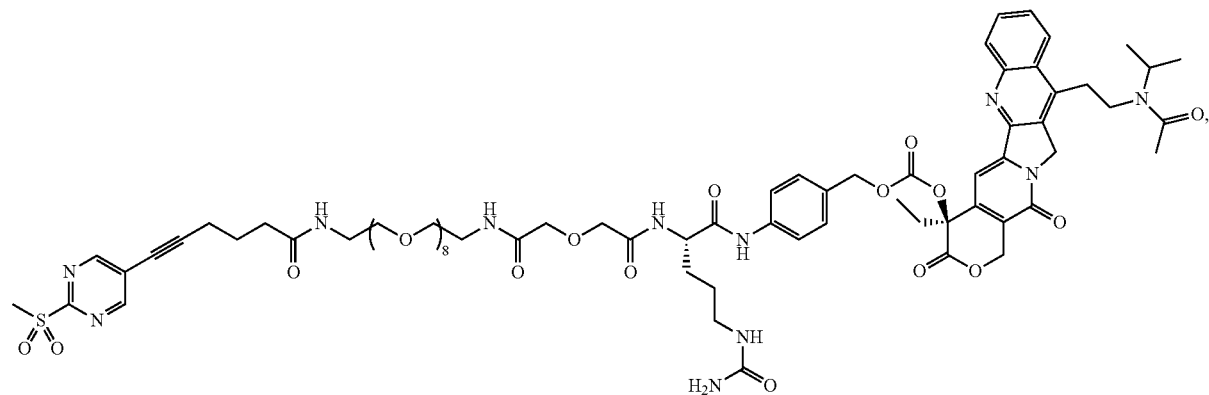
TL028
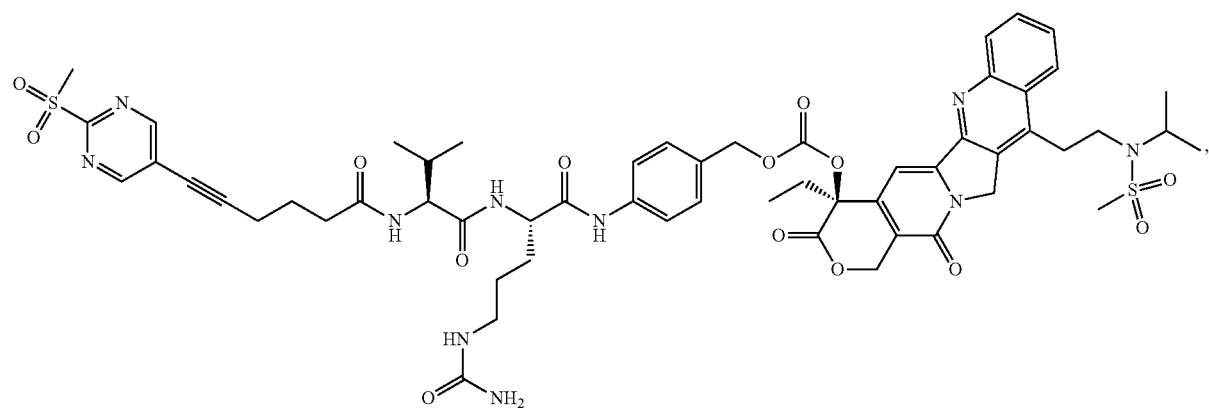
TL029
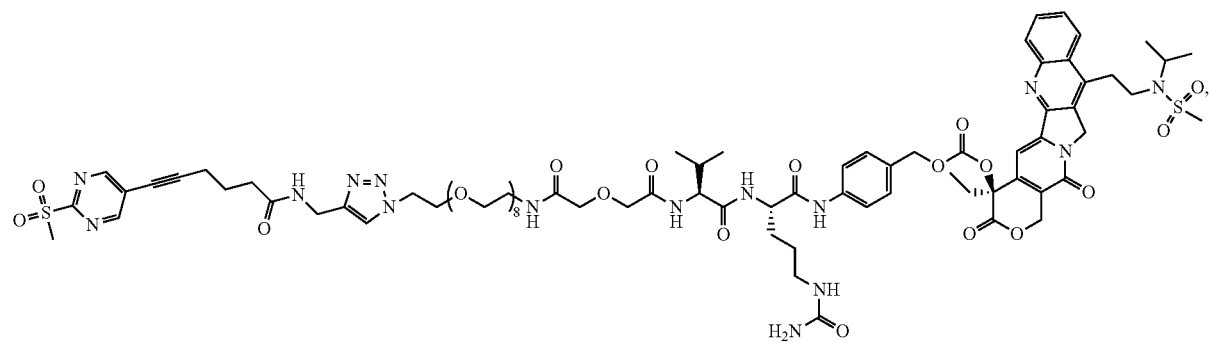
TL030
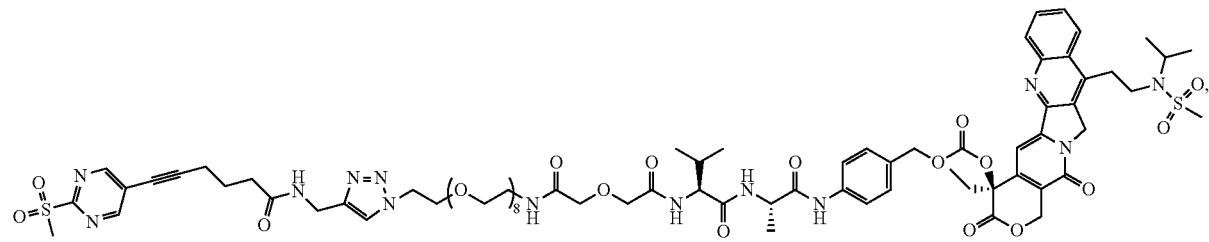

-continued
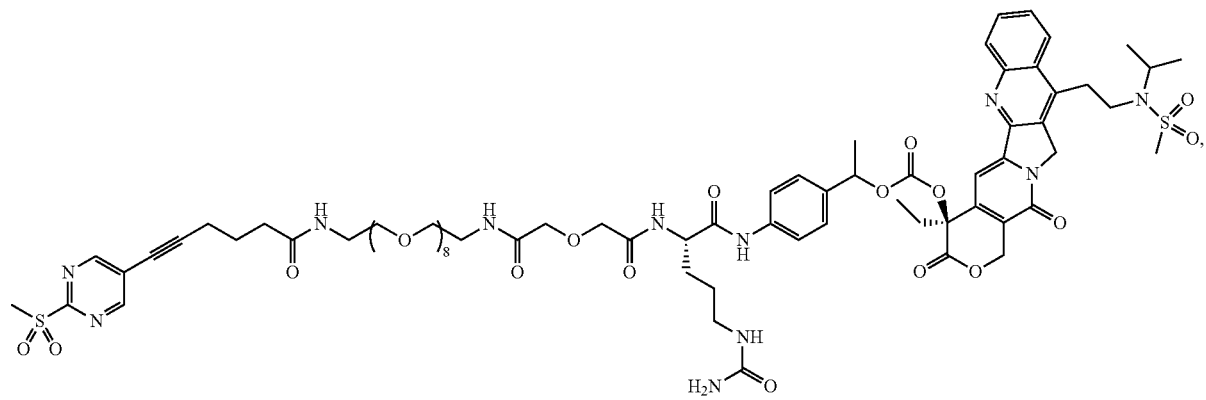
TL031
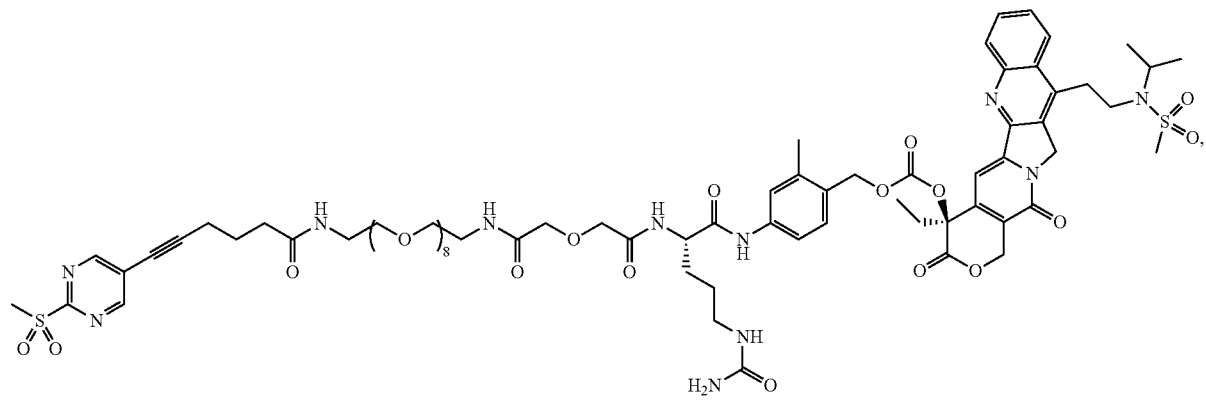
TL032
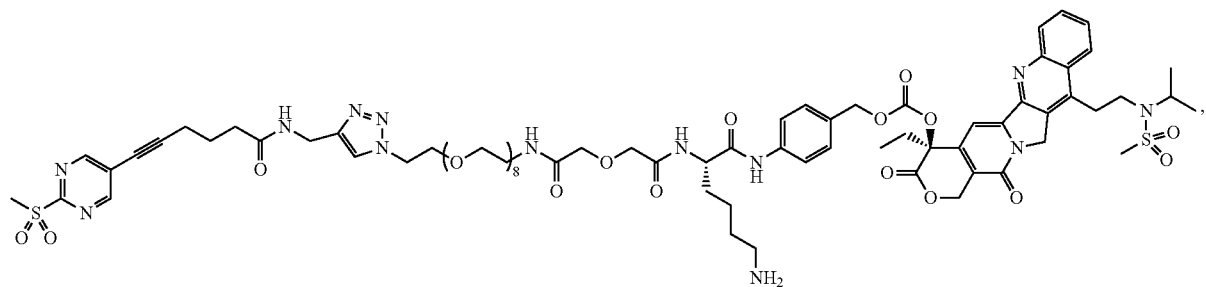
TL033
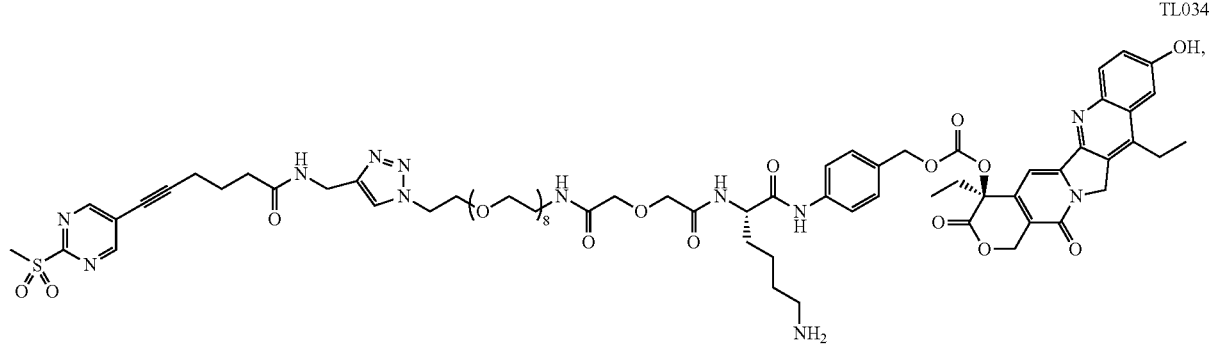
TL034

TL035
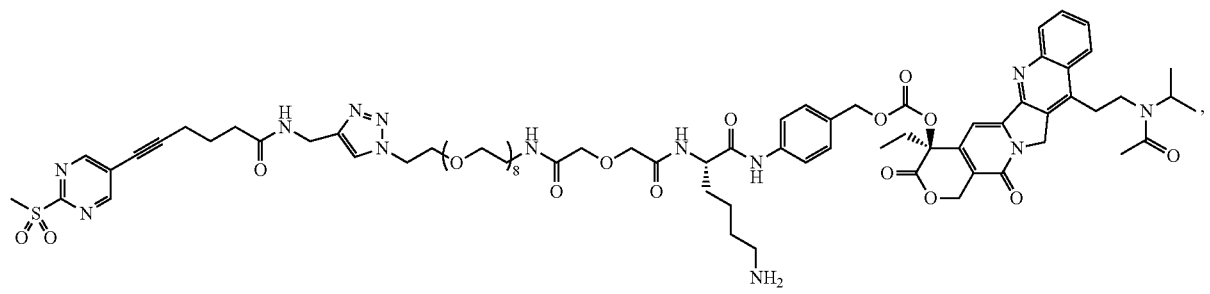
TL040
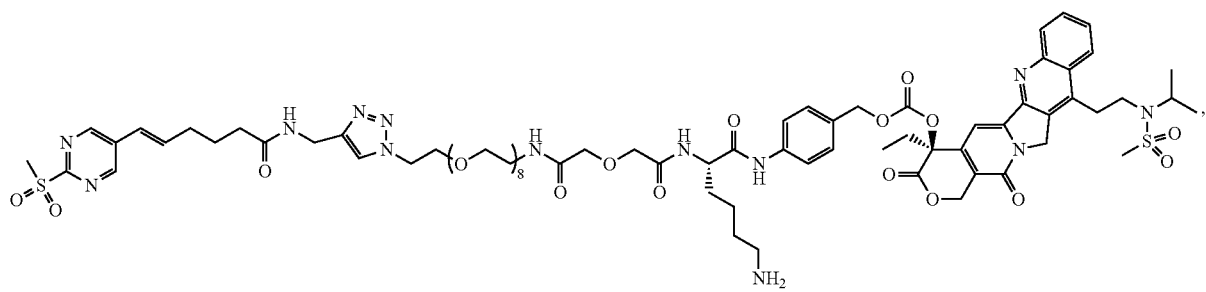
TL041
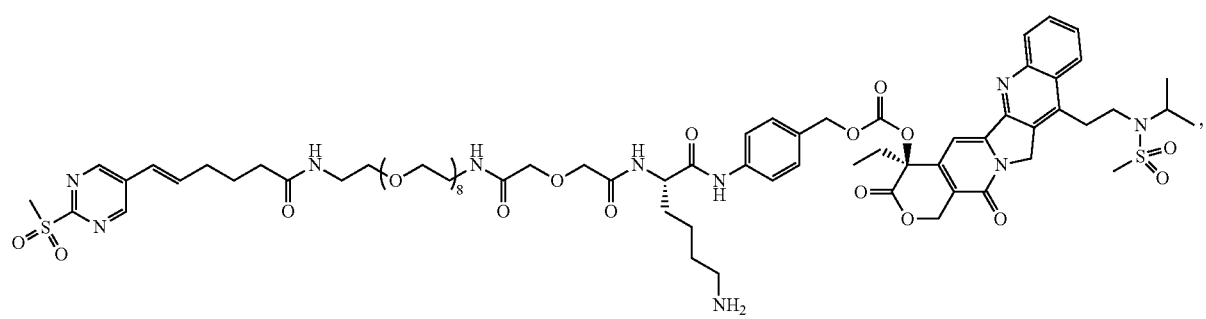
TL042
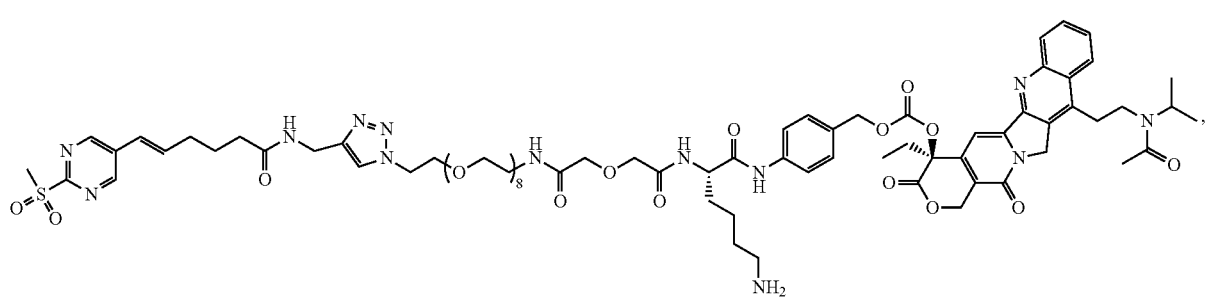
TL043
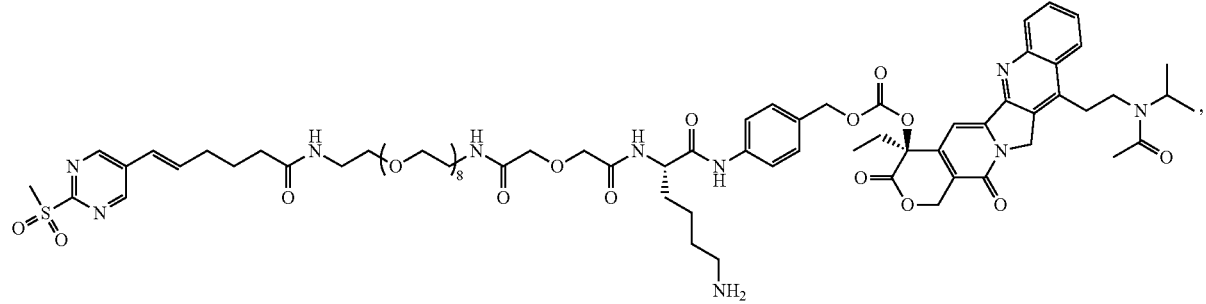

-continued
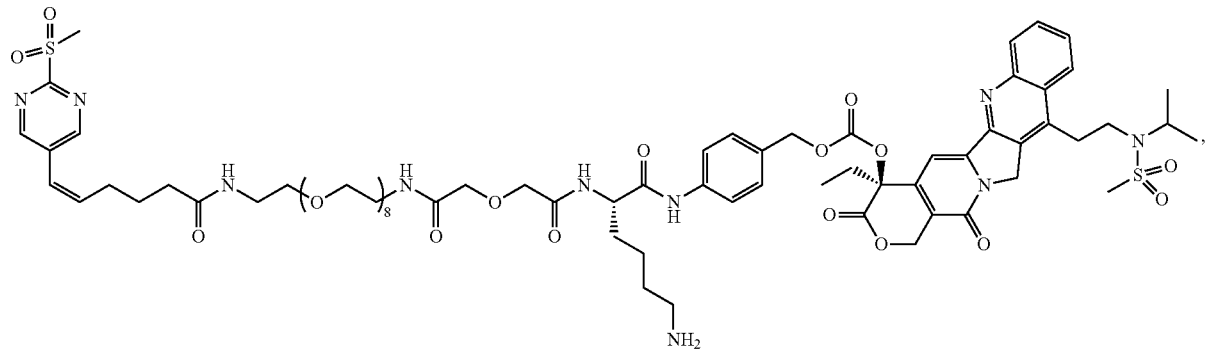
TL044
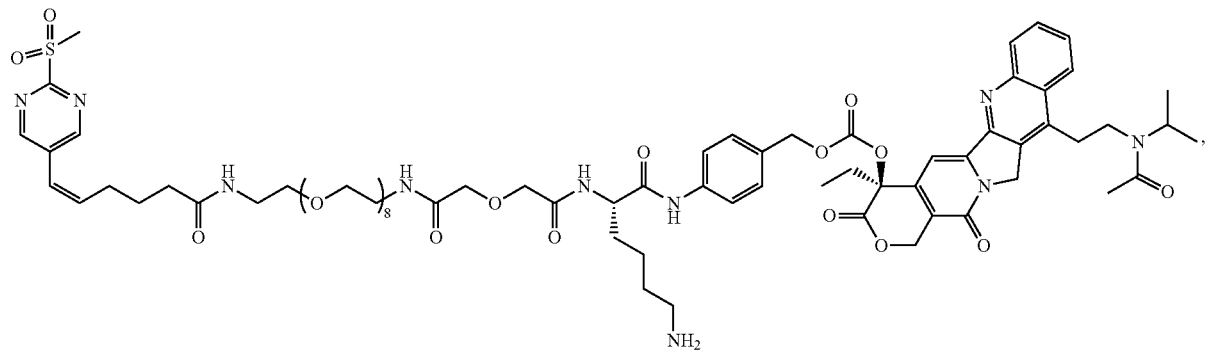
TL045
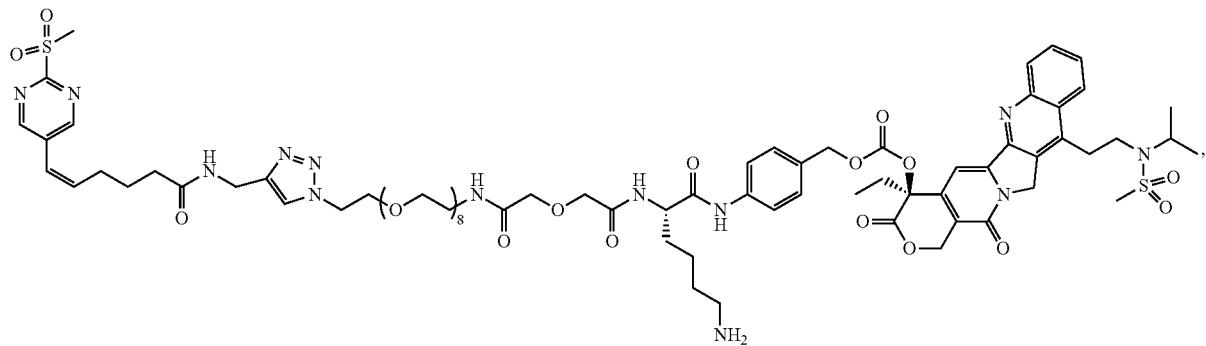
TL046
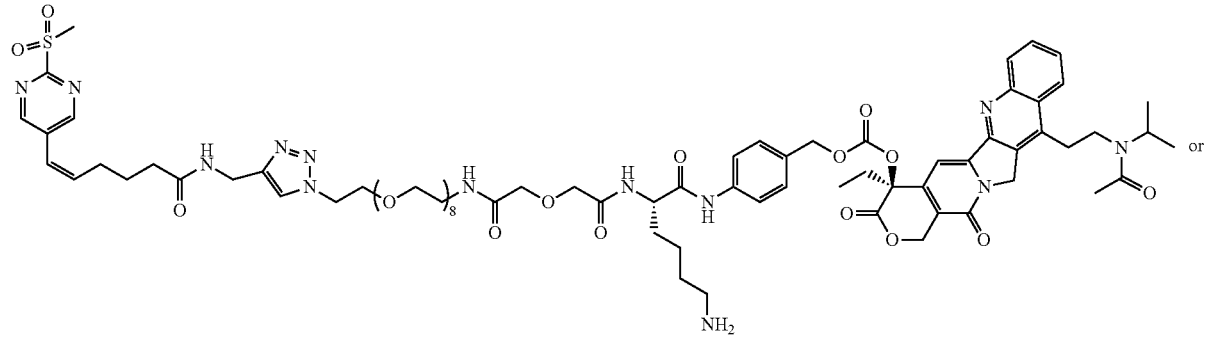
TL047
or

TL048

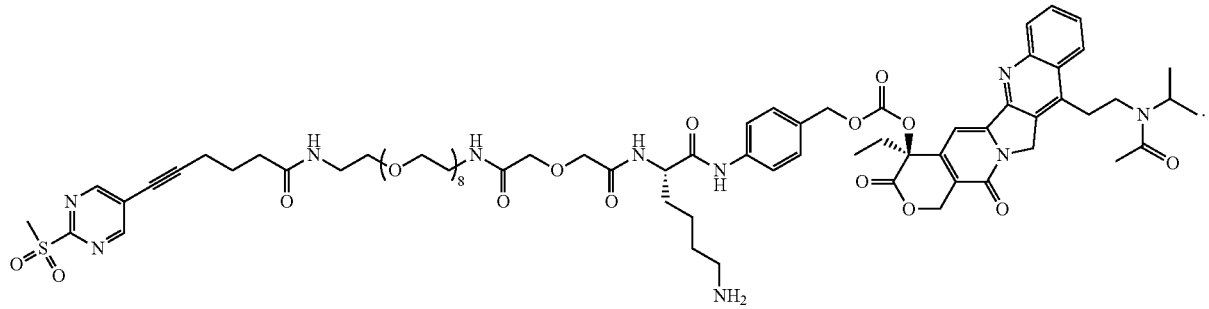

In a second aspect, the disclosure provides a conjugate, comprising a bioactive molecule, a linker and a targeting moiety. The targeting moiety is linked to the linker via an active group (e.g., a thiol group) to form a conjugate.

In some preferred embodiments, the structure of the conjugate is shown in formula (II):

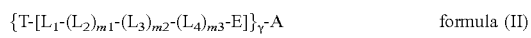

where, wherein, A is a targeting moiety (e.g., a small molecule ligand, a protein, a polypeptide or a non-protein reagent (e.g., saccharide, RNA or DNA)); γ is an integer or a decimal from 1 to 10; preferably, γ is an integer or a decimal from 5 to 8 (e.g., 5, 6, 7 or 8);

the rest groups are as described in the first aspect of the disclosure.

In some preferred embodiments, a target of A is selected from epidermal growth factor, Trop-2, CD37, HER2, CD70, EGFRvIII, Mesothelin, Folate receptor1, Mucin 1, CD138, CD20, CD19, CD30, SLTRK6, Nectin 4, Tissue factor, Mucin16, Endothelin receptor, SLC39A6, Guanylylcyclase C, PSMA, CCD79b, CD22, Sodium phosphate cotransporter 2B, GPNMB, Trophoblast glycoprotein, AGS-16, EGFR, CD33, CD66e, CD74, CD56, PD-L.sub.1, TACSTD2, DR5, E16, STEAP1, 0772P, MPF, Napi3b, Sema 5b, PSCA hlg, ETBR, MSG783, STEAP2, TrpM4, CRIPTO, CD21, CD79b, FcRH2, NCA, MDP, IL20Rα, Brevican, EphB2R, A5LG659, PSCA, GEDA, BAFF-R, CD79a, CXCR5, HLA-DOB, P2X5, CD72, LY64, FcRH1, IRTA2, TENB2, integrin α5β6, α4β7, FGF2, FGFR2, Her3, CA6, DLL3, DLL4, P-cadherin, EpCAM, pCAD, CD223, LYPD3, LY6E, EFNA4, ROR1, SLITRK6, 5T4, ENPP3, Claudin18.2, BMPR1 B, c Met, ApoE, CD1 Ic, CD40, CD45 (PTPRC), CD49D (ITGA4), CD80, CSF1R, CTSD, GZMB, Ly86, MS4A7, PIK3AP1, PIK3CD, CCR5, IFNG, IL10RA1, IL-6, ACTA2, COL7A1, LOX, LRRC15, MCPT8, MMP10, NOG, SERPINET, STAT1, TGFBR1, CTSS, PGF, VEGFA, C1 QA, C1QB, EGLN, ANGPTL4, EGLN3, BNIP3, AIF1, CCL5, CXCL10, CXCL11, IF16, PLOD2, KISS1R, STC2, DDIT4, PFKFB3, PGK1, PDK1, AKR1C1, AKR1C2, CADM1, CDH11, COL6A3, CTGF, HMOX1, KRT33A, LUM, WNT5A, IGFBP3, MMP14, CDCP1, PDGFRA, TCF4, TGF, TGFB1, TGFB2, CD1 Ib, ADGRE1, EMR2, TNFRSF21, UPK1 B, TNFSF9, MMP16, MFI2, IGF-1R, RNF43, NaPi2b, or BCMA.

In some preferred embodiments, A is a small molecule ligand, such as a folic acid derivative, a glutamate urea derivative, a somatostatin derivative, an arylsulfonamide derivative (e.g., a carbonic anhydrase IX inhibitor), a poly- ene connecting two aliphatic indoles, a cyanine dye or IR-783 or a derivative thereof.

In some preferred embodiments, A is selected from

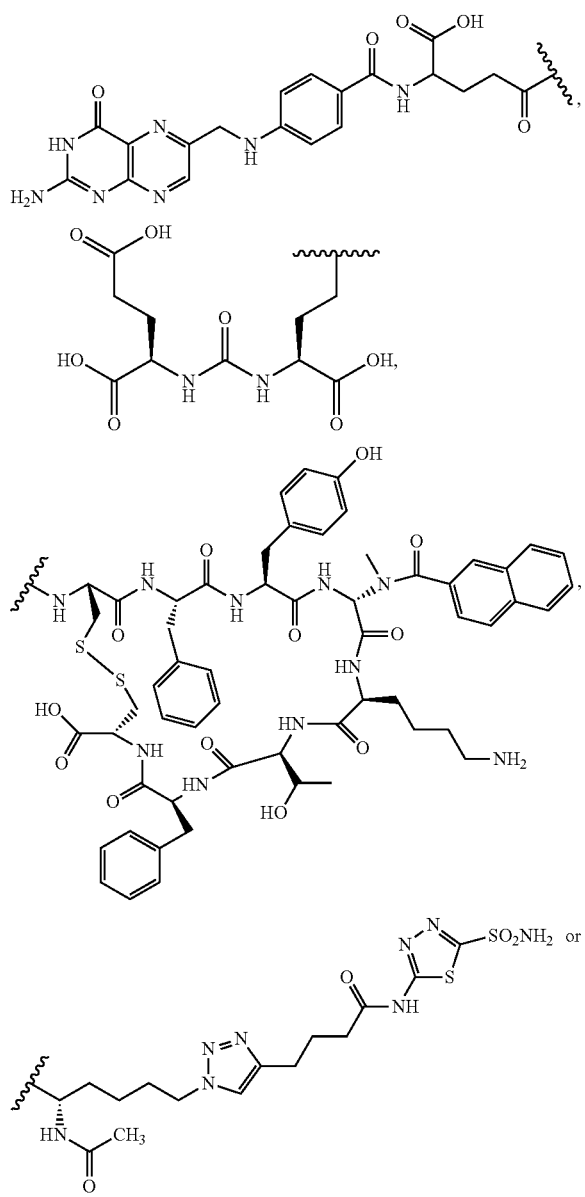

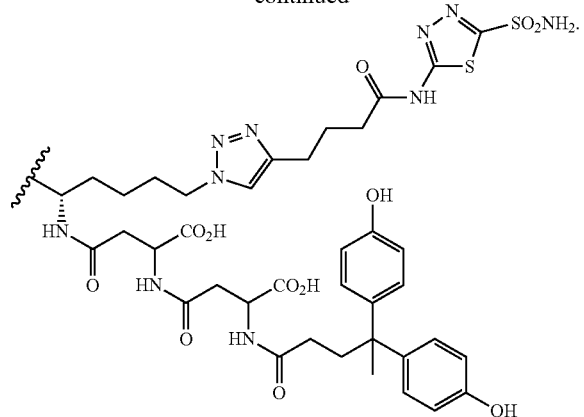

In some preferred embodiments, A is an antibody such as a monoclonal antibody or an antigen binding fragment thereof, wherein the monoclonal antibody or the antigen binding fragment thereof comprises Fab, Fab', F(ab')$_2$, Fd, Fv, dAb, a complementary determinant fragment, a single chain antibody (e.g., scFv), a non-human antibody, a humanized antibody, a chimeric antibody, a completely humanized antibody, a probody, a bispecific antibody or a multispecific antibody.

In some preferred embodiments, A is an anti-Her 2 monoclonal antibody, such as Trastuzumab, Pertuzumab; or an anti-Trop-2 monoclonal antibody, such as Sacituzumab.

In some preferred embodiments, A is an anti-Trop-2 monoclonal antibody, such as antibody M1, M2 or M3.

| Antibody | M1 | M2 | M3 |
|---|---|---|---|
| Heavy chain CDR1 | GYTFTNY (SEQ ID No.: 1) | GYTFTNY (SEQ ID No.: 1) | GYTFTNY (SEQ ID No.: 1) |
| Heavy chain CDR2 | NTDSGE (SEQ ID No.: 2) | NTDSGE (SEQ ID No.: 2) | NTDSGE (SEQ ID No.: 2) |
| Heavy chain CDR3 | GGFGSSYWYFDV (SEQ ID No.: 3) | GGFGSSYWYFDV (SEQ ID No.: 3) | GGFGSSYWYFDV (SEQ ID No.: 3) |
| Light chain CDR1 | KASQDVSSAVA (SEQ ID No.: 4) | KASQDVSSAVA (SEQ ID No.: 4) | KASQDVSIAVA (SEQ ID No.: 8) |
| Light chain CDR2 | SASYRYT (SEQ ID No.: 5) | SASYRYT (SEQ ID No.: 5) | SASYRYT (SEQ ID No.: 5) |
| Light chain CDR3 | QQHYSTPLT (SEQ ID No.: 6) | QQHYITPLT (SEQ ID No.: 7) | QQHYSTPLT (SEQ ID No.: 6) |

The assignment of amino acids in each region or domain can follow Chothia & Lesk (1987) J. Mol. Biol. 196:901-917; definition of Chothia et al. (1989) in Nature 342: 878-883.

1. Heavy chain and light chain sequences of the hydrophobically modified antibody M1 Amino acid sequence of heavy chain variable region of M1: (121 aa)

(SEQ ID No.: 11)
QVQLQQSGSELKKPGASVKVSCKASGYTFTNYGMNWVKQAPGQGLKWMGW

INTDSGEPTYTDDFKGRFAFSLDTSVSTAYLQISSLKADDTAVYFCARGG

FGSSYWYFDVWGQGSLVTVSS

Amino acid sequence of light chain variable region of M1: (107 aa)

(SEQ ID No.: 12)
DIQLTQSPSSLSASVGDRVSITCKASQDVSSAVAWYQQKPGKAPKLLIYS

ASYRYTGVPDRFSGSGSGTDFTLTISSLQPEDFAVYYCQQHYSTPLTFGA

GTKVEIK

2. Heavy chain and light chain sequences of the hydrophobically modified antibody M2 Amino acid sequence of heavy chain variable region of M2: (121 aa)

(SEQ ID No.: 13)
QVQLQQSGSELKKPGASVKVSCKASGYTFTNYGMNWVKQAPGQGLKWMGW

INTDSGEPTYTDDFKGRFAFSLDTSVSTAYLQISSLKADDTAVYFCARGG

FGSSYWYFDVWGQGSLVTVSS

Amino acid sequence of light chain variable region of M2: (107 aa)

(SEQ ID No.: 14)
DIQLTQSPSSLSASVGDRVSITCKASQDVSSAVAWYQQKPGKAPKLLIYS

ASYRYTGVPDRFSGS GS GTDFTLTIS SLQPEDFAVYYCQQHYITPLT

FGAGTKVEIK

3. Heavy chain and light chain sequences of the hydrophobically modified antibody M3 Amino acid sequence of heavy chain variable region of M3: (121 aa)

(SEQ ID No.: 15)
QVQLQQSGSELKKPGASVKVSCKASGYTFTNYGMNWVKQAPGQGLKWMGW

INTDSGEPTYTDDFKGRFAFSLDTSVSTAYLQISSLKADDTAVYFCARGG

FGSSYWYFDVWGQGSLVTVSS

Amino acid sequence of light chain variable region of M3: (107 aa)

(SEQ ID No.: 16)
DIQLTQSPSSLSASVGDRVSITCKASQDVSIAVAWYQQKPGKAPKLLIYS

ASYRYTGVPDRFSGSGSGTDFTLTISSLQPEDFAVYYCQQHYSTPLTFGA

GTKVEIK

Sequence of light chain constant regions of M1, M2, M3: (107 aa)

(SEQ ID No.: 9)
RTVAAPSVFIFPPSDEQLKSGTASVVCLLNNFYPREAKVQWKVDNALQSG

NSQESVTEQDSKDSTYSLSSTLTLSKADYEKHKVYACEVTHQGLSSPVTK

SFNRGEC

Sequence of heavy chain constant regions of M1, M2, M3: (330 aa)

(SEQ ID No.: 10)
ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKRVEP

KSCDKTHTCPPCPAPELLGGPSVFLFPPKPKDTLMISRTPEVTCVVVDVS

HEDPEVKFNWYVDGVEVHNAKTKPREEQYNSTYRVVSVLTVLHQDWLNGK

EYKCKVSNKALPAPIEKTISKAKGQPREPQVYTLPPSREEMTKNQVSLTC

LVKGFYPSDIAVEWESNGQPENNYKTTPPVLDSDGSFFLYSKLTVDKSRW

QQGNVFSCSVMHEALHNHYTQKSLSLSPGK

Terminal Lys of heavy chains is easily deleted, but such deletion does not affect bioactivity. See Dick, L. W. et al., Biotechnol. Bioeng., 100: 1132-1143. The above monoclonal antibodies M1, M2, M3 and sequences or fragments thereof with deleted Lys at terminal of heavy chains all belong to the M1, M2, M3 monoclonal antibodies of this invention.

In some preferred embodiments, A is selected from a RGD peptide that recognizes cell surface integrin receptor; a growth factor that recognizes cell surface growth factor receptor, such as EGF, PDGF or VEGF; or a peptide capable of recognizing functional cell surface plasminogen activator, bombesin, bradykinin, somatostatin or prostate-specific membrane antigen receptor.

In some preferred embodiments, A is selected from CD40 ligand, CD30 ligand, OX40 ligand, PD-1 ligand, ErbB ligand, Her2 ligand, TACSTD2 ligand, or DR5 ligand.

In some preferred embodiments, the conjugate is selected from:

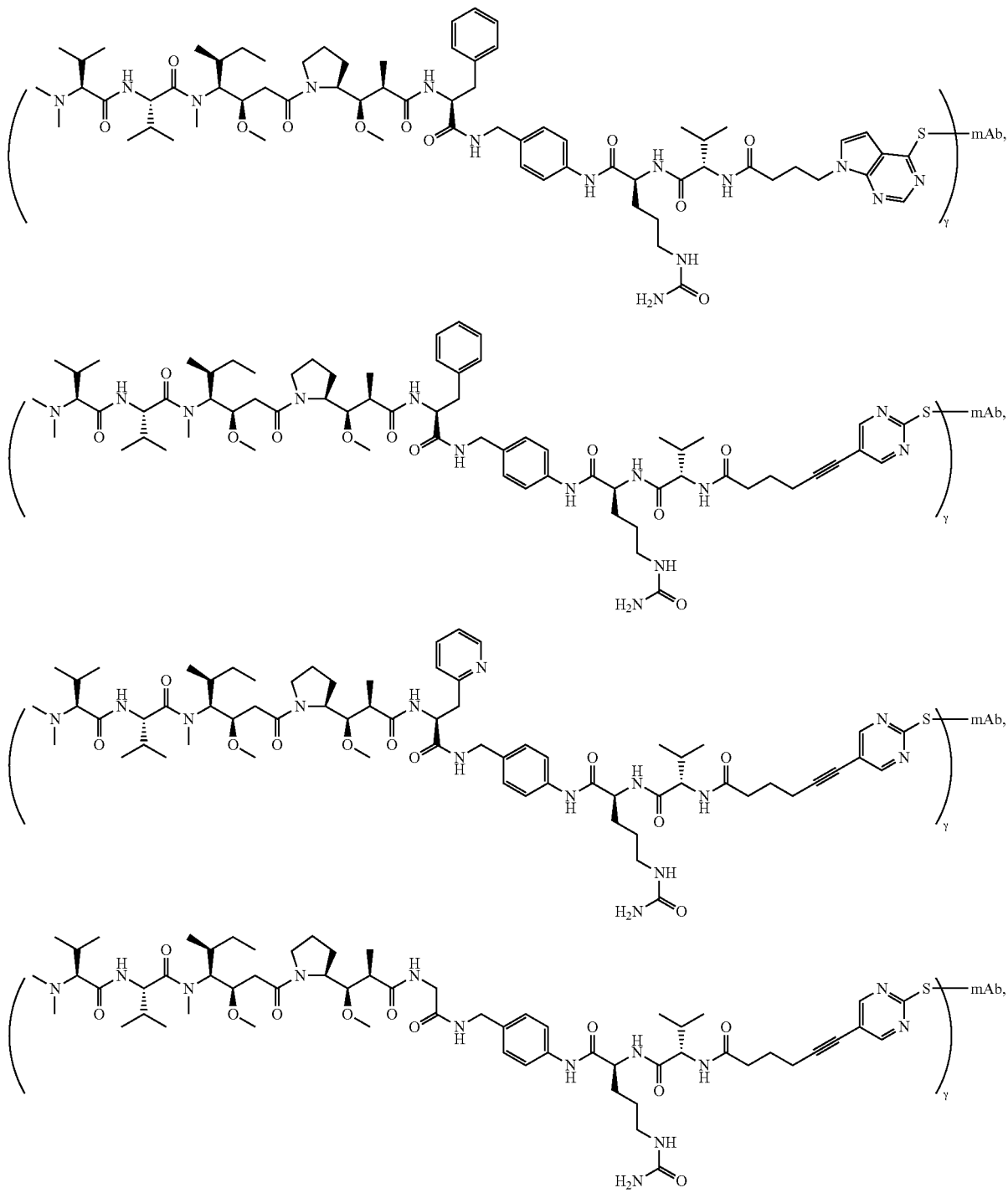

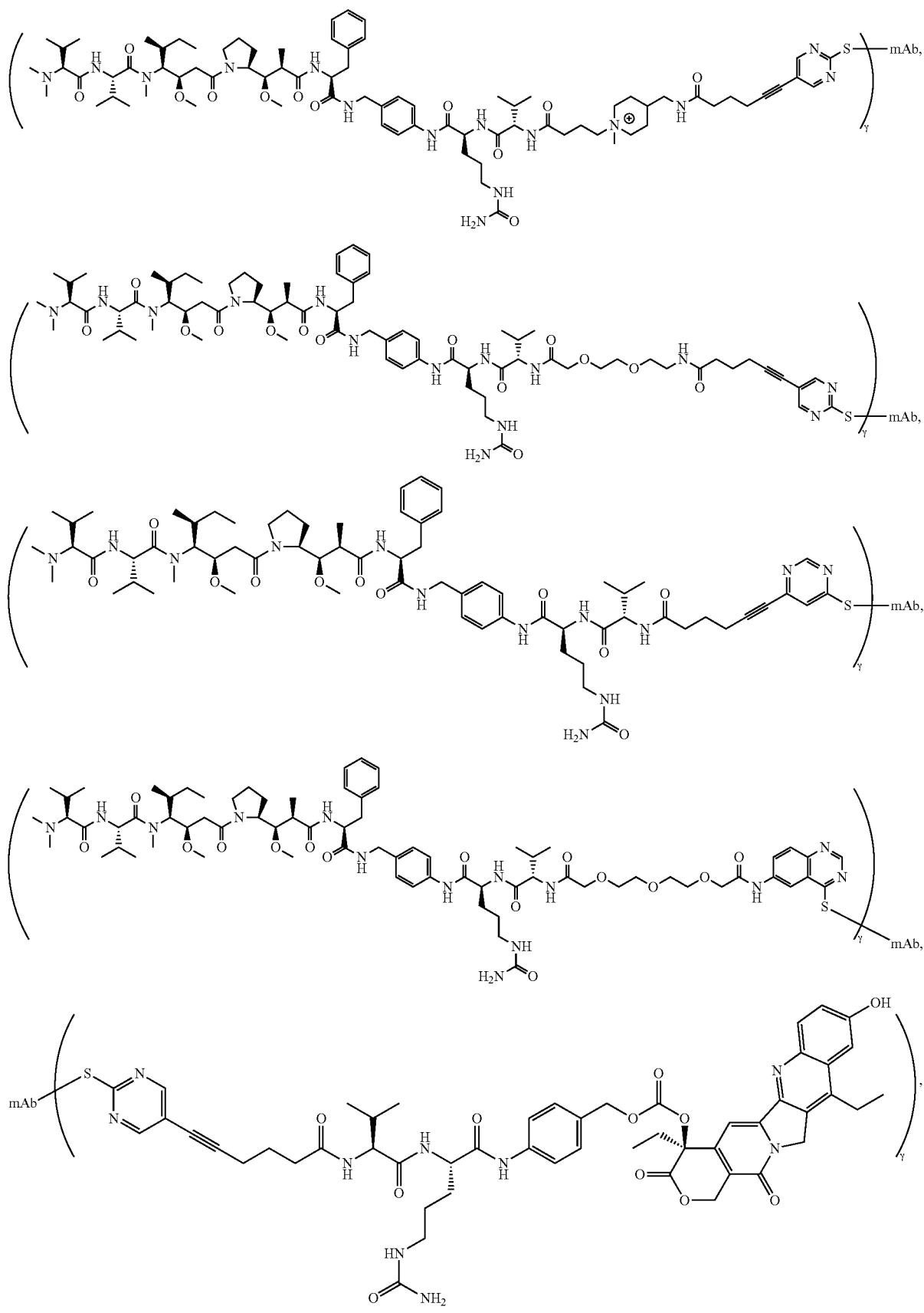

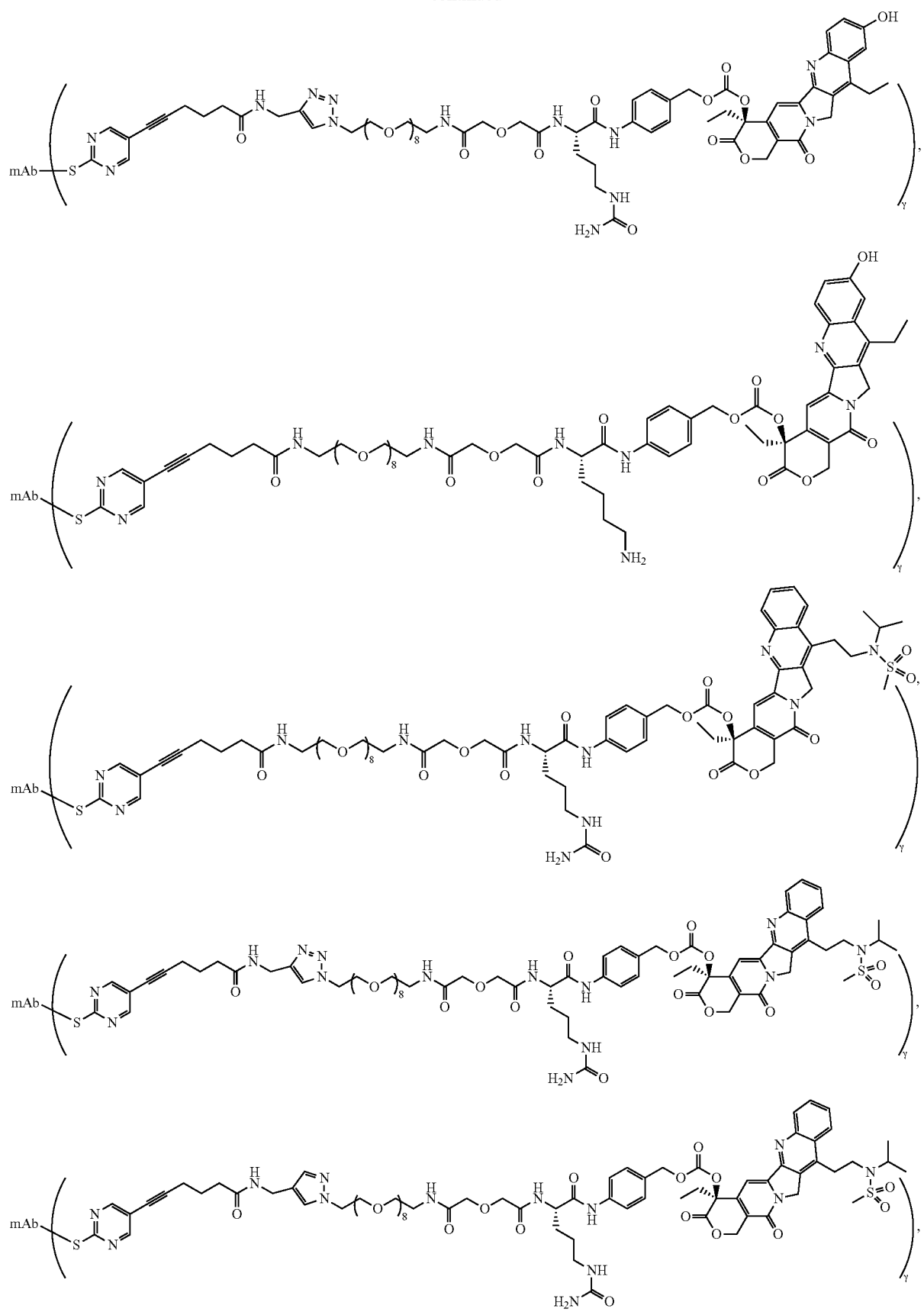

-continued
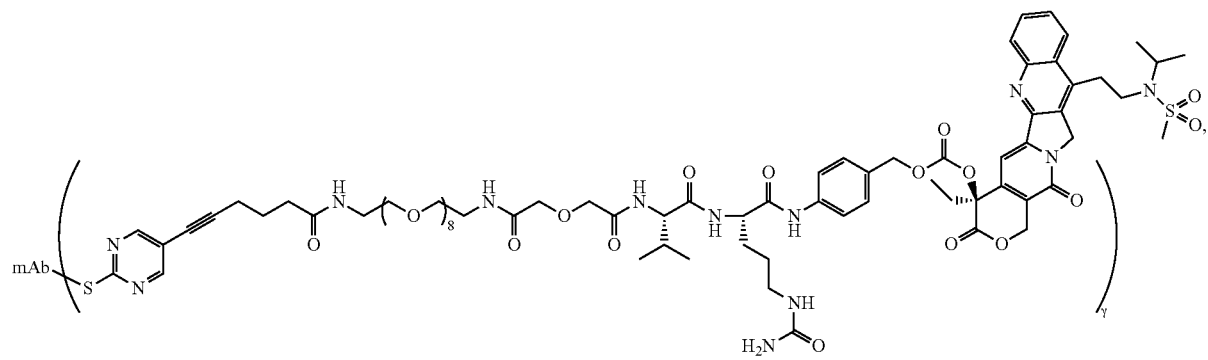
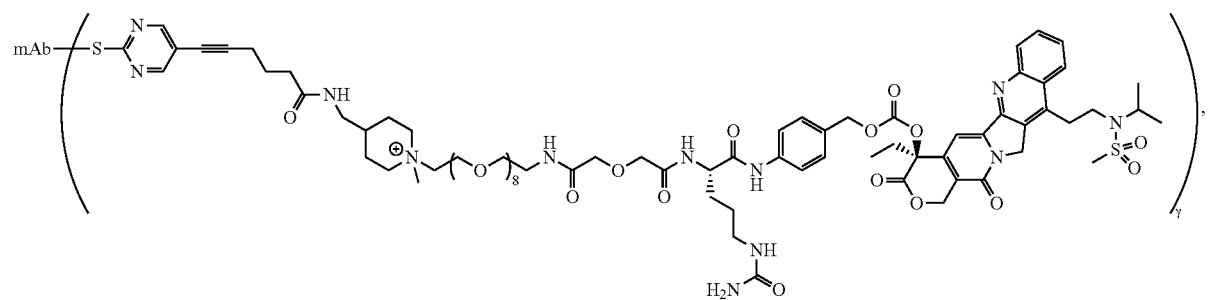
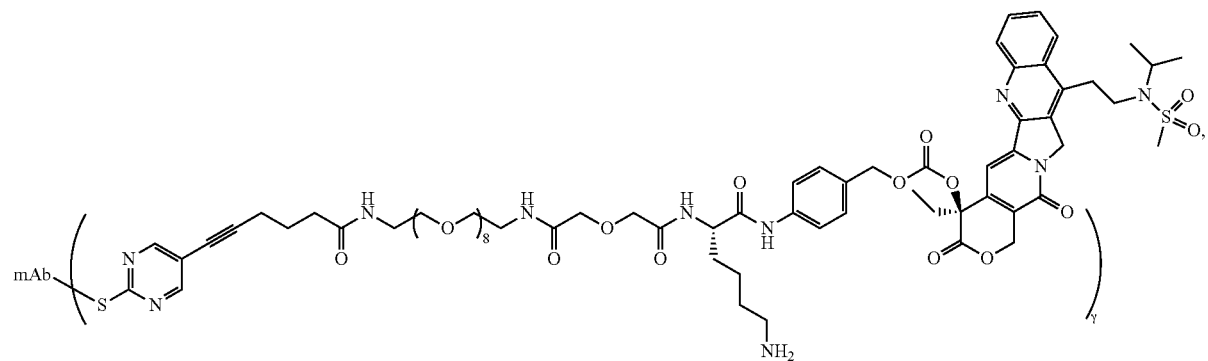
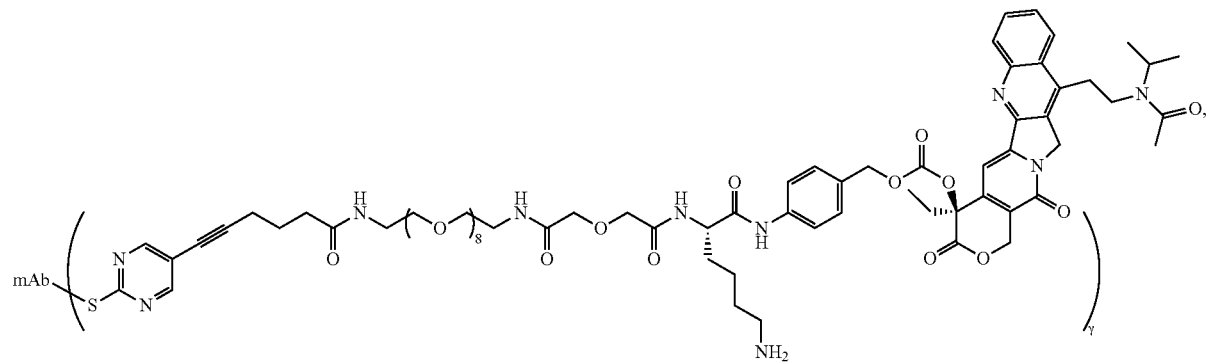

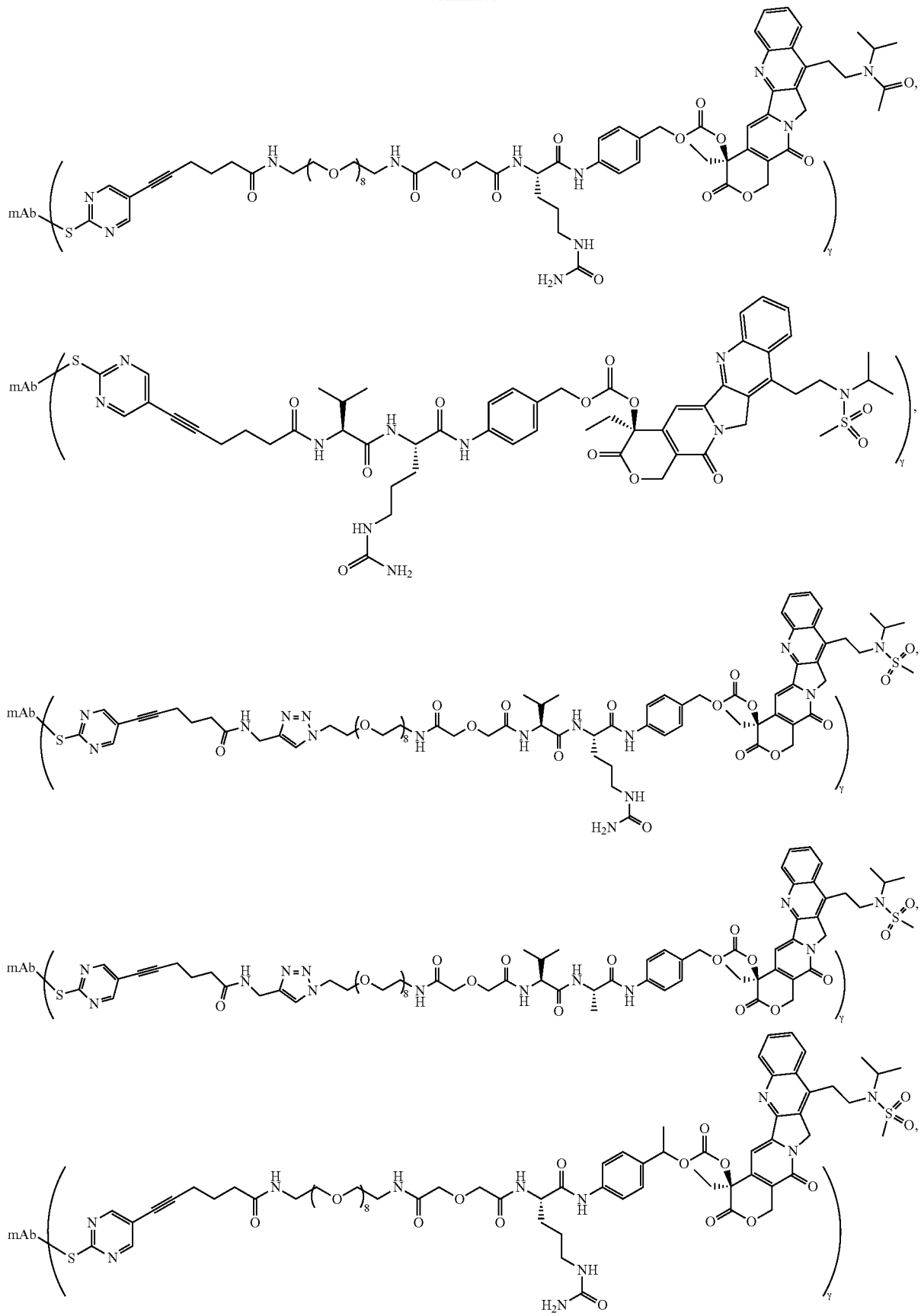

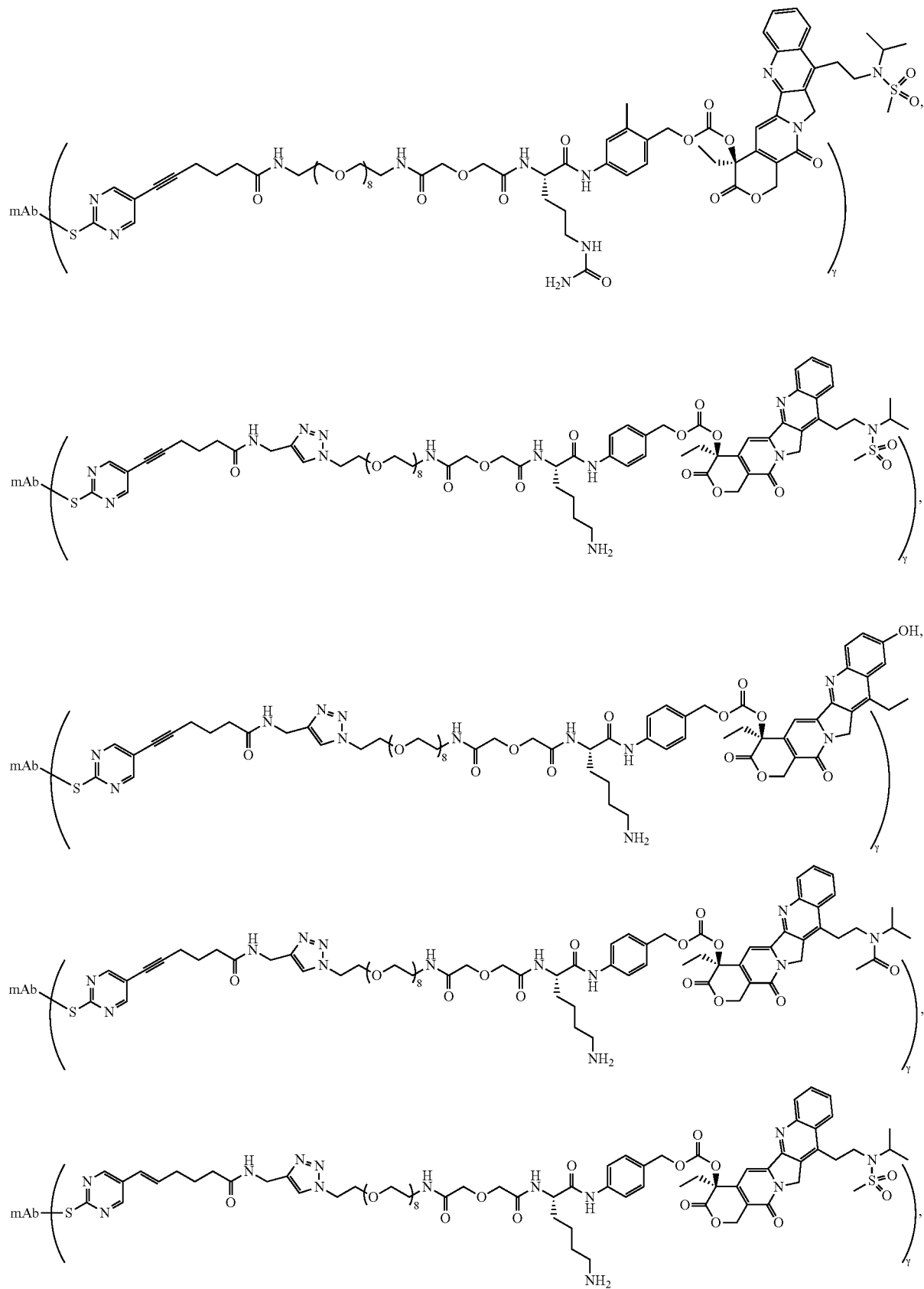

-continued
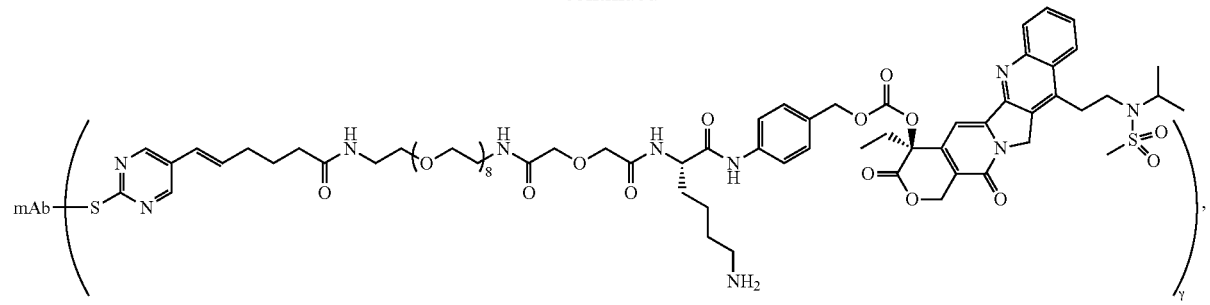
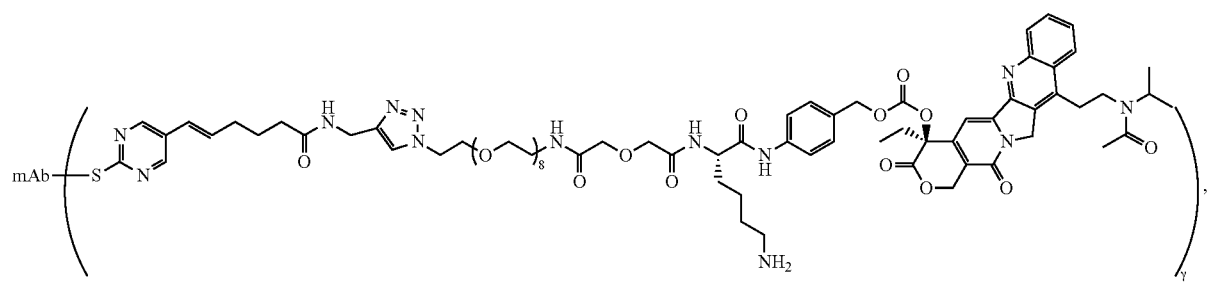
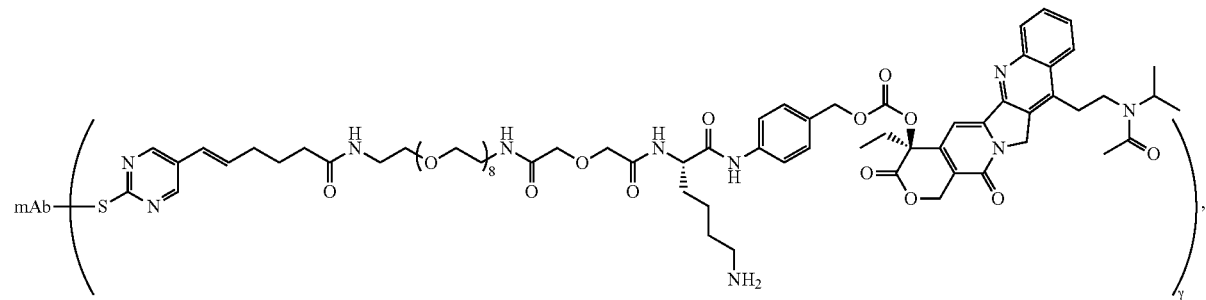
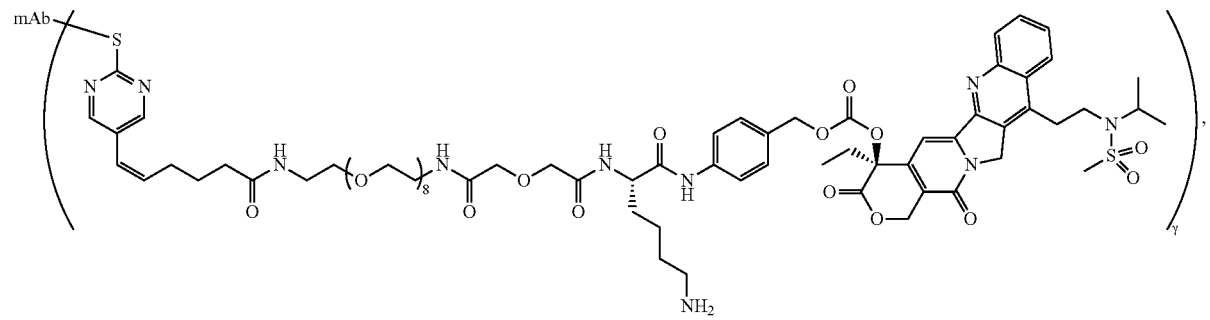
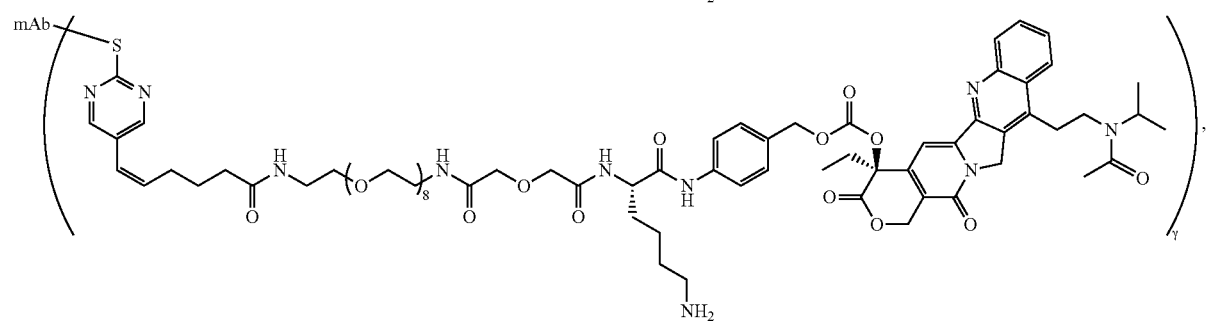

-continued
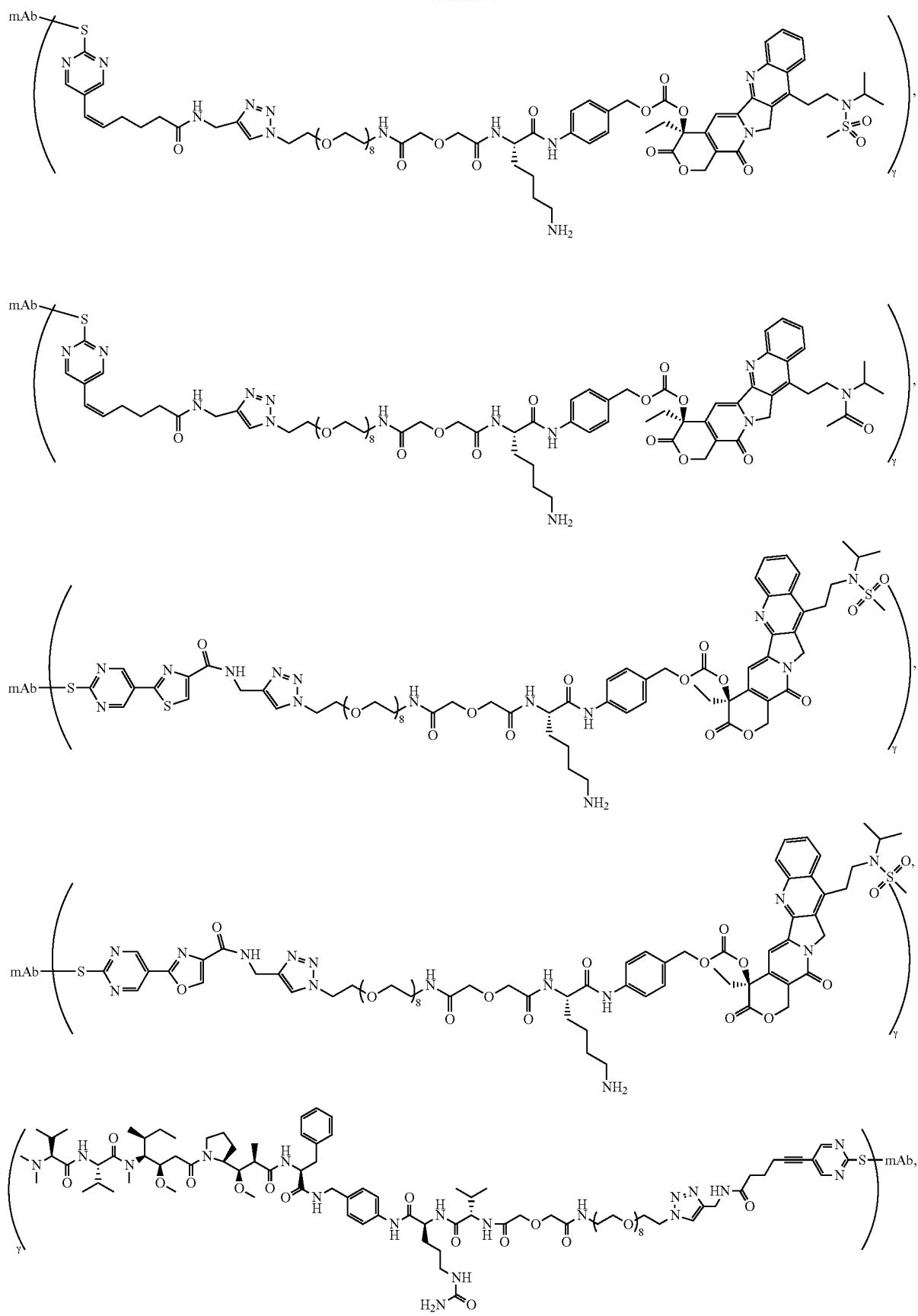

-continued
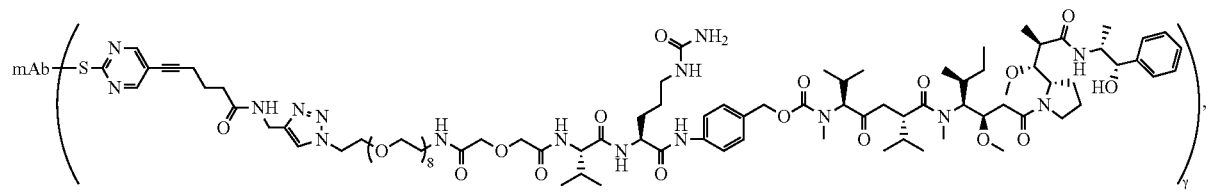
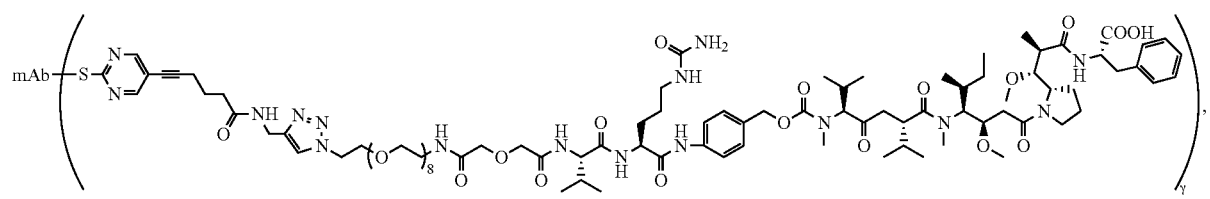
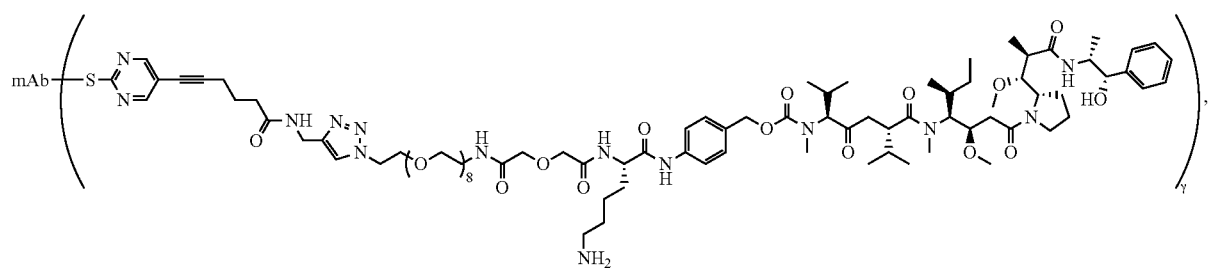
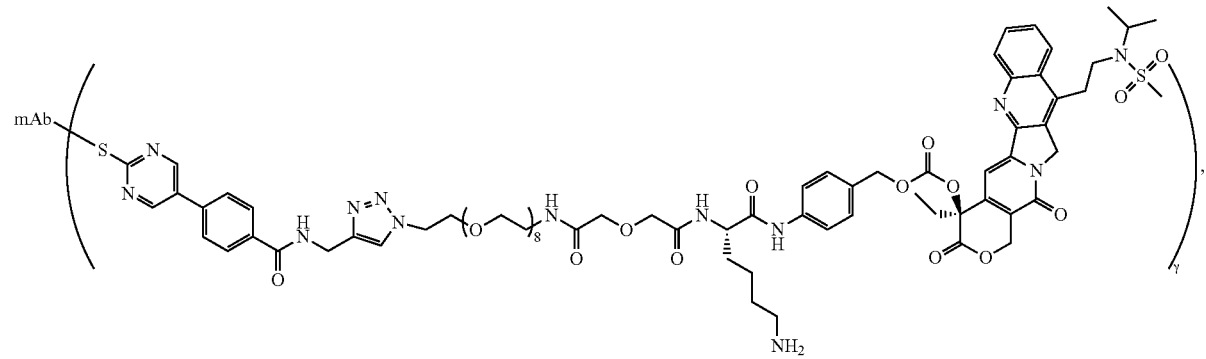
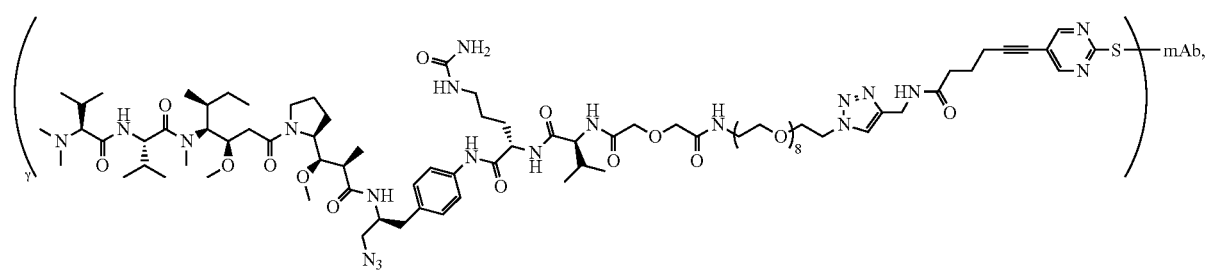
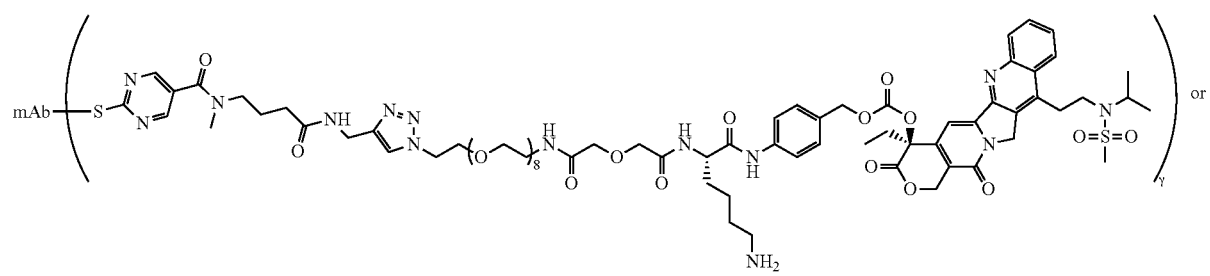

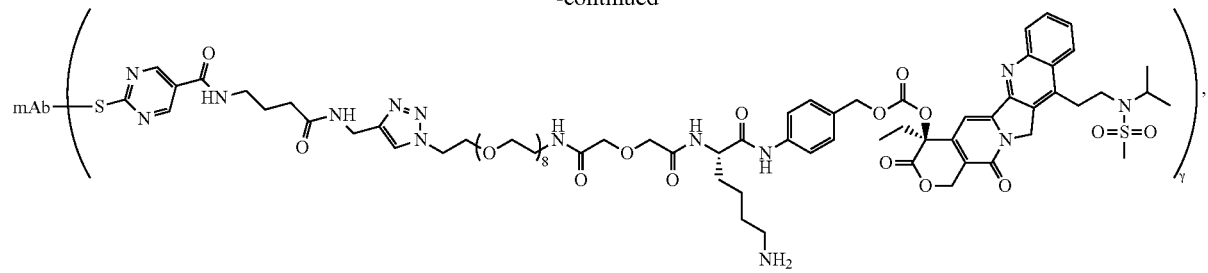

wherein, γ is an integer or a decimal from 1 to 10, and mAb is an anti-Trop-2 monoclonal antibody or an anti-Her 2 monoclonal antibody; preferably, the anti-Trop-2 monoclonal antibody is selected from antibodies of Sacituzumab, M1, M2 or M3, and the anti-Her 2 monoclonal antibody is Trastuzumab or Pertuzumab; preferably, γ is an integer or a decimal from 5 to 8 (e.g., 5, 6, 7 or 8).

In some preferred embodiments, the conjugate is selected from:

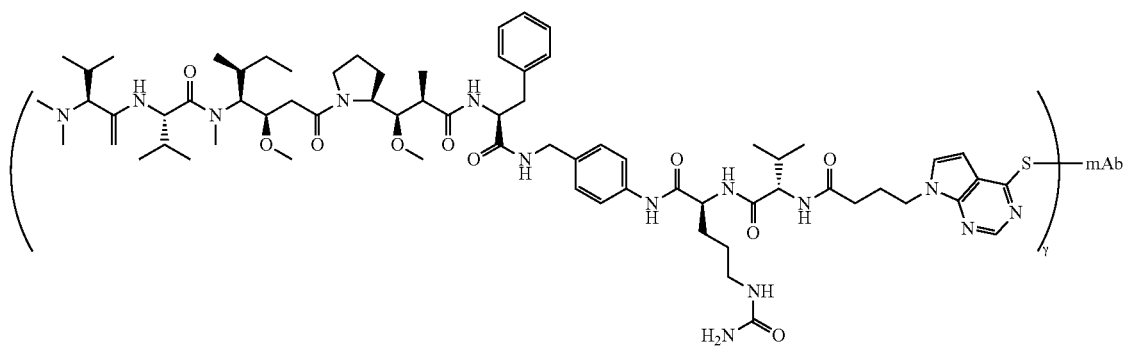

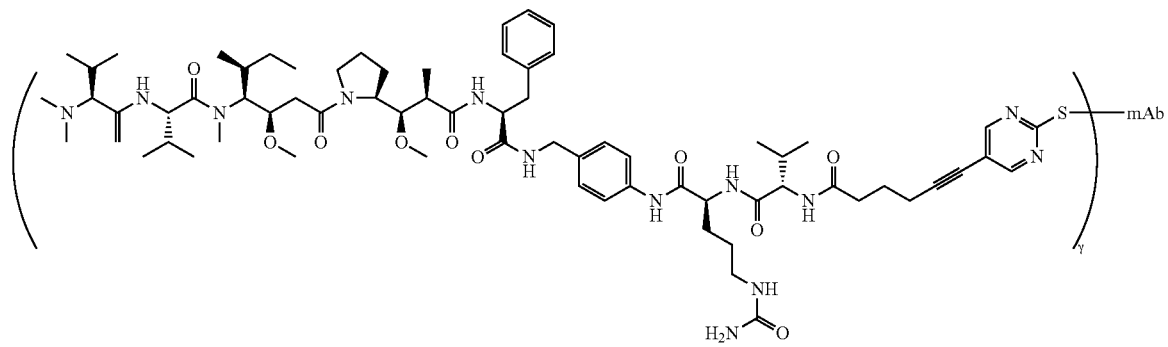

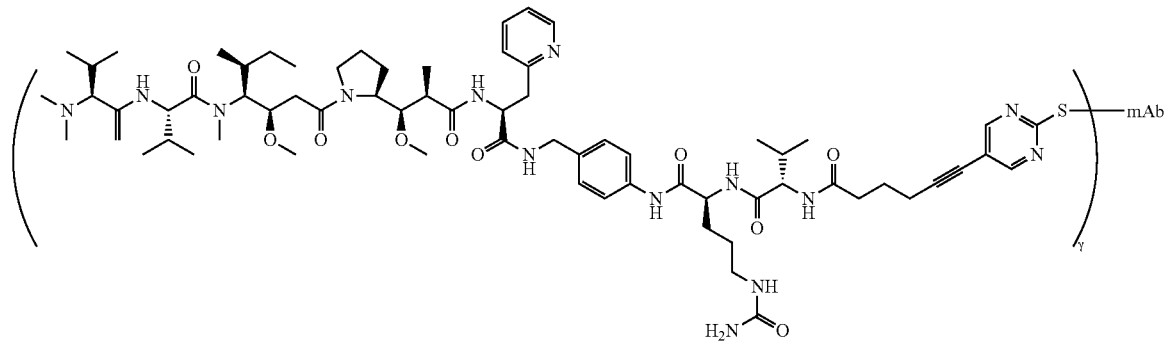

-continued
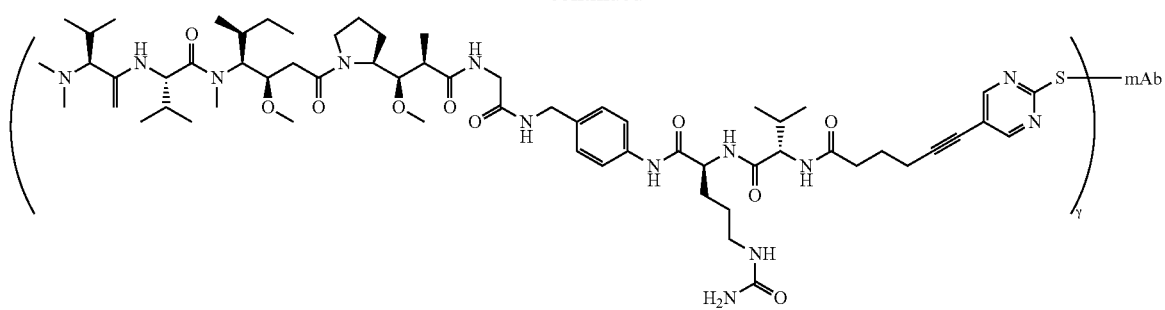
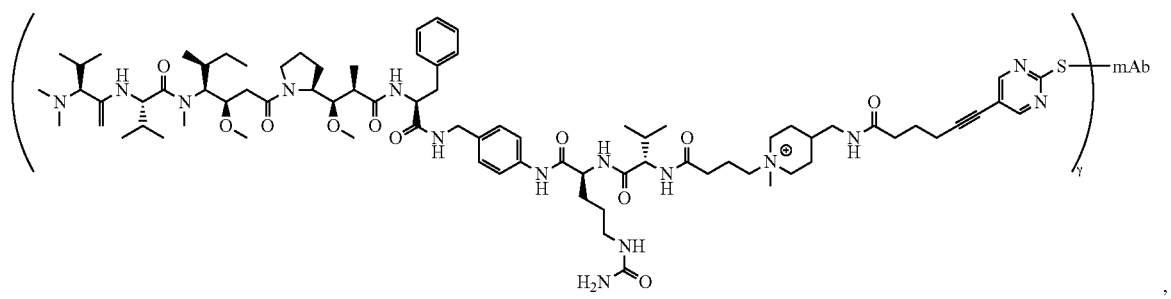
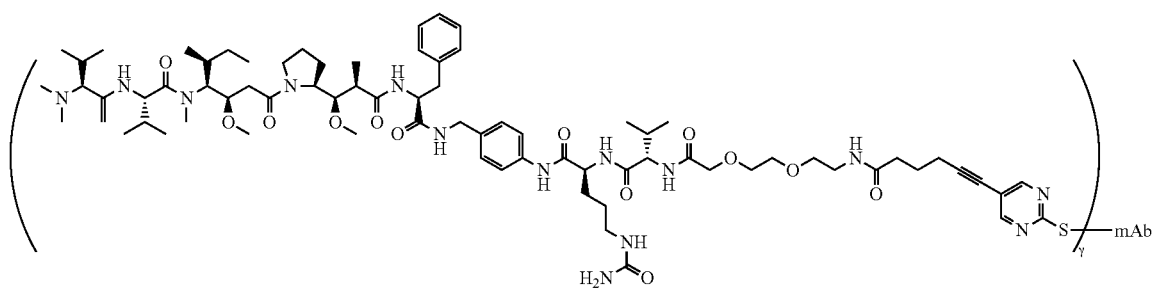
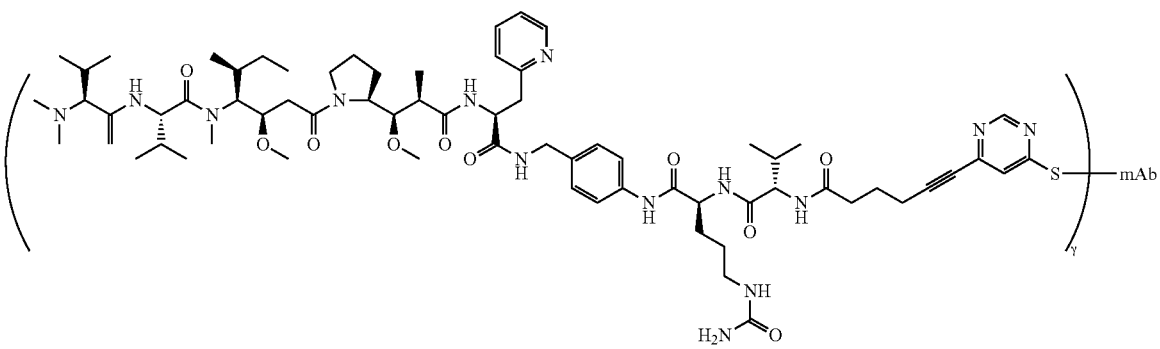
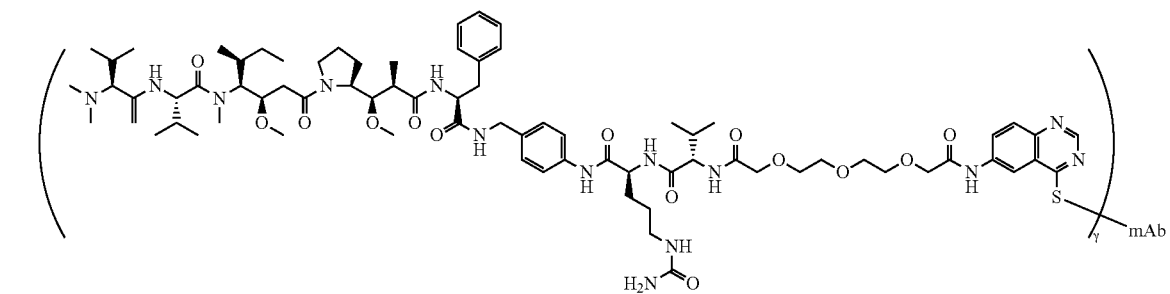

-continued
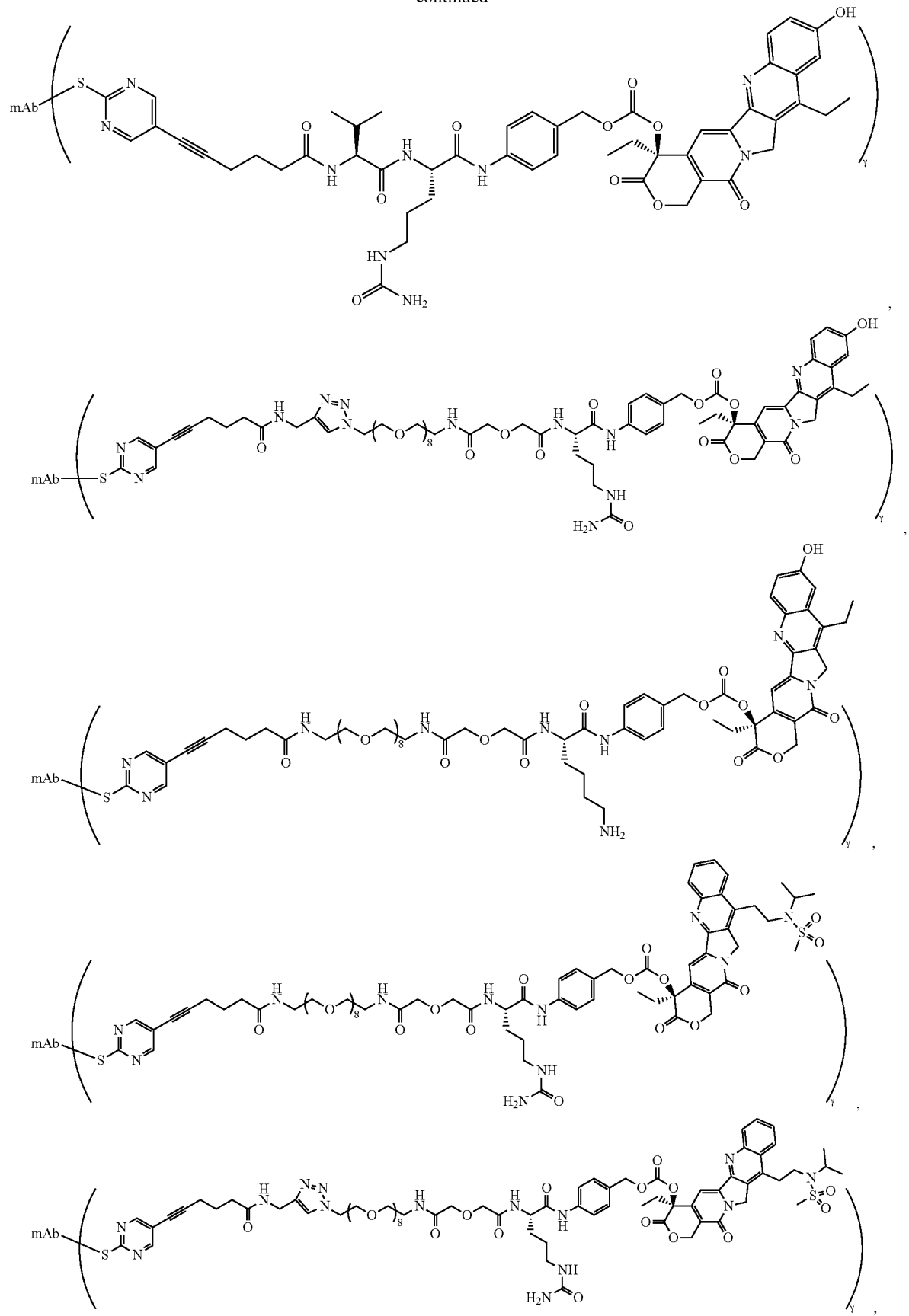

-continued
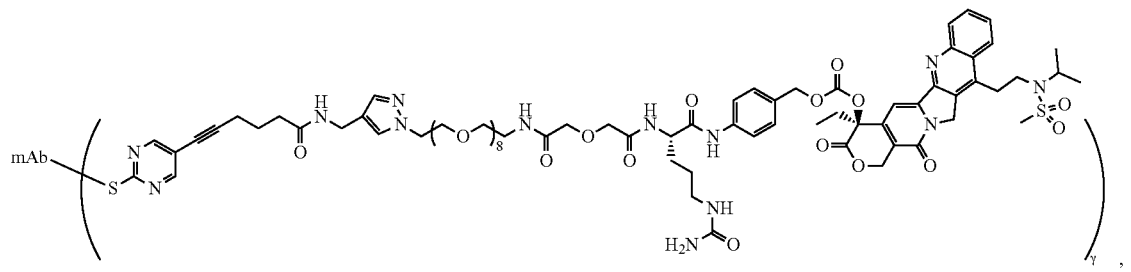
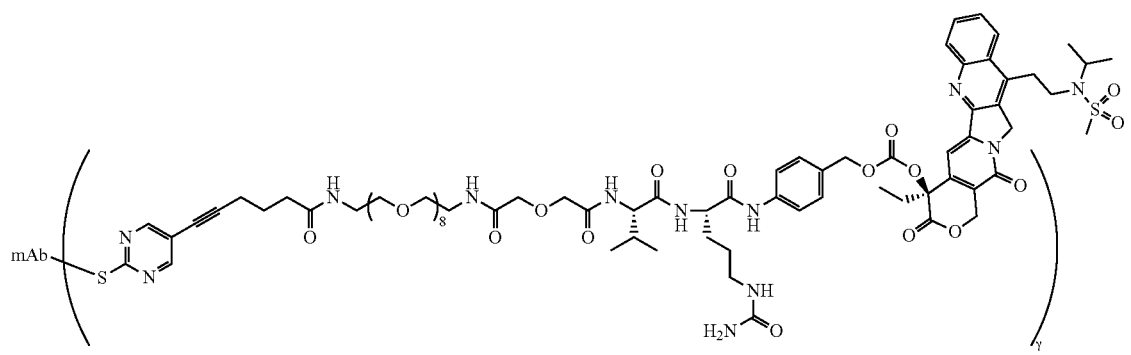
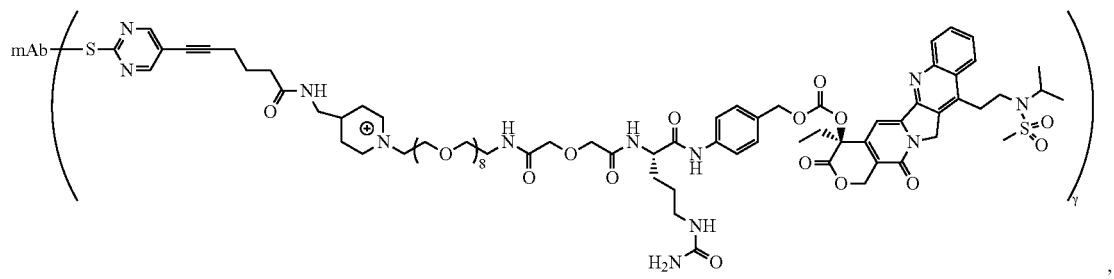
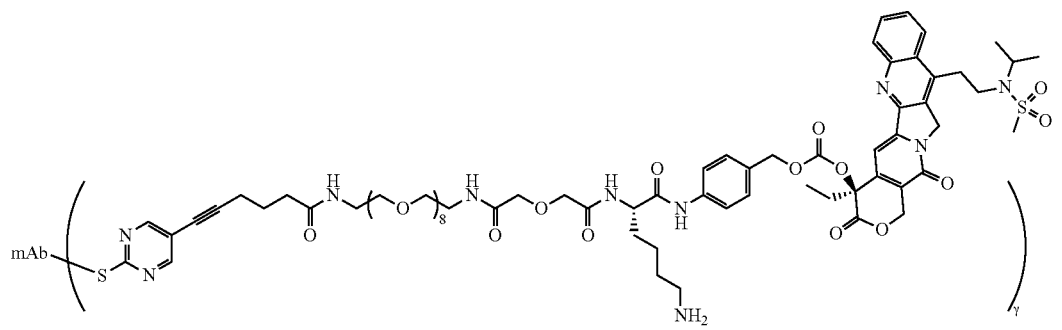
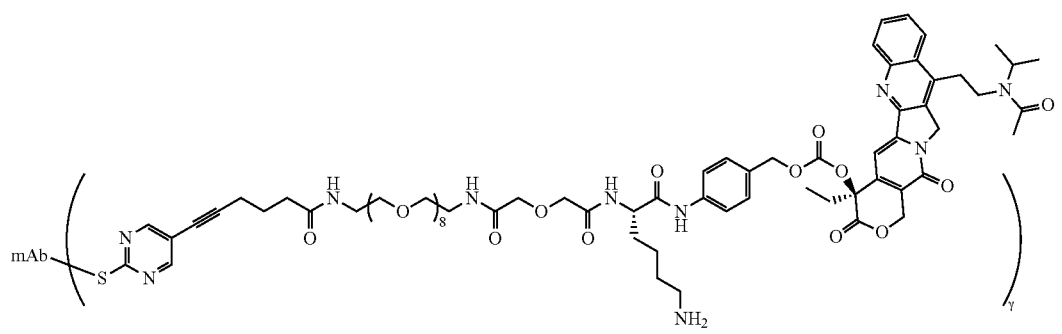

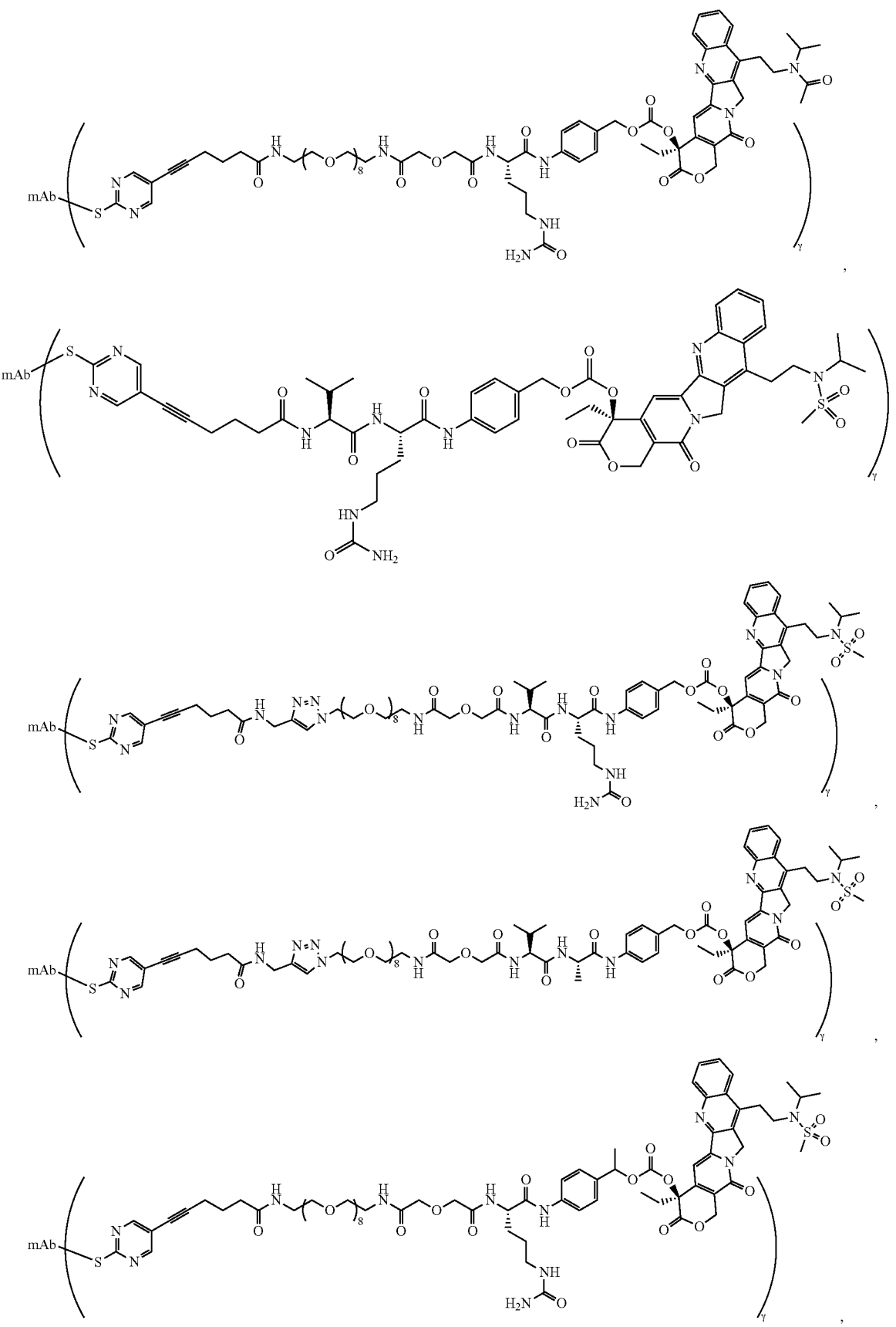

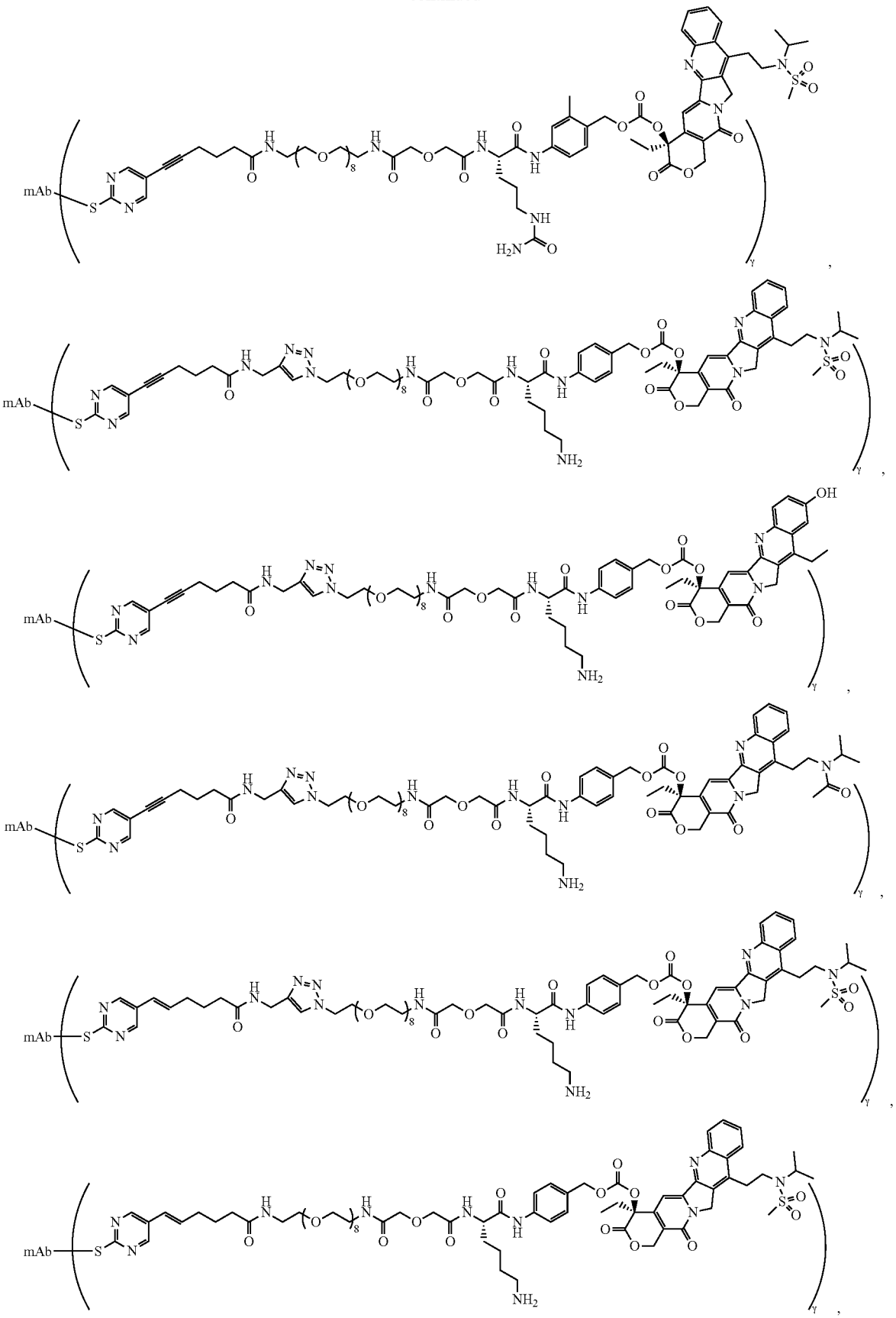

-continued
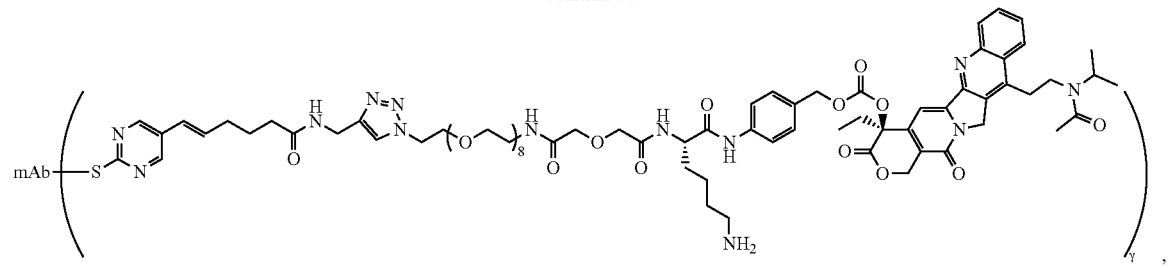
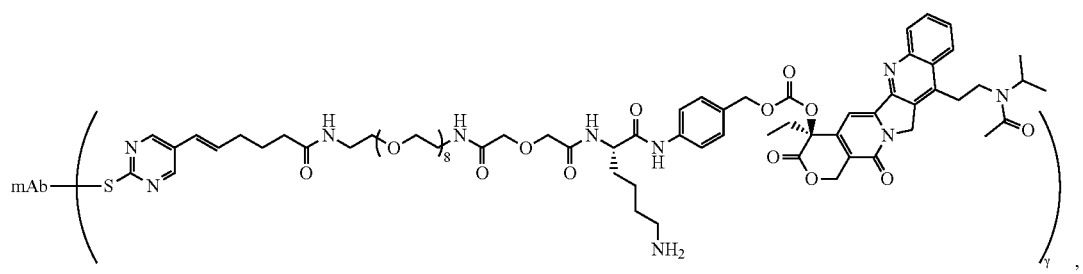
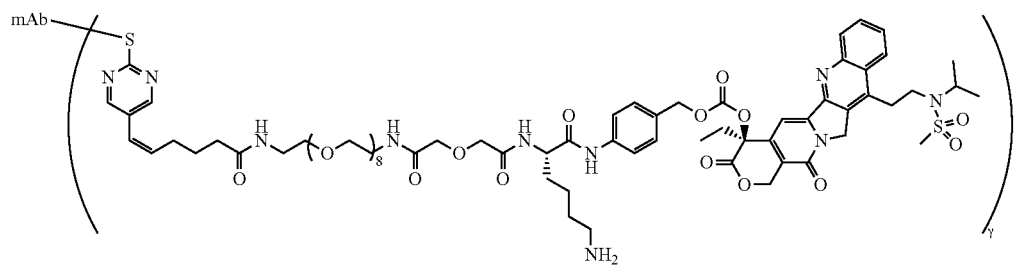
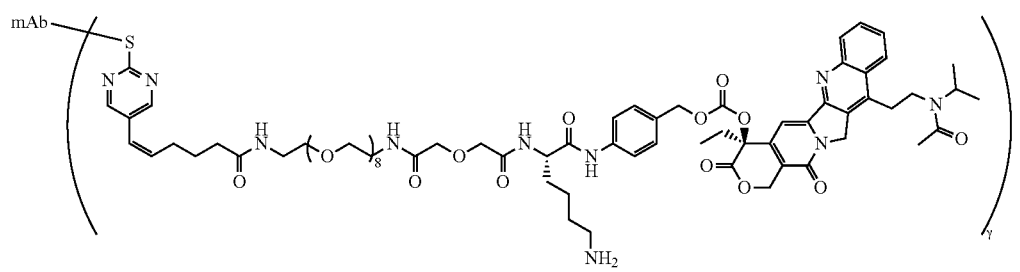
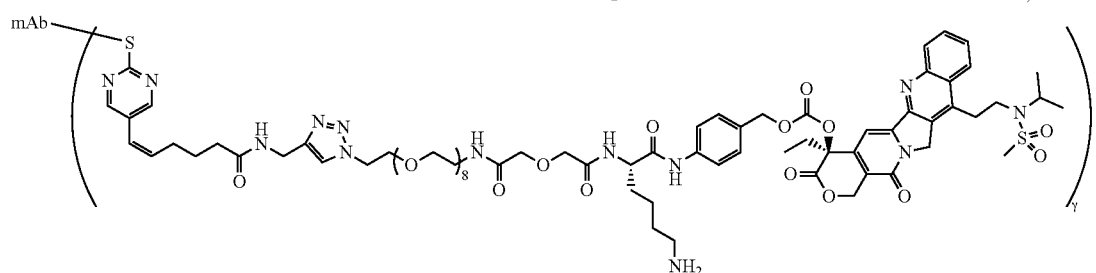
or
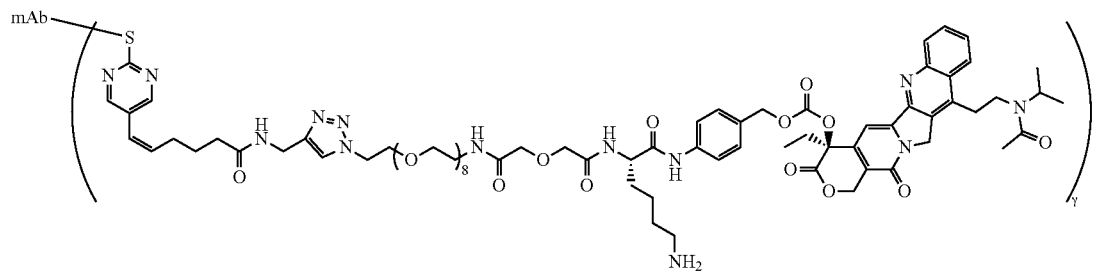

wherein, γ is an integer or a decimal from 1 to 10, and mAb is an anti-Trop-2 monoclonal antibody or an anti-Her 2 monoclonal antibody; preferably, the anti-Trop-2 monoclonal antibody is selected from Sacituzumab, and the anti-Her 2 monoclonal antibody is selected from Trastuzumab or Pertuzumab; preferably, γ is an integer or a decimal from 5 to 8 (e.g., 5, 6, 7 or 8).

In some preferred embodiments, the conjugate is:

BT001002

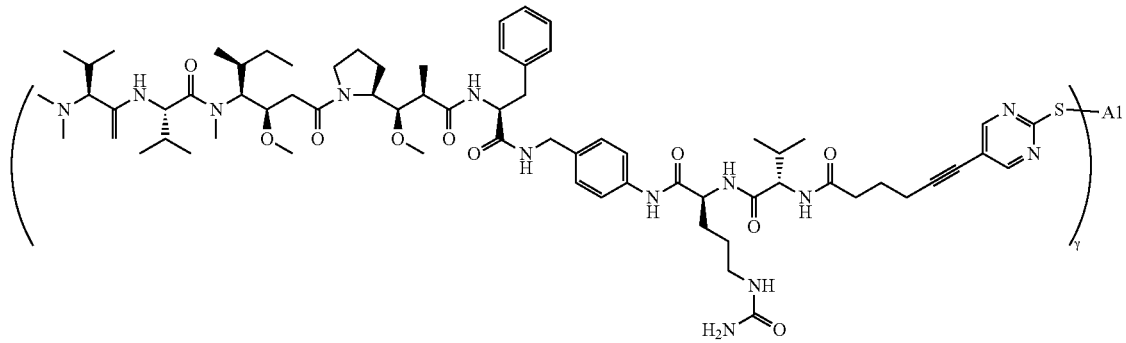

BT001004

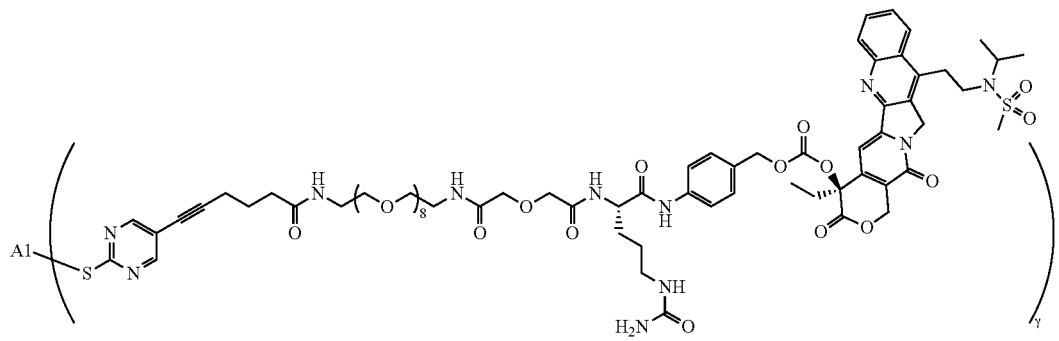

BT001012

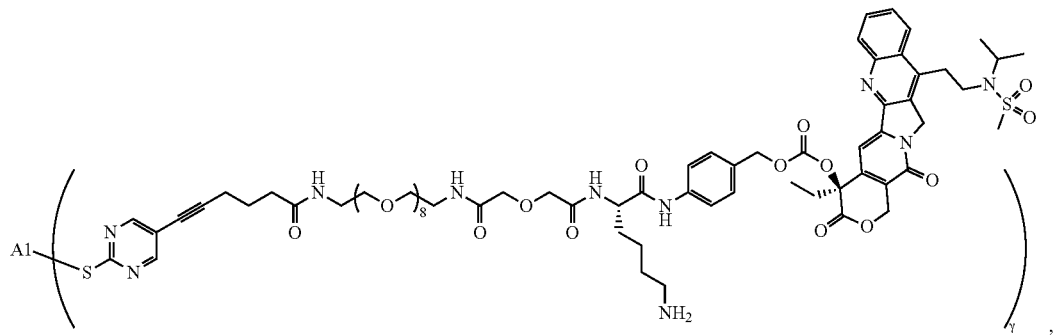

BT001013

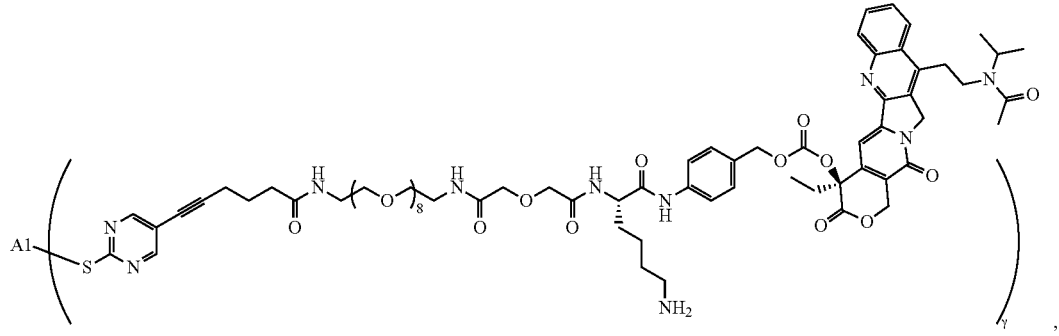

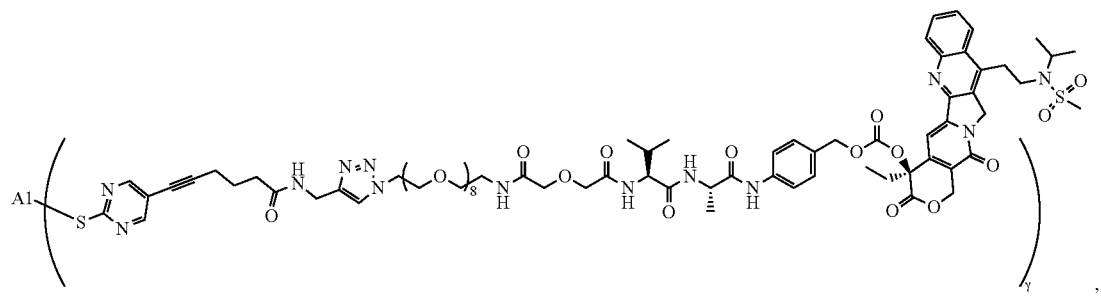
BT001018
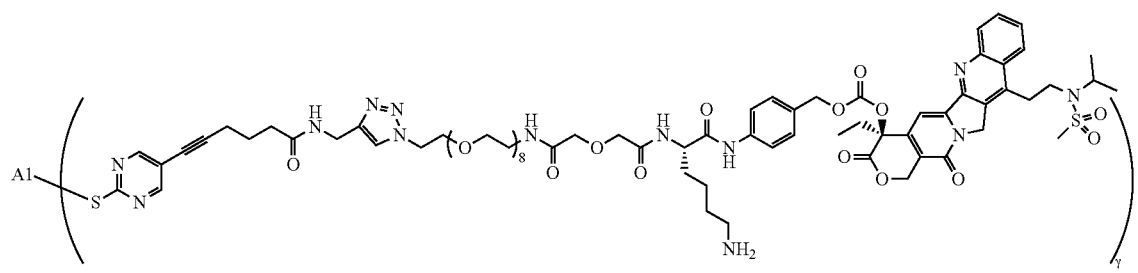
BT001021
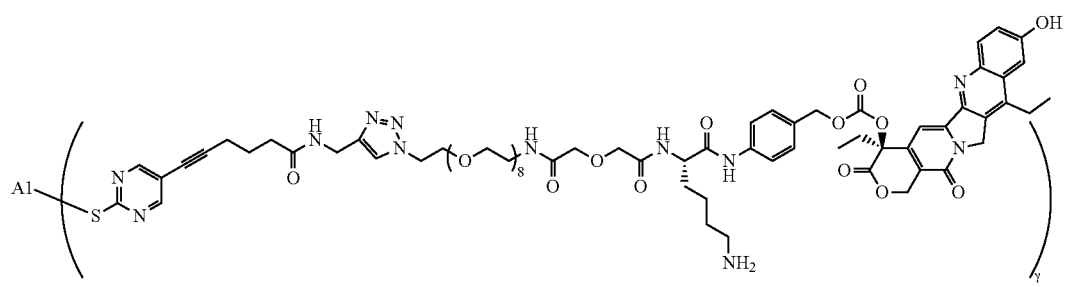
BT001022
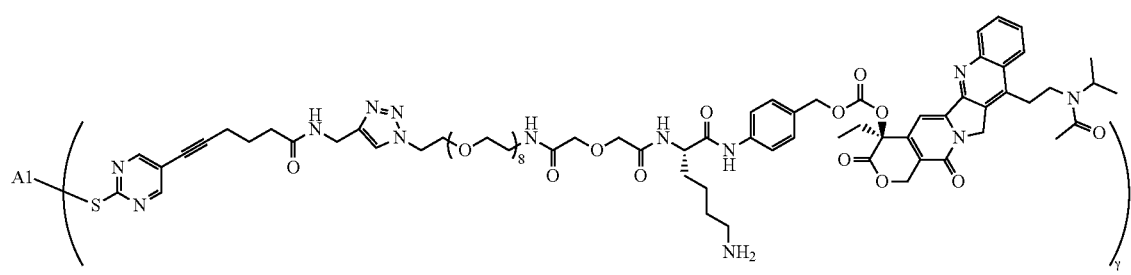
BT001023
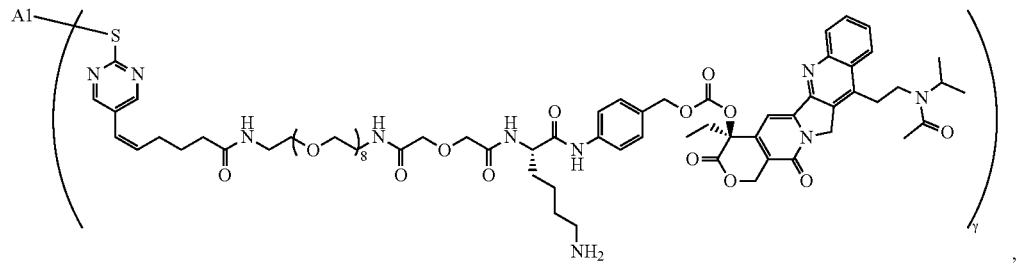
BT001032

-continued
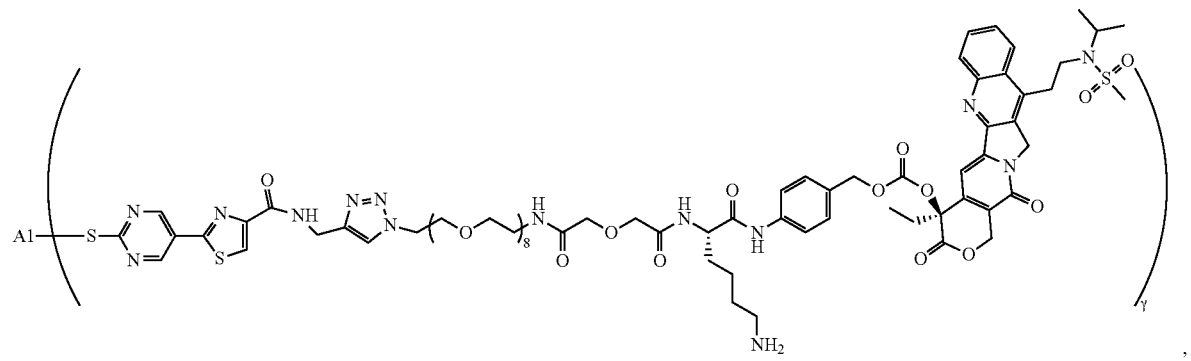
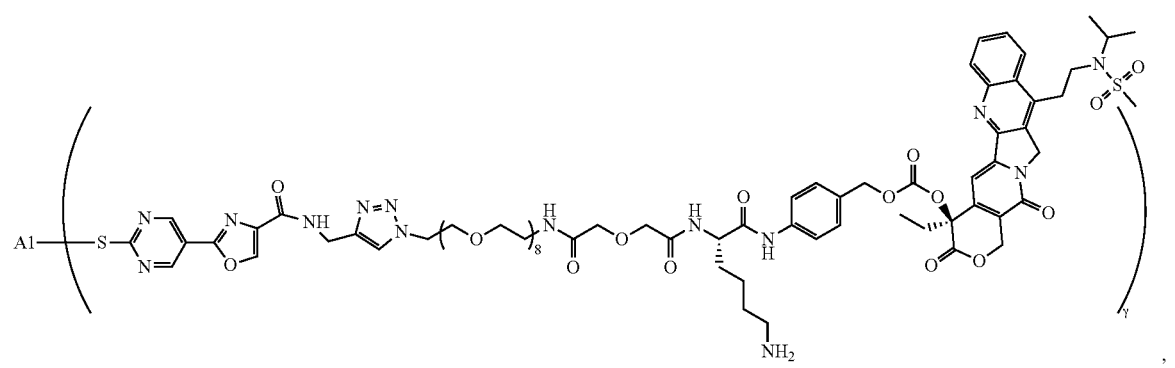
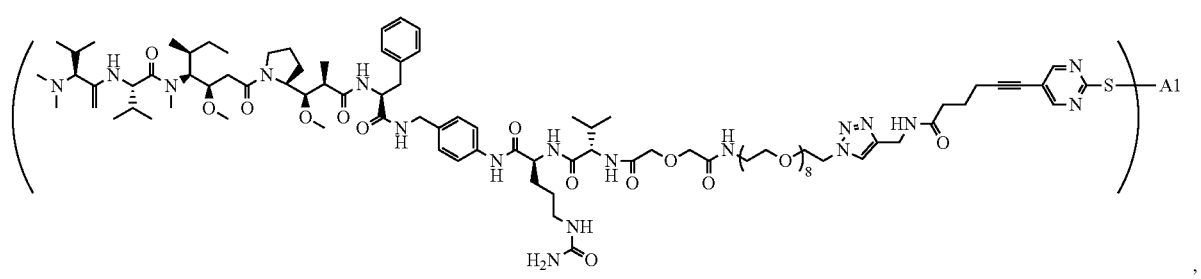
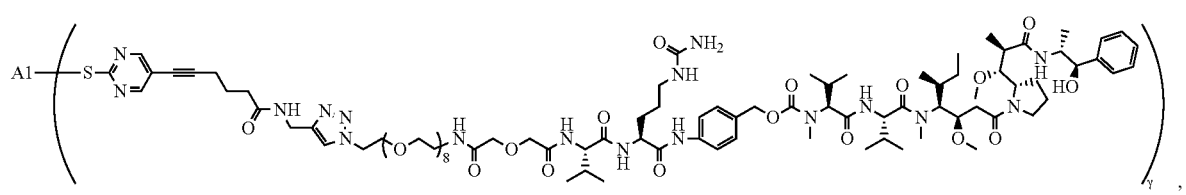
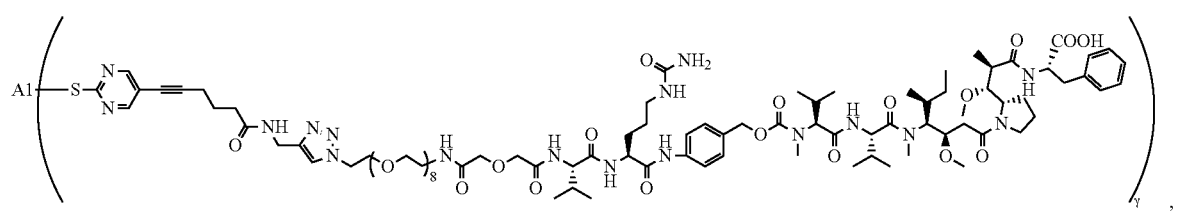

-continued
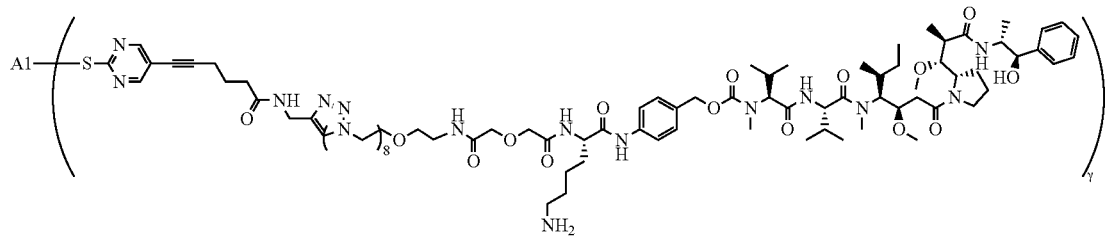
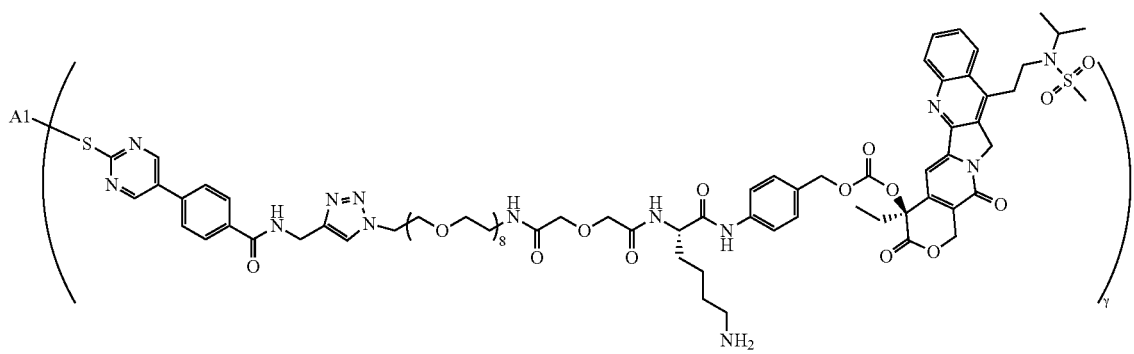
, or
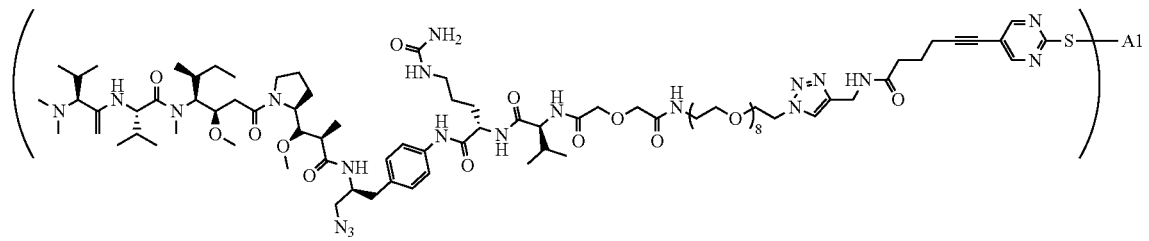
;
wherein, A1 is Sacituzumab, and γ is an integer or a decimal from 1 to 10; preferably, γ is an integer or a decimal from 5 to 8, such as an integer or a decimal from 6-7, 6-7.5, 6-8, 6.5-7, 6.5-7.5, 6.5-8, 7-8 or 7.5-8.
In some preferred embodiments, the conjugate is:
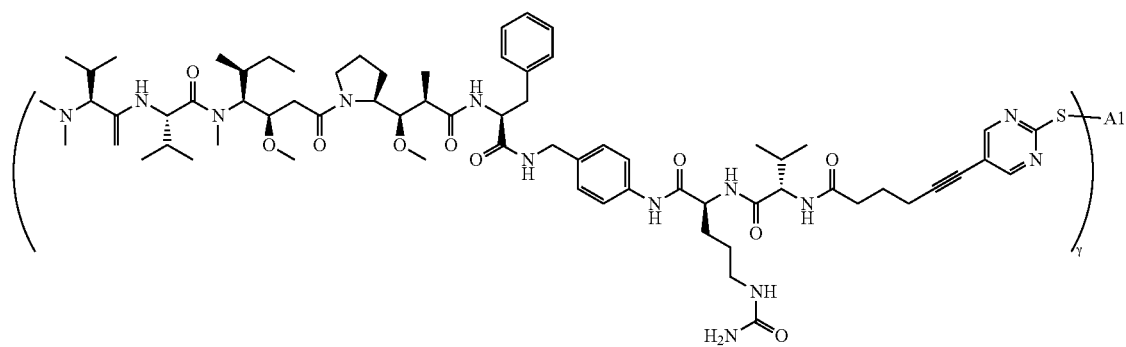
, -continued
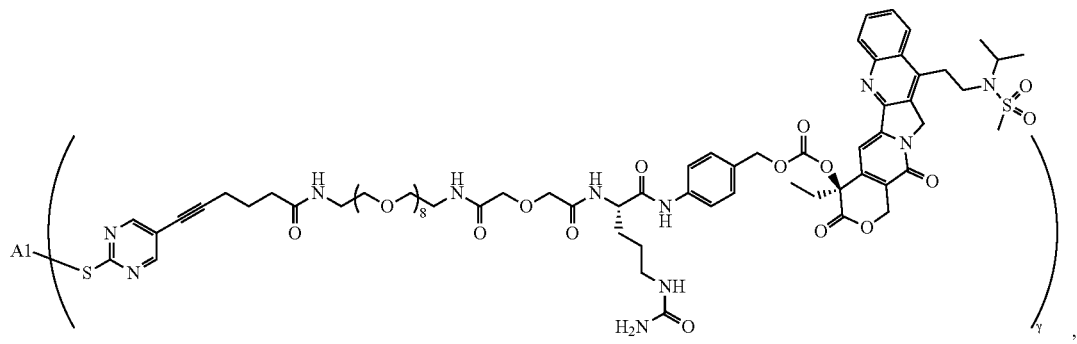
BT001004
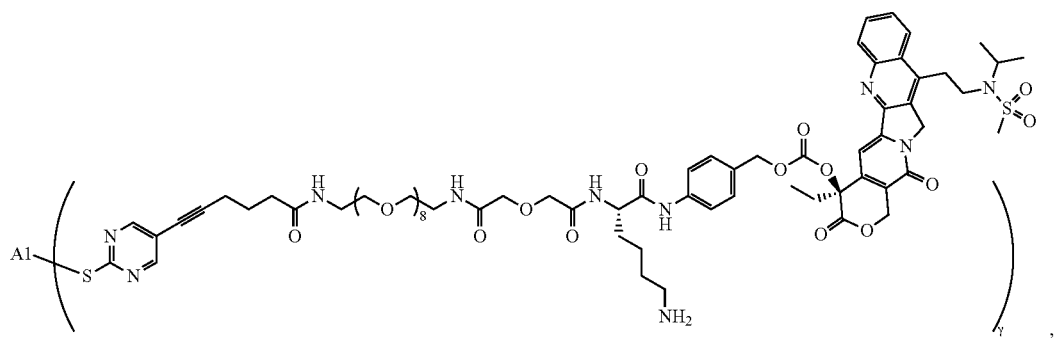
BT001012
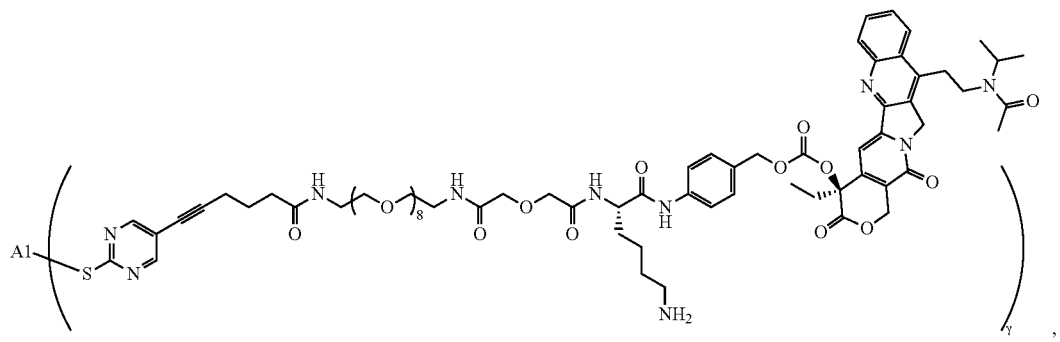
BT001013
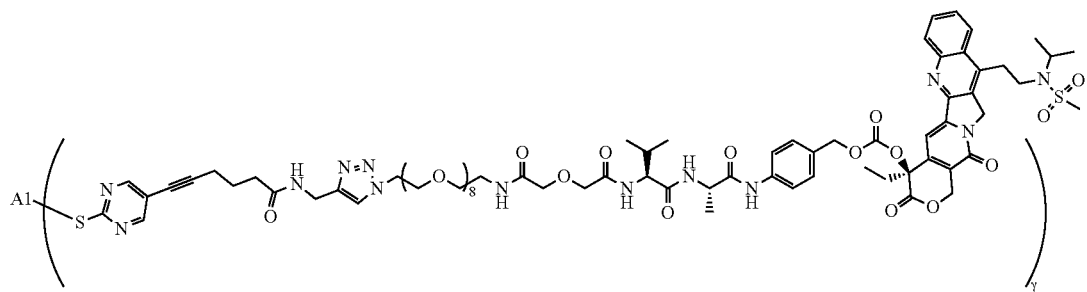
BT001018

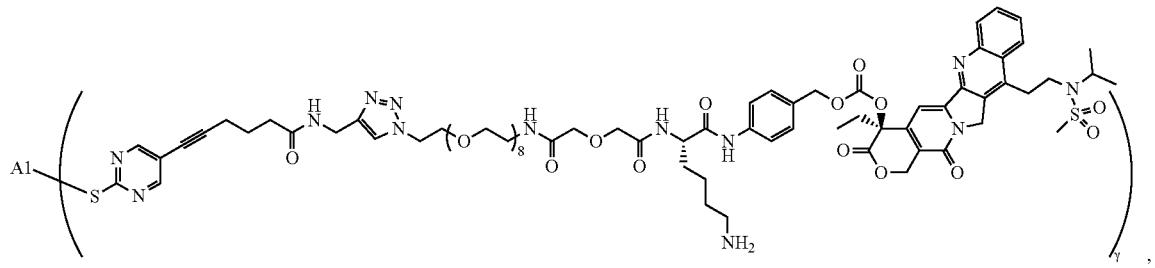
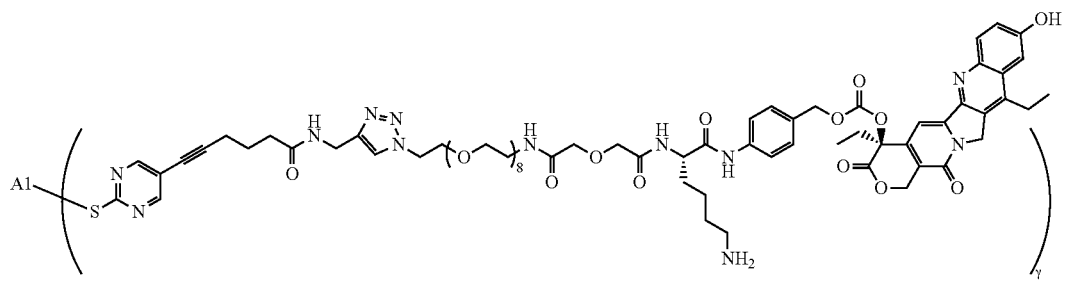
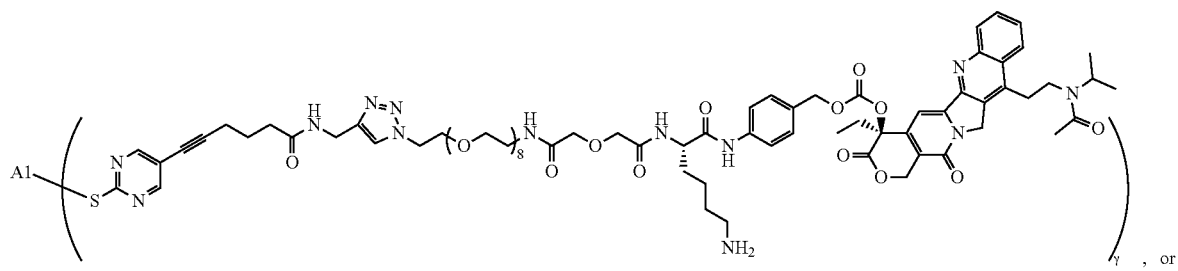
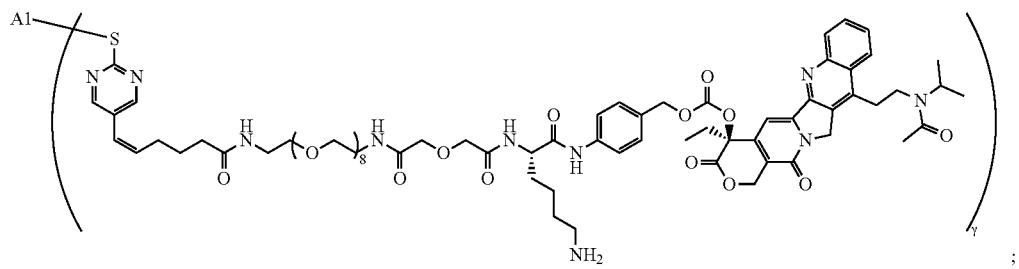
wherein, A1 is Sacituzumab, and γ is an integer or a decimal from 1 to 10; and preferably, γ is an integer or a decimal from 5 to 8, such as an integer or a decimal from 6-7, 6-7.5, 6-8, 6.5-7, 6.5-7.5, 6.5-8, 7-8 or 7.5-8.

In some preferred embodiments, the conjugate is:
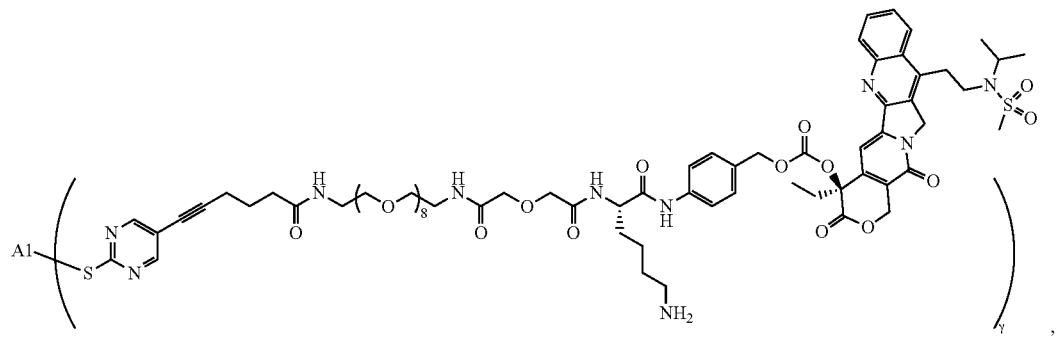
BT001012
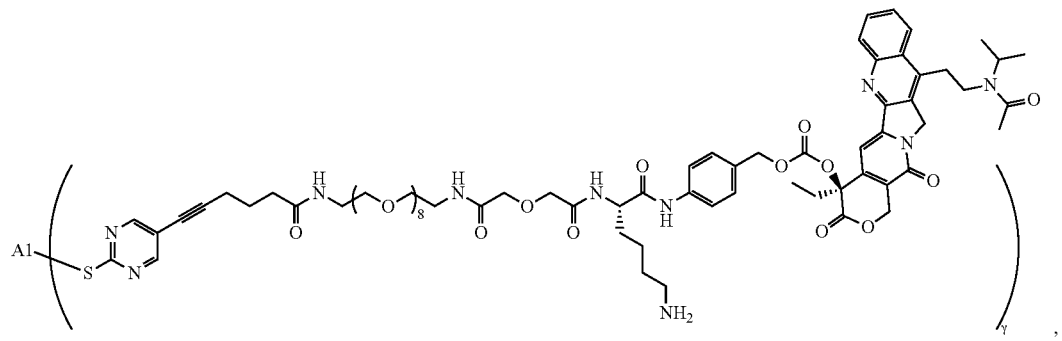
BT001013
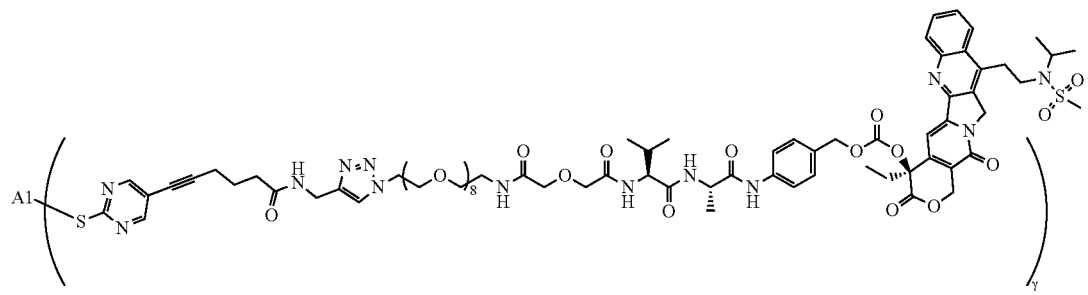
BT001018
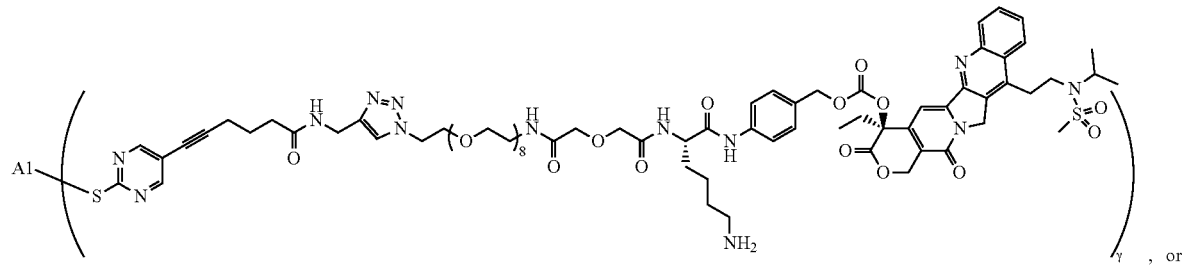
BT001021
, or

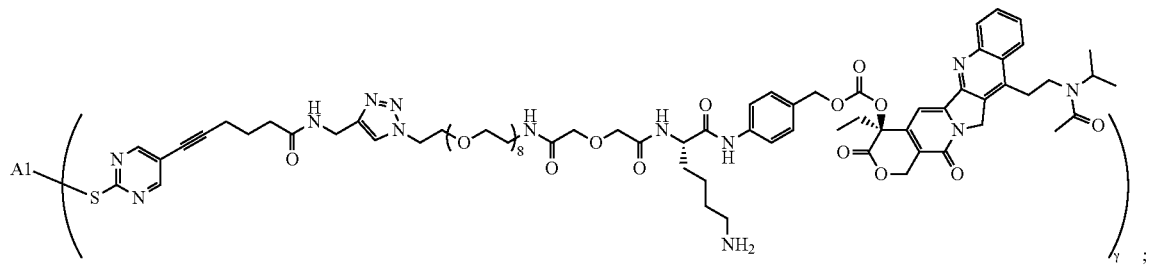
BT001023
wherein, A1 is Sacituzumab, and γ is an integer or a decimal from 1 to 10; and preferably, γ is an integer or a decimal from 5 to 8, such as an integer or a decimal from 6-7, 6-7.5, 6-8, 6.5-7, 6.5-7.5, 6.5-8, 7-8 or 7.5-8.
In some preferred embodiments, the conjugate is:
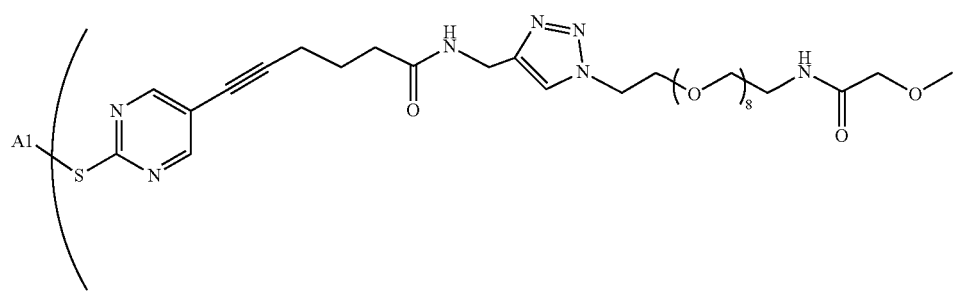
BT001021
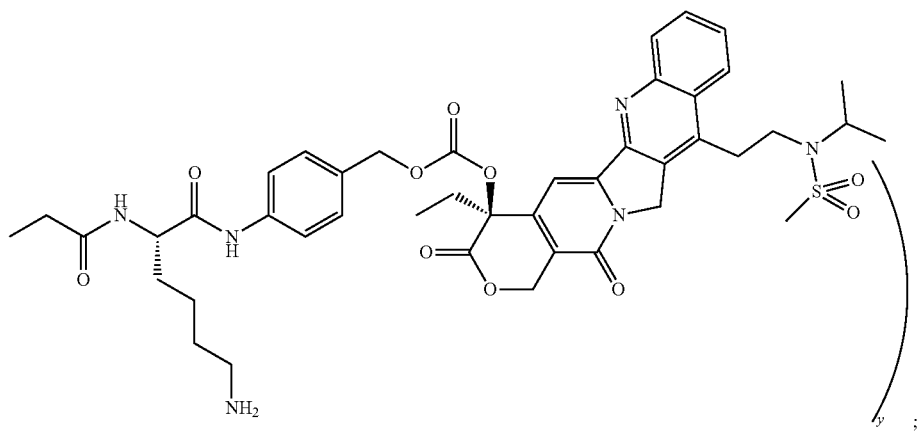

wherein, A1 is a fragment of Sacituzumab, and γ is an integer or a decimal from 1 to 10; and preferably, γ is an integer or a decimal from 5 to 8, such as an integer or a decimal from 6-7, 6-7.5, 6-8, 6.5-7, 6.5-7.5, 6.5-8, 7-8 or 7.5-8.
In some preferred embodiments, the conjugate is:
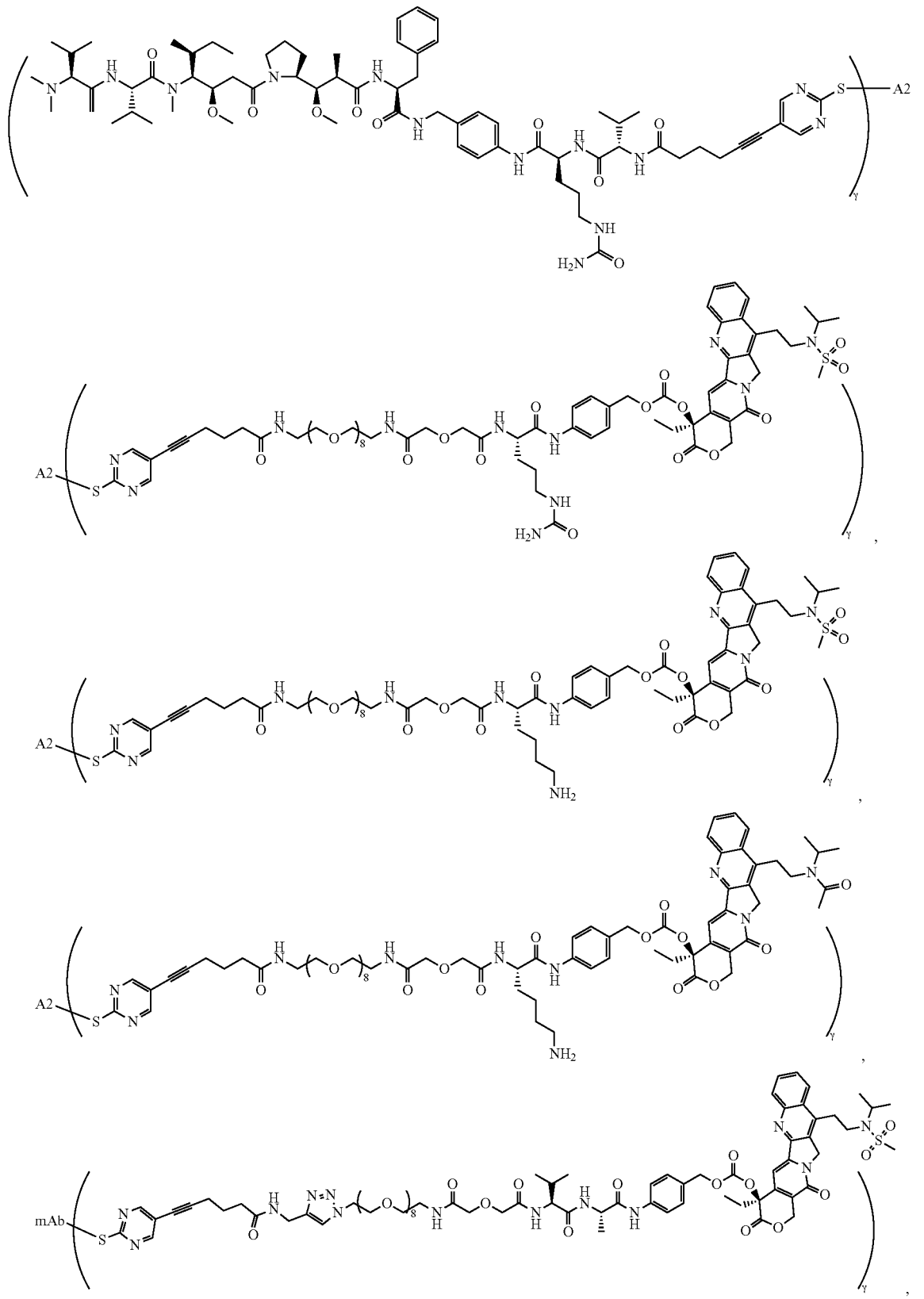

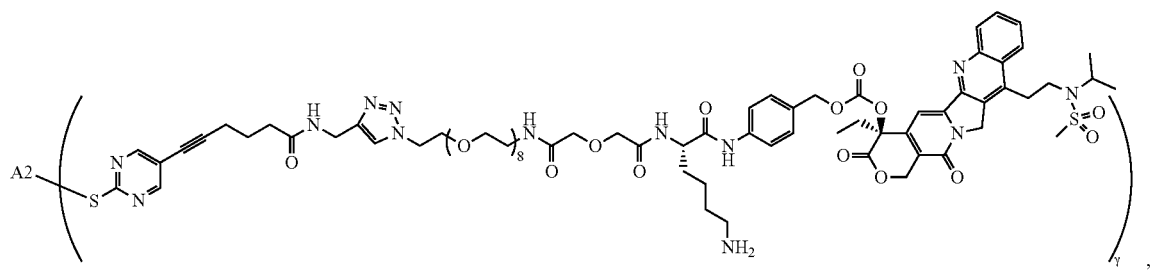
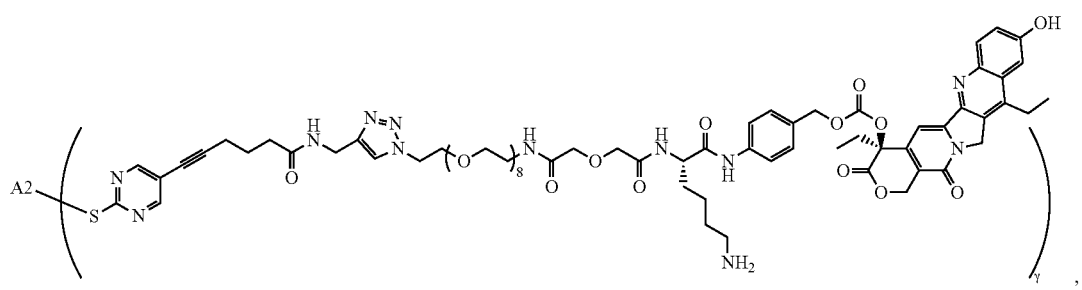
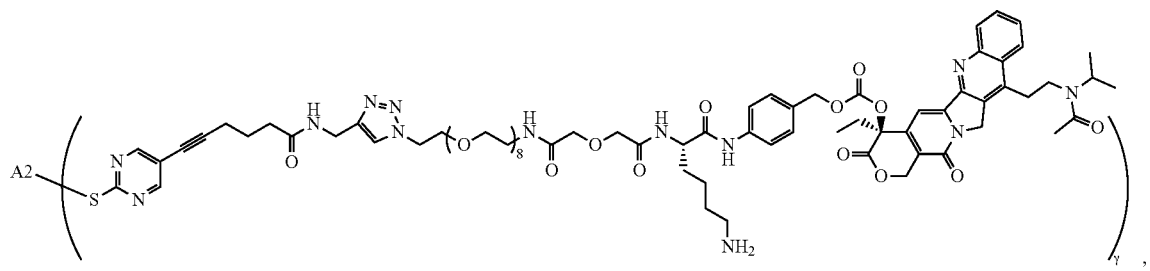
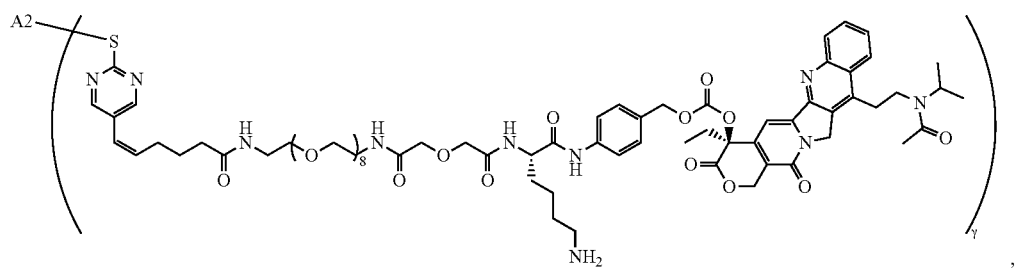
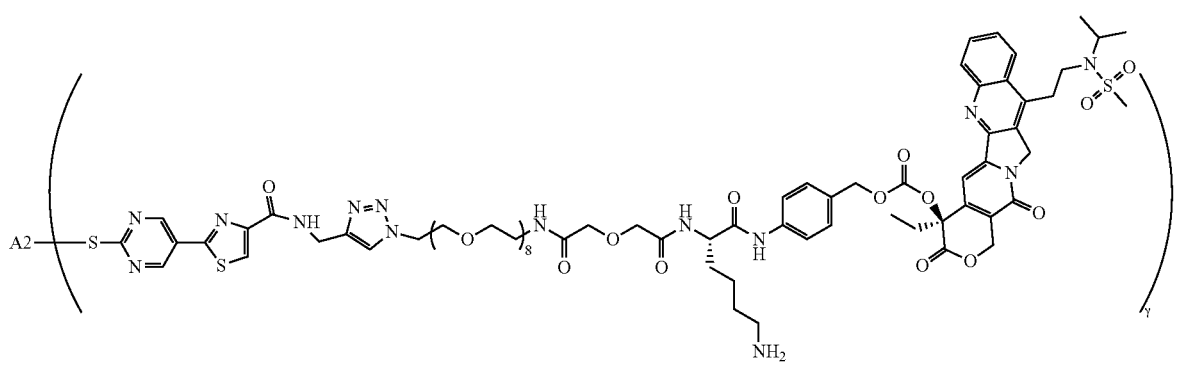

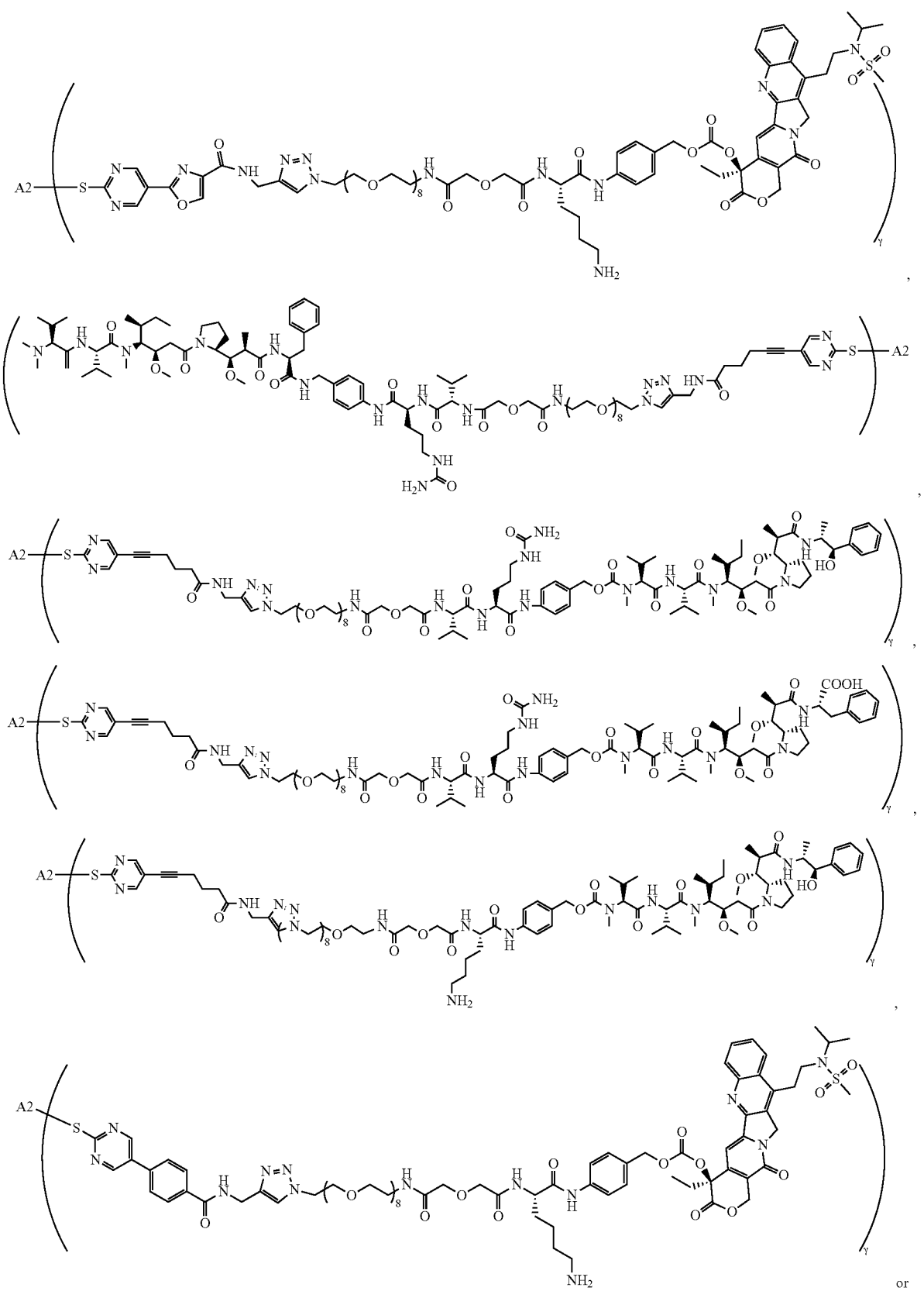

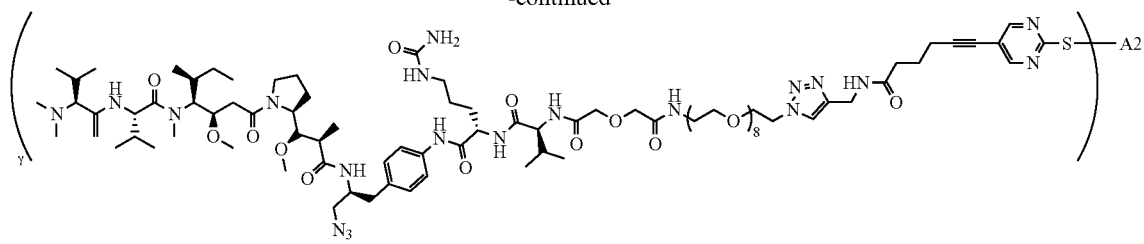
wherein, A2 is Trastuzumab, and γ is an integer or a decimal from 1 to 10; and preferably, γ is an integer or a decimal from 5 to 8, such as an integer or a decimal from 6-7, 6-7.5, 6-8, 6.5-7, 6.5-7.5, 6.5-8, 7-8 or 7.5-8.
In some preferred embodiments, the conjugate is:
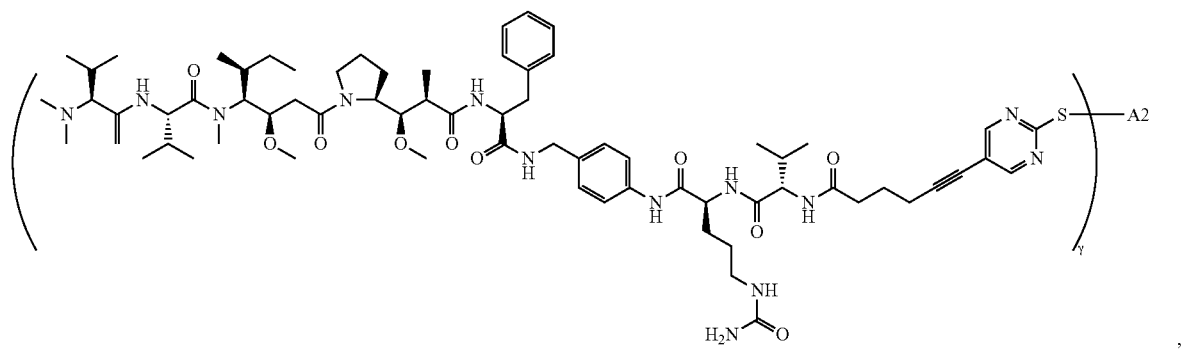
,
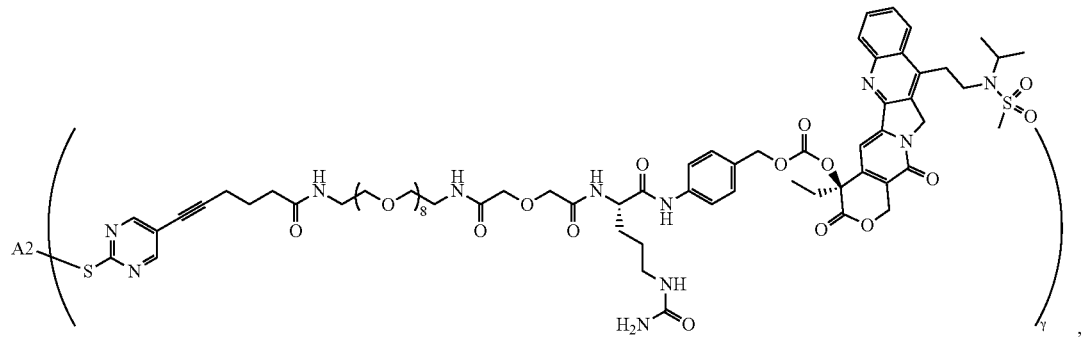
,
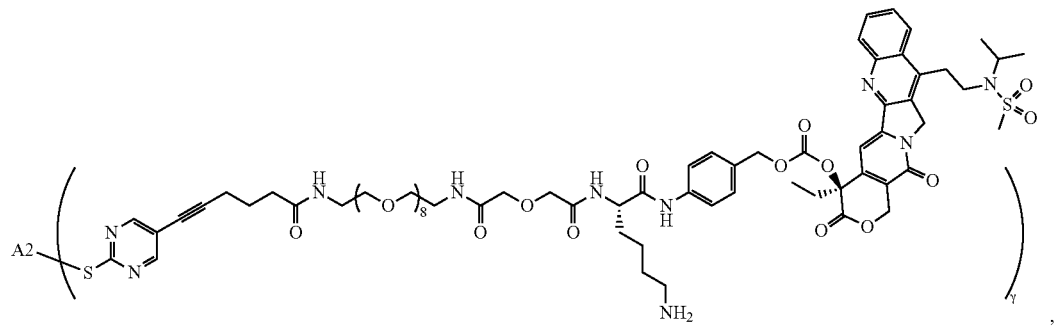
,

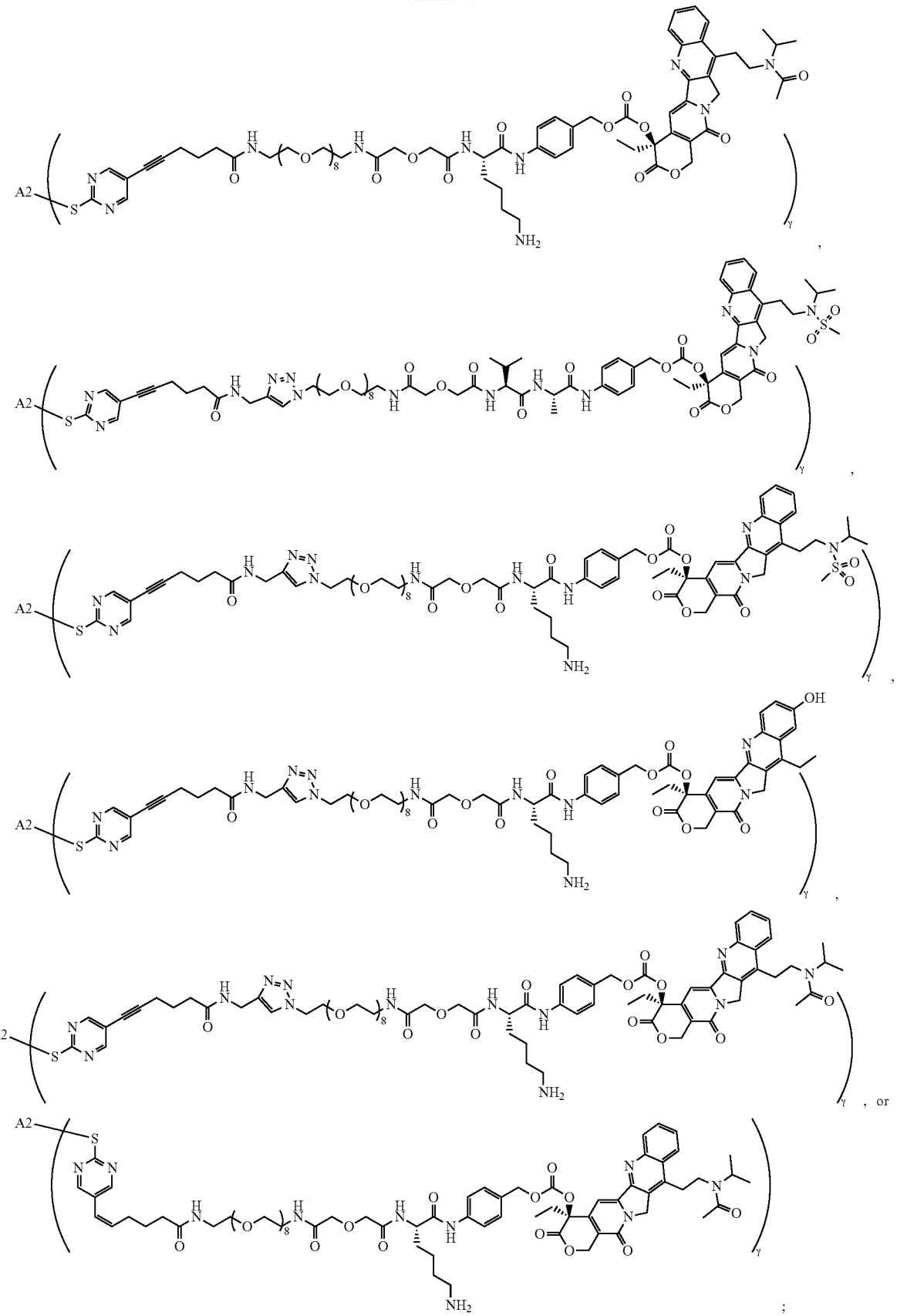

wherein, A2 is Trastuzumab, and γ is an integer or a decimal from 1 to 10; and preferably, γ is an integer or a decimal from 5 to 8, such as an integer or a decimal from 6-7, 6-7.5, 6-8, 6.5-7, 6.5-7.5, 6.5-8, 7-8 or 7.5-8.

In some preferred embodiments, the conjugate is:

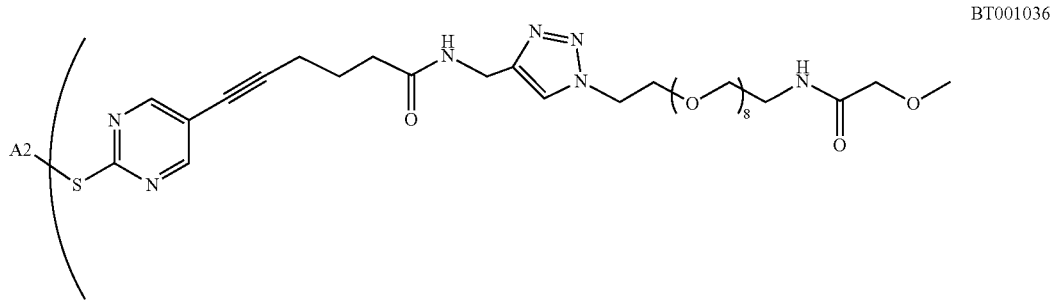

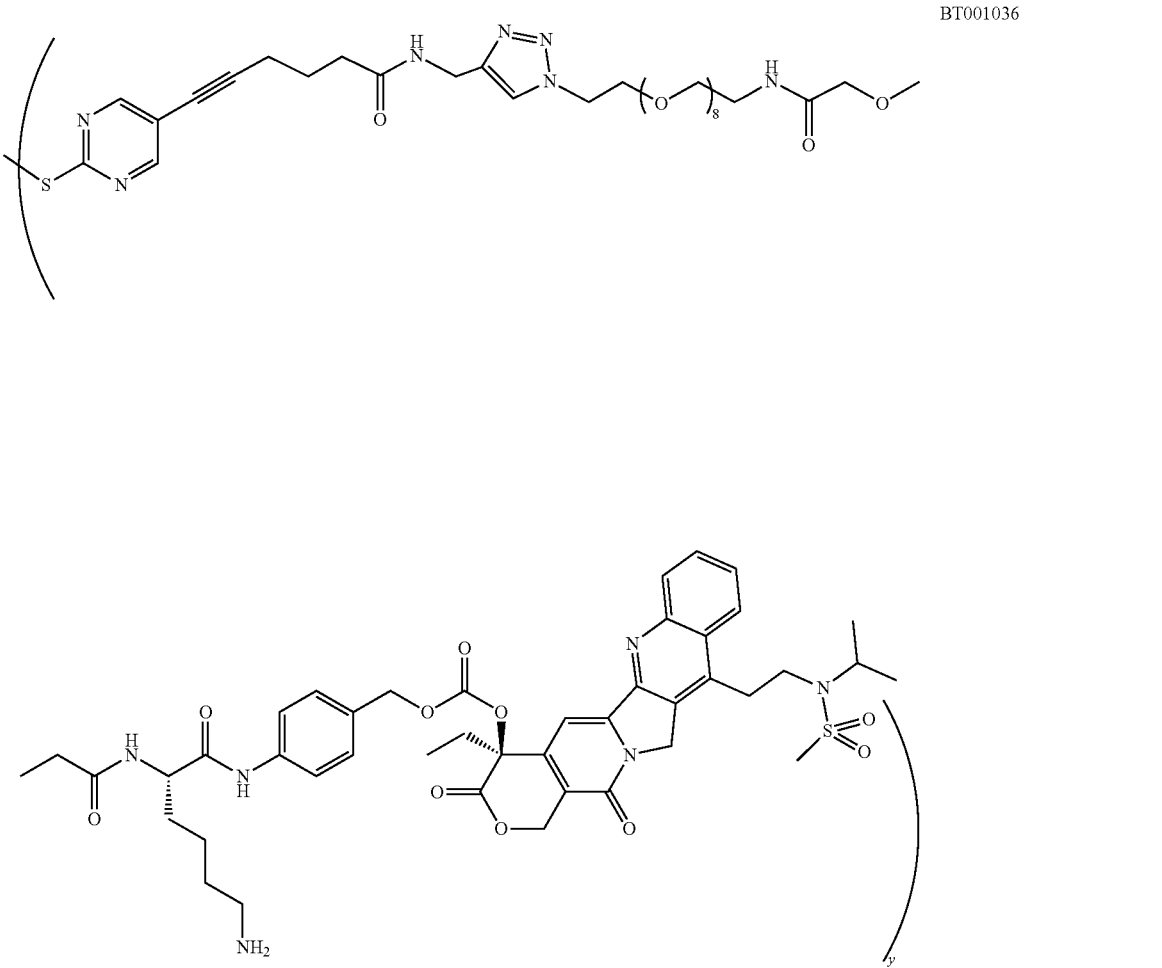

wherein, A2 is Trastuzumab, and γ is an integer or a decimal from 1 to 10; and preferably, γ is an integer or a decimal from 5 to 8, such as an integer or a decimal from 6-7, 6-7.5, 6-8, 6.5-7, 6.5-7.5, 6.5-8, 7-8 or 7.5-8.

In some preferred embodiments, the conjugate is:

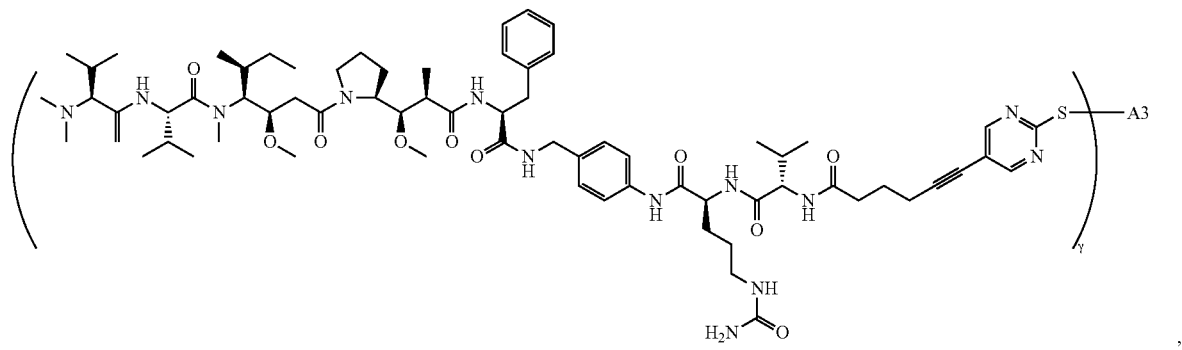

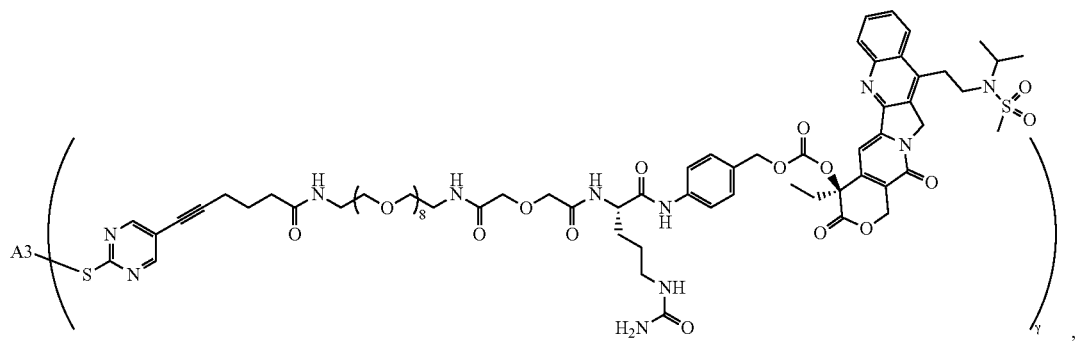
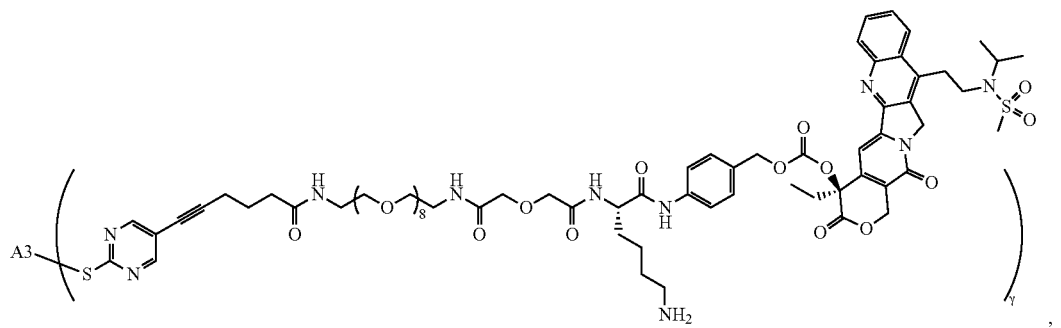
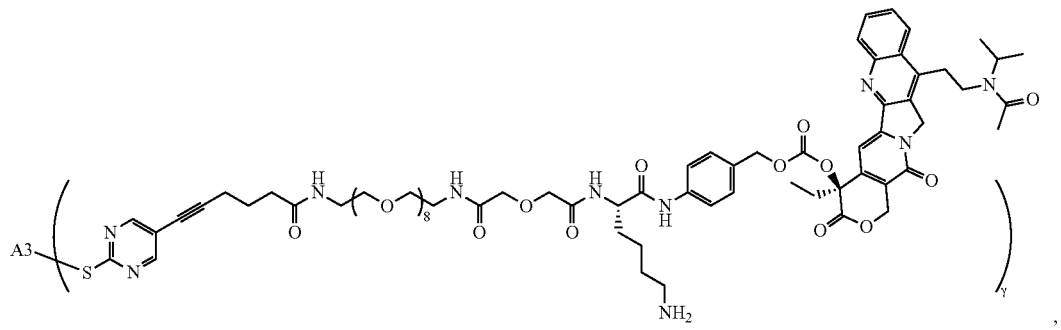
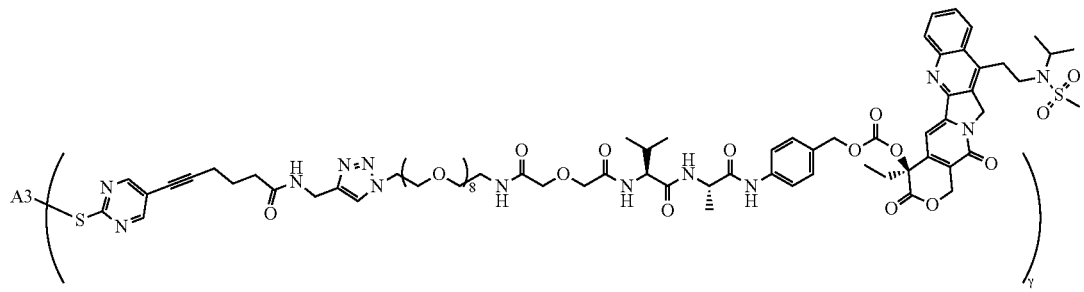
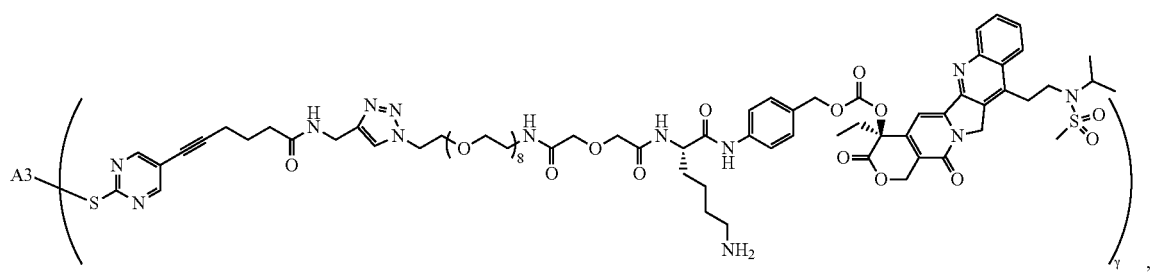

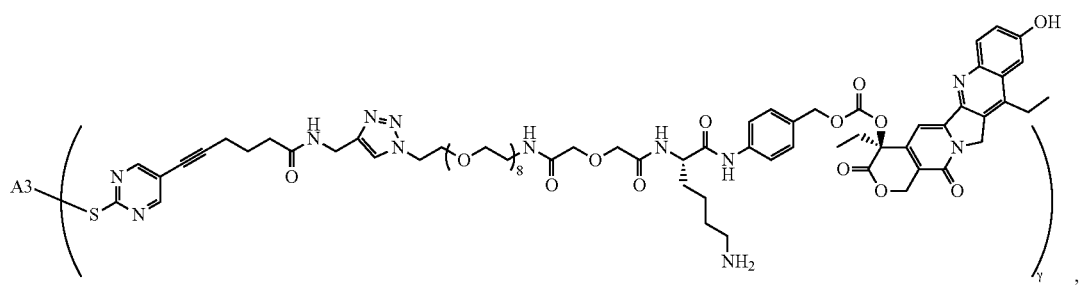
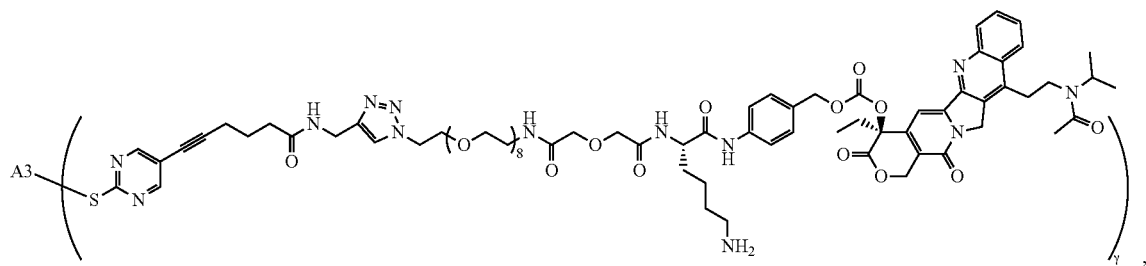
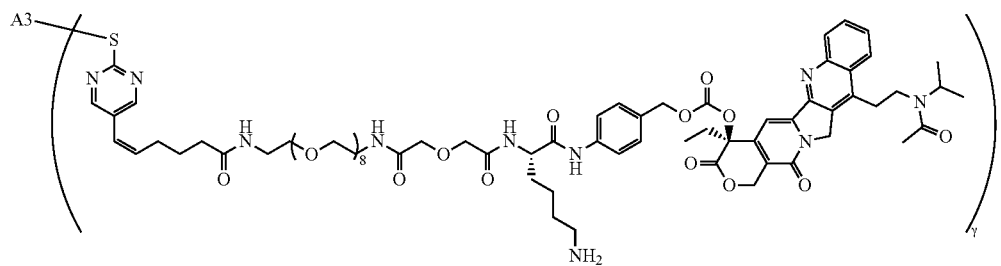
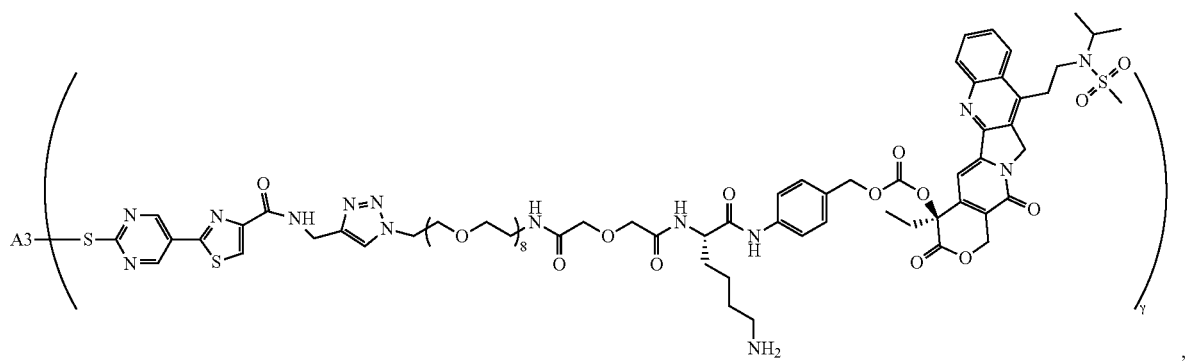
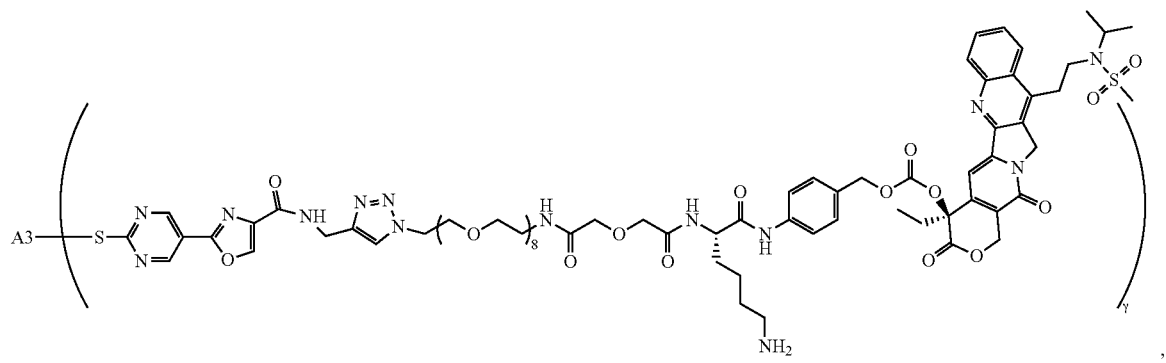

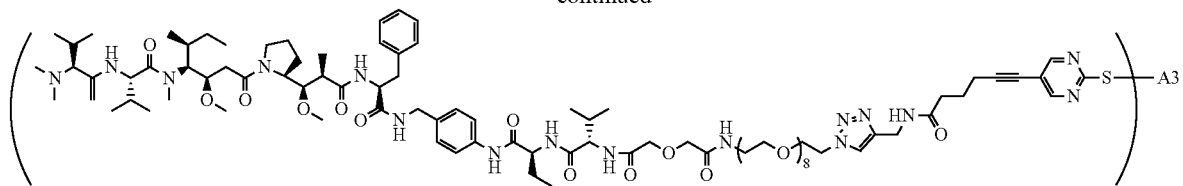
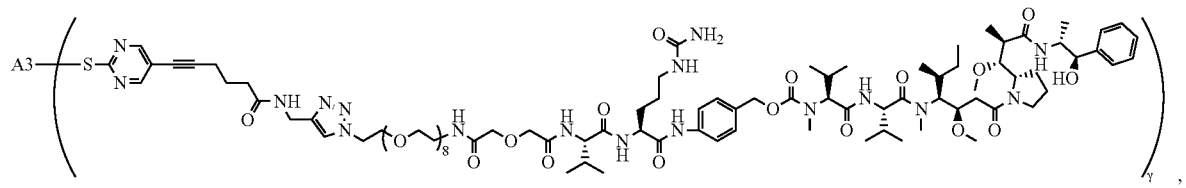
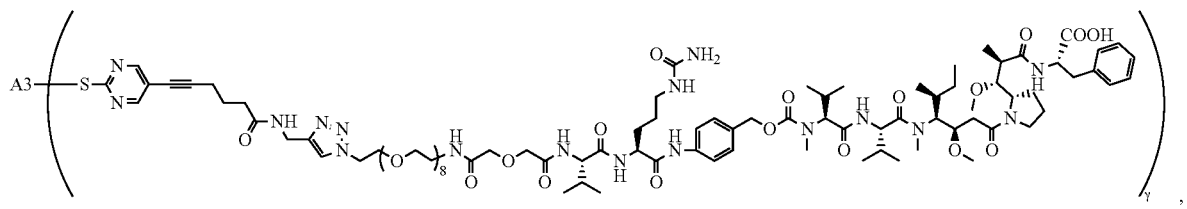
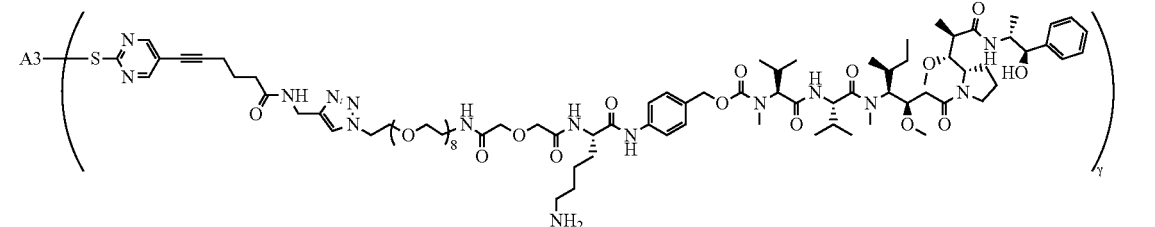
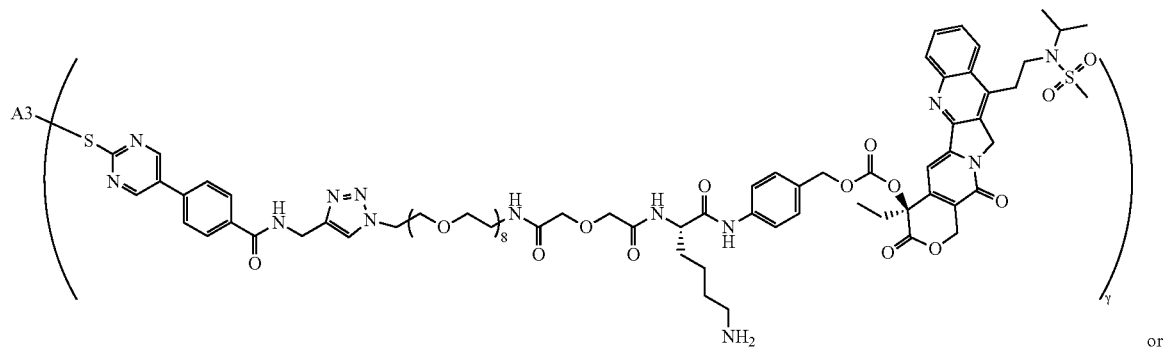
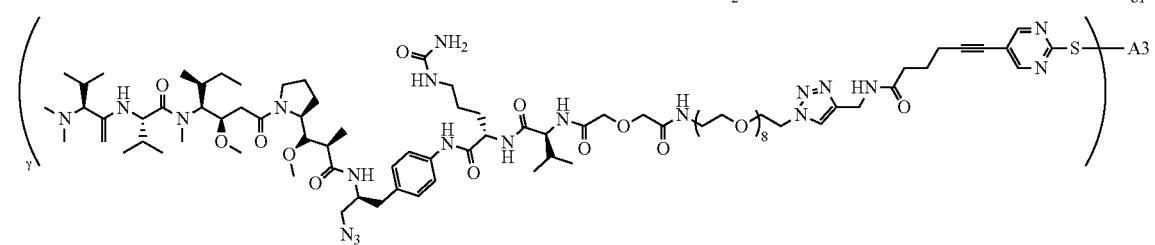
wherein, A3 is Pertuzumab, and γ is an integer or a decimal from 1 to 10; and preferably, γ is an integer or a decimal from 5 to 8, such as an integer or a decimal from 6-7, 6-7.5, 6-8, 6.5-7, 6.5-7.5, 6.5-8, 7-8 or 7.5-8.

In some preferred embodiments, the conjugate is:
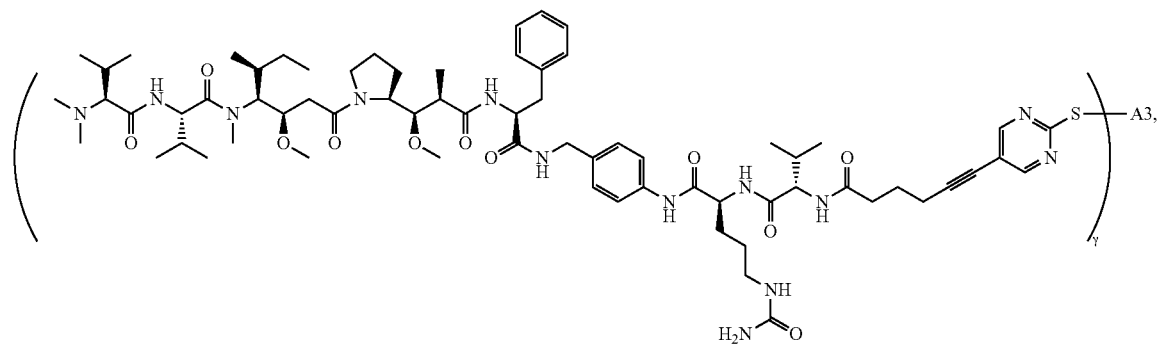
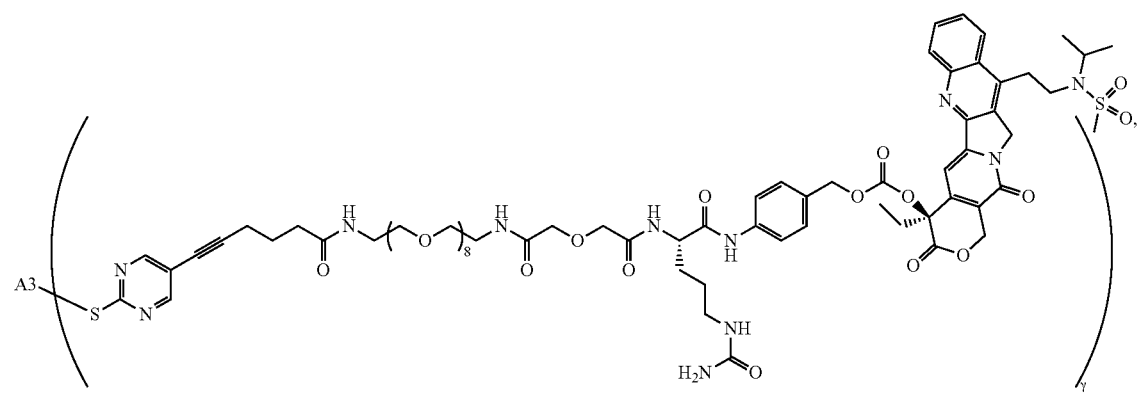
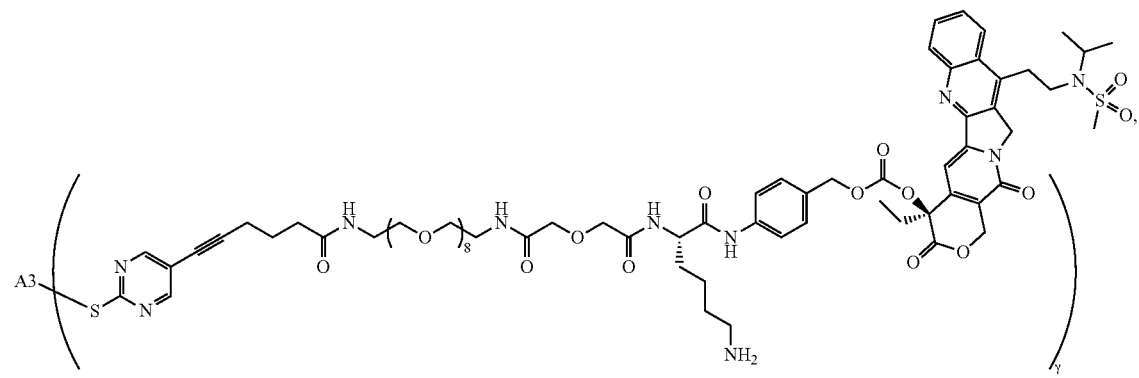
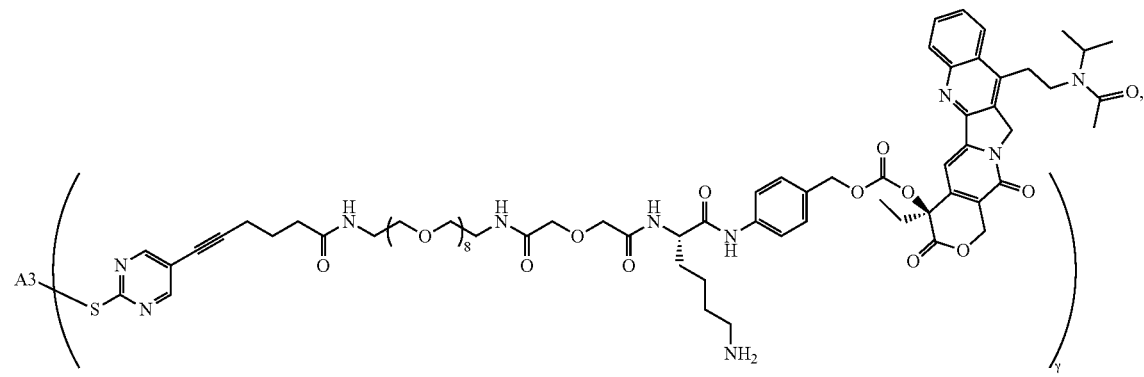

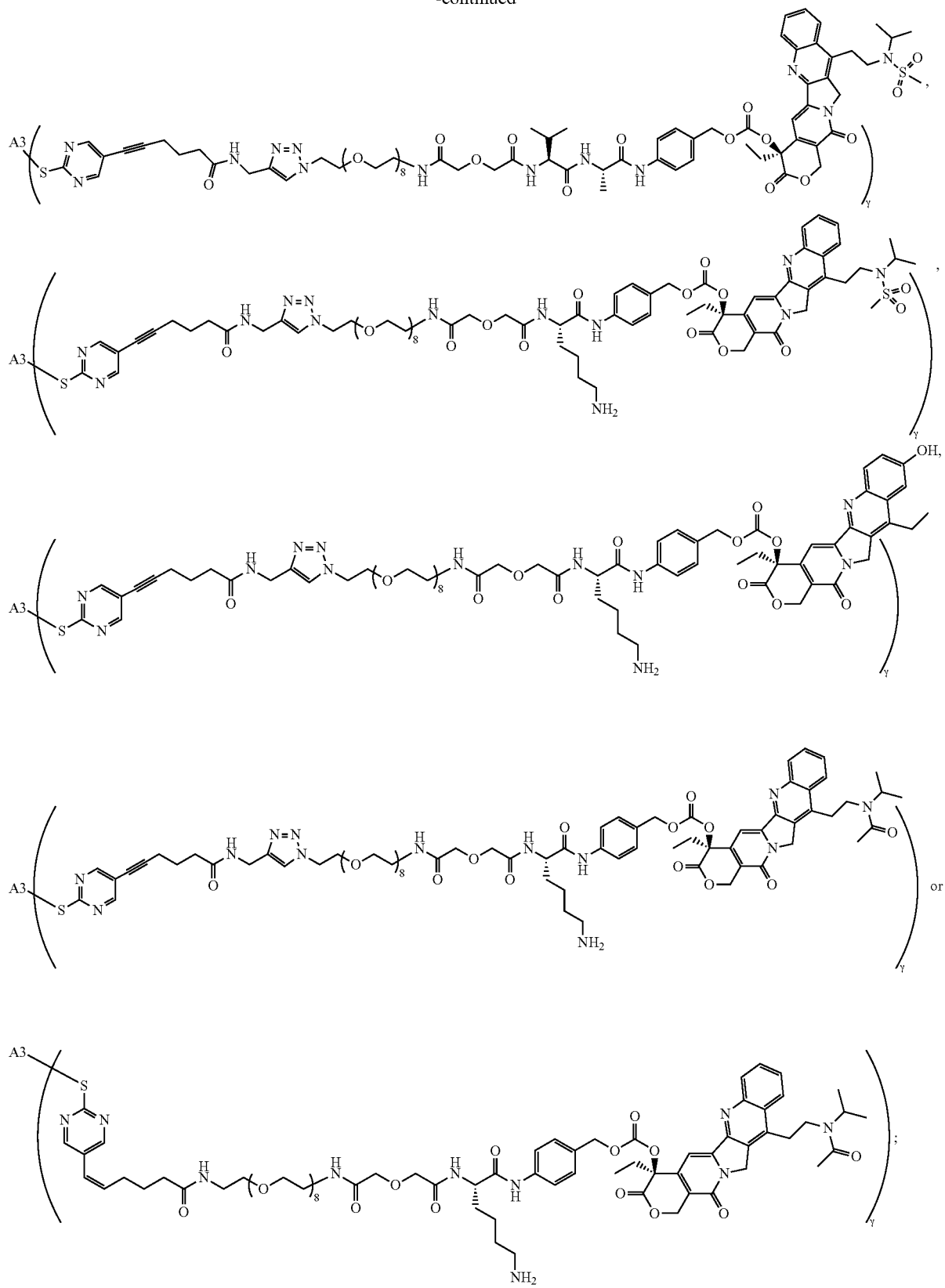
wherein, A3 is Pertuzumab, and γ is an integer or a decimal from 1 to 10; and preferably, γ is an integer or a decimal from 5 to 8, such as an integer or a decimal from 6-7, 6-7.5, 6-8, 6.5-7, 6.5-7.5, 6.5-8, 7-8 or 7.5-8.

In some preferred embodiments, the conjugate is:
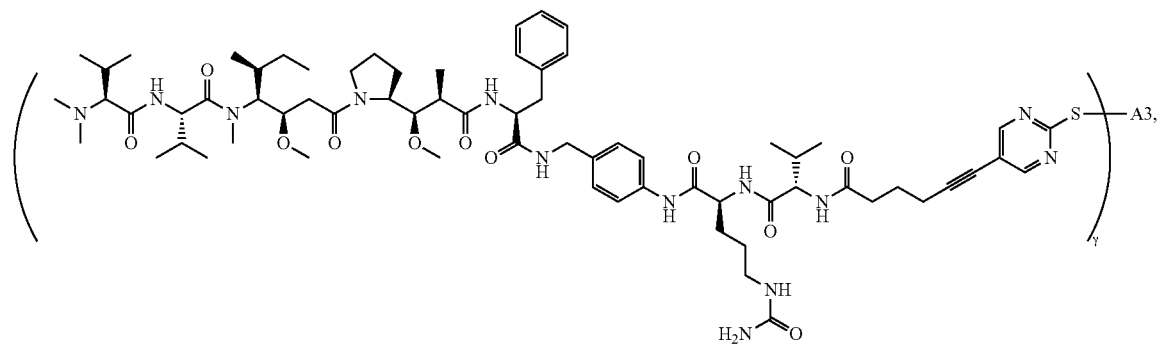
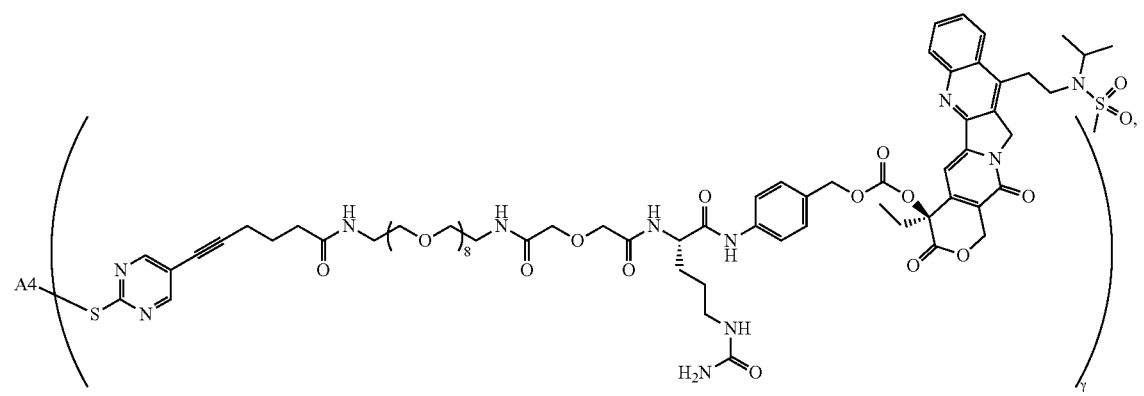
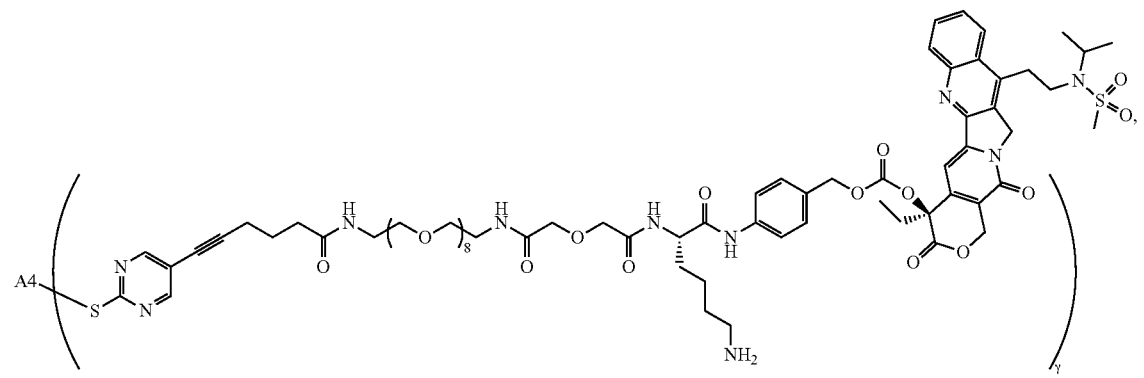
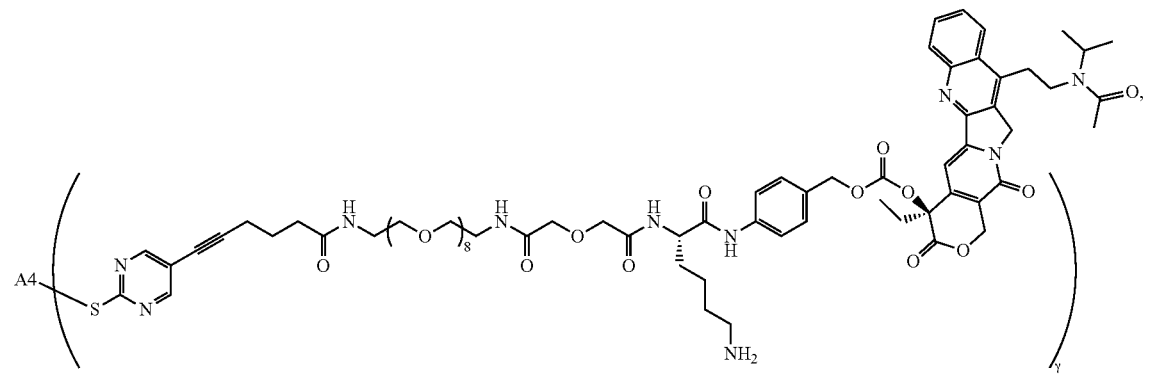

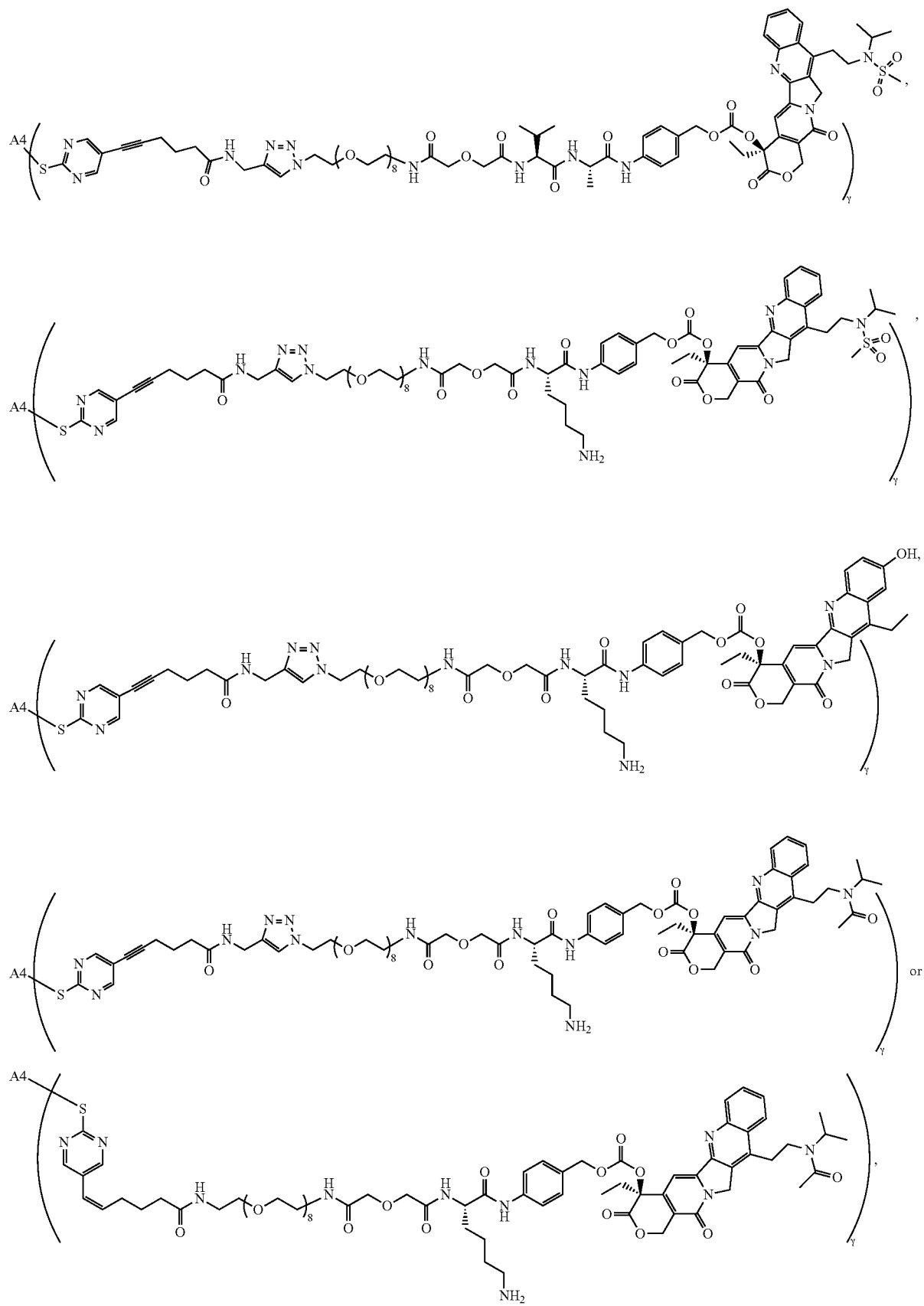

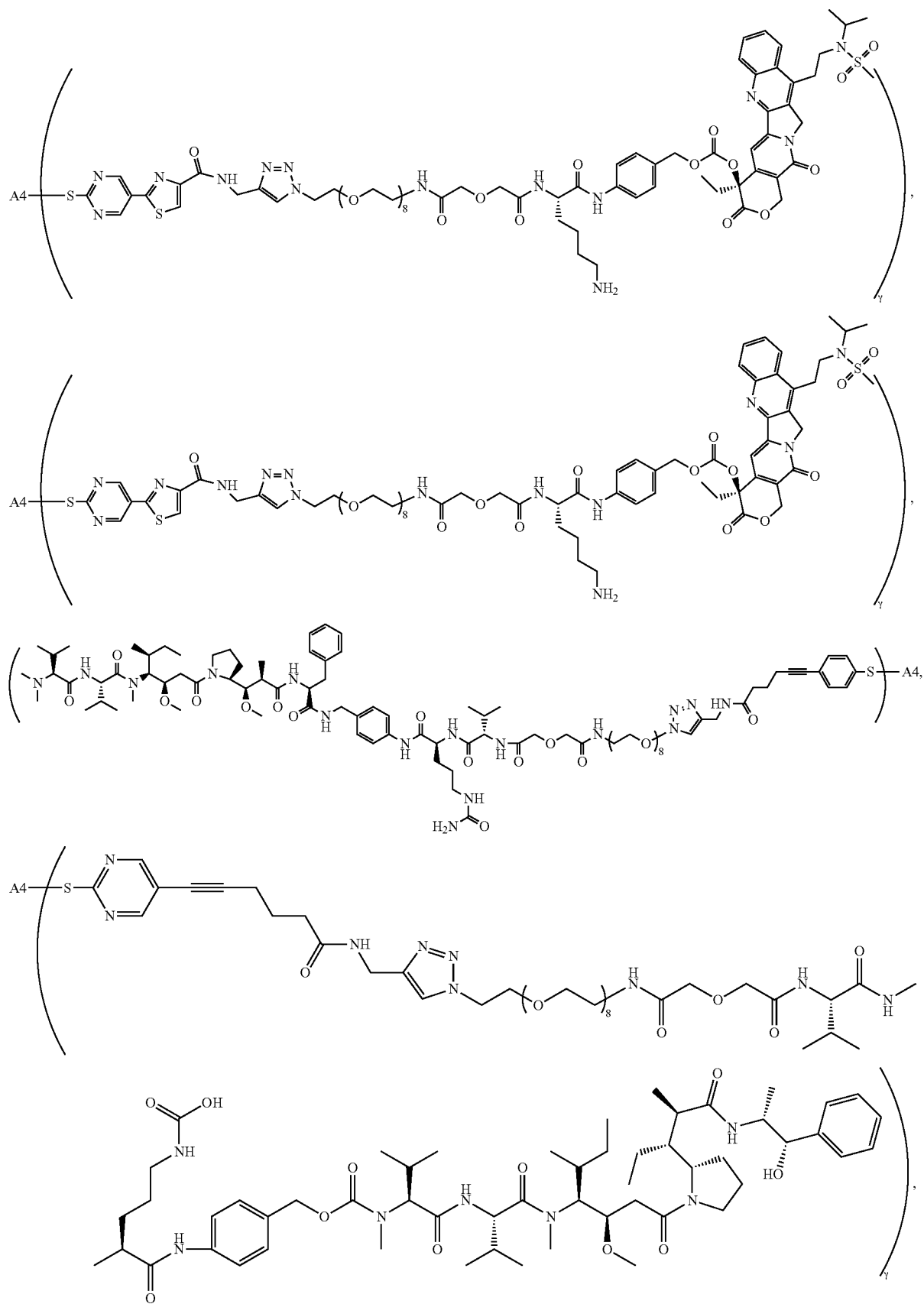

199
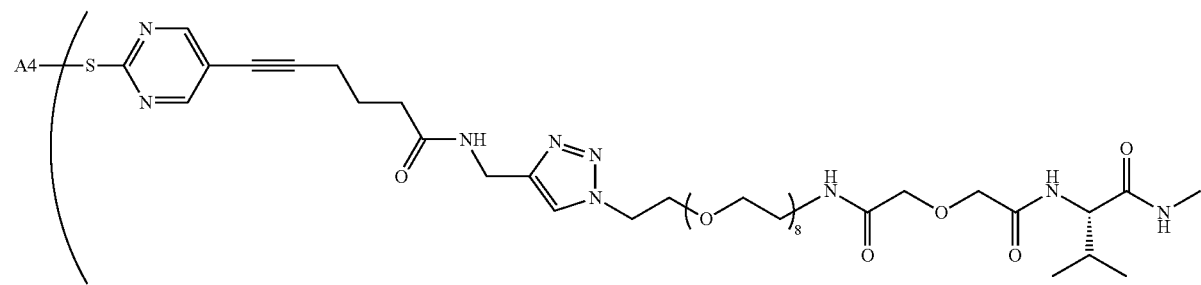
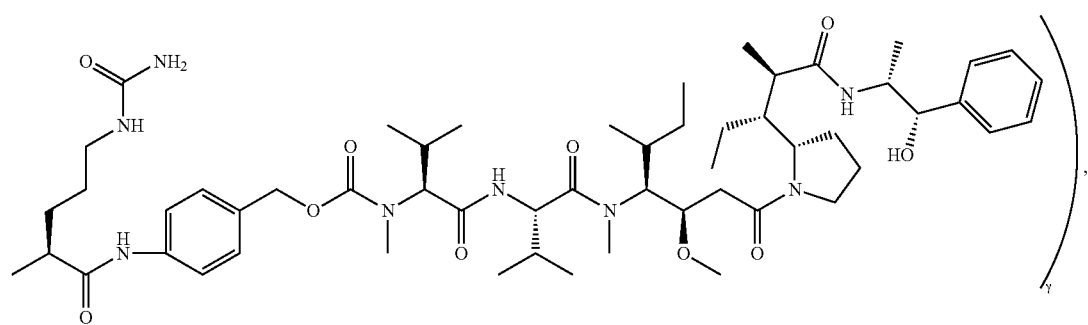
200
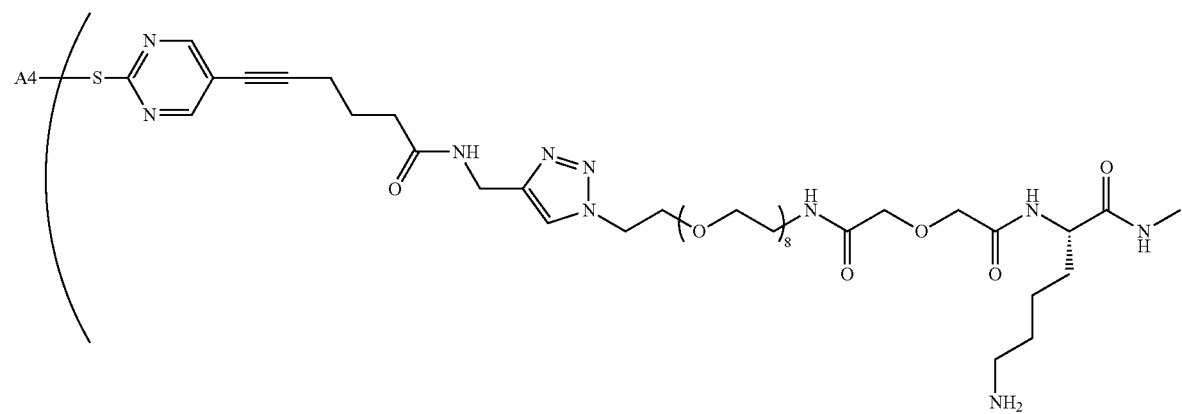
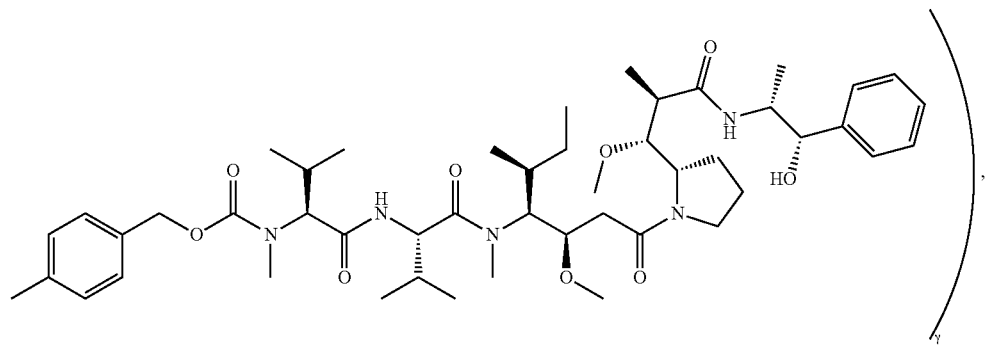

-continued
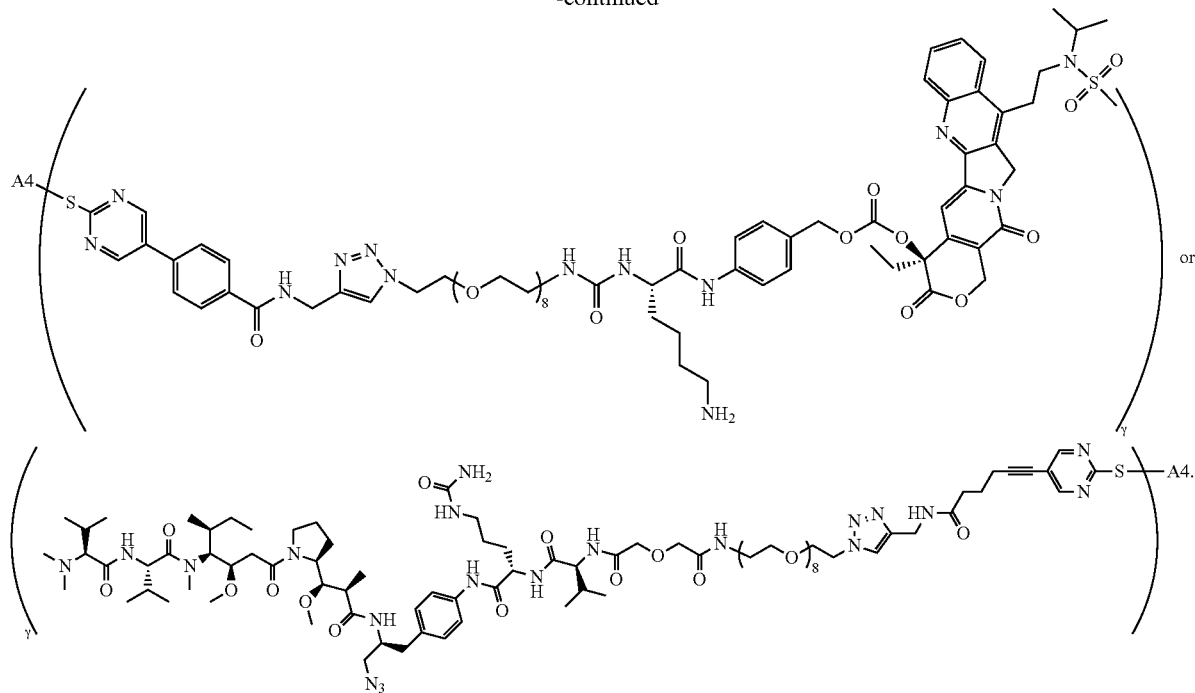
wherein, A4 is antibody M1, and γ is an integer or a decimal from 1 to 10; and preferably, γ is an integer or a decimal from 5 to 8, such as an integer or a decimal from 6-7, 6-7.5, 6-8, 6.5-7, 6.5-7.5, 6.5-8, 7-8 or 7.5-8.
In some preferred embodiments, the conjugate is:
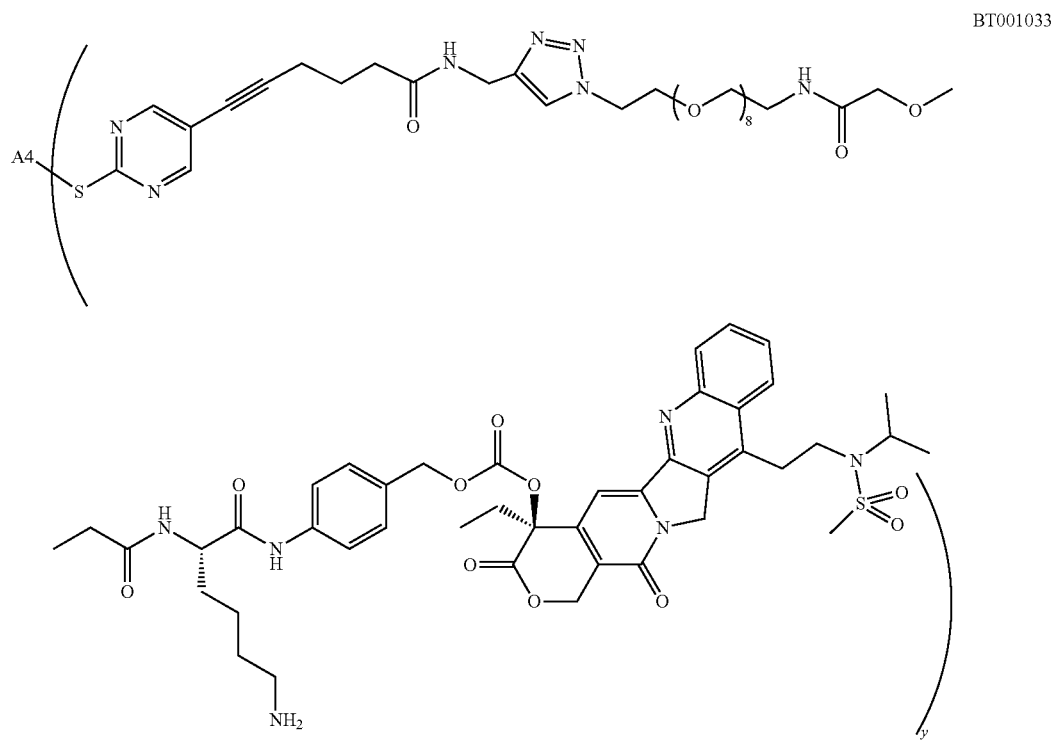

wherein, A4 is antibody M1, and γ is an integer or a decimal from 1 to 10; and preferably, γ is an integer or a decimal from 5 to 8, such as an integer or a decimal from 6-7, 6-7.5, 6-8, 6.5-7, 6.5-7.5, 6.5-8, 7-8 or 7.5-8.
In some preferred embodiments, the conjugate is:
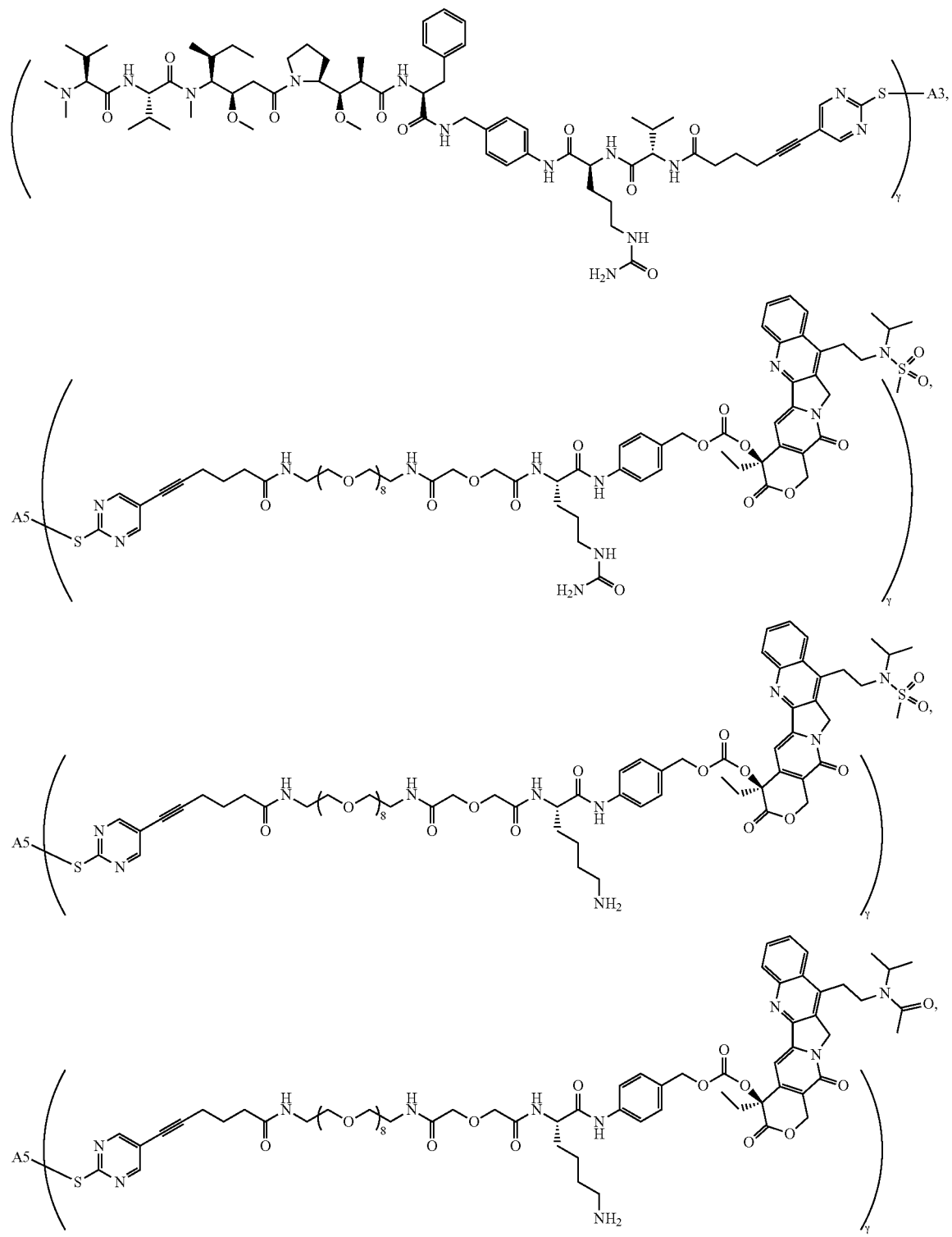

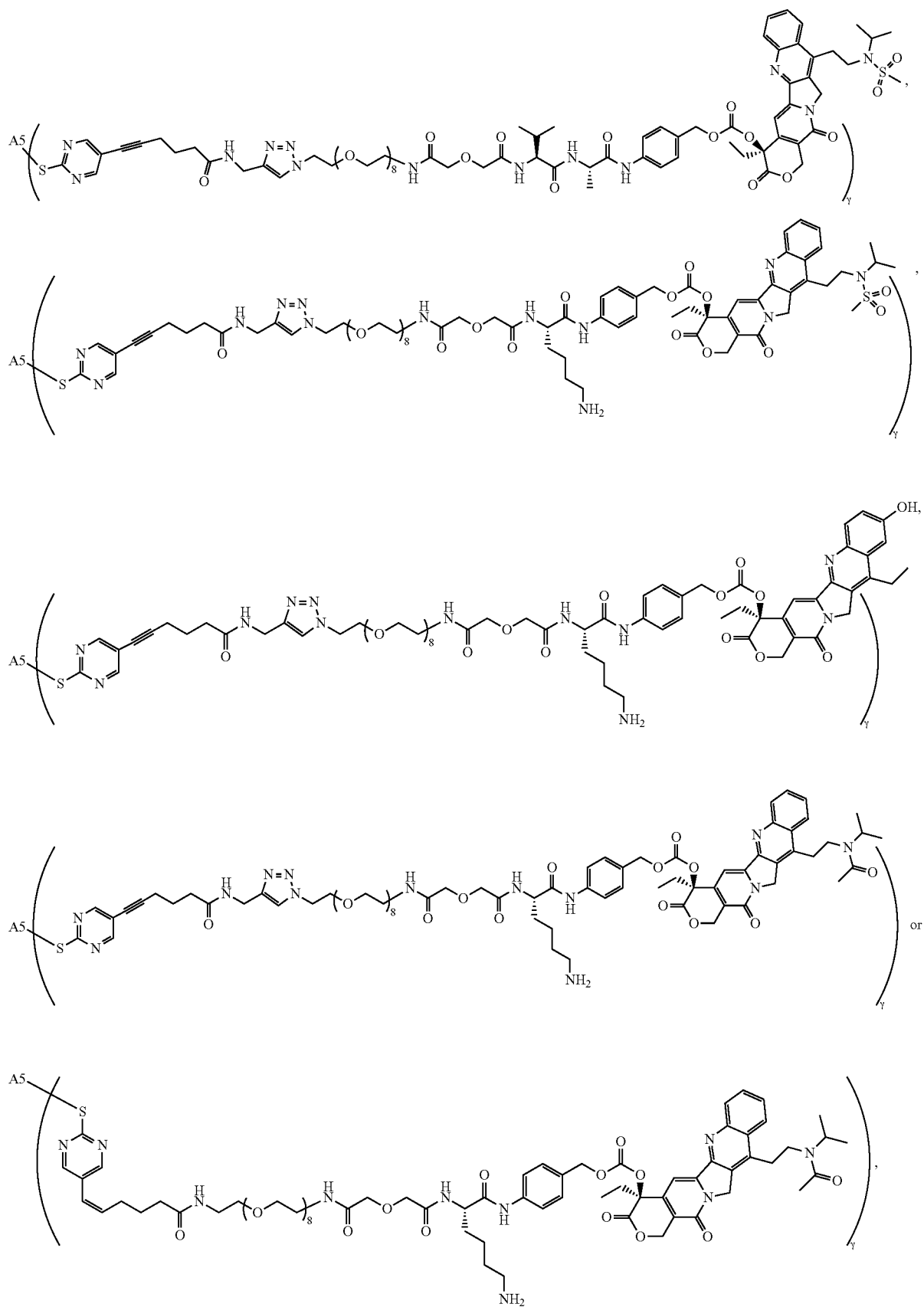

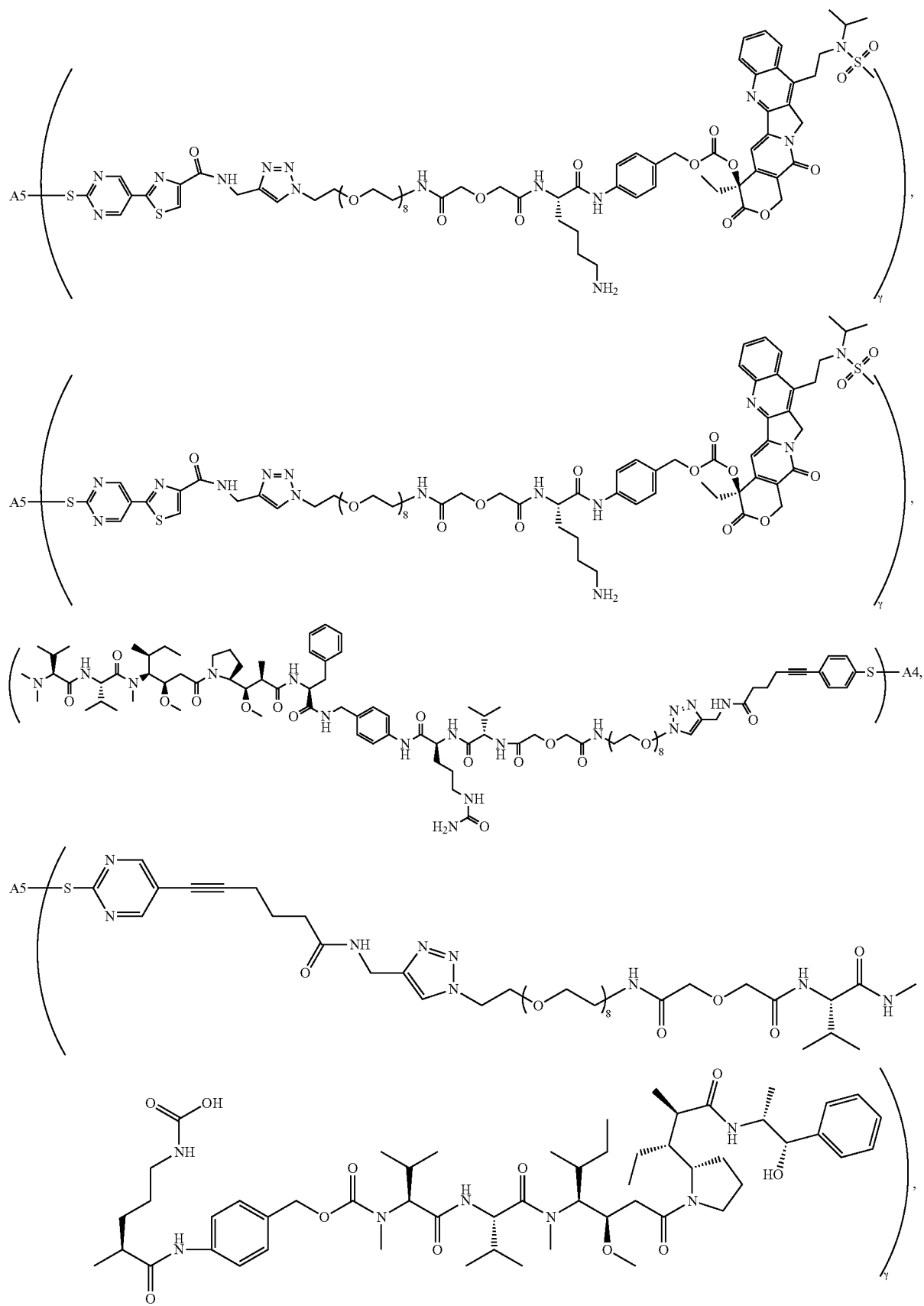

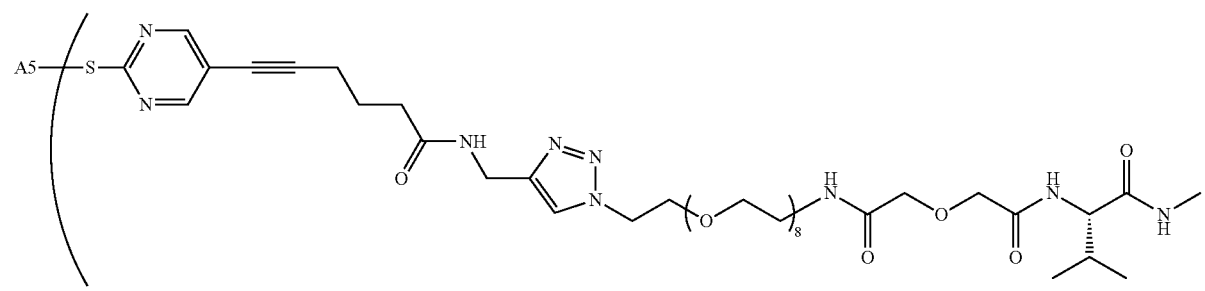
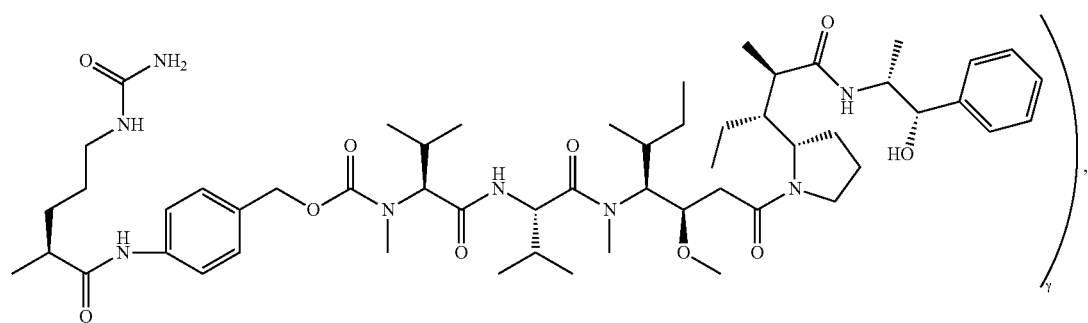
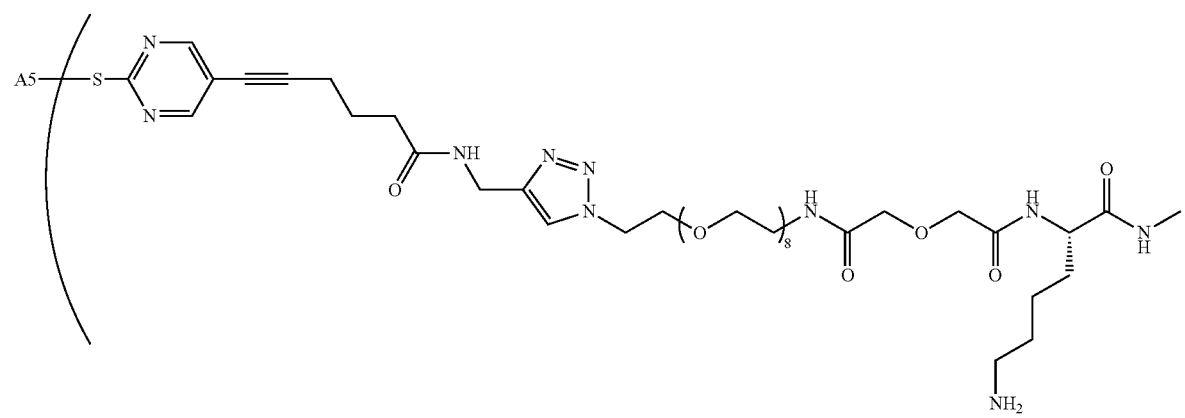
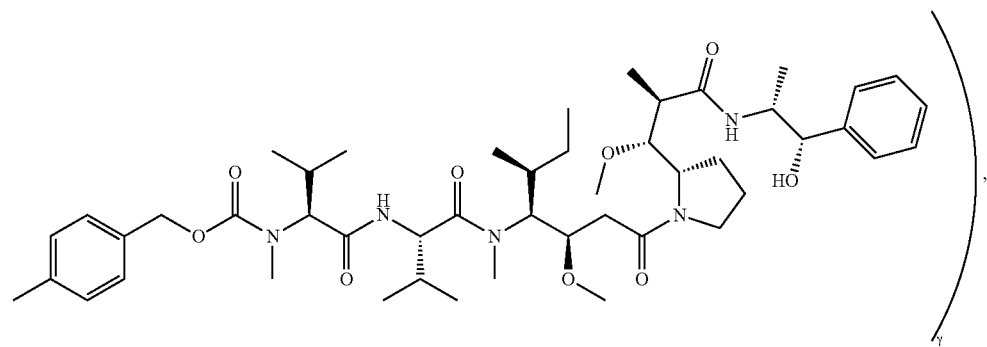

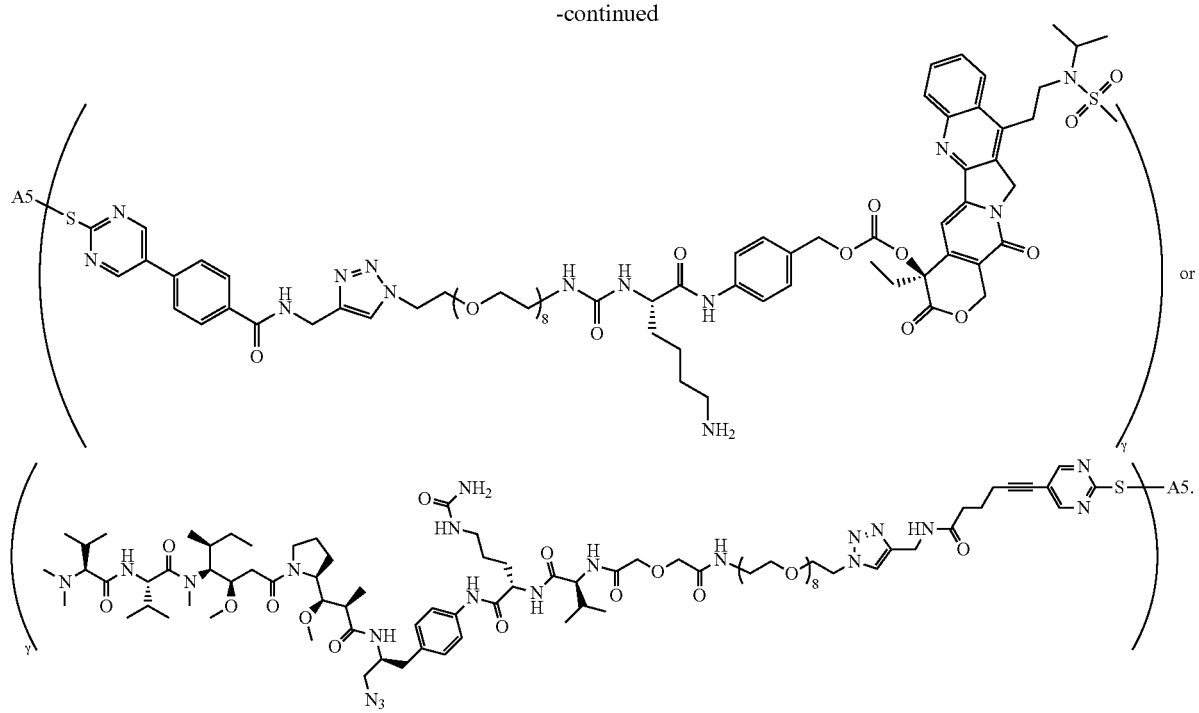
wherein, A5 is antibody M2, and γ is an integer or a decimal from 1 to 10; and preferably, γ is an integer or a decimal from 5 to 8, such as an integer or a decimal from 6-7, 6-7.5, 6-8, 6.5-7, 6.5-7.5, 6.5-8, 7-8 or 7.5-8.
In some preferred embodiments, the conjugate is:
BT001034
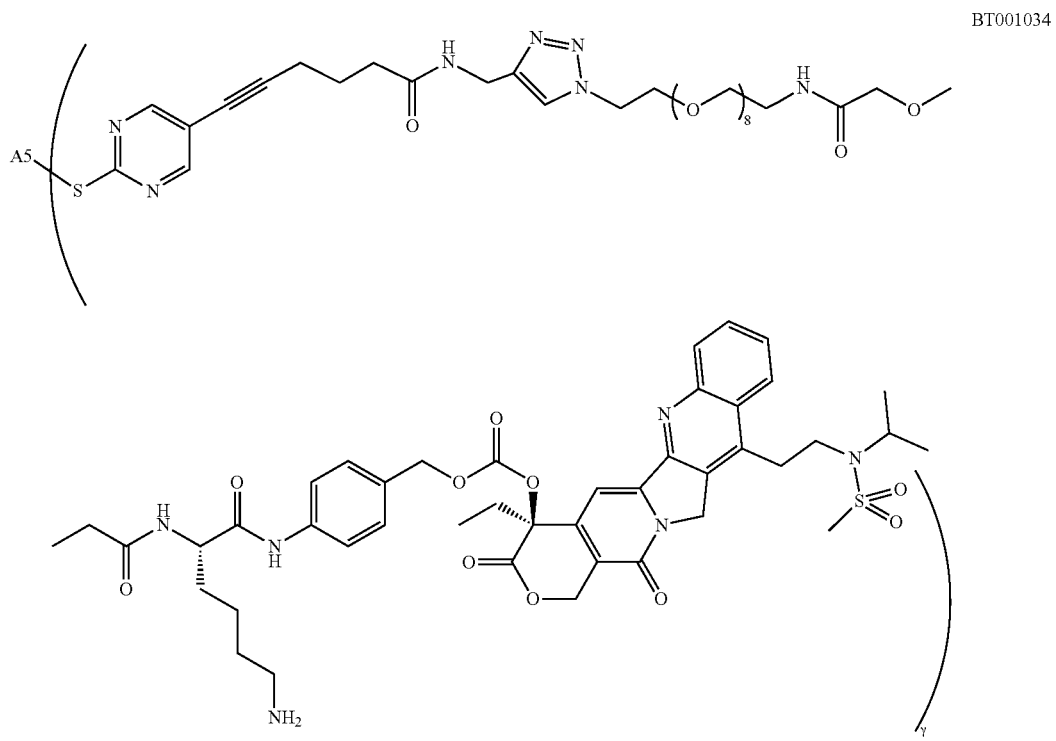

wherein, A5 is antibody M2, and γ is an integer or a decimal from 1 to 10; and preferably, γ is an integer or a decimal from 5 to 8, such as an integer or a decimal from 6-7, 6-7.5, 6-8, 6.5-7, 6.5-7.5, 6.5-8, 7-8 or 7.5-8.
In some preferred embodiments, the conjugate is:
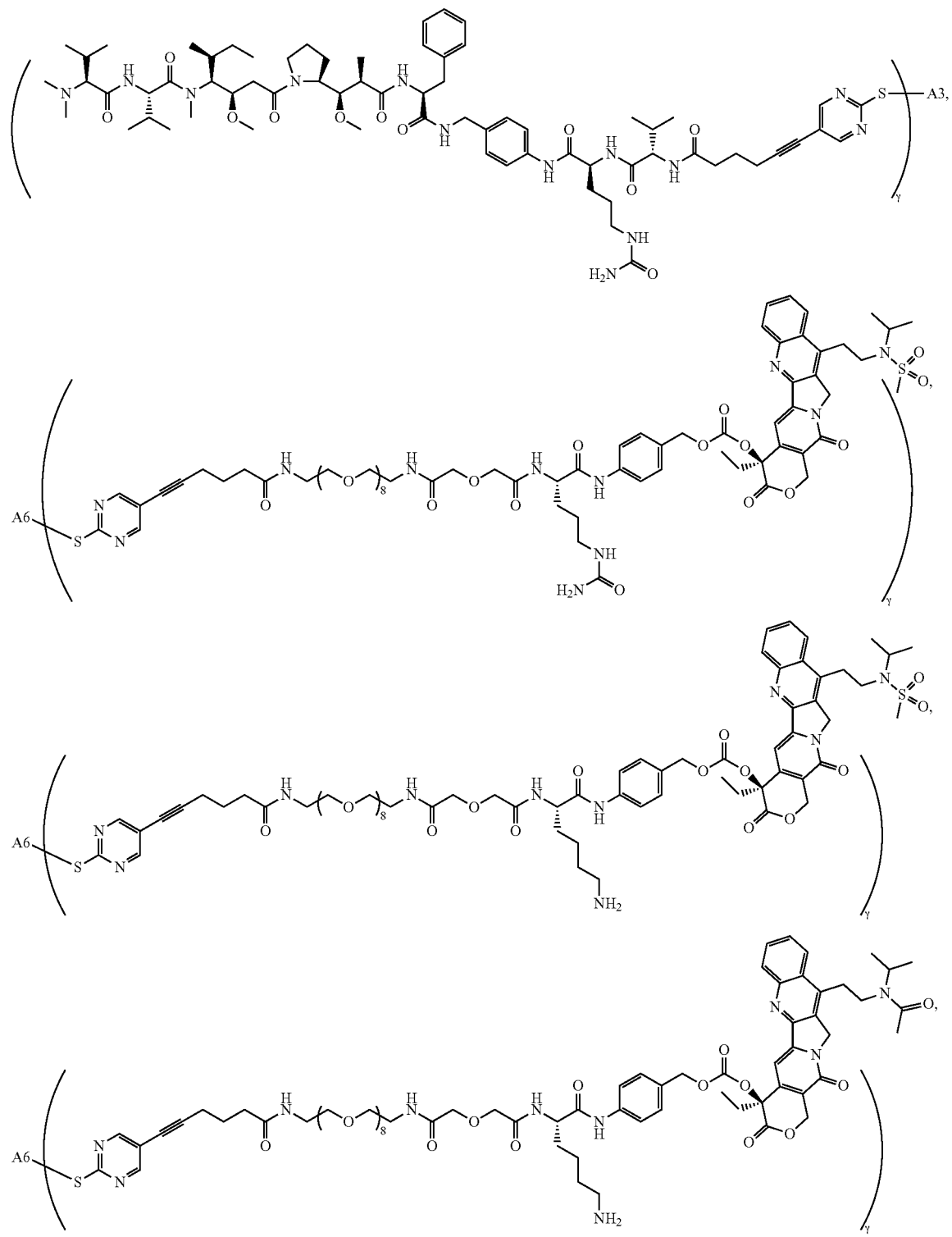

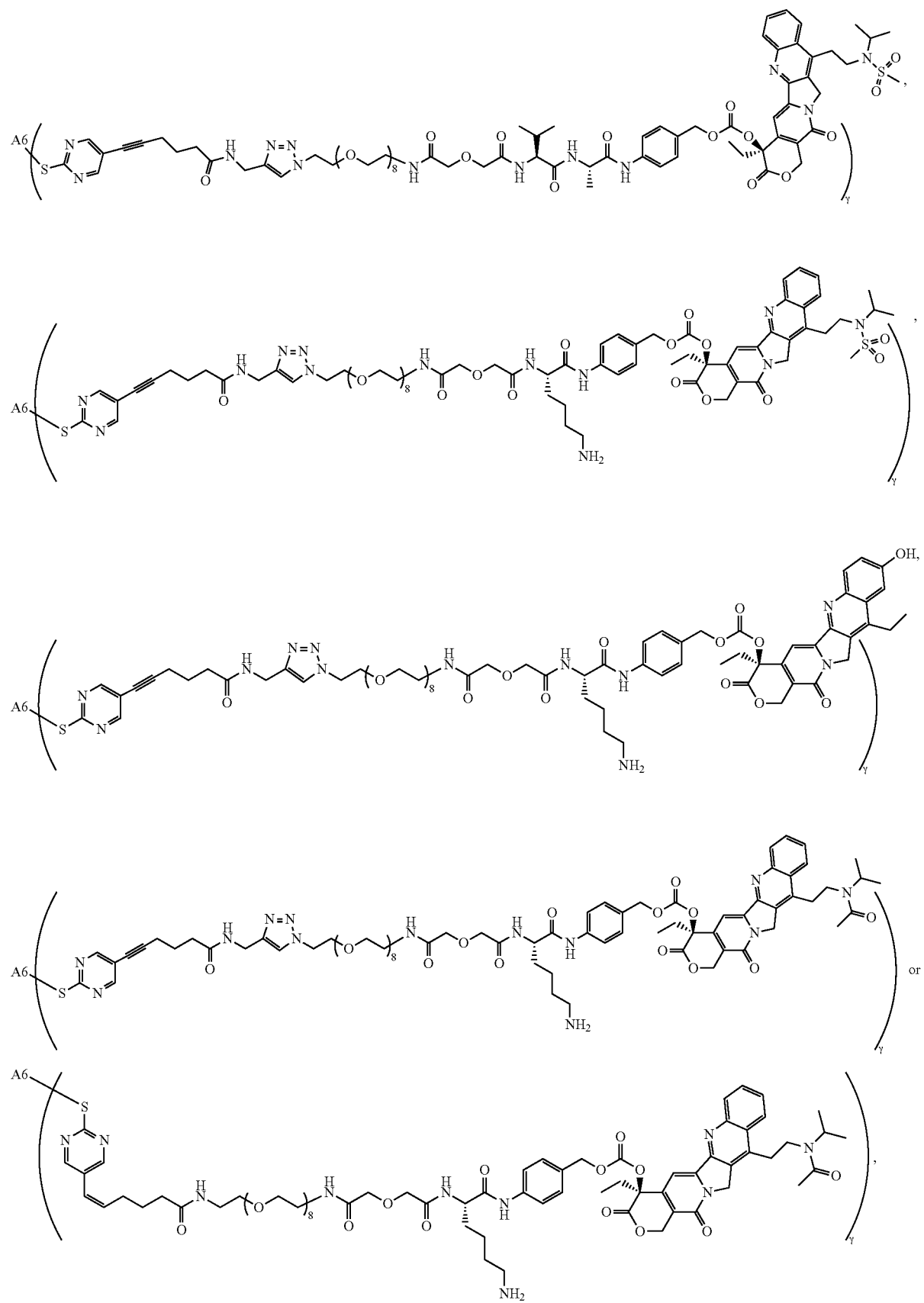

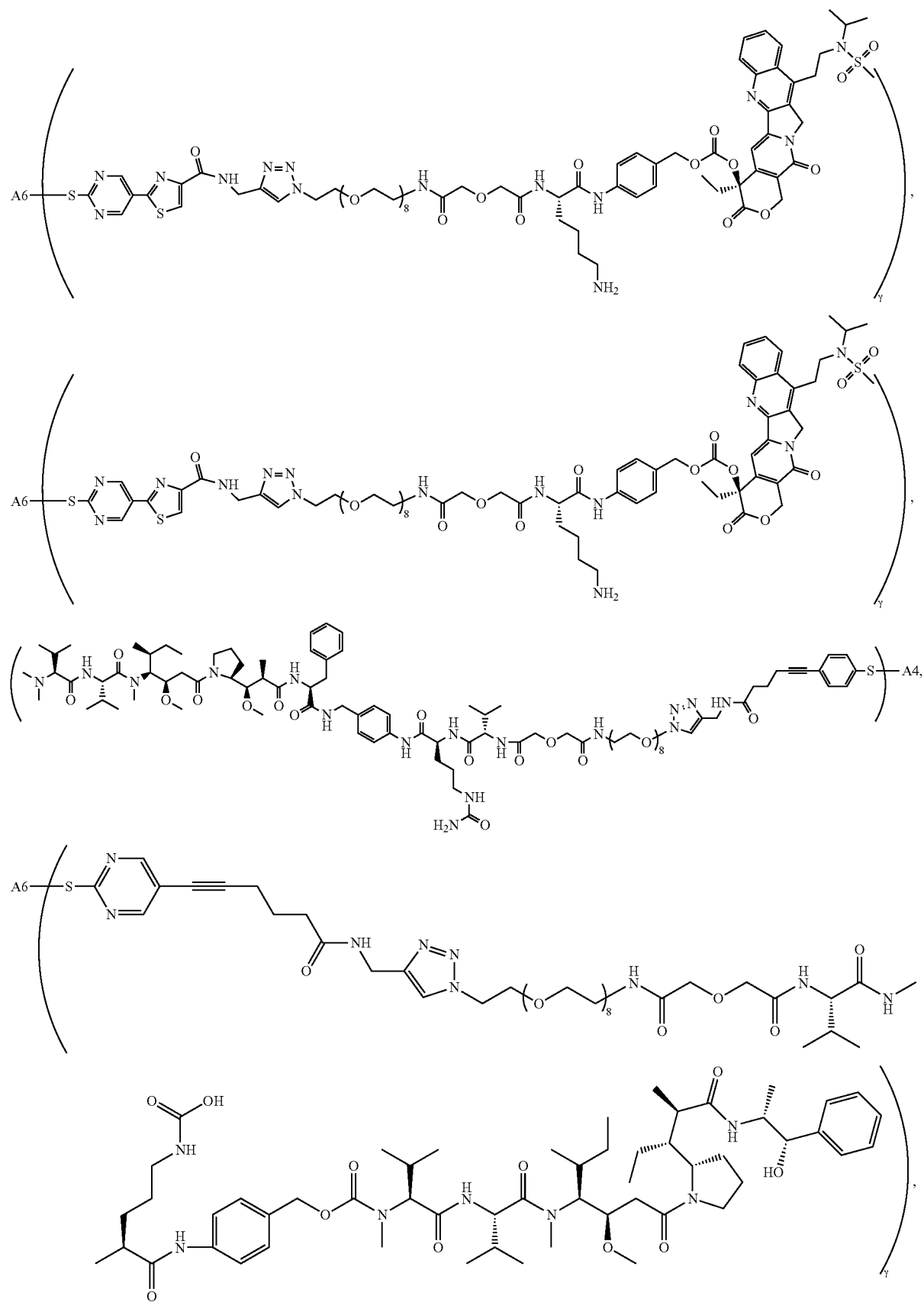

219
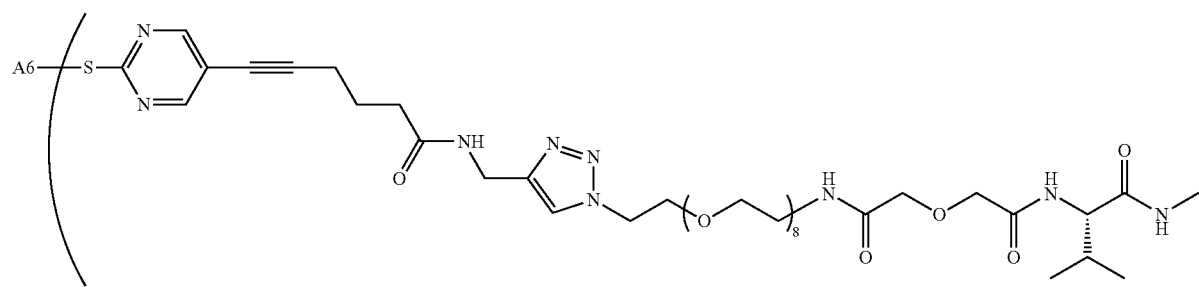
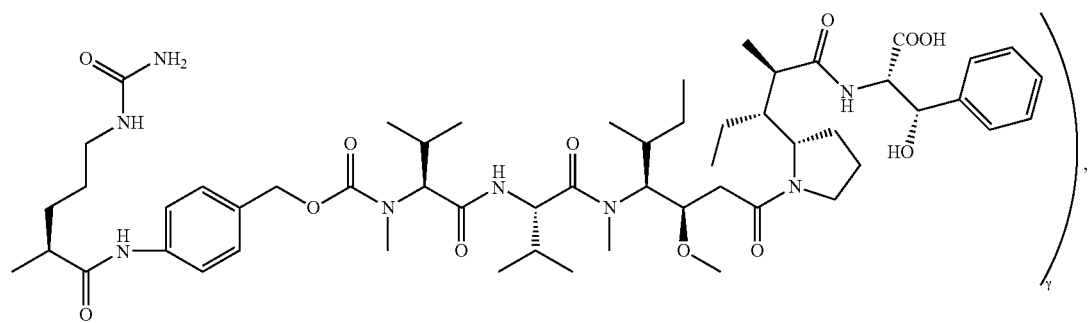
220
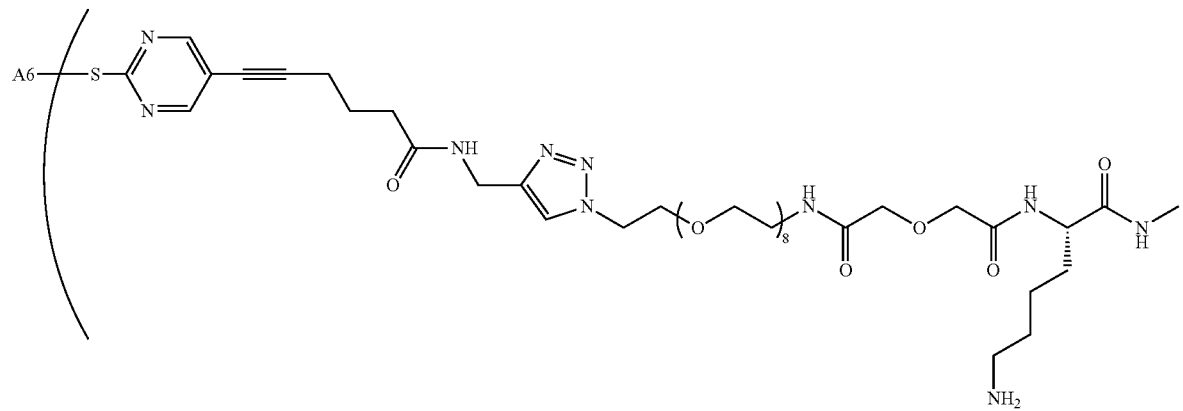
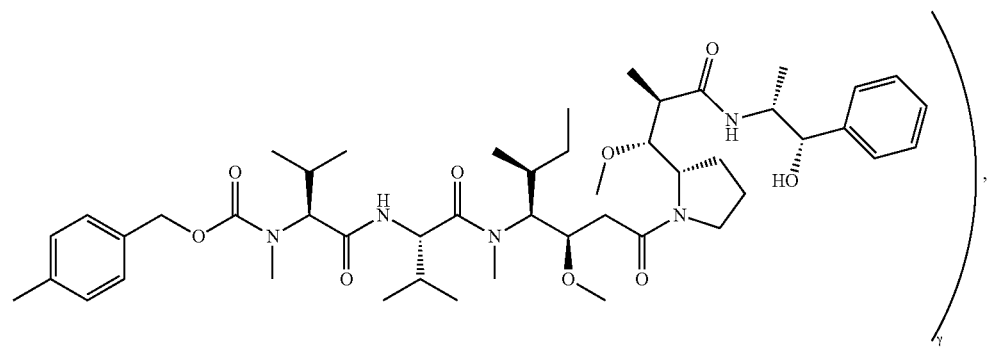

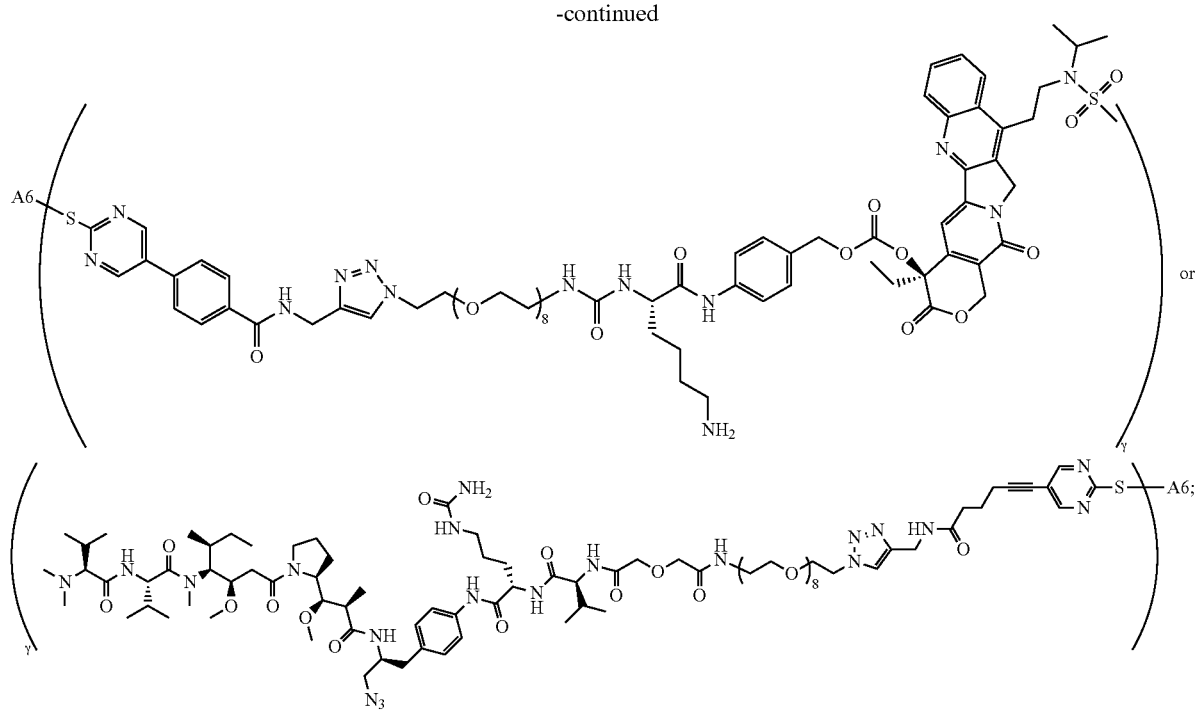
wherein A6 is antibody M3, and γ is an integer or a decimal from 1 to 10; and preferably, γ is an integer or a decimal from 5 to 8, such as an integer or a decimal from 6-7, 6-7.5, 6-8, 6.5-7, 6.5-7.5, 6.5-8, 7-8 or 7.5-8.
In some preferred embodiments, the conjugate is:
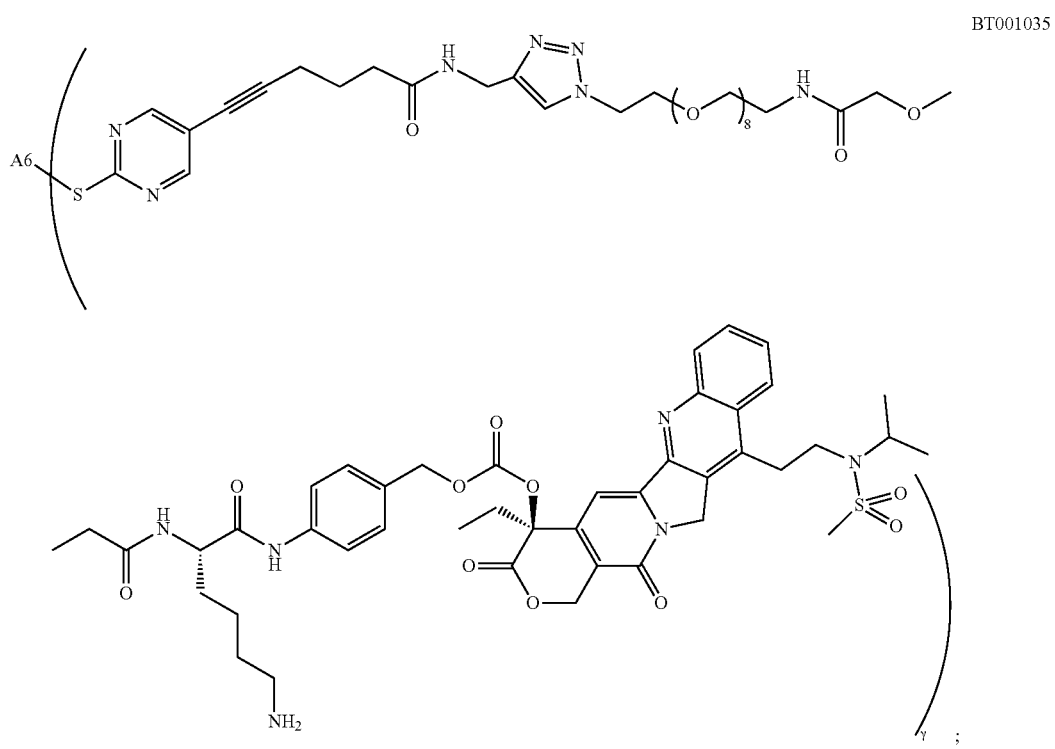

wherein A6 is antibody M3, and γ is an integer or a decimal from 1 to 10; and preferably, γ is an integer or a decimal from 5 to 8, such as an integer or a decimal from 6-7, 6-7.5, 6-8, 6.5-7, 6.5-7.5, 6.5-8, 7-8 or 7.5-8.

In another aspect, the disclosure provides a method for preparing the conjugate of the second aspect, comprising a step of coupling the linker of the compound of formula (I) with an active group of the targeting moiety.

In some preferred embodiments, the method comprises a step of opening a disulfide bond of the targeting moiety by a reductant (e.g., TCEP) to obtain a sulfydryl group.

In some preferred embodiments, the method comprises a step of forming a C—S bond between the linker of the compound of formula (I) and the sulfydryl group of the targeting moiety.

In some preferred embodiments, the targeting moiety is an anti-Her 2 monoclonal antibody (e.g., Trastuzumab, Pertuzumab) or an anti-Trop-2 monoclonal antibody (e.g., Sacituzumab, M1, M2 or M3), or an active fragment or mutant thereof.

In some preferred embodiments, the molar ratio of the targeting moiety to the compound of formula (I) is 1:(1-20); preferably, the coupling is carried out in water and/or an organic solvent; preferably, the organic solvent is selected from N,N-dimethylformamide, dimethylsulfoxide, N-methylpyrrolidone, nitriles (e.g., acetonitrile), alcohols (e.g., methanol, ethanol) or any combination thereof.

In some preferred embodiments, the method further comprises a step of purifying the coupling product; preferably, the coupling product is purified by chromatography (e.g., one or more of ion exchange chromatography, hydrophobic chromatography, reverse phase chromatography or affinity chromatography).

In another aspect, the disclosure provides a pharmaceutical composition comprising the compound of the first aspect of the disclosure or a pharmaceutically acceptable salt thereof, or the conjugate of the second aspect, and one or more pharmaceutical excipients.

In another aspect, the disclosure provides use of the compound of the first aspect or a pharmaceutically acceptable salt thereof or the conjugate of the second aspect in the manufacturer of a medicament for the treatment of a disease associated with an abnormal cell activity (e.g., cancer).

In some preferred embodiments, the cancer is a solid tumor or a non-solid tumor, such as esophageal cancer (e.g., esophageal adenocarcinoma, esophageal squamous cell carcinoma), a brain tumor, lung cancer (e.g., small cell lung cancer, non-small cell lung cancer), squamous cell carcinoma, bladder cancer, stomach cancer, ovarian cancer, peritoneal cancer, pancreatic cancer, breast cancer, head and neck cancer, cervical cancer, endometrial cancer, colorectal cancer, liver cancer, kidney cancer, non Hodgkin's lymphoma, central nervous system tumors (e.g., neuroglioma, glioblastoma multiforme, glioma or sarcoma), prostate cancer and thyroid cancer.

In another aspect, the disclosure provides use of the compound of the first aspect or a pharmaceutically acceptable salt thereof or the conjugate or pharmaceutical composition of the second aspect in treating a disease associated with an abnormal cell activity (e.g., cancer).

In another aspect, the disclosure provides a method of treating a disease associated with an abnormal cell activity (e.g., cancer), comprising a step of administering an effective amount of the compound of the first aspect or a pharmaceutically acceptable salt thereof or the conjugate or pharmaceutical composition of the second aspect to an individual in need thereof.

Unless otherwise specified, all scientific and technical terms used in the disclosure have the meanings commonly understood by those skilled in the art. Moreover, cell culture, molecular genetics, nucleic acid chemistry and immunology laboratory procedures used herein are all routine steps widely used in the corresponding art. In addition, definitions and explanations of relevant terms are given below for a better understanding of the disclosure.

In the disclosure, the pharmaceutical excipients refer to excipients and additives used in drug manufacturing and formulating, and are substances that have been reasonably evaluated in terms of safety and are contained in pharmaceutical preparations in addition to active ingredients. In addition to being used as excipients, carriers and stability enhancers, pharmaceutical excipients also have important functions such as solubilization, sustained release, and are important ingredients that may affect the quality, safety and efficacy of drugs. Pharmaceutical excipients can be divided by sources into natural substances, semi-synthetic substances and full-synthetic substances; divided by effects and uses into solvents, propellants, solubilizers, cosolvents, emulsifiers, colorants, binders, disintegrants, filling agents, lubricants, wetting agents, osmotic pressure regulators, stabilizers, glidants, flavoring agents, preservatives, suspending agents, coating materials, aromatics, anti-adhesion agents, antioxidants, chelating agents, penetration enhancers, pH regulators, buffers, plasticizers, surfactants, foaming agents, defoamers, thickeners, inclusion agents, humectants, absorbents, diluents, flocculants and deflocculants, filter aids and release retardants; and divided by administration routes into oral administration, injection, mucosal, transdermal or local administration, nasal or oral inhalation and ophthalmic administration. The same pharmaceutical excipient can be used for pharmaceutical preparations with different administration routes, and has different effects and uses.

The pharmaceutical composition can be formulated into various suitable dosage forms depending on administration routes, such as tablets, capsules, granules, oral solutions, oral suspensions, oral emulsions, powders, tinctures, syrups, injections, suppositories, ointments, creams, pastes, ophthalmic preparations, pills, subdermals, aerosols, powders and sprays. The pharmaceutical composition or suitable dosage forms may contain 0.01 mg to 1000 mg of the compound of the disclosure or a pharmaceutically acceptable salt or conjugate thereof, suitably 0.1 mg to 800 mg, preferably 0.5 to 500 mg, preferably 0.5 to 350 mg, and particularly preferably 1 to 1-250 mg.

The pharmaceutical composition can be administered in the form of injections, including liquids for injection, sterilized powders for injection, and concentrated solutions for injection. Acceptable carriers and solvents include water, Ringer's solution and isotonic sodium chloride solution. In addition, sterilized non-volatile oil can also be used as a solvent or suspending medium, such as monoglyceride or diglyceride.

In the disclosure, the term "individual" include a human individual or a non-human animal. Exemplary human individual includes a human individual with a disease (e.g., a disease described herein) (referred to as a patient) or a normal individual. The term "non-human animal" in the disclosure includes all vertebrates, such as a non-mammal (e.g., a bird, an amphibian and a reptile) and a mammal, such as a non-human primate, a domestic animal, and/or a domesticated animal (e.g., a sheep, a dog, a cat, a cow and a pig).

In the disclosure, the term "effective amount" refers to the amount of the compound that, after being administered, relieves one or more symptoms of the treated disease to some extent.

In the disclosure, the term "conjugate" refers to a substance obtained by linking a bioactive molecule with a targeting moiety. In some embodiments of the disclosure, the bioactive molecule is linked to the targeting moiety via a linker. The linker can be cleaved in a specific environment (e.g., an intracellular low pH environment) or under a specific action (e.g., the action of lysosomal protease), thereby dissociating the bioactive molecule from the target moiety. In some embodiments of the disclosure, the linker comprises cleavable or non-cleavable units, such as a peptide or disulfide bond. In some embodiments of the disclosure, the bioactive molecule is linked directly to the targeting moiety via a covalent bond that can be cleaved under a specific environment or action, thereby dissociating the bioactive molecule from the targeting moiety.

In the disclosure, the terms "bioactive substance" and "bioactive molecule" refer to a substance that inhibits or prevents cell functions and/or cause cell death or destruction. In some embodiments of the disclosure, the bioactive substance or bioactive molecule in the conjugate is a molecule with anti-tumor bioactivity. For example: a radioisotope such as $At^{211}$, $I^{131}$, $I^{125}$, $Y^{90}$, $Re^{186}$, $Re^{188}$, $Sm^{153}$, $Bi^{212}$, $p^{32}$, $Pb^{212}$ or a radioisotope of Lu; a metal complex such as a platinum metal complex, a gold metal complex or oxaliplatin; a glycopeptide antibiotic such as bleomycin or pingyangmycin; a DNA topoisomerase inhibitor such as a topoisomerase I inhibitor, e.g., camptothecin, hydroxycamptothecin, 9-aminocamptothecin, SN-38, irinotecan, topotecan, bellotencian or rubitecan, or a topoisomerase II inhibitor, e.g., actinomycin D, doxorubicin, duocarmycin, daunorubicin, mitoxantrone, podophyllotoxin, etoposide and so on; a drug interfering with DNA synthesis, such as methotrexate, 5-fluorouracil, cytarabine, gemcitabine, mercaptopurine, pentostatin, fludarabine, cladribine, narabine and so on; a drug acting on a structural protein, such as a tubulin inhibitor, a vinblastine alkaloid, a vincristine, vinblastine, paclitaxel, docetaxel, cabazitaxel and so on; a tumor cell signaling pathway inhibitor such as a serine/threonine kinase inhibitor, a tyrosine kinase inhibitor, a aspartokinase inhibitor or a histidine kinase inhibitor and so on; also includes a proteasome inhibitor; a histone deaceylase inhibitor; a tumor angiogenesis inhibitor; a cyclin inhibitor; a maytansine derivative; a calicheamicin derivative; a auristatin derivative; a Pyrrolobenzodiazepines (PBD) derivative; melphalan; mitomycin C; chlorambucil; and other active substances which inhibit the growth of tumor cells, promote the apoptosis or necrosis of tumor cells; an enzymes and fragment thereof, such as karyolytic enzyme; an antibiotic; a toxin such as a small molecule toxin or an enzymatically active toxin originated from bacterium, fungus, plants or animals, including fragment and/or variant thereof; a growth inhibitor; and a drug module. The term "toxin" refers to a substance that has deleterious effects on the growth or proliferation of cells.

In the disclosure, the term "small molecule" refers to a small molecule drug with bioactivity.

In the disclosure, the term "linker" refers to a fragment linking a bioactive molecule with a targeting moiety.

In the disclosure, the term "targeting moiety" refers to a moiety of the conjugate that can specifically bind to a target (or a portion of the target) on the cell surface. The conjugate can be delivered to a specific cell population by interaction between the targeting moiety and the target.

In the disclosure, the conjugate can be referred to as a "drug-antibody conjugate" when the targeting moiety of the conjugate is an antibody. In the disclosure, the "drug-antibody conjugate" and "immune conjugate" are interchangeable.

In the disclosure, the term "antibody" is interpreted in its broadest sense, including a complete monoclonal antibody, polyclonal antibody, and a multispecific antibody (e.g., a bispecific antibody) formed from at least two complete antibodies, provided that the antibody has required bioactivity. In the disclosure, the terms "antibody" and "immunoglobulin" are interchangeable.

In the disclosure, the term "monoclonal antibody" refers to an antibody from a group of substantially uniform antibodies, i.e., antibodies that make up the group are identical except for a small number of possible natural mutations. A monoclonal antibody has high specificity for one determinant (epitope) of an antigen, while a comparative polyclonal antibody contains different antibodies for different determinants (epitopes). In addition to specificity, the monoclonal antibody has the advantage of being free from contamination by other antibodies during synthesis. The modifier "monoclonal" here indicates that the antibody is characterized by coming from a substantially uniform antibody group and should not be construed as being prepared by a special method.

In some embodiments of the disclosure, the monoclonal antibody also specifically includes a chimeric antibody, i.e., a portion of a heavy chain and/or a light chain is the same as or homologous to a type, a class, or a subclass of antibodies, while the rest is the same as or homologous to another type, another class, or another subclass of antibodies, provided the antibody has required bioactivity (see, e.g., U.S. Pat. No. 4,816,567; and Morrison et al., 1984, PNAS, 81: 6851-6855). The chimeric antibody available in the disclosure includes a primatized antibody containing a variable region antigen binding sequence from a non-human primate (e.g., an ancient monkey or an orangutan) and a human constant region sequence.

The term "antibody fragment" refers to a portion of the antibody, preferably an antigen binding region or a variable region. Examples of antibody fragment includes Fab, Fab', F(ab')$_2$, Fd, Fv, dAb and complementary determinant fragment, diabody, linear antibody and single chain antibody molecule.

The term "bispecific antibody", also known as "bifunctional antibody conjugate", refers to a conjugate formed by a first antibody (fragment) and a second antibody (fragment) through a coupling arm. The conjugate retains the activity of each antibody and thus has bifunctional and bispecific properties.

The term "multispecific antibody" includes, for example, a trispecific antibody which is an antibody having three different antigen binding specificities, and a tetraspecific antibody which is an antibody having four different antigen binding specificities.

The term "complete antibody" refers to an antibody containing an antigen binding variable region, a light chain constant region (CL) and heavy chain constant regions (CH1, CH2 and CH3). The constant regions can be natural sequences (e.g., human natural constant region sequences) or amino acid sequence variants thereof. The complete antibody is preferably a complete antibody having one or more effector functions.

The term "probody" is a modified antibody comprising an antibody or antibody fragment that can specifically bind to a target thereof and can be coupled with a masked group, and the masked group here refers that the cleavage constant for the binding capacity of the antibody or antibody fragment to the target is at least 100 times or 1000 times or 10000 times greater than that for the binding capacity of an antibody or antibody fragment not coupled with a masked group to a target thereof.

In the disclosure, a "humanized" form of a non-human (e.g., mouse) antibody refers to a chimeric antibody that contains minimal non-human immunoglobulin sequences. Most of the humanized antibodies are those in which residues in hypervariable regions of human recipient immunoglobulins are substituted with residues in non-human (e.g., mice, rats, rabbits or non-human primates) hypervariable regions (donor antibodies) with required specificity, affinity and functions. In some embodiments, residues in frame regions (FRs) of human immunoglobulins are also substituted with non-human residues. Furthermore, the humanized antibody can also contain residues not present in recipient antibodies or donor antibodies. Such modifications are made to further optimize antibody performance A humanized antibody generally contains at least one variable region, typically two variable regions, in which all or almost all hypervanable loops correspond to non-human immunoglobulins, while all or almost all FRs are those of human immunoglobulin sequences. A humanized antibody can also contain at least a portion of an immunoglobulin constant region (Fc, usually human immunoglobulin Fc). For details, see, for example, Jones et al., 1986, Nature, 321: 522-525; Riechmann et al., 1988, Nature, 332: 323-329; and Presta, 1992, Curr Op Struct Bwl 2: 593-596.

Complete antibody can be classified into different "classes" according to amino acid sequences of heavy chain constant regions. The main five classes are IgA, IgD, IgE, IgG and IgM, and several of which can also be further classified into different "subclasses" (isotypes), such as IgG1, IgG2, IgG3, IgG4, IgA1 and IgA2. Different classes of heavy chain constant regions of antibodies are called α, β, ε, γ and μ respectively. Different classes of subunit structures and 3D configurations of immunoglobulins are well known in the art.

In the disclosure, although amino acid substitutions in antibodies are substituted with L-amino acids in most cases, the embodiments are not limited thereto. In some embodiments, an antibody peptide chain can contain one or more D-amino acids. Peptides containing D-amino acids may be more stable and less degradable in oral cavity, intestinal tract or plasma than peptides containing only L-amino acids.

Monoclonal antibody used in the disclosure can be produced by multiple methods. For example, the monoclonal antibody used in the disclosure can be obtained by hybridoma methods using multiple species (including cells of mice, hamsters, rats and humans) (see, for example, Kohler et al., 1975, Nature, 256: 495), or by recombinant DNA techniques (see, for example, U.S. Pat. No. 4,816, 567), or isolated from phage antibody libraries (see, for example, Clackson et al., 1991, Nature, 352: 624-628; and Marks et al., 1991, Journal of Molecular Biology, 222: 581-597). Monoclonal antibody that can be used in the disclosure includes, but is not limited to anti-Her 2 monoclonal antibody such as Trastuzumab and Pertuzumab, or anti-Trop-2 monoclonal antibody such as Sacituzumab (i.e., Isactuzumab or hRS7 antibody), M1, M2 or M3.

In some preferred embodiments, a target of A is selected from epidermal growth factor, Trop-2, CD37, HER2, CD70, EGFRvIII, Mesothelin, Folate receptor1, Mucin 1, CD138, CD20, CD19, CD30, SLTRK6, Nectin 4, Tissue factor, Mucin16, Endothelin receptor, SLC39A6, Guanylylcyclase C, PSMA, CCD79b, CD22, Sodium phosphate cotransporter 2B, GPNMB, Trophoblast glycoprotein, AGS-16, EGFR, CD33, CD66e, CD74, CD56, PD-L.sub.1, TACSTD2, DRS, E16, STEAP1, 0772P, MPF, Napi3b, Sema 5b, PSCA hlg, ETBR, MSG783, STEAP2, TrpM4, CRIPTO, CD21, CD79b, FcRH2, NCA, MDP, IL20Rα, Brevican, EphB2R, A5LG659, PSCA, GEDA, BAFF-R, CD79a, CXCR5, HLA-DOB, P2X5, CD72, LY64, FcRH1, IRTA2, TENB2, integrin α5β6, α4β7, FGF2, FGFR2, Her3, CA6, DLL3, DLL4, P-cadherin, EpCAM, pCAD, CD223, LYPD3, LY6E, EFNA4, ROR1, SLITRK6, 5T4, ENPP3, Claudin18.2, BMPR1 B, Tyrol, c Met, ApoE, CD1 Ic, CD40, CD45 (PTPRC), CD49D (ITGA4), CD80, CSF1R, CTSD, GZMB, Ly86, MS4A7, PIK3AP1, PIK3CD, CCR5, IFNG, IL10RA1, IL-6, ACTA2, COL7A1, LOX, LRRC15, MCPT8, MMP10, NOG, SERPINET, STAT1, TGFBR1, CTSS, PGF, VEGFA, C1QA, C1QB, EGLN, ANGPTL4, EGLN3, BNIP3, AIF1, CCL5, CXCL10, CXCL11, IFI6, PLOD2, KISS1R, STC2, DDIT4, PFKFB3, PGK1, PDK1, AKR1C1, AKR1C2, CADM1, CDH11, COL6A3, CTGF, HMOX1, KRT33A, LUM, WNT5A, IGFBP3, MMP14, CDCP1, PDGFRA, TCF4, TGF, TGFB1, TGFB2, CD1 Ib, ADGRE1, EMR2, TNFRSF21, UPK1 B, TNFSF9, MMP16, MFI2, IGF-1R, RNF43, NaPi2b, or BCMA.

In some embodiments of the disclosure, the target of the targeting moiety A is selected from a RGD peptide that recognizes cell surface integrin receptor; a growth factor that recognizes cell surface growth factor receptor, such as EGF, PDGF or VEGF; and a peptide capable of recognizing functional cell surface plasminogen activator, bombesin, bradykinin, somatostatin or prostate-specific membrane antigen receptor.

In some embodiments of the disclosure, the target of the targeting moiety A is selected from a CD40 ligand, a CD30 ligand, an OX40 ligand, a PD-1 ligand, an ErbB ligand, a Her2 ligand, a TACSTD2 ligand and a DR5 ligand.

In some embodiments of the disclosure, the targeting moiety A is an anti-Her 2 monoclonal antibody, such as Trastuzumab or Pertuzumab; or an anti-Trop-2 monoclonal antibody, such as Sacituzumab, M1, M2 or M3.

In some embodiments of the disclosure, the targeting moiety is Trastuzumab or Pertuzumab. Tratuzumab is an anti-Her 2 monoclonal antibody, an amino acid sequence thereof is known to a person skilled in the art, for a schematic sequence thereof, refer to, for example, CN103319599.

In some embodiments of the disclosure, terminal Lys of heavy chains of the targeting moiety is easily deleted, but such deletion does not affect bioactivity. See Dick, L. W. et al., Biotechnol. Bioeng., 100: 1132-1143. For example, the targeting moiety is an anti-Trop-2 monoclonal antibody, such as Sacituzumab, M1, M2 or M3 deleted terminal Lys of heavy chains, for example, the targeting moiety is an anti-Her 2 monoclonal antibody, such as Trastuzumab or Pertuzumab deleted terminal Lys of heavy chains.

Exemplary heavy and light chain sequences of Trastuzumab, refer to SEQ ID No.: 17 and SEQ ID No.: 18. In the disclosure, heavy and light chain sequences of Trastuzumab referred to or involved are described using the sequences shown in SEQ ID No.: 17 and SEQ ID No.: 18, respectively. Exemplary heavy and light chain sequences of Pertuzumab, refer to SEQ ID No.: 16 and SEQ ID No.: 15 of U.S. Pat. No. 7,560,111.

(heavy chain sequence)

SEQ ID No.: 17

EVQLVESGGGLVQPGGSLRLSCAASGFNIKDTYIHWVRQAPGKGLEWVAR

IYPTNGYTRYADSVKGRFTISADTSKNTAYLQMNSLRAEDTAVYYCSRWG

GDGFYAMDYWGQGTLVTVSSASTKGPSVFPLAPSSKSTSGGTAALGCLVK

DYFPEPVTVSWNSGALTSGVHTFPAVLQSSGLYSLSSVVTVPSSSLGTQT

YICNVNHKPSNTKVDKKVEPKSCDKTHTCPPCPAPELLGGPSVFLFPPKP

KDTLMISRTPEVTCVVVDVSHEDPEVKFNWYVDGVEVHNAKTKPREEQYN

STYRVVSVLTVLHQDWLNGKEYKCKVSNKALPAPIEKTISKAKGQPREPQ

VYTLPPSREEMTKNQVSLTCLVKGFYPSDIAVEWESNGQPENNYKTTPPV

LDSDGSFFLYSKLTVDKSRWQQGNVFSCSVMHEALHNHYTQKSLSLSPG (K)

(light chain sequence)

SEQ ID No.: 18

DIQMTQSPSSLSASVGDRVTITCRASQDVNTAVAWYQQKPGKAPKLLIYS

ASFLYSGVPSRFSGSRSGTDFTLTISSLQPEDFATYYCQQHYTTPPTFGQ

GTKVEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC

In some embodiments of the disclosure, the anti-Trop-2 antibody of the targeting moiety is RS7 (i.e., Sacituzumab of the disclosure) described in U.S. Pat. No. 7,517,964; and hRS7 (i.e., Sacituzumab of the disclosure) described in US2012/0237518. The anti-Trop-2 antibody available in the disclosure can also be obtained by screening through carrier design, construction and construction of an antibody library displaying antibodies as disclosed in CN103476941A, or can be obtained by screening a G-MAB® library of Sorrento Therapeutics, Inc.

For the heavy chain sequence and light chain amino acid sequence of the monoclonal antibody Sacituzumab, refer to, for example, SEQ ID No.: 19 and SEQ ID No.: 20, respectively.

(heavy chain sequence)

SEQ ID No.: 19

QVQLQQSGSELKKPGASVKVSCKASGYTFTNYGMNWVKQAPGQGLKWMGW

INTYTGEPTYTDDFKGRFAFSLDTSVSTAYLQISSLKADDTAVYFCARGG

FGSSYWYFDVWGQGSLVTVSSASTKGPSVFPLAPSSKSTSGGTAALGCLV

KDYFPEPVTVSWNSGALTSGVHTFPAVLQSSGLYSLSSVVTVPSSSLGTQ

TYICNVNHKPSNTKVDKRVEPKSCDKTHTCPPCPAPELLGGPSVFLFPPK

PKDTLMISRTPEVTCVVVDVSHEDPEVKFNWYVDGVEVHNAKTKPREEQY

NSTYRVVSVLTVLHQDWLNGKEYKCKVSNKALPAPIEKTISKAKGQPREP

QVYTLPPSREEMTKNQVSLTCLVKGFYPSDIAVEWESNGQPENNYKTTPP

VLDSDGSFFLYSKLTVDKSRWQQGNVFSCSVMHEALHNHYTQKSLSLSPG (K)

Terminal K (or lys) of heavy chains is easily deleted, but such deletion does not affect bioactivity. See Dick, L. W. et al., Biotechnol. Bioeng., 100: 1132-1143.

(light chain sequence)

SEQ ID No.: 20

DIQLTQSPSSLSASVGDRVSITCKASQDVSIAVAWYQQKPGKAPKLLIYS

ASYRYTGVPDRFSGSGSGTDFTLTISSLQPEDFAVYYCQQHYITPLTFGA

GTKVEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC

In the disclosure, ErbB2 and Her2/neu are interchangeable, both of which represent human Her2 proteins of natural sequences (Genebank CAS No.: X03363, see, for example, Semba et al., 1985, PNAS, 82: 6497-6501; and Yamamoto et al., 1986, Nature, 319: 230-234) and functional derivatives thereof, such as amino acid sequence variants. ErbB2 represents a gene encoding human Her2 and neu represents a gene encoding rat p185neu. In some embodiments, the compound or conjugate of the disclosure can inhibit or kill cells that express ErbB2 receptors, such as breast cancer cells, ovarian cancer cells, gastric cancer cells, endometrial cancer cells, salivary gland cancer cells, lung cancer cells, kidney cancer cells, colon cancer cells, thyroid cancer cells, pancreatic cancer cells, bladder cancer cells or liver cancer cells.

In the disclosure, Trop-2 or TROP2 refers to human trophoblast cell-surface antigen 2, also known as TACSTD2, M1S1, GA733-1, EGP-1, which is a cell surface receptor expressed in many human tumors (e.g., breast cancer, colorectal cancer, lung cancer, pancreatic cancer, ovarian cancer, prostate cancer and cervical cancer). In some embodiments, the compound or conjugates of the disclosure can inhibit or kill cells that express TROP2 receptors, such as breast cancer cells, colorectal cancer cells, lung cancer cells, pancreatic cancer cells, ovarian cancer cells, prostate cancer cells or cervical cancer cells.

As used herein,

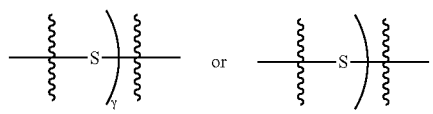

contained in the conjugate of the invention indicates a specific linking mode of a sulfydryl group and a linker in the antibody when the targeting moiety is an antibody.

As used herein, the term "$C_{1-6}$ alkyl" refers to linear or branched alkyl containing 1-6 carbon atoms, including, for example, "$C_{1-4}$ alkyl" and "$C_{1-3}$ alkyl". Specific examples include, but are not limited to methyl, ethyl, n-propyl, isopropyl, n-butyl, isobutyl, sec-butyl, tert-butyl, n-pentyl, iso-pentyl, 2-methyl butyl, neopentyl, 1-ethyl propyl, n-hexyl, isohexyl, 3-methyl pentyl, 2-methyl pentyl, 1-methyl pentyl, 3,3-dimethyl butyl, 2,2-dimethyl butyl, 1,1-dimethyl butyl, 1,2-dimethyl butyl, 1,3-dimethyl butyl, 2,3-dimethyl butyl, 2-ethyl butyl and 1,2-dimethyl propyl.

As used herein, the term "$C_{2-6}$ alkenyl" refers to linear, branched or cyclic alkenyl containing at least a double bond and 2-6 carbon atoms, including, for example, "$C_{2-4}$ alkenyl". Examples thereof include, but are not limited to vinyl, 1-propenyl, 2-propenyl, 1-butenyl, 2-butenyl, 1,3-butadienyl, 1-pentenyl, 2-pentenyl, 3-pentenyl, 1,3-pentadienyl, 1,4-pentadienyl, 1-hexenyl, 2-hexenyl, 3-hexenyl, 1,4-hexadienyl, cyclopentenyl, 1,3-cyclopentadienyl, cyclohexenyl and 1,4-cyclohexadienyl.

As used herein, the term "C$_{2-6}$ alkynyl" refers to linear or branched alkynyl containing at least a triple bond and 2-6 carbon atoms, including, for example, "C$_{2-4}$ alkynyl". Examples thereof include, but are not limited to ethynyl, propynyl, 2-butynyl, 2-pentynyl, 3-pentynyl, 4-methyl-2-pentynyl, 2-hexynyl, 3-hexynyl and 5-methyl-2-hexynyl.

As used herein, the term "halogen" includes fluorine, chlorine, bromine and iodine.

As used herein, the terms "3-8 membered cycloalkyl" or "C$_{3-8}$ cycloalkyl" refers to saturated cyclic alkyl containing 3-8 carbon atoms, including, for example, "3-6 membered cycloalkyl", "4-6 membered cycloalkyl", "5-7 membered cycloalkyl" or "5-6 membered cycloalkyl". Specific examples include, but are not limited to cyclopropanyl, cyclobutylalkyl, cyclopentanyl, cyclohexyl, cycloheptyl and cyclooctadecyl.

As used herein, the term "C$_{1-6}$ alkoxy" refers to a group having a structure of C$_{1-6}$ alkyl-O—, wherein C$_{1-6}$ alkyl is as defined previously. Specific examples include, but are not limited to methoxy, ethoxy, propoxy, isopropoxy, n-propoxy, isopropoxy, n-butoxy, isobutoxy, tert-butoxy, pentoxy and hexyloxy.

As used herein, the term "3-8 membered aliphatic heterocyclyl" refers to a cyclic group containing 3-8 ring-forming atoms (at least one of which is a heteroatom, such as a nitrogen atom, an oxygen atom or a sulfur atom). Optionally, the ring-forming atoms (e.g., carbon atoms, nitrogen atoms or sulfur atoms) in the cyclic structure can be substituted with oxygen. The "3-8 membered aliphatic heterocyclyl" includes, for example, "3-8 membered nitrogen-containing aliphatic heterocyclyl," "3-8 membered oxygen-containing aliphatic heterocyclyl," "3-6 membered aliphatic heterocyclyl," "3-6 membered oxygen-containing aliphatic heterocyclyl," "4-7 membered aliphatic heterocyclyl," "4-6 membered aliphatic heterocyclyl," "5-7 membered aliphatic heterocyclyl," "5-6 membered aliphatic heterocyclyl," "5-6 membered nitrogen-containing aliphatic heterocyclyl," including but not limited to oxiranyl, oxocyclobutyl, pyrrolidinyl, tetrahydrofuranyl, piperidinyl, piperazinyl, tetrahydropyranyl and homopiperazinyl.

As used herein, the term "6-12 membered spirocyclyl" refers to a cyclic structure containing 6-12 ring-forming carbon atoms and formed by two or more cyclic structures sharing one carbon atom. Optionally, the carbon atoms in the cyclic structure can be substituted with oxygen. The "6-12 membered spirocyclyl" includes, for example, "6-11 membered spirocyclyl", "6-10 membered spirocyclyl", "7-10 membered spirocyclyl", "7-9 membered spirocyclyl", "7-8 membered spirocyclyl", "9-10 membered spirocyclyl" and "3-10 membered spirocyclyl". Specific examples include, but are not limited to

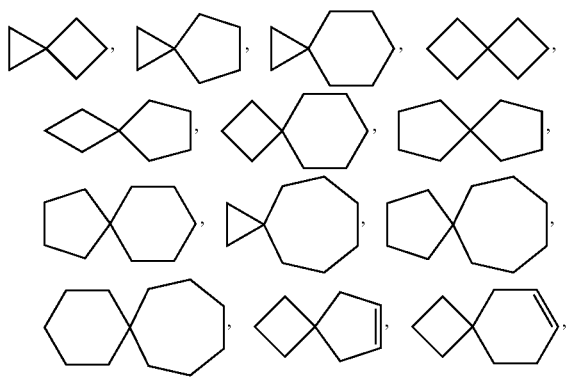

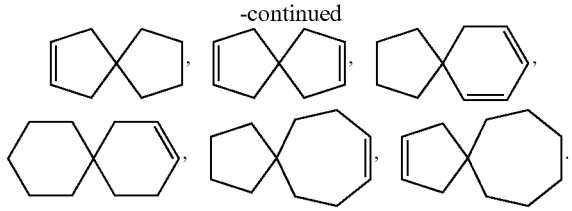

As used herein, the term "6-12 membered bridged cyclyl" refers to a cyclic structure containing 6-12 ring-forming carbon atoms and formed by two or more cyclic structures sharing two nonadjacent carbon atoms, Optionally, the carbon atoms in the cyclic structure can be substituted with oxygen. The "6-12 membered bridged cyclyl" includes, for example, "6-11 membered bridged cyclyl", "5-10 membered bridged cyclyl", "7-10 membered bridged cyclyl", "7-9 membered bridged cyclyl", "7-8 membered bridged cyclyl", "9-10 membered bridged cyclyl" and "3-10 membered bridged cyclyl". Specific examples include, but are not limited to

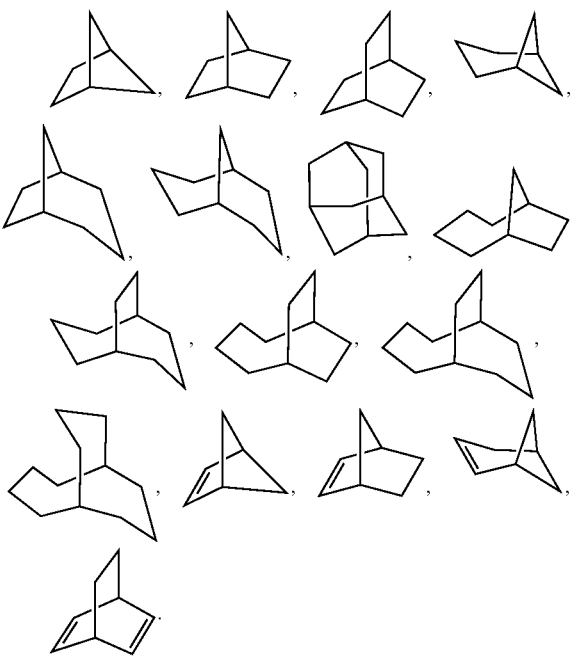

As used herein, the term "6-12 membered fused cyclyl" refers to a cyclic structure containing 6-12 ring-forming carbon atoms and formed by two or more cyclic structures sharing two adjacent atoms, including "6-11 membered fused cyclyl", "6-10 membered fused cyclyl", "6-8 membered fused cyclyl", "10-12 membered fused cyclyl", "7-10 membered fused cyclyl". Examples thereof include, but are not limited to

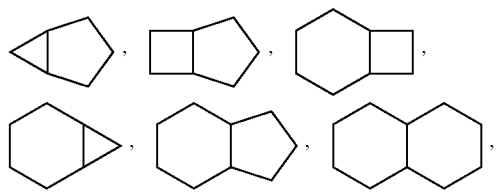

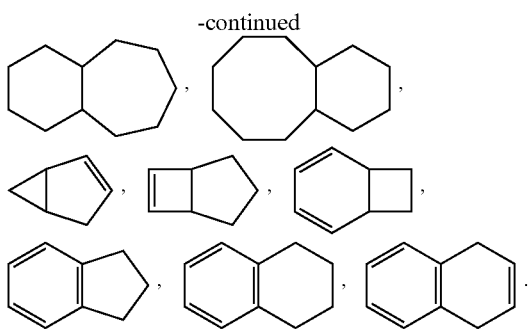

As used herein, the term "6-12 membered spiroheterocyclyl" refers to a cyclic structure containing 6-12 ring-forming atoms (at least one of which is a heteroatom, such as a nitrogen atom, an oxygen atom or a sulfur atom) and formed by two or more cyclic structures sharing one ring-forming atom. Optionally, the ring-forming atoms (e.g., carbon atoms, nitrogen atoms or sulfur atoms) in the cyclic structure can be substituted with oxygen. The "6-12 membered spiroheterocyclyl" includes, for example, "6-11 membered spiroheterocyclyl", "5-10 membered spiroheterocyclyl", "7-11 membered spiroheterocyclyl", "7-10 membered spiroheterocyclyl", "7-9 membered spiroheterocyclyl", "7-8 membered spiroheterocyclyl", "9-10 membered spiroheterocyclyl" and "3-10 membered spiroheterocyclyl". Specific examples include, but are not limited to

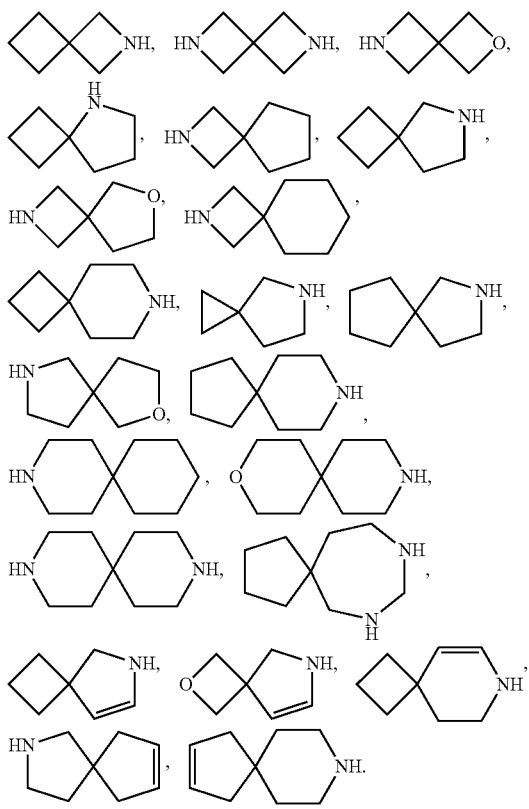

As used herein, the term "6-12 membered bridged heterocyclyl" refers to a cyclic structure containing 6-12 ring-forming atoms (at least one of which is a heteroatom, such as a nitrogen atom, an oxygen atom or a sulfur atom) and formed by two or more cyclic structures sharing two non-adjacent ring-forming atoms. Optionally, the ring-forming atoms (e.g., carbon atoms, nitrogen atoms or sulfur atoms) in the cyclic structure can be substituted with oxygen. The "6-12 membered bridged heterocyclyl" includes, for example, "6-11 membered bridged heterocyclyl", "6-9 membered bridged heterocyclyl", "6-10 membered bridged heterocyclyl", "7-10 membered bridged heterocyclyl", "7-9 membered bridged heterocyclyl", "7-8 membered bridged heterocyclyl", "8 membered bridged heterocyclyl", "9-10 membered bridged heterocyclyl" and "3-10 membered bridged heterocyclyl". Specific examples include, but are not limited to

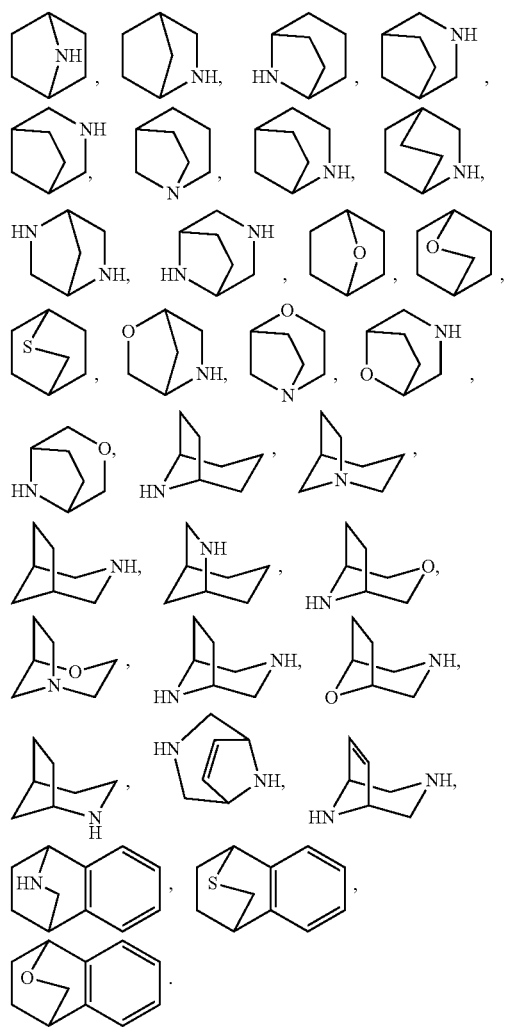

As used herein, the term "6-12 membered fused heterocyclyl" refers to a cyclic structure containing 6-12 ring-forming atoms (at least one of which is a heteroatom, such as a nitrogen atom, an oxygen atom or a sulfur atom) and formed by two or more cyclic structures sharing two adjacent atoms. Optionally, the ring-forming atoms (e.g., carbon atoms, nitrogen atoms or sulfur atoms) in the cyclic structure can be substituted with oxygen. The "6-12 membered fused heterocyclyl" includes, for example, "6-11 membered fused heterocyclyl," "5-10 membered fused heterocyclyl", "7-10 membered fused heterocyclyl", "3-10 membered fused heterocyclyl", "3-10 membered nitrogen-containing fused heterocyclyl", "9-10 membered fused heterocyclyl", "9-10 membered nitrogen-containing fused heterocyclyl" and "6-12 membered oxygen-containing fused heterocyclyl". Specific examples include, but are not limited to tetrahydroimidazo [4,5-c]pyridyl, 3,4-dihydroquinazolinyl, 1,2-dihydroquinoxalinyl, benzo[d][1,3]dioxolyl, 1,3-dihydroisobenzofuranyl, 4H-1,3-benzoxazinyl, 4,6-dihydro-1H-furo[3,4-d]imidazolyl, 3a,4,6,6a-tetrahydro-1H-furo[3,4-d]imidazolyl, 4,6-dihydro-1H-thieno[3,4-d]imidazolyl, 4,6-dihydro-1H-pyrrolo[3,4-d]imidazolyl, benzoimidazolidinyl, octahydro-benzo[d]imidazolyl, decahydroquinolyl, hexahydrothienoimidazolyl, hexahydrofuroimidazolyl, 4,5,6,7-tetrahydro-1H-benzo[d]imidazolyl, octahydrocyclopenteno[c]pyrrolyl, dihydroindolyl, dihydroisoindolyl, benzooxazolidinyl, benzothiazolidinyl, 1,2,3,4-tetrahydroisoquinolinyl, 1,2,3,4-tetrahydroquinolinyl and 4H-1,3-benzoxazinyl.

As used herein, the term "aryl" refers to a monocyclic or polycyclic hydrocarbonyl having aromaticity, such as 6-20 membered aryl, 6-10 membered aryl and 5-8 membered aryl. Specific examples include but are not limited to phenyl, naphthyl, anthracenyl and phenanthryl. The "6-20 membered aryl" refers to aryl containing 6-20 ring-forming atoms.

As used herein, the term "heteroaryl" refers to a cyclic group having aromaticity, wherein at least one ring-forming atom is a heteroatom, such as a nitrogen atom, an oxygen atom or a sulfur atom. Optionally, the ring-forming atoms (e.g., carbon atoms, nitrogen atoms or sulfur atoms) in the cyclic structure can be substituted with oxygen. Specific examples include, but are not limited to 5-10 membered heteroaryl, 5-10 membered nitrogen-containing heteroaryl, 6-10 membered oxygen-containing heteroaryl, 6-8 membered nitrogen-containing heteroaryl and 5-8 membered oxygen-containing heteroaryl, such as furyl, thienyl, pyrrolyl, thiazolyl, isothiazolyl, thiadiazolyl, oxazolyl, isoxazolyl, oxadiazolyl, imidazolyl, pyrazolyl, 1,2,3-triazolyl, 1,2,4-triazolyl, 1,2,3-oxadiazolyl, 1,2,4-oxadiazolyl, 1,2,5-oxadiazolyl, 1,3,4-oxadiazolyl, pyridyl, 2-pyridone, 4-pyridone, pyrimidinyl, 1,4-dioxacyclohexadienyl, 2H-1,2-oxazinyl, 4H-1,2-oxazinyl, 6H-1,2-oxazinyl, 4H-1,3-oxazinyl, 6H-1,3-oxazinyl, 4H-1,4-oxazinyl, pyridazinyl, pyrazinyl, 1,2,3-triazinyl, 1,3,5-triazinyl, 1,2,4,5-tetrazinyl, azacycloheptatrienyl, 1,3-diazcycloheptatrienyl and azacyclooctatetraenyl.

BENEFICIAL EFFECTS OF THE INVENTION

The disclosure obtains a kind of novel bioactive molecule conjugate by improving the coupling way of drugs and targeting moieties in ADCs or SMDCs. In some embodiments of the disclosure, the bioactive molecule conjugate is obtained through nucleophilic substitutions of the heteroaryl ring on the ADC linker by the free sulfhydryl in the antibody. The conjugate obtained by the coupling can achieve at least one of the following technical effects:
(1) high stability;
(2) high DAR, the DAR values of the conjugate can reach 5-8 in some embodiments;
(3) extremely high coupling efficiency, the coupling efficiency can reach 90% in some embodiments;
(4) the conjugate obtained by the coupling can effectively improve the stability of the drug in the circulation and reduce unexpected dissociation of the drug in non-target cells;
(5) the conjugate can also increase effective release of the bioactive molecule in cells to attain the purposes of decreasing toxicity and increasing efficacy;
(6) the conjugate has good tumor tissue targetability; and
(7) the conjugate has good efficacy on animal models of tumors.

In addition, the coupling method described in the disclosure has broad application scope and can be widely used in coupling bioactive molecules with antibodies or targeted small molecule ligands.

SPECIFIC MODE FOR CARRYING OUT THE INVENTION

Figure 1:
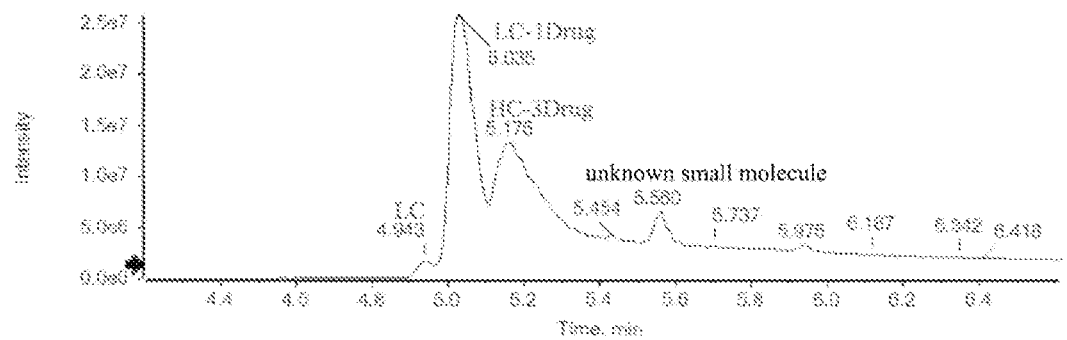
FIG. 1 shows a TIC (total ion chromatogram) of BT001002.

The disclosure will be further illustrated in combination with specific embodiments, but the disclosure is not limited thereto. It should be understood by a person skilled in the art that various modifications or improvements can be made according to the teachings of the disclosure without departing from the basic idea and scope of the disclosure.

Abbreviations in the invention have the following meanings:

| OMs | methylsulfonyloxy | FA | Formic acid |
| OTs | Trifluoromethylsulfonyloxy | ACN | Acetonitrile |
| OTf | p-toluenesulfonyloxy | CCK8 reagent | 2-(2-methoxy-4-nitrophenyl)-3-(4-nitrophenyl)-5-(2,4-disulfophenyl)-2H-tetrazole monosodium salt |
| TBS | Tert-butyldimethylsilyl | FBS | Fetal bovine serum |
| MMT | p-methoxytriphenylmethyl | DMSO | Dimethyl sulfoxide |
| PB/PBS | Phosphate buffered saline | | |

Preparation Solutions

The structures of compounds described in the following examples were determined by nuclear magnetic resonance ($^1$H NMR) or mass spectrometry (MS).

Nuclear magnetic resonance ($^1$H NMR) was determined by using a Bruker 400 MHz NMR spectrometer. Deuterated methanol (CD$_3$OD), deuterated chloroform (CDCl$_3$) or deuterated dimethyl sulfoxide (DMSO-D$_6$) was the solvent for determination, and tetramethylsilane (TMS) was an internal standard substance.

Abbreviations in nuclear magnetic resonance (NMR) spectra used in the examples were shown below.

s: singlet, d: doublet, t: triplet, q: quartet, dd: double doublet, qd: quartet doublet, ddd: double double doublet, ddt: double double triplet, dddd: double double double doublet, m: multiplet, br: broad, J: coupling constant, Hz: hertz, DMSO-d$_6$: deuterated dimethyl sulfoxide. δ value was expressed in ppm.

Mass spectra (MS) were determined using Agilent (ESI) mass spectrometer (model: Agilent 6120B).

Preparative Liquid Chromatography:

Method A:

Chromatographic column: Daisogel C18 10 μm 100×250 mm

Mobile phase A: water; Mobile phase B: acetonitrile

| Time [min] | Mobile phase A [%] | Mobile phase B [%] | Flow rate [mL/min] |
|---|---|---|---|
| 0.00 | 70.0 | 30.0 | 300.0 |
| 8.00 | 70.0 | 30.0 | |
| 50.00 | 20.0 | 80.0 | |

Method B:

Chromatographic column: Daisogel C18 10 μm 50×250 mm

Mobile phase A: water; Mobile phase B: acetonitrile

| Time [min] | Mobile phase A [%] | Mobile phase B [%] | Flow rate [mL/min] |
|---|---|---|---|
| 0.00 | 70.0 | 30.0 | 80.0 |
| 8.00 | 70.0 | 30.0 | |
| 50.00 | 20.0 | 80.0 | |

Method C:

Chromatographic column: Daisogel C18 10 μm 50×250 mm

Mobile phase A: water containing 0.1% trifluoroacetic acid; Mobile phase B: acetonitrile

| Time [min] | Mobile phase A [%] | Mobile phase B [%] | Flow rate [mL/min] |
|---|---|---|---|
| 0.00 | 90.0 | 10.0 | 80.0 |
| 10.00 | 90.0 | 10.0 | |
| 50.00 | 60.0 | 40.0 | |

Method D: chromatographic column: Waters SunFire C18 5 μm 19×250 mm

Mobile phase A: acetonitrile; Mobile phase B: water containing 0.05% formic acid Time: 0 min-16 min; Mobile phase A: 10%-90%; Flow rate: 28 mL/min I. Synthesis of Bioactive Molecules Example 1: Synthesis of (2S)—N-((3R,4S,5S)-1-((2S)-2-((1R,2R)-3-((1-((4-aminobenzyl)amino)-1-oxo-3-phenylpropan-2-yl)amino)-1-methoxy-2-methyl-3-propionyl)pyrrolidin-1-yl)-3-methoxy-5-methyl-1-heptanoyl-4-yl)-2-((S)-2-(dimethylamino)-3-methylbutyrylamino)-N,3-dimethylbutyramide (T001)

5S)-4-((S)-2-((S)-2-(dimethylamino)-3-methylbutyrylamino)-N,3-dimethylbutyrylamino)-3-methoxy-5-methylheptanoyl)pyrrolidin-2-yl)-3-methoxy-2-methylpropionyl)-L-phenylalanine (10.0 mg, 13.5 μmol, commercially available) were successively added. After being stirred for 5 min, 1H-benzotriazol-1-yl-oxytripyrrolidinophosphonium hexafluorophosphate (10.0 mg, 20.1 μmol) was added thereto, and stirred at 0° C. for 1 h. The reaction of raw materials was monitored by high performance liquid chromatography-mass spectrometry. After the raw materials were consumed up, the reaction solution was purified by preparative liquid chromatography (method D) to obtain the title compound (9.0 mg of white solid). ESI-MS (m/z): 950.5 [M+H]⁺.

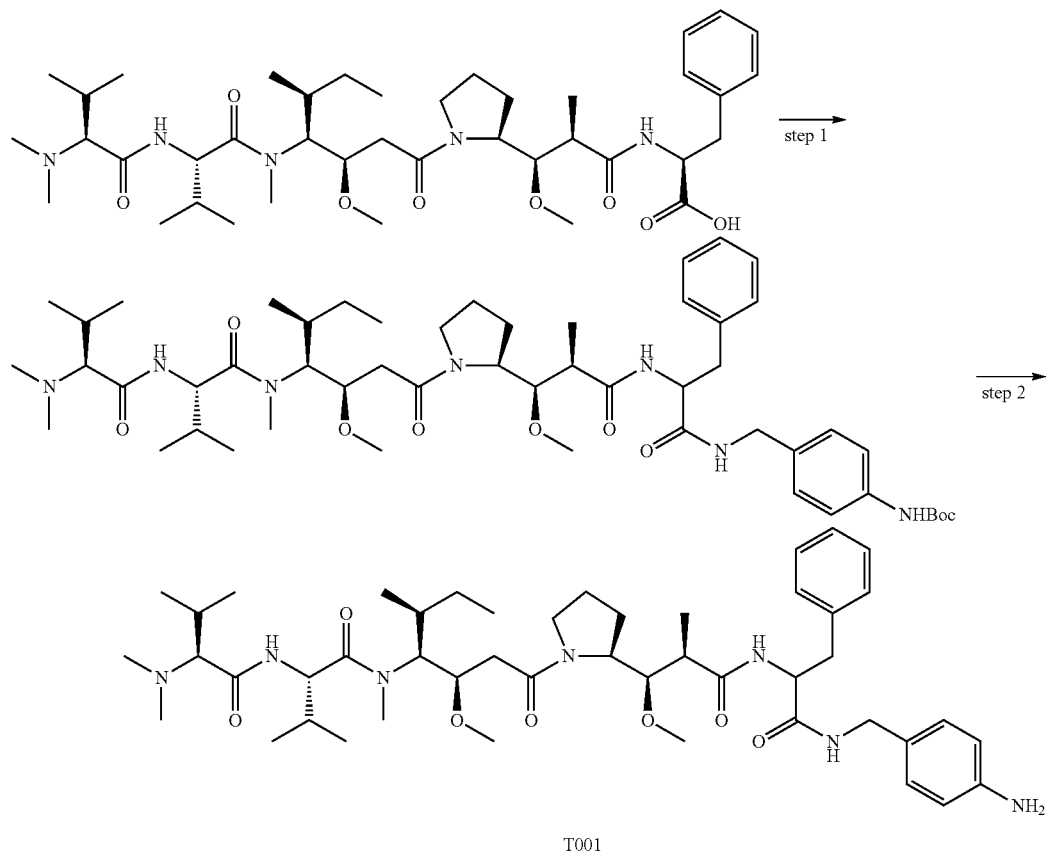

T001

Step 1: Synthesis of tert-butyl (4-((2-((2R,3R)-3-((S)-1-((3R,4S,5S)-4-((S)-2-((S)-2-(dimethylamino)-3-methylbutyrylamino)-N,3-dimethylbutyrylamino)-3-methoxy-5 methylheptanoyl)pyrrolidin-2-yl)-3-methoxy-2-methylpropionamido)-3-phenylpropionamido)methyl)phenyl) carbamate At room temperature, 1-hydroxybenzotriazole (2.0 mg, 14.74 μmol) was dissolved in N,N-dimethylformamide (4 mL), cooled to 0° C., and then tert-butyl 4-methylaminobenzyl carbamate (4.0 mg, 16.1 μmol), N,N-diisopropylethylamine (8.5 mg, 66.8 μmol), ((2R, 3R)-3-((S)-1-((3R,4S, Step 2: Synthesis of (2S)—N-((3R,4S,5S)-1-((2S)-2-((1R,2R)-3-((1-((4-aminobenzyl)amino)-1-oxo-3-phenylpropan-2-yl)amino)-1-methoxy-2-methyl-3-propionyl)pyrrolidin-1-yl)-3-methoxy-5-methyl-1-heptanoyl-4-yl)-2-((S)-2-(dimethylamino)-3-methylbutyrylamino)-N,3-dimethylbutanamide At room temperature, tert-butyl (4-((2-((2R,3R)-3-((S)-1-((3R,4S,5S)-4-((S)-2-((S)-2-(dimethylamino)-3-methylbutyrylamino)-N,3-dimethylbutyryl)-3-methoxy-5-methylheptanoyl)pyrrolidin-2-yl)-3-methoxy-2-methylpropionyl)-3-phenylpropanamide)methyl)phenyl) carbamate (9.0 mg, 0.02 mmol) was dissolved in 1,4-dioxane (0.5 mL), cooled to 0° C., and then the hydrogen chloride solution in dioxane (1 mL, 4.0 M) was added and reacted at room temperature for 3 hours under stirring. The reaction of raw materials was monitored by high performance liquid chromatography-mass spectrometry. After the raw materials were consumed up, the solvent was evaporated under reduced pressure, and the crude product was purified by preparative liquid chromatography (method C) to obtain the trifluoroacetate of the title compound (5.0 mg of white solid). ESI-MS (m/z): 850.5 [M+H]$^+$.

Example 2: Synthesis of (S)—N-((3R,4S,5S)-1-((S)-2-((1R,2R)-3-((S)-1-((4-aminobenzyl)amino)1-oxo-3-phenylprop-2-yl)amino)-1-methoxy-2-methyl-3-oxopropyl) pyrrolidin-1-yl)-3-methoxy-5-methyl-1-oxoheptyl-4-yl)-2-((S)-2-(dimethylamino)-3-methylbutyrylamino)-N,3-dimethylbutyramide (T011)

Step 1: Synthesis of tert-buty (S)-(4-((2-(((((9H-fluoren-9-yl)methoxy)carbonyl)amino)-3-phenylpropionamido) methyl)phenyl) 1 carbamate At 0° C., 4-aminobenzylamine (222 mg, 1.0 mmol) and N-methylmorpholine (306 mg, 1.5 mmol) were added to a solution of (S)-2-((((9H-fluoren-9-yl)methoxy)carbonyl)amino)-3-phenylpropionicacid (387 mg, 1.0 mmol) in N,N-dimethylformamide (5 mL), then 1-hydroxybenzotriazole (203 mg, 1.5 mmol) and 1-(3-dimethylaminopropyl)-3-ethylcarbodiimide hydrochloride (288 mg, 1.5 mmol) were successively added. The resulting mixture was reacted overnight at 0° C. The reaction solution was poured into water (50 mL), and a white solid was precipitated. The solid was filtered, the filter cake was washed with water (20 mL×3).

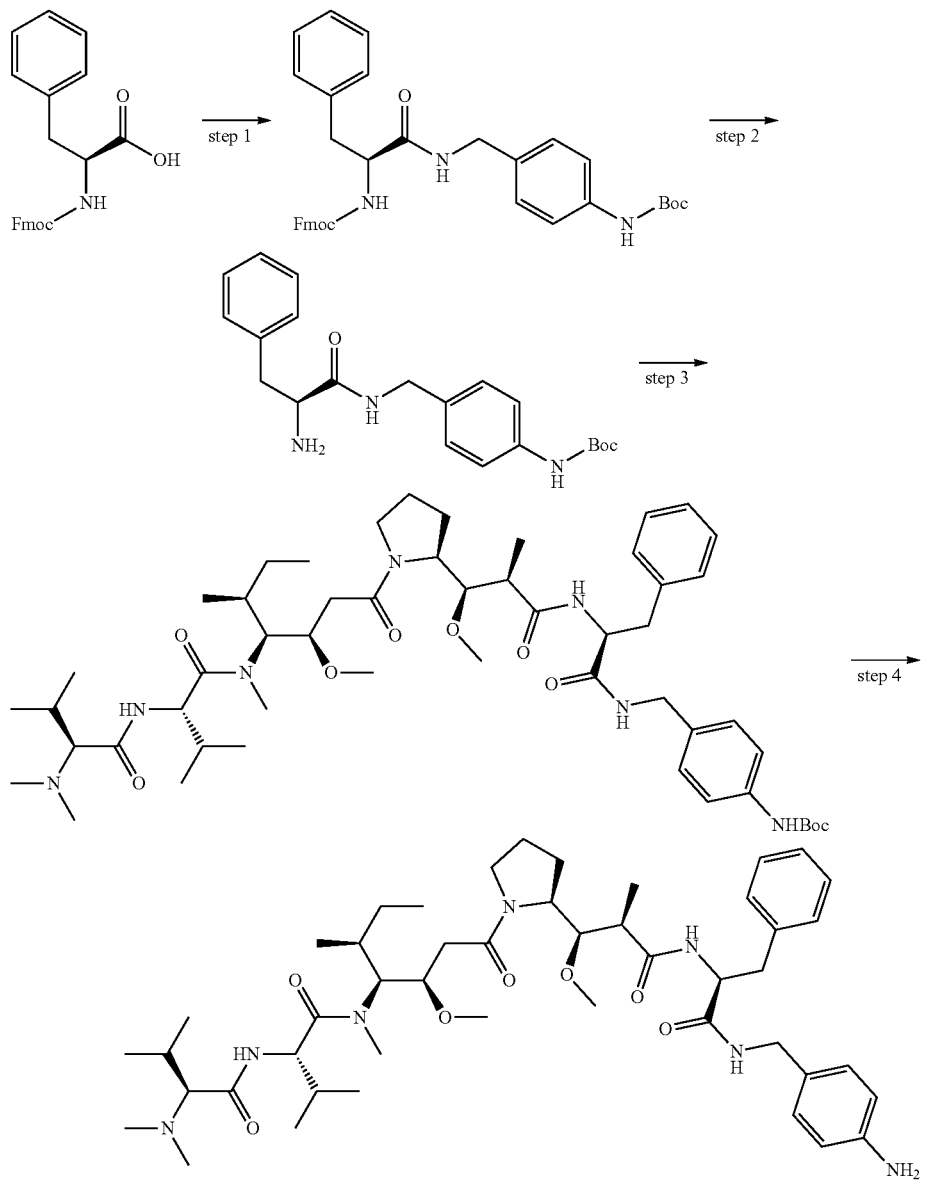

T011

The solid was purified by silica gel column chromatography to obtain the title compound (a 380 mg white solid). ESI-MS (m/z): 592.3 [M+H]+.

Step 2: Synthesis of tert-butyl (S)-(4-((2-amino-3-phenylpropionamido) methyl)phenyl) carbamate Lithium hydroxide monohydrate (21 mg, 0.51 mmol) was dissolved in water (1 mL) and added to a tetrahydrofuran (2 mL) solution of tert-butyl (S)-(4-((2-((((9H-fluoren-9-yl) methoxy)carbonyl)amino)-3-phenylpropionamido)methyl) phenyl) carbamate (102 mg, 0.17 mmol). The resulting mixture was reacted at room temperature for 2 hours. The reaction solution was added with water (20 mL) and extracted with ethyl acetate (30 mL×4). The organic phases were combined, washed with saturated saline (30 mL×2) and dried over anhydrous sodium sulfate. Then the desiccant was removed by filtration, the solvent was evaporated under reduced pressure, and the residues were purified by preparative liquid chromatography (method D) to obtain the title compound (65 mg of white solid). ESI-MS (m/z): 370.2 [M+H]+.

Step 3: Synthesis of (4-((S)-2-((2R,3R)-3-((S)-1-((3R,4S,5S)-4-((S)-3-((methylamino)-3-methylbutyrylamino)-N,3-dimethylbutyrylamino)-3-methoxy-5-methylheptanoyl)pyrrolidin-2-yl)-3-methoxy-2-methylpropionamido)-3-phenylpropionamido) methyl)phenyl)carbamate At 0° C., tert-butyl (S)-(4-((2-amino-3-phenylpropionamido)methyl)phenyl) carbamate (15 mg, 0.04 mmol) and N-methylmorpholine (12 mg, 0.12 mmol) were added to a solution of (2R,3R)-3-((S)-1-((3R,4S,5S)-4-((S)-2-((S)-2-(dimethylamino)-3-methylbutyrylamino)-N,3-dimethylbutyrylamino)-3-methoxy-5-methylheptanoyl)pyrrolidin-2-yl-3-methoxy-2-methylpropionic acid (24 mg, 0.04 mmol) in N,N-dimethylformamide (2 mL), then 1-hydroxybenzotriazole (8 mg, 0.06 mmol) and 1-(3-dimethylaminopropyl)-3-ethylcarbodiimide hydrochloride (12 mg, 0.06 mmol) were successively added. The resulting mixture was reacted overnight at 0° C. The reaction solution was purified by preparative liquid chromatography (method D) to obtain the title compound (24 mg of white solid). ESI-MS (m/z): 950.6 [M+H]+.

Step 4: Synthesis of (S)—N-((3R,4S,5S)-1-((S)-2-((1R,2R)-3-((S)-1-((4-aminobenzyl)amino)-1-oxo-3-phenylprop-2-yl)amino)-1-methoxy-2-methyl-3-oxopropyl)pyrrolidin-1-yl)-3-methoxy-5-methyl-1-oxoheptyl-4-yl)-2-((S)-2-(dimethylamino)-3-methylbutyrylamino)-N,3-dimethylbutyramide Trifluoroacetic acid (0.5 mL) was added to a solution of (4-((S)-2-((2R,3R)-3-((S)-1-(3R,4S,5S)-4-((S)-3-(methylamino)-3-methylbutyrylamino)-N, 3-dimethylbutyrylamino)-3-methoxy-5-methylheptanoyl)pyrrolidin-2-yl)-3-methoxy-2-methylpropanamido)-3-phenylpropionamido) methyl)phenyl) carbamate (14.0 mg, 0.015 mmol) in dichloromethane (1.5 mL). The resulting mixture was reacted at room temperature for 1 h. Then the solvent was evaporated under reduced pressure, and the residue was purified by preparative liquid chromatography (method C) to obtain the trifluoroacetate of the title compound (4.2 mg of white solid). ESI-MS (m/z): 850.6 [M+H]+.

The following molecules can be synthesized by a similar synthetic method:

| Name | Structure | ESI-MS |
|------|-----------|--------|
| T012 | 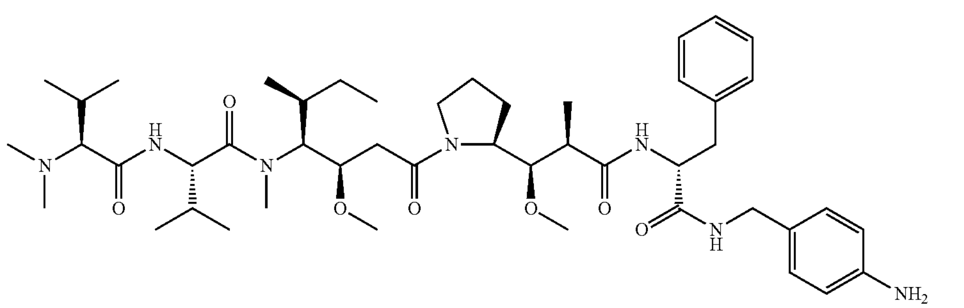 [SMILES: CC[C@H](C)[C@@H]([C@@H](CC(=O)N1CCC[C@H]1[C@H](OC)[C@@H](C)C(=O)N[C@H](Cc1ccccc1)C(=O)NCc1ccc(N)cc1)OC)N(C)C(=O)[C@@H](NC(=O)[C@H](C(C)C)N(C)C)C(C)C] | 850.6 |
| T013 | 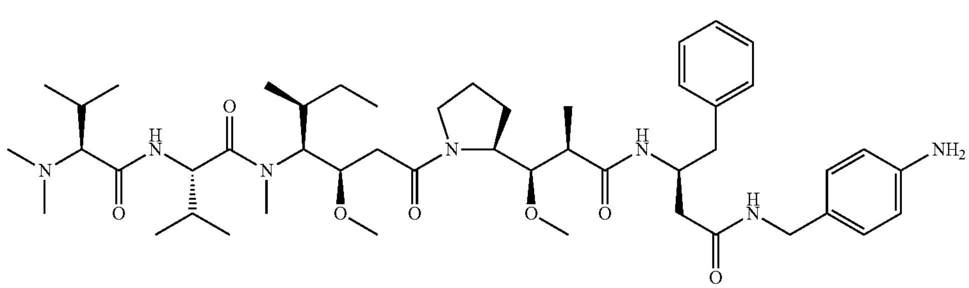 [SMILES: CC[C@H](C)[C@@H]([C@@H](CC(=O)N1CCC[C@H]1[C@H](OC)[C@@H](C)C(=O)N[C@H](CC(=O)NCc1ccc(N)cc1)Cc1ccccc1)OC)N(C)C(=O)[C@@H](NC(=O)[C@H](C(C)C)N(C)C)C(C)C] | 864.6 |

| Name | Structure | ESI-MS |
|---|---|---|
| T015 | 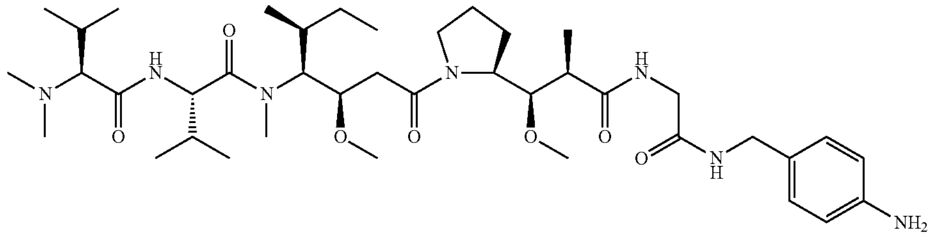 [SMILES: CC[C@H](C)[C@@H]([C@@H](CC(=O)N1CCC[C@H]1[C@H](OC)[C@@H](C)C(=O)NCC(=O)NCc1ccc(N)cc1)OC)N(C)C(=O)[C@@H](NC(=O)[C@H](C(C)C)N(C)C)C(C)C] | 760.6 |
| T021 | 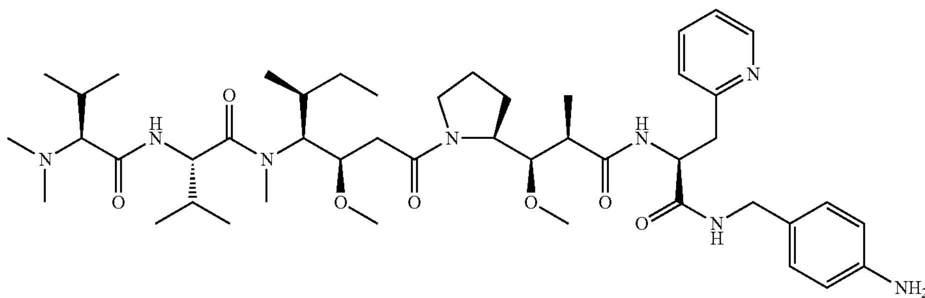 [SMILES: CC[C@H](C)[C@@H]([C@@H](CC(=O)N1CCC[C@H]1[C@H](OC)[C@@H](C)C(=O)N[C@@H](Cc1ccccn1)C(=O)NCc1ccc(N)cc1)OC)N(C)C(=O)[C@@H](NC(=O)[C@H](C(C)C)N(C)C)C(C)C] | 851.6 |

Example 3: Synthesis of (S)—N-(2-(4-ethyl-4-hydroxyl-3,14-dione-3,4,12,14-tetrahydro-1H-pyrano[3',4',6,7]indolizino[1,2-b]quinolin-11-yl)ethyl)-N-isopropylacetamide

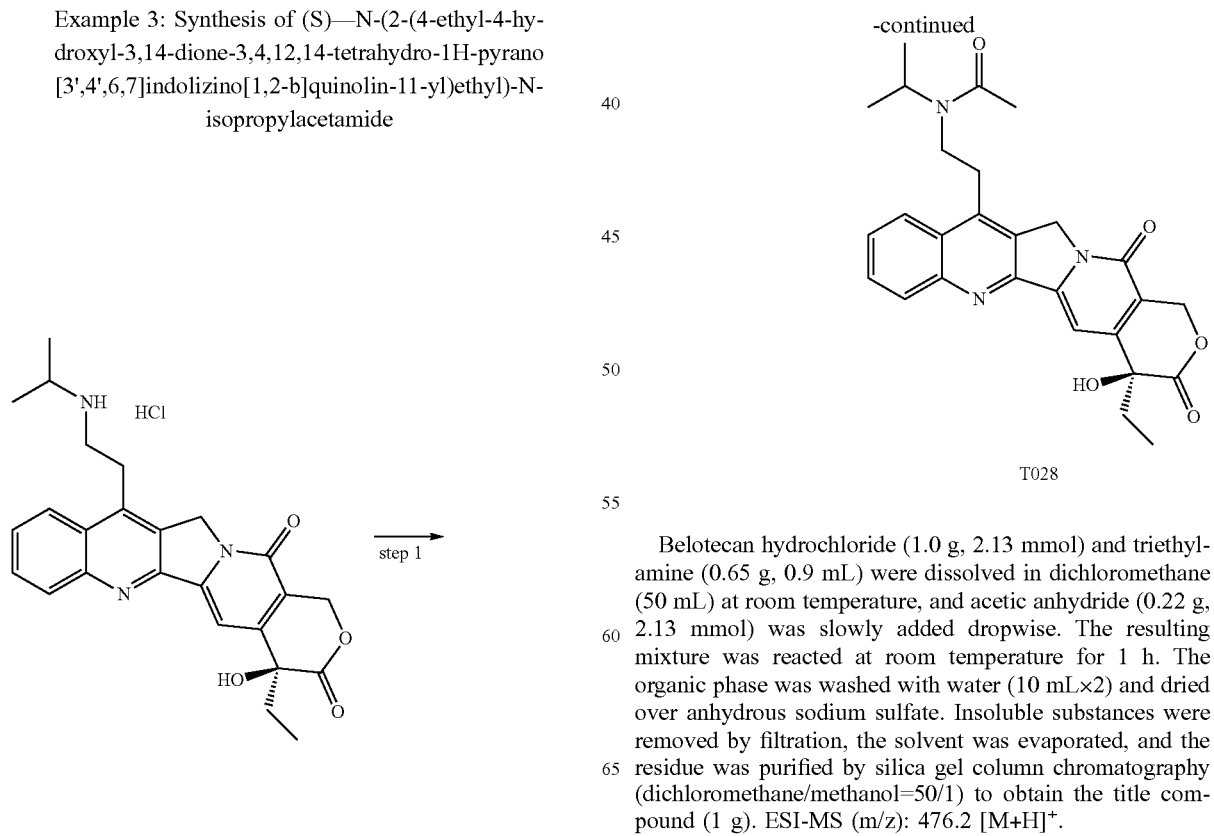

T028

Belotecan hydrochloride (1.0 g, 2.13 mmol) and triethylamine (0.65 g, 0.9 mL) were dissolved in dichloromethane (50 mL) at room temperature, and acetic anhydride (0.22 g, 2.13 mmol) was slowly added dropwise. The resulting mixture was reacted at room temperature for 1 h. The organic phase was washed with water (10 mL×2) and dried over anhydrous sodium sulfate. Insoluble substances were removed by filtration, the solvent was evaporated, and the residue was purified by silica gel column chromatography (dichloromethane/methanol=50/1) to obtain the title compound (1 g). ESI-MS (m/z): 476.2 [M+H]$^+$.

Example 4: Synthesis of (S)—N-(2-(4-ethyl-4-hydroxyl-3,14-dione-3,4,12,14-tetrahydro-1H-pyrano[3',4',6,7]indolizino[1,2-b]quinolin-11-yl)ethyl)-N-isopropylmethanesulfonamide

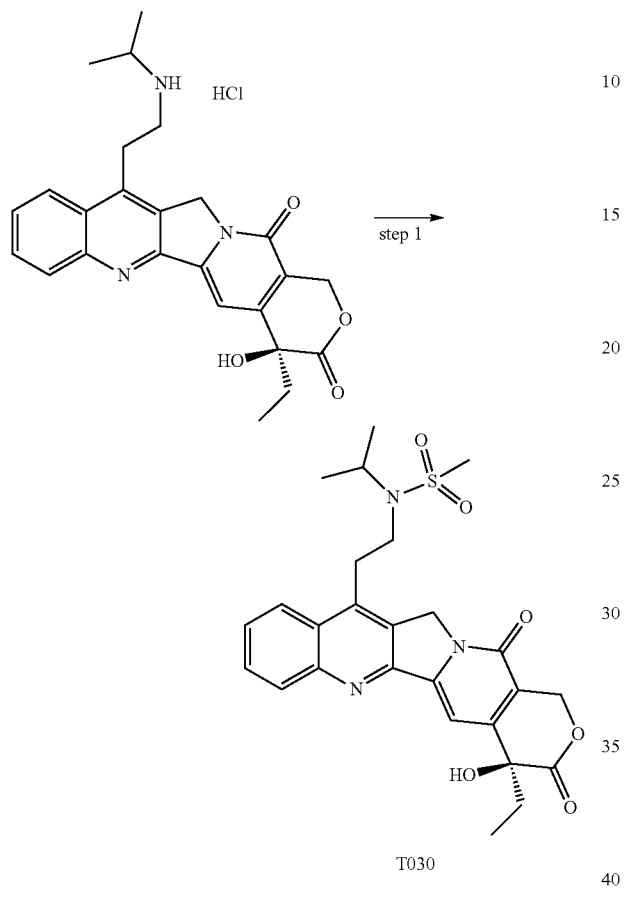

Methylsulfonyl chloride (462 mg, 12.77 mmol, purity: about 70%) was added dropwise to a solution of belotecan hydrochloride (3 g, 6.38 mmol) and triethylamine (2.58 g, 25.54 mmol) in dichloromethane (40 mL). The resulting mixture was reacted at room temperature for 2 h. Suction filtration was performed, and the filter cake was washed three times with dichloromethane (3 mL) to obtain the title compound (2.2 g).

Structural characterization data are as follows:

$^1$H NMR (400 MHz, DMSO-$d_6$) δ 8.32 (d, J=8.4 Hz, 1H), 8.20 (dd, J=8.4, 1.2 Hz, 1H), 7.93-7.84 (m, 1H), 7.79 (t, J=7.6 Hz, 1H), 7.35 (s, 1H), 6.56 (s, 1H), 5.44 (d, J=9.2 Hz, 4H), 3.98 (p, J=6.7 Hz, 1H), 3.50 (t, J=8.0 Hz, 2H), 3.42-3.35 (m, 2H), 3.00 (s, 3H), 1.93-1.82 (m, 2H), 1.15 (d, J=6.7 Hz, 6H), 0.88 (t, J=7.3 Hz, 3H). ESI-MS (m/z): 512.2 [M+H]$^+$. $[α]_D^{20}$ is +28.19° (c=0.101 g/100 mL, CH$_3$CN).

The rest bioactive molecules without illustration of synthetic method are commercially available or can be prepared by the method disclosed in the prior art.

II. Synthesis of Compounds Containing Bioactive Molecules and Linkers

Example 5: Synthesis of (S)-2-((S)-2-(4-(4-chloro-7H-pyrrolo[2,3-d]pyrimidin-7-yl)butyrylamido)-3-methylbutyrylamido)-N-(4-(((S)-2-((2R,3R)-3-((S)-1-((3R,4S,5S)-4-((S)-2-((S)-2-(dimethylamino)-3-methylbutyrylamino)-N,3-dimethylbutyrylamino)-3-methoxy-5-methylheptanoyl)pyrrolidin-2-yl)-3-methoxy-2-methylpropionamido)-3-phenylpropionamido)methyl)phenyl)-5-ureidovaleramide

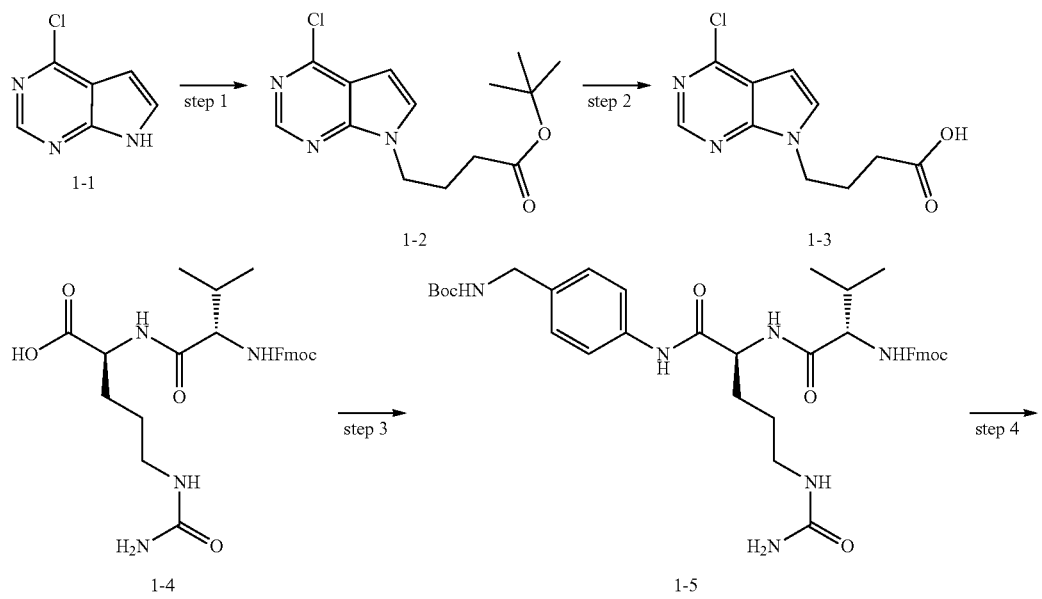

-continued
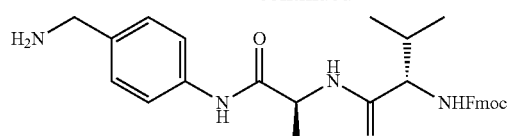
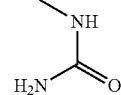
1-6
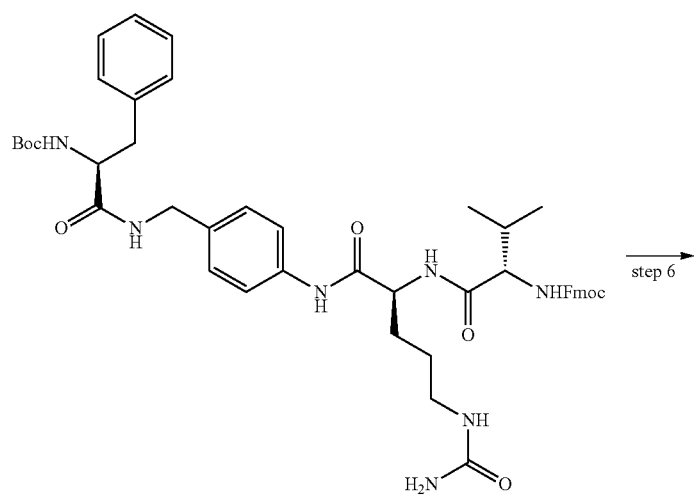
1-7
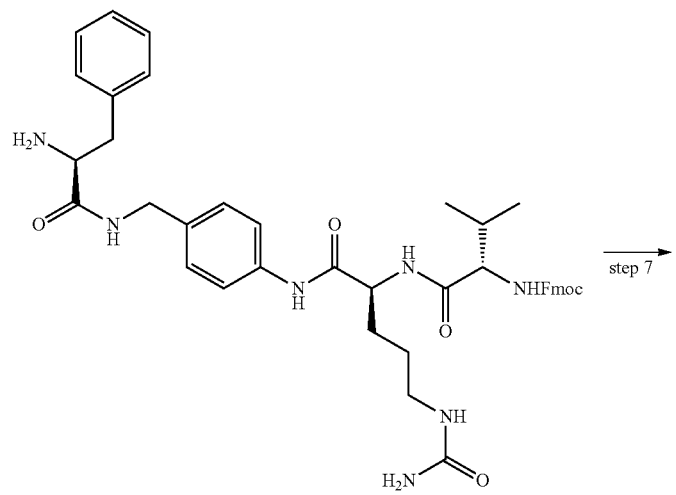
1-8

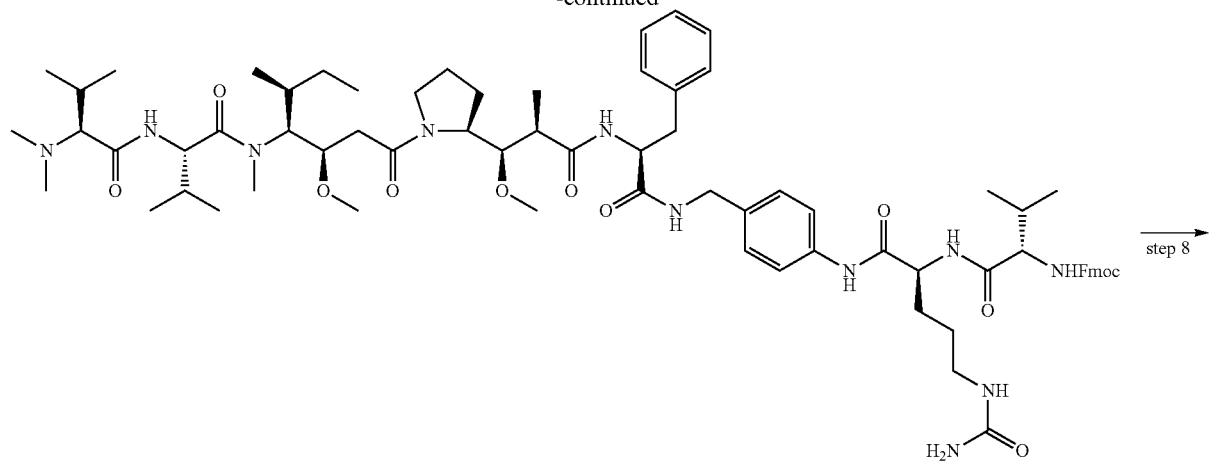

Step 1: Synthesis of tert-butyl 4-(4-chloro-7H-pyrrolo[2,3-d]pyrimidin-7-yl) butyrate (Compound 1-2)

At room temperature, compound 1-1 (500 mg, 3.27 mmol) was dissolved in N,N-dimethylformamide (10 mL), sodium hydride (130 mg, 3.27 mmol) was slowly added in batches thereto. The resulting mixture was stirred at room temperature for 10 min, followed by the dropwise addition of t-butyl 4-bromobutyrate (725 mg, 3.27 mmol), and then reacted at room temperature for 2 hours. The reaction was quenched with saturated ammonium chloride aqueous solution, and extracted with ethyl acetate (50 mL×3). Then organic phases were combined, washed with saturated saline solution (50 mL×3) and dried over anhydrous sodium sulfate. The desiccant was removed by filtration, and the solvent was evaporated under reduced pressure to obtain the title compound (500 mg). ESI-MS (m/z): 296.1 [M+H]$^+$.

Step 2: Synthesis of 4-(4-chloro-7H-pyrrolo[2,3-d]pyrimidin-7-yl)butyric Acid (Compound 1-3)

At room temperature, compound 1-2 (500 mg, 1.69 mmol) was dissolved in dichloromethane (6 mL), and trifluoroacetic acid (3 mL) was added and reacted at room temperature for 4 hours. Then the solvent was evaporated under reduced pressure to obtain the title compound (400 mg). ESI-MS (m/z): 240.1 [M+H]$^+$.

Step 3: Synthesis of (9H-fluoren-9-yl)-methyl-((S)-1-(((S)-1-((4-(((tert-butoxycarbonyl)amino)methyl)phenyl)amino)-1-oxo-5-ureidopentyl-2-yl)amino)-3-methyl-1-oxobutyl-2-yl)-carbamate (Compound 1-5)

At room temperature, 4-(N-Boc-aminomethyl)-aniline (6.0 g, 27 mmol), compound 1-4 (3.35 g, 6.75 mmol), and 2-ethyoxyl-1-ethoxycarboxyl-1,2-dihydroquinoline (3.34 g, 13.5 mmol) were dissolved in the mixed solvent of dichloromethane (140 mL) and methanol (70 mL), then warmed to 45° C. and reacted at the temperature for 8.0 hours. After being cooled to room temperature, a large amount of solid was precipitated, which was subject to suction filtration to obtain the title compound (3.65 g). ESI-MS (m/z): 701.4 [M+H]$^+$.

Step 4: Synthesis of (9H-fluoren-9-yl)-methyl-((S)-1-(((S)-1-((4-(aminomethyl)phenyl))amino)-1-oxo-5-5-ureidopentyl-2-yl)amino)-3-methyl-1-oxobutyl-2-yl)-carbamate (Compound 1-6)

At room temperature, trifluoroacetic acid (15 mL) was added to compound 1-5 (3.0 g, 4.29 mmol) and stirred at room temperature for 1.0 h. Then the solvent was evaporated under reduced pressure to obtain a yellow oil. Anhydrous diethyl ether (20 mL) was added, and a large amount of solid was precipitated. After vigorous stirring for 0.5 h, suction filtration was carried out to obtain the trifluoroacetate of the title compound (3.06 g). ESI-MS (m/z): 601.3[M+H]$^+$.

Step 5: Synthesis of (9H-fluoren-9-yl)-methyl-((S)-1-(((S)-1-((4-(((R)-2-((t-butyloxycarbonyl)amino)-3-phenylpropionamido)methyl)phenyl)amino-1-oxo-5-ureidopentyl-2-yl)amino)-3-methyl-1-oxobutyl-2-yl)-carbamate (Compound 1-7)

At room temperature, Boc-D-phenylalanine (1.1 g, 4.2 mmol) and the trifluoroacetate of compound 1-6 (3.0 g, 4.2 mmol) were dissolved in N,N-dimethylformamide (40 mL), cooled to 0° C., and then 1-(3-dimethylaminopropyl)-3-ethylcarbodiimide hydrochloride (1.2 g, 6.3 mmol), 1-hydroxybenzotriazole (0.9 g, 6.3 mmol) and N-methylmorpholine (1.7 g, 16.8 mmol) were successively added. The reaction system was stirred for 1.0 h at the temperature. The reaction solution was then added dropwise to ice water (400 mL) and stirred vigorously for 0.5 h, a large amount of solid was precipitated, and suction filtration was carried out to obtain the title compound (3.3 g). ESI-MS (m/z): 848.4 [M+H]$^+$.

Step 6: Synthesis of (9H-fluoren-9-yl)-methyl-((S)-1-(((S)-1-((4-(((R)-2-amino-3-phenylpropionamido)methyl)phenyl)amino)-1-oxo-5-ureidopentyl-2-yl)amino)-3-methyl-1-oxobutyl-2-yl)-carbamate (Compound 1-8)

At room temperature, compound 1-7 (3.0 g, 3.3 mmol) was dissolved in trifluoroacetic acid (30 mL) and stirred at room temperature for 1.0 h. The solvent was evaporated under reduced pressure to obtain a yellow oil. Anhydrous diethyl ether (100 mL) was added and stirred vigorously for 0.5 h, and a large amount of solid was precipitated. Suction filtration was carried out to obtain the trifluoroacetate of the title compound (2.1 g). ESI-MS (m/z): 748.4 [M+H]$^+$.

Step 7: Synthesis of (9H-fluoren-9-yl)-methyl-((S)-1-(((S)-1-((4-(((S)-2-((2R,3R)-3-((S)-1-((3R,4S,5S)-4-((S)-2-((S)-2-(dimethylamino)-3-butyrylamido)-N,3-dimethylamino)-3-methoxy-5-methylheptanoyl)pyrro-2-yl)-3-methoxy-2-methylpropionamido)-3-phenylpropionamido)methyl)phenyl)amino)-1-oxo-5-ureidopent-2-yl)amino)-3-methyl-1-oxobutan-2-yl) carbamate (Compound 1-9)

At room temperature, (2R,3R)-3-((S)-1-((3R,4S,5S)-4-((S)-2-((S)-(dimethylamino)-3-butyrylamino)-N,3-dimethylbutyrylamino)-3-methoxy-5-methylheptanoyl)pyrro-2-yl)-3-methoxy-2-methylpropionic acid (1.3 g, 2.17 mmol) and trifluoroacetate of compound 1-8 (1.8 g, 2.17 mmol) were dissolved in N,N-dimethylformamide (20 mL), cooled to 0° C., then 1-hydroxybenzotriazole (440 mg, 3.26 mmol) and N-methylmorpholine (658 mg, 6.51 mmol) were successively added, and 1-(3-dimethylaminopropyl)-3-ethyl-carbodiimide hydrochloride (624 mg, 1.38 mmol) was added at last, the reaction solution was stirred at 0° C. for 5 hours, and purified by preparative liquid chromatography (method D) to obtain the title compound (1.8 g). ESI-MS (m/z): 1329.2 [M+H]$^+$.

Step 8: Synthesis of (S)-2-((S)-2-amino-3-butyrylamino)-N-(4-(((S)-2-((2R,3R)-3-((S)-1-((3R,4S,5S)-4-((S)-2-((S)-2-(dimethylamino)-3-butyrylamino)-N,3-dimethylbutyrylamino)-3-methoxy-5-methylheptanoyl)pyrro-2-yl)-3-methoxy-2-methylpropionamido)-3-phenylpropionamido)methyl)phenyl)-5-ureidovaleramide (Compound 1-10)

At room temperature, compound 1-9 (500 mg, 0.38 mmol) was dissolved in N,N-dimethylformamide (5 mL), added with piperidine (324 mg, 3.8 mmol) and stirred at room temperature for 3 h. Then the purification was performed on preparative liquid chromatography (method D) to obtain the title compound (350 mg). ESI-MS (m/z): 1107.2 [M+H]$^+$.

Step 9: Synthesis of (S)-2-((S)-2-(4-(4-chloro-7H-pyrrolo[2,3-d]pyrimidin-7-yl)butyrylamido)-3-methylbutyrylamido)-N-(4-(((S)-2-((2R,3R)-3-((S)-1-((3R,4S,5S)-4-((S)-2-((S)-2-(dimethylamino)-3-methylbutyrylamino)-N,3-dimethylbutyrylamino)-3-methoxy-5-methylheptanoyl)pyrrolidin-2-yl)-3-methoxy-2-methylpropionamido)-3-phenylpropionamido)methyl)phenyl)-5-ureidovaleramide (Compound TL001)

At room temperature, compound 1-10 (60 mg, 0.054 mmol) and 4-(4-chloro-7H-pyrrolo[2,3-d]pyrimidin-7-yl)butyric acid (26 mg, 0.066 mmol) were dissolved in N,N-dimethylformamide (3 mL), cooled to 0° C., and N,N-diisopropylethylamine (105 mg, 0.81 mmol) and 1H-benzotriazole-1-oxytripyrrolidinophosphonium hexafluorophosphate (281 mg, 0.54 mmol) were successively added. The reaction system was stirred at room temperature for 3 hours. Then purification was performed on preparative liquid chromatography (method D) to obtain the title compound (30 mg). ESI-MS (m/z): 664.5 [M/2+H]$^+$.

Example 6: (S)—N-(4-(((S)-2-((2R,3R)-3-((S)-1-((3R,4S,5S)-4-((S)-2-((S)-2-(dimethylamino)-3-methylbutyrylamino)-N,3-dimethylbutyrylamino)-3-methoxy-5-methylheptanoyl)pyrrolidin-2-yl)-3-methoxy-2-methylpropionamido)-3-phenylpropionamido)methyl)phenyl)-2-((S)-3-methyl-2-(4-(4-(methylsulfonyl)-7H-pyrrolo[2,3-d]pyrimidin-7-yl)-butyrylamido)-butyrylamido)-5-ureidovaleramide

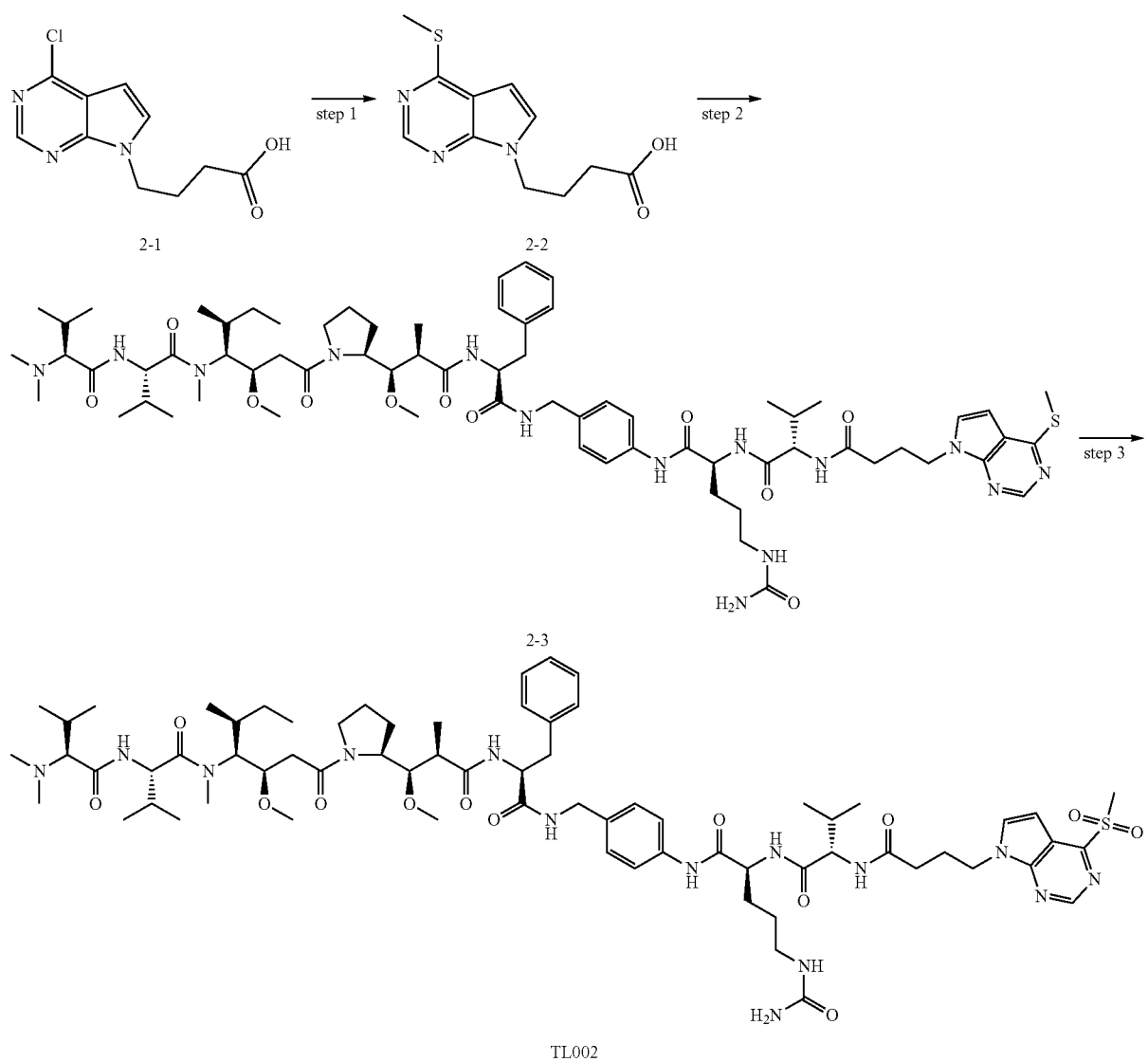

Step 1: Synthesis of 4-(4-(methylthio)-7H-pyrrolo[2,3-d]pyrimidin-7-yl)butyric Acid (Compound 2-2)

At room temperature, 4-(4-chloro-7H-pyrrolo[2,3-d]pyrimidin-7-yl) butyric acid (300 mg, 1.25 mmol) was dissolved in methanol (8 mL), sodium methanethiol (351 mg, 5.02 mmol) was added in one batch, and then warmed to 50° C. and reacted overnight. Purification was performed on preparative liquid chromatography (method D) to obtain the title compound (120 mg). ESI-MS (m/z): 252.1 [M+H]$^+$.

Step 2: Synthesis of (S)—N-(4-(((S)-2-((2R,3R)-3-((S)-1-((3R,4S,5S)-4-((S)-2-((S)-2-(dimethylamino)-3-methylbutyrylamino)-N,3-dimethylbutyrylamino)-3-methoxy-5-methylheptanoyl)pyrrolidin-2-yl)-3-methoxy-2-methylpropionamido)-3-phenylpropionamido)methyl)phenyl)-2-((S)-3-methyl-2-(4-(4-(methylthio)-7H-pyrrolo[2,3-d]pyrimidin-7-yl)-butyrylamido)-butyrylamido)-5-ureidovaleramide (Compound 2-3)

Operations similar to those described in step 9 of example 5, except that 4-(4-chloro-7H-pyrrolo[2,3-d]pyrimidin-7-yl)

butyric acid was replaced with 4-(4-(methylthio)-7H-pyrrolo[2,3-d]pyrimidin-7-yl) butyric acid, were carried out, and purification was performed by using preparative liquid chromatography (method D) to obtain the title compound (20 mg). ESI-MS (m/z): 670.5 [M/2+H]⁺.

Step 3: Synthesis of (S)—N-(4-(((S)-2-((2R,3R)-3-((S)-1-((3R,4S,5S)-4-((S)-2-((S)-2-(dimethylamino)-3-methylbutyrylamino)-N,3-dimethylbutyrylamino)-3-methoxy-5-methylheptanoyl)pyrrolidin-2-yl)-3-methoxy-2-methylpropionamido)-3-phenylpropionamido)methyl)phenyl)-2-((S)-3-methyl-2-(4-(methylsulfonyl)-7H-pyrrolo[2,3-d]pyrimidin-7-yl)-butyrylamido)-butyrylamido)-5-ureidovaleramide (Compound TL002)

At room temperature, compound 2-3 (20 mg, 0.015 mmol) was dissolved in dichloromethane (2 mL), and m-chloroperoxybenzoic acid (4.0 mg, 0.022 mmol) was added. The resulting mixture was reacted at room temperature for 2 hours. Purification was performed on preparative liquid chromatography (method D) to obtain the title compound (5.0 mg). ESI-MS (m/z): 686.5 [M/2+H]⁺.

Example 7: N—((S)-1-(((S)-1-((4-(((S)-2-((2R,3R)-3-((S)-1-((3R,4S,5S)-4-((S)-2-((S)-2-(dimethylamino)-3-methylbutyrylamino)-N,3-dimethylbutyrylamino)-3-methoxy-5-methylheptanoyl)pyrrolidin-2-yl)-3-methoxy-2-methylpropionamido-3-phenylpropionamido)methyl)phenyl)amino)-1-oxo-5-ureido-2-yl)amino)-3-methyl-1-oxybutan-2-yl)-6-(2-(methylsulfonyl)pyrimidin-5-yl)-5-hexynamide

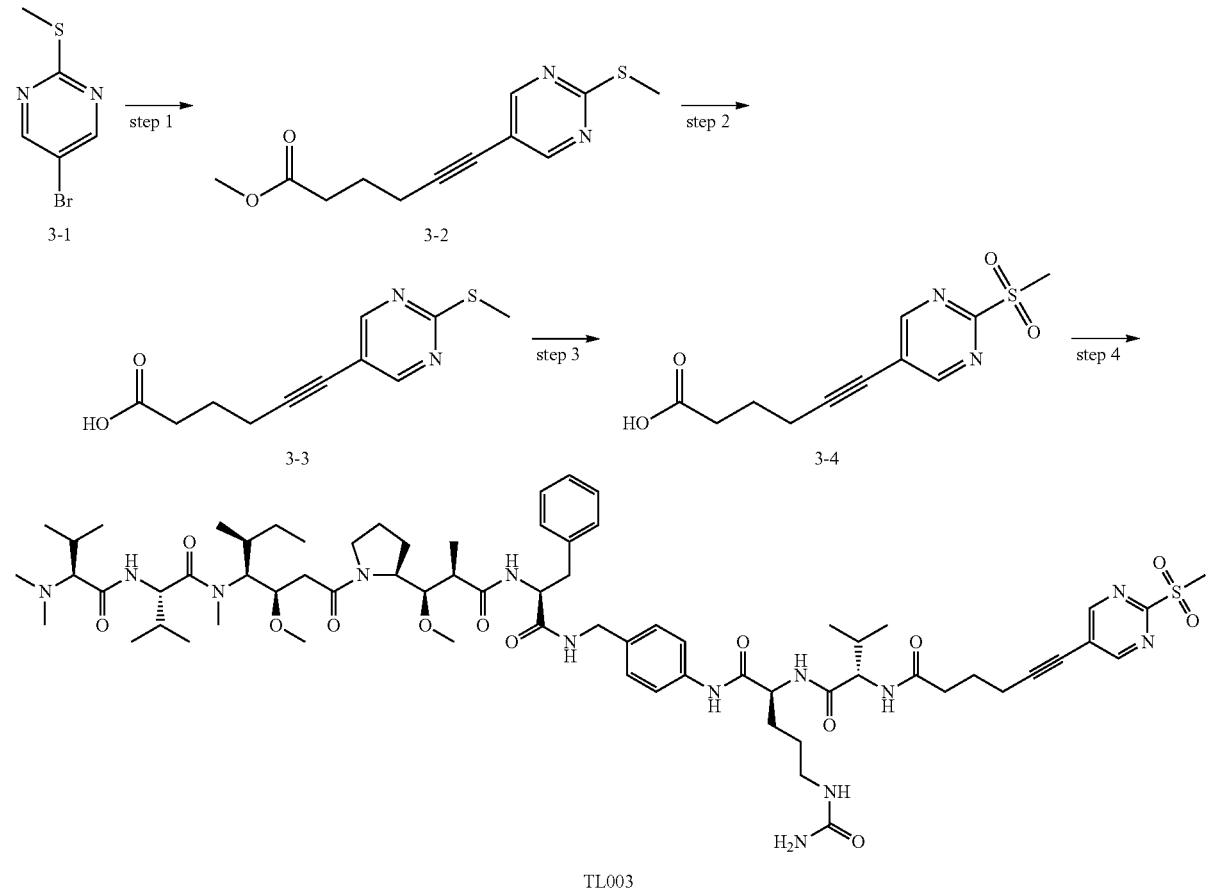

TL003

Step 1: Synthesis of methyl 6-(2-(methylthio)pyrimidin-5-yl)-5-hexynoate (Compound 3-2)

At room temperature, methyl 5-hexynoate (500 mg, 3.97 mmol) and 5-bromo-2-methylthiopyrimidine were dissolved in N,N-dimethylformamide (3 ml), then triethylamine (3 ml), cuprous iodide (75 mg, 0.4 mmol) and Bis (triphenylphosphine) palladium (II) dichloride (279 mg, 0.4 mmol) were successively added. The resulting mixture was heated to 95° C. under nitrogen protection and reacted for 6 h under stirring, quenched with water, and extracted with ethyl acetate (20 mL×3). Organic phases were combined, washed with saturated saline (20 mL×2) and dried over anhydrous sodium sulfate. The desiccant was removed by filtration, and the solvent was evaporated under reduced pressure. Purification was performed on preparative liquid chromatography (method D) to obtain the title compound (300 mg). ESI-MS (m/z): 251.3 [M+H]⁺.

Step 2: Synthesis of 6-(2-(methylthio)pyrimidin-5-yl)-5-hexynoic Acid (Compound 3-3)

At room temperature, compound 3-2 (200 mg, 0.8 mmol) was dissolved in a mixed solution of tetrahydrofuran and water (4 mL/4 mL), and lithium hydroxide monohydrate (235 mg, 5.6 mmol) was added, and reacted at room temperature under stirring for 4 h, then diluted with water and extracted with ethyl acetate (20 ml×2). The aqueous phase was adjusted to pH=3 with 1N hydrochloric acid, and extracted with ethyl acetate (20 mL×3), then organic phases were combined, washed with saturated saline (20 mL×2) and dried over anhydrous sodium sulfate. The desiccant was removed by filtration, and the solvent was evaporated under reduced pressure to obtain the title compound (120 mg).

Step 3: Synthesis of 6-(2-(methylsulfonyl)pyrimidin-5-yl)-5-hexynoic Acid (Compound 3-4)

At room temperature, compound 3-3 (20 mg, 0.085 mmol) was dissolved in dichloromethane (4 mL), and m-chloroperoxybenzoic acid (22 mg, 0.127 mmol) was added for reaction at room temperature overnight under stirring. Purification was performed on preparative liquid chromatography (method D) to obtain the title compound (20 mg). ESI-MS (m/z): 269.1 [M+H]⁺.

Step 4: N—((S)-1-(((S)-1-((4-(((S)-2-((2R,3R)-3-((S)-1-((3R,4S,5S)-4-((S)-2-((S)-2-(dimethylamino)-3-methylbutyrylamino)-N,3-dimethylbutyrylamino)-3-methoxy-5-methylheptanoyl)pyrrolidin-2-yl)-3-methoxy-2-methylpropionamido)-3-phenylpropionamido)methyl)phenyl)amino)-1-oxo-5-ureido-2-yl)amino)-3-methyl-1-oxybutan-2-yl)-6-(2-(methylsulfonyl)pyrimidin-5-yl)-5-hexynamide (Compound TL003)

Operations similar to those described in step 9 of example 5, except that 4-(4-chloro-7H-pyrrolo[2,3-d]pyrimidin-7-yl)butyric acid was replaced with 6-(2-(methylsulfonyl)pyrimidin-5-yl)-5-hexynoic acid, were carried out, and purification was performed by using preparative liquid chromatography (method D) to obtain the title compound (14 mg). ESI-MS (m/z): 679.0 [M/2+H]⁺.

Example 8: (S)-4-ethyl-11-(2-(N-isopropylmethyl-sulfonamide)-ethyl)-3,14-dioxo-3,4,12,14-tetra-hydro-1H-pyrano[3',4',6,7]-indolizino[1,2-b]-quino-lin-4-yl(4-((S)-42-(2-(methylsulfonyl)pyrimidin-5-yl)-4,8,37-trioxo-2-(3-ureidopropyl)-6,12,15,18,21,24,27,30,33-nonoxy-3,9,36-azatetracosan-41-amido)benzyl)carbonate

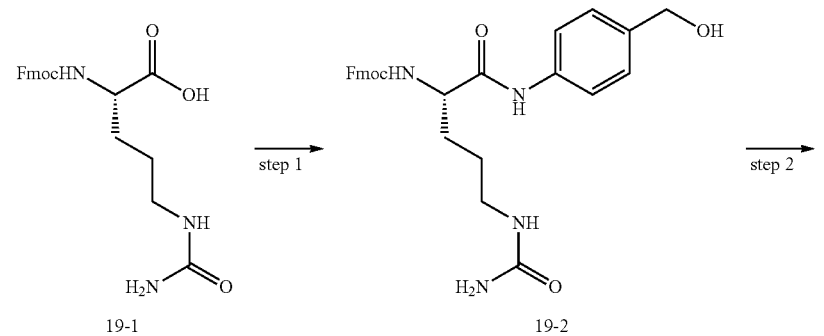

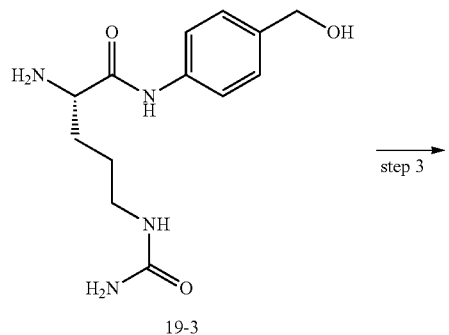

-continued
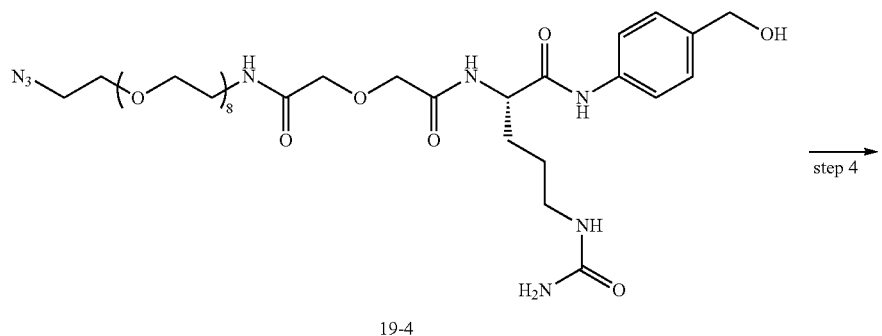
19-4
step 4 →
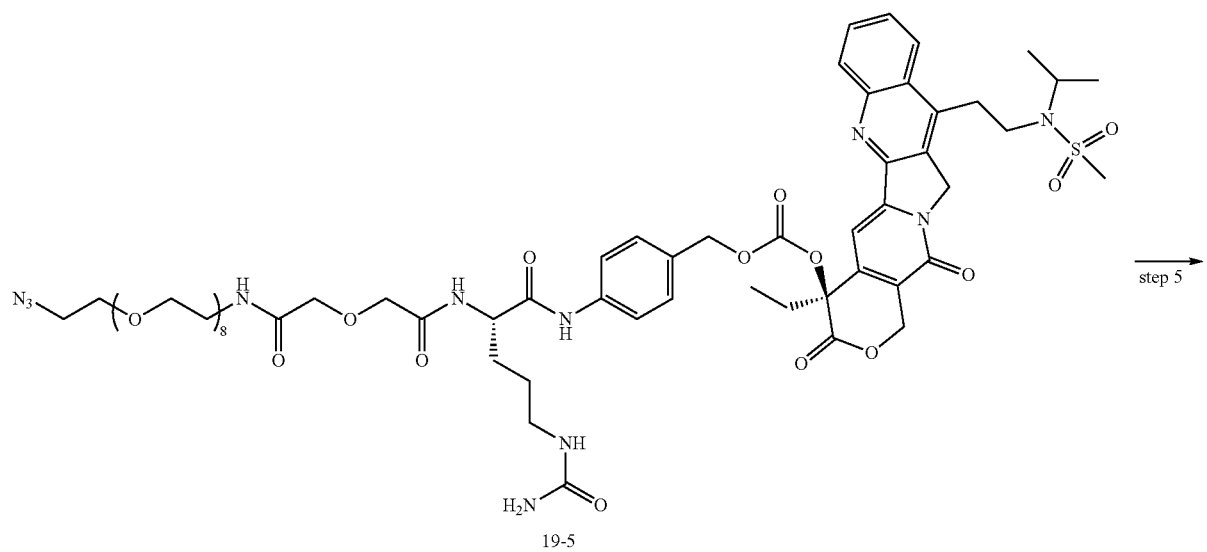
19-5
step 5 →
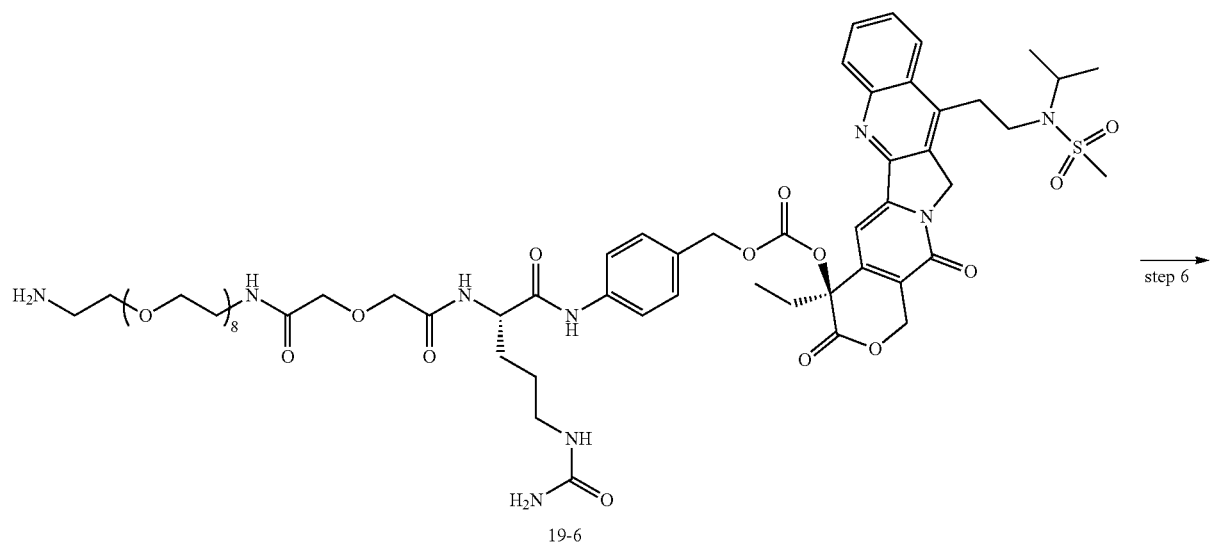
19-6
step 6 →

-continued

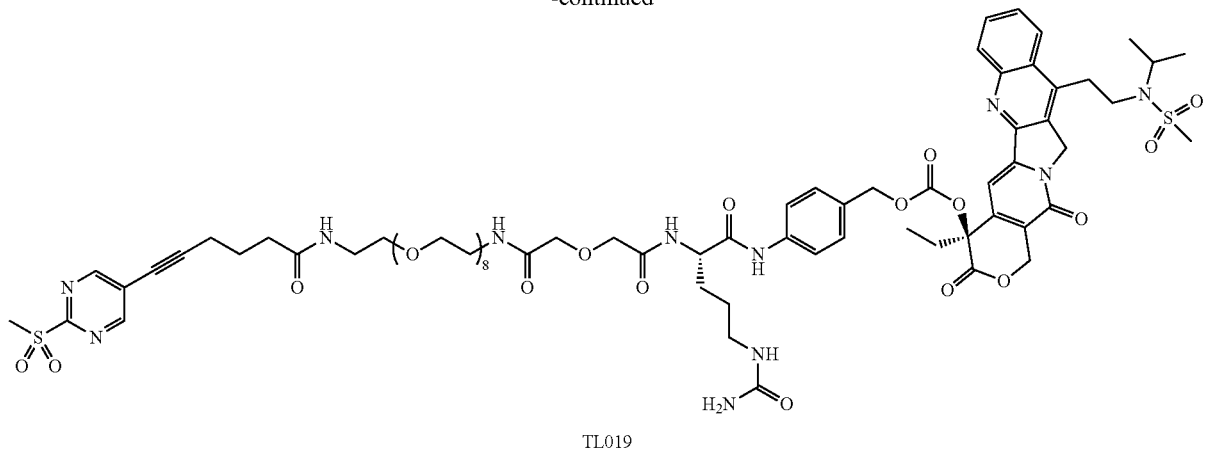

TL019

Step 1: Synthesis of methyl (S)-(1-((4-(hydroxymethyl)phenyl)amino)-1-oxo-5-ureidopentan-2-yl)-(9H-fluorenyl) carbamate (Compound 19-2)

At room temperature, Fmoc-L-citrulline (5.0 g, 12.58 mmol), p-aminobenzyl alcohol (6.20 g, 50.32 mmol) and 2-ethoxy-1-ethoxycarboxyl-1, 2-dihydroquinoline (6.22 g, 25.16 mmol) were dissolved in dichloromethane (100 mL), and heated to 45° C. and reacted for 6 h. The reaction solution was concentrated under reduced pressure, and beaten with anhydrous diethyl ether (100 mL) to obtain the title compound (6.0 g). ESI-MS (m/z): 503.3 [M+H]$^+$.

Step 2: Synthesis of (S)-2-amino-N-(4-(hydroxymethyl)phenyl)-5-ureidovaleramide (Compound 19-3)

At room temperature, compound 19-2 (1.0 g, 1.99 mmol) was dissolved in N,N-dimethylformamide (8 mL), and piperidine (339 mg, 3.98 mmol) was added dropwise for reaction at room temperature for 30 min, then dichloromethane (10 mL) was added, followed by stirring for 10 min. The reaction solution was concentrated under reduced pressure, and purified by flash column chromatography to obtain the title compound (400 mg). ESI-MS (m/z): 281.2 [M+H]$^+$.

Step 3: Synthesis of (S)-2-(32-azido-5-oxo-3,9,12,15,18,21,24,27,30-nonyloxa-6-azatriacetamido)-N-(4-(hydroxymethyl)phenyl)-5-ureidovaleramide (Compound 19-4)

Compound 19-3 (150 mg, 0.54 mmol) and 32-azido-5-oxo-3,9,12,15,18,21,24,27,30-nonoxy-6-azatricycloundecanoic acid (296 mg, 0.54 mmol) were dissolved in dichloromethane (10 mL) and cooled to 0° C., then 2-ethoxy-1-ethoxycarboxyl-1,2-dihydroquinoline (145 mg, 0.58 mmol) was added. The resulting mixture was moved to room temperature and reacted overnight. The reaction solution was concentrated under reduced pressure, and purified by flash column chromatography to obtain the title compound (200 mg). ESI-MS (m/z): 817.5 [M+H]$^+$.

Step 4: Synthesis of 4-((S)-35-azido-4,8-dioxo-2-(3-ureidopropyl)-6,12,15,18,21,24,27,30,33-nonoxy-3,9-azatetracosane)benzyl((S)-4-ethyl-11-(2-(N-isopropylmethylsulfonylamino)ethyl)-3,14-dioxo-3,4,12,14-tetrahydro-1H-pyrano[3',4',6,7]indolizino[1,2-b]quinolin-4-yl)carbonate (Compound 19-5)

At room temperature, (S)—N-(2-(4-ethyl-4-hydroxy-3,14-dione-3,4,12,14-tetrahydro-1H-pyrano[3',4',6,7]indolizino[1,2-b]quinolin-11-yl)ethyl)-N-isopropylmethanesulfonamide (200 mg, 0.39 mmol) was dissolved in dichloromethane (10 mL) and cooled to 0° C., a solution of 4-dimethylaminopyridine (573 mg, 4.69 mmol) in dichloromethane (1.0 ml) was added, and then a solution of triphosgene (116 mg, 0.39 mmol) in dichloromethane (1.0 ml) was slowly added dropwise. The resulting mixture was reacted at 0° C. for 1 h under stirring. A solution of the compound 19-4 (159 mg, 0.18 mmol) in dichloromethane (2.0 mL) was added to the reaction solution and reacted at room temperature for 1 h. Purification was performed on preparative high performance liquid chromatography (method D) to obtain the title compound (160 mg). ESI-MS (m/z): 678.0 [M/2+H]$^+$.

Step 5: Synthesis of 4-((S)-35-amino-4,8-dioxo-2-(3-ureidopropyl)-6,12,15,18,21,24,27,30,33-nonoxy-3,9-azatetracosane)benzyl((S)-4-ethyl-11-(2-(N-isopropylmethylsulfonylamino)ethyl)-3,14-dioxo-3,4,12,14-tetrahydro-1H-pyrano[3',4',6,7]indolizino[1,2-b]quinolin-4-yl)carbonate (Compound 19-6)

At room temperature, compound 19-5 (80 mg, 0.059 mmol) was dissolved in tetrahydrofuran (1.0 ml) and cooled to 0° C., then a solution of 4-dimethylaminopyridine (573 mg, 4.69 mmol) in dichloromethane (1.0 ml) was added, and platinum dioxide (15 mg, 0.059 mmol) was added in one batch under nitrogen protection, then air was substituted with hydrogen for three times and reacted at room temperature for 6 hours. The reaction solution was filtered, and the filtrate was concentrated to obtain a crude product which was purified by preparative high performance liquid chromatography (method D) to obtain the title compound (40 mg). ESI-MS (m/z): 665.0 [M/2+H]$^+$.

Step 6: Synthesis of (S)-4-ethyl-11-(2-(N-isopropylmethylsulfonamide)ethyl)-3,14-dioxo-3,4,12,14-tetrahydro-1H-pyrano[3',4',6,7]indolizino[1,2-b]quinolin-4-yl(4-((S)-42-(2-(methylsulfonyl)pyrimidin-5-yl)-4,8,37-trioxo-2-(3-ureidopropyl)-6,12,15,18,21,24,27,30,33-nonoxy-3,9,36-azatetracosan-41-amido)benzyl)carbonate (Compound TL019)

Compound 19-6 (30 mg, 0.016 mmol) and 6-(2-methylsulfonylpyrimidin-5-yl)-5-hexynoic acid (6.4 mg, 0.024 mmol) were dissolved in N,N-dimethylformamide (1 mL) and cooled to 0° C., then benzotriazol-1-yl-oxytripyrrolidinyl hexafluorophosphate (16.5 mg, 0.032 mmol), N,N-diisopropylethylamine (6.2 mg, 0.047 mmol) were successively added. The resulting mixture was reacted at room temperature for 2 hours. Purification was performed on preparative high performance liquid chromatography (method D) to obtain the title compound (10 mg). ESI-MS (m/z): 790.0 [M/2+H]⁺.

Example 9: (S)-4-ethyl-11-(2-(N-isopropylmethane-sulfonamide)ethyl)-3,14-dioxo-3,4,12,14-tetrahydro-1H-pyrano[3',4',6,7]indolizino[1,2-b]quinolin-4-yl-(4-((S)-2-((S)-3-methyl-2-(6-(2-(methylsulfonyl)pyrimidin-5-yl))-5-hexynamido)butyramido-5-ureidovalerylamido)benzyl)carbonate

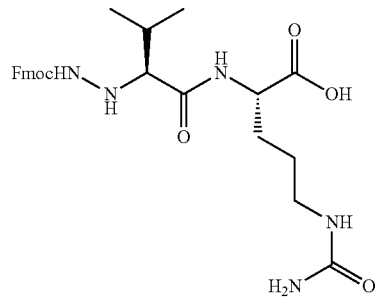

28-1

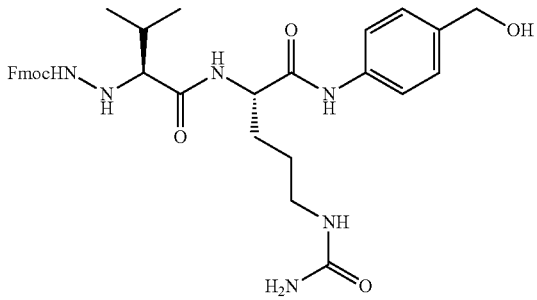

28-2

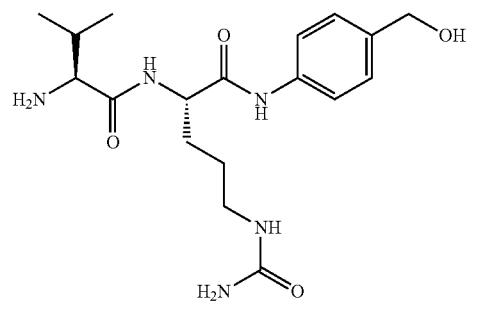

28-3

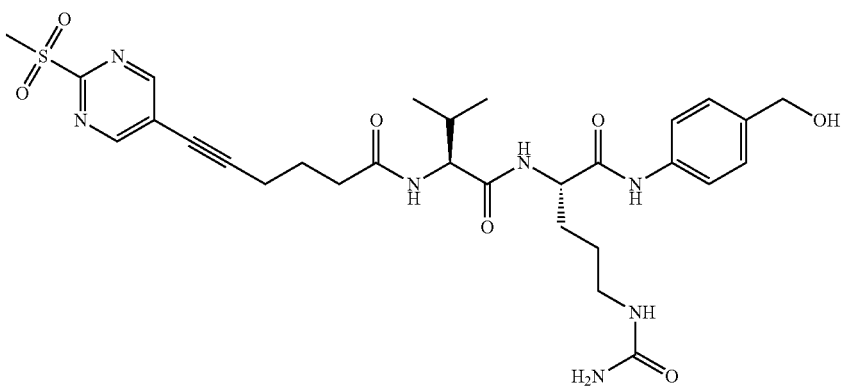

28-4

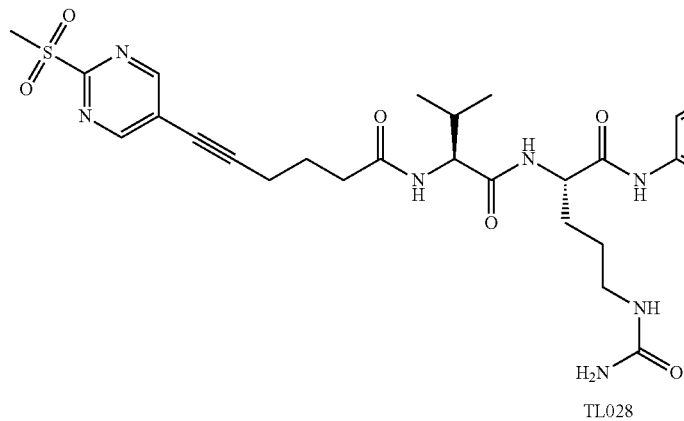
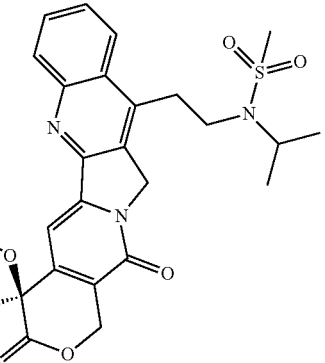

TL028

Step 1: methyl ((S)-1-(((S)-1-((4-(hydroxymethyl)phenyl)amino)-1-oxo-5-ureidovalerylamido-2-yl)amino))-3-methyl-butyramido-2-yl)-(9H-fluorenyl) carbamate Operations similar to those described in step 1 of example 8 were carried out to obtain the title compound (310 mg), except that compound 19-1 was replaced with compound 28-1. ESI-MS (m/z): 602.3 [M+H]$^+$.

Step 2: Synthesis of (S)-2-((S)-2-amino-3-methylbutyramido)-N-(4-(hydroxymethyl)phenyl)-5-ureidovaleramide (compound 28-2)

Operations similar to those described in step 2 of example 8 were carried out to obtain the title compound (150 mg), except that compound 19-2 was replaced with compound 28-2. ESI-MS (m/z): 380.3[M+H]$^+$.

Step 3: Synthesis of N—((S)-1-(((S)-1-((4-hydroxymethyl)phenyl)amino)-1-oxo-5-ureidopent-2-yl)amino)-3-methyl-1-oxobutan-2-yl)-6-(2-(methylsulfonyl)pyrimidin-5-yl)-5-hexynamide (Compound 28-4)

At room temperature, benzotriazol-1-yl-oxytripyrrolidinyl hexafluorophosphate (313 mg, 0.6 mmol) and N,N-diisopropylethylamine (194 mg, 1.50 mmol) were added to a solution of 6-(2-methylsulfonylpyrimidin-5-yl)-5-hexynoic acid (135 mg, 0.5 mmol) and (2S)-2-(((2S)-2-amino-3-methyl-butyryl)amino)-N-(4-(hydroxymethyl)phenyl)-5-ureido-valeramide (190 mg, 0.5 mmol) in N,N-dimethylformamide (10 mL) and reacted at room temperature for 3 hours under stirring. The reaction solution was purified by preparative high performance liquid chromatography (method D) to obtain the title compound (78 mg). ESI-MS (m/z): 630.3 [M+H]$^+$.

Step 4: Synthesis of (S)-4-ethyl-11-(2-(N-isopropyl-methanesulfonamide)ethyl)-3,14-dioxo-3,4,12,14-tetrahydro-1H-pyrano[3',4',6,7]indolizino[1,2-b]quinolin-4-yl-(4-((S)-2-((S)-3-methyl-2-(6-(2-(methylsulfonyl)pyrimidin-5-yl))-5-hexynamido)butyramido-5-ureidovalerylamido)benzyl)carbonate (Compound TL028)

Operations similar to those described in step 4 of example 8 were carried out to obtain the title compound (1.76 mg), except that compound 19-4 was replaced with compound 28-4. ESI-MS (m/z): 1167.4 [M+H]$^+$.

Example 10: (S)-4-ethyl-11-(2-(N-isopropylmethylsulfonamide)ethyl)-3,14-dioxo-3,4,12,14-tetrahydro-1H-pyrano[3',4',6,7]indolizino[1,2-b]quinolin-4-yl-(4-((2S,5S)-5-isopropyl-38-(4-((6-(2-(methylsulfonyl)pyrimidin-5-yl)-5-hexynamido)methyl)-1H-1,2,3-triazol-1-yl)-4,7,11-trioxo-2-(3-ureidopropyl)-9,15,18,21,24,27,30,33,36-nonoxy-3,6,12-triazotritriacontylamido)benzyl)carbonate

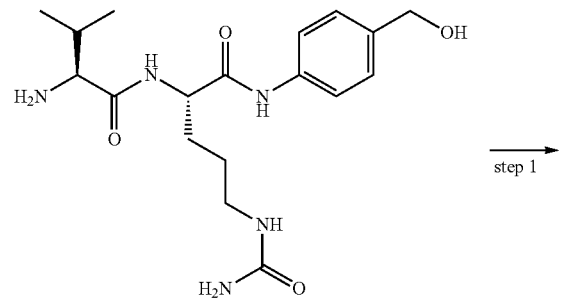

28-3 step 1

-continued

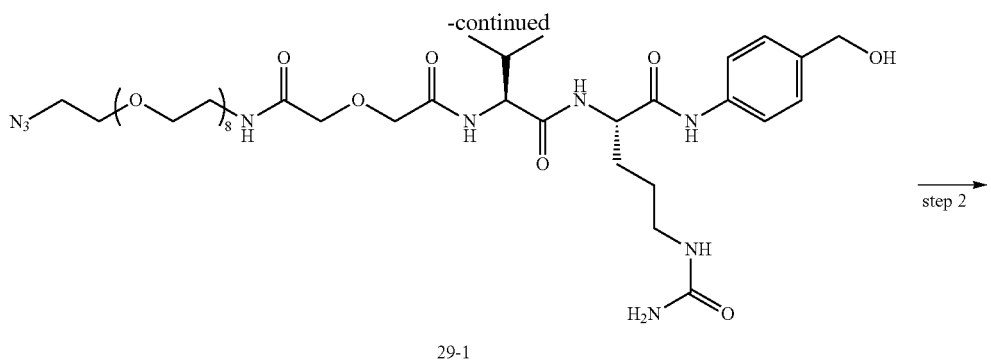

29-1

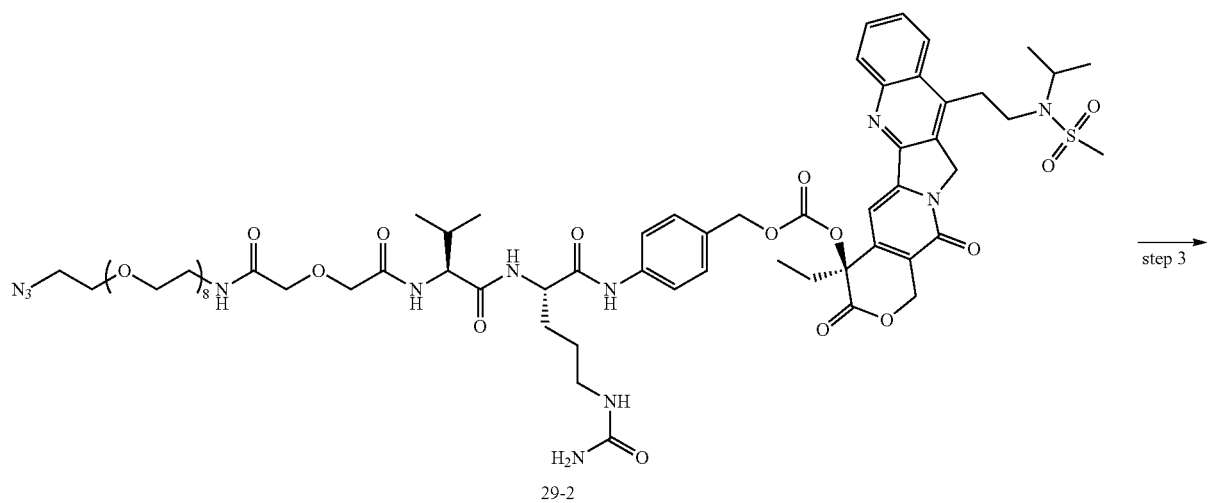

29-2

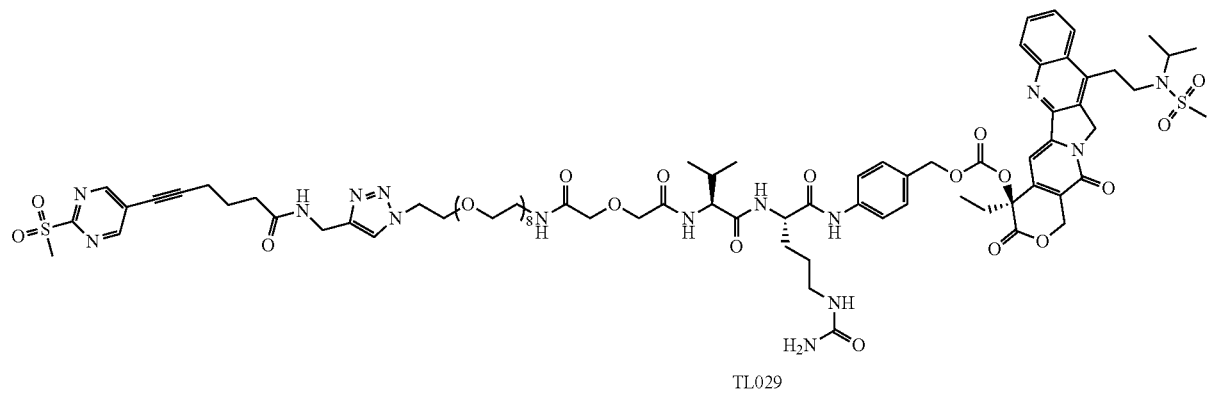

TL029

Step 1: Synthesis of (S)-2-((S)-35-azido-2-isopropyl-4,8-dioxo-6,12,15,18,21,24,27,30,33-nonoxy-3,9-azatetracosyl)-N-(4-(hydroxymethyl)phenyl)-5-ureidovaleramide (Compound 29-1)

Operations similar to those described in step 3 of example 8 were carried out to obtain the title compound (180 mg), except that compound 19-3 was replaced with compound 28-3. ESI-MS (m/z): 916.5[M+H]$^+$.

Step 2: Synthesis of 4-((2S,5S)-38-azido-5-isopropyl-4,7,11-trioxo-2-(3-ureidopropyl)-9,15,18,21,24,27,30,33,36-nonoxy-3,6,12-triazatritriacontylamido)benzyl((S)-4-ethyl-11-(2-(N-isopropylmethylsulfonamido)ethyl)-3,14-dioxo-3,4,12,14-tetrahydro-1H-pyrano[3',4',6,7]indolizino[1,2-b]quinolin-4-yl)carbonate (Compound 29-2)

Operations similar to those described in step 4 of example 8 were carried out to obtain the title compound (30 mg), except that compound 19-4 was replaced with compound 29-1. ESI-MS (m/z): 727.5[M/2+H]$^+$.

Step 3: Synthesis of (S)-4-ethyl-11-(2-(N-isopropyl-methylsulfonamide)ethyl)-3,14-dioxo-3,4,12,14-tetrahydro-1H-pyrano[3',4',6,7]indolizino[1,2-b]quinolin-4-yl-(4-((2S,5S)-5-isopropyl-38-(4-((6-(2-(methylsulfonyl)pyrimidin-5-yl)-5-hexynamido)methyl)-1H-1,2,3-triazol-1-yl)-4,7,11-trioxo-2-(3-ureidopropyl)-9,15,18,21,24,27,30,33,36-nonoxy-3,6,12-triazotritriacontylamido)benzyl)carbonate (Compound TL029)

At room temperature, compound 29-2 (20 mg, 0.014 mmol) and 6-(2-(methylsulfonyl)pyrimidin-5-yl)-N-(2-propyn-1-yl)-5-hexynamide (4.3 mg, 0.014 mmol) were dissolved in a mixed solvent (1 mL/0.25 mL) of dimethyl sulfoxide and water, then cuprous bromide (3.95 mg, 0.027 mmol) was added and reacted for 1 h under stirring. Purification was performed on preparative high performance liquid chromatography (method D) to obtain the title compound (15 mg). ESI-MS (m/z): 880.0[M/2+H]$^+$.

Example 11: (S)-4-ethyl-11-(2-(N-isopropylmethanesulfonamido)ethyl)-3,14-dioxo-3,4,12,14-tetrahydro-1H-pyrano[3',4':6,7]indolizino[1,2-b]quinolin-4-yl(4-((2S,5S)-5-isopropyl-45-(2-(methylsulfonyl)pyrimidin-5-yl)-4,7,11,40-tetraoxo-2-(3-ureidopropyl)-9,15,18,21,24,27,30,33,36-nonoxy-3,6,12,39-tetraazapentatetracontane-((4-carbamoyl)benzyl)carbonate

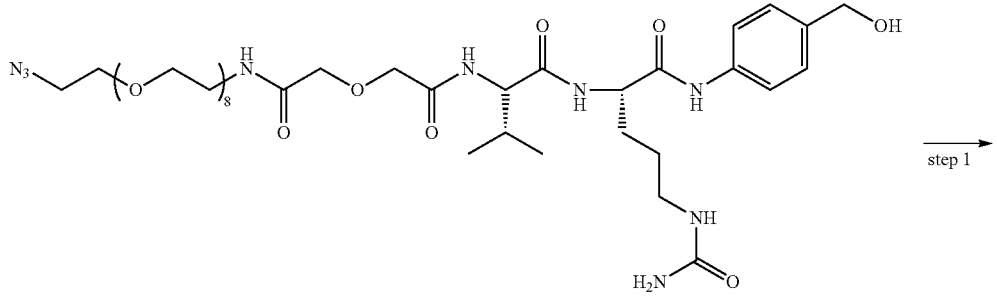

29-1

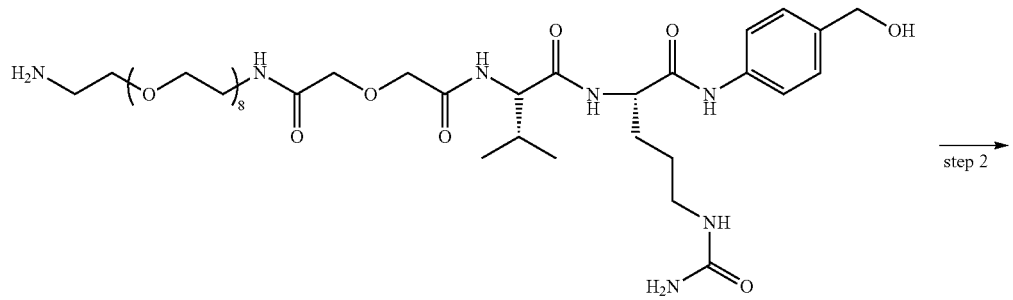

22-1

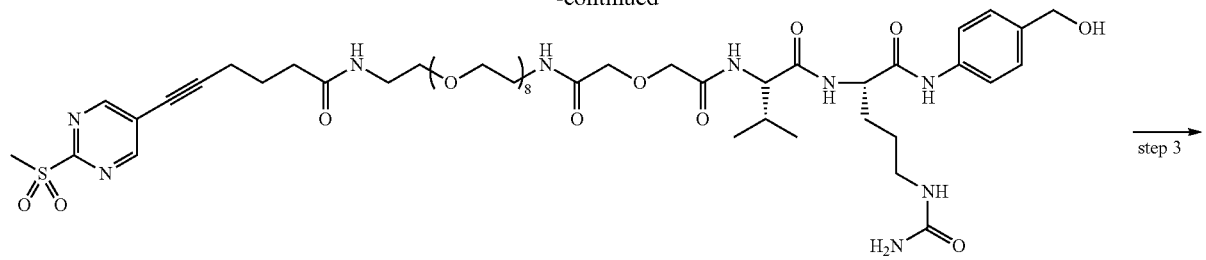

22-2

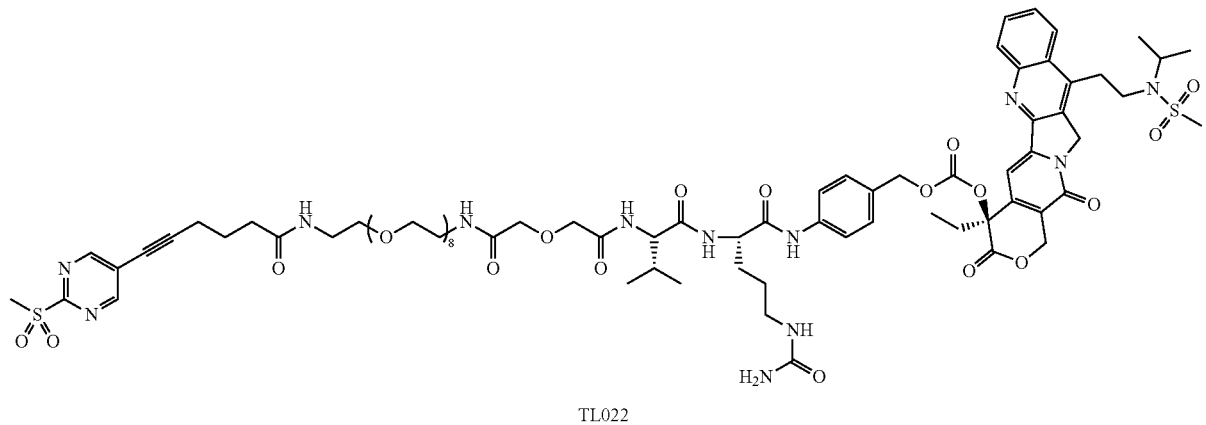

TL022

Step 1: Synthesis of (S)-2-((S)-35-amino-2-isopropyl-4,8-dioxo-6,12,15,18,21,24,27,30,33-nonoxy-3,9-diazapentatriacontamido)-N-(4-(hydroxymethyl)phenyl)-5-ureidovaleramide At 20° C., compound 29-1 (400 mg, 0.44 mmol) was dissolved in methanol and tetrahydrofuran (2.0 mL: 4.0 mL). After complete dissolution, platinum dioxide (40 mg) was added in one batch under nitrogen protection, then the mixed solution was subject to hydrogen substitution for three times. Hydrogenation was conducted at 20° C. for 2 hours. The reaction solution was filtered. The filter cake was washed with methanol. The filtrate was concentrated under reduced pressure. The residue was purified by preparative high performance liquid chromatography (method D) to obtain the title compound (200 mg). ESI-MS (m/z): 890.4 [M+H]$^+$.

Step 2: Synthesis of N-(((6S,9S)-1-amino-6-((4-(hydroxymethyl)phenyl)carbamoyl)-9-isopropyl-1,8,11,15-tetraoxo-13,19,22,25,28,31,34,37,40-nonoxy-2,7,10,16-tetraazadotetracont-42-yl)-6-(2-(methylsulfonyl)pyrimidin-5-yl)hex-5-ynylamide At 20° C., compound 22-1 (250 mg, 0.28 mmol) was dissolved in N,N-dimethylformamide (1.0 mL), then HATU (160 mg, 0.42 mmol) and N,N-diisopropylethylamine (109 mg, 0.84 mmol) were successively added, followed by stirring overnight at room temperature. Purification was performed on preparative high performance liquid chromatography (method D) to obtain the title compound (250 mg).

Step 3: Synthesis of (S)-4-ethyl-11-(2-(N-isopropylmethanesulfonamido)ethyl)-3,14-dioxo-3,4,12,14-tetrahydro-1H-pyrano[3',4':6,7]indolizino[1,2-b]quinolin-4-yl(4-(((2S,5S)-5-isopropyl-45-(2-(methylsulfonyl)pyrimidin-5-yl)-4,7,11,40-tetraoxo-2-(3-ureidopropyl)-9,15,18,21,24,27,30,33,36-nonoxy-3,6,12,39-tetraazapentatetracontane-((4-carbamoyl)benzyl)carbonate (Compound TL022)

At 20° C., (S)—N-(2-(4-ethyl-4-hydroxy-3,14-dione-3,4,12,14-tetrahydro-1H-pyrano[3',4':6,7]indolizino[1,2-b]quinolin-11-yl)ethyl)-N-isopropylmethanesulfonamide (70 mg, 0.14 mmol) was dissolved in dichloromethane (4.0 mL) and cooled to 0° C., then a solution of p-dimethylaminopyridine (200 mg, 1.64 mmol) in dichloromethane (1.0 ml) was added, and a solution of triphosgene (40.6 mg, 0.14 mmol) in dichloromethane (1.0 ml) was slowly added dropwise. The resulting mixture was reacted at 0° C. for 1 h under stirring. The unreacted triphosgene was blown off with nitrogen, and a solution of compound 22-2 (139 mg, 012 mmol) in dichloromethane (2.0 mL) was added to the reaction solution and reacted at 0° C. for 1 h under stirring. Purification was performed on preparative high performance liquid chromatography (method D) to obtain the title compound (1.5 mg). ESI-MS (m/z): 839.5 [M/2+H]$^+$.

Example 12: 4-((S)-2-(4-aminobutyl)-42-(2-(methylsulfonyl)pyrimidin-5-yl)-4,8,37-trioxo-6,12,15,18, 21,24,27,30,33-nonaoxa-3,9,36-triazadedotetracontyl-41-alkynamido)benzyl-((S)-4-ethyl-11-(2-(N-isopropylmethylsulfonyl)ethyl)-3,14-dioxo-3,4,12, 14-tetrahydro-1H-pyrone[3',4': 6,7]indolizino[1,2-b]quinolin-4-yl)carbonate

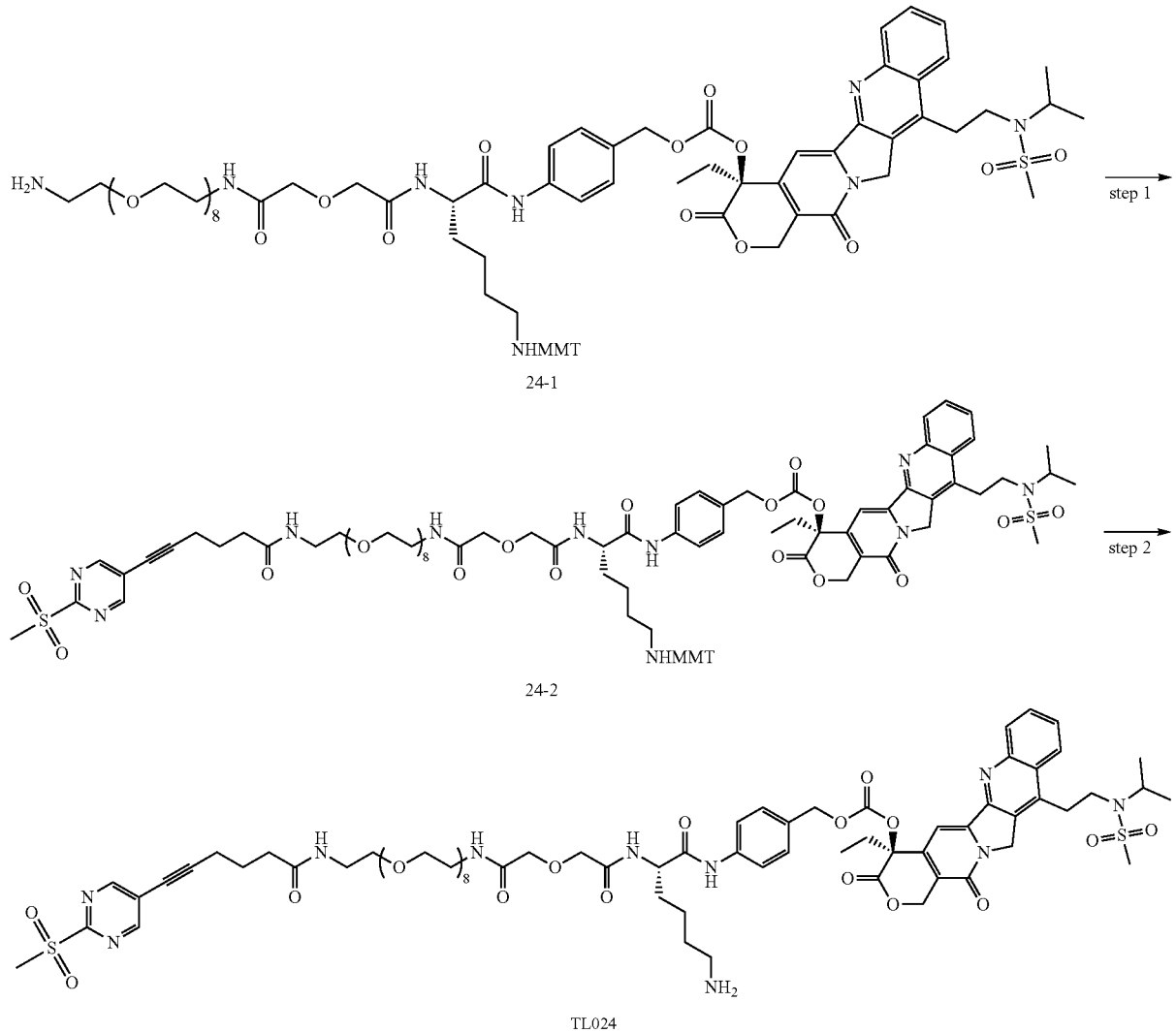

Step 1: Synthesis of (S)-4-ethyl-11-(2-(N-isopropylmethanesulfonamido)ethyl)-3,14-dioxo-3,4,12,14-tetrahydro-1H-pyrone[3',4':6,7]indolizino[1,2-b]quinolin-4-yl(4-((S)-2-(4-(((4-methoxyphenyebenzhydryl)amino)butyl)-42-(2-(methylsulfonyl)pyrimidin-5-yl)-4,8,37-trioxo-6,12, 15,18,21,24,27,30,33-nonaoxa-3,9,36-triazadotetracontyl-41-alkynamido)benzylcarbonate At room temperature, 6-(-2-(methylsulfonyl)pyrimidin-5-yl)hex-5-ynoic acid (12 mg, 0.045 mmol) was dissolved in dichloromethane (2 mL), then 2-(7-azobenzotriazol)-N,N,N',N'-tetramethylureahexafluorophosphate (21.2 mg, 0.056 mmol) and N,N-diisopropylethylamine (8.6 mg, 0.067 mmol) were added and stirred for 10 min, and compound 24-1 (35 mg, 0.022 mmol) was added and reacted for 1 h under stirring. Purification was performed on preparative high performance liquid chromatography (method B) to obtain the title compound (20 mg). ESI-MS (m/z): 1821.8 [M+H]+.

Step 2: Synthesis of 4-((S)-2-(4-aminobutyl)-42-(2-(methylsulfonyl)pyrimidin-5-yl)-4,8,37-trioxo-6,12, 15,18,21,24,27,30,33-nonaoxa-3,9,36-triazadedotetracontyl-41-alkynamido)benzyl-((S)-4-ethyl-11-(2-(N-isopropylmethylsulfonyl)ethyl)-3,14-dioxo-3,4, 12,14-tetrahydro-1H-pyrone[3',4':6,7]indolizino[1,2-b]quinolin-4-yl)carbonate (Compound TL024)

At room temperature, compound 24-2 (20 mg, 0.011 mmol) was dissolved in acetonitrile (1 mL), and a solution of trifluoroacetic acid (0.5 ml) in acetonitrile (0.5 ml) was added dropwise and stirred for 20 min. Purification was performed on preparative high performance liquid chromatography (method C) to obtain the trifluoroacetate of the title compound (12 mg). ESI-MS (m/z): 1549.6[M+H]$^+$.

Example 13: Synthesis of (S)-4-ethyl-11-(2-(N-isopropylmethylsulfonamide)ethyl)-3,14-dioxo-3,4,12,14-tetrahydro-1H-pyrano[3',4':6,7]indolizino[1,2-b]quinolin-4-yl-4-((2S,5S)-5-isopropyl-2-methyl-38-(4-((6-(2-(methylsulfonyl)pyrimidin-5-yl)yl)hex-5-ynamido)methyl)-1H-1,2,3-triazol-1-yl)-4,7,11-trioxo-9,15,18,21,24,27,30,33,36-nonoxy-3,6,12-triazatriacontazanamido)benzyl)carbonate

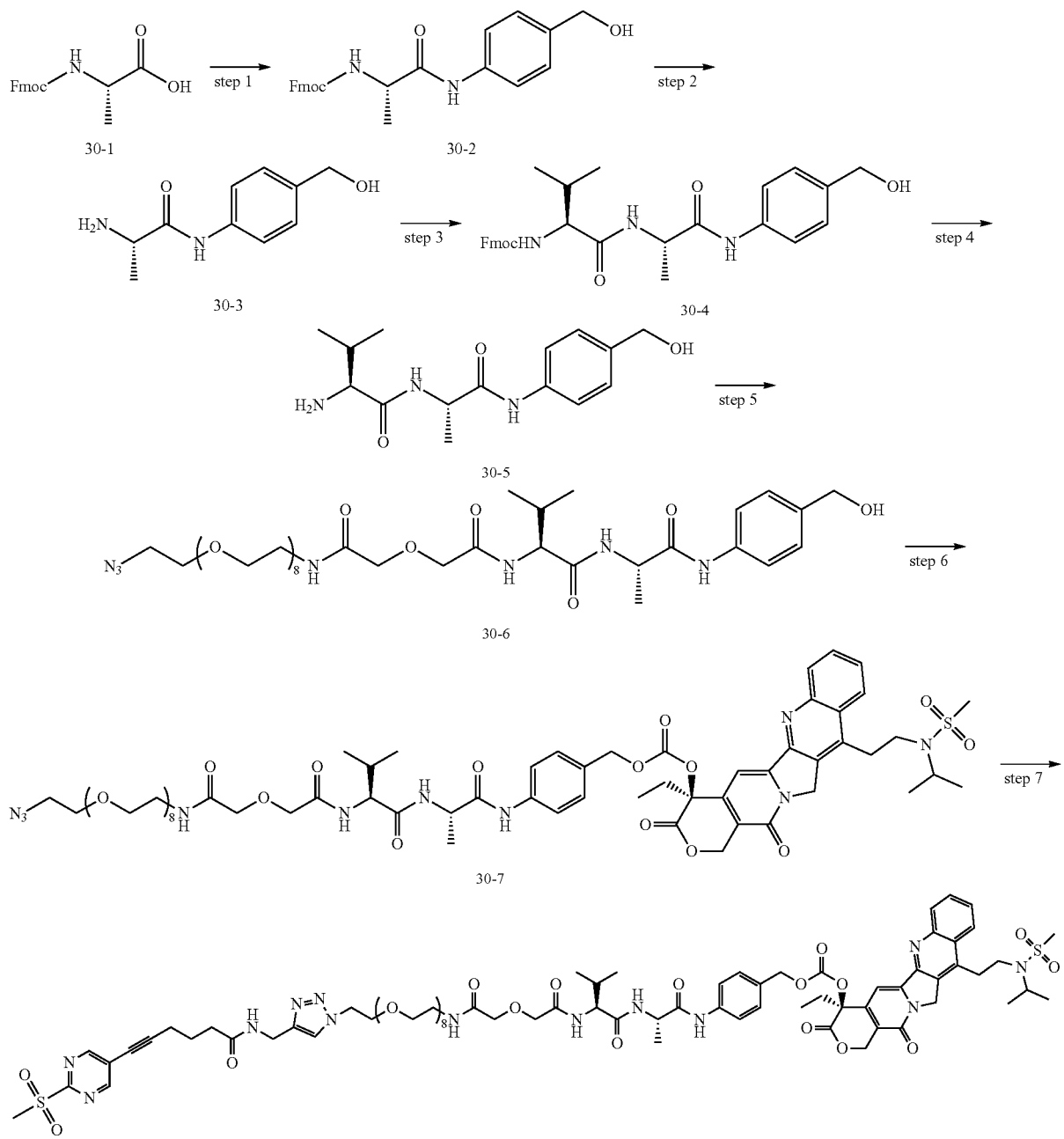

Step 1: Preparation of (S)-(9H-fluoren-9-yl)-methyl (1-((4-(hydroxymethyl)phenyl)amino)-1-oxopropyl-2-yl)carbamate At room temperature, 2-ethoxy-1-ethoxycarboxyl-1,2-dihydroquinoline (1.31 g, 5.30 mmol) and p-aminobenzyl alcohol (593 mg, 4.82 mmol) were added to a solution of the compound 30-1 (1.5 g, 4.82 mmol) in dichloromethane (35 mL) and reacted for 3 hours under stirring. Purification was performed on silica gel column chromatography to obtain the title compound (1.8 g). ESI-MS (m/z): 417.2 [M+H]+

Step 2: Preparation of (S)-2-amino-N-(4-(hydroxymethyl)phenyl)propionamide

At room temperature, ethylenediamine (5 mL) was added to a solution of compound 30-2 (1.8 g, 4.32 mmol) in dichloromethane (20 mL) and reacted for 2 hours. Purification was performed on silica gel column chromatography to obtain the title compound (820 mg). ESI-MS (m/z): 195.1 [M+]+

Step 3: Preparation of (9H-fluoren-9-yl)-methyl ((S)-1-(((S)-1-((4-(hydroxymethyl)phenyl)amino)-1-oxopropan-2-yl)amino)-3-methyl-1-oxobutan-2-yl)-carbamate At room temperature, (2S)-2-(9H-fluoren-9-ylmethoxycarbonylamino)-3-methyl-butyricacid (875 mg, 2.58 mmol), O-benzotriazolyl-tetramethyluronium hexafluorophosphate (1.45 g, 3.83 mmol), N,N-diisopropylethylamine (1.00 g, 7.74 mmol) and 1-hydroxybenzotriazole (525 mg, 3.89 mmol) were successively added to a solution of the compound 30-3 (503 mg, 2.58 mmol) in dichloromethane (2 mL) and reacted for 4 hours under stirring. Purification was performed on silica gel column chromatography to obtain the title compound (1.1 g). ESI-MS (m/z): 516.2 [M+H]+

Step 4: Preparation of (S)-2-amino-N—((S)-1-((4-(hydroxymethyl)phenyl)amino)-1-oxoprop-2-yl)-3-methylbutanamide At room temperature, ethylenediamine (2 mL) was added to a solution of the compound 30-4 (1.1 g, 2.13 mmol) in dichloromethane (8 mL) and reacted for 1 h under stirring. Purification was performed on silica gel column chromatography to obtain the title compound (610 mg). ESI-MS (m/z): 294.2 [M+H]+

Step 5: Preparation of (S)-2-(32-azido-5-oxo-3,9,12,15,18,21,24,27,30-nonoxy-6-diazapentatriacontamido)-N—((S)-1-((4-(hydroxymethyl)phenyl)amino)-1-oxopropan-2-yl)-3-methylbutyramide At room temperature, O-benzotriazolyl-tetramethyluroniumhexafluorophosphate (160 mg, 0.42 mmol), 1-hydroxybenzotriazole (57 mg, 0.42 mmol), N,N-diisopropylethylamine (109 mg, 0.84 mmol) and 32-azido-5-oxo-3,9,12,15,18,21,24,27,30-nonoxy-6-azatricyclodecane-1-acid (156 mg, 0.28 mmol) were added to a solution of compound 30-5 (84 mg, 0.28 mmol) in dichloromethane (3 mL) and reacted for 4 hours under stirring. Purification was performed on silica gel column chromatography to obtain the title compound (163 mg). ESI-MS (m/z): 830.4 [M+H]+

Step 6: Preparation of 4-((2S,5S)-38 azido-5-isopropyl-2-methyl-4,7,11-trioxo-9,15,18,21,24,27,30,33,36-nonoxy-3,6,12-triazatriacontamino)benzyl ((S)-4-ethyl-11-(2-(N-isopropylmethylsulfonylamino)ethyl)-3,14-dioxo-3,4,12,14-tetrahydro-1H-pyrano[3',4': 6,7]indolizino[1,2-b]quinolin-4-yl)carbonate Under nitrogen protection and at 0° C., a solution of triphosgene (16 mg, 0.05 mmol) in dichloromethane (0.3 mL) was added dropwise to a mixed solution of 4-dimethylaminopyridine (65 mg, 0.53 mmol) and (S)—N-(2-(4-ethyl-4-hydroxy-3,14-dioxo-3,4,12,14-tetrahydro-1H-pyrano[3',4':6,7]indolizino[1,2-b]quinolin-11-yl)ethyl)-N-isopropylmethanesulfonamide (45 mg, 0.09 mmol) in dichloromethane (0.7 mL) and reacted at 0° C. for 1 h. Then a solution of the compound 30-6 (73 mg, 0.09 mmol) in dichloromethane (1 mL) was added dropwise to the reaction solution and reacted at 0° C. for 1 h. Purification was performed on silica gel column chromatography to obtain the title compound (33 mg). ESI-MS (m/z): 1367.6 [M+H]+

Step 7: Preparation of (S)-4-ethyl-11-(2-(N-isopropylmethylsulfonamide)ethyl)-3,14-dioxo-3,4,12,14-tetrahydro-1H-pyrano[3',4':6,7]indolizino[1,2-b]quinolin-4-yl-4-((2S,5S)-5-isopropyl-2-methyl-38-(4-((6-(2-(methylsulfonyl)pyrimidin-5-yl)yl)hex-5-ynamido)methyl)-1H-1,2,3-triazol-1-yl)-4,7,11-trioxo-9,15,18,21,24,27,30,33,36-nonoxy-3,6,12-triazatriacontazanamido)benzylcarbonate (Compound TL030)

At room temperature, cuprous bromide (5 mg, 0.04 mmol) and compound 30-7 (20 mg, 15 umol) were added dropwise to a solution of 6-(2-(methylsulfonyl)pyrimidin-5-yl)-N-(prop-2-yn-1-yl)-hex-5-ynylamide (9 mg, 0.007 mmol) in water and N,N-dimethylformamide (0.2 ml: 0.8 ml) and reacted for 4 hours under stirring. Purification was performed on preparative high performance liquid chromatography (method D) to obtain the title compound (4.15 mg). ESI-MS (m/z): 1672.7 [M+H]+

Example 14: 4-((S)-2-(4-aminobutyl)-35-(4-((6-(2-(methylsulfonyl)pyrimidin-5-yl)hex-5-ynamido)methyl)-1H-1,2,3-triazol-1-yl)-4,8-dioxo-6,12,15,18,21,24,27,30,33-nonaoxa-3,9-diazapentatriacontamido)benzyl((S)-4-ethyl-11-(2-(N-isopropylmethylsulfonamido)ethyl)-3,14-dioxo-3,4,12,14-tetrahydro-1H-pyrano[3',4': 6,7]indolizino[1,2-b]quinolin-4-yl)carbonate
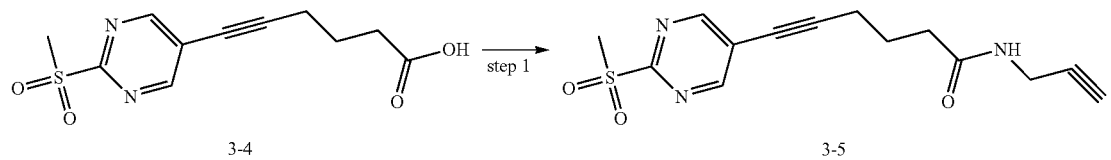
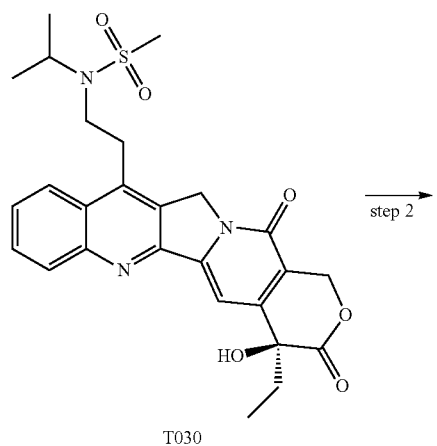
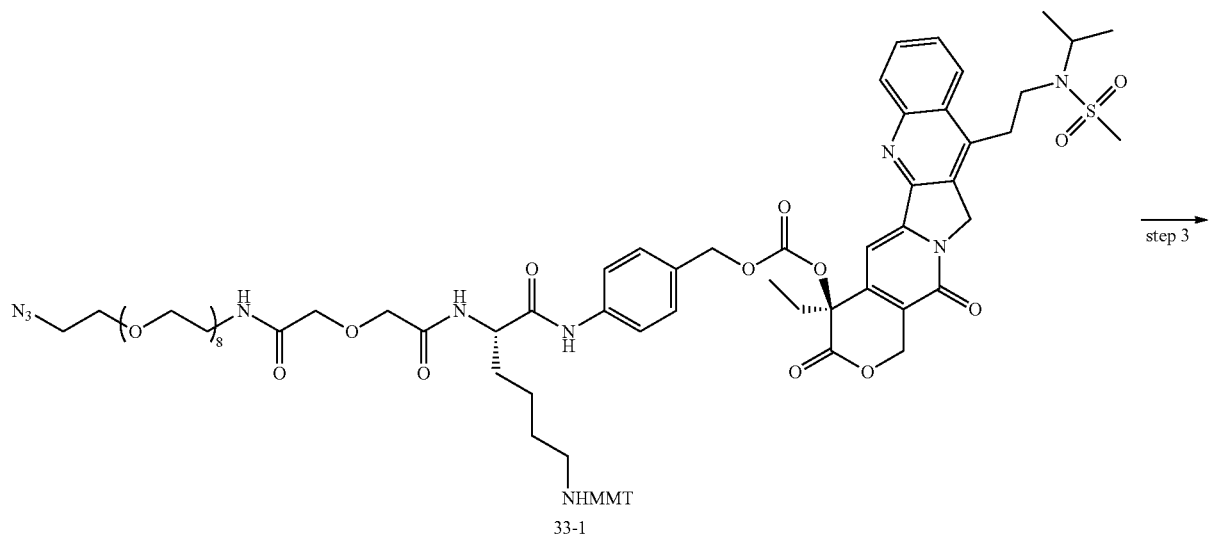

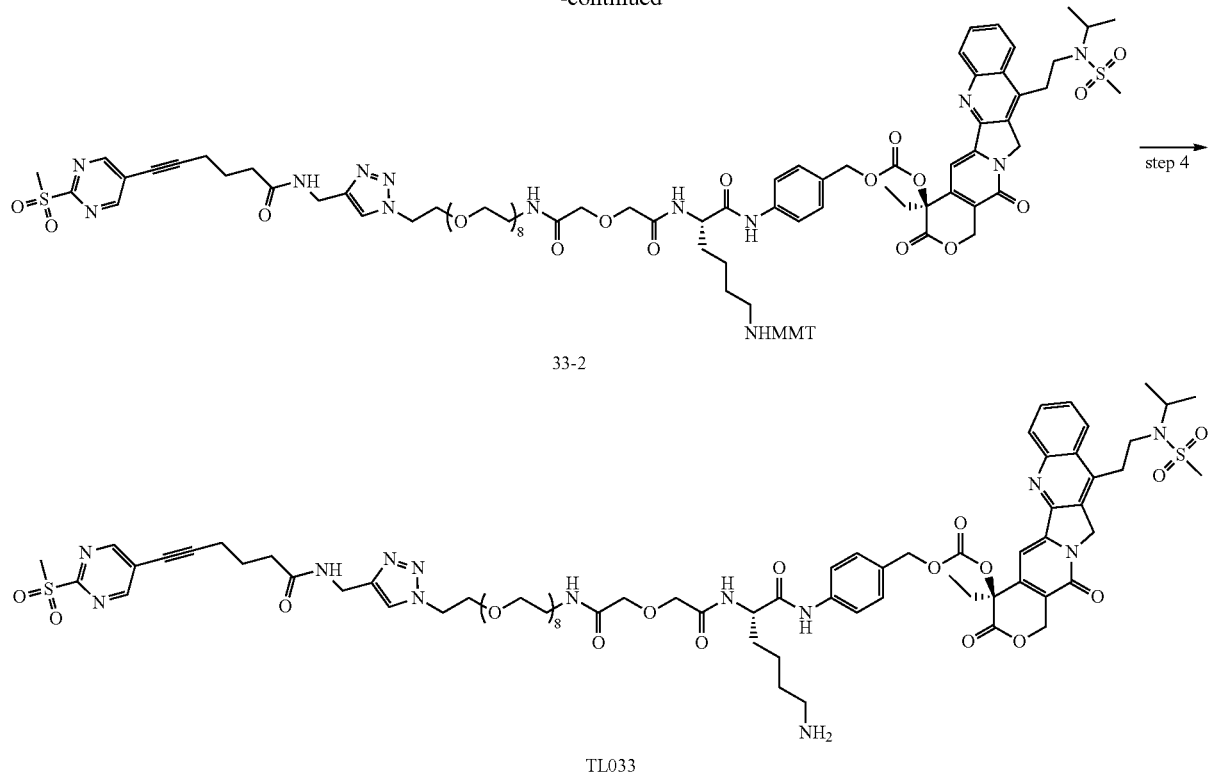

33-2

TL033

Step 1: Synthesis of 6-(2-(methylsulfonyl)pyrimidin-5-yl)-N-(prop-2-yn-1-yl)hex-5-ynamide At 25° C., prop-2-ynyl-1-amine (189 mg, 3.4 mmol) and compound 3-4 (800 mg, 2.83 mmol) were dissolved in dichloromethane (10 mL), then N,N-diisopropylethylamine (738 mg, 5.67 mmol) and O-(7-azabenzotriazol-1-yl)-N,N,N',N'-tetramethyluronium hexafluorophosphate (1.63 g, 4.25 mmol) were successively added and reacted for 2 hours under stirring. The reaction solution was concentrated under reduced pressure, and the residue was purified by flash silica gel column chromatography (ethyl acetate/petroleum ether=3/1) to obtain the title compound (700 mg). ESI-MS (m/z): 306.1[M+H]$^+$.

Step 2: Synthesis of 4-((S)-35-azido-2-(4-(((4-methoxyphenyl)benzhydryl)amino)butyl)-4,8-dioxo-6,12,15,18,21,24,27,30,33-nonazo-3,9-diazapentatriacontamino)benzyl((S)-4-ethyl-11-(2-(N-isopropylmethanesulfonamide)ethyl)-3,14-dioxo-3,4,12,14-tetrahydro-2H-pyrano[2,3-b]-1H-pyrano[3',4':6,7]indolizino[1,2-b]quinolin-4-yl)carbonate At 25° C. and under nitrogen protection, T-030 (250 mg, 0.49 mmol) was dissolved in dichloromethane (10 mL) and cooled to 0° C., then a solution of 4-dimethylaminopyridine (478 mg, 3.91 mmol) in dichloromethane (3 mL) was added, followed by the slow and dropwise addition of a solution of triphosgene (72 mg, 0.24 mmol) in dichloromethane (10 mL) and reacted at 0° C. for 20 min under stirring. The reaction solution was bubbled with nitrogen for 20 min, then a solution of (S)-2-(32-azido-5-oxo-3,9,12,15,18,21,24,27,30-nonaoxa-6-azatriacetamido)-N-(4-(hydroxymethyl)phenyl)-6-(((4-methoxyphenyl)benzhydryl)amino)acetamide (518 mg, 0.49 mmol) in dichloromethane (7 mL) was added and reacted at 0° C. for 1 h under stirring. The reaction solution was concentrated under reduced pressure, the residue was purified by preparative high performance liquid chromatography (method A) to obtain the title compound (500 mg). ESI-MS (m/z): 1597.5[M+H]$^+$.

Step 3: Synthesis of (S)-4-ethyl-11-(2-(N-isopropylmethanesulfonamido)ethyl)-3,14-dioxo-3,4,12,14-tetrahydro-1H-pyrano[3',4':6,7]indolizino[1,2-b]quinolin-4-yl(4-((S)-2-(4-(((4-methoxyphenyl)diphenylmethyl)amino)butyl)-35-(4-((6-(2-(methylsulfonyl)pyrimidin-5-yl)hex-5-ynamido)methyl)-1H-1,2,3-triazol-1-yl)-4,8-dioxo-6,12,15,18,21,24,27,30,33-nonoxy-3,9-diazapentatriacontamido)benzyl)carbonate At room temperature, compound 33-1 (14 mg, 0.05 mmol) was dissolved in dimethyl sulfoxide and water (2.0 mL: 0.5 mL), followed by an addition of cuprous bromide (11 mg, 0.08 mmol) and reacted for 1 h under stirring. Purification was performed on preparative high performance liquid chromatography (method B) to obtain the title compound (30 mg). ESI-MS (m/z): 815.9 [(M−273)/2+H]$^+$.

Step 4: Synthesis of 4-((S)-2-(4-aminobutyl)-35-(4-((6-(2-(methylsulfonyl)pyrimidin-5-yl)hex-5-ynamido)methyl)-1H-1,2,3-triazol-1-yl)-4,8-dioxo-6,12,15,18,21,24,27,30,33-nonaoxa-3,9-diazapentatriacontamido)benzyl((S)-4-ethyl-11-(2-(N-isopropylmethylsulfonamido)ethyl)-3,14-dioxo-3,4,12,14-tetrahydro-1H-pyrano[3',4':6,7]indolizino[1,2-b]quinolin-4-yl)carbonate (Compound TL033)

Compound 33-2 (30 mg, 0.02 mmol) was dissolved in dichloromethane (1.0 mL), and trifluoroacetic acid (0.2 mL)

was added to the reaction solution and reacted at room temperature for 30 min. Purification was performed on preparative high performance liquid chromatography (method C) to obtain the trifluoroacetate of the title compound (20.0 mg). Identification of the title compound is as follows:

$^1$H NMR (400 MHz, DMSO-d$_6$) δ 10.18 (s, 1H), 9.10 (s, 2H), 8.38 (t, J=5.56 Hz, 1H), 8.32 (d, J=8.40 Hz, 1H), 8.22-8.20 (m, 2H), 8.09 (t, J=5.68 Hz, 1H), 7.91-7.87 (m, 2H), 7.82-7.78 (m, 1H), 7.69 (brs, 3H), 7.61 (d, J=8.56 Hz, 2H), 7.32 (d, J=8.56 Hz, 2H), 7.06 (s, 1H), 5.56 (d, J=16.96 Hz, 1H), 5.51 (d, J=16.96 Hz, 1H), 5.47 (d, J=19.28 Hz, 1H), 5.42 (d, J=19.28 Hz, 1H), 5.14 (d, J=12.20 Hz, 1H), 5.07 (d, J=12.16 Hz, 1H), 4.48 (t, J=5.24 Hz, 2H), 4.46-4.43 (m, 1H), 4.29 (d, J=5.60 Hz, 2H), 4.08-3.95 (m, 5H), 3.79 (t, J=5.28 Hz, 2H), 3.51-3.43 (m, 32H), 3.40 (s, 3H), 3.39-3.35 (m, 2H), 3.30-3.26 (m, 2H), 3.00 (s, 3H), 2.82-2.74 (m, 2H), 2.56 (t, J=7.08 Hz, 2H), 2.29 (t, J=7.36 Hz, 2H), 2.23-2.13 (m, 2H), 1.82 (p, J=7.24 Hz, 2H), 1.78-1.63 (m, 2H), 1.61-1.49 (m, 2H), 1.42-1.27 (m, 2H), 1.15 (d, J=6.80 Hz, 3H), 1.13 (d, J=6.76 Hz, 3H), 0.90 (t, J=7.32 Hz, 3H). ESI-MS (m/z): 816.01 [M/2+H]$^+$. [α]$_D^{20}$ is −19.55° (c=1.000 g/100 mL, CH$_3$CN).

Example 15: 4-((S)-2-(4-aminobutyl)-35-(4-((6-(2-(methylsulfonyl)pyrimidin-5-yl)hex-5-ynamido)methyl)-1H-1,2,3-triazol-1-yl)-4,8-dioxo-6,12,15,18,21,24,27,30,33-nonoxy-3,9-diazapentatriacontamido)benzyl((S)-11-diethyl-9-hydroxy-3,14-dioxo-3,4,12,14-tetrahydro-1H-pyrano[3',4':6,7]indolizino[1,2-b]quinolin-4-carbonate

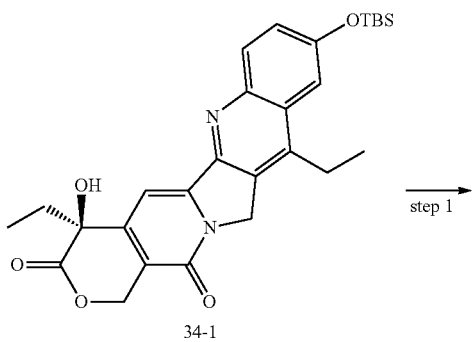

34-1

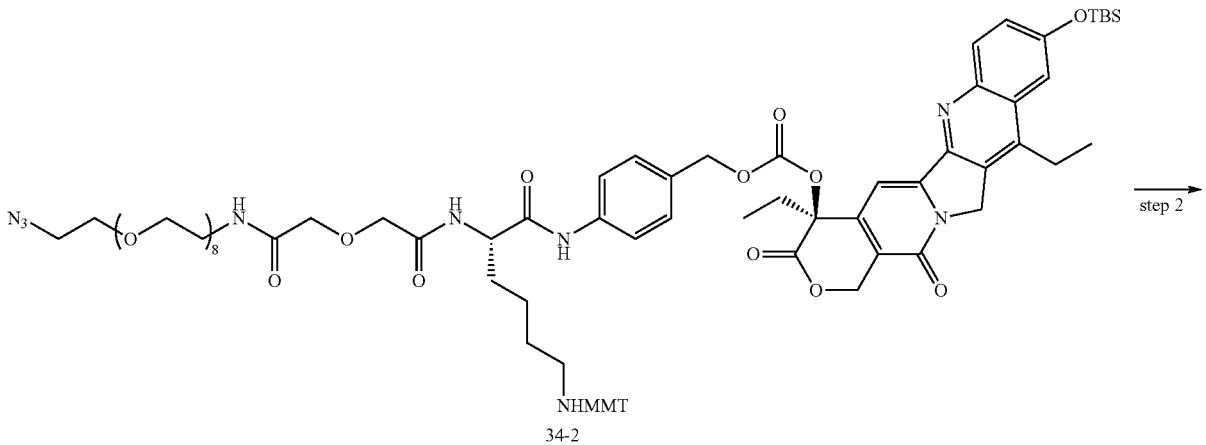

34-2

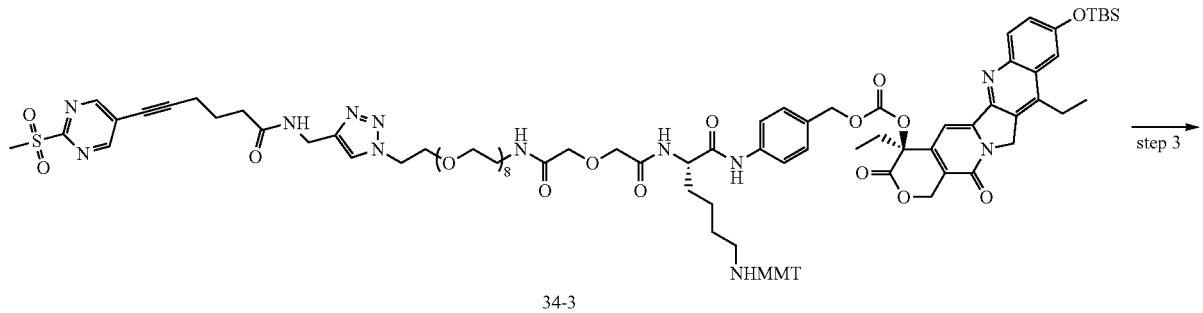

34-3

-continued

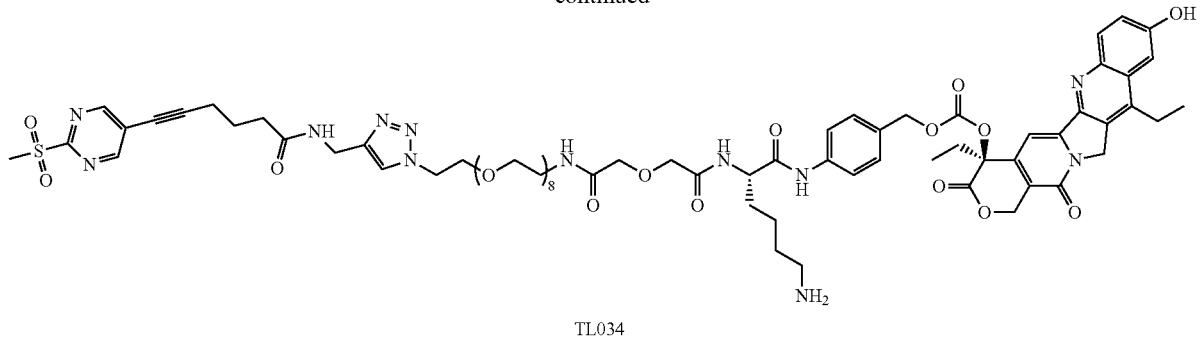

TL034

Step 1: Synthesis of 4-((S)-35-azido-2-(4-(((4-methoxyphenyl)diphenylmethyl)amino)butyl)-4,8-dioxo 6,12,15,18,21,24,27-nonoxy-((S)-9-((tert-butyldimethylsilyl)oxy)-4,11-diethyl-3,14-dioxo-3,4,12,14-tetrahydro-1,2,3,4-tetrahydroquinolin-1H-pyrano[3',4':6,7]indolizino[1,2-b]quinolin-4-yl) carbonate At room temperature, compound 34-1 (100 mg, 0.2 mmol) was dissolved in anhydrous dichloromethane (2 ml) under nitrogen protection, then cooled to 0° C., followed by an addition of a solution of 4-dimethylaminopyridine (144 mg, 1.18 mmol) in anhydrous dichloromethane (0.5 ml), then a solution of triphosgene (41 mg, 0.14 mmol) in dry dichloromethane (0.5 ml) was slowly added dropwise. The resulting mixture was reacted at 0° C. for 1 h under stirring. Then a solution of (S)-2-(32-azido-5-oxo-3,9,12,15,18,21,24,27,30-nonaoxa-6-azatriacetamido)-N-(4-(hydroxymethyl)phenyl)-6-(((4-methoxyphenyl)benzhydryl)amino)acetamide (160 mg, 0.15 μmol) in dry dichloromethane (0.5 mL) was added to the reaction solution and reacted at room temperature for 1 h. Purification was performed on preparative high performance liquid chromatography (method B) to obtain the title compound (60 mg). ESI-MS (m/z): 1592.7 [M+H]$^+$.

Step 2: Synthesis of (S)-9-(tert-butyldimethylsilyl)oxy)-4,11-diethyl-3,14-dioxo-3,4,12,14-tetrahydro-1H-pyrano[3',4':6,7]indolizino[1,2-b]quinolin-4-yl-4-((S)-2-(4-(((6-2-(methylsulfonyl)pyrimidin-5-yl)-35-(4-((6-2-(methylsulfonyl)pyrimidin-5-yl)hex-5-ynamido)methyl)-1H-1,2,3-triazol-1-yl)-dioxo 6,12,15,18,21,24,27,30,33-nonoxy-3,9-diazapentatriacontamido)carbonate At room temperature, compound 34-2 (40 mg, 0.03 mmol) and 6-(2-(methylsulfonyl)pyrimidin-5-yl)-N-(prop-2-yn-1-yl)hex-5-ynylamide (11.50 mg, 0.04 mmol) were dissolved in dimethyl sulfoxide and water (0.5 ml: 0.1 ml), and cuprous bromide (9.01 mg, 0.06 mmol) was added. The resulting mixture was reacted for 1 h under stirring. Purification was performed on preparative high performance liquid chromatography (method B) to obtain the title compound (20 mg). ESI-MS (m/z): 1897.5 [M+H].

Step 3: Synthesis of 4-((S)-2-(4-aminobutyl)-35-(4-((6-(2-(methylsulfonyl)pyrimidin-5-yl)hex-5-ynamido)methyl)-1H-1,2,3-triazol-1-yl)-4,8-dioxo-6,12,15,18,21,24,27,30,33-nonoxy-3,9-diazapentatriacontamido)benzyl((S)-11-diethyl-9-hydroxy-3,14-dioxo-3,4,12,14-tetrahydro-1H-pyrano[3',4':6,7]indolizino[1,2-b]quinolin-4-carbonate (Compound TL034)

At room temperature, compound 34-3 (30 mg, 0.018 mmol) was dissolved in acetonitrile and water (0.4 mL: 0.1 mL), then a mixed solution of trifluoroacetic acid and acetonitrile (0.5 mL: 0.5 mL) was added dropwise, and stirred at room temperature for 2 hours. Purification was performed on preparative high performance liquid chromatography (method C) to obtain the trifluoroacetate of the title compound (12 mg). ESI-MS (m/z): 1511.5 [M+H]$^+$.

Example 16: Synthesis of 4-((S)-2-(4-aminobutyl)-35-(4-((6-(2-(methylsulfonyl)pyrimidin-5-yl)hex-5-ynamido)methyl)-1H-1,2,3-triazol-1-yl)-4,8-dioxo-6,12,15,18,21,24,27,30,33-nonaoxa-3,9-diazapentatriacontamido)benzyl((S)-4-ethyl-11-(2-(N-isopropylmethylsulfonamido)ethyl)-3,14-dioxo-3,4,12,14-tetrahydro-1H-pyrano[3',4':6,7]indolizino[1,2-b]quinolin-4-yl)carbonate

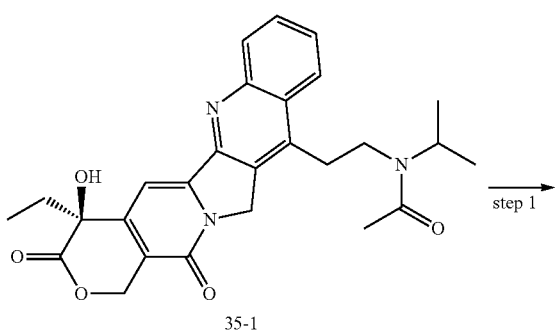

35-1

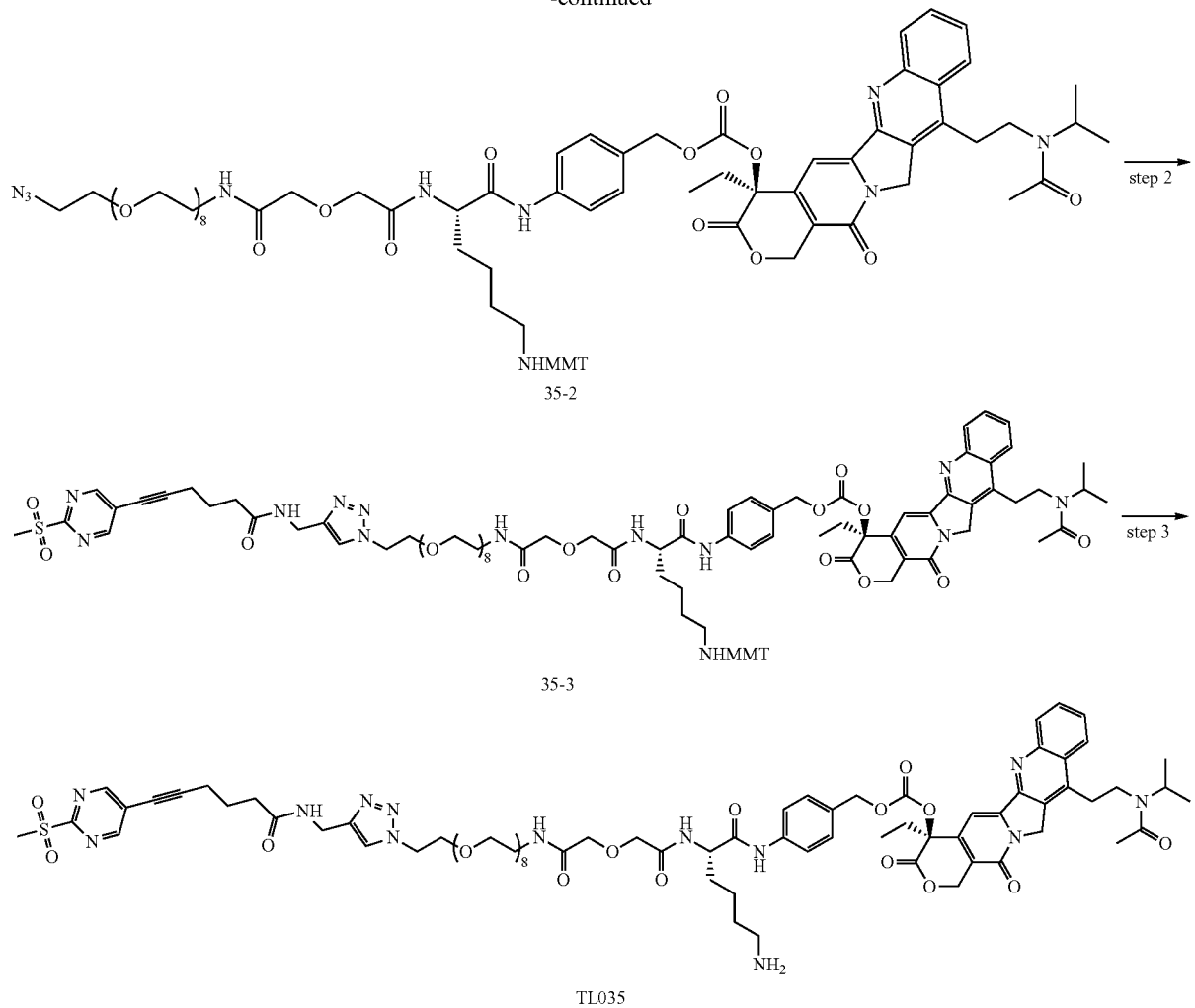

Step 1: Synthesis of ((S)-35-azido-2-(4-(((4-methoxyphenyl)diphenylmethyl)amino)butyl)-4,8-dioxo-6,12,15,18,21,24,27,30,33-nonoxy-3,9-diazapentatriacontamido)benzyl((S)-4-ethyl-11-(2-(N-isopropylacetamido)ethyl)-3,14-dioxo-3,4,12,14-tetrahydro-1,2,3,6-triazacycloheptane-1H-pyrano[3',4':6,7]indolizino[1,2-b]quinolin-4-yl)carbonate Operations similar to those described in step 1 of example 15 were carried out to obtain the title compound (60 mg), except that compound 34-1 was replaced with compound 35-1. ESI-MS (m/z): 1561.5 [M+H]⁺.

Step 2: Synthesis of (S)-4-ethyl-11-(2-(N-isopropylacetamido)ethyl)-3,14-dioxo3,4,12,14-tetrahydro-1H-pyrano[3',4':6,7]indolizino[1,2-b]quinolin-4-yl)-4-((S)-2-(4-(((4-methoxyphenyl)diphenylmethyl)amino)butyl)-35-(4-((6-2-(methylsulfonyl)pyrimidin-5-yl)hex-5-ynamido)methyl)-1H-1,2,3-triazol-1-yl)-4,8-dioxo-6,12,15,18,21,24,27,30,33-nonoxy-3,9-diazapentatriacontamido]carbonate A synthetic method similar to that as described in step 2 of example 15 was adopted to obtain the title compound (20 mg), except that compound 34-2 was replaced with compound 35-2. ESI-MS (m/z): 1866.5 [M+H].

Step 3: Synthesis of 4-((S)-2-(4-aminobutyl)-35-(4-(((6-(2-(methylsulfonyl)pyrimidin-5-yl)hex-5-ynamido)methyl)-1H-1,2,3-triazol-1-yl)-4,8-dioxo-6,12,15,18,21,24,27,30,33-nonaoxa-3,9-diazapentatriacontamido)benzyl((S)-4-ethyl-11-(2-(N-isopropylacetamido)ethyl)-3,14-dioxo-3,4,12,14-tetrahydro-1H-pyrano[3',4':6,7]indolizino[1,2-b]quinolin-4-yl)carbonate (Compound TL035)

A synthetic method similar to that as described in step 3 of example 15 was adopted to obtain the trifluoroacetate of the title compound (4.9 mg), except that compound 34-3 was replaced with compound 35-3. ESI-MS (m/z): 1594.5 [M+H]⁺.

Example 17: Synthesis of 4-((S,Z)-2-(4-aminobutyl)-42-(2-(methylsulfonyl)pyrimidin-5-yl)-4,8,37-trioxo-6,12,15,18,21,24,27,30,33-nonaoxa-3,9,36-triazadotetracontyl-41-alkenamido)benzyl-((S)-4-ethyl-11-(2-(N-isopropylacetamido)ethyl)-3,14-dioxo-3,4,12,14-tetrahydro-1H-pyrone[3',4':6,7]indolizino[1,2-b]quinolin-4-yl)carbonate

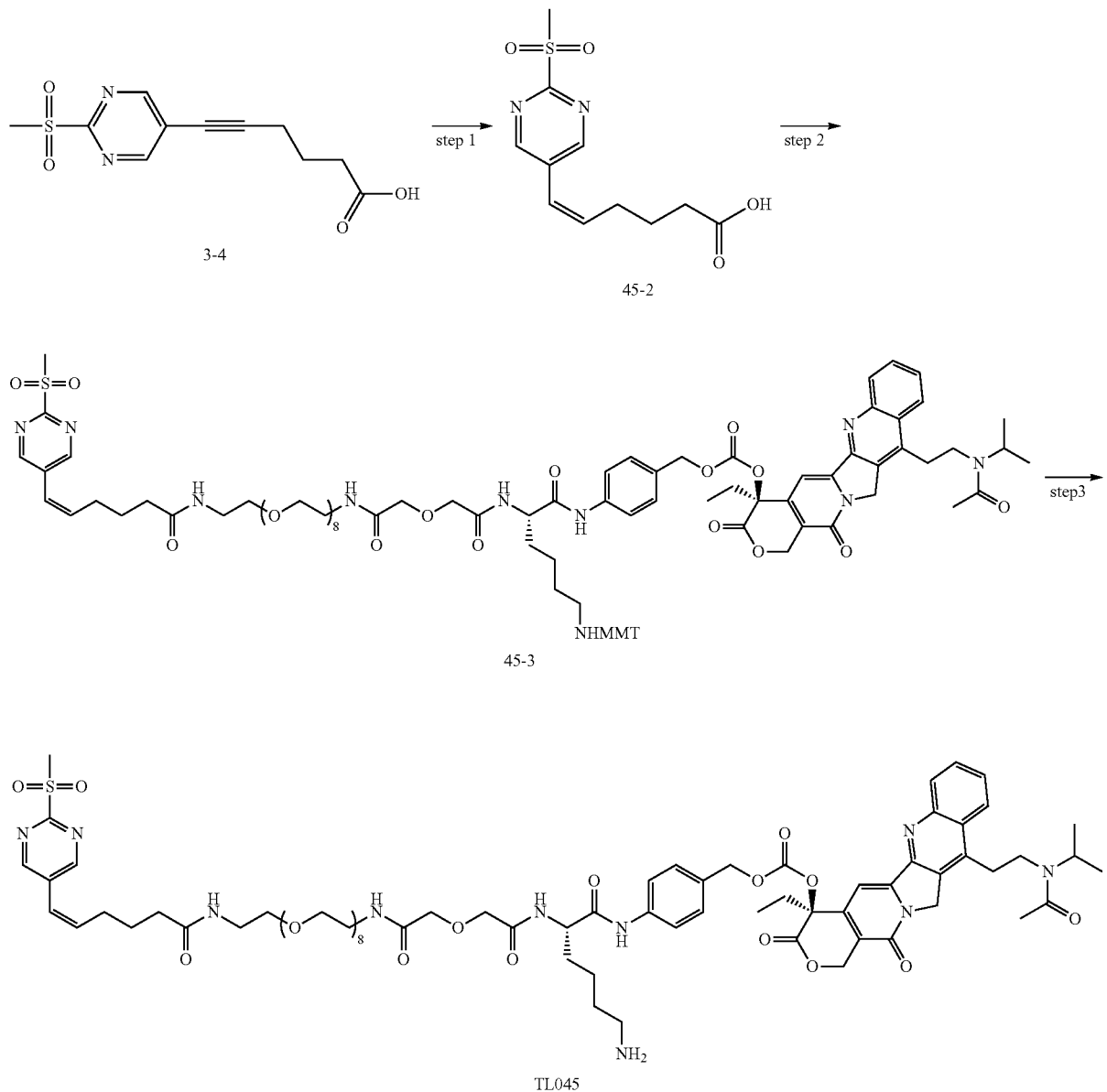

Step 1: Synthesis of (Z)-6-(2-(methylsulfonyl)pyrimidin-5-yl)hex-5-enoic Acid

At 20° C., compound 3-4 (200 mg, 0.67 mmol) was dissolved in methanol (8.0 mL), and a Lindlar catalyst (20 mg) was added under nitrogen protection, then the solution was subject to hydrogen substitution for three times. Hydrogenation was conducted at 20° C. for 3 hours. After filtration, the filtrate was subject to spin drying to obtain the title compound (150 mg). ESI-MS (m/z): 271.1 [M+H]⁺.

Step 2: Synthesis of (S)-4-ethyl-11-(2-(N-isopropylacetamido)ethyl)-3,14-dioxo-3,4,12,14-tetrahydro-1H-pyrone[3',4':6,7]indolizino[1,2-b]quinolin-4-yl (4-((S,Z)-2-(4-(((4-methoxyphenyebenzhydryl)amino)butyl)-42-(2-(methylsulfonyl)pyrimidin-5-yl)-4,8,37-trioxo-6,12,15,18,21,24,27,30,33-nonaoxa-3,9,36-triazadotetracontyl-41-alkenamido)benzylcarbonate At room temperature, compound 45-2 (8 mg, 0.030 mmol) was dissolved in dichloromethane (2 mL), then 2-(7-azobenzotriazol)-N,N,N',N'-tetramethyluronium hexafluorophosphate (14.9 mg, 0.039 mmol) and N,N-diisopropylethylamine (8.8 mg, 0.068 mmol) were added. The reaction solution was stirred at room temperature for 10 min, then compound 48-1 (30 mg, 0.020 mmol) was added and reacted at room temperature for 1 h under stirring. Purification was performed on preparative high performance liquid chromatography (method B) to obtain the title compound (30 mg). ESI-MS (m/z): 1787.8[M+H]$^+$.

Step 3: Synthesis of 4-((S,Z)-2-(4-aminobutyl)-42-(2-(methylsulfonyl)pyrimidin-5-yl)-4,8,37-trioxo-6,12,15,18,21,24,27,30,33-nonaoxa-3,9,36-triazadedotetracontyl-41-alkenamido)benzyl-((S)-4-ethyl-11-(2-(N-isopropylacetamido)ethyl)-3,14-dioxo-3,4,12,14-tetrahydro-1H-pyrone[3',4':6,7]indolizino[1,2-b]quinolin-4-yl)carbonate (Compound TL045)

At room temperature, compound 45-3 (30 mg, 0.017 mmol) was dissolved in acetonitrile (1 ml), and a solution of trifluoroacetic acid (0.5 ml) in acetonitrile (0.5 ml) was added dropwise. The reaction solution was stirred at room temperature for 20 min. Purification was performed on preparative high performance liquid chromatography (method C) to obtain the trifluoroacetate of the title compound (9 mg). ESI-MS (m/z): 1515.6 [M+H]$^+$.

Example 18: 4-((S)-2-(4-aminobutyl)-42-(2-(methylsulfonyl)pyrimidin-5-yl)-4,8,37-trioxo-6,12,15,18,21,24,27,30,33-nonaoxa-3,9,36-triazadedotetracontyl-41-alkynamido)benzyl-((S)-4-ethyl-11-(2-(N-isopropylacetamido)ethyl)-3,14-dioxo-3,4,12,14-tetrahydro-1H-pyrone[3',4':6,7]indolizino[1,2-b]quinolin-4-yl)carbonate

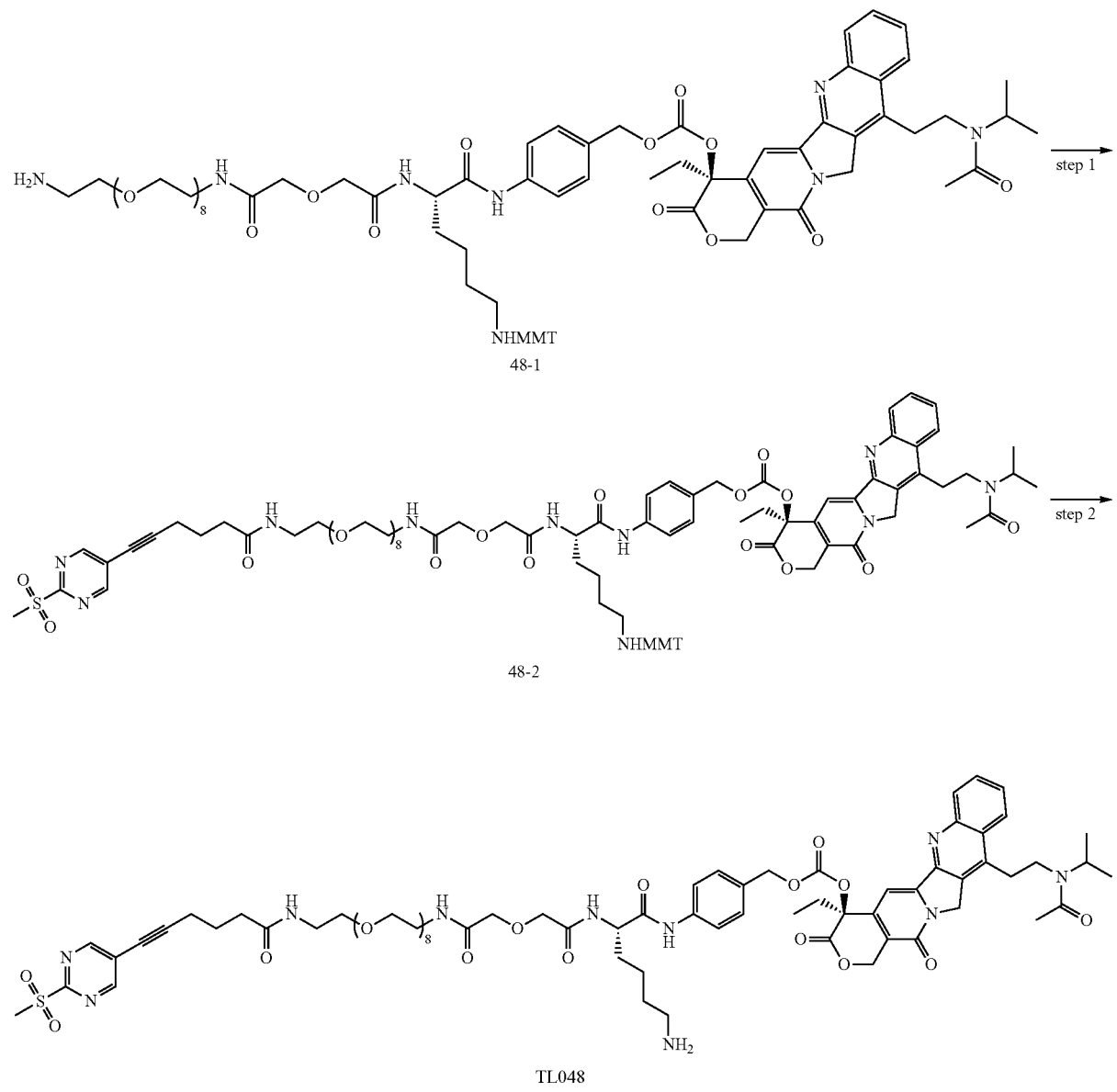

Step 1: Synthesis of (S)-4-ethyl-11-(2-(N-isopropy-lacetamido)ethyl)-3,14-dioxo-3,4,12,14-tetrahydro-1H-pyrone[3',4':6,7]indolizino[1,2-b]quinolin-4-yl (4-((S)-2-(4-(((4-methoxyphenyebenzhydryl)amino)butyl)-42-(2-(methylsulfonyl)pyrimidin-5-yl)-4,8,37-trioxo-6,12,15,18,21,24,27,30,33-nonaoxa-3,9,36-triazadotetracontyl-41-alkynamido)benzylcarbonate A synthetic method similar to that described in step 1 of example 12 was adopted to obtain the title compound (15 mg), except that compound 24-1 was replaced with compound 48-1. ESI-MS (m/z): 1785.8 [M+H]⁺.

Step 2: Synthesis of 4-((S)-2-(4-aminobutyl)-42-(2-(methylsulfonyl)pyrimidin-5-yl)-4,8,37-trioxo-6,12,15,18,21,24,27,30,33-nonaoxa-3,9,36-triazadedotetracontyl-41-alkynamido)benzyl-((S)-4-ethyl-11-(2-(N-isopropylacetamido)ethyl)-3,14-dioxo-3,4,12,14-tetrahydro-1H-pyrone[3',4':6,7]indolizino[1,2-b]quinolin-4-yl)carbonate (Compound TL048)

A synthetic method similar to that described in step 2 of example 12 was adopted to obtain the trifluoroacetate of the title compound (11.35 mg), except that compound 24-2 was replaced with compound 48-2. ESI-MS (m/z): 1513.7 [M+H]⁺.

Example 19: 4-((S)-2-(4-aminobutyl)-35-(4-((2-(2-((methylsulfonyl)pyrimidin-5-yl)thiazol-4-carbox-amido)methyl)-1H-1,2,3-triazol-1-yl)-4,8-dioxo-6,12,15,18,21,24,27,30,33-nonaoxa-3,9-diazapentatriacontamino)benzyl((S)-4-ethyl-11-(2-(N-isopropylmethylsulfonamido)ethyl)-3,14-dioxo-3,4,12,14-tetrahydro-1H-pyrone[3',4':6,7]indolizino[1,2-b]quinolin-4-yl)carbonate

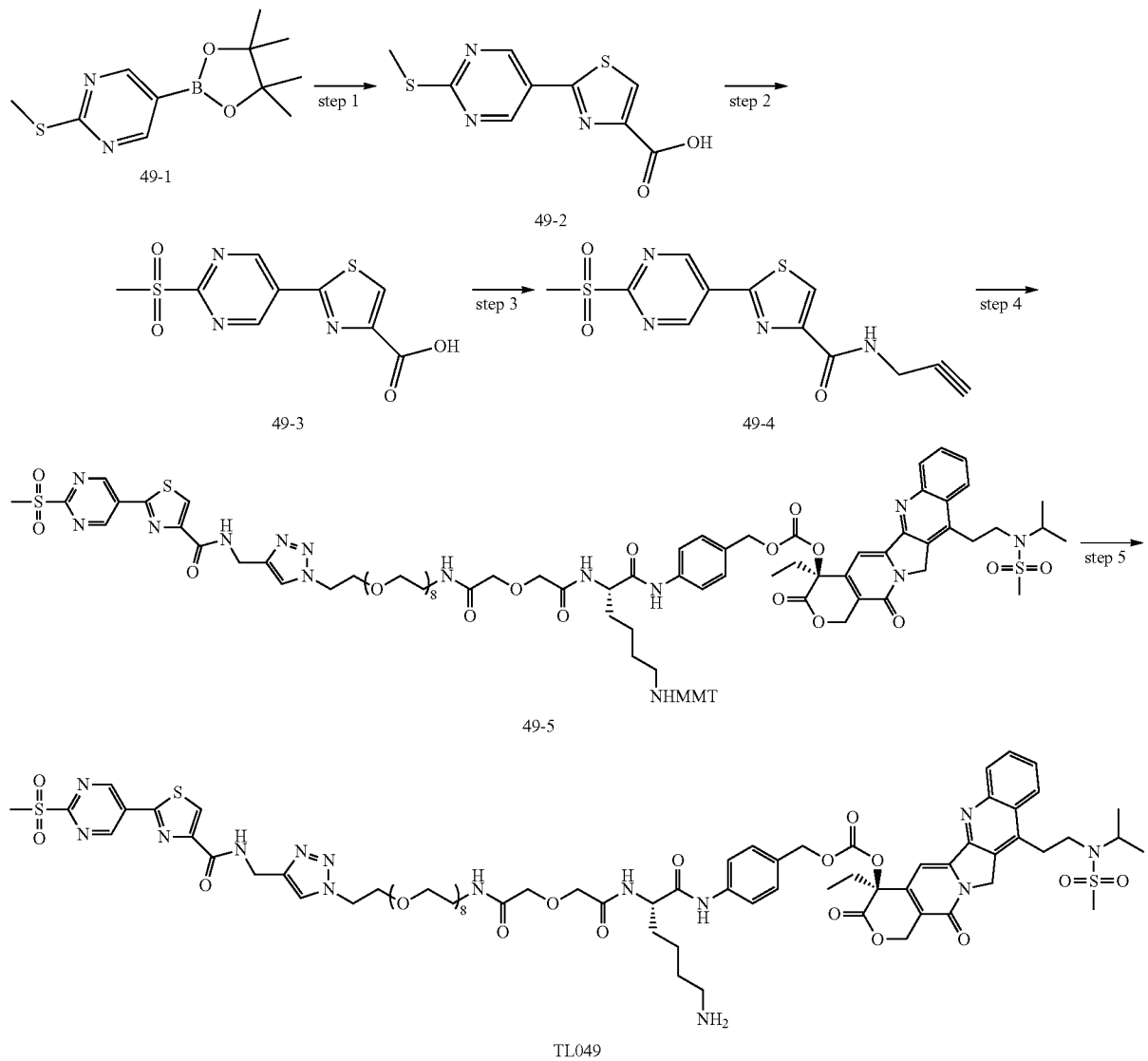

Step 1: Synthesis of 2-(2-(methylthio)pyrimidin-5-yl)thiazol-4-carboxylic Acid Compound 49-1 (100 mg, 0.40 mmol), 2-bromo-4-thiazolecarboxylic acid (99.01 mg, 0.48 mmol), potassium carbonate (137.03 mg, 0.99 mmol) and [1,1'-bis(diphenylphosphino)ferrocenyl]palladium dichloride (29.02 mg, 0.04 mmol) were dissolved in N,N-dimethylformamide (4 mL) and water (1 ml), under nitrogen protection, the reaction system was heated to 100° C. and stirred for 4 h. Then the reaction solution was cooled to room temperature and dropped into water. After filtration, the filtrate was collected and extracted with ethyl acetate (10 mL×3). The aqueous phase was collected and adjusted with dilute hydrochloric acid to pH=3 to precipitate a solid, and filtered. The filter cake was collected to obtain the title compound (70 mg). ESI-MS (m/z): 254.0 [M+H]$^+$.

Step 2: Synthesis of 2-(2-(methylsulfonyl)pyrimidin-5-yl)thiazol-4-carboxylic Acid Compound 49-2 (73 mg, 0.29 mmol) was dissolved in dichloromethane (15 mL), and m-chloroperoxybenzoic acid (175.53 mg, 0.87 mmol, 85%) was added. The reaction system was stirred overnight at room temperature. The solvent was concentrated under reduced pressure. Purification was performed on preparative high performance liquid chromatography (method D) to obtain the title compound (20 mg). ESI-MS (m/z): 286.0[M+H]$^+$.

Step 3: Synthesis of 2-(2-(methylsulfonyl)pyrimidin-5-yl)-N-(prop-2-yn-1-yl)thiazol-4-carboxamide Compound 49-3 (20 mg, 0.07 mmol) was dissolved in dichloromethane (2 mL), and O-(7-benzotriazol-N,N,N,N-tetramethyluronium hexafluorophosphate (39.98 mg, 0.11 mmol) was added. The obtained reaction system was cooled to 0° C., then N, N-diisopropylethylamine (22.65 mg, 0.18 mmol) and propargylamine (4.63 mg, 0.09 mmol) were added thereto. The reaction solution was stirred at room temperature for 3 hours. Purification was performed on preparative high performance liquid chromatography (method D) to obtain the title compound (10 mg). ESI-MS (m/z): 323.0 [M+H]$^+$.

Step 4: Synthesis of (S)-4-ethyl-11-(2-(N-isopropylmethanesulfonamido)ethyl)-3,14-dioxo-3,4,12,14-tetrahydro-1H-pyrone[3',4':6,7]indolizino[1,2-b]quinolin-4-yl-(4-((S)-2-(4-(((4-methoxyphenyebenzhydryl)amino)butyl)-35-(4-((2-(2-(methylsulfonyl)pyrimidin-5-yl)thiazol-4-carboxamido)methyl)-1H-1,2,3-triazol-1-yl)-4,8-dioxo-6,12,15,18,21,24,27,30,33-nonazeza-3,9-diazapentatriacontamino)benzyl)carbonate At room temperature, compound 33-1 (30 mg, 0.02 mmol) and compound 49-4 (9.08 mg, 0.03 mmol) were dissolved in dimethyl sulfoxide and water (2 mL/0.5 mL), and cuprous bromide (5.39 mg, 0.04 mmol) was added and reacted for 2 hours under stirring. After filtration, the filtrate was purified by preparative high performance liquid chromatography (method B) to obtain the title compound (20 mg). ESI-MS (m/z): 1647.3 [M+H–273]$^+$.

Step 5: Synthesis of 4-((S)-2-(4-aminobutyl)-35-(4-((2-(2-((methylsulfonyl)pyrimidin-5-yl)thiazol-4-carboxamido)methyl)-1H-1,2,3-triazol-1-yl)-4,8-dioxo-6,12,15,18,21,24,27,30,33-nonaoxa-3,9-diazapentatriacontamino)benzyl((S)-4-ethyl-11-(2-(N-isopropylmethylsulfonamido)ethyl)-3,14-dioxo-3,4,12,14-tetrahydro-1H-pyrone[3',4':6,7]indolizino[1,2-b]quinolin-4-yl)carbonate At room temperature, compound 49-5 (20 mg, 0.01 mmol) was dissolved in dichloromethane (2 mL), and trifluoroacetic acid (0.2 mL) was added dropwise. The obtained reaction solution was stirred at room temperature for 20 min. The reaction solution was then concentrated. The residue was purified by preparative high performance liquid chromatography (method C) to obtain the trifluoroacetate of the title compound (8 mg). ESI-MS (m/z): 1647.9 [M+H]$^+$.

Example 20: 4-((S)-2-(4-aminobutyric acid)-35-(4-((2-(2-(methylsulfonyl)pyrimidin-5-yl)-oxazol-4-formylamino)methyl)-1H-1,2,3-triazol-1-yl)-4,8-dioxo-6,12,15,18,21,24,27,30,33-nonoxy-3,9-diazapentatriacontamido)benzyl-((S)-4-ethyl-11-(2-(N-isopropylmethylsulfonamido)ethyl)-3,14-dioxo-3,4,12,14-tetrahydro-1H-pyrano[3',4':6,7]indolizino[1,2-b]quinolin-4-yl)carbonate

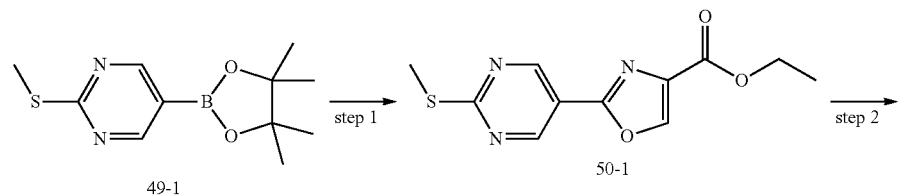

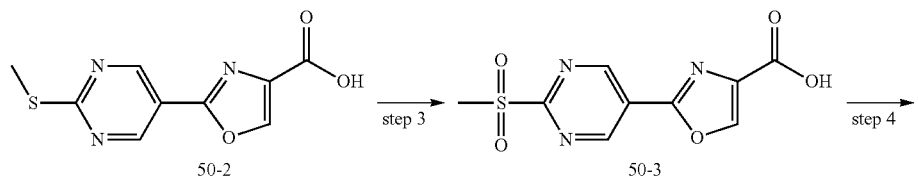

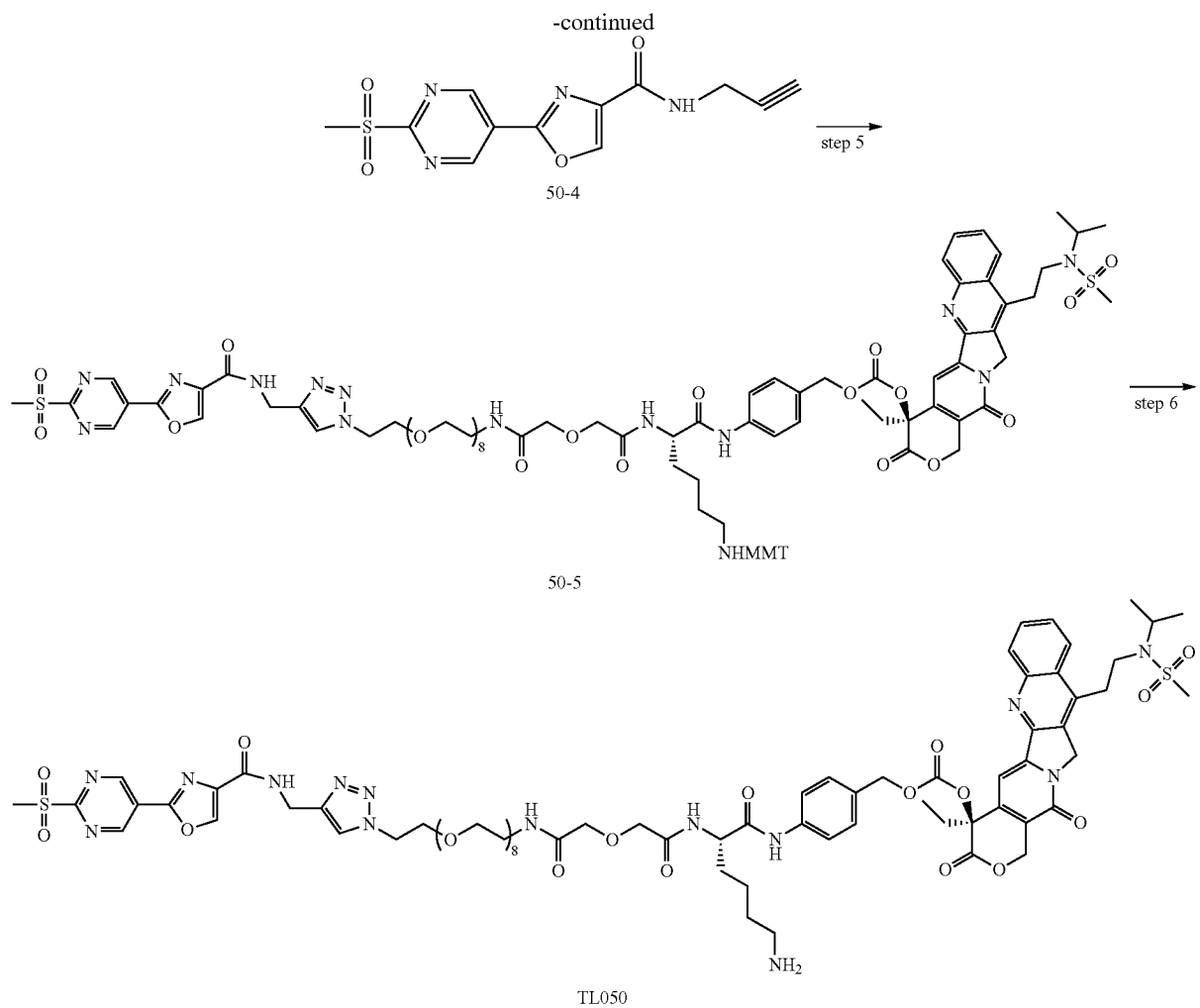

Step 1: Synthesis of ethyl 2-(2-(methylthio)pyrimidin-5-yl)oxazol-4-carboxylate At 25° C., ethyl 2-bromooxazol-4-carboxylate (100 mg, 0.45 mmol) and compound 49-1 (126 mg, 0.50 mmol) were dissolved in a mixed solvent of 1,4-dioxane and water (4 mL/2 mL), then potassium carbonate (125 mg, 0.9 mmol) and [1,1'-bis(diphenylphosphino)ferrocene]palladium dichloride (33 mg, 0.05 mmol) were successively added, under N2 protection, the mixture was heated to 90° C. and reacted for 3 hours. The reaction solution was filtered through diatomite. The filtrate was diluted with water (50 mL) and extracted with ethyl acetate (30 mL×3). The organic phases were combined and dried. The desiccant was removed by filtration, the filtrate was concentrated under reduced pressure to obtain a crude product which was purified by preparative thin layer chromatography (petroleum ether/ethyl acetate=2/1) to obtain the title compound (40 mg). ESI-MS (m/z): 266.1[M+H]+.

Step 2: Synthesis of 2-(2-(methylthio)pyrimidin-5-yl)oxazol-4-carboxylic Acid At 25° C., compound 50-1 (50 mg, 0.19 mmol) was dissolved in a mixed solvent of tetrahydrofuran and water (4 mL/2 mL), after complete dissolution, lithium hydroxide monohydrate (40 mg, 0.94 mmol) was added thereto and reacted at 25° C. for 1 h. The reaction solution was diluted with water (15 mL) and extracted with ethyl acetate (20 mL×2). The aqueous phase was adjusted with 1N dilute hydrochloric acid to pH=2-3, then extracted with a mixed solvent of dichloromethane/methanol (v:v=10:1) (20 mL×3). The organic phases were combined, washed with saturated saline (30 mL×1) and dried over anhydrous sodium sulfate. The desiccant was removed by filtration and the filtrate was concentrated to obtain the title compound (40 mg), which was directly used in further reaction without purification. ESI-MS (m/z): 238.1 [M+H]+.

Step 3: Synthesis of 2-(2-(methylsulfonyl)pyrimidin-5-yl)oxazol-4-carboxylic Acid At 25° C., compound 50-2 (40 mg, 0.17 mmol) was dissolved in dichloromethane (6 mL), after complete dissolution, m-chloroperoxybenzoic acid (29 mg, 0.17 mmol) was added thereto and reacted at 25° C. for 14 hours under stirring. The reaction solution was concentrated, and the residue was purified by preparative high performance liquid chromatography (method D) to obtain the title compound (20 mg). ESI-MS (m/z): 269.9[M+H]+.

Step 4: Synthesis of 2-(2-(methylsulfonyl)pyrimidin-5-yl)-N-(prop-2-yn-1-yl)-oxazol-4-formamide At 25° C., compound 50-3 (20 mg, 0.07 mmol) was dissolved in dichloromethane (4 mL), then O-(7-azabenzotriazol-1-yl)-N,N,N',N'-tetramethyluronium hexafluorophosphate (42 mg, 0.11 mmol) and N,N-diisopropylethylamine (19 mg, 0.15 mmol) were successively added and stirred for 5 min, followed by an addition of propargylamine (5.0 mg, 0.09 mmol) and then the resulting mixture was stirred at room temperature for 30 min. The reaction solution was concentrated, the residue was purified by preparative high performance liquid chromatography (method D) to obtain the title compound (5.0 mg). ESI-MS (m/z): 306.9 [M+H]$^+$.

Step 5: Synthesis of (S)-4-ethyl-11-(2-(N-isopropylmethanesulfonamido)ethyl)-3,14-dioxo-3,4,12,14-tetrahydro-1H-pyrano[3',4':6,7]indolizino[1,2-b]quinolin-4-yl4-((S)-2-(4-(((4-methoxyphenyl)diphenylmethyl)amino)butyl)-35-(4-((2-(2-(methylsulfonyl)pyrimidin-5-yl)oxazol-4-formylamino)methyl)-1H-1,2,3-triazol-1-yl)-4,8-dioxo-6,12,15,18,21,24,27,30,33-nonoxy-3,9-diazapentatriacontamido)benzyl)carbonate At 25° C., compound 50-4 (6.0 mg, 0.02 mmol) and compound 33-1 (30 mg, 0.02 mmol) were dissolved in a mixed solvent (2 mL/0.5 mL) of dimethyl sulfoxide and water, and cuprous bromide (5.0 mg, 0.04 mmol) was added in one batch. The resulting mixture was reacted at room temperature for 2 hours. The reaction solution was filtered and purified by preparative high performance liquid chromatography (method B) to obtain the title compound (25 mg). ESI-MS (m/z): 1631.3 [(M−273+H]$^+$.

Step 6: Synthesis of 4-((S)-2-(4-aminobutyric acid)-35-(4-((2-(2-(methylsulfonyl)pyrimidin-5-yl)oxazol-4-formylamino)methyl)-1H-1,2,3-triazol-1-yl)-4,8-dioxo-6,12,15,18,21,24,27,30,33-nonoxy-3,9-diazapentatriacontamido)benzyl-((S)-4-ethyl-11-(2-(N-isopropylmethylsulfonamido)ethyl)-3,14-dioxo-3,4,12,14-tetrahydro-1H-pyrano[3',4':6,7]indolizino[1,2-b]quinolin-4-yl)carbonate At 25° C., compound 50-5 (20 mg, 0.01 mmol) was dissolved in dichloromethane (2.0 mL). After complete dissolution, the reaction mixture was added with trifluoroacetic acid (0.2 mL) and reacted at 25° C. for 10 min. The reaction solution was concentrated, and the residue was purified by preparative high performance liquid chromatography (method C) to obtain the trifluoroacetate of the title compound (3.0 mg). ESI-MS (m/z): 816.5 [M/2+H]$^+$.

Example 21: N-((1-((6S,9S)-1-amino-6-((4-(((S)-2-((2R,3R)-3-((S)-1-((3R,4S,5S)-4-((S)-2-((S)-2-(dimethylamino)-3-methylbutanamido)-N,3-dimethylbutanamido)-3-methoxy-5-methylheptanoyl)pyrrolidin-2-yl)-3-methoxy-2-methylpropanamido)-3-phenylpropanamido)methyl)phenyl)carbamoyl)-9-isopropyl-1,8,11,15-tetraoxy-13,19,22,25,28,31,34,37,40-nonaoxa-2,7,10,16-tetraazaanthracen-42-yl)-1H-1,2,3-triazol-4-yl)methyl)-6-(2-(methylsulfonyl)pyrimidin-5-yl)-5-hexynamide

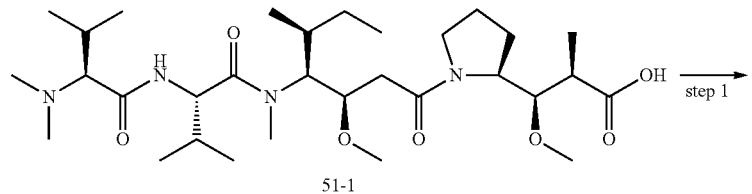

51-1

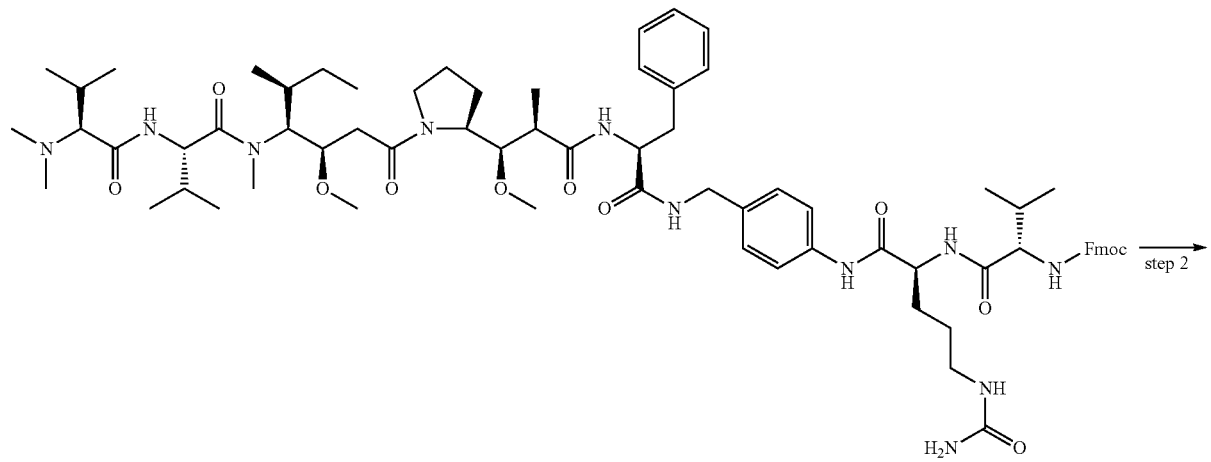

51-2

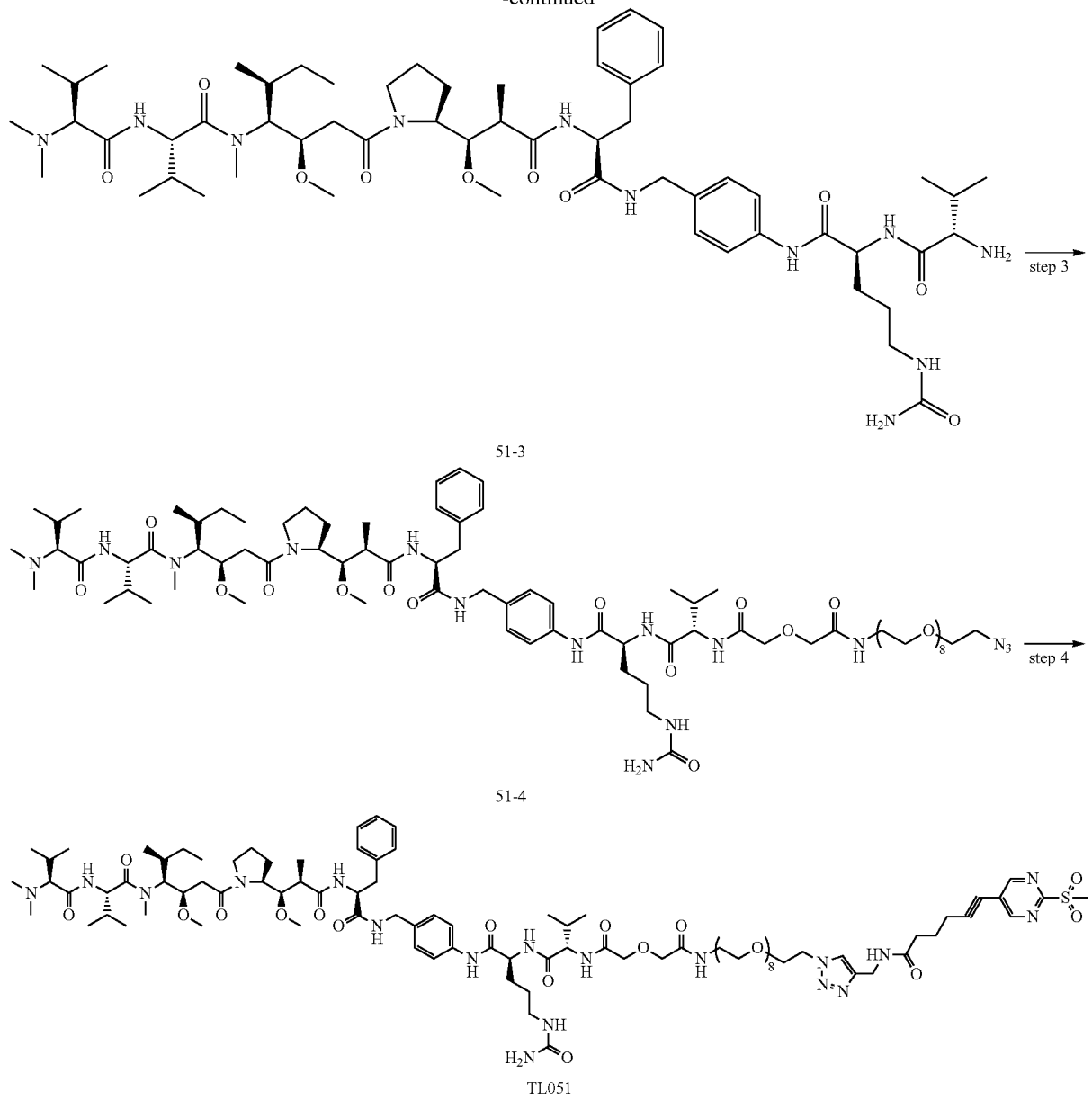

Step 1: Synthesis of 9-fluorenylmethyl ((S)-1-(((S)-1-((4-(((S)-2-((2R,3R)-3-((S)-1-((3R,4S,5S)-4-((S)-2-((S)-2-(dimethylamino)-3-butyrylamido)-N,3-dimethylbutyrylamido)-3-methoxy-5-methylheptanoyl)pyrro-2-yl)-3-methoxy-2-methylpropionamido)-3-phenylpropionamido)methyl)phenyl)amino)-1-oxo-5-ureidopent-2-yl)amino)-3-methyl-1-oxobutan-2-yl)carbamate At room temperature, compound 51-1 (100 mg, 0.17 mmol) and 9-fluorenylmethyl ((S)-1-(((S)-1-((4-(((S)-2-amino-3-phenylpropanamido)methyl)phenyl)amino)-1-oxo-5-pentylureido-2-yl)amino)-3-methyl-1-oxobutan-2-yl) carbamate trifluoroacetate (144 mg, 0.17 mmol) were dissolved in N,N-dimethylformamide (2 mL) and cooled to 0° C., then 1-hydroxybenzotriazole (34 mg, 0.25 mmol), N-methylmorpholine (51 mg, 0.51 mmol) and 1-(3-dimethylaminopropyl)-3-ethylcarbodiimide hydrochloride (48 mg, 0.25 mmol) were successively added. After addition, the reaction solution was stirred at 0° C. for 5 hours. The reaction solution was poured into water (20 mL) to precipitate a white solid, followed by suction filtration. The filter cake was washed and dried to obtain the title compound (200 mg). ESI-MS (m/z): 1329.2 [M+H]$^+$.

Step 2: Synthesis of (S)-2-((S)-2-amino-3-butyrylamino)-N-(4-(((S)-2-((2R,3R)-3-((S)-1-((3R,4S,5S)-4-((S)-2-((S)-2-(dimethylamino)-3-butyrylamino)-N,3-dimethylbutyrylamino)-3-methoxy-5-methylheptanoyl)pyrro-2-yl)-3-methoxy-2-methylpropionamido)-3-phenylpropionamido)methyl)phenyl)-5-ureidovaleramide At room temperature, compound 51-2 (200 mg, 0.12 mmol) was dissolved in N, N-dimethylformamide (5 mL), and piperidine (0.5 mL) was added. The reaction solution was stirred at room temperature for 2 hours, and then purified by preparative high performance liquid chromatography (method D) to obtain the title compound (65 mg). ESI-MS (m/z): 1107.2 [M+H]⁺.

Step 3: Synthesis of (S)-2-((S)-35-azido-2-isopropyl-4,8-dioxo-6,12,15,18,21,24,27,30,33-nonaoxa-3,9-diazapentatriacontamino)-N-(4-(((S)-2-((2R,3R)-3-((S)-1-((3R,4S,5S)-4-((S)-2-((S)-2-(dimethylamino)-3-methylbutanamido)-N,3-dimethylbutanamido)-3-methoxy-5-methylheptanoyl)pyrrolidin-2-yl)-3-methoxy-2-methylpropanamido)-3-phenylpropanamido)methyl)phenyl)-5-ureidovaleramide 32-azido-5-oxo-3,9,12,15,18,21,24,27,30-nonaoxa-6-azatricarboxylic acid (33.1 mg, 0.06 mmol) was dissolved in N,N-dimethylformamide (5 mL), then O-(7-azabenzotriazol)-N,N,N,N-tetramethyluronium hexafluorophosphate (38 mg, 0.10 mmol) and N,N-diisopropylethylamine (26 mg, 0.20 mmol) were added. The reaction solution was stirred at room temperature for 10 min, then cooled to 0° C., and added with compound 51-3 (55 mg, 0.05 mmol). The reaction solution was stirred at room temperature for 2 hours, and purified by preparative high performance liquid chromatography (method D) to obtain the title compound (56 mg). ESI-MS (m/z): 821.8 [M/2+H]⁺.

Step 4: Synthesis of N-((1-((6S,9S)-1-amino-6-((4-(((S)-2-((2R,3R)-3-((S)-1-((3R,4S,5S)-4-((S)-2-((S)-2-(dimethylamino)-3-methylbutanamido)-N,3-dimethylbutanamido)-3-methoxy-5-methylheptanoyl)pyrrolidin-2-yl)-3-methoxy-2-methylpropanamido)-3-phenylpropanamido)methyl)phenyl)carbamoyl)-9-isopropyl-1,8,11,15-tetraoxy-13,19,22,25,28,31,34,37,40-nonaoxa-2,7,10,16-tetraazaanthracen-42-yl)-1H-1,2,3-triazol-4-yl)methyl)-6-(2-(methylsulfonyl)pyrimidin-5-yl)-5-hexynamide At room temperature, compound 51-4 (56 mg, 0.04 mmol) and 6-(2-(methylsulfonyl)pyrimidin-5-yl)-N-(prop-2-yn-1-yl)-5-hexynamide (16 mg, 0.05 mmol) were dissolved in a mixed solution of dimethyl sulfoxide and water (2 mL/0.5 mL), and cuprous bromide (10 mg, 68.17 umol) was added. The obtained mixture was stirred for 2 hours, and then filtered. The filtrate was purified by preparative high performance liquid chromatography (method D) to obtain the title compound (50 mg). ESI-MS (m/z): 974.3[M/2+H]⁺.

Example 22: 4-((2S,5S)-5-isopropyl-38-(4-((6-(2-(methylsulfonyl)pyrimidin-5-yl)-5-hexynamido)methyl)-1H-1,2,3-triazol-1-yl)-4,7,11-trioxo-2-(3-ureidopropyl)-9,15,18,21,24,27,30,33,36-nonaoxa-3,6,12-triazadotetracontyl)benzyl-((S)-1-(((S)-1-(43R,4S,5S)-1-((S)-2-((1R,2R)-3-(((1S,2R)-1-hydroxy-1-phenylpropan-2-yl)amino)-1-methoxy-2-methyl-3-oxypropyl)pyrrolidin-1-yl)-3-methoxy-5-methyl-1-oxyheptan-4-yl)(methyl)amino)-3-methyl-1-oxobutan-2-yl)(methyl)carbamate

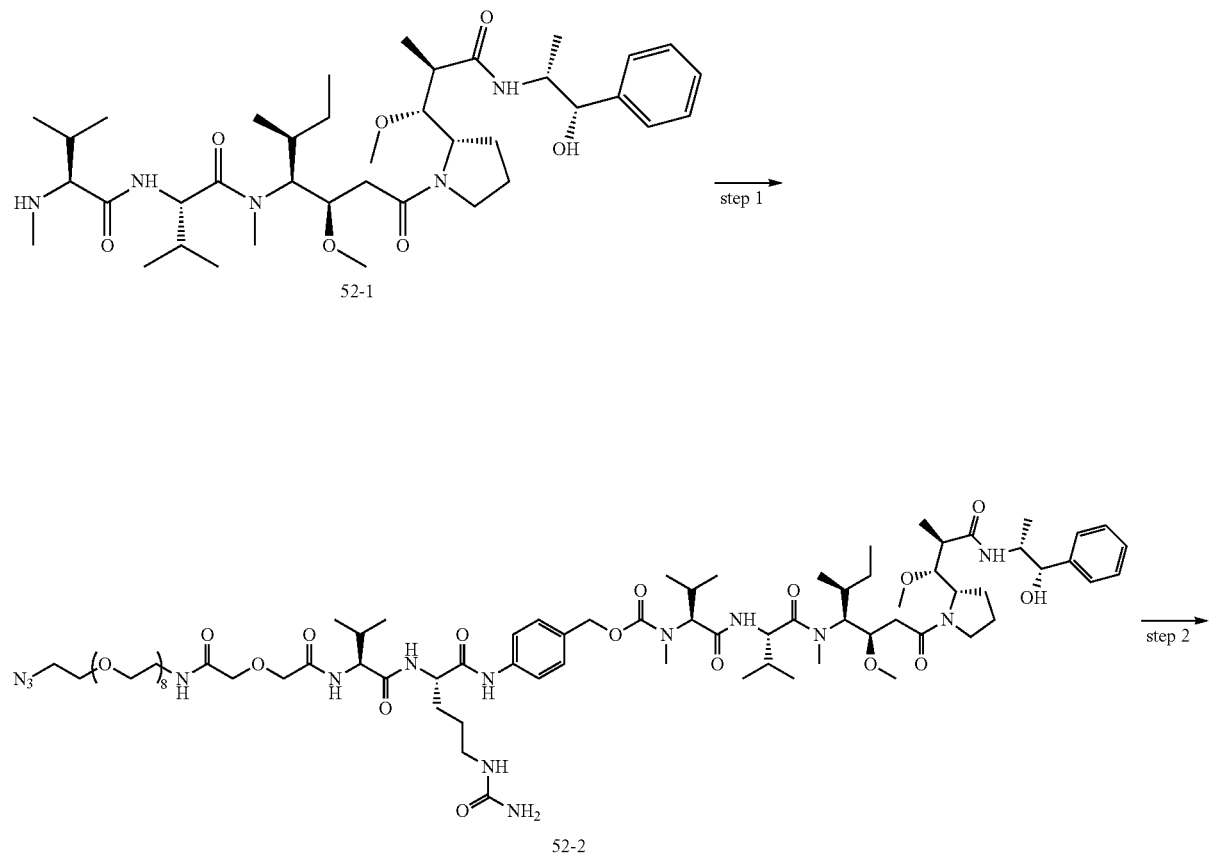

52-1

52-2

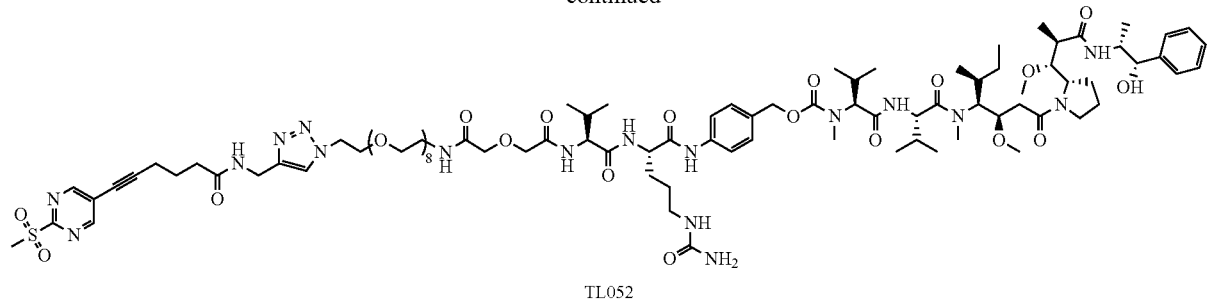

TL052

Step 1: 4-((2S,5S)-38-azido-5-isopropyl-4,7,11-tri-oxo-2-(3-ureidopropyl)-9,15,18,21,24,27,30,33,36-nonaoxa-3,6,12-triazadotetracontyl)benzyl-((S)-1-(((S)-1-(((3R,4S,5S)-1-((S)-2-((1R,2R)-3-(((1S,2R)-1-hydroxy-1-phenylpropan-2-yl)amino)-1-methoxy-2-methyl-3-oxypropyl)pyrrolidin-1-yl)-3-methoxy-5-methyl-1-oxyheptan-4-yl)(methyl)amino)-3-methyl-1-oxobutan-2-yl)(methyl)carbamate At room temperature, compound 53-1 (100 mg, 0.09 mmol) was dissolved in N,N-dimethylformamide (3 mL), then 1-hydroxybenzotriazole (13 mg, 0.09 mmol), N,N-diisopropylethylamine (36 mg, 0.28 mmol) and compound 52-1 (67 mg, 0.09 mol) were added. The reaction solution was stirred at room temperature for 16 hours, and then purified by preparative high performance liquid chromatography (method D) to obtain the title compound (120 mg). ESI-MS (m/z): 830.1 [M/2+H]$^+$.

Step 2: Synthesis of 4-((2S,5S)-5-isopropyl-38-(4-((6-(2-(methylsulfonyl)pyrimidin-5-yl)-5-hexynamido)methyl)-1H-1,2,3-triazol-1-yl)-4,7,11-trioxo-2-(3-ureidopropyl)-9,15,18,21,24,27,30,33,36-nonaoxa-3,6,12-triazadotetracontyl)benzyl-((S)-1-(((S)-1-((43R,4S,5S)-1-((S)-2-((1R,2R)-3-(((1S,2R)-1-hydroxy-1-phenylpropan-2-yl)amino)-1-methoxy-2-methyl-3-oxypropyl)pyrrolidin-1-yl)-3-methoxy-5-methyl-1-oxyheptan-4-yl)(methyl)amino)-3-methyl-1-oxobutan-2-yl)(methyl)carbamate At room temperature, compound 52-2 (22 mg, 0.07 mmol) was dissolved in a mixed solution of dimethyl sulfoxide and water (3 mL/0.3 mL), then cuprous bromide (18 mg, 0.13 mmol) was added and stirred for 1 h. The reaction solution was filtered. The filtrate was purified by preparative high performance liquid chromatography (method D) to obtain the title compound (92 mg). ESI-MS (m/z): 982.8 [M/2+H]$^+$.

Example 23: Synthesis of (S)-2-((2R,3R)-3-((2S)-1-((3R,4S,5S)-4-((S)—N,3-dimethyl-2-((S)-3-methyl2-(methyl(((4-((S)-2-((S)-3-methyl-2-(32-(4-((6-(2-(methylsulfonyl)pyrimidin-5-yl)hex-5-carbamoyl)methyl)-1H-1,2,3-triazol-1-yl)-5-oxo-3,9,12,15,18,21,24,27,30-nonoxy-6-azatriacontamino)butyrylamino)-5-ureidovalerylamino)benzyl)oxy)carbonyl)amino)butyrylamino)-3-methoxy-5-methylheptyl)pyrrolidin-2-yl)-3-methoxy-2-methylpropionyl)-L-phenylalanine

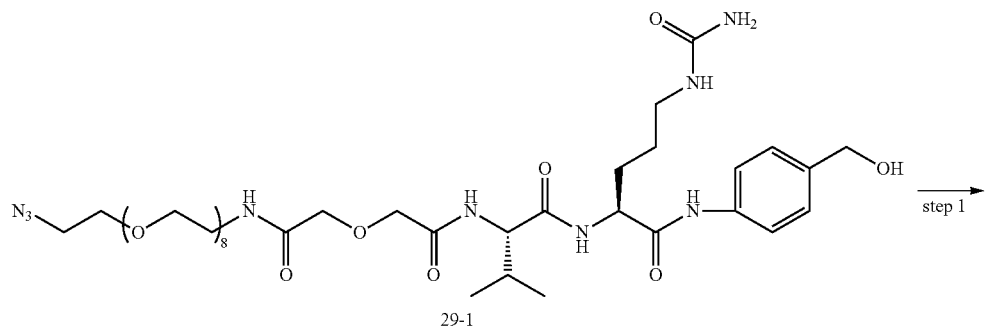

29-1 step 1

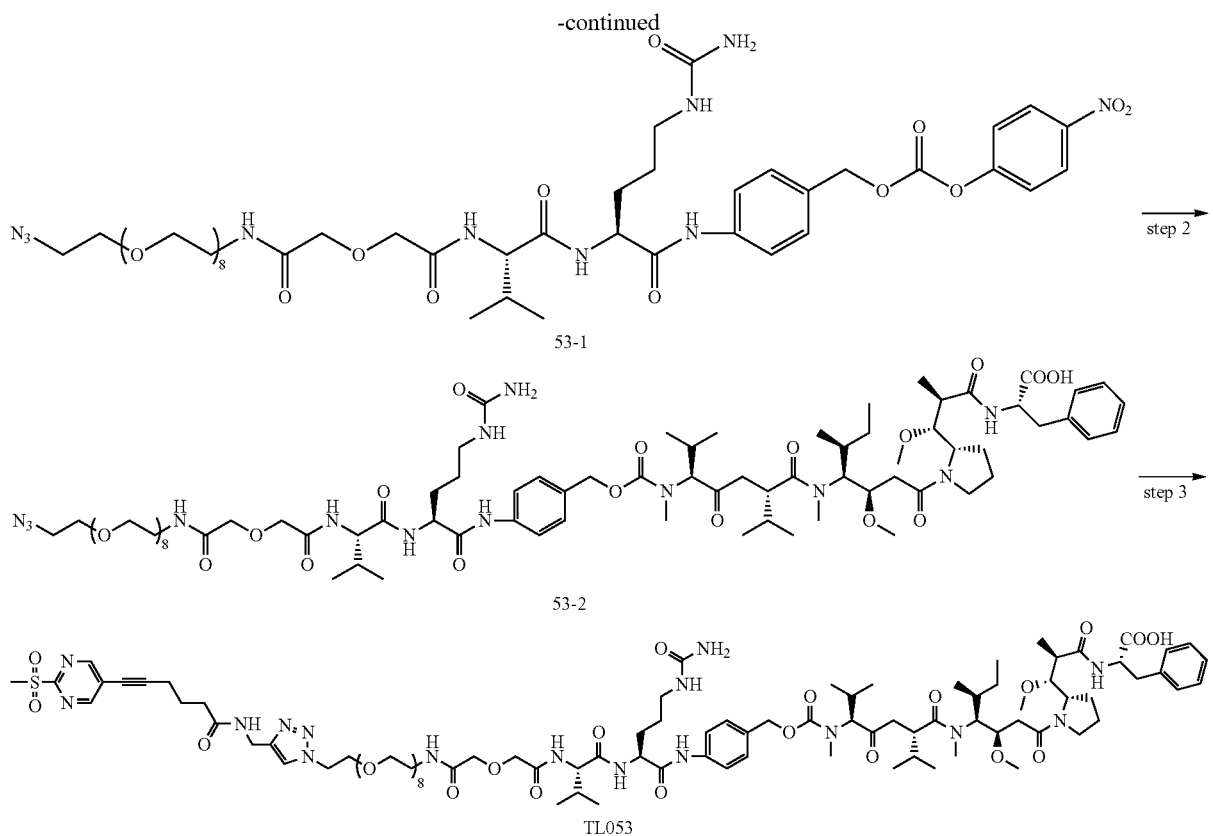

Step 1: Synthesis of 4-((2S,5S)-38-azido-5-isopropyl-4,7,11-trioxo-2-(3-ureidopropyl)-9,15,18,21,24, 27,30,33,36-nonoxy-3,6,12-triazaoctatriacontamino) benzyl-(4-nitrophenyl)-carbonate At 25° C., compound 29-1 (500 mg, 0.55 mmol) was dissolved in N,N-dimethylformamide (10 mL), and added with N,N-diisopropylethylamine (141 mg, 1.09 mmol), then followed by a dropwise addition of a solution of di(p-nitrobenzol)carbonate (332 mg, 1.09 mmol) in dichloromethane (1 mL). After the addition, the mixture was reacted at 25° C. for 3 hours under stirring. The reaction solution was purified by reverse column (C18) chromatography (acetonitrile/water=1:2) to obtain the title compound (400 mg). ESI-MS (m/z): 1081.9 [M+H]⁺.

Step 2: Synthesis of (S)-2-((2R,3R)-3-((2S)-1-((3R, 4S,5S)-4-((S)-2-((S)-2-((((4-((S)-2-((S)-2-(32-azido-5-oxo-3,9,12,15,18,21,24,27,30-nonoxy-6-azatriacontamido)-3-methylbutyrylamino)-5-ureidopentanoylamino)benzyl)oxy)carbonyl)(methyl)amino)-3-methylbutyrylamino)-N,3-dimethylbutyrylamino)-3-methoxy-5-methylheptyl) pyrrolidin-2-yl)-3-methoxy-2-methylpropionyl)-L-phenylalanine At 25° C., compound 53-1 (60 mg, 0.06 mmol) and ((2R)-3-((2S)-1-((3R, 5S)-4-((S)—N,3-dimethyl-2-((S)-3-methyl-2-(methylamino)butyrylamino)butyrylamino)-3-methoxy-5-methylheptyl)pyrrolidine-2-yl)-3-methoxy-2-methypropionyl)-L-phenylalanine (41 mg, 0.06 mmol) were dissolved in N,N-dimethylformamide (2 mL). After complete dissolution, 1-hydroxybenzotriazole (8 mg, 0.06 mmol) was added. After the addition, the mixture was stirred at 25° C. for 16 hours. The reaction solution was purified by preparative high performance liquid chromatography (method D) to obtain the title compound (38 mg). ESI-MS (m/z): 837.2 [M/2+H]⁺.

Step 3: Synthesis of (S)-2-((2R,3R)-3-((2S)-1-((3R, 4S,5S)-4-((S)—N,3-dimethyl-2-((S)-3-methyl2-(methyl(((4-((S)-2-((S)-3-methyl-2-(32-(4-((6-(2-(methylsulfonyl)pyrimidin-5-yl)hex-5-carbamoyl) methyl)-1H-1,2,3-triazol-1-yl)-5-oxo-3,9,12,15,18, 21,24,27,30-nonoxy-6-azatriacontamino) butyrylamino)-5-ureidovalerylamino)benzyl)oxy) carbonyl)amino)butyrylamino)-3-methoxy-5-methylheptyl)pyrrolidin-2-yl)-3-methoxy-2-methylpropionyl)-L-phenylalanine At 25° C., 2-(2-(methylsulfonyl)pyrimidin-5-yl)-N-(prop-2-yn-1-yl)-oxazol-4-formamide (9 mg, 0.03 mmol) and compound 53-2 (50 mg, 0.03 mmol) were dissolved in a mixed solvent of dimethyl sulfoxide and water (1 mL/0.25 mL). After complete dissolution, cuprous bromide (11 mg, 0.08 mmol) was added. After the addition, the mixture was stirred for 1 h under N₂ protection. Filtration was then conducted, and the filtrate was purified by preparative high performance liquid chromatography (method D) to obtain the title compound (25 mg). ESI-MS (m/z): 989.9 [M/2+H]⁺.

Example 24: 4-((S)-2-(4-aminobutyl)-35-(4-((6-(2-(methylsulfonyl)pyrimidin-5-yl)-5-hexynamido)methyl)-1H-1,2,3-triazol-1-yl)-4,8-dioxo-6,12,15,18,21,24,27,30,33-nonaoxa-3,9-diazapentatriacontamino)benzyl-((S)-1-(((S)-1-(43R,4S,5S)-1-((S)-2-((1R,2R)-3-(((1S,2R)-1-hydroxy-1-phenylpropan-2-yl)amino)-1-methoxy-2-methyl-3-oxypropyl)pyrrolidin-1-yl)-3-methoxy-5-methyl-1-oxyheptan-4-yl)(methyl)amino)-3-methyl-1-oxobutan-2-yl)amino)-3-methyl-1-oxobutan-2-yl)(methyl)carbamate
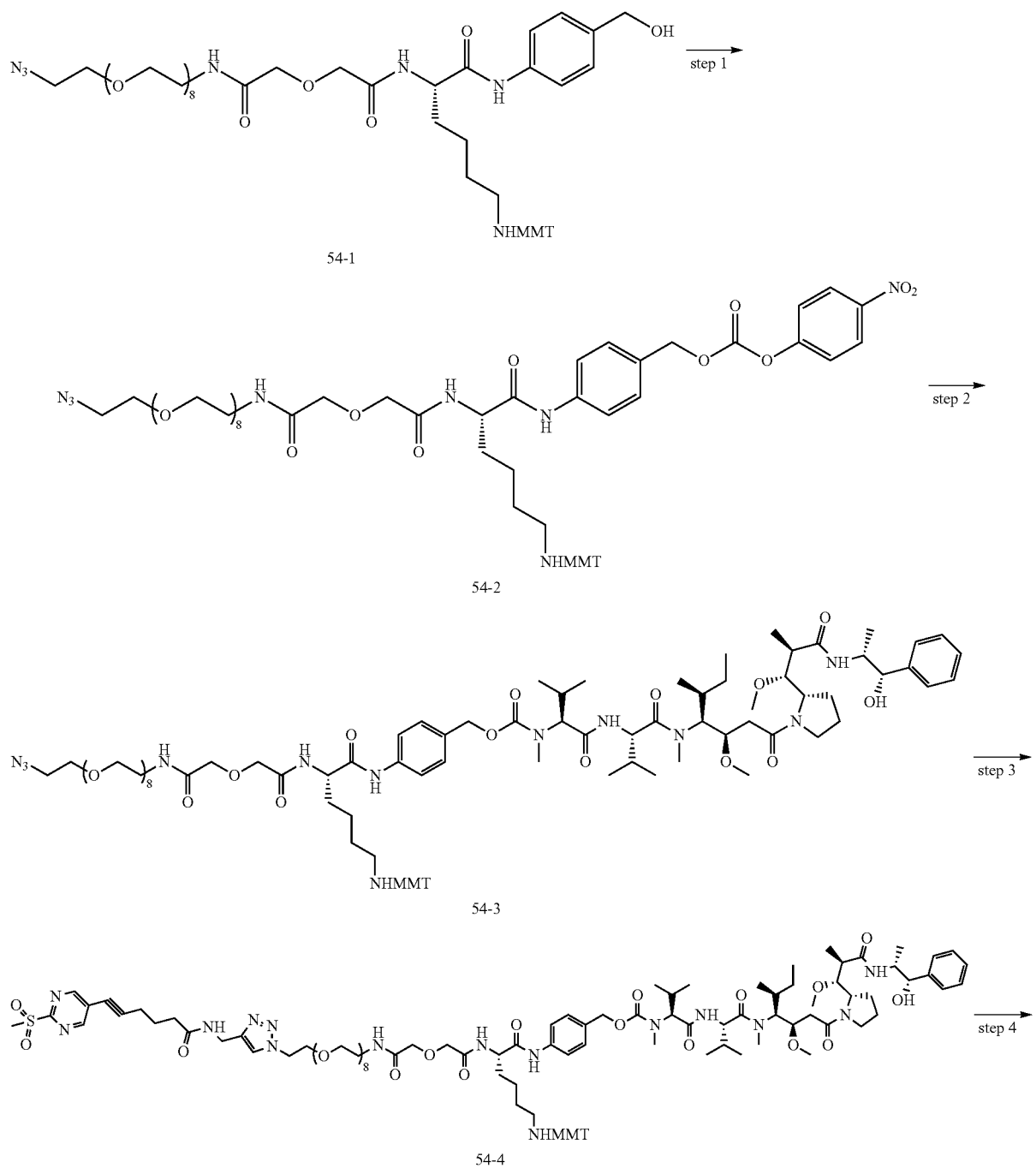

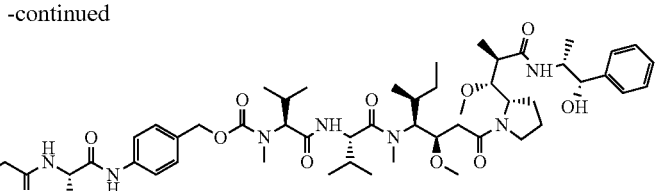
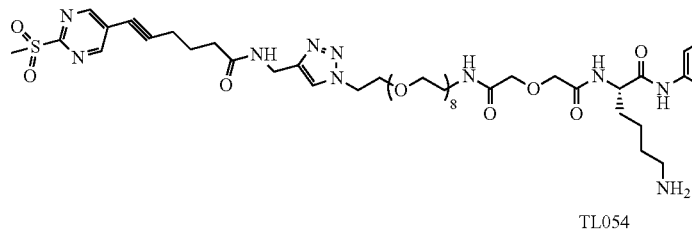

TL054

Step 1: Synthesis of (S)-4-(35-azido-2-(4-(((4-methoxyphenyl)benzhydryl)amino)butyryl)-4,8-dioxo-6,12,15,18,21,24,27,30,33-nonaoxa-3,9-diazapentatriacontamino)benzyl-(4-nitrophenyl)-carbonate At room temperature, compound 54-1 1 g, 0.95 mmol) was dissolved in dichloromethane (20 ml), then added with N,N-diisopropylethylamine (488 mg, 3.77 mmol), followed by a dropwise addition of a solution of di-(p-nitrophenyl)-carbonate (860 mg, 2.83 mmol) in dichloromethane (10 mL). The resulting reaction solution was stirred at room temperature for 6 hours and purified by silica gel column chromatography (dichloromethane/methanol=40/1) to obtain the title compound (900 mg). ESI-MS (m/z): 953.0 [M+H−273]⁺.

Step 2: Synthesis of 4-((S)-35-azide-2-(4-(((4-methoxyphenyl)benzhydryl)amino)butyryl)-4,8-dioxo-6,12,15,18,21,24,27,30,33-nonaoxa-3,9-diazapentatriacontamino)benzyl((S)-1-(((S)-1-(43R,4S,5S)-1-((S)-2-((1R,2R)-3-(((1S,2R)-1-hydroxy-1-phenylpropan-2-yl)amino)-1-methoxy-2-methyl-3-oxypropyl)pyrrolidin-1-yl)-3-methoxy-5-methyl-1-oxyheptan-4-yl)(methyl)amino)-3-methyl-1-oxobutan-2-yl)amino)-3-methyl-1-oxobutan-2-yl)(methyl)carbamate At room temperature, to compound 54-2 (2 ml) were added 1-hydroxybenzotriazole (33 mg, 0.25 mmol), N,N-diisopropylethylamine (48 mg, 0.37 mmol), and then compound 52-1 (88 mg, 0.12 mmol). The obtained reaction solution was stirred at room temperature for 16 hours and then purified by preparative high performance liquid chromatography (method B) to obtain the title compound (150 mg). ESI-MS (m/z): 1803.6 [M+H]⁺.

Step 3: Synthesis of 4-((S)-2-(4-(((4-methoxyphenyl)benzhydryl)amino)butyryl)-35-(4-((6-(2-(methylsulfonyl)pyrimidin-5-yl)-5-hexynamido)methyl)-1H-1,2,3-triazol-1-yl)-4,8-dioxo-6,12,15,18,21,24,27,30,33-nonaoxa-3,9-diazapentatriacontamino)benzyl((S)-1-(((S)-1-(((3R,4S,5S)-1-((S)-2-((1R,2R)-3-(((1S,2R)-1-hydroxy-1-phenylpropan-2-yl)amino)-1-methoxy-2-methyl-3-oxypropyl)pyrrolidin-1-yl)-3-methoxy-5-methyl-1-oxyheptan-4-yl)(methyl)amino)-3-methyl-1-oxobutan-2-yl)amino)-3-methyl-1-oxobutan-2-yl)(methyl)carbamate At room temperature, compound 54-3 (100 mg, 0.06 mmol) and 6-(2-(methylsulfonyl)pyrimidin-5-yl)-N-(prop-2-yn-1-yl)-5-hexynamide (26 mg, 0.08 mmol) were dissolved in dimethyl sulfoxide (2 mL) and water (0.5 mL), then cuprous bromide (16 mg, 0.11 mmol) was added and stirred for 2 hours. Filtration was then performed, and the filtrate was purified by preparative high performance liquid chromatography (method B) to obtain the title compound (70 mg). ESI-MS (m/z): 1936.6 [M+H−273]⁺.

Step 4: Synthesis of 4-((S)-2-(4-aminobutyl)-35-(4-((6-(2-(methylsulfonyl)pyrimidin-5-yl)-5-hexynamido)methyl)-1H-1,2,3-triazol-1-yl)-4,8-dioxo-6,12,15,18,21,24,27,30,33-nonaoxa-3,9-diazapentatriacontamino)benzyl-((S)-1-(((S)-1-(((3R,4S,5S)-1-((S)-2-((1R,2R)-3-(((1S,2R)-1-hydroxy-1-phenylpropan-2-yl)amino)-1-methoxy-2-methyl-3-oxypropyl)pyrrolidin-1-yl)-3-methoxy-5-methyl-1-oxyheptan-4-yl)(methyl)amino)-3-methyl-1-oxobutan-2-yl)amino)-3-methyl-1-oxobutan-2-yl)(methyl)carbamate At room temperature, compound 54-4 (70 mg, 0.04 mmol) was dissolved in dichloromethane (2 mL), and trifluoroacetic acid (0.2 mL) was added dropwise. The obtained reaction solution was stirred at room temperature for 20 min, then concentrated, and the residue was purified by preparative high performance liquid chromatography (method C) to obtain the trifluoroacetate of the title compound (55 mg). ESI-MS (m/z): 918.8[M/2+H]⁺.

Example 25: Synthesis of 4-((S)-2-(4-aminobutyl)-35-(4-((4-(2-(methylsulfonyl)pyrimidin-5-yl)benzamido)methyl)-1H-1,2,3-triazol-1-yl)-4,8-dioxo-6,12,15,18,21,24,27,30,33-nonoxy-3,9-diazapentatriacontamido)benzyl((S)-4-ethyl-11-(2-(N-isopropylmethylsulfonamido)ethyl)-3,14-dioxo-3,4,12,14-tetrahydro-1H-pyrano[3',4':6,7]indolizino[1,2-b]quinolin-4-yl)carbonate
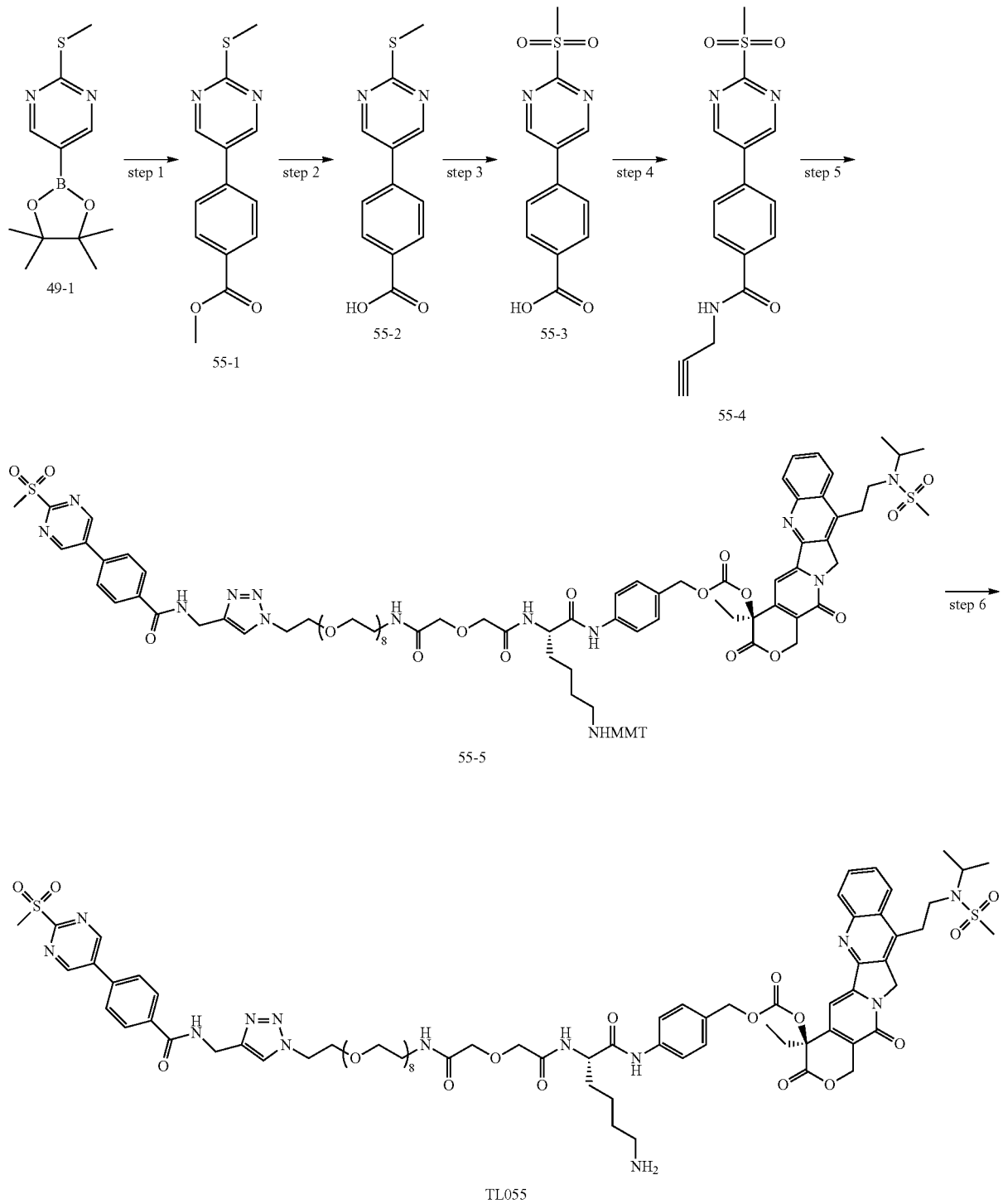

Step 1: Synthesis of methyl 4-(2-(methylthio)pyrimidin-5-yl)benzoate

At 25° C., compound 49-1 (252 mg, 1.0 mmol), water (3 mL), Pd(dppf)Cl$_2$ (40 mg, 0.05 mmol) and potassium carbonate (277 mg, 2.0 mmol) were added successively to a solution of methyl p-bromobenzoate (215 mg, 1.0 mmol) in 1,4-dioxane (5 mL) and stirred at 80° C. for 4 hours. The reaction solution was extracted with ethyl acetate (30 mL×3). The organic phases were combined and dried, then the insoluble substances were removed by filtration, and the residue was purified by silica gel column chromatography to obtain the title compound (220 mg). ESI-MS (m/z): 261.0 [M+H]$^+$.

Step 2: Synthesis of 4-(2-(methylthio)pyrimidin-5-yl)benzoic Acid

At 25° C., lithium hydroxide monohydrate (322 mg, 7.68 mmol) and water (3 ml) were respectively added to a solution of compound 55-1 (500 mg, 1.92 mmol) in tetrahydrofuran (3 ml) and stirred for 4 hours. The reaction solution was adjusted with 1N hydrochloric acid to pH=3-4, and extracted with ethyl acetate (20 mL×3). The organic phases were combined and dried. The insoluble substances were removed by filtration, and the residue was purified by preparative high performance liquid chromatography (method D) to obtain the title compound (430 mg). ESI-MS (m/z): 246.9 [M+H]$^+$.

Step 3: Synthesis of 4-(2-(methylsulfonyl)pyrimidin-5-yl)benzoic Acid

At 25° C., m-chloroperoxybenzoic acid (420 mg, 2.44 mmol) was added to a solution of compound 55-2 (200 mg, 0.81 mmol) in dichloromethane (5 ml), and stirred for 5 hours, and then purified by silica gel column chromatography to obtain the title compound (180 mg). ESI-MS (m/z): 279.0 [M+H]$^+$.

Step 4: Synthesis of 4-(2-(methylsulfonyl)pyrimidin-5-yl)-N-(prop-2-yn-1-yl)benzamide At 25° C., benzotriazole-N,N,N',N'-tetramethyluronium hexafluorophosphate (100 mg, 0.26 mmol) was added to a solution of compound 55-3 (50 mg, 0.18 mmol) in dichloromethane (10 mL), and stirred for 30 min, then propynylamine (10 mg, 0.2 mmol) and N,N-diisopropylethylamine (70 mg, 0.5 mmol) were added to the reaction solution and reacted for 2.5 h under stirring. The reaction solution was purified by silica gel column chromatography to obtain the title compound (20 mg). ESI-MS (m/z): 316.0 [M+H]$^+$.

Step 5: Synthesis of (S)-4-ethyl-11-(2-(N-isopropylmethanesulfonamido)ethyl)-3,14-dioxo-3,4,12,14-tetrahydro-1H-pyrano[3',4':6,7]indolizino[1,2-b]quinolin-4-yl(4-((S)-2-(4-(((4-methoxyphenyl)diphenylmethyl)amino)butyl)-35-(4-((4-(2-(methylsulfonyl)pyrimidin-5-yl)benzamido)methyl)-1H-1,2,3-triazol-1-yl)-4,8-dioxo-6,12,15,18,21,24,27,30,33-nonoxy-3,9-diazapentatriacontamido)benzyl)carbonate At 25° C. and under N2 protection, cuprous iodide (10 mg, 0.05 mmol) and water (2 mL) were successively added to dimethyl sulfoxide solution (2 mL) of compound 55-4 (16 mg, 0.05 mmol) and compound 33-1 (80 mg, 0.05 mmol) and reacted for 1 h under stirring. Purification (method B) was performed to obtain the title compound (79 mg). ESI-MS (m/z): 1641.5 [M−273+H]$^+$.

Step 6: Synthesis of 4-((S)-2-(4-aminobutyl)-35-(4-((4-(2-(methylsulfonyl)pyrimidin-5-yl)benzamido)methyl)-1H-1,2,3-triazol-1-yl)-4,8-dioxo-6,12,15,18,21,24,27,30,33-nonoxy-3,9-diazapentatriacontamido)benzyl((S)-4-ethyl-11-(2-(N-isopropylmethylsulfonamido)ethyl)-3,14-dioxo-3,4,12,14-tetrahydro-1H-pyrano[3',4':6,7]indolizino[1,2-b]quinolin-4-yl)carbonate At 25° C., compound 55-5 (55 mg, 0.029 mmol) was added to trifluoroacetic acid (0.5 mL) in a mixed solvent of water/acetonitrile (0.1 mL/0.5 mL), and reacted for 15 min under stirring. The reaction solution was purified by preparative high performance liquid chromatography (method C) to obtain the trifluoroacetate of the title compound (42 mg). ESI-MS (m/z): 821.0 [M/2+H]$^+$.

Example 26: N-((1-((6S,9S)-1-amino-6-((4-((S)-3-azido-2-((2R,3R)-3-((S)-1-((3R,4S,5S)-4-((S)-2-((S)-2-(dimethylamino)-3-methylbutyrylamino)-N,3-dimethylbutyrylamino)-3-methoxy-5-methylheptyl)pyrrolidin-2-yl)-3-methoxy-2-methylpropionamido)propyl)phenyl)carbamoyl)-9-isopropyl-1,8,11,15-tetraoxo-13,19,22,25,28,31,34,37,40-nonoxy-2,7,10,16-tetraazadotetracont-42-yl)-1H-1,2,3-triazol-4-yl)methyl)-6-(2-(methylsulfonyl)pyrimidin-5-yl)hex-5-ynylamide

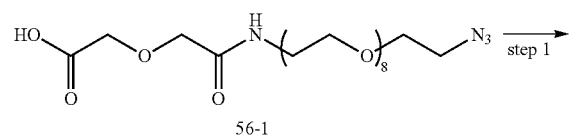

56-1

-continued
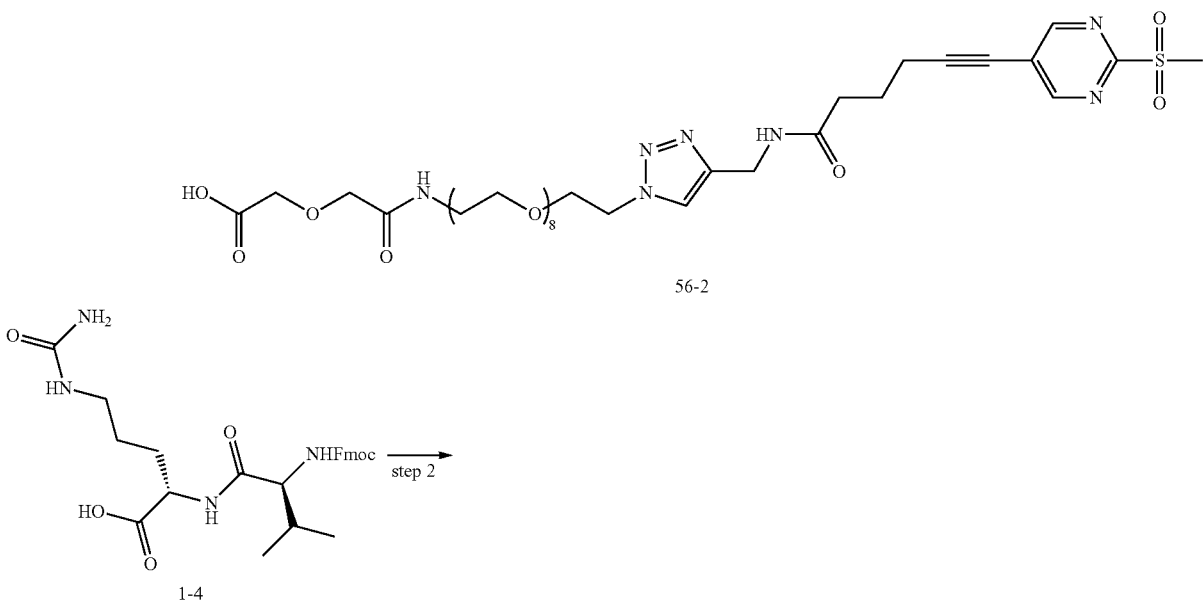
56-2
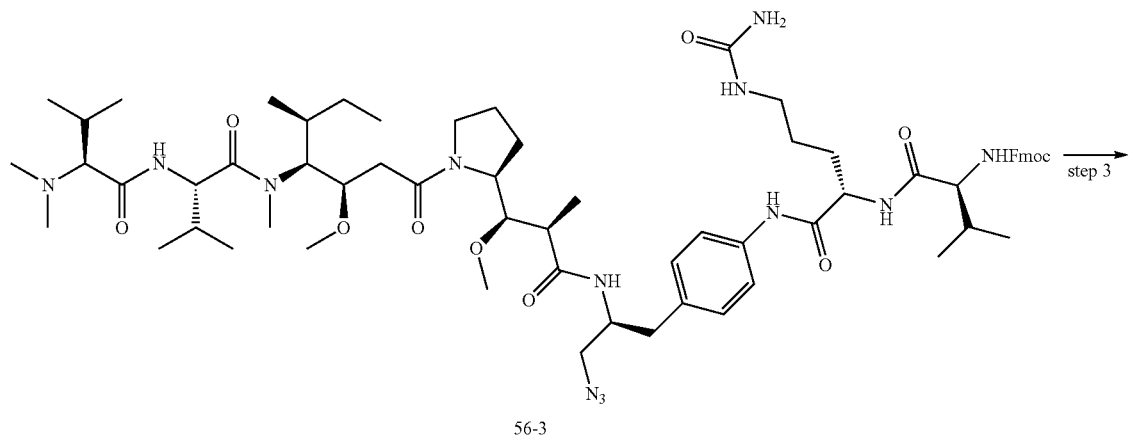
56-3
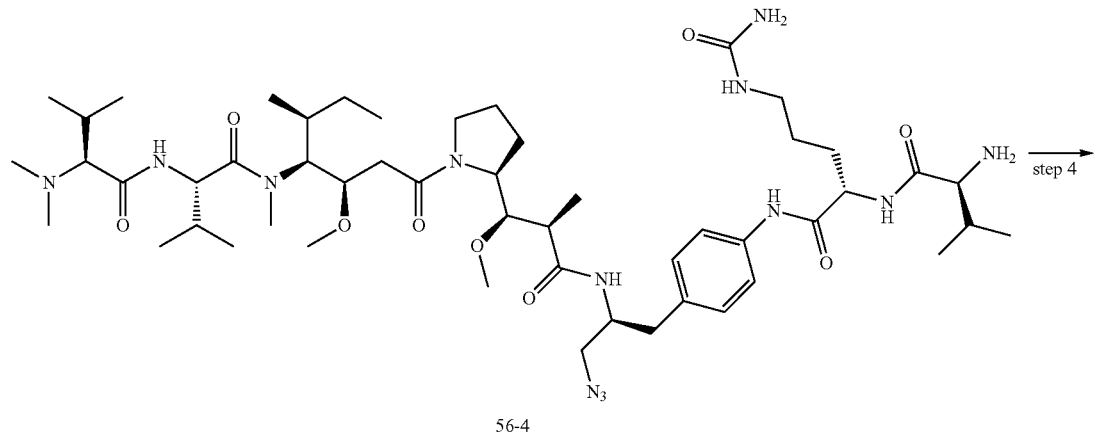
56-4

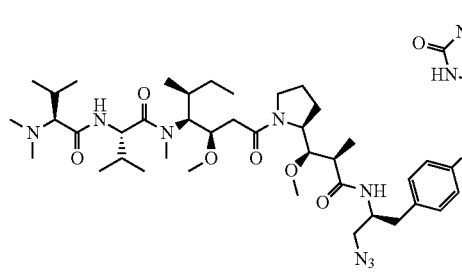

TL056

Step 1: Synthesis of 32-(4-((6-(2-(methylsulfonyl)pyrimidin-5-yl)hex-5-ynamido)methyl)-1H-1,2,3-triazol-1-yl)-5-oxo-3,9,12,15,18,21,24,27,30-nonoxy-6-azadotriacontanoic Acid At 20° C., compound 56-1 (750 mg, 1.28 mmol) and 6-(2-(methylsulfonyl)pyrimidin-5-yl)-N-(prop-2-yn-1-yl)hex-5-ynylamide (496 mg, 1.54 mmol) were dissolved in dimethyl sulfoxide (10 mL), and cuprous bromide (465 mg, 3.21 mmol) was added in one batch. After the addition, the mixture was reacted for 12 hours under stirring. The reaction solution was filtered, and the filtrate was purified by preparative high performance liquid chromatography (method D) to obtain the title compound (500 mg). ESI-MS (m/z): 860.4 [M+H]+.

Step 2: Synthesis of (9H-fluoren-9-yl)methyl((S)-1-(((S)-1-((4-((S)-3-azido-2-((2R,3R)-3-((S)-1-((3R,4S,5S)-4-((S)-2-((S)-2-(dimethylamino)-3-methylbutyrylamino)-N,3-dimethylbutyrylamino)-3-methoxy-5-methylheptyl)pyrrolidin-2-yl)-3-methoxy-2-methylpropionamido)propyl)phenyl)amino)-1-oxo-5-ureidopentanoylamino-2-yl)amino)-3-methyl-1-oxobutan-2-yl)carbamate At 25° C., (S)—N-((3R,4S,5S)-1-((S)-2-((1R,2R)-3-(((S)-1-(4-aminophenyl)-3-azidopropyl-2-yl)amino)-1-methoxy-2-methyl-3-oxopropyl)pyrrolidin-1-yl)-3-methoxy-5-methyl-1-oxoheptyl-4-yl)-2-((S)-2-(dimethylamino)-3-methylbutyrylamino)-N,3-dimethylbutyrylamine (185 mg, 0.24 mmol) was dissolved in N,N-dimethylformamide (5 mL), then HATU (137 mg, 0.36 mmol) was added and stirred for 5 min, followed by an addition of (S)-2-((S)-2-((((9H-fluoren-9-yl)methoxy)carbonyl)amino)-3-methylbutyrylamino)-5-ureidopentanoic acid (131 mg, 0.26 mmol). The mixture was stirred at room temperature for 30 min. The reaction solution was directly used in further reaction. ESI-MS (m/z): 626.0 [M/2+H]+.

Step 3: Synthesis of (S)-2-((S)-2-amino-3-methylbutyrylamino)-N-(4-((S)-3-azido-2-((2R,3R)-3-((S)-1-((3R,4S,5S)-4-((S)-2-((S)-2-(dimethylamino)-3-methylbutyrylamino)-N,3-dimethylbutyrylamino)-3-methoxy-5-methylheptyl)pyrrolidin-2-yl)-3-methoxy-2-methylpropionamido)propyl)phenyl)-5-ureidovaleramide At 25° C., diethylamine (0.5 mL) was added to the reaction solution obtained in step 2, and stirred for reaction for 30 min after the addition. The reaction solution was purified by preparative high performance liquid chromatography (method D) to obtain the title compound (70 mg). ESI-MS (m/z): 515.0 [M/2+H]+.

Step 4: Synthesis of N-((1-(((6S,9S)-1-amino-6-((4-((S)-3-azido-2-((2R,3R)-3-((S)-1-((3R,4S,5S)-4-((S)-2-((S)-2-(dimethylamino)-3-methylbutyrylamino)-N,3-dimethylbutyrylamino)-3-methoxy-5-methylheptyl)pyrrolidin-2-yl)-3-methoxy-2-methylpropionamido)propyl)phenyl)carbamoyl)-9-isopropyl-1,8,11,15-tetraoxo-13,19,22,25,28,31,34,37,40-nonoxy-2,7,10,16-tetraazadotetracont-42-yl)-1H-1,2,3-triazol-4-yl)methyl)-6-(2-(methylsulfonyl)pyrimidin-5-yl)hex-5-ynylamide At 25° C., (S)-2-((S)-2-amino-3-methylbutyrylamino)-N-(4-((S)-3-azido-2-((2R,3R)-3-((S)-1-((3R,4S,5S)-4-((S)-2-((S)-2-(dimethylamino)-3-methylbutyrylamino)-N,3-dimethylbutyrylamino)-3-methoxy-5-methylheptyl)pyrrolidin-2-yl)-3-methoxy-2-methylpropionamido)propyl)phenyl)-5-ureidovaleramide (95 mg, 0.092 mmol) and 32-(4-((6-(2-(methylsulfonyl)pyrimidin-5-yl)hex-5-ynamido)methyl)-1H-1,2,3-triazol-1-yl)-5-oxo-3,9,12,15,18,21,24,27,30-nonoxy-6-azadotriacontanic acid (79 mg, 0.092 mmol) were dissolved in N,N-dimethylformamide (4 mL), and HATU (70 mg, 0.184 mmol) was added in one batch. The mixture was stirred at room temperature for 1 h. The reaction solution was purified by preparative high performance liquid chromatography (method D) to obtain the title compound (30 mg). ESI-MS (m/z): 935.8[M/2+H]+.

III. Coupling of the Compound Containing the Bioactive Molecule and the Linker with an Antibody Example 27: Preparation of BT001002

0.3 mL of antibody Sacituzumab (anti-Trop-2, 33.5 mg/mL) was diluted with 0.25 ml of a solution (pH 7.6) containing 20 mM PB, 150 mM NaCl and 20 mM sodium edetate, to which 0.45 ml of a solution (pH 7.6) containing 20 mM PB and 150 mM NaCl was added and evenly mixed. The mixture was adjusted with 1M $K_2HPO_4$ solution to pH=7.4, and then 10 mM TCEP (tris(2-carboxyethyl)phosphine) solution was added and evenly mixed, which was allowed to stand at room temperature for 30 min. To the solution system, TL003 dissolved in dimethyl sulfoxide was added in an amount of 15 equiv. and evenly mixed, which was allowed to stand at room temperature for 2 hours. After the addition, 6.1 μl of 100 mM cysteine was added to terminate the reaction. At last, the buffer was replaced with a 20 mM PB buffer solution of pH 6.44 by G-25 gel column to obtain the coupling product of TL003 with Sacituzumab, which was named as BT001002.

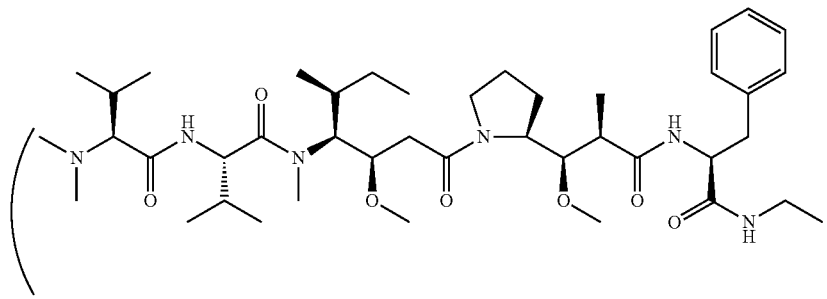

BT001002

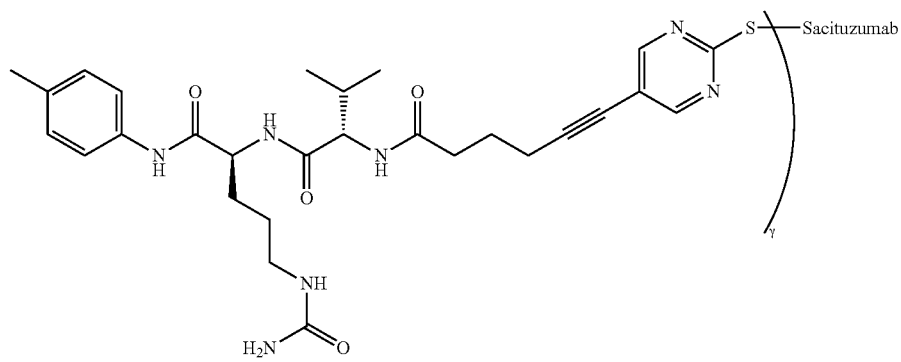

Example 28: Preparation of BT001004

0.285 mL of Sacituzumab (anti-Trop-2, 17.6 mg/mL) was diluted with 0.095 mL of a diluent (a solution containing 20 mM PB, 150 mM NaCl and 20 mM sodium edetate, pH 7.6). Then the diluted solution was adjusted with 1M $Na_2HPO_4$ solution to pH 7.4, and 10 mM TCEP solution was added and evenly mixed, which was allowed to stand at room temperature for 30 min. To the solution system, TL019 dissolved in dimethyl sulfoxide was added in an amount of 9 equiv. and evenly mixed, which was allowed to stand at room temperature for 2h. At last, the buffer was replaced with a PBS buffer solution of pH 6.5 by G-25 gel column to obtain the coupling product of TL019 with Sacituzumab, which was named as BT001004.

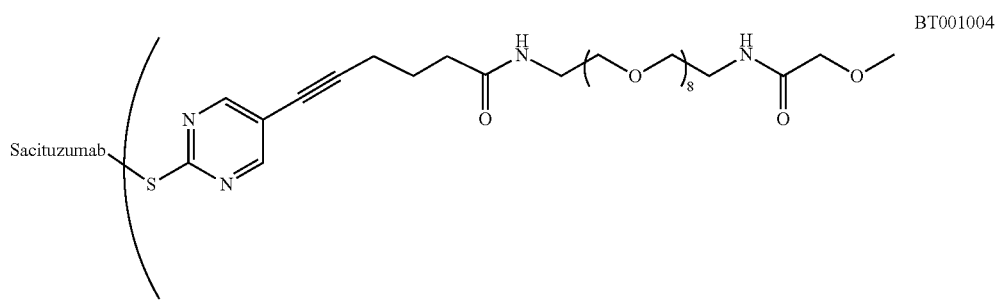

BT001004

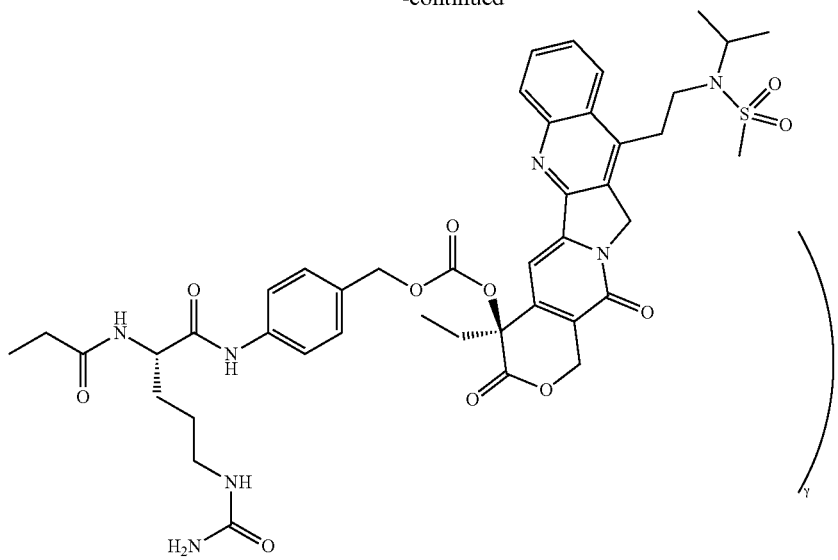
Example 29: Preparation of BT001012
A method similar to that described in example 27 was adopted to obtain the coupling product of TL024 with Sacituzumab, which was named as BT001012, except that TL003 was replaced by trifluoroacetate of TL024.
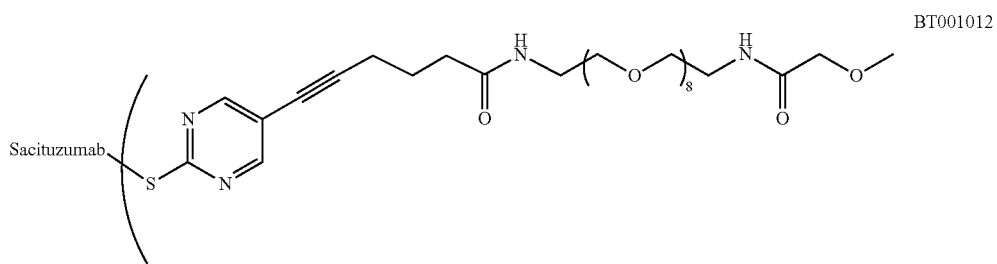
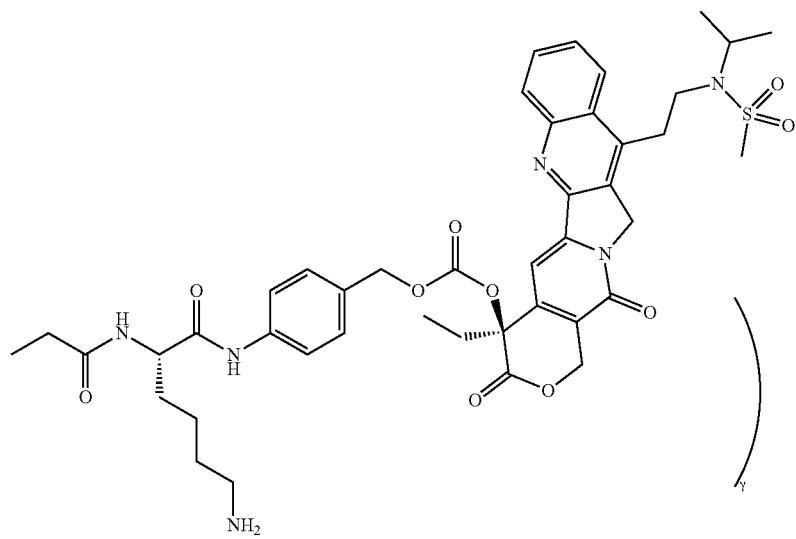

Example 30: Preparation of BT001013

A method similar to that described in example 27 was adopted to obtain the coupling product of TL048 with Sacituzumab, which was named as BT001013, except that TL003 was replaced by trifluoroacetate of TL048.

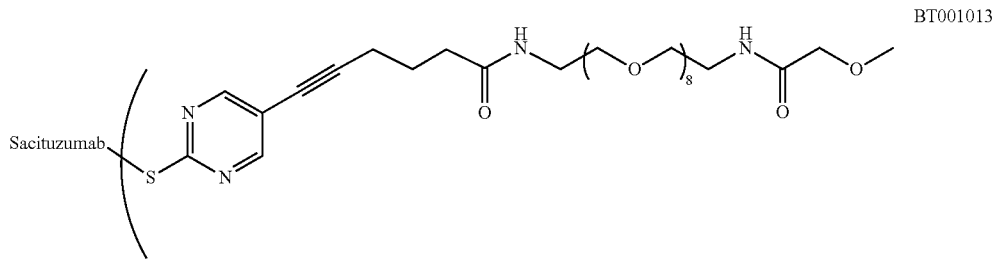

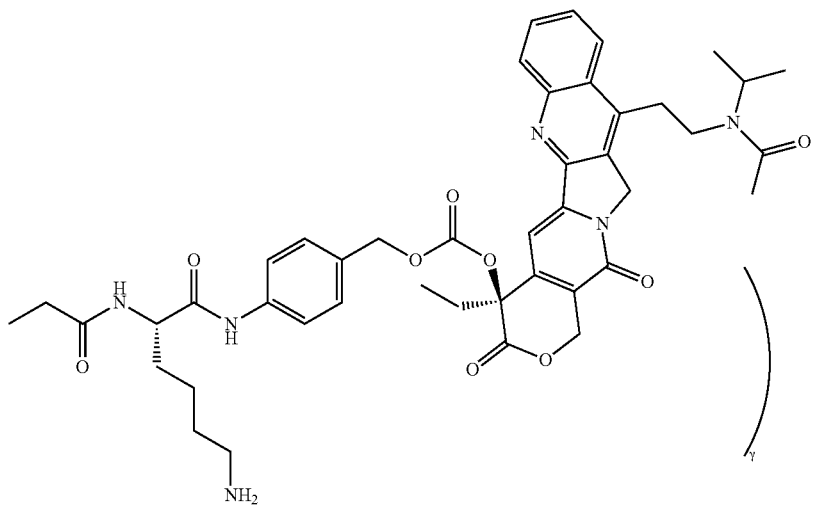

Example 31: preparation of BT001018

A method similar to that described in example 27 was adopted to obtain the coupling product of TL030 with Sacituzumab, which was named as BT001018, except that TL003 was replaced by TL030.

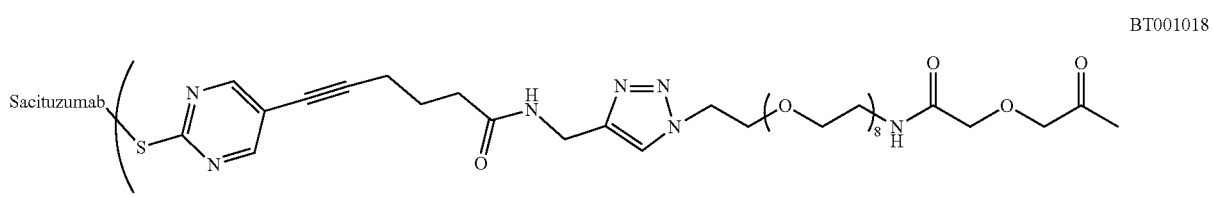

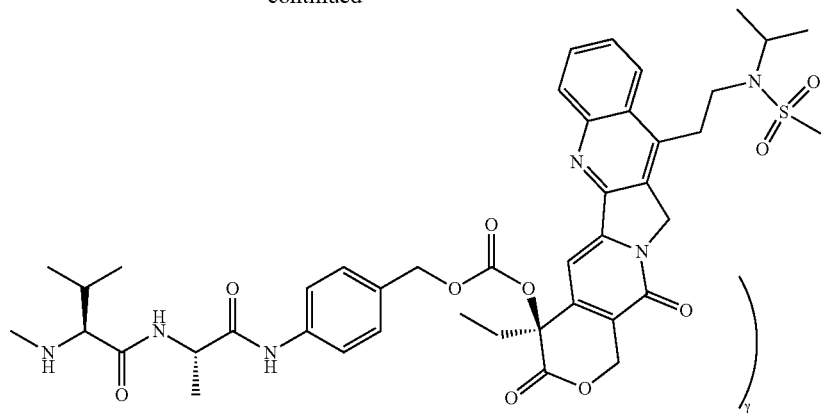

Example 32: Preparation of BT001021

0.3 mL of Sacituzumab (anti-Trop-2, 33.5 mg/mL) was diluted with 0.25 ml of a solution (pH 7.6) containing 20 mM PB, 150 mM NaCl and 20 mM sodium edetate, then 0.45 mL of a solution (pH 7.6) containing 20 mM PB and 150 mM NaCl was added and evenly mixed. The mixture was adjusted with 1M $Na_2HPO_4$ solution to pH=7.4, then 10 mM TCEP (tris(2-carboxyethyl)phosphine) solution was added and evenly mixed, which was allowed to stand at room temperature for 30 min. To the solution system, trifluoroacetate of TL033 dissolved in dimethyl sulfoxide was added in an amount of 10 equiv. and evenly mixed, which was allowed to stand at room temperature for 2 hours. Then 6.1 μl of 100 mM cysteine was added to terminate the reaction. At last, the buffer was replaced by a PBS buffer solution of pH 6.5 by G-25 gel column to obtain the coupling product of TL033 with Sacituzumab, which was named as BT001021.

BT001021

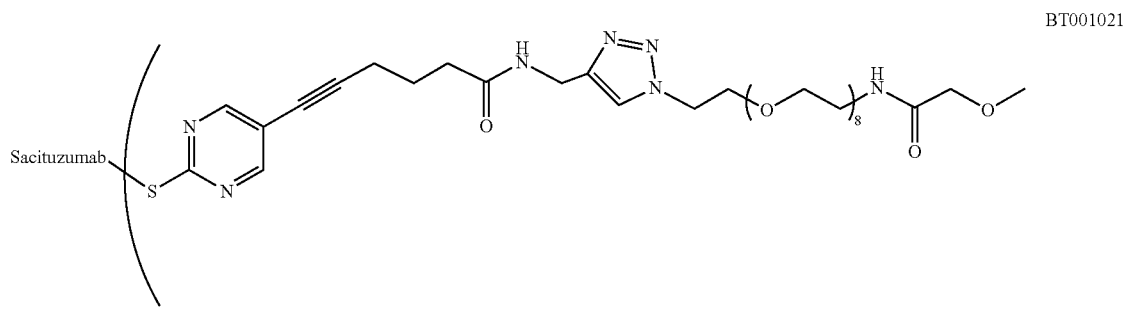

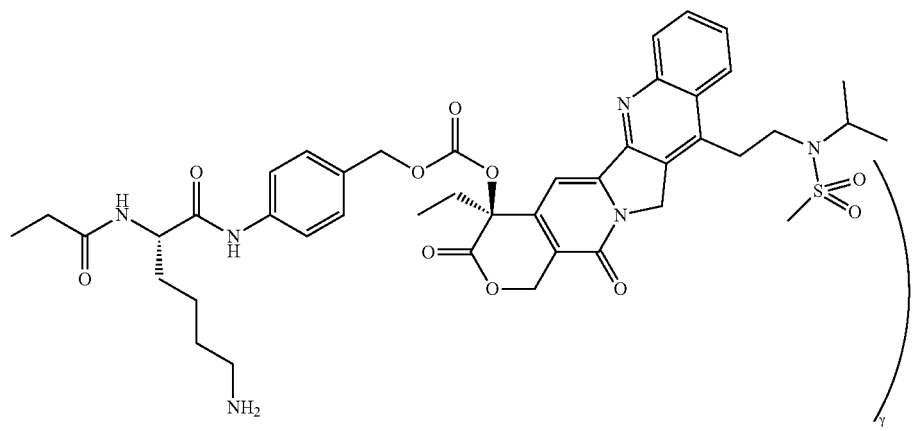

Example 33: Preparation of BT001022

A method similar to that described in example 27 was adopted to obtain the coupling product of TL034 with Sacituzumab, which was named as BT001022, except that TL003 was replaced by trifluoroacetate of TL034.

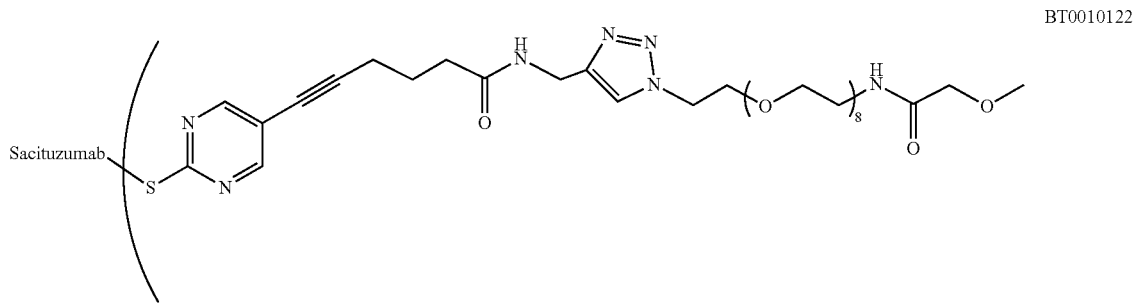

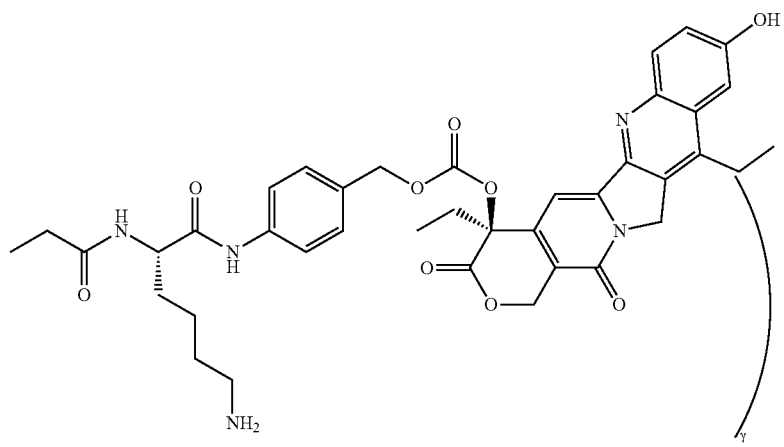

Example 34: Preparation of BT001023

A method similar to that described in example 27 was adopted to obtain the coupling product of TL035 with Sacituzumab, which was named as BT001023, except that TL003 was replaced by trifluoroacetate of TL035.

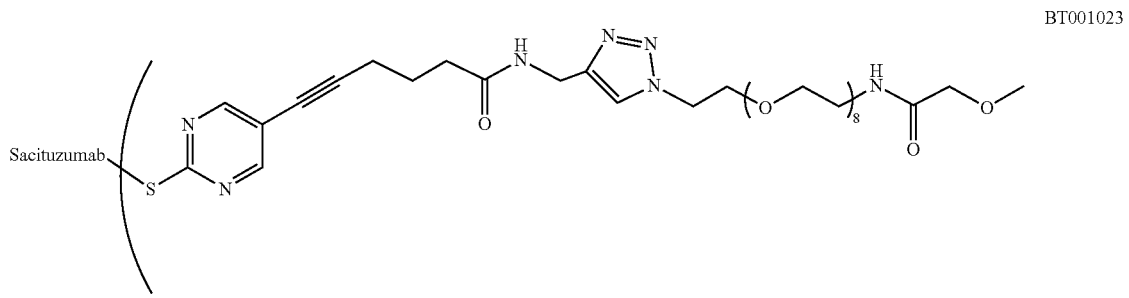

-continued
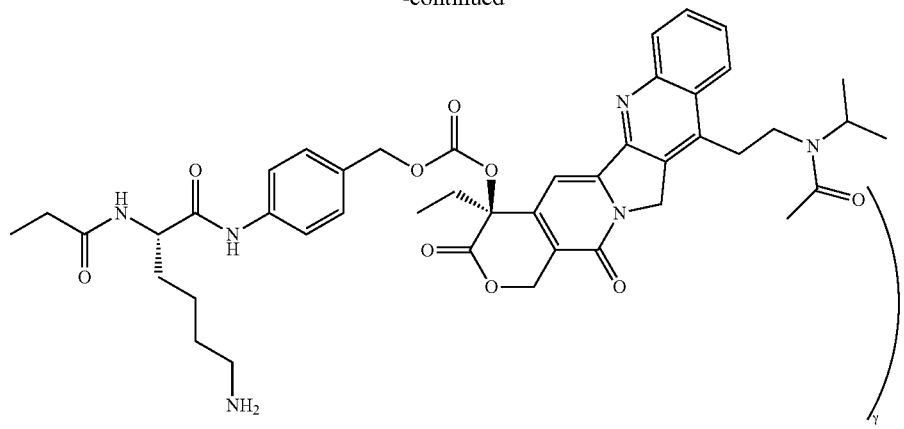
Example 35: Preparation of BT001032
A method similar to that described in example 27 was adopted to obtain the coupling product of TL045 with Sacituzumab, which was named as BT001032, except that TL003 was replaced by trifluoroacetate of TL045.
BT001032
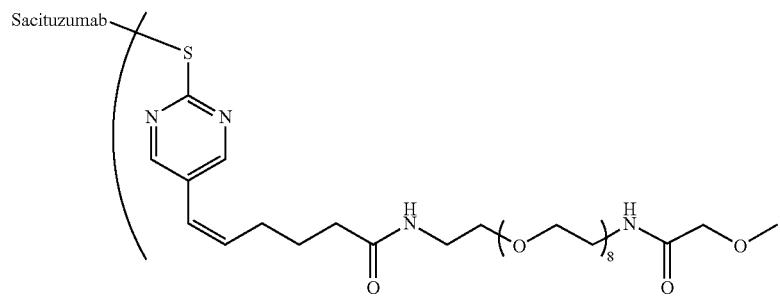
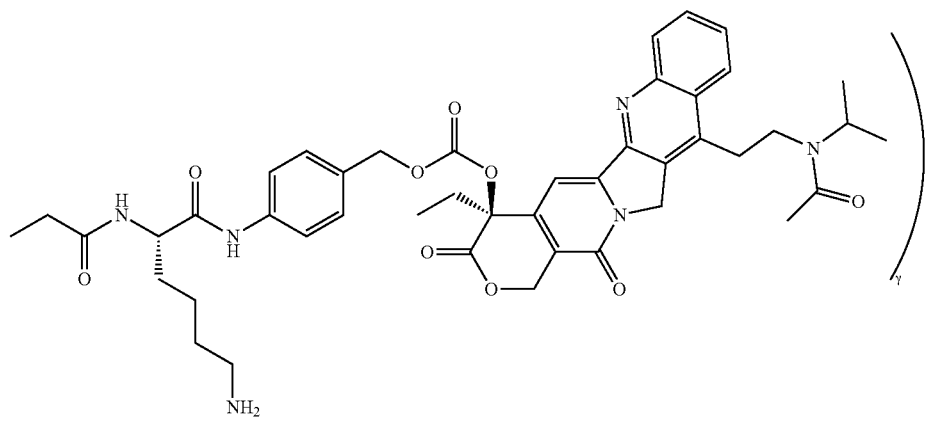

Example 36: Preparation of BT001033

A method similar to that described in example 27 was adopted to obtain the coupling product of TL033 with antibody M1, which was named as BT001033, except that TL003 was replaced by trifluoroacetate of TL033 and Sacituzumab was replaced by antibody M1.

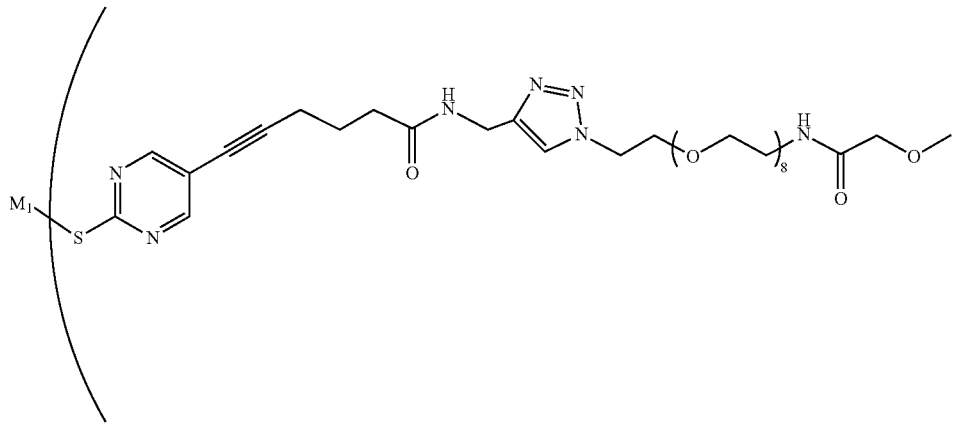

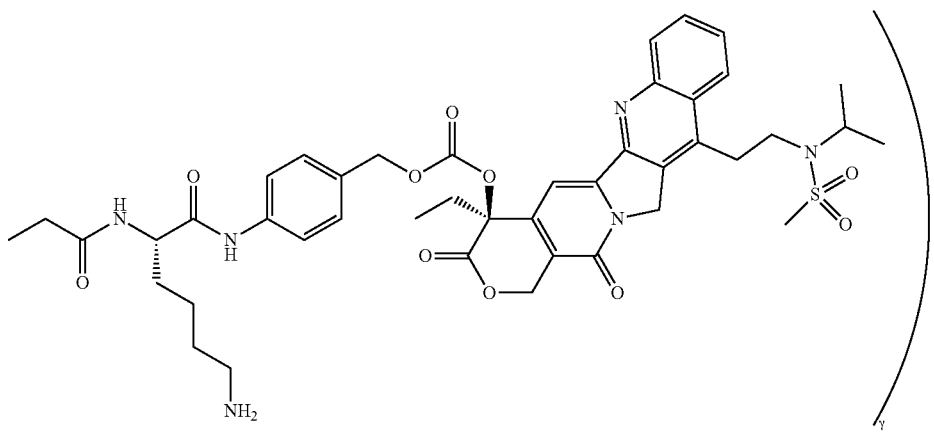

Example 37: Preparation of BT001034

A method similar to that described in example 27 was adopted to obtain the coupling product of TL033 with antibody M2, which was named as BT001034, except that TL003 was replaced by trifluoroacetate of TL033 and Sacituzumab was replaced by antibody M2.

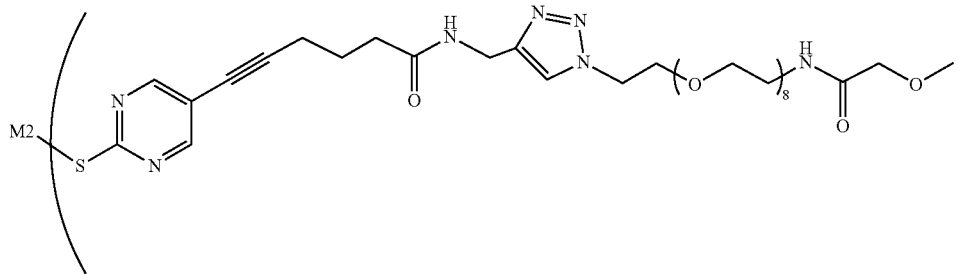

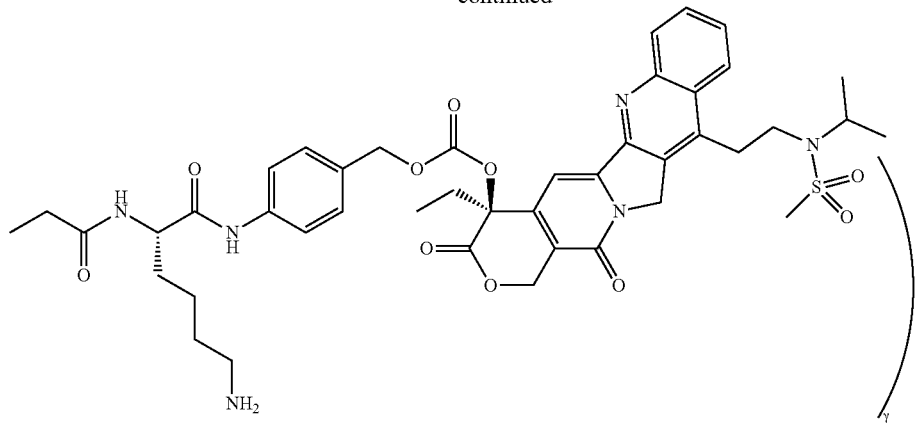

Example 38: Preparation of BT001035

0.3 mL of antibody M3 (anti-Trop-2, 33.5 mg/mL) was diluted with 0.25 ml of a solution (pH 7.6) containing 20 mM PB, 150 mM NaCl and 20 mM sodium edetate, then 0.45 mL of a solution (pH 7.6) containing 20 mM PB and 150 mM NaCl was added and evenly mixed. The mixture was adjusted with 1M $Na_2HPO_4$ solution to pH=7.4, then 10 mM TCEP (tris(2-carboxyethyl)phosphine) solution was added and evenly mixed, which was allowed to stand at room temperature for 30 min. To the solution system, trifluoroacetate of TL033 dissolved in dimethyl sulfoxide was added in an amount of 10 equiv. and evenly mixed. The resulting mixture was allowed to stand at room temperature for 2 hours. Then 6.1 μl of 100 mM cysteine was added to terminate the reaction. At last, the buffer was replaced with a PBS buffer solution of pH 6.5 by G-25 gel column to obtain a coupling product of TL033 with antibody M3, which was named as BT001035.

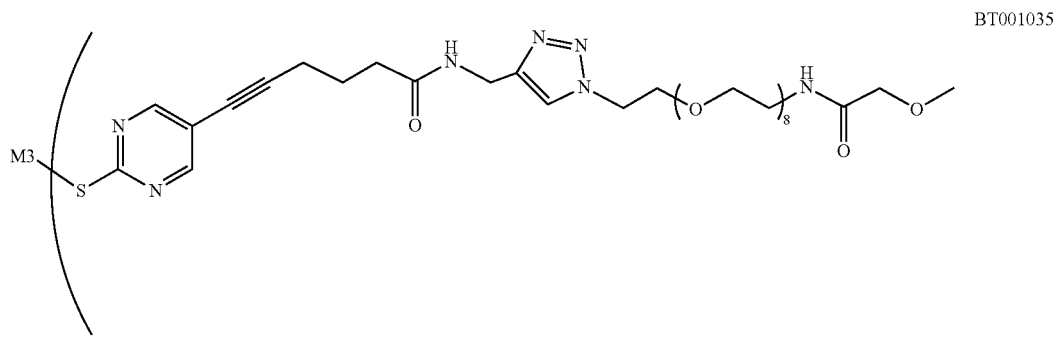

BT001035

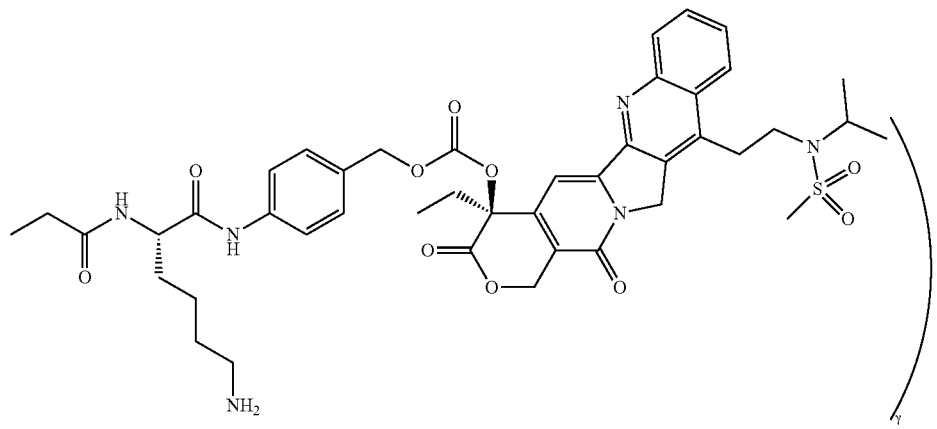

Example 39: Preparation of BT001036

A method similar to that described in example 27 was adopted to obtain the coupling product of TL033 with Trastuzumab, which was named as BT001036, except that TL003 was replaced by trifluoroacetate of TL033 and Sacituzumab was replaced by Trastuzumab.

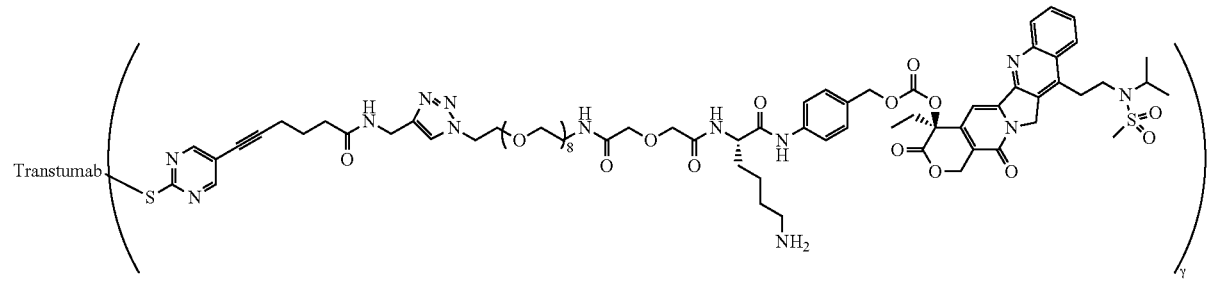

Example 40: Preparation of BT001040

A method similar to that described in example 27 was adopted to obtain the coupling product of TL049 with Sacituzumab, which was named as BT001040, except that TL003 was replaced by trifluoroacetate of TL049.

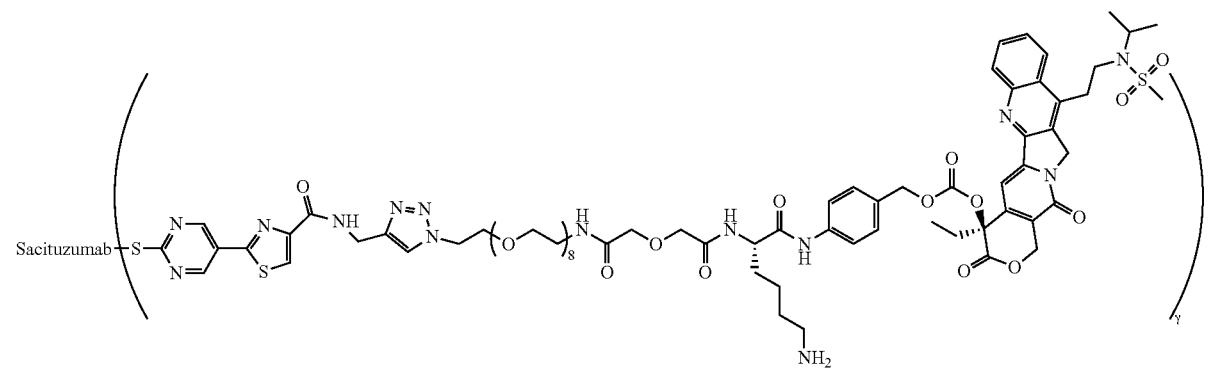

Example 41: Preparation of BT001041

A method similar to that described in example 27 was adopted to obtain the coupling product of TL050 with Sacituzumab, which was named as BT001041, except that TL003 was replaced by trifluoroacetate of TL050.

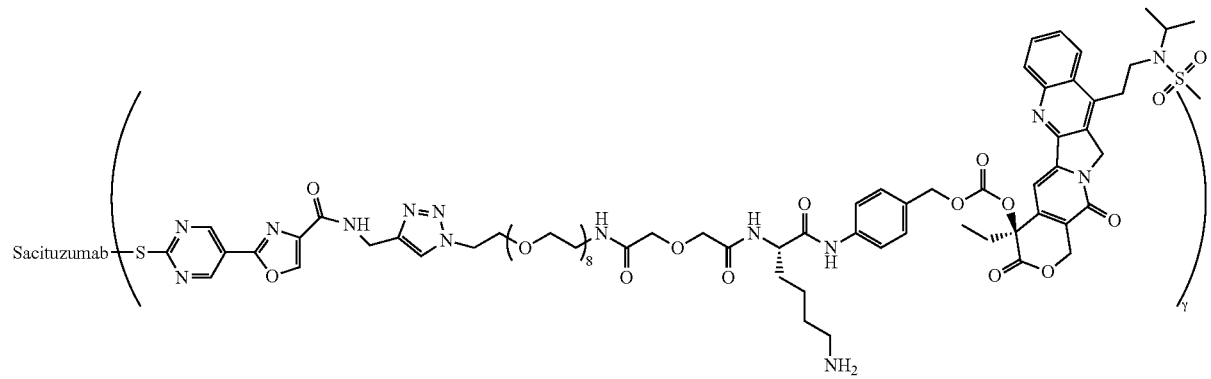

Example 42: Preparation of BT001042

A method similar to that described in example 27 was adopted to obtain the coupling product of TL051 with Sacituzumab, which was named as BT001042, except that TL003 was replaced by TL051.

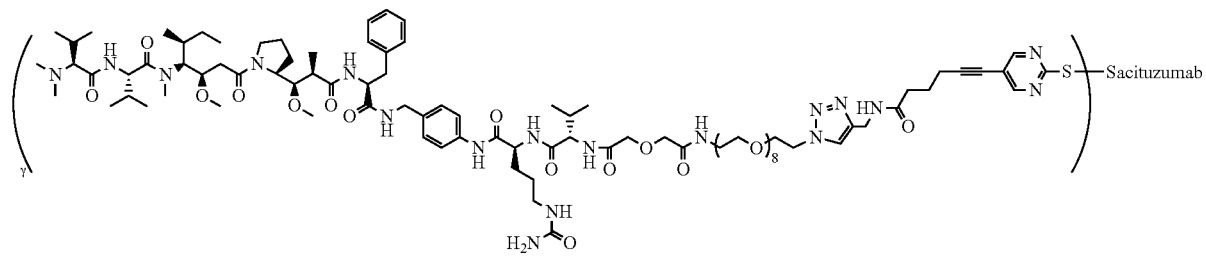
BT001042

Example 43: Preparation of BT001043

A method similar to that described in example 27 was adopted to obtain the coupling product of TL052 with Sacituzumab, which was named as BT001043, except that TL003 was replaced by TL052.

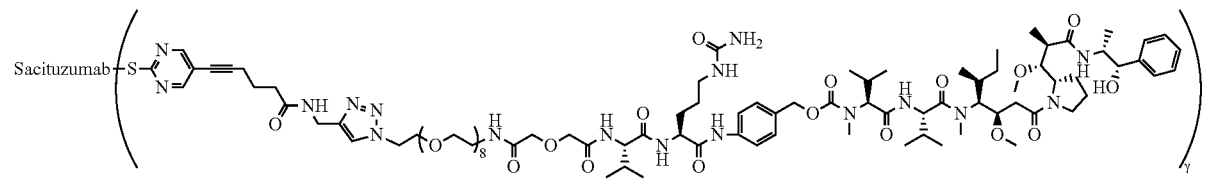
BT001043

Example 44: Preparation of BT001044

A method similar to that described in example 27 was adopted to obtain the coupling product of TL053 with Sacituzumab, which was named as BT001044, except that TL003 was replaced by TL053.

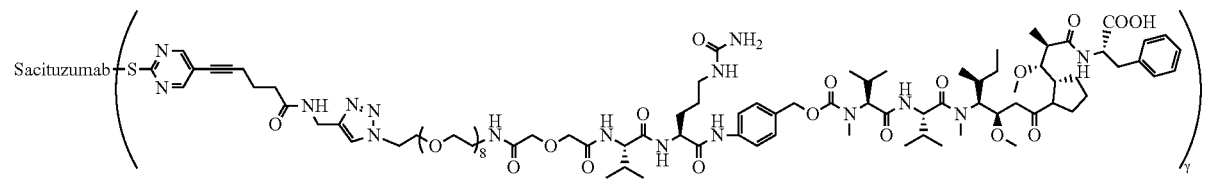
BT001044

Example 45: Preparation of BT001045

A method similar to that described in example 27 was adopted to obtain the coupling product of TL054 with Sacituzumab, which was named as BT001045, except that TL003 was replaced by trifluoroacetate of TL054.

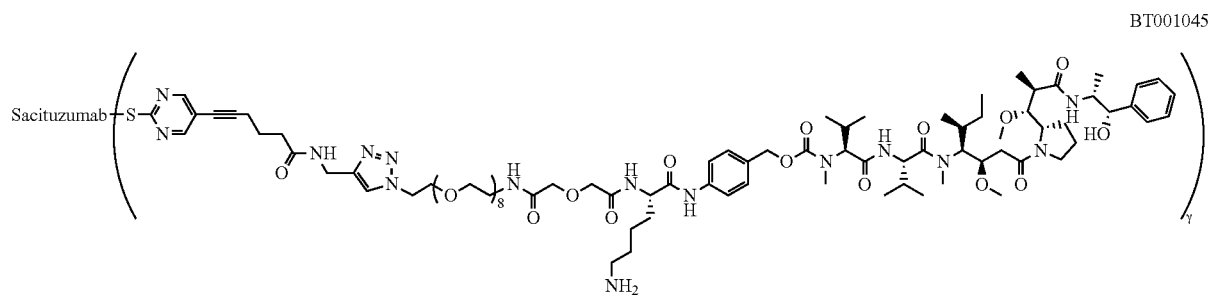

Example 46: Preparation of BT001046

A method similar to that described in example 27 was adopted to obtain the coupling product of TL055 with Sacituzumab, which was named as BT001046, except that TL003 was replaced by trifluoroacetate of TL055.

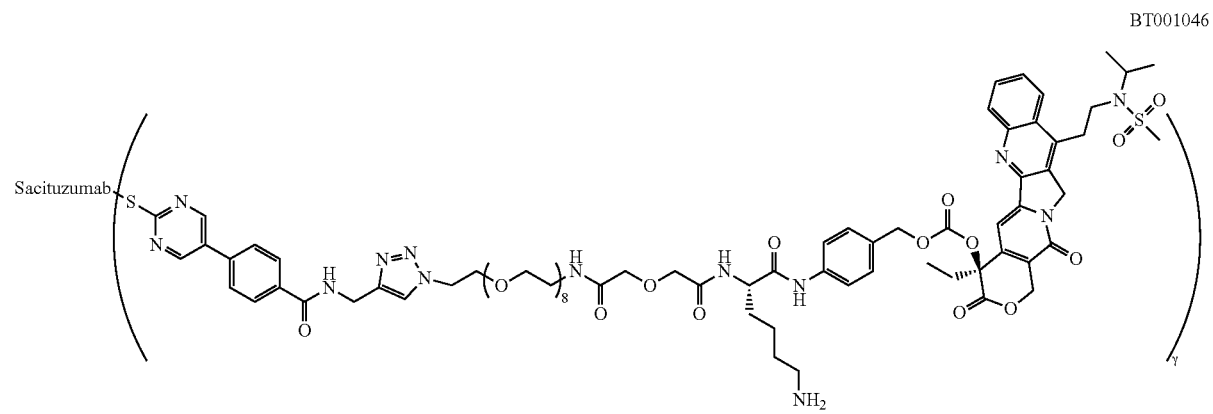

Example 47: Preparation of BT001047

A method similar to that described in example 27 was adopted to obtain the coupling product of TL056 with Sacituzumab, which was named as BT001047, except that TL003 was replaced by TL056.

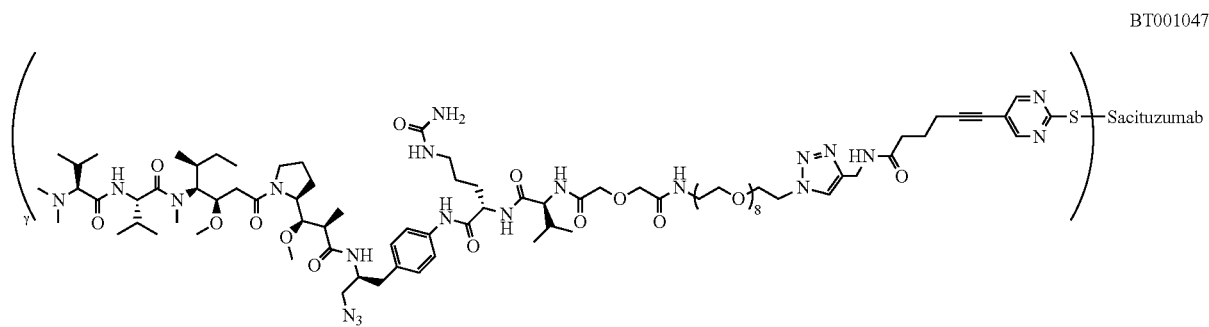

Example 48: Determination of Molecular Weight of BT001002 by LC-MS

The molecular weight of BT001002 obtained by coupling was analyzed by LC-MS.
LC conditions:
Liquid chromatographic column: ACQUITU UPLC® Protein BEH C4 1.7 µm, 2.1 mm×100 mm;
Mobile phase A: 0.1% FA/98% $H_2O$/2% ACN; Mobile phase B: 0.1% FA/2% $H_2O$/98% ACN;
Flow rate: 0.25 mL/min; Sample room temperature: 8° C.; Column temperature: 60° C.; Sample size: 1 µg;

| Time (min.) | 1 | 7 | 8 | 9 | 13 |
|---|---|---|---|---|---|
| Mobile phase A (% volume) | 90 | 20 | 20 | 90 | 90 |
| Mobile phase B (% volume) | 10 | 80 | 80 | 10 | 10 |

MS conditions:
Mass spectrometer model: Triple TOF 5600+;
GS1 60; GS2 60; CUR30; TEM600; ISVF5000; DP300; CE10 m/z600-5000;
Results were shown in FIG. 1-3.
Theoretical molecular weight and measured molecular weight of BT001002

| Peptide chain | | mAb | DAR1 | DAR2 | DAR3 | DAR4 |
|---|---|---|---|---|---|---|
| LC | Theoretical value | 23334.0 | 24610.7 | 25887.3 | 27163.9 | 28440.5 |
| | Measured value | Not detected | 24611.1 | Not detected | Not detected | Not detected |
| HC | Theoretical value | 50734.0 | 52010.6 | 53287.2 | 54563.8 | 55840.4 |
| | Measured value | Not detected | Not detected | Not detected | 54563.1 | Not detected |

In the table, mAb stands for a monoclonal antibody; LC stands for the light chain of an antibody; HC stands for the heavy chain of an antibody; DAR1 stands for a conjugate containing a light chain/heavy chain of an antibody and a bioactive molecule; DAR2 stands for a conjugate containing a light chain/heavy chain of an antibody and two bioactive molecules; DAR3 stands for a conjugate containing a light chain/heavy chain of an antibody and three bioactive molecules; DAR4 stands for a conjugate containing a light chain/heavy chain of an antibody and four bioactive molecules; glycoform stands for the structure of glycan of the two heavy chains: GOF stands for fucosylation and free of galactosylation. The mAb, LC, HC, DAR1, DAR2, DAR3, DAR4, and GOF hereinafter are as described above.

Figure 2:
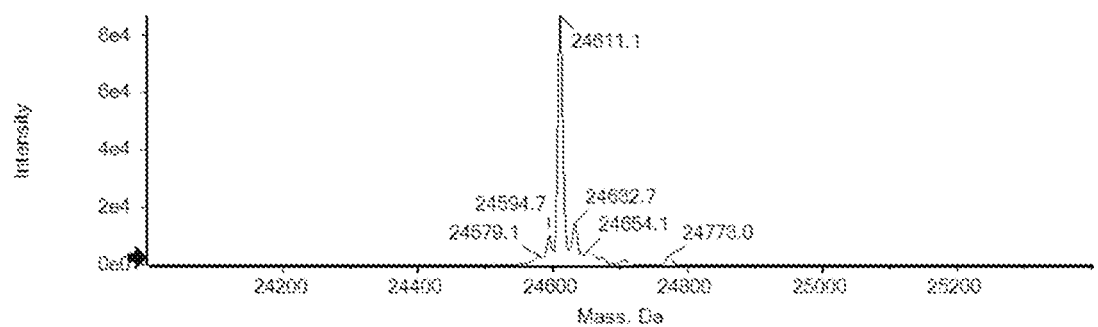
FIG. 2 shows a deconvolution diagram of a coupled light chain of BT001002.
Figure 3:
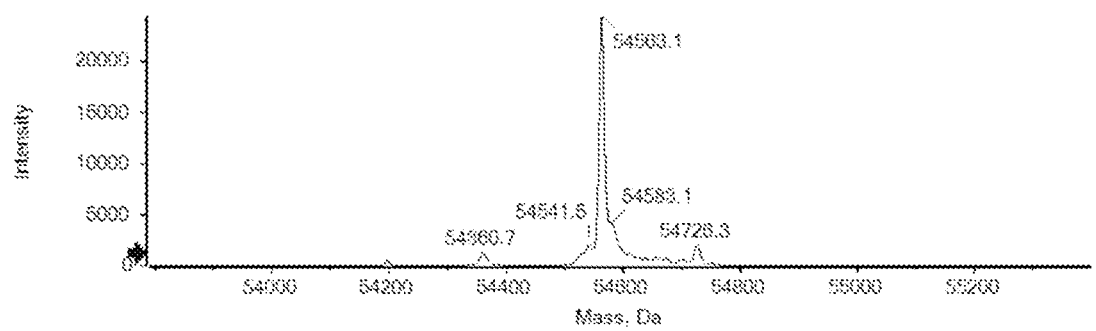
FIG. 3 shows a deconvolution diagram of a coupled heavy chain of BT001002.

As can be seen from FIGS. 1-3, both the molecular weights of the light chain and the heavy chain of the antibody are changed after being coupled with TL003, wherein the light chain was coupled with 1 bioactive molecule and the heavy chain was coupled with 3 bioactive molecules. Therefore, it could be inferred that the DAR of the antibody to the bioactive molecule was 8.

Example 49: Determination of Molecular Weight of BT001004 by LC-MS

The molecular weight of BT001004 obtained from coupling was analyzed by LC-MS.

LC conditions:
Liquid chromatographic column: ACQUITU UPLC® Protein BEH C18 1.7 µm, 2.1 mm×100 mm;
Mobile phase A: 0.1% FA/98% $H_2O$/2% ACN; Mobile phase B: 0.1% FA/2% $H_2O$/98% ACN;
Flow rate: 0.25 mL/min; Sample room temperature: 8° C.; Column temperature: 60° C.; Sample size: 1 µg;

| Time (min.) | 2 | 20 | 22 | 25 | 26 | 30 |
|---|---|---|---|---|---|---|
| Mobile phase A (% volume) | 80 | 60 | 10 | 10 | 80 | 80 |
| Mobile phase B (% volume) | 20 | 40 | 90 | 90 | 20 | 20 |

MS conditions:
Mass spectrometer model: Triple TOF 5600+;
GS1 60; GS2 60; CUR30; TEM 350; ISVF5500; DP300; CE10; m/z 600-5000;
Results were shown in FIG. 4-6.
Theoretical molecular weight and measured molecular weight of BT001004

| Peptide chain | | mAb | DAR1 | DAR2 | DAR3 | DAR4 |
|---|---|---|---|---|---|---|
| LC | Theoretical value | 23334.04 | 24832.7 | 26331.4 | 27830.0 | 29328.7 |
| | Measured value | 23334.9 | 24833.7 | Not detected | Not detected | Not detected |
| HC | Theoretical value | 50734.0 | 52232.6 | 53731.3 | 55230.0 | 56728.6 |
| | Measured value | Not detected | 52232.1 | 53730.8 | 55229.3 | Not detected |

LC stands for the light chain of an antibody; and HC stands for the heavy chain of an antibody.

Figure 4:
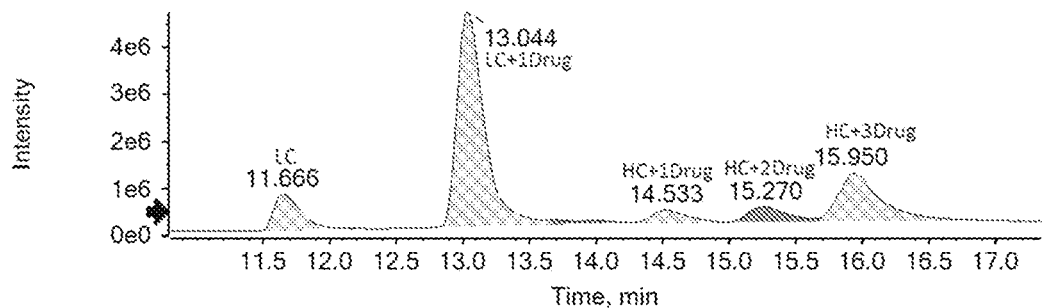
FIG. 4 shows a TIC (total ion chromatogram) of BT001004.
Figure 5:
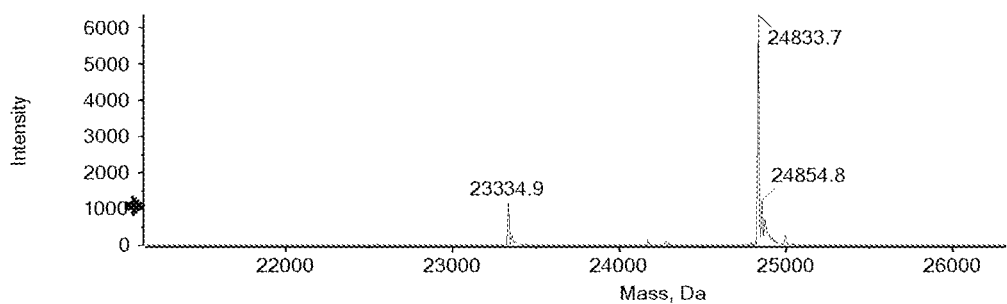
FIG. 5 shows a deconvolution diagram of a coupled light chain of BT001004.
Figure 6:
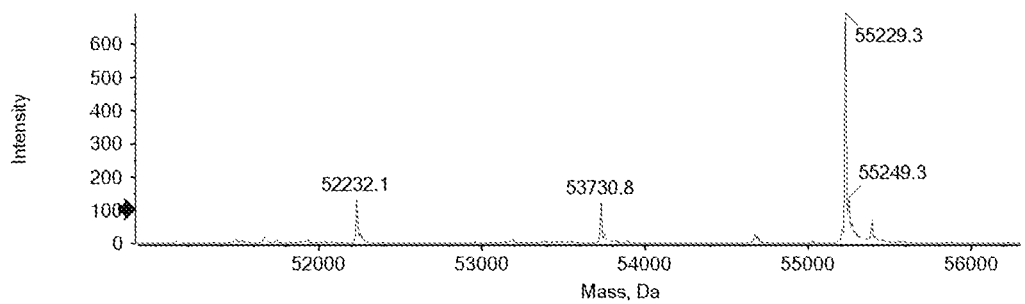
FIG. 6 shows a deconvolution diagram of a coupled heavy chain of BT001004.

As can be seen from FIGS. 4-6, in BT001004, the light chain of the antibody was coupled with 0-1 bioactive molecule (LC and DAR1 accounted for 14% and 86%, respectively), and the heavy chain was coupled with 1-3 bioactive molecules (DAR1, DAR2 and DAR3 accounted for 13%, 19% and 68%, respectively). Therefore, it could be calculated that the DAR of the antibody to the bioactive molecule was 7.0.

Example 50: Determination of Molecular Weight of BT001012 by LC-MS

Figure 10:
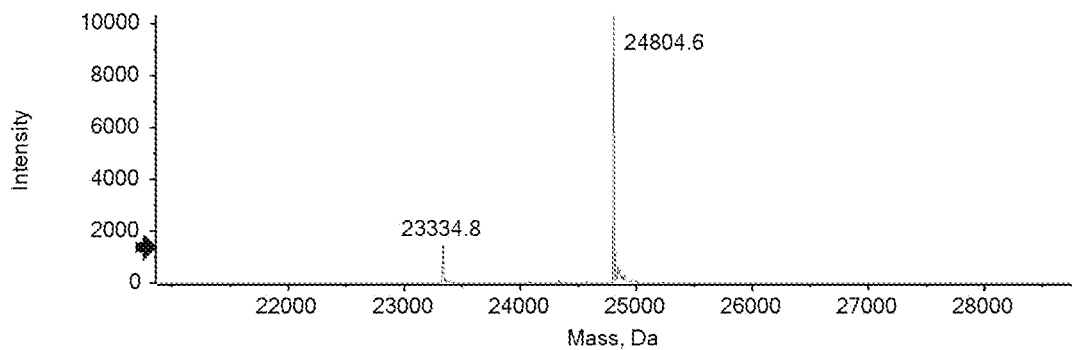
FIG. 10 shows a deconvolution diagram of a coupled light chain of BT001012.
Figure 11:
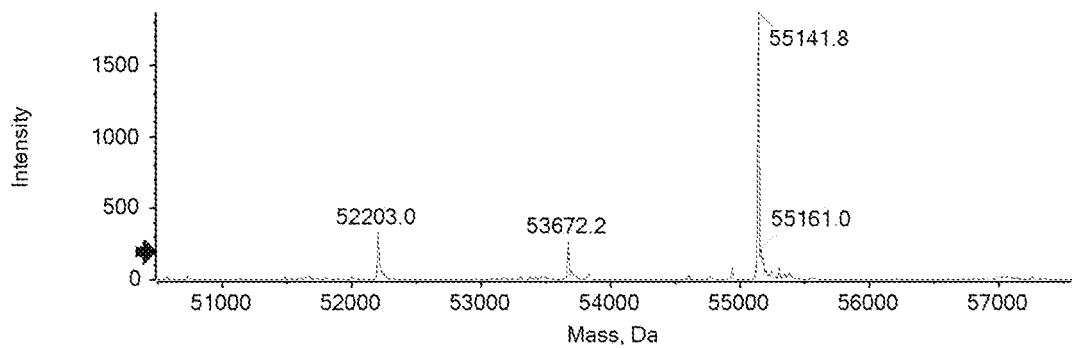
FIG. 11 shows a deconvolution diagram of a coupled heavy chain of BT001012.

A method similar to that as described in example 48 was adopted, and results were shown in FIGS. 10 and 11.

The theoretical molecular weight and measured molecular weight of the light chain and heavy chain of BT001012 obtained by coupling TL024 and the antibody (calculated from main glycoform GOF) were shown in the table below:

| Peptide chain | | mAb | DAR1 | DAR2 | DAR3 | DAR4 |
|---|---|---|---|---|---|---|
| LC | Theoretical value | 23334.04 | 24803.7 | 26273.4 | 27743.0 | 29212.7 |
| | Measured value | 23334.8 | 24804.6 | Not detected | Not detected | Not detected |
| HC | Theoretical value | 50734.0 | 52203.6 | 53673.3 | 55143.0 | 56612.6 |
| | Measured value | Not detected | 52203.0 | 53672.2 | 55141.8 | Not detected |

As can be seen from FIGS. 10 and 11, in BT001012, the light chain of the antibody was coupled with 0-1 toxin (LC and DAR1 accounted for 12.9% and 87.1%, respectively), and the heavy chain was coupled with 1-3 toxins (DAR1, DAR2 and DAR3 accounted for 13.4%, 10.8% and 75.8%, respectively). Therefore, it could be calculated that the DAR of the antibody to toxins was 7.0.

Example 51: Determination of Molecular Weight of BT001013 by LC-MS

Figure 12:
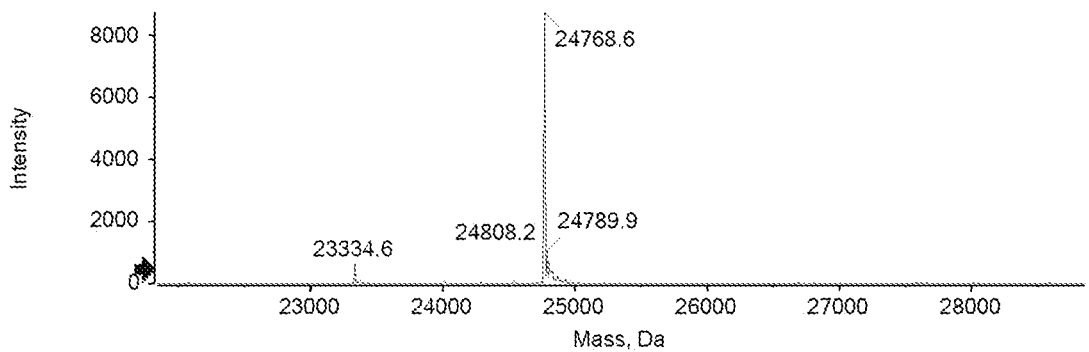
FIG. 12 shows a deconvolution diagram of a coupled light chain of BT001013.
Figure 13:
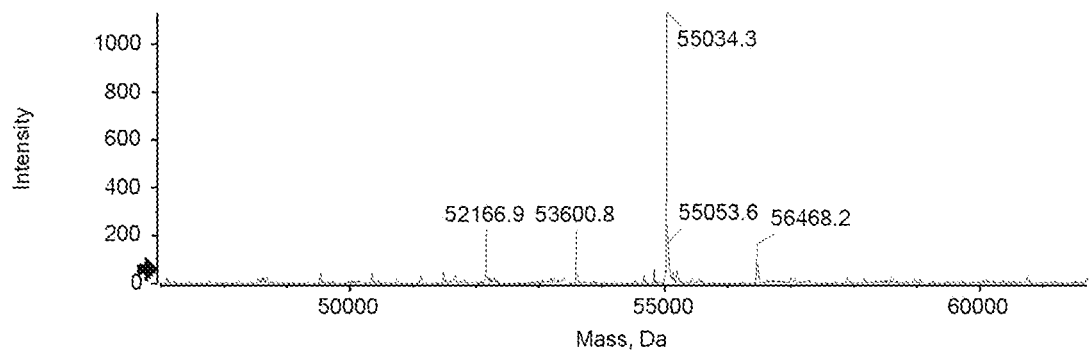
FIG. 13 shows a deconvolution diagram of a coupled heavy chain of BT001013.

A method similar to that as described in example 48 was adopted, and results were shown in FIGS. 12 and 13.

The theoretical molecular weight and measured molecular weight of the light chain and the heavy chain of BT001013 obtained from coupling TL048 and the antibody (calculated based on main glycoform GOF) were shown in the table below:

| Peptide chain | | mAb | DAR1 | DAR2 | DAR3 | DAR4 |
|---|---|---|---|---|---|---|
| LC | Theoretical value | 23334.04 | 24767.7 | 26201.3 | 27634.9 | 29068.5 |
| | Measured value | 23334.6 | 24768.6 | Not detected | Not detected | Not detected |
| HC | Theoretical value | 50734.0 | 52167.6 | 53601.2 | 55034.8 | 56468.4 |
| | Measured value | Not detected | 52166.9 | 53600.8 | 55034.3 | 56468.2 |

As can be seen from FIGS. 12 and 13, in BT001013, the light chain of the antibody was coupled with 0-1 toxin (LC and DAR1 accounted for 6.8% and 93.2%, respectively), and the heavy chain was coupled with 1-4 toxins (DAR1, DAR2, DAR3 and DAR4 accounted for 12.8%, 12.8%, 64.9% and 9.5%, respectively). Therefore, it could be calculated that the DAR of the antibody to toxins was 7.3.

Example 52: Determination of Molecular Weight of BT001018 by LC-MS

Figure 14:
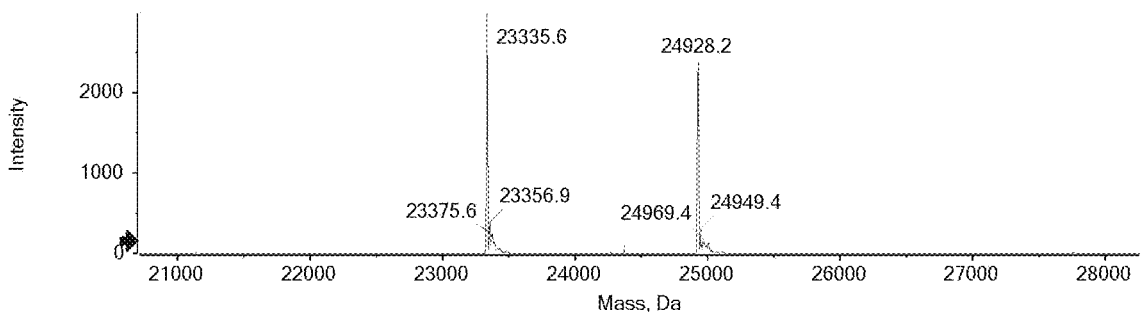
FIG. 14 shows a deconvolution diagram of a coupled light chain of BT001018.
Figure 15:
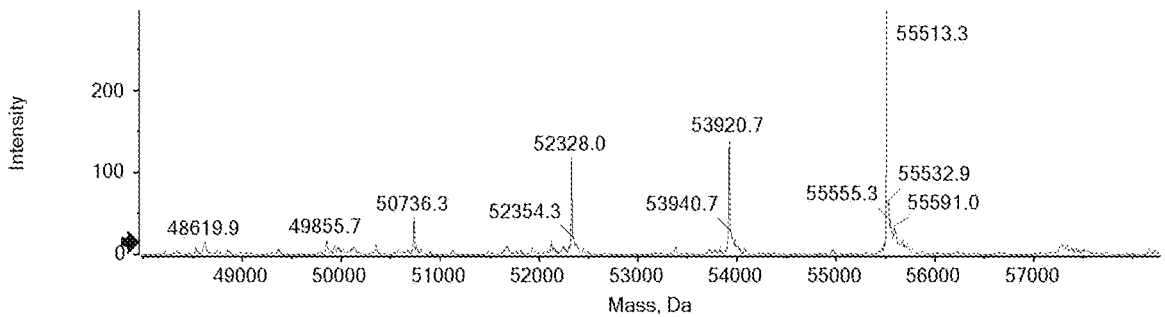
FIG. 15 shows a deconvolution diagram of a coupled heavy chain of BT001018.

A method similar to that as described in example 48 was adopted, and results were shown in FIGS. 14 and 15.

The theoretical molecular weight and measured molecular weight of the light chain and the heavy chain of BT001018 obtained from coupling TL030 and the antibody (calculated based on main glycoform GOF) were shown in the table below:

| Peptide chain | | mAb | DAR1 | DAR2 | DAR3 | DAR4 |
|---|---|---|---|---|---|---|
| LC | Theoretical value | 23334.04 | 24926.8 | 26519.6 | 28112.3 | 29705.1 |
| | Measured value | 23335.6 | 24928.2 | Not detected | Not detected | Not detected |
| HC | Theoretical value | 50734.0 | 52326.7 | 53919.5 | 55512.3 | 57105.0 |
| | Measured value | 50736.3 | 52328.0 | 53920.7 | 55513.3 | Not detected |

As can be seen from FIGS. 14 and 15, in BT001018, the light chain of the antibody was coupled with 0-1 toxin (LC and DAR1 accounted for 55.3% and 44.7%, respectively), and the heavy chain was coupled with 1-3 toxins (DAR1, DAR2 and DAR3 accounted for 19.6%, 23.3% and 49.6%, respectively). Therefore, it could be calculated that the DAR of the antibody to toxins was 5.2.

Example 53: Determination of Molecular Weight of BT001021 by LC-MS

The molecular weight of the coupled BT001021 was analyzed by LC-MS.

LC conditions:
Liquid chromatographic column: ACQUITU UPLC® Protein BEH C4 1.7 µm, 2.1 mm×100 mm;
Mobile phase A: 0.1% FA/98% $H_2O$/2% ACN; Mobile phase B: 0.1% FA/2% $H_2O$/98% ACN;
Flow rate: 0.25 mL/min; Sample room temperature: 8° C.; Column temperature: 60° C.; Sample size: 1 µg;

| Time (min.) | 1 | 7 | 8 | 9 | 13 |
|---|---|---|---|---|---|
| Mobile phase A (% volume) | 90 | 20 | 20 | 90 | 90 |
| Mobile phase B (% volume) | 10 | 80 | 80 | 10 | 10 |

MS conditions:
Mass spectrometer model: Triple TOF 5600+;
GS1 60; GS2 60; CUR30; TEM600; ISVF5000; DP300; CE10 m/z600-5000;
Results were shown in FIGS. 16 and 17.

The theoretical molecular weight and measured molecular weight of the light chain and the heavy chain of BT001021 obtained from coupling TL033 and the antibody (calculated based on main glycoform GOF) were shown in the table below:

| Peptide chain | | mAb | DAR1 | DAR2 | DAR3 | DAR4 |
|---|---|---|---|---|---|---|
| LC | Theoretical value | 23334.04 | 24884.8 | 26435.5 | 27986.3 | 29537.0 |
| | Measured value | 23334.6 | 24885.9 | Not detected | Not detected | Not detected |
| HC | Theoretical value | 50734.0 | 52284.7 | 53835.5 | 55386.2 | 56937.0 |
| | Measured value | Not detected | 52284.3 | 53834.5 | 55385.4 | Not detected |

Figure 16:
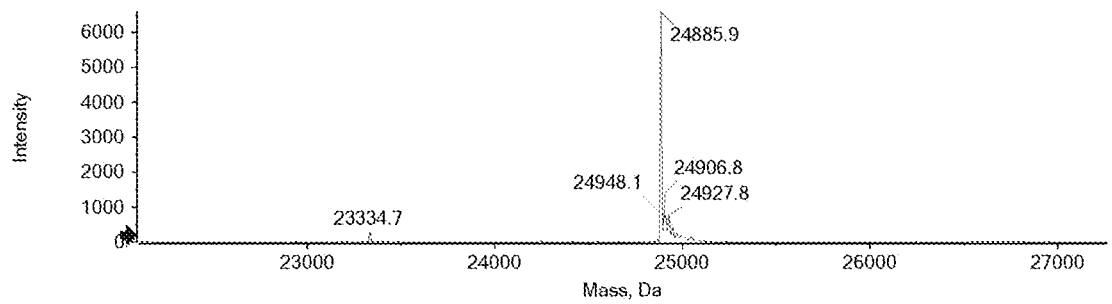
FIG. 16 shows a deconvolution diagram of a coupled light chain of BT001021.
Figure 17:
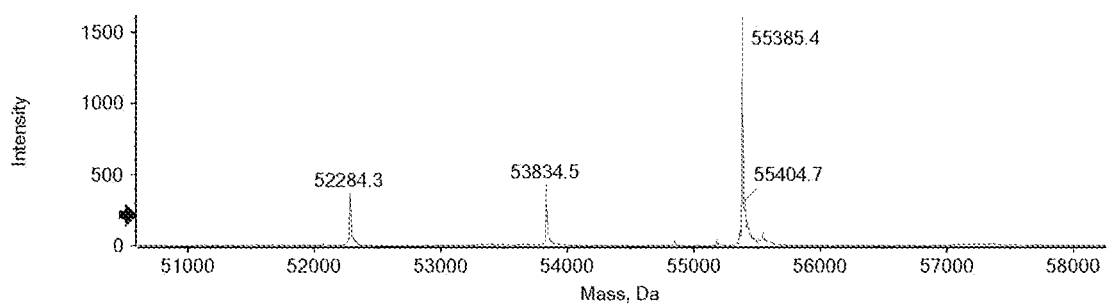
FIG. 17 shows a deconvolution diagram of a coupled heavy chain of BT001021.

As can be seen from FIGS. 16 and 17, in BT001021, the light chain of the antibody was coupled with 0-1 toxin (LC and DAR1 accounted for 4.5% and 95.5%, respectively), and the heavy chain was coupled with 1-3 toxins (DAR1, DAR2 and DAR3 accounted for 15.3%, 17.6% and 67.1%, respectively). Therefore, it could be calculated that the DAR of the antibody to toxins was 6.9.

Example 54: Determination of Molecular Weight of BT001023 by LC-MS

Figure 18:
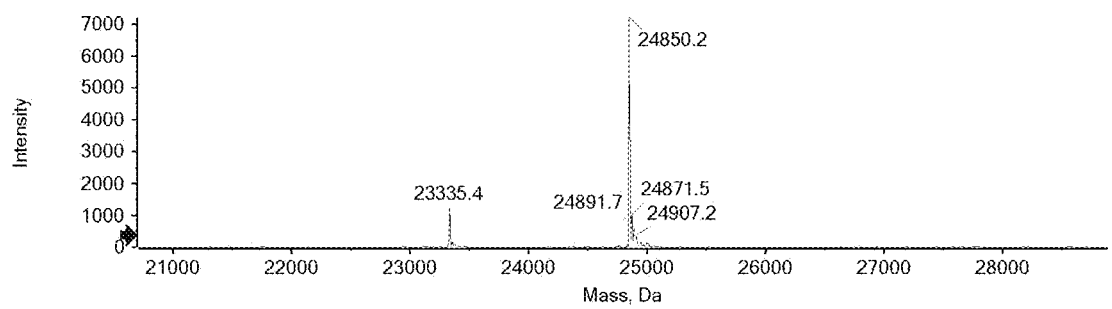
FIG. 18 shows a deconvolution diagram of a coupled light chain of BT001023.
Figure 19:
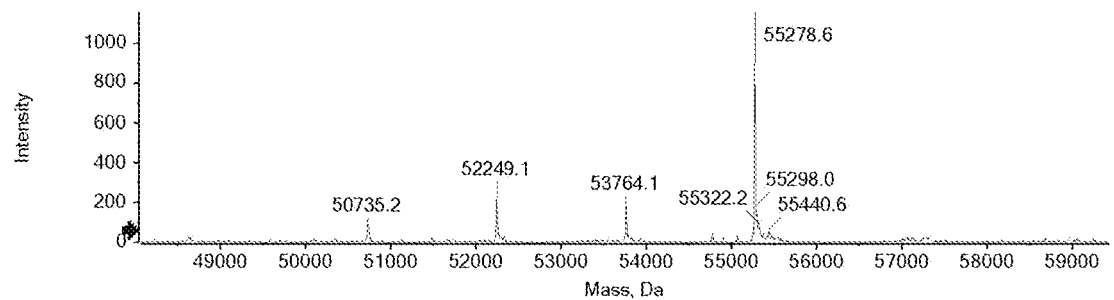
FIG. 19 shows a deconvolution diagram of a coupled heavy chain of BT001023.

A method similar to that as described in example 48 was adopted, and results were shown in FIGS. 18 and 19.

The theoretical molecular weight and measured molecular weight of the light chain and the heavy chain of BT001023 obtained by coupling TL035 and the antibody (calculated based on main glycoform GOF) were shown in the table below:

| Peptide chain | | mAb | DAR1 | DAR2 | DAR3 | DAR4 |
|---|---|---|---|---|---|---|
| LC | Theoretical value | 23334.04 | 24848.7 | 26363.4 | 27878.1 | 29392.7 |
| | Measured value | 23335.4 | 24850.2 | Not detected | Not detected | Not detected |
| HC | Theoretical value | 50733.98 | 52248.7 | 53763.3 | 55278.0 | 56792.7 |
| | Measured value | 50735.2 | 52249.1 | 53764.1 | 55278.6 | Not detected |

As can be seen from FIGS. 18 and 19, in BT001023, the light chain of the antibody was coupled with 0-1 toxin (LC and DAR1 accounted for 15% and 85%, respectively), and the heavy chain was coupled with 0-3 toxins (HC, DAR1, DAR2 and DAR3 accounted for 6.7%, 16.7%, 12.7% and 63.9%, respectively). Therefore, it could be calculated that the DAR of the antibody to toxins was 6.4.

Example 55: Determination of Molecular Weight of BT001040 by LC-MS

The molecular weight of BT001040 obtained by coupling was analyzed by LC-MS.
Liquid chromatographic column: Thermo MabPac™ RP 4 μm, 3.0 mm*100 mm
Mobile phase A: 0.1% FA/98% $H_2O$/2% ACN; Mobile phase B: 0.1% FA/2% $H_2O$/98% ACN
Flow rate: 0.25 mL/min; Sample room temperature: 8° C.; Column temperature: 60° C.; Sample size: 1 μg

| Time (min.) | 2 | 20 | 22 | 25 | 26 | 30 |
|---|---|---|---|---|---|---|
| Mobile phase A (% volume) | 80 | 60 | 10 | 10 | 80 | 80 |
| Mobile phase B (% volume) | 20 | 40 | 90 | 90 | 20 | 20 |

MS conditions:
Mass spectrometer model: Triple TOF 5600+
GS1 35; GS2 35; CUR30; TEM 350; ISVF5000; DP250; m/z 600-5000

The theoretical molecular weight and measured molecular weight of the light chain and the heavy chain of BT001040 obtained by coupling TL049 with the antibody (calculated based on main glycoform G0F) were shown in the table below:

| Peptide chain | | mAb | DAR1 | DAR2 | DAR3 | DAR4 |
|---|---|---|---|---|---|---|
| LC | Theoretical value | 23334.04 | 24901.8 | 26469.5 | 28037.3 | 29605.0 |
| | Measured value | 23334.2 | 24902.8 | Not detected | Not detected | Not detected |
| HC | Theoretical value | 50733.98 | 52301.7 | 53869.5 | 55437.2 | 57005.0 |
| | Measured value | Not detected | 52301.6 | 53869.2 | 55437.4 | 57005.3 |

Figure 20:
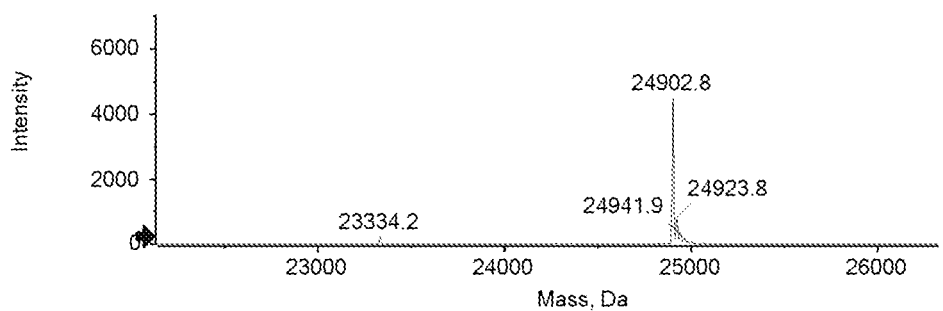
FIG. 20 shows a deconvolution diagram of a coupled light chain of BT001040.
Figure 21:
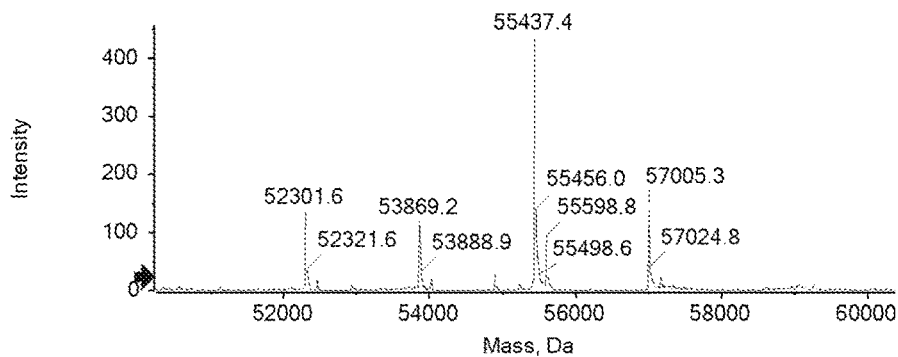
FIG. 21 shows a deconvolution diagram of a coupled heavy chain of BT001040.

As can be seen from FIGS. 20 and 21, in BT001040, the light chain of the antibody was coupled with 0-1 bioactive molecule (LC and DAR1 accounted for 4.9% and 95.1%, respectively), and the heavy chain was coupled with 1-4 bioactive molecules (DAR1, DAR2, DAR3 and DAR4 accounted for 16.5%, 14.3%, 52.6% and 16.6%, respectively). Therefore, it could be calculated that the DAR of the antibody to bioactive molecules was 7.3.

Example 56: Determination of Molecular Weight of BT001041 by LC-MS

Figure 22:
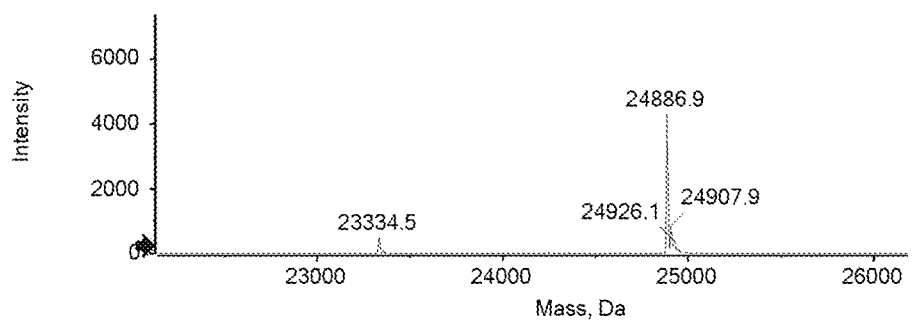
FIG. 22 shows a deconvolution diagram of a coupled light chain of BT001041.
Figure 23:
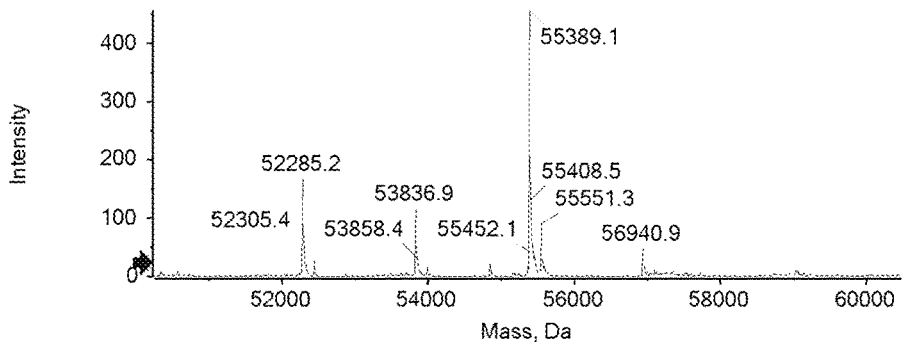
FIG. 23 shows a deconvolution diagram of a coupled heavy chain of BT001041.

A method similar to that as described in example 55 was adopted, and results were shown in FIGS. 22 and 23.
The theoretical molecular weight and measured molecular weight of the light chain and the heavy chain of BT001041 obtained by coupling TL050 with the antibody (calculated based on main glycoform G0F) were shown in the table below:

| Peptide chain | | mAb | DAR1 | DAR2 | DAR3 | DAR4 |
|---|---|---|---|---|---|---|
| LC | Theoretical value | 23334.04 | 24885.7 | 26437.4 | 27989.1 | 29540.8 |
| | Measured value | 23334.5 | 24886.9 | Not detected | Not detected | Not detected |
| HC | Theoretical value | 50733.98 | 52285.7 | 53837.3 | 55389.0 | 56940.7 |
| | Measured value | Not detected | 52285.2 | 53836.9 | 55389.1 | 56940.9 |

As can be seen from FIGS. 22 and 23, the light chain of the antibody in BT001041 was coupled with 0-1 bioactive molecule (LC and DAR1 accounted for 10.5% and 89.5%, respectively), and the heavy chain was coupled with 1-4 bioactive molecules (DAR1, DAR2, DAR3 and DAR4 accounted for 21.3%, 14.8%, 57.9% and 6.0%, respectively). Therefore, it could be calculated that the DAR of the antibody to bioactive molecules was 6.8.

Example 57: Determination of Molecular Weight of BT001042 by LC-MS

Figure 24:
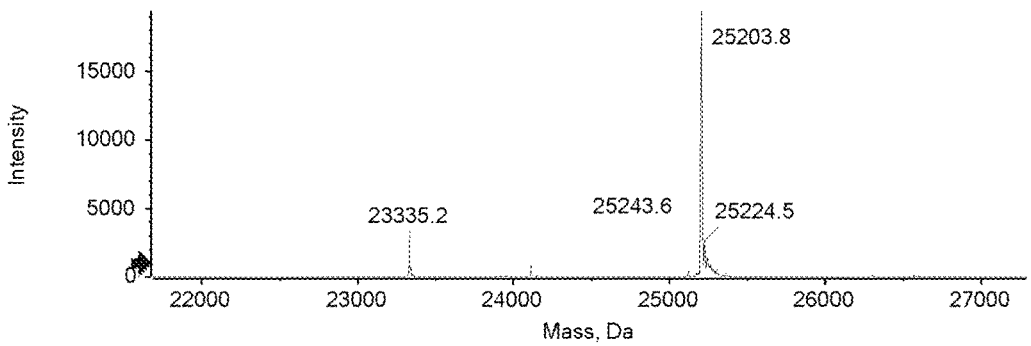
FIG. 24 shows a deconvolution diagram of a coupled light chain of BT001042.
Figure 25:
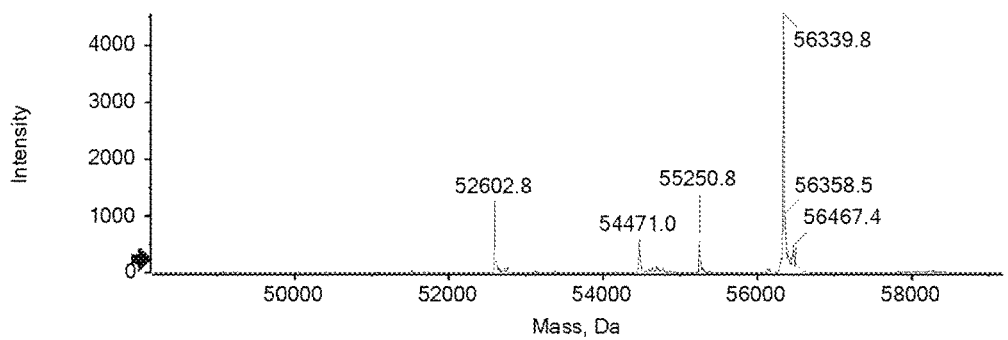
FIG. 25 shows a deconvolution diagram of a coupled heavy chain of BT001042.

A method similar to that as described in example 55 was adopted, and results were shown in FIGS. 24 and 25.
The theoretical molecular weight and measured molecular weight of the light chain and the heavy chain of BT001042 obtained by coupling TL051 with the antibody (calculated based on main glycoform G0F) were shown in the table below:

| Peptide chain | | mAb | DAR1 | DAR2 | DAR3 | DAR4 |
|---|---|---|---|---|---|---|
| LC | Theoretical value | 23334.04 | 25202.3 | 27070.6 | 28938.9 | 30807.2 |
| | Measured value | 23335.2 | 25203.8 | Not detected | Not detected | Not detected |
| HC | Theoretical value | 50733.98 | 52602.3 | 54470.6 | 56338.9 | 58207.2 |
| | Measured value | Not detected | 52602.8 | 54471.0 | 56339.8 | Not detected |

As can be seen from FIGS. 24 and 25, the light chain of the antibody in BT001042 was coupled with 0-1 bioactive molecule (LC and DAR1 accounted for 14.9% and 85.1%, respectively), and the heavy chain was coupled with 1-3 bioactive molecules (DAR1, DAR2 and DAR3 accounted for 19.7%, 9.4% and 70.9%, respectively). Therefore, it could be calculated that the DAR of the antibody to bioactive molecules was 6.7.

Example 58: Determination of Molecular Weight of BT001043 by LC-MS

Figure 26:
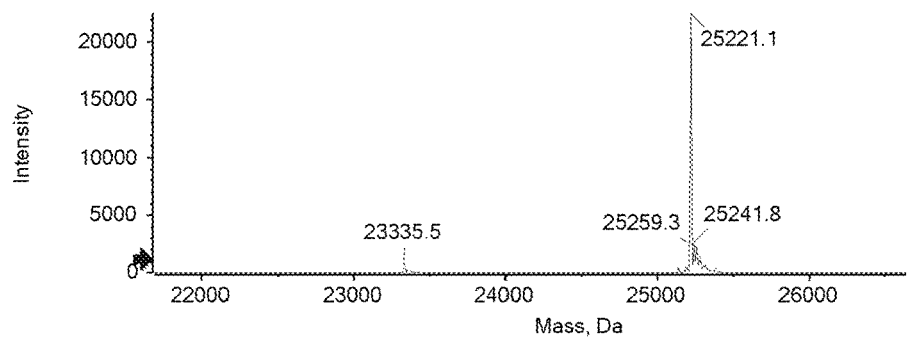
FIG. 26 shows a deconvolution diagram of a coupled light chain of BT001043.
Figure 27:
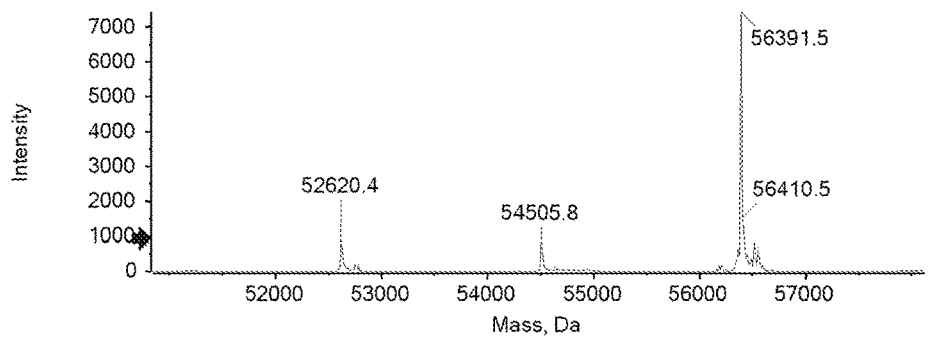
FIG. 27 shows a deconvolution diagram of a coupled heavy chain of BT001043.

A method similar to that as described in example 55 was adopted, and results were shown in FIGS. 26 and 27.
The theoretical molecular weight and measured molecular weight of the light chain and the heavy chain of BT001043 obtained by coupling TL052 with the antibody (calculated based on main glycoform G0F) were shown in the table below:

| Peptide chain | | mAb | DAR1 | DAR2 | DAR3 | DAR4 |
|---|---|---|---|---|---|---|
| LC | Theoretical value | 23334.04 | 25202.3 | 27100.6 | 28983.9 | 30867.2 |
| | Measured value | 23335.5 | 25221.1 | Not detected | Not detected | Not detected |

| Peptide chain | | mAb | DAR1 | DAR2 | DAR3 | DAR4 |
|---|---|---|---|---|---|---|
| HC | Theoretical value | 50733.98 | 52617.3 | 54500.6 | 56383.9 | 58267.2 |
| | Measured value | Not detected | 52620.4 | 54505.8 | 56391.5 | Not detected |

As can be seen from FIGS. 26 and 27, the light chain of the antibody in BT001043 was coupled with 0-1 bioactive molecule (LC and DAR1 accounted for 9.1% and 90.9%, respectively), and the heavy chain was coupled with 1-3 bioactive molecules (DAR1, DAR2 and DAR3 accounted for 20.1%, 11.4% and 68.4%, respectively). Therefore, it could be calculated that the DAR of the antibody to bioactive molecules was 6.8.

Example 59: Determination of Molecular Weight of BT001044 by LC-MS

Figure 28:
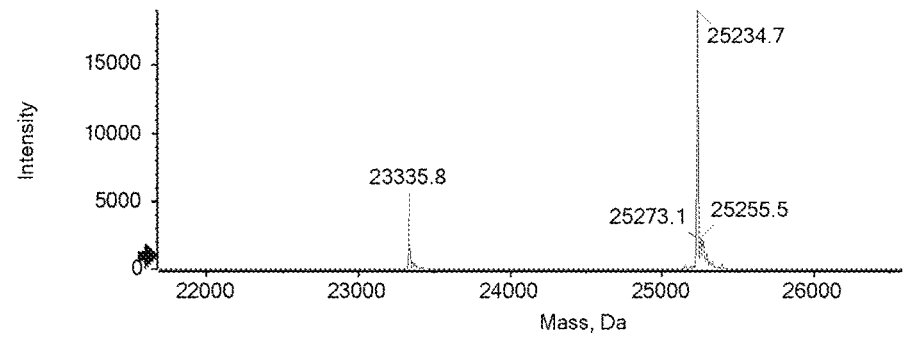
FIG. 28 shows a deconvolution diagram of a coupled light chain of BT001044.
Figure 29:
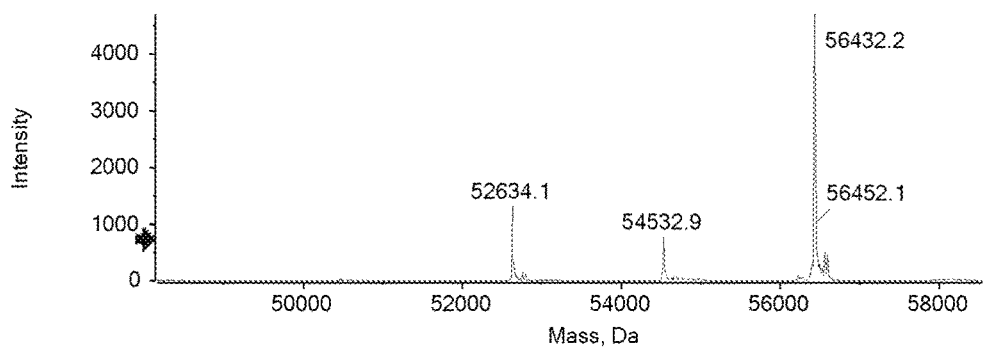
FIG. 29 shows a deconvolution diagram of a coupled heavy chain of BT001044.

A method similar to that as described in example 55 was adopted, and results were shown in FIGS. 28 and 29.

The theoretical molecular weight and measured molecular weight of the light chain and the heavy chain of BT001044 obtained by coupling TL053 with the antibody (calculated based on main glycoform GOF) were shown in the table below:

| Peptide chain | | mAb | DAR1 | DAR2 | DAR3 | DAR4 |
|---|---|---|---|---|---|---|
| LC | Theoretical value | 23334.04 | 25233.3 | 27132.5 | 29031.8 | 30931.1 |
| | Measured value | 23335.5 | 25234.7 | Not detected | Not detected | Not detected |
| HC | Theoretical value | 50733.98 | 52633.2 | 54532.5 | 56431.7 | 58331.0 |
| | Measured value | Not detected | 52634.1 | 54532.9 | 56432.1 | Not detected |

As can be seen from FIGS. 28 and 29, in BT001044, the light chain of the antibody was coupled with 0-1 bioactive molecule (LC and DAR1 accounted for 23.0% and 77.0%, respectively), and the heavy chain was coupled with 1-3 bioactive molecules (DAR1, DAR2 and DAR3 accounted for 19.4%, 11.4% and 69.3%, respectively). Therefore, it could be calculated that the DAR of the antibody to bioactive molecules was 6.5.

Example 60: Determination of Molecular Weight of BT001046 by LC-MS

Figure 30:
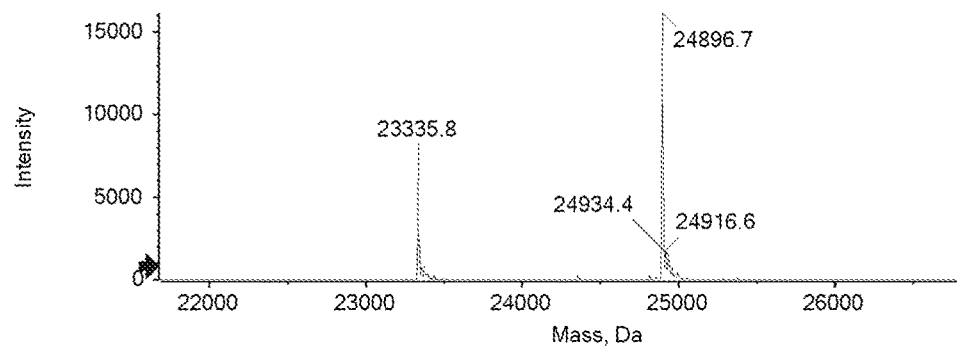
FIG. 30 shows a deconvolution diagram of a coupled light chain of BT001046.
Figure 31:
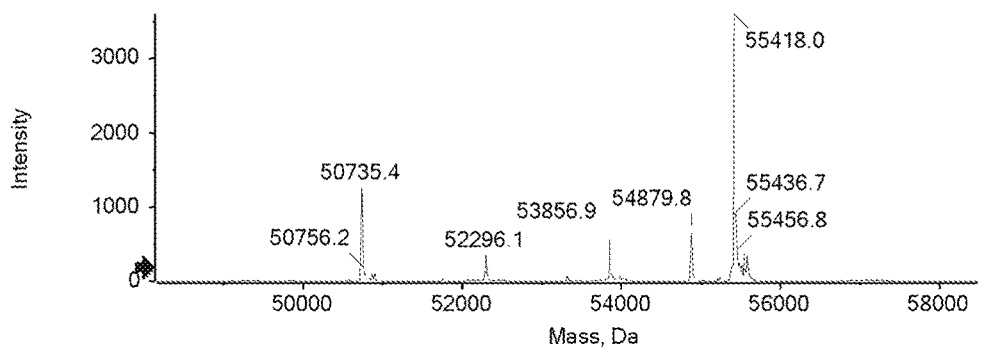
FIG. 31 shows a deconvolution diagram of a coupled heavy chain of BT001046.

A method similar to that as described in example 55 was adopted, and results were shown in FIGS. 30 and 31.

The theoretical molecular weight and measured molecular weight of the light chain and the heavy chain of BT001046 obtained by coupling TL055 with the antibody (calculated based on main glycoform GOF) were shown in the table below:

| Peptide chain | | mAb | DAR1 | DAR2 | DAR3 | DAR4 |
|---|---|---|---|---|---|---|
| LC | Theoretical value | 23334.04 | 24894.8 | 26455.5 | 28016.2 | 29577.0 |
| | Measured value | 23335.5 | 24896.7 | Not detected | Not detected | Not detected |
| HC | Theoretical value | 50733.98 | 52294.7 | 53855.4 | 55416.2 | 56976.9 |
| | Measured value | 50735.4 | 52296.1 | 53856.9 | 55418.0 | Not detected |

As can be seen from FIGS. 30 and 31, in BT001046, the light chain of the antibody was coupled with 0-1 bioactive molecule (LC and DAR1 accounted for 33.8% and 66.2%, respectively), and the heavy chain was coupled with 0-3 bioactive molecules (DAR0, DAR1, DAR2 and DAR3 accounted for 21.9%, 6.1%, 9.6% and 62.3%, respectively). Therefore, it could be calculated that the DAR of the antibody to bioactive molecules was 5.6.

Example 61: Determination of Molecular Weight of BT001047 by LC-MS

Figure 32:
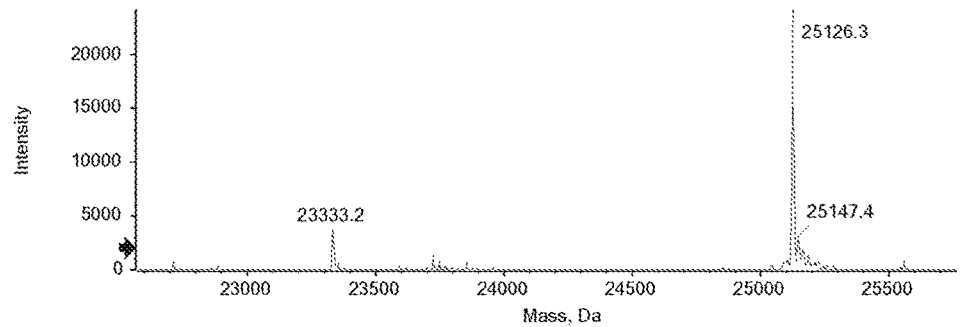
FIG. 32 shows a deconvolution diagram of a coupled light chain of BT001047.
Figure 33:
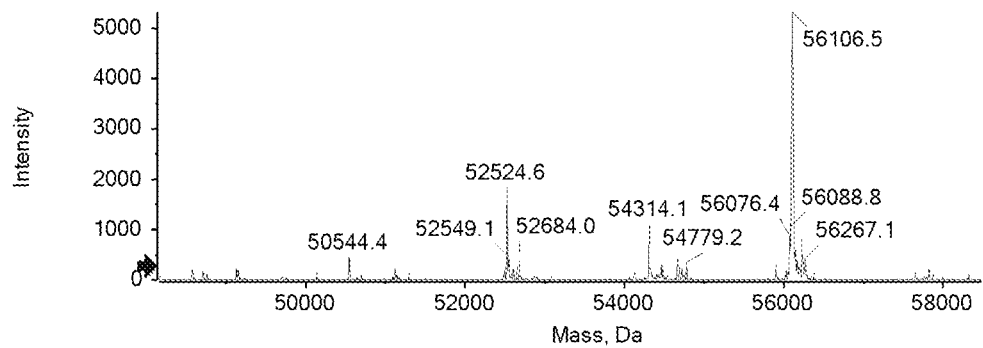
FIG. 33 shows a deconvolution diagram of a coupled heavy chain of BT001047.

A method similar to that as described in example 55 was adopted, and results were shown in FIGS. 32 and 33.

The theoretical molecular weight and measured molecular weight of the light chain and the heavy chain of BT001047 obtained by coupling TL056 with the antibody (calculated based on main glycoform GOF) were shown in the table below:

| Peptide chain | | mAb | DAR1 | DAR2 | DAR3 | DAR4 |
|---|---|---|---|---|---|---|
| LC | Theoretical value | 23334.04 | 25124.2 | 26914.4 | 28704.6 | 30494.8 |
| | Measured value | 23335.5 | 25126.3 | Not detected | Not detected | Not detected |
| HC | Theoretical value | 50733.98 | 52524.2 | 54314.3 | 56104.5 | 57894.7 |
| | Measured value | 50735.4 | 52524.6 | 54314.1 | 56106.5 | Not detected |

As can be seen from FIGS. 32 and 33, in BT001047, the light chain of the antibody was coupled with 0-1 bioactive molecule (LC and DAR1 accounted for 13.7% and 86.3%, respectively), and the heavy chain was coupled with 1-3 bioactive molecules (DAR1, DAR2 and DAR3 accounted for 22.2%, 13.5% and 64.3%, respectively). Therefore, it could be calculated that the DAR of the antibody to bioactive molecules was 6.6.

Example 62: Size Exclusion Chromatography Analysis

Figure 7:
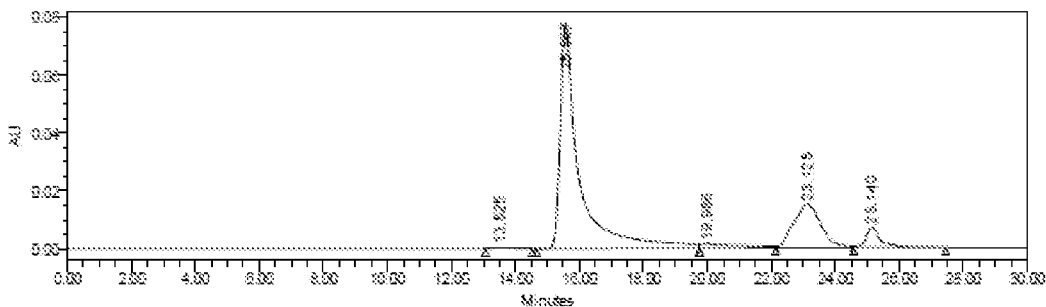
FIG. 7 shows a SEC chromatogram of BT001002.
Figure 8:
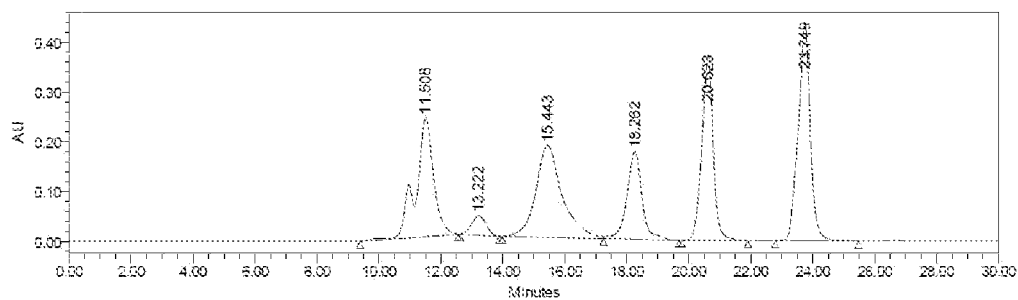
FIG. 8 shows a SEC chromatogram of molecular weight Marker of BT001002.

The coupling reaction was monitored by SEC-HPLC, and the conjugates were tested by SEC.
Chromatographic Conditions:
Liquid chromatographic column: TOSOH TSKgel SuperSW mAb, 4 μm, 7.8 mm×300 mm;
Mobile phase: 100 mmol/L $Na_2HPO_4$, 100 mmol/L NaCl, 5% isopropanol, pH7.0;
Flow rate: 0.5 ml/min; Detection wavelength: 280 nm; Column temperature: room temperature; Sample room temperature: 8° C.;
Sample size: 30 μg; Isocratic operation: 30 min.
The SEC chromatogram and molecular weight Marker SEC chromatogram of BT001002 obtained by coupling TL003 with the antibody were shown in FIGS. 7 and 8 respectively. According to the molecular weight Marker, it is confirmed that the molecular weight of the main peak of the coupling product is about 150 kD, i.e., for BT001002 obtained by coupling TL003 with the antibody, the light chain and the heavy chain are not dissociated, and the antibody still maintains its integral structure.

Figure 9:
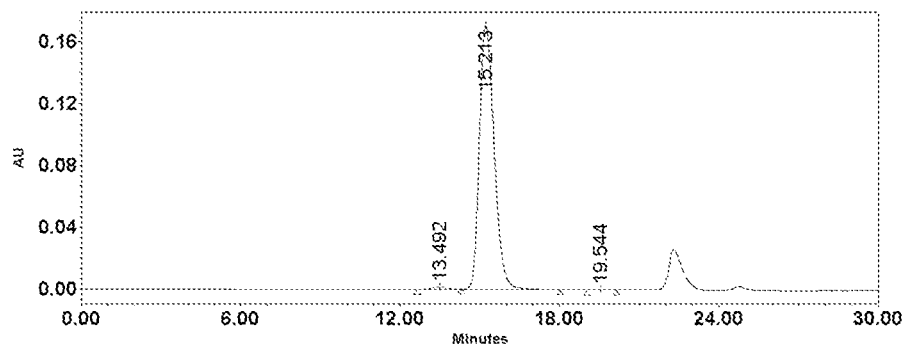
FIG. 9 shows a SEC chromatogram of BT001004.

The SEC chromatogram of BT001004 obtained by coupling TL019 with the antibody is shown in FIG. 9. According to the retention time and peak area ratio in the SEC, it is confirmed that the molecular weight of the main coupling product is about 150 kD, i.e., BT001004 obtained by coupling TL019 with the antibody still maintains the integral structure of the antibody.

Figure 34:
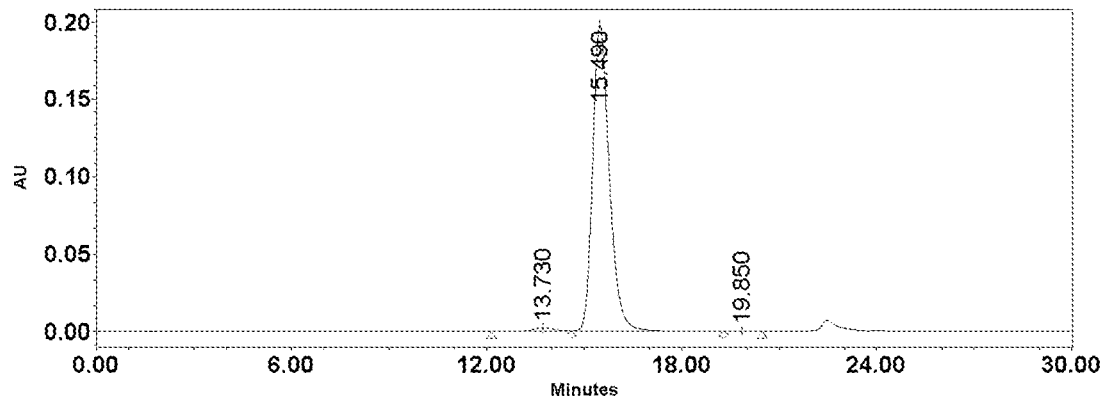
FIG. 34 shows a SEC chromatogram of BT001012.

The SEC chromatogram of BT001012 obtained by coupling TL024 with the antibody is shown in FIG. 34. According to the retention time and peak area ratio in the SEC, it is confirmed that the molecular weight of the main coupling product is about 150 kD, i.e., BT001012 obtained by coupling TL024 with the antibody still maintains the integral structure of the antibody.

Figure 35:
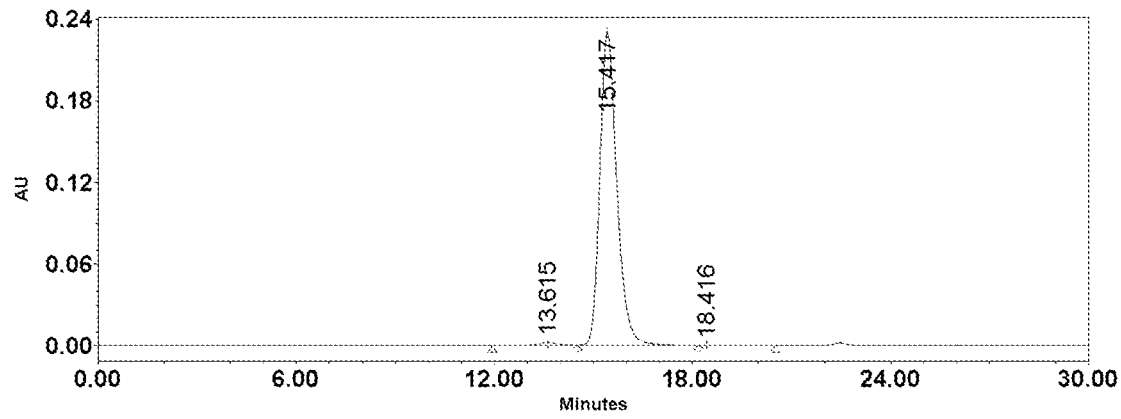
FIG. 35 shows a SEC chromatogram of BT001013.

The SEC chromatogram of BT001013 obtained by coupling TL048 with the antibody is shown in FIG. 35. According to the retention time and peak area ratio in the SEC, it is confirmed that the molecular weight of the main coupling product is about 150 kD, i.e., BT001013 obtained by coupling TL048 with the antibody still maintains an integral structure of the antibody.

Figure 36:
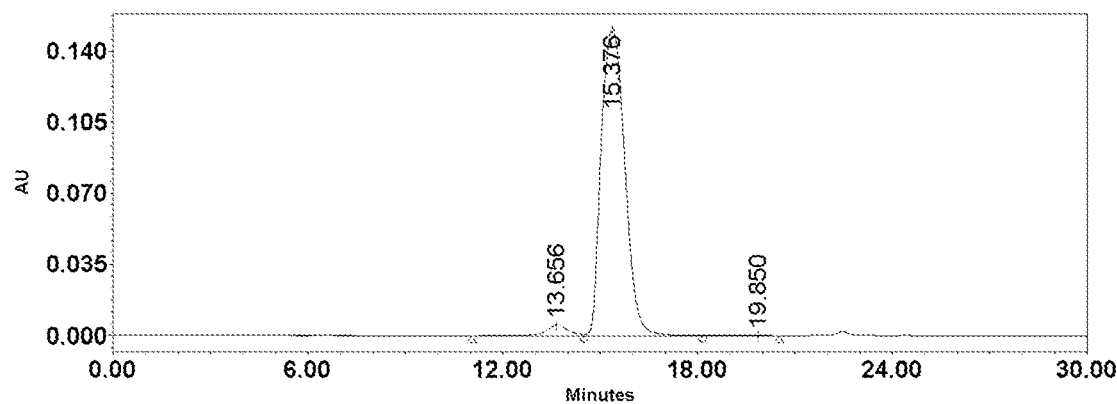
FIG. 36 shows a SEC chromatogram of BT001018.

The SEC chromatogram of BT001018 obtained by coupling TL030 with the antibody is shown in FIG. 36. According to the retention time and peak area ratio in the SEC, it is confirmed that the molecular weight of the main coupling product is about 150 kD, i.e., BT001018 obtained by coupling TL030 with the antibody still maintains an integral structure of the antibody.

Figure 37:
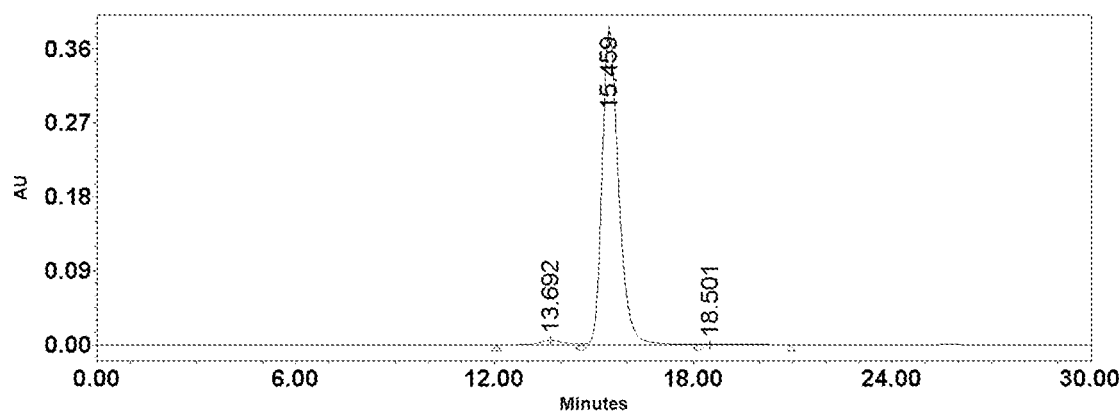
FIG. 37 shows a SEC chromatogram of BT001021.

The SEC chromatogram of BT001021 obtained by coupling TL033 with the antibody is shown in FIG. 37. According to the retention time and peak area ratio in the SEC, it is confirmed that the molecular weight of the main coupling product is about 150 kD, i.e., BT001021 obtained by coupling TL033 with the antibody still maintains an integral structure of the antibody.

Figure 38:
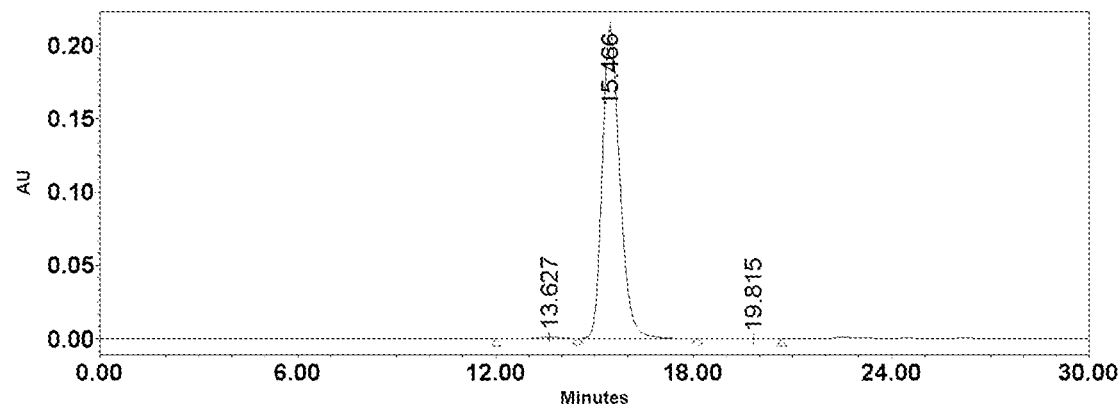
FIG. 38 shows a SEC chromatogram of BT001023.

The SEC chromatogram of BT001023 obtained by coupling TL035 with the antibody is shown in FIG. 38. According to the retention time and peak area ratio in the SEC, it is confirmed that the molecular weight of the main coupling product is about 150 kD, i.e., BT001023 obtained by coupling TL035 with the antibody still maintains an integral structure of the antibody.

Figure 39:
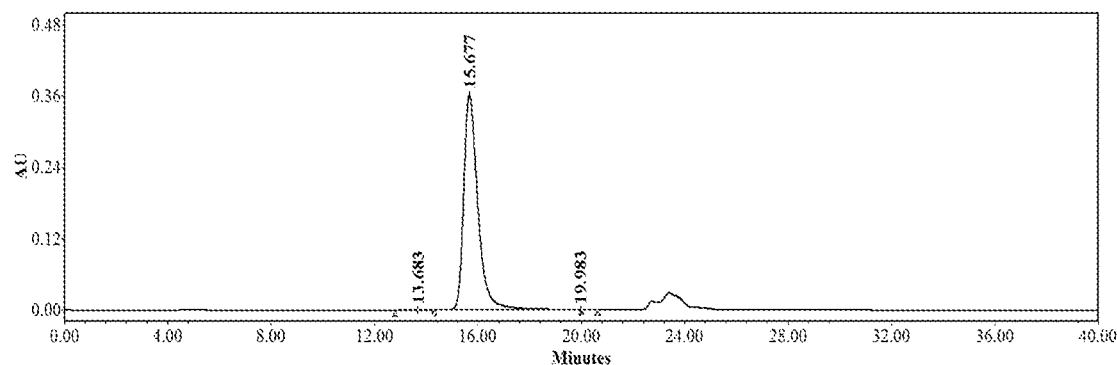
FIG. 39 shows a SEC chromatogram of BT001042.

The SEC chromatogram of BT001042 obtained by coupling TL051 with an antibody is shown in FIG. 39. According to the retention time and peak area ratio in the SEC, it is confirmed that the molecular weight of the main coupling product is about 150 kD, i.e., BT001042 obtained by coupling TL051 with the antibody still maintains the integral structure of the antibody.

Figure 40:
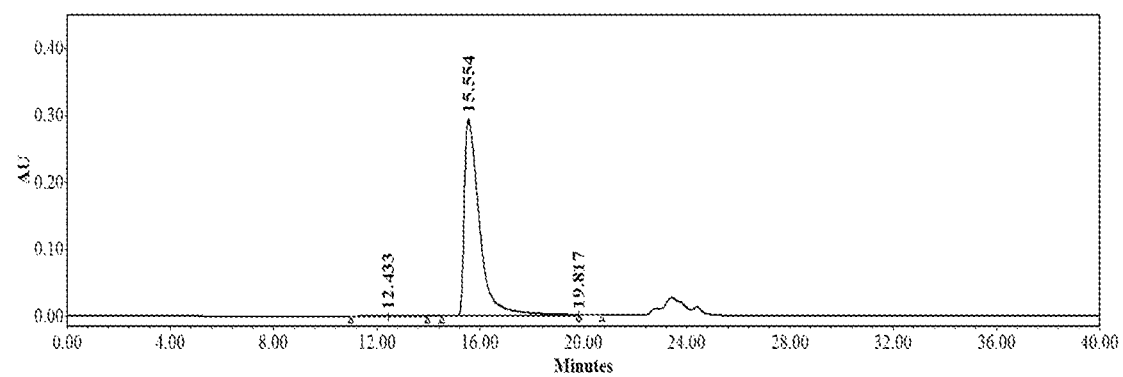
FIG. 40 shows a SEC chromatogram of BT001043.

The SEC chromatogram of BT001043 obtained by coupling TL052 with the antibody is shown in FIG. 40. According to the retention time and peak area ratio in the SEC, it is confirmed that the molecular weight of the main coupling product is about 150 kD, i.e., BT001043 obtained by coupling TL052 with the antibody still maintains the integral structure of the antibody.

Figure 41:
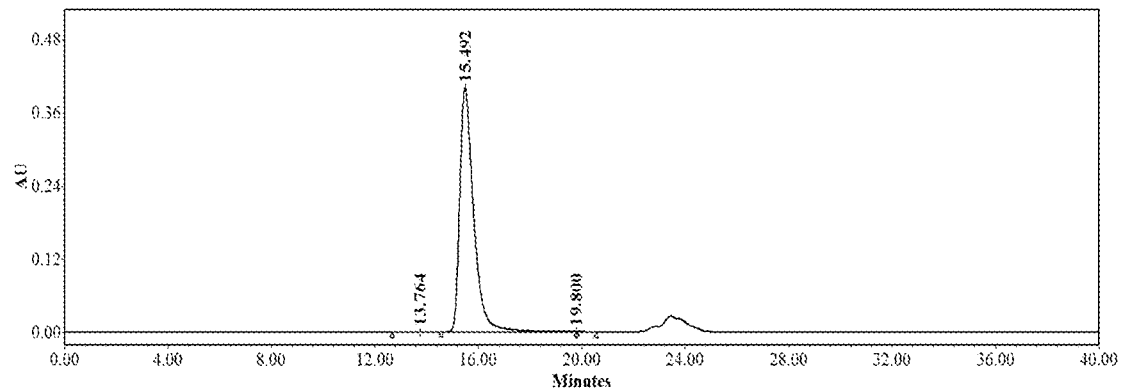
FIG. 41 shows a SEC chromatogram of BT001044.

The SEC chromatogram of BT001044 obtained by coupling TL053 with the antibody is shown in FIG. 41. According to the retention time and peak area ratio in the SEC, it is confirmed that the molecular weight of the main coupling product is about 150 kD, i.e., BT001044 obtained by coupling TL053 with the antibody still maintains the integral structure of the antibody.

Figure 42:
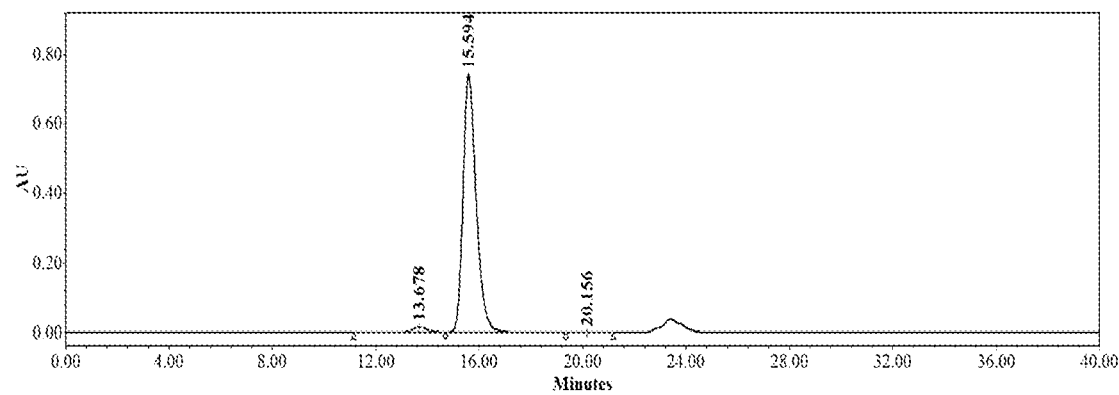
FIG. 42 shows a SEC chromatogram of BT001046.

The SEC chromatogram of BT001046 obtained by coupling TL055 with the antibody is shown in FIG. 42. According to the retention time and peak area ratio in the SEC, it is confirmed that the molecular weight of the main coupling product is about 150 kD, i.e., BT001046 obtained by coupling TL055 with the antibody still maintains the integral structure of the antibody.

Figure 43:
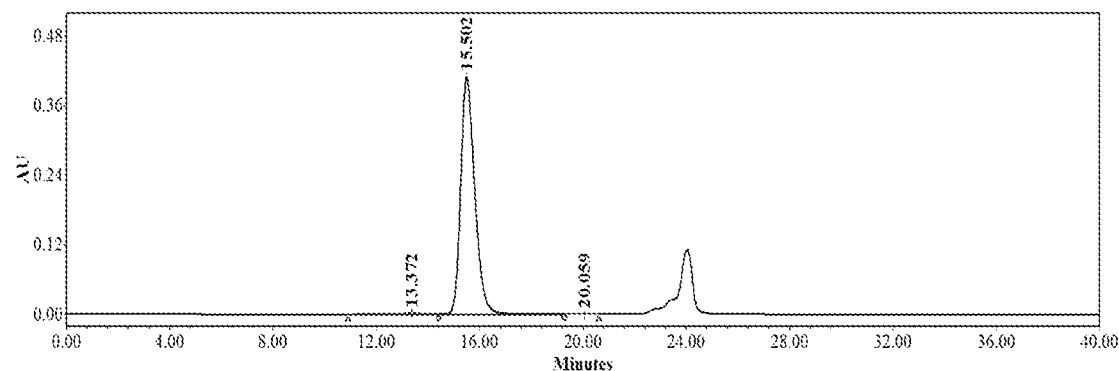
FIG. 43 shows a SEC chromatogram of BT001047.

The SEC chromatogram of BT001047 obtained by coupling TL056 with the antibody is shown in FIG. 43. According to the retention time and peak area ratio in the SEC, it is confirmed that the molecular weight of the main coupling product is about 150 kD, i.e., BT001047 obtained by coupling TL056 with the antibody still maintains the integral structure of the antibody.

Example 63: Test of Inhibitory Effects of Bioactive Molecules and Antibody Drug Conjugates on Activity of Cells In Vitro First, tumor cells MDA-MB-468 (Trop-2 positive cell lines) and HCC1806 (Trop-2 positive cell lines) were cultured. The bioactive molecules and ADC molecules disclosed in the disclosure were co-cultured with the tumor cells, then a CCK8 reagent (Dojindo Molecular Technologies, Inc., Cat: CK04, Lot: JJ744) was added. The activity of dehydrogenase in mitochondria was tested through readings (detection wave length was 450 nm) from a microplate reader (manufacturer: Molecular Devices, model: SpectraMax M2) so as to evaluate the inhibitory effect of ADC on cell proliferation. Sources of the tumor cells were shown in table 1.

TABLE 1

| Cell name | Tumor type | Source |
|---|---|---|
| MDA-MB-468 | Breast cancer | Concortis |
| HCC1806 | Breast cancer | Cobioer Biosciences Co., Ltd. |

In-vitro cell activity testing: bioactive molecules or ADCs were diluted (12 concentration gradients) with corresponding test media (containing 2% FBS). The tumor cells were trypsinized with trypsin by a conventional method, collected and counted, and then resuspended with corresponding test media (containing 2% FBS). Diluted bioactive molecules or ADCs were added to a 96-well plate, and then cells were added. 20 μL of the CCK8 reagent was added to each well and reacted for 4 h, and readings (detection wavelength was 450 nm) were taken from a microplate reader. Experimental conditions and test results were shown in Table 2 and Table 3.

TABLE 2

| Killing effects of bioactive molecules on cells | | |
|---|---|---|
| Name | Cell name | $EC_{50}(nM)$ |
| T001 | MDA-MB-468 | 1.126 |
| T011 | (7500 cells/well, 4 days) | 0.211 |
| T012 | | 1.621 |
| T013 | | 0.414 |
| T015 | | 7.428 |
| T-028 | HCC1806 | 6.016 |
| T-030 | (7500 cells/well, 3 days) | 6.734 |

The test results indicated that all of the bioactive molecules had killing effects on the tumor cells.

TABLE 3

Killing effects of conjugates (ADCs) on cell lines

| Name | Cell name | EC50(nM) |
| --- | --- | --- |
| BT001002 | MDA-MB-468 | 0.072 |
| | (10000 cells/well, 3 days) | |
| BT001004 | HCC1806 | 6.139 |
| BT001012 | (7500 cells/well, 3 days) | 14.41 |
| BT001013 | | 48.01 |
| BT001018 | | 13.42 |
| BT001021 | | 13.15 |
| BT001022 | | 23.43 |
| BT001023 | | 21.65 |
| BT001040 | | 11.08 |
| BT001041 | | 10.34 |
| BT001042 | | 0.0186 |
| BT001043 | | 0.062 |
| BT001044 | | 0.0051 |
| BT001046 | | 0.81 |
| BT001047 | | 0.23 |

The test results indicated that ADC molecules obtained by a novel coupling way had killing effects on tumor cells, indicating that the ADCs formed by the novel coupling method had killing effects on the tumor cells, and the novel coupling method was workable in the synthesis of ADC molecules.

Example 64: Pharmacodynamic Test of Antibody Drug Conjugates and Bioactive Molecules in Vivo Drugs Under Test Drug name, source and preparation method:

BT001021, liquid aliquots were stored at −20° C. at a concentration of 5.44 mg/ml, and diluted with physiological saline by dosage before use to obtain a test solution;

Immu-132 (prepared according to example 2 of WO2015/012904A2, DAR=5.4, also described as IMMU-132), liquid aliquots were stored at −20° C. at a concentration of 13.158 mg/ml, and diluted with physiological saline by dosage before use to obtain a test solution;

Solid powder of T-030 was prepared with 100% DMSO (Sigma) into a solution at a concentration of 5.2 mg/mL, and liquid aliquots were stored at −20° C., and diluted with physiological saline to a desired dose before use to obtain a test solution;

Solid powder of SN-38 (also described as SN38) was prepared with 100% DMSO (Sigma) into a solution at a concentration of 3.23 mg/ml, liquid aliquots were stored at −20° C., and diluted with physiological saline by dosage before use to obtain a test solution.

Note: Toxin was prepared and administered in an equi-molar ratio of ADC samples.

Structures of T-030, SN-38 and Immu-132 were as follows:

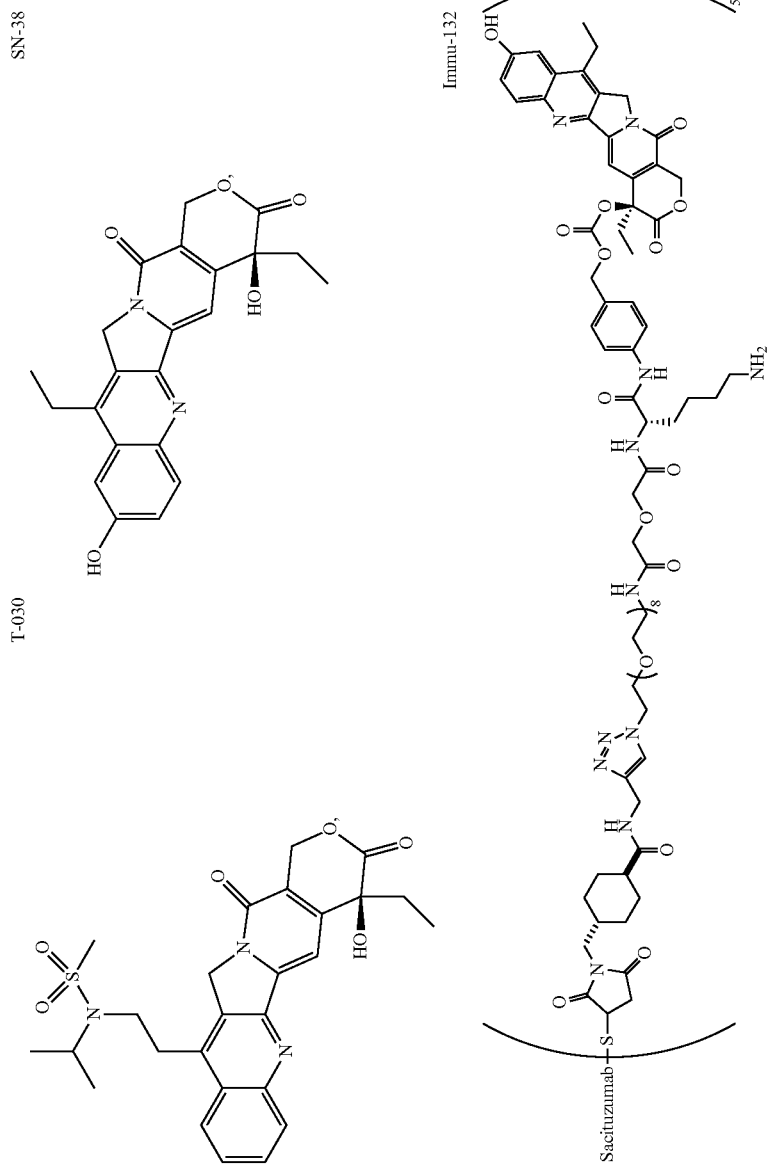

Experimental Animals and Cell Lines

Balb/c-nu mice (Beijing Vital River Laboratory Animal Technology Co., Ltd., production license No.: SCXK (Beijing) 2016-0011); Gastric cancer cell line NCI-N87 (ATCC), breast cancer cell line HCC1806 (COBIOER Nanjing).

Experimental Grouping and Evaluation Method

Tumor-bearing mice (6 mice/group) with tumor volume of 100-200 mm$^3$ were randomly grouped (the number of groups was determined according to sample number). The administration volume was 10 m$_l$/kg, and the administration route was tail intravenous injection. The mice were administered twice a week, and tumor diameter was measured with a vernier caliper, and tumor volume was calculated based on the following calculation formula: V=0.5 a×b$^2$, wherein a and b stand for the long diameter and short diameter of a tumor respectively. Animal deaths were observed and recorded every day.

The tumor growth inhibition rate TGI (%) was calculated from the following formula to evaluate tumor inhibitory effect of antibody drug conjugates:

$$TGI\ (\%)=[1-(V_{Tend}-V_{Tstart})/(V_{Cend} \times V_{Cstart})]*100\%$$

wherein, $V_{Tend}$: average tumor volume at the end of the experiment in the treatment group $V_{Tstart}$: average tumor volume at the beginning of administration in the treatment group $V_{Cend}$: average tumor volume at the end of the experiment in the control group $V_{Cstart}$: average tumor volume at the beginning of administration in the control group In the following experimental examples 1 and 2, the inhibition of the antibody conjugate BT001021 on tumor proliferation of tumor-bearing mice constructed by subcutaneous xenograft of human tumor cells was evaluated. Specifically, in the experimental examples 1 and 2, tumor-bearing mice models were constructed by subcutaneous xenograft of a human gastric cancer cell line NCI-N87 or a human triple negative breast cancer cell line HCC1806. After the tumor volume was about 100 mm$^3$, the mice were randomly grouped, and intravenously administered with BT001021 twice a week for a total of 6 times. Changes in tumor volume and animal body weight were measured twice a week to evaluate the efficacy (tumor inhibitory effect) of the antibody drug conjugate on tumor-bearing mice.

Experimental Example 1. Inhibition of NCI-N87 by Antibody Drug Conjugates and Bioactive Molecules Experimental Methods:

NCI-N87 cells were cultured in a 1640 culture medium containing 10% fetal bovine serum at 37° C. and 5% CO$_2$. NCI-N87 cells in the exponential growth stage were collected, resuspended in PBS to a suitable concentration, and inoculated subcutaneously into female Balb/c-nu mice to construct gastric cancer models. When the mean tumor volume was about 90 mm$^3$, the mice were randomly grouped into a physiological saline group, a BT001021 (3 mg/kg, IV, BIW×3W) group, a positive drug Immu-132 (3 mg/kg, IV, BIW×3W) group, a T030 group and a SN38 group according to the tumor size, followed by tail intravenous injection of corresponding drugs twice a week for a total of 6 times. After administration, the tumor volume and body weight of the mice were observed and measured regularly. Specific results were shown in Table 4, FIGS. 44 and 45.

Conclusion:

In the experimental example, a human gastric cancer cell line NCI-N87 was used to construct subcutaneous xenograft models of human gastric cancer, and the efficacy of BT001021 in the NCI-N87 human gastric cancer tumor-bearing mice models was evaluated.

Experimental results showed that BT001021 (3 mg/kg, IV, BIW×3W) could significantly inhibit the tumor growth of xenograft model mice of NCI-N87 gastric cancer, and tumor regression occurred at the end of administration, with anti-tumor activity superior to that of positive control Immu-132. Neither animal death nor significant animal weight loss occurred in all treatment groups during the observation period, indicating that BT001021 had no significant toxicity.

TABLE 4

NCI-N87 model of gastric cancer

| | | D 21 after administration | | |
|---|---|---|---|---|
| Group No. | Regimen | Tumor volume (mm$^3$) ($\bar{x} \pm S$) | Tumor growth inhibition rate (%) | P value (vs group 1) |
| Group 1 | Physiological saline | 405.67 ± 91.81 | | |
| Group 2 | BT001021 | 42.78 ± 21.87 | 114.61 | 0.0000 |
| Group 3 | Immu-132 | 259.04 ± 42.41 | 46.46 | 0.0053 |
| Group 4 | T-030 | 339.02 ± 152.80 | 21.48 | 0.3813 |
| Group 5 | SN-38 | 416.11 ± 195.15 | −2.75 | 0.9079 |

Experimental Example 2. Inhibition of HCC1806 by Antibody Drug Conjugates

Experimental Methods:

HCC1806 cells were cultured in a 1640 culture medium containing 10% fetal bovine serum at 37° C. and 5% CO$_2$. HCC1806 cells in the exponential growth stage were collected, resuspended in PBS in a suitable concentration, and inoculated subcutaneously into female Balb/c-nu to construct breast cancer models. When the mean tumor volume was about 130 mm$^3$, the mice were randomly grouped into a physiological saline group, a BT001021 (10 mg/kg, IV, BIW×3W) group and a positive drug Immu-132 (10 mg/kg, IV, BIW×3W) group according to the tumor size, followed by tail intravenous injection of corresponding drugs twice a week for a total of 5 times. After administration, the tumor volume of the mice was observed and measured regularly. Specific results were shown in Table 5 and FIG. 46.

Conclusion:

In the experimental example, a human breast cancer cell line HCC1806 was used to construct subcutaneous xenograft models of human breast cancer, and the efficacy of BT001021 in the HCC1806 human breast cancer tumor-bearing mice models was evaluated.

Experimental results showed that BT001021 (10 mg/kg, IV, BIW×3W) could significantly inhibit the tumor growth of xenograft model mice of HCC1806 breast cancer, with anti-tumor activity superior to that of positive Immu-132.

TABLE 5

HCC1806 model of breast cancer

D 17 after administration

| Group No. | Regimen | Tumor Volume (mm³) (x̄ ± S) | Tumor growth inhibition rate (%) | P value (vs group 1) |
|---|---|---|---|---|
| Group 1 | Physiological saline | 2638.22 ± 553.81 | | |
| Group 2 | BT001021 | 1260.87 ± 415.60 | 54.93 | 0.0006 |
| Group 3 | Immu-132 | 2347.05 ± 317.79 | 11.62 | 0.2901 |

Figure 44:
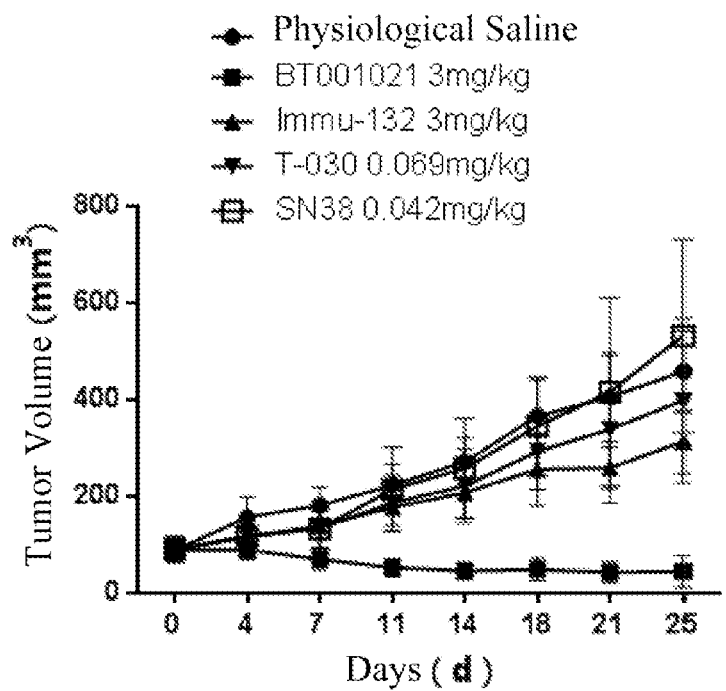
FIG. 44 shows changes in growth of tumor volume of each group of mice in a NCI-N87 human gastric cancer model.
Figure 45:
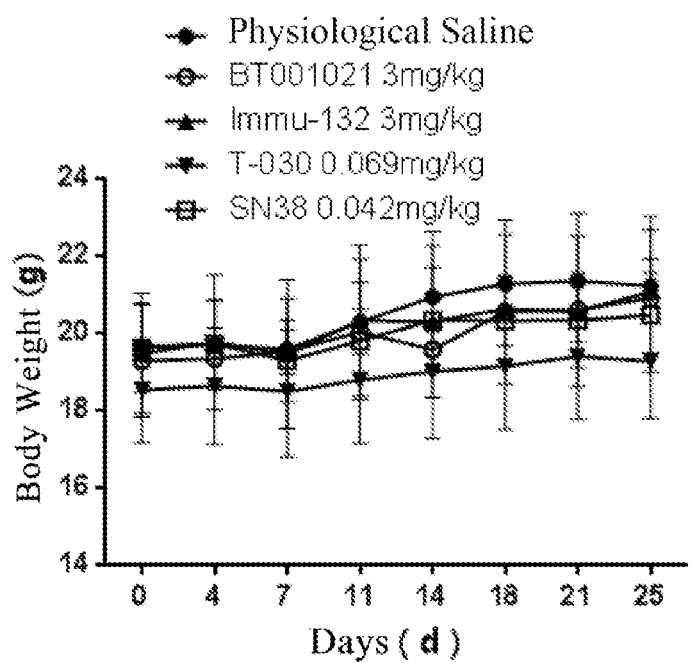
FIG. 45 shows changes in body weight of each group of mice in a NCI-N87 human gastric cancer model.
Figure 46:
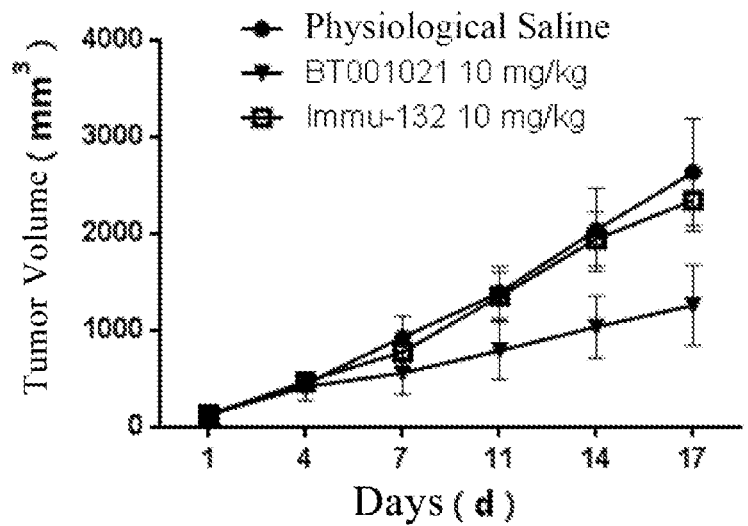
FIG. 46 shows changes in growth of tumor volume of each group of mice in an HCC1806 human breast cancer model.

According to Table 4, Table 5 and FIGS. 44-46, the antibody drug BT001021 of the invention could significantly inhibit tumor growth in NCI-N87 mice models. It was significantly superior to Immu-132 at the same dosage, and had neither significant weight loss nor significant drug toxicity. In the HCC1806 mice models, when the dosage increased to 10 mg/kg due to high malignancy of the tumor, Immu-132 did not show significant inhibitory activity, whereas BT001021 could significantly inhibit tumor growth. The results indicated that BT001021 of the invention had good efficacy and excellent safety.

In the subcutaneous xenograft models of the experimental examples 1 and 2, the anti-tumor activity of BT001021 was significantly superior to that of Immu-132 at the same dosage, suggesting that BT001021 had the potential to treat solid tumors, and was expected to benefit more patients clinically than Immu-132.

Experimental Example 3. Inhibition of HCC827 by Antibody Drug Conjugates

The experimental example 3 was used to evaluate the inhibitory effect of BT001021 and BT001035 on proliferation of tumor-bearing mice models constructed by subcutaneous xenograft human tumor cells of HCC827 non-small cell lung cancer. Specifically, in the experiment, tumor-bearing mice models were constructed by subcutaneous xenograft of a human non-small cell lung cancer cell line HCC827. After the tumor volume was about 100 mm³, the mice were randomly grouped, and intravenously administrated with BT001021 and BT001035 twice a week for a total of 6 times. Then changes in tumor volume and animal body weight were measured twice a week to calculate the efficacy (tumor inhibitory effect) of BT001021 and BT001035 on the tumor-bearing mice.

Experimental Methods:

HCC827 cells were cultured in a 1640 culture medium containing 10% fetal bovine serum at 37° C. and 5% $CO_2$. HCC827 cells in the exponential growth stage were collected, resuspended in PBS in a suitable concentration, and inoculated subcutaneously into female Balb/c-nu mice to construct xenograft models of lung cancer. When the mean tumor volume was about 80 mm³, the mice were randomly grouped into a physiological saline group, a positive drug Immu-132 (10 mg/kg, IV, BIW×3W) group, a BT001021 (10 mg/kg, IV, BIW×3W) group and a BT001035 (10 mg/kg, IV, BIW×3W) group according to the tumor size, followed by tail intravenous injection of corresponding drugs twice a week for a total of 6 times. After administration, the tumor volume and body weight of the mice were observed and measured regularly. Results were shown in Table 6, FIG. 47A and FIG. 47B.

Conclusion:

Experimental results showed that BT001021 and BT001035 could significantly inhibit the tumor growth of xenograft model mice of HCC827 non-small cell lung cancer, and tumor regression occurred at the end of administration, with anti-tumor activity superior to that of the positive control Immu-132 group. During the observation period, no animal death and significant animal weight loss occurred in all treatment groups, and no significant drug toxicity was observed. During the treatment period, the mice showed good tolerance to all drugs to be evaluated.

TABLE 6

HCC827 model of lung cancer

D 21 after administration

| Group No. | Regimen | Tumor Volume (mm³) (x̄ ± S) | TGI (%) | P value (vs group 1) |
|---|---|---|---|---|
| 1 | Physiological saline | 515.25 ± 165.09 | | |
| 2 | Immu-132 | 145.94 ± 19.72 | 85.19 | 0.0003 |
| 3 | BT001021 | 40.26 ± 8.36 | 108.70 | 0.0001 |
| 4 | BT001035 | 48.61 ± 9.99 | 106.95 | 0.0000 |

Figure 47A:
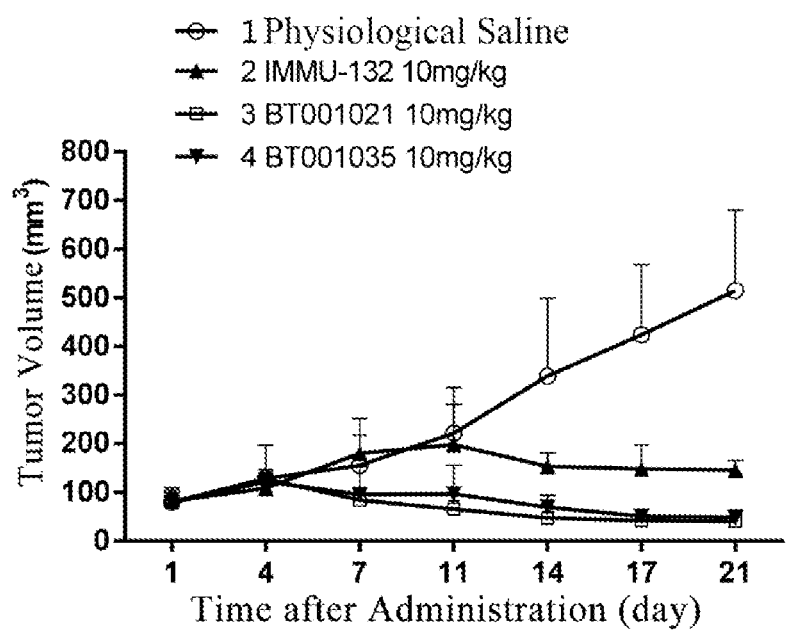
FIG. 47A shows changes in growth of tumor volume of each group of mice in a xenograft model of HCC827 human non-small cell lung cancer.
Figure 47B:
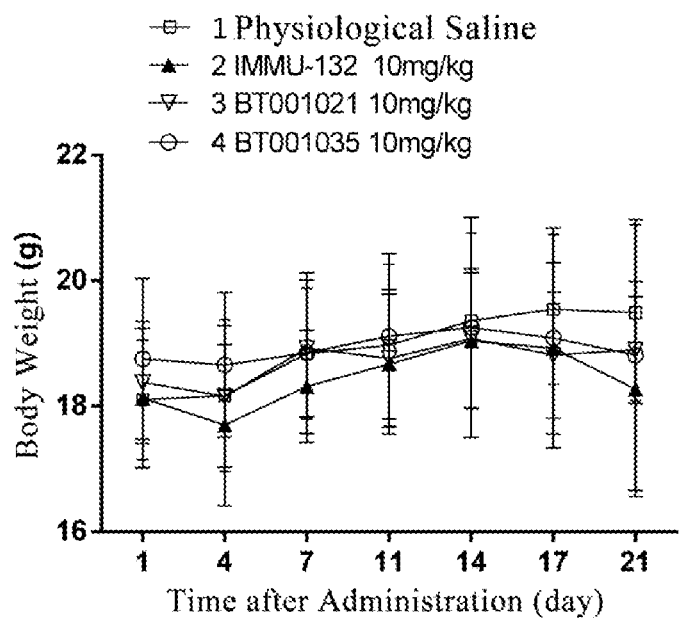
FIG. 47B shows changes in body weight of each group of mice in a xenograft model of HCC827 human non-small cell lung cancer.

According to Table 6, FIG. 47A and FIG. 47B, both BT001021 and BT001035 had significant inhibitory activity on tumor growth during the evaluation period, and they are significantly superior to that of Immu-132 at the same dosage. During treatment, no significant weight loss and drug toxicity were observed in all groups. The results indicated that both BT001021 and BT001035 had excellent anti-tumor activity.

In the subcutaneous xenograft models, the anti-tumor activity of both BT001021 and BT001035 was significantly superior to that of Immu-132 at the same dosage, suggesting that both BT001021 and BT001035 had the potential to treat solid tumors, and was expected to benefit more patients clinically than Immu-132.

Experimental Example 4. Inhibition of NCI-N87 by Antibody Drug Conjugates

The experimental example 4 was used to evaluate the inhibition of the antibody drug conjugate BT001036 on tumor proliferation of tumor-bearing mice constructed by subcutaneous xenograft of human tumor cells. Specifically, in the experiment, tumor-bearing mice models were constructed by subcutaneous xenograft of a human gastric cancer cell line NCI-N87. After the tumor volume was about 140 mm³, the mice were randomly grouped, and intravenously administrated with BT001036 twice a week for a total of 6 times. Changes in tumor volume and animal body weight were measured twice a week to evaluate the efficacy (tumor inhibitory effect) of the antibody drug conjugate on tumor-bearing mice.

Figure 48A:
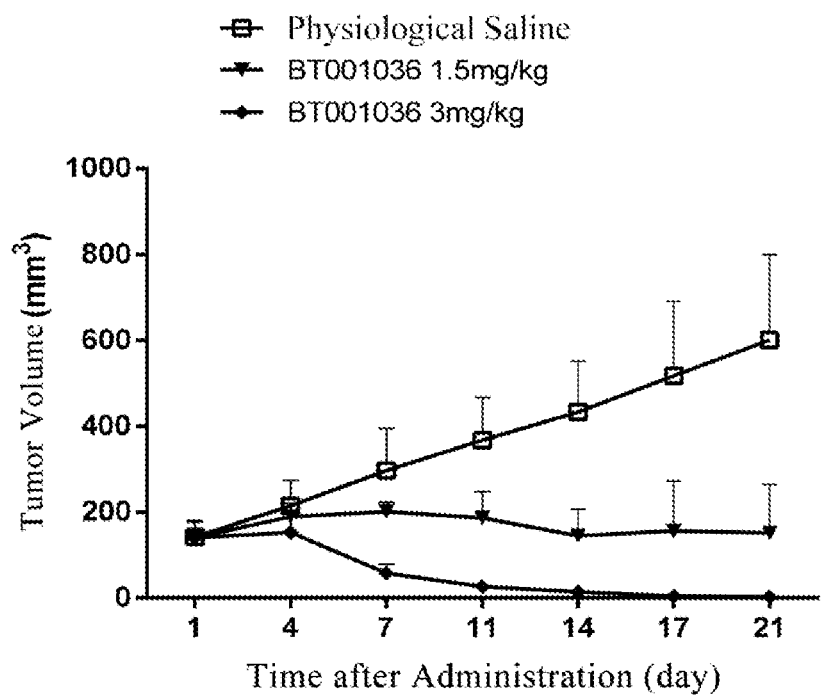
FIG. 48A shows changes in growth of tumor volume of each group of mice in a xenograft model of NCI-N87 human gastric cancer.
Figure 48B:
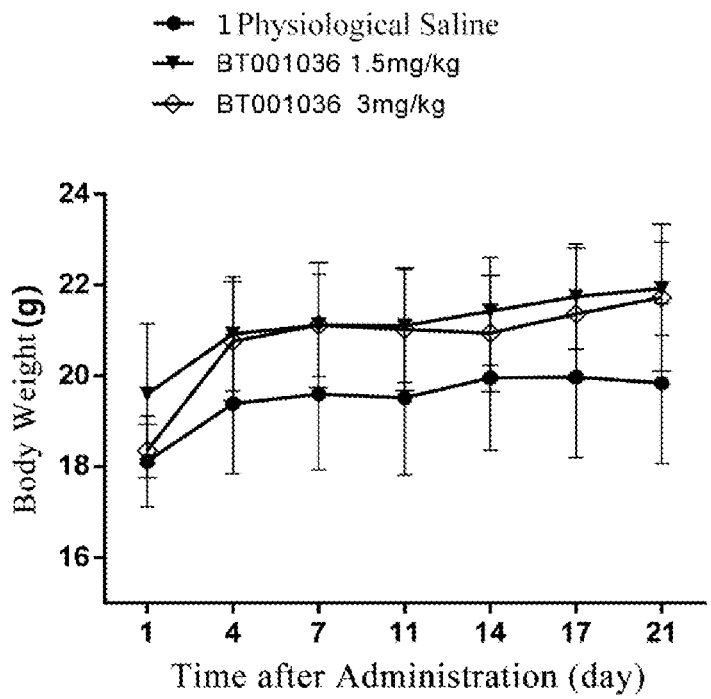
FIG. 48B shows changes in body weight of each group of mice in a xenograft model of NCI-N87 human gastric cancer.

Experimental Methods:

NCI-N87 cells were cultured in a 1640 culture medium containing 10% fetal bovine serum at 37° C. and 5% $CO_2$. NCI-N87 cells in the exponential growth stage were collected, resuspended in PBS in a suitable concentration, and inoculated subcutaneously into female Balb/c-nu mice to construct xenograft models of gastric cancer. When the mean tumor volume was about 140 mm³, the mice were randomly grouped into a physiological saline group, a BT001036 (1.5 mg/kg, IV, BIW×3W) group and a BT001036 (3 mg/kg, IV, BIW×3W) group according to the tumor size, followed by tail intravenous injection of corresponding drugs twice a week for a total of 6 times. After administration, the tumor volume and body weight of the mice were observed and measured regularly. Specific results were shown in Table 7, FIG. 48A and FIG. 48B.

TABLE 7

NCI-N87 model of gastric cancer

| Group No. | Regimen | D 21 after administration | | |
|---|---|---|---|---|
| | | Tumor Volume $(mm^3)$ $\bar{x}$ ($\pm S$) | TGI (%) | P value (vs group 1) |
| Group 1 | Physiological saline | 601.29 ± 198.92 | | |
| Group 2 | BT001036 (1.5 mg/kg) | 150.87 ± 112.84 | 97.78 | 0.0017 |
| Group 3 | BT001036 (3 mg/kg) | 2.74 ± 0.64 | 129.95 | 0.0000 |

Conclusion:

In the experimental example, subcutaneous xenograft models of human gastric cancer were constructed by subcutaneous xenograft of a human gastric cancer cell line NCI-N87, and the efficacy of BT001036 in the NCI-N87 human gastric cancer tumor-bearing mice models was evaluated.

Experimental results showed that both the high and low dosages of BT001036 (1.5 mg/kg, 3 mg/kg) could significantly inhibit the tumor growth of xenograft model mice of NCI-N87 gastric cancer, and tumor regression occurred at the end of administration, with excellent anti-tumor activity. During the observation period, no animal death and significant animal weight loss occurred in all treatment groups, and no significant drug toxicity was observed. During the treatment period, the mice showed good tolerance to all drugs to be evaluated.

Experimental Example 5. Inhibition of MDA-MB-231 by Antibody Drug Conjugates

The experimental example 5 was used to evaluate the inhibitory effect of BT001021 on the proliferation of tumor-bearing mice models constructed by subcutaneous xenograft human tumor cells of MDA-MB-231 breast cancer. Specifically, in the experiment, tumor-bearing mice models were constructed by subcutaneous xenograft of a human breast cancer cell line MDA-MB-231. After the tumor volume was about 130 $mm^3$, the mice were randomly grouped, and intravenously administered with BT001021 twice a week for a total of 6 times. Then changes in tumor volume and animal body weight were measured to calculate the efficacy (tumor inhibitory effect) of BT001021 on the tumor-bearing mice.

Figure 49A:
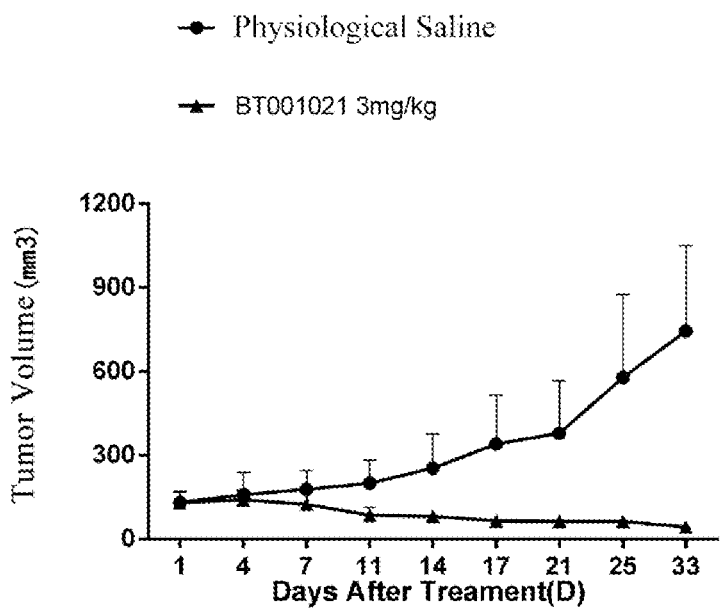
FIG. 49A shows changes in growth of tumor volume of each group of mice in a tumor-bearing mice model of MDA-MB-231 human breast cancer.
Figure 49B:
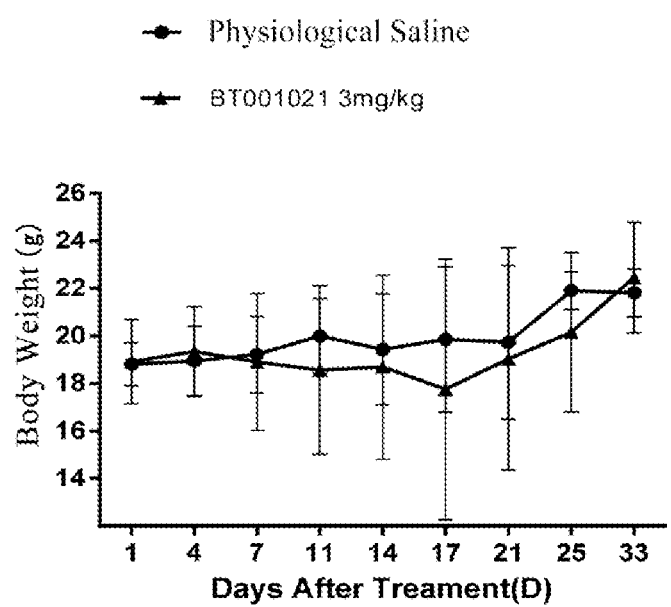
FIG. 49B shows changes in body weight of each group of mice in a tumor-bearing mice model of MDA-MB-231 human breast cancer.

Experimental Methods:

NCI-MDA-MB-231 cells were cultured in a RPMI1640 culture medium containing 10% fetal bovine serum at 37° C. and 5% CO.sub.2. MDA-MB-231 cells in the exponential growth stage were collected, resuspended in PBS in a suitable concentration, and inoculated subcutaneously into female Balb/c-nu mice to construct xenograft models of breast cancer. When the mean tumor volume was about 130 mm.sup.3, the mice were randomly grouped into a physiological saline group and a BT001021 (3 mg/kg) group according to the tumor size, followed by tail intravenous injection of corresponding drugs twice a week for a total of 6 times. After administration, the tumor volume and body weight of the mice were observed and measured regularly. Results were shown in Table 8, FIG. 49A and FIG. 49B.

Conclusion:

Results showed that BT001021 could significantly inhibit the tumor growth of xenograft model mice of MDA-MB-231 breast cancer, and tumor regression occurred at the end of administration. During the observation period, neither animal death nor significant animal weight loss occurred in all treatment groups, no significant drug toxicity was observed, either. During the treatment period, the mice showed good tolerance to all drugs to be evaluated.

TABLE 8

MDA-MB-231 model of breast cancer

| Group No. | Regimen | D 33 after administration | | |
|---|---|---|---|---|
| | | Tumor Volume $(mm^3)$ $\bar{x}$ ($\pm S$) | TGI (%) | P value (vs group 1) |
| 1 | Physiological saline | 744.53 ± 306.66 | | |
| 2 | BT001021 | 43.96 ± 7.72 | 114.18 | 0.0119 |

In the subcutaneous xenograft models, BT001021 had significant anti-tumor activity. During the observation period, neither animal death nor significant animal weight loss occurred in all treatment groups, no significant drug toxicity was observed, either. During the treatment period, the mice showed good tolerance to all drugs to be evaluated.

Example 65: Test of Pharmacokinetics of Antibody Drug Conjugates and Bioactive Molecules In Vivo Experimental example 6 was used to evaluate pharmacokinetics of antibody drug conjugates and bioactive molecules in vivo. Specifically, in the experiment, a tumor-bearing mice model was constructed by subcutaneous xenograft of a human gastric cancer cell line NCI-N87 to Balb/c-nu mice. After the tumor volume was 100-200 $mm^3$, the mice were randomly grouped, and intravenously administrated with a single dose of BT001021 and T-030. The concentration of the T-030 in tumor tissues and serum was determined to evaluate the pharmacokinetics in vivo of the antibody conjugate BT001021 and the bioactive molecule T-030 in the tumor-bearing mice.

Drugs Under Test

Drug Names and Preparation Methods:

BT001021, liquid aliquots were stored at −20° C. at a concentration of 20 mg/ml, and diluted with physiological saline to the desired doses before use to obtain a test solution;

T-030, which was prepared into 1 mg/ml with dimethyl sulfoxide and diluted with physiological saline to a desired dose to obtain a test solution.

Experimental Animals and Cell Lines:

Balb/c-nu mice (Beijing Vital River Laboratory Animal Technology Co., Ltd., production license No.: SCXK (Beijing) 2016-0011); Gastric cancer cell line NCI-N87 (ATCC).

Experimental Groups and Evaluation Method:

Tumor-bearing mice (4 mice/group) with tumor volume of 100-200 $mm^3$ were randomly grouped (the number of groups was determined according to sample number), and the administration route was single tail intravenous injection.

Experimental Example 6. Test of Pharmacokinetics of BT001021 and T-030 in Tumor-Bearing Mice In Vivo Experimental Method:

NCI-N87 cells were cultured in a 1640 culture medium containing 10% heat-inactivated fetal bovine serum at 37° C. and 5% CO.sub.2. NCI-N87 cells in the exponential growth stage were collected, resuspended in PBS to a suitable concentration, and inoculated subcutaneously into Balb/c-nu mice to construct xenograft models of gastric cancer. When the mean tumor volume was about 100-200 mm.sup.3, the mice were randomly grouped into a physiological saline group, a T-030 (0.23 mg/kg, IV, single dose) group and a BT001021 (10 mg/kg, IV, single dose) group according to the tumor size, followed by tail intravenous injection of corresponding drugs. For the T-030 group, serum and tumor tissues were collected 1 h, 2h, 4h, 8h, 24h and 72h after administration (T-030 was not detected in the serum and tumor tissues 72h after administration, therefore, serum and tumor tissues were not collected 168h after administration). For BT001021 group, serum and tumor tissues were collected 1 h, 2h, 4h, 8h, 24h, 72h and 168h after administration to test the concentration of the T-030 in the serum and the tumors by LC-MS/MS. Specific results were shown in Table 9. The administration dose of the T-030 (0.23 mg/kg) was converted to isomolar dose (10 mg/kg) of BT001021.

TABLE 9

Pharmacokinetic parameters of T-030 in tumors and serum of tumor-bearing mice after intravenous administration of T-030 and BT001021

| Regimen | T-030 (0.23 mg/kg) administration group | | BT001021 (10 mg/kg) administration group | |
|---|---|---|---|---|
| | Tumor | Serum | Tumor | Serum |
| $AUC_{last}$(h*ng/ml) | 3.85 | 5.58 | 850.1 | 174.97 |
| $C_{max}$(ng/ml) | 1.20 | 1.81 | 7.82 | 11.7 |
| $MRT_{INF}$(h) | 1.52 | 1.11 | 64.24 | 42.9 |
| $T_{max}$(h) | 1.00 | 1.00 | 8.00 | 1.00 |
| $T_{1/2}$(h) | 2.55 | 1.76 | 93.14 | 44.35 |

Conclusion:

$AUC_{last}$ of the drug in the tumors and serum of BT001021 (10 mg/kg) administration group was 850.1 h*ng/ml and 174.97 h*ng/ml, respectively, whereas the $AUC_{last}$ of the drug in the tumors and serum of the T-030 administration group was 3.85 h*ng/ml and 5.58 h*ng/ml, respectively. The comparison indicated that the exposure doses of T-030 of BT001021 administration group was significantly increased compared with those of the T-030 administration group. In addition, the exposure doses of the bioactive molecule T-030 in the tumors of BT001021 administration group was significantly higher than those in the serum, whereas, the exposure doses of the active biomolecule in the serum and tumors of the T-030 administration group was basically the same, indicating that the antibody drug conjugate (BT001021) had high tumor tissue targetability.

$C_{max}$ of the bioactive molecule T-030 in the tumors and serum of BT001021 (10 mg/kg) administration group was 7.82 ng/ml and 11.7 ng/ml, respectively, whereas the $C_{max}$ of the bioactive molecule T-030 in the tumors and serum of the T-030 administration group was 1.20 ng/ml and 1.81 ng/ml, respectively, indicating that the antibody drug conjugate (BT001021) had higher concentration of the bioactive molecule (T-030) in tumor tissues and serum.

$T_{1/2}$ of the bioactive molecule T-030 in the tumors of BT001021 (10 mg/kg) administration group was 93.14 h, whereas the $T_{1/2}$ of the bioactive molecule T-030 in the tumors of the T-030 administration group was 2.55 h, indicating that the antibody drug conjugate (BT001021) had a longer half life in the tumor tissues.

In conclusion, BT001021 had significant tumor tissue targetability and good pharmacokinetic properties compared with the corresponding bioactive molecule (T-030).

Experimental Example 7. Test of Pharmacokinetics of Antibody Drug Conjugates BT001021 and Immu-132 In Vivo In the experiment, tumor-bearing mice models were constructed by subcutaneous xenograft of a human gastric cancer cell line NCI-N87 to Balb/c-nu mice. After the tumor volume was 100-200 mm³, the mice were randomly grouped, and intravenously given a single dose of BT001021 and Immu-132. The concentration of the bioactive molecule T-030 and the SN-38 corresponding to BT001021 and Immu-132 in tumor tissues and serum was respectively measured to evaluate the pharmacokinetics of the antibody conjugates BT001021 and Immu-132 in tumor-bearing mice in vivo.

Drugs Under Test

Drug Names and Preparation Methods:

BT001021, liquid aliquots were stored at −20° C. at a concentration of 20 mg/ml, and diluted with physiological saline to the desired doses before use to obtain the test solution;

Immu-132 was diluted with physiological saline to the desired dose to obtain the test solution.

Experimental Animals and Cell Lines:

Balb/c-nu mice (Beijing Vital River Laboratory Animal Technology Co., Ltd., production license No.: SCXK (Beijing) 2016-0011); Gastric cancer cell line NCI-N87 (ATCC).

Experimental Groups and Evaluation Method:

Tumor-bearing mice (4 mice/group) with tumor volume of 100-200 mm³ were randomly grouped (the number of groups was determined according to sample number), and the administration route was single tail intravenous injection.

Experimental Methods:

NCI-N87 cells were cultured in a 1640 culture medium containing 10% heat-inactivated fetal bovine serum at 37° C. and 5% CO.sub.2. NCI-N87 cells in the exponential growth stage were collected, resuspended in PBS to a suitable concentration, and inoculated subcutaneously into Balb/c-nu mice to construct an xenograft model of gastric cancer. When the mean tumor volume was about 100-200 mm.sup.3, the mice were randomly grouped into a BT001021 (5 mg/kg, IV, single dose) group and an lmmu-132 (5 mg/kg, IV, single dose) group according to the tumor size, followed by tail intravenous injection of corresponding drugs. Serum and tumor tissues were collected at 2h, 24h, 48h and 72h after administration respectively to test the concentration of the T-030 or SN-38 in the serum and tumors by LC-MS/MS.

TABLE 10

Pharmacokinetic parameters of T-030 and SN-38 in tumors and serum of tumor-bearing mice after intravenous administration of BT001021 and Immu-132

| Regimen | Immu-132 (5 mg/kg) administration group | | BT001021 (5 mg/kg) administration group | |
|---|---|---|---|---|
| | Tumor | Serum | Tumor | Serum |
| $AUC_{last}$ (h*ng/ml) | 116.8 | 422.7 | 427.2 | 115.3 |
| $C_{max}$ (ng/ml) | 2.8 | 19.58 | 6.8 | 5.08 |
| $MRT_{last}$ (h) | 21.5 | 15.66 | 31.9 | 17.6 |

Conclusion:

$AUC_{last}$ of small toxin molecules in the tumors and serum of BT001021 administration group was 427.2 h*ng/ml and 115.3 h*ng/ml respectively, whereas the $AUC_{last}$ of small toxin molecules in the tumors and serum of Immu-132 administration group was 116.8 h*ng/ml and 422.7 h*ng/ml respectively. C. of small toxin molecules in the tumors of BT001021 administration group was 6.8 ng/ml, whereas the C. of small toxin molecules in the tumors of Immu-132 administration group was 2.8 ng/ml. The results showed that BT001021 had better tumor tissue targetability, better pharmacokinetic properties and better therapeutic window, compared with Immu-132.

Even though specific modes for carrying out the invention have been described in detail, it should be understood by a person skilled in the art that various modifications and alternatives can be made to the details according to all published teachings, and such changes are within the protection scope of the invention. The full scope of the invention is given by the attached claims and any equivalent thereof.

The invention claimed is:

1. An antibody-drug conjugate, wherein the conjugate is

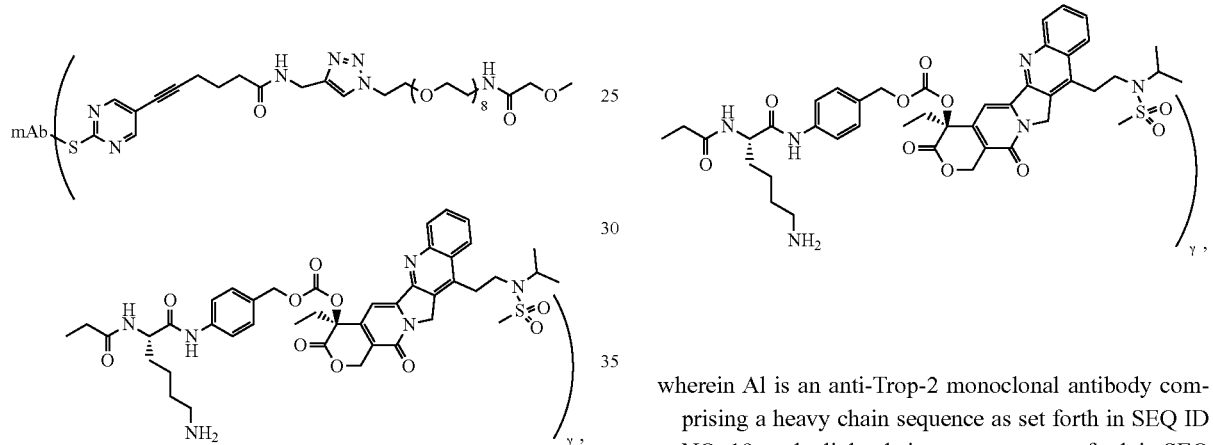

wherein γ is an integer from 1 to 10, and mAb is an anti-Trop-2 monoclonal antibody.

2. An antibody-drug conjugate, wherein the conjugate is

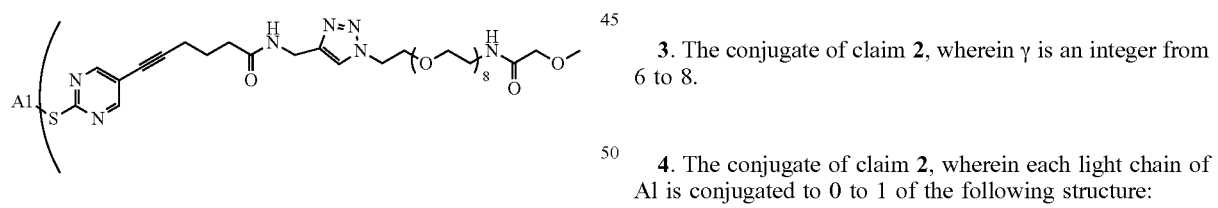

wherein A1 is an anti-Trop-2 monoclonal antibody comprising a heavy chain sequence as set forth in SEQ ID NO: 19, and a light chain sequence as set forth in SEQ ID NO: 20, wherein A1 is linked via one or more thiol group(s) to form the conjugate, and γ is an integer from 1 to 8.

3. The conjugate of claim 2, wherein γ is an integer from 6 to 8.

4. The conjugate of claim 2, wherein each light chain of A1 is conjugated to 0 to 1 of the following structure:

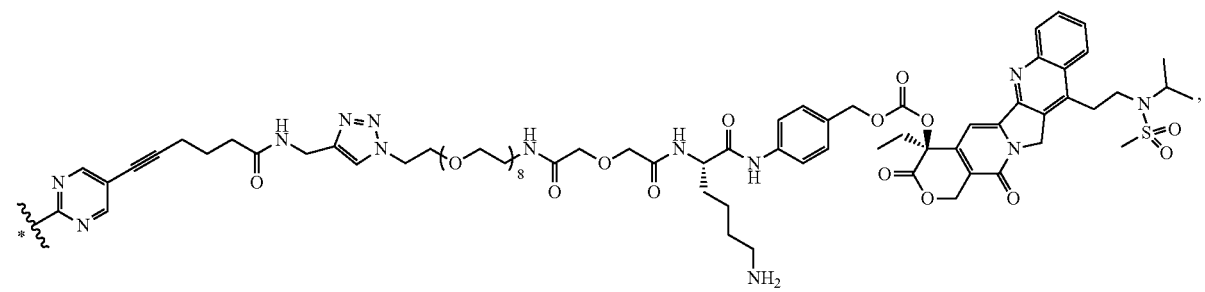

and each heavy chain of A1 is conjugated to 1 to 3 of the following structure:

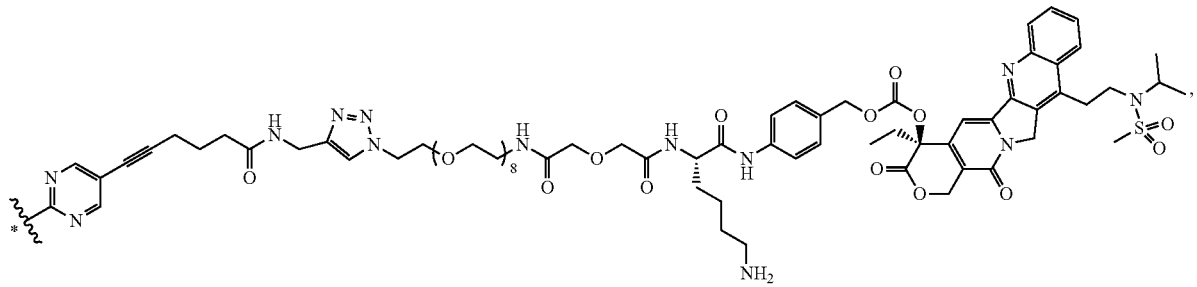

wherein* is the point of attachment to a cysteine of A1.

5. A pharmaceutical composition comprising one or more of the conjugate of claim 1, and one or more pharmaceutical excipients.

6. A pharmaceutical composition comprising one or more of the conjugate of claim 2, and one or more pharmaceutical excipients.

7. The pharmaceutical composition of claim 6, which has a drug-to-antibody ratio ("DAR") of from 5 to 8.

8. The pharmaceutical composition of claim 6, which has a DAR of about 6.9.

9. An antibody-drug conjugate, wherein the conjugate is

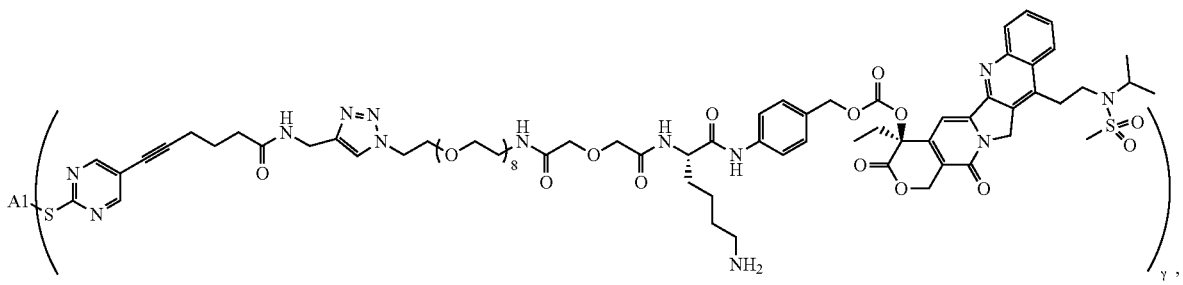

wherein A1 is sacituzumab, wherein the sacituzumab is linked via one or more thiol group(s) to form the conjugate, and γ is an integer from 1 to 8.

10. The conjugate of claim 9, wherein y is an integer from 6 to 8.

11. The conjugate of claim 9, wherein each light chain of sacituzumab is conjugated to 0 to 1 of the following structure:

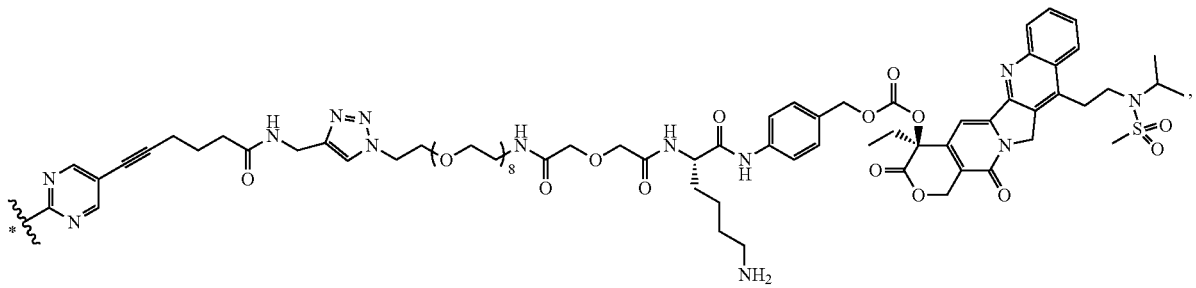

and each heavy chain of sacituzumab is conjugated to 1 to 3 of the following structure:

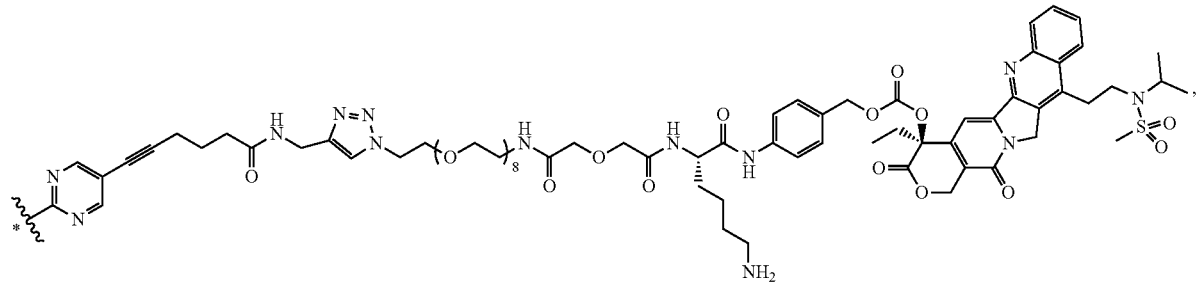

wherein* is the point of attachment to a cysteine of sacituzumab.

12. A pharmaceutical composition comprising one or more of the conjugate of claim 9, and one or more pharmaceutical excipients.

13. The pharmaceutical composition of claim 12, which has a drug-to-antibody ratio ("DAR") of from 7 to 8.

14. The pharmaceutical composition of claim 12, which has a DAR of about 6.9.

15. The pharmaceutical composition of claim 5, which has a drug-to-antibody ratio ("DAR") of from 5 to 8.

16. The pharmaceutical composition of claim 5, which has a DAR of about 6.9.

17. An antibody-drug conjugate, wherein the conjugate is

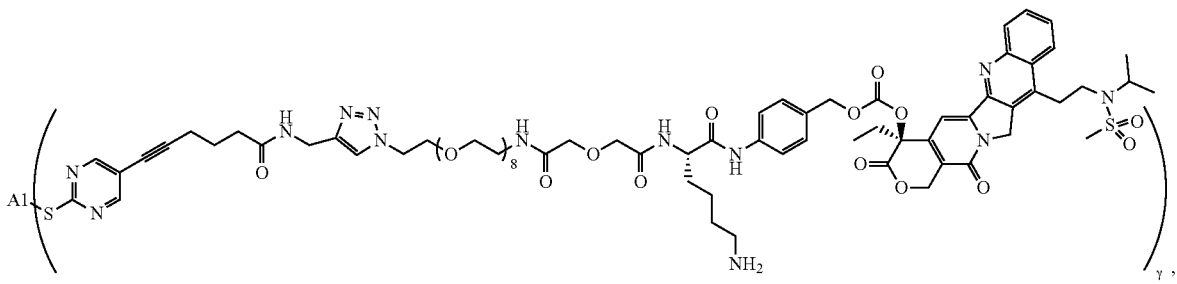

wherein A1 is an anti-Trop-2 monoclonal antibody comprising a heavy chain variable region comprising the amino acid sequences of the complementarity determining regions (CDRs) in the heavy chain sequence set forth in SEQ ID NO: 19, and a light chain variable region comprising the amino acid sequences of the CDRs in the light chain sequence set forth in SEQ ID NO: 20, wherein A1 is linked via one or more thiol group(s) to form the conjugate, and γ is an integer from 1 to 8.

18. The conjugate of claim 17, wherein y is an integer from 6 to 8.

19. The conjugate of claim 17, wherein each light chain of the anti-Trop-2 monoclonal antibody is conjugated to 0 to 1 of the following structure:

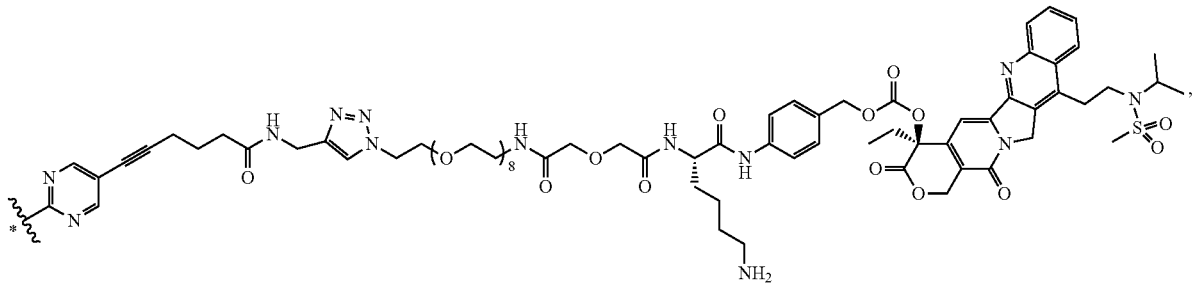

and each heavy chain of the anti-Trop-2 monoclonal antibody is conjugated to 1 to 3 of the following structure:

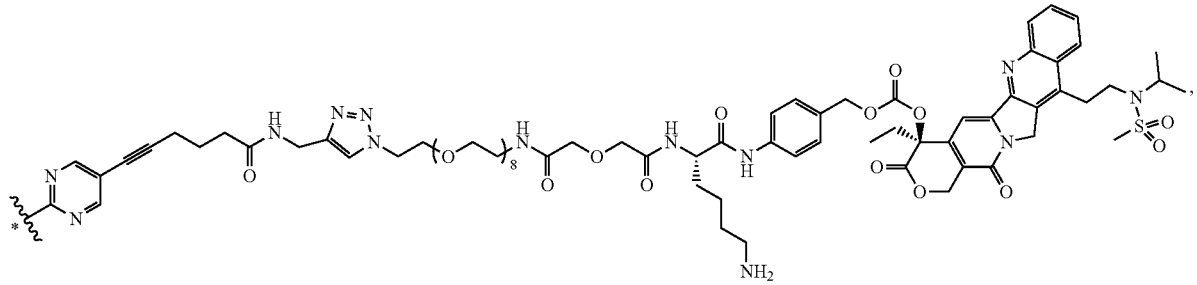

wherein* is the point of attachment to a cysteine of the anti-Trop-2 monoclonal antibody.

20. A pharmaceutical composition comprising one or more of the conjugate of claim 17, and one or more pharmaceutical excipients.

21. The pharmaceutical composition of claim 20, which has a drug-to-antibody ratio ("DAR") of from 5 to 8.

22. The pharmaceutical composition of claim 20, which has a DAR of about 6.9.

* * * * *